US012565647B2

(12) United States Patent
Doudna et al.

(10) Patent No.: US 12,565,647 B2
(45) Date of Patent: Mar. 3, 2026

(54) COMPOSITIONS AND METHODS FOR TARGETED DELIVERY OF CRISPR-Cas EFFECTOR POLYPEPTIDES AND TRANSGENES

(71) Applicant: The Regents of the University of California, Oakland, CA (US)

(72) Inventors: Jennifer A. Doudna, Berkeley, CA (US); Jennifer Hamilton, Berkeley, CA (US); Connor Tsuchida, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/824,626

(22) Filed: May 25, 2022

(65) Prior Publication Data

US 2022/0403379 A1 Dec. 22, 2022

Related U.S. Application Data

(60) Provisional application No. 63/194,679, filed on May 28, 2021.

(51) Int. Cl.
| | |
|---|---|
| *C12N 15/11* | (2006.01) |
| *C07K 14/16* | (2006.01) |
| *C12N 9/22* | (2006.01) |
| *C12N 15/86* | (2006.01) |

(52) U.S. Cl.
CPC .......... *C12N 15/111* (2013.01); *C07K 14/161* (2013.01); *C12N 9/22* (2013.01); *C12N 15/86* (2013.01); *C12N 2310/20* (2017.05); *C12N 2740/16023* (2013.01); *C12N 2740/16043* (2013.01)

(58) Field of Classification Search
CPC ........ C12N 15/111; C12N 9/22; C12N 15/86; C12N 2310/20; C12N 2740/16023; C12N 2740/16043; C12N 2740/16222; C07K 14/161; C07K 2319/09; C07K 2319/50; C07K 14/005; C07K 14/7051; A61K 48/0041
See application file for complete search history.

(56) References Cited

U.S. PATENT DOCUMENTS

| | | | |
|---|---|---|---|
| 5,175,099 | A | 12/1992 | Wills |
| 9,322,037 | B2 | 4/2016 | Liu et al. |
| 10,968,253 | B2 | 4/2021 | Ohlmann |
| 11,649,264 | B2 | 5/2023 | Ohlmann |
| 12,049,480 | B2 | 7/2024 | Ohlmann |
| 12,202,860 | B2 | 1/2025 | Ohlmann |
| 2002/0168346 | A1 | 11/2002 | Leboulch et al. |
| 2005/0009743 | A1 | 1/2005 | Sundquist et al. |
| 2018/0200359 | A1 | 7/2018 | Puckette et al. |
| 2019/0055288 | A1* | 2/2019 | Ohlmann ............... C12N 15/90 |

| | | | |
|---|---|---|---|
| 2020/0255864 | A1 | 8/2020 | Frost et al. |
| 2023/0071283 | A1* | 3/2023 | Golosov ................. A61P 19/02 |
| 2023/0193255 | A1* | 6/2023 | Doudna ................. C12N 15/11 |
| | | | 435/455 |

FOREIGN PATENT DOCUMENTS

| | | |
|---|---|---|
| WO | WO 2010/040023 | 4/2010 |
| WO | WO 2017/068077 | 4/2017 |
| WO | WO 2017/181119 | 10/2017 |
| WO | WO 2020/102709 | 5/2020 |
| WO | WO 2022/183072 A1 | 9/2022 |
| WO | 2023/102550 A2 | 6/2023 |
| WO | WO 2024/015605 A1 | 1/2024 |
| WO | 2024/044557 A1 | 2/2024 |

OTHER PUBLICATIONS

Liu et al. "CRISPR-Cas9-mediated multiplex gene editing in CAR-T cells." Cell research 27.1 (2017): 154-157 (Year: 2017).*
Voelkel, PNAS | Apr. 27, 2010 | vol. 107 | No. 17 | 7805-7810; Abstract (Year: 2010).*
Voet et al., Biochemistry, John Wiley and Sons, 1990, p. 126-129 (Year: 1990).*
Paul et al. (Biomedical journal 43.1 (2020): 8-17.) (Year: 2020).*
Choi et al. (Gene therapy 23.7 (2016): 627-633. (Year: 2016).*
Guo et al. (Cell Research 29.3 (2019): 183-192.) (Year: 2019).*
Münch et al. (Molecular Therapy 19.4 (2011): 686-693. (Year: 2011).*
Hamilton, Jennifer R., et al. "Targeted delivery of CRISPR-Cas9 and transgenes enables complex immune cell engineering." Cell reports 35.9 (2021) (Year: 2021).*
Cebrian-Serrano, et al.; "CRISPR-Cas orthologues and variants: optimizing the repertoire, specificity and delivery of genome engineering tools"; Mamm Genome; vol. 28, pp. 247-261 (2017).
Choi, et al.; "Lentivirus pre-packed with Cas9 protein for safer gene editing"; Gene Therapy; vol. 23, pp. 627-633 (2016).
Cronin, et al.; "Altering the Tropism of Lentiviral Vectors through Pseudotyping"; Curr Gene Ther; vol. 5, No. 4, pp. 387-398 (Aug. 2005).

(Continued)

*Primary Examiner* — Maria Marvich
*Assistant Examiner* — Brendan Thomas Tinsley
(74) *Attorney, Agent, or Firm* — Kyle A. Gurley; Bozicevic, Field & Francis LLP

(57) ABSTRACT

The present disclosure provides virus-like particles (VLPs) comprising: i) a CRISPR-Cas effector polypeptide; ii) a recombinant lentivirus comprising a nucleotide sequence encoding a therapeutic polypeptide having a length of from about 250 amino acids to about 3,000 amino acids, where the VLP comprises a pseudotyping viral glycoprotein and/or a polypeptide that provides for binding to a target cell. The present disclosure provides systems for producing a VLP. The present disclosure provides methods of delivering a therapeutic protein, using a VLP of the present disclosure.

33 Claims, 32 Drawing Sheets

Specification includes a Sequence Listing.

(56)  References Cited

OTHER PUBLICATIONS

Hewitt; "The MHC class I antigen presentation pathway: strategies for viral immune evasion"; Immunology; vol. 110, pp. 163-169 (2003).

Mangeot, et al.; "Efficient genome editing in primary cells and in vivo using viral-derived "Nanoblades" loaded with Cas9/sgRNA ribonucleoproteins"; bioRxiv; doi: https://doi.org/10.1101/202010 (Oct. 12, 2017).

Montagna, et al.; "VSV-G-Enveloped Vesicles for Traceless Delivery of CRISPR-Cas9"; Molecular Therapy: Nucleic Acids; vol. 12, pp. 453-462 (Sep. 2018).

Muriaux, et al.; "Properties and functions of the nucleocapsid protein in virus assembly"; RNA Biology; vol. 7, No. 6, pp. 744-753 (Nov./Dec. 2010).

Pyzocha, et al.; "Diverse Class 2 CRISPR-Cas Effector Proteins for Genome Engineering Applications"; ACS Chemical Biology; vol. 13, pp. 347-356 (2018).

Shao, et al.; "Inhibition of antigen presentation during AAV gene therapy using virus peptides"; Human Molecular Genetics; vol. 27, No. 4, pp. 601-613 (2018).

Staahl, et al.; "Efficient genome editing in the mouse brain by local delivery of engineered Cas9 ribonucleoprotein complexes"; Nature Biotechnology; vol. 35, No. 5, pp. 431-434 (May 2017).

Yewdell, et al.; "Mechanisms of Viral Interference with MHC Class I Antigen Processing and Presentation"; Annu Rev Cell Dev Biol; vol. 15, pp. 579-606 (1999).

Zhou, et al.; "Exclusive Transduction of Human CD4+ T Cells upon Systemic Delivery of CD4-Targeted Lentiviral Vectors"; The Journal of Immunology; vol. 195, No. 5, pp. 2493-2501 (Sep. 1, 2015).

Kim, et al.; "CReVIS-Seq: A highly accurate and multiplexable method for genome-wide mapping of lentiviral integration sites"; Molecular Therapy, Methods & Clinical Development; vol. 20, pp. 792-800 (Mar. 2020).

Schenkwein, et al.; "Efficient Nuclease-Directed Integration of Lentivirus Vectors into the Human Ribosomal DNA Locus"; Molecular Therapy; vol. 28, No. 8, pp. 1858-1875 (Aug. 2020).

Anzalone, et al.; "Search-and-replace genome editing without double-strand breaks or donor DNA"; Nature; vol. 576, pp. 149-157 (2019).

Banskota, et al.; "Engineered virus-like particles for efficient in vivo delivery of therapeutic proteins"; Cell; vol. 185, No. 2, pp. 250-265 (Jan. 20, 2022).

Dobson, et al.; "Antigen identification and high-throughput interaction mapping by reprogramming viral entry"; Nature Methods; vol. 19, pp. 449-460 (2022).

Hamilton, et al.; "In vivo human T cell engineering with enveloped delivery vehicles"; Nature Biotechnology; vol. 42, pp. 1684-1692 (Nov. 2024).

Hamilton, et al.; "Targeted delivery of CRISPR-Cas9 and transgenes enables complex immune cell engineering"; Cell Reports; vol. 35, No. 9, Article 109207, pp. 1-11 (Jun. 1, 2021).

Koblan, et al.; "Improving cytidine and adenine base editors by expression optimization and ancestral reconstruction"; Nature Biotechnology; vol. 36, pp. 843-846 (2018).

Mangeot, et al.; "Genome editing in primary cells and in vivo using viral-derived Nanoblades loaded with Cas9-sgRNA ribonucleoproteins"; Nature Communications; vol. 10, No. 45, pp. 1-15 (2019).

Munch, et al.; "DARPins: An Efficient Targeting Domain for Lentiviral Vectors"; Molecular Therapy; vol. 19, No. 4, pp. 686-693 (Apr. 2011).

Ngo, et al.; "Mechanism-guided engineering of a minimal biological particle for genome editing"; PNAS; vol. 122, No. 1, e2413519121, pp. 1-9 (Dec. 30, 2024), includes Supporting Information.

Nikolic, et al.; "Structural basis for the recognition of LDL-receptor family members by VSV glycoprotein"; Nature Communications; vol. 9, No. 1029, pp. 1-12 (2018).

Richardson, et al.; "Enhancing homology-directed genome editing by catalytically active and inactive CRISPR- Cas9 using asymmetric donor DNA"; Nature Biotechnology; vol. 34, pp. 339-344 (2016).

Yu, et al.; "Systematic discovery of receptor-ligand biology by engineered cell entry and single-cell genomics"; bioRxiv; pp. 1-53 (Dec. 14, 2021).

Gutierrez-Guerrero et al. (2021) "Baboon Envelope Pseudotyped "Nanoblades" Carrying Cas9/gRNA Complexes Allow Efficient Genome Editing in Human T, B, and CD34+ Cells and Knock-in of AAV6-Encoded Donor DNA in CD34+ Cells", Front Genome Ed., 3: 604371 Jan. 2021.

Hübner et al. (2007) "Sequence of human immunodeficiency virus type 1 (HIV-1) Gag localization and oligomerization monitored with live confocal imaging of a replication-competent, fluorescently tagged HIV-1", Journal of Virology, 81:22 12596-12607.

Mangeot et al. (2019) "Genome editing in primary cells and in vivo using viral-derived Nanoblades loaded with Cas9-sgRNA ribonucleoproteins", Nature Communications 10:45 1-15.

Zila et al. (2021) "Cone-shaped HIV-1 capsids are transported through intact nuclear pores", Cell, 184:4 1032-1046.

* cited by examiner

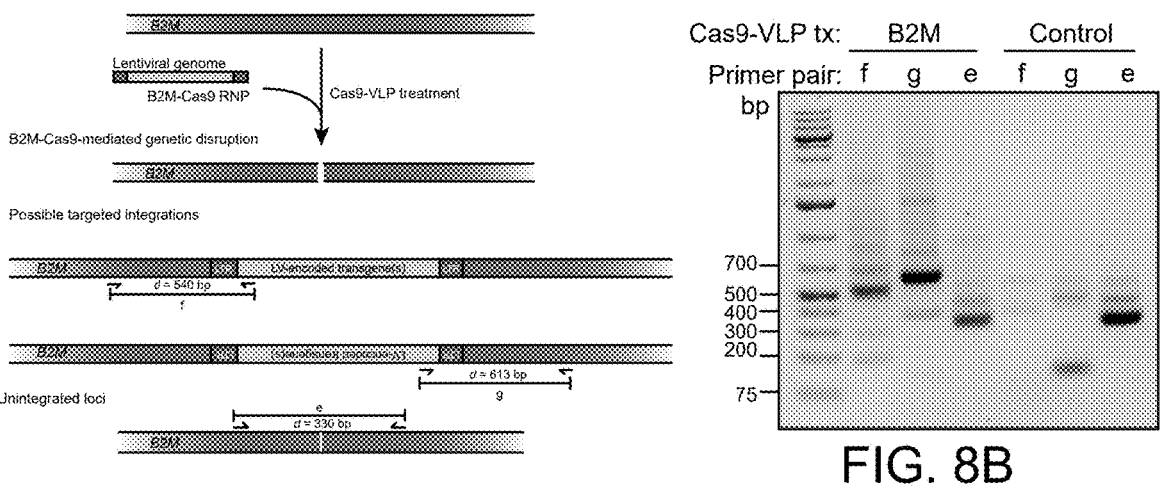
FIG. 8A
FIG. 8B
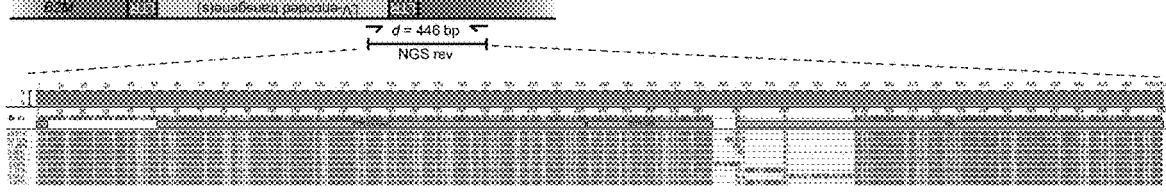
FIG. 8C
FIG. 8D

FIG. 14

Table S1. Protospacer sequences for mammalian genome editing, Related to STAR Methods.

| Target | Spacer sequence | PAM |
|---|---|---|
| B2M | 5'-GAGTAGCGCGAGCACAGCTA | AGG |
| TRAC | 5'-AGAGTCTCTCAGCTGGTACA | CGG |
| BFP | 5'-GCTGAAGCACTGCACGCCAT | GGG |
| Control (tdTom298) | 5'-AAGTAAAACCTCTACAAATG | TGG |
| Control (non-targeting guide used for integration site analysis) | 5'-GTATTACTGATATTGGTGGG | |

FIG. 15

Table S2. Genomic amplification and sequencing primers. Related to STAR Methods.

| Target | Sequence |
|---|---|
| B2M_Sanger_F | 5'-TCACCCAGTCTAGTGCATGC |
| B2M_Sanger_R | 5'-GACGCTTATCGACGCCCTAA |
| TRAC_Sanger_F | 5'-CATCACTGGCATCTGGACTCCA |
| TRAC_Sanger_R | 5'-TGCTCTTGAAGTCCATAGACCTCA |
| B2M_NGS1_F | 5'-GCTCTTCCGATCTTGCGGGCCTTGTCCTGATTG |
| B2M_NGS1_R | 5'-GCTCTTCCGATCTAGATCCAGCCCTGGACTAGC |
| B2M_NGS2_F | 5'-GCTCTTCCGATCTAAGCTGACAGCATTCGGGC |
| B2M_NGS2_R | 5'-GCTCTTCCGATCTGAAGTCACGGAGCGAGAGAG |
| Integration_a_F | 5'-GCTCTTCCGATCTTGCGGGCCTTGTCCTGATTG |
| Integration_a_R | 5'-GTTCGGGCGCCACTGCTAGA |
| Integration_b_F | 5'-TTAAGCCTCAATAAAGCTTGCC |
| Integration_b_R | 5'-GCTCTTCCGATCTAGATCCAGCCCTGGACTAGC |
| Integration_c_F | 5'-GCTCTTCCGATCTTGCGGGCCTTGTCCTGATTG |
| Integration_c_R | 5'-TTAAGCCTCAATAAAGCTTGCC |
| Integration_d_F | 5'-GTTCGGGCGCCACTGCTAGA |
| Integration_d_R | 5'-GCTCTTCCGATCTAGATCCAGCCCTGGACTAGC |
| Integration_e_F | 5'-GCTCTTCCGATCTTGCGGGCCTTGTCCTGATTG |
| Integration_e_R | 5'-GCTCTTCCGATCTAGATCCAGCCCTGGACTAGC |
| Integration_f_F | 5'-GCTCTTCCGATCTTGCGGGCCTTGTCCTGATTG |
| Integration_f_R | 5'-TACTGACGCTCTCGCACCCAT |
| Integration_g_F | 5'-TACTGACGCTCTCGCACCCAT |
| Integration_g_R | 5'-GCTCTTCCGATCTAGATCCAGCCCTGGACTAGC |
| Integration_NGS fwd_F | 5'-GCTCTTCCGATCTAAGCTGACAGCATTCGGGC |
| Integration_NGS fwd_R | 5'-GCTCTTCCGATCTGAGAGCTCCTCTGGTTTCCC |
| Integration_NGS rev_F | 5'-GCTCTTCCGATCTGAGAGCTCCTCTGGTTTCCC |

FIG. 15 (cont'd)

| Integration_NGS rev_R | 5'-GCTCTTCCGATCTGAAGTCACGGAGCGAGAGAG |
|---|---|
| Integration_Nested_1_F | 5'-TCACCCAGTCTAGTGCATGC |
| Integration_Nested_1_R | 5'-GACGCTTATCGACGCCCTAA |
| Integration_Nested_2_F | 5'-GCTCTTCCGATCTAGGTCCGAGCAGTTAACTGG |
| Integration_Nested_2_R | 5'-GCTCTTCCGATCTACTTAGCGGGCGCCTAGA |

Illumina adapter sequences used for library prep are in bold.

FIG. 16

Table S3. HDR template, Related to Fig. S1, STAR Methods.

| Target | Sequence |
|---|---|
| BFP_GFP_HDRT | 5'-GCCACCTACGGCAAGCTGACCCTGAAGTTCATCTGCACCA CCGGCAAGCTGCCCGTGCCCTGGCCCACCCTCGTGACCACC CTGACGTACGGCGTGCAGTGCTTCAGCCGCTACCCCGACCA CATGA |

FIG. 17

Table S4. Primary human T cell donors, Related to STAR Methods.

| Treatment | Figures | Number of Donors |
|---|---|---|
| Nucleofection | Fig. 4, Supp. Fig. 5 | 2 (Donors A-B) |
| VSV-G Cas9-VLP | Fig. 4, Supp. Fig. 5, Supp. Fig. 7 | 4 (Donors A-D) |
| Env Cas9-VLP | Fig. 4, Supp. Fig. 9 | 2 (Donors A-B) |
| B2M Cas9-VLP + TRAC Cas9-VLP | Fig. 4, Supp. Fig. 6 | 2 (Donors E-F) |
| B2M CAR-P2A-mCherry Cas9-VLP | Fig. 4, Supp. Fig. 6, Supp. Fig. 7 | 4 (Donors C-D, E-F) |
| TRAC CAR-P2A-mCherry Cas9-VLP | Fig. 4, Supp. Fig. 6 | 2 (Donors E-F) |

FIG. 18A

*Streptococcus pyogenes* Cas9

```
MDKKYSIGLDIGTNSVGWAVITDEYKVPSKKFKVLGNTDRHSIKKNLIGALLFDSGETAEATRLKRTARRRYTRRKNRICYLQEIFSNEM
AKVDDSFFHRLEESFLVEEDKKHERHPIFGNIVDEVAYHEKYPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPGEKKNGLFGNLIALSLGLTPNFKSNFDLAEDAKLQLSKDTYD
DDLDNLLAQIGDQYADLFLAAKNLSDAILLSDILRVNTEITKAPLSASMIKRYDEHHQDLTLLKALVRQQLPEKYKEIFFDQSKNGYAGYID
GGASQEEFYKFIKPILEKMDGTEELLVKLNREDLLRKQRTFDNGSIPHQIHLGELHAILRRQEDFYPFLKDNREKIEKILTFRIPYYVGPLA
RGNSRFAWMTRKSEETITPWNFEEVVDKGASAQSFIERMTNFDKNLPNEKVLPKHSLLYEYFTVYNELTKVKYVTEGMRKPAFLSGE
QKKAIVDLLFKTNRKVTVKQLKEDYFKKIECFDSVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRNFMQLIHDDSLTFKEDIQKAQVSGQGDSLHEHIA
NLAGSPAIKKGILQTVKVVDELVKVMGRHKPENIVIEMARENQTTQKGQKNSRERMKRIEEGIKELGSQILKEHPVENTQLQNEKLYLYY
LQNGRDMYVDQELDINRLSDYDVDHIVPQSFLKDDSIDNKVLTRSDKNRGKSDNVPSEEVVKKMKNYWRQLLNAKLITQRKFDNLTKA
ERGGLSELDKAGFIKRQLVETRQITKHVAQILDSRMNTKYDENDKLIREVKVITLKSKLVSDFRKDFQFYKVREINNYHHAHDAYLNAVV
GTALIKKYPKLESEFVYGDYKVYDVRKMIAKSEQEIGKATAKYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGFDSPTVAYSVLVVAKVEKGKSKKLKSVKELLGITIMERSSF
EKNPIDFLEAKGYKEVKKDLIIKLPKYSLFELENGRKRMLASAGELQKGNELALPSKYVNFLYLASHYEKLKGSPEDNEQKQLFVEQHK
HYLDEIIEQISEFSKRVILADANLDKVLSAYNKHRDKPIREQAENIIHLFTLTNLGAPAAFKYFDTTIDRKRYTSTKEVLDATLIHQSITGLYE
TRIDLSQLGGD
(SEQ ID NO:200)
```

FIG. 18B

SpCas9 (SpCas9 D10A)

MDKKYSIGLAIGTNSVGWAVITDEYKVPSKKFKVLGNTDRHSIKKNLIGALLFDSGETAEATRLKRTARRRYTRRKNRICYLQEIFSNEM
AKVDDSFFHRLEESFLVEEDKKHERHPIFGNIVDEVAYHEKYPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPGEKKNGLFGNLIALSLGLTPNFKSNFDLAEDAKLQLSKDTYD
DDLDNLLAQIGDQYADLFLAAKNLSDAILLSDILRVNTEITKAPLSASMIKRYDEHHQDLTLLKALVRQQLPEKYKEIFFDQSKNGYAGYI
DGGASQEEFYKFIKPILEKMDGTEELLVKLNREDLLRKQRTFDNGSIPHQIHLGELHAILRRQEDFYPFLKDNREKIEKILTFRIPYYVGPLA
RGNSRFAWMTRKSEETITPWNFEEVVDKGASAQSFIERMTNFDKNLPNEKVLPKHSLLYEYFTVYNELTKVKYVTEGMRKPAFLSGEQ
KKAIVDLLFKTNRKVTVKQLKEDYFKKIECFDSVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRNFMQLIHDDSLTFKEDIQKAQVSGQGDSLHEHIA
NLAGSPAIKKGILQTVKVVDELVKVMGRHKPENIVIEMARENQTTQKGQKNSRERMKRIEEGIKELGSQILKEHPVENTQLQNEKLYLY
YLQNGRDMYVDQELDINRLSDYDVDHIVPQSFLKDDSIDNKVLTRSDKNRGKSDNVPSEEVVKMKNYWRQLLNAKLITQRKFDNLTK
AERGGLSELDKAGFIKRQLVETRQITKHVAQILDSRMNTKYDENDKLIREVKVITLKSKLVSDFRKDFQFYKVREINNYHHAHDAYLNA
VVGTALIKKYPKLESEFVYGDYKVYDVRKMIAKSEQEIGKATAKYFFYSNIMNFFKTEITLANGEIRKRPLIETNGETGEIVWDKGRDFAT
VRKVLSMPQVNIVKKTEVQTGGFSKESILPKRNSDKLIARKKDWDPKKYGGFDSPTVAYSVLVVAKVEKGKSKKLKSVKELLGITIMER
SSFEKNPIDFLEAKGYKEVKKDLIIKLPKYSLFELENGRKRMLASAGELQKGNELALPSKYVNFLYLASHYEKLKGSPEDNEQKQLFVEQ
HKHYLDEIIEQISEFSKRVILADANLDKVLSAYNKHRDKPIREQAENIIHLFTLTNLGAPAAFKYFDTTIDRKRYTSTKEVLDATLIHQSITG
LYETRIDLSQLGGD
(SEQ ID NO:201)

FIG. 18C

SpCas9 (H840A)

MDKKYSIGLDIGTNSVGWAVITDEYKVPSKKFKVLGNTDRHSIKKNLIGALLFDSGETAEATRLKRTARRRYTRRKNRICYLQEIFSNEM
AKVDDSFFHRLEESFLVEEDKKHERHPIFGNIVDEVAYHEKYPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPGEKKNGLFGNLIALSLGLTPNFKSNFDLAEDAKLQLSKDTYD
DDLDNLLAQIGDQYADLFLAAKNLSDAILLSDILRVNTEITKAPLSASMIKRYDEHHQDLTLLKALVRQQLPEKYKEIFFDQSKNGYAGYID
GGASQEEFYKFIKPILEKMDGTEELLVKLNREDLLRKQRTFDNGSIPHQIHLGELHAILRRQEDFYPFLKDNREKIEKILTFRIPYYVGPLA
RGNSRFAWMTRKSEETITPWNFEEVVDKGASAQSFIERMTNFDKNLPNEKVLPKHSLLYEYFTVYNELTKVKYVTEGMRKPAFLSGE
QKKAIVDLLFKTNRKVTVKQLKEDYFKKIECFDSVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRNFMQLIHDDSLTFKEDIQKAQVSGQGDSLHEHIA
NLAGSPAIKKGILQTVKVVDELVKVMGRHKPENIVIEMARENQTTQKGQKNSRERMKRIEEGIKELGSQILKEHPVENTQLQNEKLYLYY
LQNGRDMYVDQELDINRLSDYDVDAIVPQSFLKDDSIDNKVLTRSDKNRGKSDNVPSEEVVKKMKNYWRQLLNAKLITQRKFDNLTKA
ERGGLSELDKAGFIKRQLVETRQITKHVAQILDSRMNTKYDENDKLIREVKVITLKSKLVSDFRKDFQFYKVREINNYHHAHDAYLNAVV
GTALIKKYPKLESEFVYGDYKVYDVRKMIAKSEQEIGKATAKYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGFDSPTVAYSVLVVAKVEKGKSKKLKSVKELLGITIMERSSF
EKNPIDFLEAKGYKEVKKDLIIKLPKYSLFELENGRKRMLASAGELQKGNELALPSKYVNFLYLASHYEKLKGSPEDNEQKQLFVEQHK
HYLDEIIEQISEFSKRVILADANLDKVLSAYNKHRDKPIREQAENIIHLFTLTNLGAPAAFKYFDTTIDRKRYTSTKEVLDATLIHQSITGLYE
TRIDLSQLGGD (SEQ ID NO:202)

FIG. 18D

SpCas9 (D10A; H840A)

MDKKYSIGLAIGTNSVGWAVITDEYKVPSKKFKVLGNTDRHSIKKNLIGALLFDSGETAEATRLKRTARRRYTRRKNRICYLQEIFSNEM
AKVDDSFFHRLEESFLVEEDKKHERHPIFGNIVDEVAYHEKYPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPGEKKNGLFGNLIALSLGLTPNFKSNFDLAEDAKLQLSKDTYD
DDLDNLLAQIGDQYADLFLAAKNLSDAILLSDILRVNTEITKAPLSASMIKRYDEHHQDLTLLKALVRQQLPEKYKEIFFDQSKNGYAGYID
GGASQEEFYKFIKPILEKMDGTEELLVKLNREDLLRKQRTFDNGSIPHQIHLGELHAILRRQEDFYPFLKDNREKIEKILTFRIPYYVGPLA
RGNSRFAWMTRKSEETITPWNFEEVVDKGASAQSFIERMTNFDKNLPNEKVLPKHSLLYEYFTVYNELTKVKYVTEGMRKPAFLSGE
QKKAIVDLLFKTNRKVTVKQLKEDYFKKIECFDSVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRNFMQLIHDDSLTFKEDIQKAQVSGQGDSLHEHIA
NLAGSPAIKKGILQTVKVVDELVKVMGRHKPENIVIEMARENQTTQKGQKNSRERMKRIEEGIKELGSQILKEHPVENTQLQNEKLYLYY
LQNGRDMYVDQELDINRLSDYDVDAIVPQSFLKDDSIDNKVLTRSDKNRGKSDNVPSEEVVKKMKNYWRQLLNAKLITQRKFDNLTKA
ERGGLSELDKAGFIKRQLVETRQITKHVAQILDSRMNTKYDENDKLIREVKVITLKSKLVSDFRKDFQFYKVREINNYHHAHDAYLNAVV
GTALIKKYPKLESEFVYGDYKVYDVRKMIAKSEQEIGKATAKYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGFDSPTVAYSVLVVAKVEKGKSKKLKSVKELLGITIMERSSF
EKNPIDFLEAKGYKEVKKDLIIKLPKYSLFELENGRKRMLASAGELQKGNELALPSKYVNFLYLASHYEKLKGSPEDNEQKQLFVEQHK
HYLDEIIEQISEFSKRVILADANLDKVLSAYNKHRDKPIREQAENIIHLFTLTNLGAPAAFKYFDTTIDRKRYTSTKEVLDATLIHQSITGLYE
TRIDLSQLGGD
(SEQ ID NO:203)

FIG. 18E enSpCas9 (nCas9 with K848A/K1003A/R1060A mutations)

MDKKYSIGLAIGTNSVGWAVITDEYKVPSKKFKVLGNTDRHSIKKNLIGALLFDSGETAEATRLKRTARRRYTRRKNRICYLQEIFSNEM
AKVDDSFFHRLEESFLVEEDKKHERHPIFGNIVDEVAYHEKYPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPGEKKNGLFGNLIALSLGLTPNFKSNFDLAEDAKLQLSKDTYD
DDLDNLLAQIGDQYADLFLAAKNLSDAILLSDILRVNTEITKAPLSASMIKRYDEHHQDLTLLKALVRQQLPEKYKEIFFDQSKNGYAGYI
DGGASQEEFYKFIKPILEKMDGTEELLVKLNREDLLRKQRTFDNGSIPHQIHLGELHAILRRQEDFYPFLKDNREKIEKILTFRIPYYVGPLA
RGNSRFAWMTRKSEETITPWNFEEVVDKGASAQSFIERMTNFDKNLPNEKVLPKHSLLYEYFTVYNELTKVKYVTEGMRKPAFLSGEQ
KKAIVDLLFKTNRKVTVKQLKEDYFKKIECFDSVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRNFMQLIHDDSLTFKEDIQKAQVSGQGDSLHEHIA
NLAGSPAIKKGILQTVKVDELVKVMGRHKPENIVIEMARENQTTQKGQKNSRERMKRIEEGIKELGSQILKEHPVENTQLQNEKLYLY
YLQNGRDMYVDQELDINRLSDYDVDHIVPQSFLADDSIDNKVLTRSDKNRGKSDNVPSEEVVKKMKNYWRQLLNAKLITQRKFDNLTK
AERGGLSELDKAGFIKRQLVETRQITKHVAQILDSRMNTKYDENDKLIREVKVITLKSKLVSDFRKDFQFYKVREINNYHHAHDAYLNA
VVGTALIKKYPALESEFVYGDYKVYDVRKMIAKSEQEIGKATAKYFFYSNIMNFFKTEITLANGEIRKAPLIETNGETGEIVWDKGRDFA
TVRKVLSMPQVNIVKKTEVQTGGFSKESILPKRNSDKLIARKKDWDPKKYGGFDSPTVAYSVLVVAKVEKGKSKKLKSVKELLGITIME
RSSFEKNPIDFLEAKGYKEVKKDLIIKLPKYSLFELENGRKRMLASAGELQKGNELALPSKYVNFLYLASHYEKLKGSPEDNEQKQLFVE
QHKHYLDEIIEQISEFSKRVILADANLDKVLSAYNKHRDKPIREQAENIIHLFTLTNLGAPAAFKYFDTTIDRKRYTSTKEVLDATLIHQSIT
GLYETRIDLSQLGGD
(SEQ ID NO:204)

FIG. 18F nSpCas9-HF1

DKKYSIGLAIGTNSVGWAVITDEYKVPSKKFKVLGNTDRHSIKKNLIGALLFDSGETAEATRLKRTARRRYTRRKNRICYLQEIFSNEMA
KVDDSFFHRLEESFLVEEDKKHERHPIFGNIVDEVAYHEKYPTIYHLRKKLVDSTDKADLRLIYLALAHMIKFRGHFLIEGDLNPDNSDVD
KLFIQLVQTYNQLFEENPINASGVDAKAILSARLSKSRRLENLIAQLPGEKKNGLFGNLIALSLGLTPNFKSNFDLAEDAKLQLSKDTYDD
DLDNLLAQIGDQYADLFLAAKNLSDAILLSDILRVNTEITKAPLSASMIKRYDEHHQDLTLLKALVRQQLPEKYKEIFFDQSKNGYAGYID
GGASQEEFYKFIKPILEKMDGTEELLVKLNREDLLRKQRTFDNGSIPHQIHLGELHAILRRQEDFYPFLKDNREKIEKILTFRIPYYVGPLAR
GNSRFAWMTRKSEETITPWNFEEVVDKGASAQSFIERMTAFDKNLPNEKVLPKHSLLYEYFTVYNELTKVKYVTEGMRKPAFLSGEQK
KAIVDLLFKTNRKVTVKQLKEDYFKKIECFDSVEISGVEDRFNASLGTYHDLLKIIKDKDFLDNEENEDILEDIVLTLTLFEDREMIEERLK
TYAHLFDDKVMKQLKRRRYTGWGALSRKLINGIRDKQSGKTILDFLKSDGFANRNFMALIHDDSLTFKEDIQKAQVSGQGDSLHEHIAN
LAGSPAIKKGILQTVKVVDELVKVMGRHKPENIVIEMARENQTTQKGQKNSRERMKRIEEGIKELGSQILKEHPVENTQLQNEKLYLYYL
QNGRDMYVDQELDINRLSDYDVDHIVPQSFLKDDSIDNKVLTRSDKNRGKSDNVPSEEVVKKMKNYWRQLLNAKLITQRKFDNLTKAE
RGGLSELDKAGFIKRQLVETRAITKHVAQILDSRMNTKYDENDKLIREVKVITLKSKLVSDFRKDFQFYKVREINNYHHAHDAYLNAVV
GTALIKKYPKLESEFVYGDYKVYDVRKMIAKSEQEIGKATAKYFFYSNIMNFFKTEITLANGEIRKRPLIETNGETGEIVWDKGRDFATVR
KVLSMPQVNIVKKTEVQTGGFSKESILPKRNSDKLIARKKDWDPKKYGGFDSPTVAYSVLVVAKVEKGKSKKLKSVKELLGITIMERSSF
EKNPIDFLEAKGYKEVKKDLIIKLPKYSLFELENGRKRMLASAGELQKGNELALPSKYVNFLYLASHYEKLKGSPEDNEQKQLFVEQHK
HYLDEIIEQISEFSKRVILADANLDKVLSAYNKHRDKPIREQAENIIHLFTLTNLGAPAAFKYFDTTIDRKRYTSTKEVLDATLIHQSITGLY
ETRIDLSQLGGD (SEQ ID NO:205)

FIG. 18G

*Staphylococcus aureus* Cas9

MKRNYILGLDIGITSVGYGVIIDYETRDVIDAGVRLFKEANVENNEGRRSKRGARRLKRRRRHRIQRVKKLLFDYNLLTDHSELSGINPYE
ARVKGLSQKLSEEEFSAALLHLAKRRGVHNVNEVEEDTGNELSTKEQISRNSKALEEKYVAELQLERLKKDGEVRGSINRFKTSDYVK
EAKQLLKVQKAYHQLDQSFIDTYIDLLETRRTYYEGPGEGSPFGWKDIKEWYEMLMGHCTYFPEELRSVKYAYNADLYNALNDLNNLV
ITRDENEKLEYYEKFQIIENVFKQKKKPTLKQIAKEILVNEEDIKGYRVTSTGKPEFTNLKVVHDIKDITARKEIIENAELLDQIAKILTIYQSS
EDIQEELTNLNSELTQEEIEQISNLKGYTGTHNLSLKAINLILDELWHTNDNQIAIFNRLKLVPKKVDLSQQKEIPTTLVDDFILSPVVKRSFI
QSIKVINAIIKKYGLPNDIIIELAREKNSKDAQKMINEMQKRNRQTNERIEEIIRTTGKENAKYLIEKIKLHDMQEGKCLYSLEAIPLEDLLNN
PFNYEVDHIIPRSVSFDNSFNNKVLVKQEENSKKGNRTPFQYLSSSDSKISYETFKKHILNLAKGKGRISKTKKEYLLEERDINRFSVQK
DFINRNLVDTRYATRGLMNLLRSYFRVNNLDVKVKSINGGFTSFLRRKWKFKKERNKGYKHHAEDALIIANADFIFKEWKKLDKAKKVM
ENQMFEEKQAESMPEIETEQEYKEIFITPHQIKHIKDFKDYKYSHRVDKKPNRELINDTLYSTRKDDKGNTLIVNNLNGLYDKDNDKLKK
LINKSPEKLLMYHHDPQTYQKLKLIMEQYGDEKNPLYKYYEETGNYLTKYSKKDNGPVIKKIKYYGNKLNAHLDITDDYPNSRNKVVKLS
LKPYRFDVYLDNGVYKFVTVKNLDVIKKENYYEVNSKCYEEAKKLKKISNQAEFIASFYNNDLIKINGELYRVIGVNNDLLNRIEVNMIDIT
YREYLENMNDKRPPPRIIKTIASKTQSIKKYSTDILGNLYEVKSKKHPQIIKKG (SEQ ID NO:206)

FIG. 18H

*Francisella tularensis* Cpf1 (Cas12a)

```
   1  MSIYQEFVNK  YSLSKTLRFE  LIPQGKTLEN  IKARGLILDD  EKRAKDYKKA  KQIIDKYHQF
  61  FIEEILSSVC  ISEDLLQNYS  DVYFKLKKSD  DDNLQKDFKS  AKDTIKKQIS  EYIKDSEKFK
 121  NLFNQNLIDA  KKGQESDLIL  WLKQSKDNGI  ELFKANSDIT  DIDEALEIIK  SFKGWTTYFK
 181  GFHENRKNVY  SSNDIPTSII  YRIVDDNLPK  FLENKAKYES  LKDKAPEAIN  YEQIKKDLAE
 241  ELTFDIDYKT  SEVNQRVFSL  DEVFEIANFN  NYLNQSGITK  FNTIIGGKFV  NGENTKRKGI
 301  NEYINLYSQQ  INDKTLKKYK  MSVLFKQILS  DTESKSFVID  KLEDDSDVVT  TMQSFYEQIA
 361  AFKTVEEKSI  KETLSLLFDD  LKAQKLDLSK  IYFKNDKSLT  DLSQQVFDDY  SVIGTAVLEY
 421  ITQQIAPKNL  DNPSKKEQEL  IAKKTEKAKY  LSLETIKLAL  EEFNKHRDID  KQCRFEEILA
 481  NFAAIPMIFD  EIAQNKDNLA  QISIKYQNQG  KKDLLQASAE  DDVKAIKDLL  DQTNNLLHKL
 541  KIFHISQSED  KANILDKDEH  FYLVFEECYF  ELANIVPLYN  KIRNYITQKP  YSDEKFKLNF
 601  ENSTLANGWD  KNKEPDNTAI  LFIKDDKYYL  GVMNKKNNKI  FDDKAIKENK  GEGYKKIVYK
 661  LLPGANKMLP  KVFFSAKSIK  FYNPSEDILR  IRNHSTHTKN  GSPQKGYEKF  EFNIEDCRKF
 721  IDFYKQSISK  HPEWKDFGFR  FSDTQRYNSI  DEFYREVENQ  GYKLTFENIS  ESYIDSVVNQ
 781  GKLYLFQIYN  KDFSAYSKGR  PNLHTLYWKA  LFDERNLQDV  VYKLNGEAEL  FYRKQSIPKK
 841  ITHPAKEAIA  NKNKDNPKKE  SVFEYDLIKD  KRFTEDKFFF  HCPITINFKS  SGANKFNDEI
 901  NLLLKEKAND  VHILSIDRGE  RHLAYYTLVD  GKGNIIKQDT  FNIIGNDRMK  TNYHDKLAAI
 961  EKDRDSARKD  WKKINNIKEM  KEGYLSQVVH  EIAKLVIEYN  AIVVFEDLNF  GFKRGRFKVE
1021  KQVYQKLEKM  LIEKLNYLVF  KDNEFDKTGG  VLRAYQLTAP  FETFKKMGKQ  TGIIYVPAG
1081  FTSKICPVTG  FVNQLYPKYE  SVSKSQEFFS  KFDKICYNLD  KGYFEFSFDY  KNFGDKAAKG
1141  KWTIASFGSR  LINFRNSDKN  HNWDTREVYP  TKELEKLLKD  YSIEYGHGEC  IKAAICGESD
1201  KKFFAKLTSV  LNTILQMRNS  KTGTELDYLI  SPVADVNGNF  FDSRQAPKNM  PQDADANGAY
1261  HIGLKGLMLL  GRIKNNQEGK  KLNLVIKNEE  YFEFVQNRNN
```

(SEQ ID NO:207)

FIG. 18I

*Acidaminococcus sp. BV3L6* type V CRISPR-associated protein Cpf1 (Cas12a)

TQFEGFTNLYQVSKTLRFELIPQGKTLKHIQEQGFIEEDKARNDHYKELKPIIDRIYKTYADQCLQLVQLDWENLSAAIDSYRKEKTEETR
NALIEEQATYRNAIHDYFIGRTDNLTDAINKRHAEIYKGLFKAELFNGKVLKQLGTVTTEHENALLRSFDKFTYFSGFYENRKNVFSAE
DISTAIPHRIVQDNFPKFKENCHIFTRLITAVPSLREHFENVKKAIGIFVSTSIEEVFSFPFYNQLLTQTQIDLYNQLLGGISREAGTEKIKGLN
EVLNLAIQKNDETAHIIASLPHRFIPLFKQILSDRNTLSFILEEFKSDEEVIQSFCKYKTLLRNENVLETAEALFNELNSIDLTHIFISHKKLETI
SSALCDHWDTLRNALYERRISELTGKITKSAKEKVQRSLKHEDINLQEIISAAGKELSEAFKQKTSEILSHAHAALDQPLPTTLKKQEEKEI
LKSQLDSLLGLYHLLDWFAVDESNEVDPEFSARLTGIKLEMEPSLSFYNKARNYATKKPYSVEKFKLNFQMPTLASGWDVNKEKNNGAI
LFVKNGLYYLGIMPKQKGRYKALSFEPTEKTSEGFDKMYYDYFPDAAKMIPKCSTQLKAVTAHFQTHTTPILLSNNFIEPLEITKEIYDLN
NPEKEPKKFQTAYAKKTGDQKGYREALCKWIDFTRDFLSKYTKTTSIDLSSLRPSSQYKDLGEYYAELNPLLYHISFQRIAEKEIMDAVET
GKLYLFQIYNKDFAKGHHGKPNLHTLYWTGLFSPENLAKTSIKLNGQAELFYRPKSRMKRMAHRLGEKMLNKKLKDQKTPIPDTLYQE
LYDYVNHRLSHDLSDEARALLPNVITKEVSHEIIKDRRFTSDKFFFHVPITLNYQAANSPSKFNQRVNAYLKEHPETPIIGIDRGERNLIYIT
VIDSTGKILEQRSLNTIQQFDYQKKLDNREKERVAARQAWSVVGTIKDLKQGYLSQVIHEIVDLMIHYQAVVLENLNFGFKSKRTGIAE
KAVYQQFEKMLIDKLNCLVLKDYPAEKVGGVLNPYQLTDQFTSFAKMGTQSGFLFYVPAPYTSKIDPLTGFVDPFVWKTIKNHESRKHF
LEGFDFLHYDVKTGDFILHFKMNRNLSFQRGLPGFMPAWDIVFEKNETQFDAKGTPFIAGKRIVPVIENHRFTGRYRDLYPANELIALLEE
KGIVFRDGSNILPKLLENDDSHAIDTMVALIRSVLQMRNSNAATGEDYINSPVRDLNGVCFDSRFQNPEWPMDADANGAYHIALKGQLL
LNHLKESKDLKLQNGISNQDWLAYIQELRN
(SEQ ID NO:208)

FIG. 18J

Cpf1 (AsCpf1 R1225A)

TQFEGFTNLYQVSKTLRFELIPQGKTLKHIQEQGFIEEDKARNDHYKELKPIIDRIYKTYADQCLQLVQLDWENLSAAIDSYRKEKTEETR
NALIEEQATYRNAIHDYFIGRTDNLTDAINKRHAEIYKGLFKAELFNGKVLKQLGTVTTEHENALLRSFDKFTIYFSGFYENRKNVFSAE
DISTAIPHRIVQDNFPKFKENCHIFTRLITAVPSLREHFENVKKAIGIFVSTSIEEVFSFPFYNQLLTQTQIDLYNQLLGGISREAGTEKIKGLN
EVLNLAIQKNDETAHIIASLPHRFIPLFKQILSDRNTLSFILEEFKSDEEVIQSFCKYKTLLRNENVLETAEALFNELNSIDLTHIFISHKKLETI
SSALCDHWDTLRNALYERRISELTGKITKSAKEKVQRSLKHEDINLQEIISAAGKELSEAFKQKTSEILSHAHAALDQPLPTTLKKQEEKEI
LKSQLDSLLGLYHLLDWFAVDESNEVDPEFSARLTGIKLEMEPSLSFYNKARNYATKKPYSVEKFKLNFQMPTLASGWDVNKEKNNGAI
LFVKNGLYYLGIMPKQKGRYKALSFEPTEKTSEGFDKMYYDYFPDAAKMIPKCSTQLKAVTAHFQTHTTPILLSNNFIEPLEITKEIYDLN
NPEKEPKKFQTAYAKKTGDQKGYREALCKWIDFTRDFLSKYTKTTSIDLSSLRPSSQYKDLGEYYAELNPLLYHISFQRIAEKEIMDAVET
GKLYLFQIYNKDFAKGHHGKPNLHTLYWTGLFSPENLAKTSIKLNGQAELFYRPKSRMKRMAHRLGEKMLNKKLKDQKTPIPDTLYQE
LYDYVNHRLSHDLSDEARALLPNVITKEVSHEIIKDRRFTSDKFFFHVPITLNYQAANSPSKFNQRVNAYLKEHPETPIIGIDRGERNLIYIT
VIDSTGKILEQRSLNTIQQFDYQKKLDNREKERVAARQAWSVVGTIKDLKQGYLSQVIHEIVDLMIHYQAVVLENLNFGFKSKRTGIAE
KAVYQQFEKMLIDKLNCLVLKDYPAEKVGGVLNPYQLTDQFTSFAKMGTQSGFLFYVPAPYTSKIDPLTGFVDPFVWKTIKNHESRKHF
LEGFDFLHYDVKTGDFILHFKMNRNLSFQRGLPGFMPAWDIVFEKNETQFDAKGTPFIAGKRIVPVIENHRFTGRYRDLYPANELIALLEE
KGIVFRDGSNILPKLLENDDSHAIDTMVALIRSVLQMANSNAATGEDYINSPVRDLNGVCFDSRFQNPEWPMDADANGAYHIALKGQLL
LNHLKESKDLKLQNGISNQDWLAYIQELRN (SEQ ID NO:209)

FIG. 18K

> Listeria seeligeri (WP_012985477.1)

```
MWISIKTLIHHLGVLFFCDYMYNRREKKIIEVKTMRITKVEVDRKKVLISRDKNGGKLVYENEMQDNTEQIMHHKKSSFYKSVVNKTICRPEQKQMKK
LVHGLLQENSQEKIKVSDVTKLNISNFLNHRFKKSLYYFPENSPDKSEEYRIEINLSQLLEDSLKKQQGTFICWESFSKDMELYINWAENYISSKTKL
IKKSIRNNRIQSTESRSGQLMDRYMKDILNKNKPFDIQSVSEKYQLEKLTSALKATFKEAKKNDKEINYKLKSTLQNHERQIIEELKENSELNQFNIE
IRKHLETYFPIKKTNRKVGDIRNLEIGEIQKIVNHRLKNKIVQRILQEGKLASYEIESTVNSNSLQKIKIEEAFALKFINACLFASNNLRNMVYPVCK
KDILMIGEFKNSFKEIKHKKFIRQWSQFFSQEITVDDIELASWGLRGAIAPIRNEIIHLKKHSWKKFFNNPTFKVKKSKIINGKTKDVTSEFLYKETL
FKDYFYSELDSVPELIINKMESSKILDYYSSDQLNQVFTIPNFELSLLTSAVPFAPSFKRVYLKGFDYQNQDEAQPDYNLKLNIYNEKAFNSEAFQAQ
YSLFKMVYYQVFLPQFTTNNDLFKSSVDFILTLNKERKGYAKAFQDIRKMNKDEKPSEYMSYIQSQLMLYQKKQEEKEKINHFEKFINQVFIKGFNSF
IEKNRLTYICHPTKNTVPENDNIEIPFHTDMDDSNIAFWLMCKLLDAKQLSELRNEMIKFSCSLQSTEEISTFTKAREVIGLALLNGEKGCNDWKELF
DDKEAWKKNMSLYVSEELLQSLPYTQEDGQTPVINRSIDLVKKYGTETILEKLFSSSDDYKVSAKDIAKLHEYDVTEKIAQQESLHKQWIEKPGLARD
SAWTKKYQNVINDISNYQWAKTKVELTQVRHLHQLTIDLLSRLAGYMSIADRDFQFSSNYILERENSEYRVTSWILLSENKNKNYNDYELYNLKNAS
IKVSSKNDPQLKVDLKQLRLTEYLELFDNRLKEKRNNISHFNYLNGQLGNSILELFDDARDVLSYDRKLKNAVSKSLKEILSSHGMEVTFKPLYQTN
HHLKIDKLQPKKIHHLGEKSTVSSNQVSNEYCQLVRTLLTMK   (SEQ ID NO:210)
```

FIG. 18L

>Leptotrichia buccalis (WP_015770004.1)

```
MKVTKVGGISHKKYTSEGRLVKSESEENRTDERLSALLNMRLDMYIKNPSSTETKENQKR
IGKLKKFSNKMVYLKDNTLSLKNGKKENIDREYSETDILESDVRDKKNFAVLKKIYLNE
NVNSEELEVFRNDIKKKLNKINSLKYSFEKNKANYQKINENNIEKVEGKSKRNIIYDYYR
ESAKRDAYVSNVKEAFDKLYKEEDIAKLVLEIENLTKLEKYKIREFYHEIIGRKNDKENF
AKIIYEEIQNVNNMKELIEKVPDMSELKKSQVFYKYYLDKEELNDKNIKYAFCHFVEIEM
SQLLKNYVYKRLSNISNDKIKRIFEYQNLKKLIENKLLNKLDTYVRNCGKYNYYLQDGEI
ATSDFIARNRQNEAFLRNIIGVSSVAYFSLRNILETENENDITGRMRGKTVKNNKGEEKY
VSGEVDKIYNENKKNEVKENLKMFYSYDFNMDNKNEIEDFFANIDEAISSIRHGIVHFNL
ELEGKDIFAFKNIAPSEISKKMFQNEINEKKLKLKIFRQLNSANVFRYLEKYKILNYLKR
TREFVNKNIPFVPSFTKLYSRIDDLKNSLGIYWKTPKTNDDNKTKEIIDAQIYLLKNIY
YGEFLNYFMSNNGNFFEISKEIIELNKNDKRNLKTGFYKLQKFEDIQEKIPKEYLANIQS
LYMINAGNQDEEKDTYIDFIQKIFLKGFMTYLANNGRLSLIYIGSDEETNTSLAEKKQE
FDKFLKKYEQNNNIKIPYEINEFLREIKLGNILKYTERLNMFYLILKLLNHKELTNLKGS
LEKYQSANKEEAFSDQLELINLLNLDNNRVTEDFELEADEIGKFLDFNGNKVKDNKELKK
FDTNKIYFDGENIIKHRAFYNIKKYGMINLLEKIADKAGYKISIEELKKYSNKKNEIEKN
HKMQENLHRKYARPRKDEKFTDEDYESYKQAIENIEEYTHLKNKVEFNELNLLQGLLLRI
LHRLVGYTSIWERDLRFRLKGEFPENQYIEEIFNFENKKNVKYKGGQIVEKYIKFYKELH
QNDEVKINKYSSANIKVLKQEKKDLYIRNYIAHFNYIPHAEISLLEVLENLRKLLSYDRK
LKNAVMKSVVDILKEYGFVATFKIGADKKIGIQTLESEKIVHLKNLKKKKLMTDRNSEEL
CKLVKIMFEYKMEEKKSEN    (SEQ ID NO:211)
```

FIG. 18M

> Leptotrichia shahii   (WP_018451595.1)

```
MGNLFGHKRWYEVRDKKDFKIKRKVKVKRNYDGNKYILNINENNNKEIDNNKEIRKYIN
YKKNDNILKEFTRKFHAGNILFKLKGKEGIIRIENNDFELETEEVVLYIEAYGKSEKLKA
LGITKKKIIDEAIRQGITKDDKKIEIKRQENEEEIEIDIRDEYTNKTLNDCSIIRIIEN
DELETKKSIYEIFKNINMSLYKIIEKIIENETEKVFENRYYEEHLREKLLKDDKIDVLT
NFMEIREKIKSNLEILGFVKFYLNVGGDKKKSKNKKMLVEKILNINVDLTVEDIADFVIK
ELEFWNITKRIEKVKKVNNEFLEKRRNRTYIKSYVLLDKHEKFKIERENKKDKIVKFFVE
NIKNNSIKEKIEKILAEFKIDELIKKLEKELKKGNCDTEIFGIFKKHYKVNFDSKKFSKK
SDEEKELYKIIYRYLKGRIEKILVNEQKVRLKKMEKIEIEKILNESILSEKILKRVKQYT
LEHIMYLGKLRHNDIDMTTVNTDFSRLHAKEELDLELITFFASTNMELNKIFSRENINN
DENIDFFGGDREKNYVLDKIILNSKIKIIRDLDFIDNKNNITNNFIRKFTKIGTNERNRI
LHAISKERDLQGTQDDYNKVINIIQNLKISDEEVSKALNLDVVFKDKKNIITKINDIKIS
EENNNDIKYLPSFSKVLPEILNLYRNNPKNEPFDTIETEKIVLNALIYVNKELYKKLILE
DDLEENESKNIFLQELKKTLGNIDEIDENIIENYYKNAQISASKGNNKAIKKYQKKVIEC
YIGYLRKNYEELFDFSDFKMNIQEIKKQIKDINDNKTYERITVKTSDKTIVINDDFEYII
SIFALLNSNAVINKIRNRFFATSVWLNTSEYQNIIDILDEIMQLNTLRNECITENWNLNL
EEFIQRMKEIEKDEFDDFKIQTKKEIFNNYYEDIKNNILTEFKDDINGCDVLEKKLEKIVI
FDDETKFEIDKKSNILQDEQRKLSNINKKDLKKKVDQYIKDKDQEIKSKILCRIIFNSDF
LKKYKKEIDNLIEDMESENENKFQEIYYPKERKNELYIYKKNLFLNIGNPNFDKIYGLIS
NDIKMADAKFLFNIDGKNIRKNKISEIDAILKNLNDKLNGYSKEYKEKYIKKLKENDDFF
AKNIQNKNYKSFEKDYNRVSEYKKIRDLVEFNYLNKIESYLIDINWKLAIQMARFERDMH
YIVNGLRELGIIKLSGYNTGISRAYPKRNGSDGFYTTTAYYKFFDEESYKKFEKICYGFG
IDLSENSEINKPENESIRNYISHFYIVRNPFADYSIAEQIDRVSNLLSYSTRYNNSTYAS
VFEVFKKDVNLDYDELKKKFKLIGNNDILERLMKPKKVSVLELESYNSDYIKNLIIELLT
KIENTNDTL   (SEQ ID NO:212)
```

FIG. 18N

> Rhodobacter capsulatus (R121) (ETD76934.1) ( U717_11515)

MQIGKVQGRTISEFGDPAGGLKRKISTDGKNRKELPAHLSSDPKALIGQWISGIDKIYRKPDSRKSDGKAIHSPTPSKMQFDARDDLGEAFWKLVSEA
GLAQDSDYDQFKRRLHPYGDKFQPADSGAKLKFEADPPEPQAFHGRWYGAMSKRGNDAKELAAALYEHLHVDEKRIDGQPKRNPKTDKFAPGLVVARA
LGIESSVLPRGMARLARNWGEEIQTYFVVDVAASVKEVAKAAVSAAQAFDPPRQVSGRSLSPKVGFALAEHLERVTGSKRCSFDPAAGPSVLALHDE
VKKTYKRLCARGKNAARAFPADKTELLALMRHTHENRVRNQMVRMGRVSEYRGQQAGDLAQSHYWTSAGQTEIKESEIFVRLWVGAFALAGRSMKAWI
DPMGKIVNTEKNDRDLTAAVNIRQVISNKEMVAEAMARRGIYFGETPELDRLGAEGNEGFVFALLRYLRGCRNQTFH**LGARAGFLKEIRKELEKTRWG
KAKEAEHVVLTDKTVAAIRAIIDNDAKALGARLLADLSGAFVAHYASKEHFSTLYSEIVKAVKDAPEVSSGLPRLKLLLKRADGVRGVVHGLRDTRKH
AFATKLPPPAPRELDDPATKARYIALLRLYDGPFRAYASGITGTALAGPAARAKEAATALAQSVNVTKAYSDVMEGRSSRLRPPNDGETLREYLSAL
TGETATEFRVQIGYESDSENARKQAEFIENYRRDMLAFMFEDYIRAKGFDWILKIEPGATAMTRAPVLPEPIDTRGQYEHWQAALYLVMHFVPASDVS
NLLHQLRKWEALQGKYELVQDGDATDQADARREALDLVKRFRDVLVLFLKTGEARFEGRAAPFDLKPFRALEANPATFDRLFMATPTTARPAEDDPEG
DGASEPELRVARTLRGLRQIARYNHMAVLSDLFAKHKVRDEEVARLAEIEDETQEKSQIVAAQELRTDLHDKVMKCHPKTISPEERQSYAAAIKTIEE
HRFLVGRVYLGDHLRLHRLMMDVIGRLIDYAGAYERDTGTFLINASKQLGAGADWAVTIAGAANTDARTQTRKDLAH**FNVLDRADGTPDLTALVNRAR
EMMAYDRKRKNAVPRSILDMLARLGLTLKWQMKDHLLQDATITQAAIKHLDKVRLTVGGPAAVTEARFSQDYLQMVAAVENGSVQNPKPRRRDDGDAW
HKPPKPATAQSOPDQKPPNKAPSAGSRLPPPQVGEVYEGVVVKVIDTGSLGFLAVEGVAGNIGLHISRLRRIREDAIIVGRRYRFRVEIYVPPKSNTS
KLNAADLVRID (SEQ ID NO:213)

FIG. 18O

>WP_034560163.1 WP_034560163.1 hypothetical protein [Carnobacterium gallinarum]

MRITKVKIKLDNKLYQVTMQKEEKYGTLKLNEESRKSTAEILRLKKASFNKSFHSKTINSQKENKNATIKKNGDYISQIFEKLVGVDTNKNIRKPKMS
LTDLKDLPKKDLALFIKRKFKNDDIVEIKNLDLISLFYNALQKVPGEHFTDESWADFCQEMMPYREYKNKFIERKILLANSIEQNKGFSINPETFSK
RKRVLHQWAIEVQERGDFSILDEKLSKLAEIYNFKKMCKRVQDELNDLEKSMKKGKNPEKEKEAYKKQKNFKIKTIWKDYPYKTHIGLIEKIKENEEL
NQFNIEIGKYFEHYFPIKKERCTEDEPYYLNSETIATTVNYQLKNALISYLMQIGKYKQFGLENQVLDSKKLQEIGIYEGFQTKFMDACVFATSSLKN
IIEPMRSGDILGKREFKEAIATSSFVNYHHFFPYFPFELKGMKDRESELIPFGEQTEAKQMQNIWALRGSVQQIFRNEIFHSFDKNQKFNLPQLDKSNF
EFDASENSTGKSQSYIETDYKFLFEAEKNQLEQFFIERIKSSGALEYYPLKSLEKLFAKKEMKFSLGSQVVAFAPSYKKLVKKGHSYQTATEGTANYL
GLSYYNRYELKEESFQAQYLLKLIYQYVFLPNFSQGNSPAFRETVKAILRINKDEARKMKKNKFLRKYAFEQVREMEFKETPDQYMSYLQSEMRE
EKVRKAEKNDKGFEKNITMNFEKLLMQIFVKGFDVFLTTFAGKELLLSSEEKVIKETEISLSKKINEREKTLKASIQVEHQLVATNSAISYWLFCKLL
DSRHLNELRNEMIKFKQSRIKFNHTQHAELIQNLLPIVELTILSNDYDEKNDSQNVDVSAYFEDKSLYETAPYVQTDDRTRVSFRPILKLEKYHTKSL
IEALLKDNPQFRVAATDIQEWMHKREEIGELVEKRKNLHTEWAEGQQTLGAEKREEYRDYCKKIDRFNWKANKVTLTYLSQLHYLITDLLGRMVGFSA
LFERDLVYFSRSFSELGGETYHISDYKNLSGVLRLNAEVKPIKIKNIKVIDNEENPYKGNEPEVKPFLDRLHAYLENVIGIKAVHGKIFRNQTAHLSVL
QLELSMIESMNNLRDLMAYDRKLIKNAVTKSMIKILDKHGMILKLKIDENHKKNFEIESLIPKEIIHLKDKAIKTNQVSEEYCQLVLALLTTNPGNQLN
(SEQ ID NO:214)

FIG. 18P

>CRZ35554.1 Herbinix hemicellulosilytica genome assembly TUM3/55, contig 02_T3/55T_contig26, whole genome shotgun sequence

```
MKLTRRRISGNSVDQKITAAFYRDMSQGLLYDSEDNDCTDKVIESMDFERSWRGRILKNGEDDKNPFYMFVKGLVGSNDKIVCEPIDVDSDPDNLDI
LINKNLTGFGRNLKAPDSNDTLENLIRKIQAGIPEEEVLPELKKIKEMIQKDIVNRKEQLLKSIKNNRIPFSLEGSKLVPSTKKMKWLFKLIDVPNKT
FNEKMLEKYWEIYDYDKLKANITNRLDKTDKKARSISRAVSEELREYHKNLRTNYNRFVSGDRPAAGLDNGGSAKYNPDKEFLLFLKEVEQYFKKYF
PVKSKHSNKSKDKSLVDKYKNYCSYKVKKEVNRSIINQLVAGLIQQGKLLYFYFYNDTWQEDFLNSYGLSYIQVEEAFKKSVMTLSWGINRLTSFF
IDDSNTVKFDDITTKKAKEAIESNYFNKLRTCSRMQDHFKEKLAFFYPVYVKDKKDRPDDDIENLIVLVKNAIESVSYLRNRTFHFKESSLLELLKEL
DDKNSGQNKIDYSVAAEFIKRDIENLYDVFREQIRSLGIAEYYKADMISDCFKTCGLEFALYSPKNSLMPAFKNVYKRGANLNKAYIRDKGPKETGDQ
GQNSYKALEEYRELTWYIEVKNNDQSYNAYKNLLQLIYHAFLPEVRENEALITDFINRTKEWNRKETEERLNTKNNKKHKNFDENDDITVNTYRYES
IPDYQGESLDDYLKVLQRKQMARAKEVNEKEEGNNNYIQFIRDVVVWAFGAYLENKLKNYKNELQPPLSKENIGLNDTLKELFPEEKVKSPFNIKCRF
SISTFIDNKGKSTDNTSAEAVKTDGKEDEKDKKNIKRKDLLCFYLFLRLLDENEICKLQHQFIKYRCSLKERRFPGNRTKLEKETELLAELEELMELV
RFTMPSIPEISAKAESGYDTMIKKYFKDFIEKKVFKNPKTSNLYYHSDSKTPVTRKYMALLMRSAPLHLYKDIFKGYYLITKKECLEYIKLSNIIKDY
QNSLNELHEQLERIKLKSEKQNGKDSLYLDKKDFYKVKEYVENLEQVARYKHLQHKINFEESLYRIFRIHVDIAARMVGYTQDWERDMHFLFKALVYNG
VLEERRFEAIFNNNDDNNDGRIVKKIQNNLNNKNRELVSMLCWNKKLNKNEFGAIIWKRNPIAHLNHFTQTEQNSKSSLESLINSLRILLAYDRKRQN
AVTKTINDLLLNDYHIRIKWEGRVDEGQIYFNIKEKEDIENEPIIHLKHLHKKDCYIYKNSYMFDKQKEWICNGIKEEVYDKSILKCIGNLFKFDYED
KNKSSANPKHT  (SEQ ID NO:215)
```

COMPOSITIONS AND METHODS FOR TARGETED DELIVERY OF CRISPR-Cas EFFECTOR POLYPEPTIDES AND TRANSGENES

CROSS-REFERENCE

This application claims the benefit of U.S. Provisional Patent Application No. 63/194,679, filed May 28, 2021, which application is incorporated herein by reference in its entirety.

INCORPORATION BY REFERENCE OF SEQUENCE LISTING PROVIDED AS A TEXT FILE

A Sequence Listing is provided herewith as a text file, "BERK-449_SEQ_LIST_ST25.txt" created on May 9, 2022, and having a size of 569 KB. The contents of the text file are incorporated by reference herein in their entirety.

INTRODUCTION

Engineering target specificity into immune cells enables the antigen-specific elimination of cells expressing cancer-associated epitopes. Currently approved cell therapies require isolation of patient T cells, viral introduction of a chimeric antigen receptor (CAR) to redirect cytotoxic activity towards target cells, and subsequent reintroduction into the body.

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. Genome editing can be carried out using a CRISPR-Cas system comprising a CRISPR-Cas effector polypeptide and a guide RNA. CRISPR-Cas systems are revolutionizing the field of gene editing and genome engineering. Efficient methods for delivering CRISPR-Cas genome editing components into target cells are needed, for both ex vivo and in vivo applications. Current delivery strategies have drawbacks. For example, delivery of a recombinant virus encoding a CRISPR-Cas effector polypeptide leads to prolonged CRISPR-Cas effector polypeptide expression in target cells, thus increasing the likelihood for off-target gene editing events. Others have used a ribonucleoprotein (RNP) comprising a CRISPR-Cas effector polypeptide and guide RNA (gRNA) to deliver the genome editing components into a cell.

There is a need in the art for strategies for modifying immune cells.

SUMMARY

The present disclosure provides virus-like particles (VLPs) comprising: i) a CRISPR-Cas effector polypeptide; ii) a recombinant lentivirus comprising a nucleotide sequence encoding a therapeutic polypeptide having a length of from about 250 amino acids to about 3,000 amino acids, where the VLP comprises a pseudotyping viral glycoprotein and/or a polypeptide that provides for binding to a target cell. The present disclosure provides systems for producing a VLP. The present disclosure provides methods of delivering a therapeutic protein, using a VLP of the present disclosure.

BRIEF DESCRIPTION OF THE DRAWINGS

FIG. 1A-1G depict production and characterization of Cas9-VLPs.

FIG. 8A-8D depict targeted integration of the lentiviral genome into the Cas9 RNP target site. FIG. 8C presents, from top to bottom SEQ ID NOs:185-189. FIG. 8D presents, from top to bottom, SEQ ID NOs:190-199.

FIG. 14 provides Table 1, which includes protospacer sequences (from top to bottom SEQ ID NOs:166-170).

FIG. 15 provides Table 2, which provides genomic amplification and sequencing primers (from top to bottom SEQ ID NOs:171-178, 175, 179, 180, 176, 175, 180, 179, 176, 175, 176, 175, 181, 181, 176, 177, 182, 182, 178, 171, 172, 182, 183).

FIG. 16 provides Table 3 (SEQ ID NO:184).

FIG. 17 provides Table 4.

FIG. 18A-18P provide amino acid sequences of CRISPR-Cas effector polypeptides.

DEFINITIONS

Figure 1E:
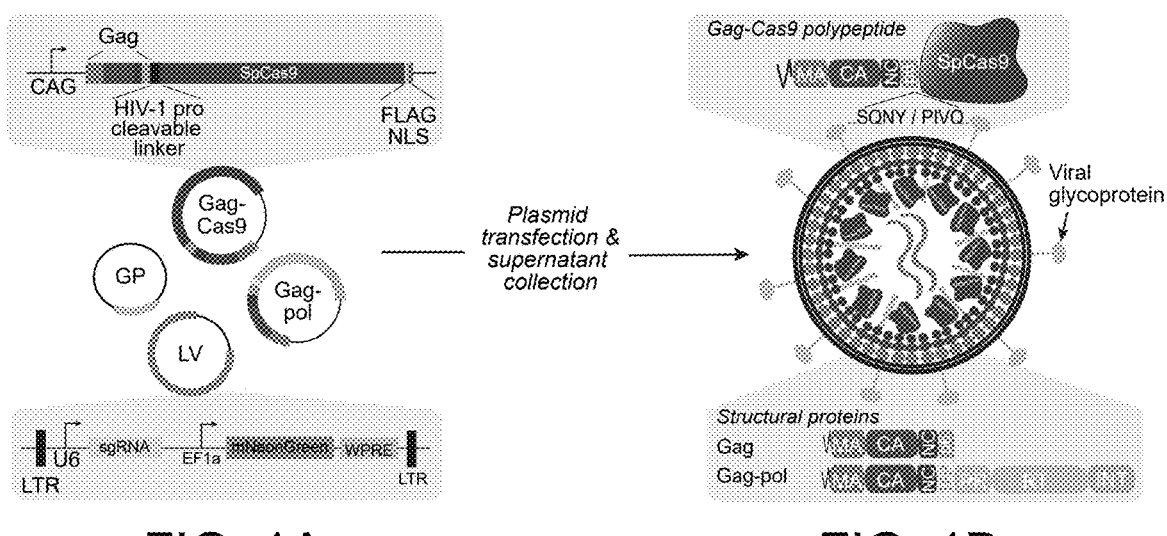
Figure 1E:
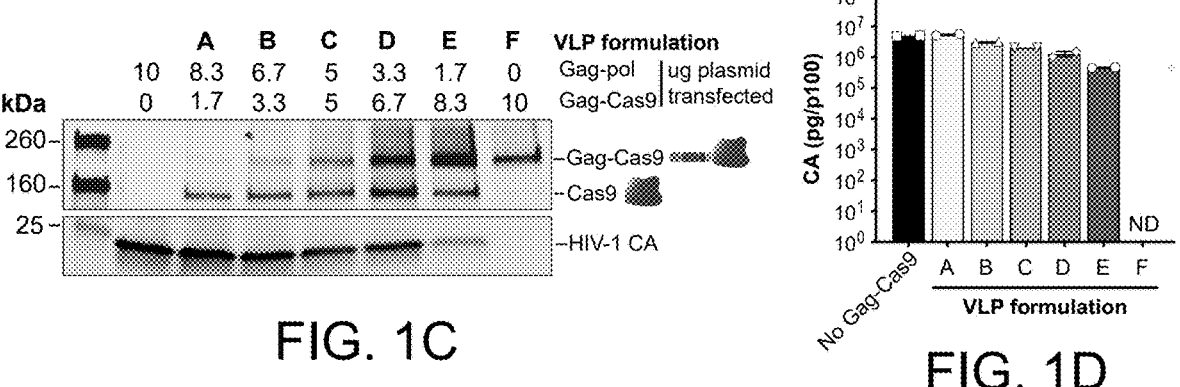
Figure 1E:
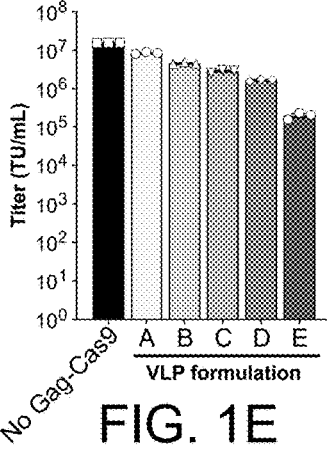

"Heterologous," as used herein, means a nucleotide or polypeptide sequence that is not found in the native nucleic acid or protein, respectively. For example, in the context of a retroviral gag polyprotein, a "heterologous" protease cleavage site is a protease cleavage site that is not found naturally in a retroviral gag polyprotein. Similarly, in the context of a retrovirus (e.g., a lentivirus), a "heterologous" protease is a protease that is not normally encoded by the retrovirus. As another example, relative to a CRISPR-Cas effector polypeptide, a heterologous polypeptide comprises an amino acid sequence from a protein other than the CRISPR-Cas effector polypeptide. As another example, a CRISPR-Cas effector protein (e.g., a dead CRISPR-Cas effector protein) can be fused to an active domain from a non-CRISPR-Cas effector protein (e.g., a cytidine deaminase), and the sequence of the active domain could be considered a heterologous polypeptide (it is heterologous to the CRISPR-Cas effector protein).

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "naturally-occurring" as used herein as applied to a nucleic acid, a protein, a cell, or an organism, refers to a nucleic acid, cell, protein, or organism that is found in nature.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

"Heterologous," as used herein, refers to a nucleotide or amino acid sequence that is not found in the native nucleic acid or protein, respectively. For example, relative to a Cas9 polypeptide, a heterologous polypeptide comprises an amino acid sequence from a protein other than the Cas9 polypeptide. Thus, for example, a polymerase polypeptide is heterologous to a Cas9 polypeptide.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, nucleotide sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant nucleotide sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such artificial combination can be carried out to join together nucleic acid segments of desired functions to generate a desired combination of functions.

Similarly, the term "recombinant" polypeptide refers to a polypeptide which is not naturally occurring, e.g., is made by the artificial combination of two otherwise separated segments of amino acid sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change can be achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. The term CAR is not limited specifically to CAR molecules but also includes CAR variants. CAR variants include split CARs wherein the extracellular portion (e.g., the ligand binding portion) and the intracellular portion (e.g., the intracellular signaling portion) of a CAR are present on two separate molecules. CAR variants also include ON-switch CARs which are conditionally activatable CARs, e.g., comprising a split CAR wherein conditional hetero-dimerization of the two portions of the split CAR is pharmacologically controlled. CAR variants also include bispecific CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. CAR molecules and derivatives thereof (i.e., CAR variants) are described, e.g., in PCT Application No. US2014/016527; Fedorov et al. Sci Transl Med (2013); 5(215):215ra172; Glienke et al. Front Pharmacol (2015) 6:21; Kakarla & Gottschalk 52 Cancer J (2014) 20(2):151-5; Riddell et al. Cancer J (2014) 20(2):141-4; Pegram et al. Cancer J (2014) 20(2):127-33; Cheadle et al Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety.

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, nanobodies, bi-specific antibodies, multi-specific antibodies, evibodies, minobodies, diabodies, and fusion proteins comprising an antigen-binding (also referred to herein as antigen binding) portion of an antibody and a non-antibody protein.

The term "nanobody" (Nb), as used herein, refers to the smallest antigen binding fragment or single variable domain ($V_{HH}$) derived from naturally occurring heavy chain antibody and is known to the person skilled in the art. They are derived from heavy chain only antibodies, seen in camelids. In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama glama, Llama guanicoe* and *Llama vicugna*). A single variable domain heavy chain antibody is referred to herein as a nanobody or a $V_{HH}$ antibody.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

As used herein, the term "antibody mimetic" refers to compounds which, like antibodies, can specifically and/or selectively bind antigens or other targets, but which are not structurally related to antibodies. Antibody mimetics are usually artificial peptides or proteins, but they are not limited to such embodiments. Typically, antibody mimetics are smaller than antibodies, with a molar mass of about 3-20 kDa (whereas antibodies are generally about 150 kDa). Non-limiting examples of antibody mimetics include peptide aptamers, affimers, affilins, affibodies, affitins, alphabodies, anticalins, avimers, DARPins, fynomers, Kunitz domain peptides, nanoCLAMPs, affinity reagents and scaffold proteins.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, non-human primates, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a guide RNA" includes a plurality of such guide RNAs and reference to "the CRISPR-Cas effector polypeptide" includes reference to one or more CRISPR-Cas effector polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides virus-like particles (VLPs) comprising: i) a CRISPR-Cas effector polypeptide; ii) a recombinant lentivirus comprising a nucleotide sequence encoding a therapeutic polypeptide having a length of from about 250 amino acids to about 3,000 amino acids, where the VLP comprises a pseudotyping viral glycoprotein and/or a polypeptide that provides for binding to a target cell. The present disclosure provides systems for producing a VLP. The present disclosure provides methods of delivering a therapeutic protein, using a VLP of the present disclosure.

Virus-Like Particles

The present disclosure provides virus-like particles (VLPs) comprising: i) a CRISPR-Cas effector polypeptide; ii) a recombinant lentivirus comprising a nucleotide sequence encoding a therapeutic polypeptide having a length of from about 250 amino acids to about 3,000 amino acids, where the VLP comprises a pseudotyping viral glycoprotein and/or a polypeptide that provides for binding to a target cell. In some cases, a VLP comprises a CRISPR-Cas effector guide RNA (referred to herein as a "guide RNA"), or a nucleic acid comprising a nucleotide sequence encoding a guide RNA. In some cases, the VLP also includes a donor template nucleic acid.

Where a VLP of the present disclosure comprises a guide RNA, in some instances, the guide RNA provides for knockout of a nucleic acid targeted by the guide RNA. Thus, in some cases, a VLP of the present disclosure provides for: i) delivery of a therapeutic protein; and ii) knockout of a target nucleic acid. As one non-limiting example, a VLP of the present disclosure can both: i) provide for delivery of a therapeutic protein (such as a chimeric antigen receptor (CAR)); and ii) knock out an endogenous nucleic acid encoding a beta-2 microglobulin (β2M) polypeptide, where the guide RNA present in the VLP (or encoded by a nucleic acid present in the VLP) would comprise a nucleotide sequence targeting a β2M-encoding nucleic acid in a target cell. Such a VLP would be useful for generating T cells that express a CAR ("CAR-T cells") that do not express endogenous major histocompatibility complex (MHC) class I antigens on their cell surface and thus could be useful for delivery of allogeneic CAR-T cells. As another non-limiting example, a VLP of the present disclosure can both: i) provide for delivery of a therapeutic protein (such as an antibody, e.g., a cancer-specific antibody or other therapeutic antibody); and ii) knock out an endogenous nucleic acid encoding an antibody light chain (e.g., a kappa light chain) or an immunoglobulin (Ig) Fc polypeptide (e.g., an Ig Fc polypeptide of a particular isotype such as IgG1). Such a VLP would be useful for generating B cells that produce a therapeutic antibody.

CRISPR-Cas Effector Polypeptides

As noted above, a VLP of the present disclosure comprises a CRISPR-Cas effector polypeptide. The CRISPR-Cas effector polypeptide can be any of a variety of CRISPR-Cas effector polypeptides. Suitable CRISPR-Cas effector polypeptides are described in detail below. For example, in some cases, the CRISPR-Cas effector polypeptide is a type II CRISPR-Cas effector polypeptide. In some cases, the type II CRISPR-Cas effector polypeptide is a Cas9 polypeptide. In some cases, the CRISPR-Cas effector polypeptide is a type V CRISPR-Cas effector polypeptide, e.g., a Cas12a, a Cas12b, a Cas12c, a Cas12d, or a Cas12e polypeptide. In some cases, the CRISPR-Cas effector polypeptide is a type VI CRISPR-Cas effector polypeptide, e.g., a Cas13a polypeptide, a Cas13b polypeptide, a Cas13c polypeptide, or a Cas13d polypeptide. In some cases, the CRISPR-Cas effector polypeptide is a Cas14 polypeptide. In some cases, the CRISPR-Cas effector polypeptide is a Cas14a polypeptide, a Cas14b polypeptide, or a Cas14c polypeptide. Also suitable for use is a variant CRISPR-Cas effector polypeptide, where the variant CRISPR-Cas effector polypeptide has reduced nucleic acid cleavage activity. Also suitable for use is a CRISPR-Cas effector fusion polypeptide comprising: i) a CRISPR-Cas effector polypeptide is a variant that has reduced nucleic acid cleavage activity; and ii) a heterologous fusion polypeptide. In some cases, the heterologous fusion polypeptide is a protein modifying enzyme. In some cases, the heterologous fusion polypeptide is a nucleic acid modifying enzyme. In some cases, the heterologous fusion polypeptide is a transcription factor. In some cases, the heterologous fusion polypeptide is a transcription activator. In some cases, the heterologous fusion polypeptide is a transcription repressor. Suitable protein-modifying enzymes and nucleic acid modifying enzymes are described in detail below. For example, in some cases, the nucleic acid modifying enzyme is a cytidine deaminase. In some cases, the nucleic acid modifying enzyme is an adenosine deaminase. In some cases, the nucleic acid modifying enzyme is a prime editor. As described in more detail below, in some cases, the CRISPR-Cas effector polypeptide comprises one or more nuclear localization signals.

Examples of CRISPR-Cas effector polypeptides are CRISPR-Cas endonucleases (e.g., class 2 CRISPR-Cas effector polypeptide such as a type II, type V, or type VI CRISPR-Cas effector polypeptide). Where a CRISPR-Cas effector polypeptide has endonuclease activity, the CRISPR-Cas effector polypeptide may also be referred to as a "CRISPR-Cas endonuclease." A CRISPR-Cas effector polypeptide can also have reduced or undetectable endonuclease activity. A CRISPR-Cas effector polypeptide can also be a fusion CRISPR-Cas effector polypeptide comprising a heterologous fusion partner. In some cases, a suitable CRISPR-Cas effector polypeptide is a class 2 CRISPR-Cas effector polypeptide. In some cases, a suitable CRISPR-Cas effector polypeptide is a class 2 type II CRISPR-Cas effector polypeptide (e.g., a Cas9 protein). In some cases, a suitable CRISPR-Cas effector polypeptide is a class 2 type V CRISPR-Cas endonuclease (e.g., a Cpf1 protein, a C2c1 protein, or a C2c3 protein). In some cases, a suitable CRISPR-Cas effector polypeptide is a class 2 type VI CRISPR-Cas effector polypeptide (e.g., a C2c2 protein; also referred to as a "Cas13a" protein). Also suitable for use is a CasX protein. Also suitable for use is a CasY protein.

In some cases, a CRISPR/Cas effector polypeptide suitable for inclusion in a fusion polypeptide of the present disclosure comprises an amino acid sequence having at least 85%, at least 90%, at least 95%, at least 98%, at least 99%, or 100%, amino acid sequence identity to the amino acid sequence depicted in any one of FIG. 18A-18P.

In some cases, the CRISPR-Cas effector polypeptide is a Type II CRISPR-Cas effector polypeptide. In some cases, the CRISPR-Cas effector polypeptide is a Cas9 polypeptide. The Cas9 protein is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA. In some cases, a Cas9 polypeptide comprises an amino acid sequence having at least 50%, at least 60%, at least 70%, at least 80%, at least 90%, at least 95%, at least 98%, at least 99%, or more than 99%, amino acid sequence identity to the *Streptococcus pyogenes* Cas9 depicted in FIG. 18A.

In some cases, the Cas9 polypeptide is a *Staphylococcus aureus* Cas9 (saCas9) polypeptide. In some cases, the saCas9 polypeptide comprises an amino acid sequence having at least 85%, at least 90%, at least 95%, at least 98%, at least 99%, or 100%, amino acid sequence identity to the saCas9 amino acid sequence depicted in FIG. 18G.

In some cases, a suitable Cas9 polypeptide is a high-fidelity (HF) Cas9 polypeptide. Kleinstiver et al. (2016) *Nature* 529:490. For example, amino acids N497, R661, Q695, and Q926 of the amino acid sequence depicted in FIG. 18A are substituted, e.g., with alanine. For example, an HF Cas9 polypeptide can comprise an amino acid sequence having at least 90%, at least 95%, at least 98%, at least 99%, or 100%, amino acid sequence identity to the amino acid sequence depicted in FIG. 18A, where amino acids N497, R661, Q695, and Q926 are substituted, e.g., with alanine. In some cases, a suitable Cas9 polypeptide exhibits altered PAM specificity. See, e.g., Kleinstiver et al. (2015) Nature 523:481.

In some cases, a suitable CRISPR-Cas effector polypeptide is a type V CRISPR-Cas effector polypeptide. In some cases, a type V CRISPR-Cas effector polypeptide is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence depicted in FIG. 18H, FIG. 18I, or FIG. 18J.

In some cases, a suitable CRISPR-Cas effector polypeptide is a CasX or a CasY polypeptide. CasX and CasY polypeptides are described in Burstein et al. (2017) Nature 542:237.

In some cases, a suitable CRISPR-Cas effector polypeptide is a fusion protein comprising a CRISPR-Cas effector polypeptide that is fused to a heterologous polypeptide (also referred to as a "fusion partner"). In some cases, a CRISPR-Cas effector polypeptide is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.).

A nucleic acid that binds to a class 2 CRISPR-Cas effector polypeptide (e.g., a Cas9 protein; a type V or type VI CRISPR-Cas protein; a Cpf1 protein; etc.) and targets the complex to a specific location within a target nucleic acid is referred to herein as a "guide RNA" or "CRISPR-Cas guide nucleic acid" or "CRISPR-Cas guide RNA." A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

In some cases, a guide RNA includes two separate nucleic acid molecules: an "activator" and a "targeter" and is referred to herein as a "dual guide RNA", a "double-molecule guide RNA", a "two-molecule guide RNA", or a "dgRNA." In some cases, the guide RNA is one molecule (e.g., for some class 2 CRISPR-Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

In some cases, a VLP of the present disclosure comprises a CRISPR-Cas effector polypeptide, or both a CRISPR-Cas effector polypeptide and a guide RNA. In some cases, e.g., where a target nucleic acid comprises a deleterious mutation in a defective allele (e.g., a deleterious mutation in a retinal cell target nucleic acid), the CRISPR-Cas effector polypeptide/guide RNA complex, together with a donor nucleic acid comprising a nucleotide sequence that corrects the deleterious mutation (e.g., a donor nucleic acid comprising a nucleotide sequence that encodes a functional copy of the protein encoded by the defective allele), can be used to correct the deleterious mutation, e.g., via homology-directed repair (HDR).

In some cases, a VLP of the present disclosure comprises: i) a CRISPR-Cas effector polypeptide; and ii) one guide RNA. In some cases, the guide RNA is a single-molecule (or "single guide") guide RNA (an "sgRNA"). In some cases, the guide RNA is a dual-molecule (or "dual-guide") guide RNA ("dgRNA").

In some cases, a VLP of the present disclosure comprises: i) a CRISPR-Cas effector polypeptide; and ii) 2 or more gRNAs, where the two or more gRNAs provide for multiplexed gene knockout, e.g., each of the 2 or more guide RNAs is targeted to a different gene. In some cases, the guide RNAs are sgRNAs. In some cases, the guide RNAs are dgRNAs.

In some cases, a VLP of the present disclosure comprises: i) a CRISPR-Cas effector polypeptide; and ii) 2 separate sgRNAs, where the 2 separate sgRNAs provide for deletion of a target nucleic acid via non-homologous end joining (NHEJ). In some cases, the guide RNAs are sgRNAs. In some cases, the guide RNAs are dgRNAs.

Class 2 CRISPR-Cas Effector Polypeptides

In class 2 CRISPR systems, the functions of the effector complex (e.g., the cleavage of target DNA) are carried out by a single endonuclease (e.g., see Zetsche et al., Cell. 2015 Oct. 22; 163(3):759-71; Makarova et al., Nat Rev Microbiol. 2015 November; 13(11):722-36; Shmakov et al., Mol Cell. 2015 Nov. 5; 60(3):385-97); and Shmakov et al. (2017) *Nature Reviews Microbiology* 15:169. As such, the term "class 2 CRISPR-Cas protein" is used herein to encompass the CRISPR-Cas effector polypeptide (e.g., the target nucleic acid cleaving protein) from class 2 CRISPR systems. Thus, the term "class 2 CRISPR-Cas effector polypeptide" as used herein encompasses type II CRISPR-Cas effector polypeptides (e.g., Cas9); type V-A CRISPR-Cas effector polypeptides (e.g., Cpf1 (also referred to a "Cas12a")); type V-B CRISPR-Cas effector polypeptides (e.g., C2c1 (also referred to as "Cas12b")); type V-C CRISPR-Cas effector polypeptides (e.g., C2c3 (also referred to as "Cas12c")); type V-U1 CRISPR-Cas effector polypeptides (e.g., C2c4); type V-U2 CRISPR-Cas effector polypeptides (e.g., C2c8); type V-U5 CRISPR-Cas effector polypeptides (e.g., C2c5); type V-U4 CRISPR-Cas proteins (e.g., C2c9); type V-U3 CRISPR-Cas effector polypeptides (e.g., C2c10); type VI-A CRISPR-Cas effector polypeptides (e.g., C2c2 (also known as "Cas13a")); type VI-B CRISPR-Cas effector polypeptides (e.g., Cas13b (also known as C2c4)); and type VI-C CRISPR-Cas effector polypeptides (e.g., Cas13c (also known as C2c7)). To date, class 2 CRISPR-Cas effector polypeptides encompass type II, type V, and type VI CRISPR-Cas effector polypeptides, but the term is also meant to encompass any class 2 CRISPR-Cas effector polypeptide suitable for binding to a corresponding guide RNA and forming an RNP complex.

In some cases, a CRISPR-Cas effector polypeptide is a fusion polypeptide comprising: i) a CRISPR-Cas effector polypeptide; and ii) one or more heterologous fusion partners (one or more heterologous fusion polypeptides). In some cases, a fusion CRISPR-Cas effector polypeptide comprises one or more localization signal peptides. In some cases, a fusion CRISPR-Cas effector polypeptide comprises one or more localization signal peptides. Suitable localization signals ("subcellular localization signals") include, e.g., a nuclear localization signal (NLS) for targeting to the nucleus; a sequence to keep the fusion protein out of the nucleus, e.g., a nuclear export sequence (NES); a sequence to keep the fusion protein retained in the cytoplasm; a mitochondrial localization signal for targeting to the mitochondria; a chloroplast localization signal for targeting to a chloroplast; an endoplasmic reticulum (ER) retention signal; and ER export signal; and the like. In some cases, a fusion CRISPR-Cas effector polypeptide does not include a NLS so that the protein is not targeted to the nucleus (which can be advantageous, e.g., when the target nucleic acid is an RNA that is present in the cytosol).

In some cases, a fusion CRISPR-Cas effector polypeptide includes (is fused to) a nuclear localization signal (NLS) (e.g., in some cases 2 or more, 3 or more, 4 or more, or 5 or more NLSs). Thus, in some cases, a fusion polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

Non-limiting examples of NLSs include an NLS sequence derived from: the NLS of the SV40 virus large T-antigen, having the amino acid sequence PKKKRKV (SEQ ID NO:1); the NLS from nucleoplasmin (e.g., the nucleoplasmin bipartite NLS with the sequence KRPAATKK-AGQAKKKK (SEQ ID NO:2)); the c-myc NLS having the amino acid sequence PAAKRVKLD (SEQ ID NO:3) or RQRRNELKRSP (SEQ ID NO:4); the hRNPA1 M9 NLS having the sequence NQSSNFGPMKGGNFG-GRSSGPYGGGGQYFAKPRNQGGY (SEQ ID NO:5); the sequence RMRIZFKNKGKDTAELRRRRVEVS-VELRKAKKDEQILKRRNV (SEQ ID NO:6) of the IBB domain from importin-alpha; the sequences VSRKRPRP (SEQ ID NO:7) and PPKKARED (SEQ ID NO:8) of the myoma T protein; the sequence PQPKKKPL (SEQ ID NO:9) of human p53; the sequence SALIKKKKKMAP (SEQ ID NO:10) of mouse c-abl IV; the sequences DRLRR (SEQ ID NO:11) and PKQKKRK (SEQ ID NO:16) of the influenza virus NS1; the sequence RKLKKKIKKL (SEQ ID NO:12) of the Hepatitis virus delta antigen; the sequence REKKKFLKRR (SEQ ID NO:13) of the mouse Mx1 protein; the sequence KRKGDEVDGVDEVAKKKSKK (SEQ ID NO:14) of the human poly(ADP-ribose) polymerase; and the sequence RKCLQAGMNLEARKTKK (SEQ ID NO:15) of the steroid hormone receptors (human) glucocorticoid. In some cases, an NLS comprises the amino acid sequence MDSLLMNRRKFLYQFKNVRWAKGRRE-TYLC (SEQ ID NO:17). In general, NLS (or multiple NLSs) are of sufficient strength to drive accumulation of the fusion polypeptide in a detectable amount in the nucleus of a eukaryotic cell. Detection of accumulation in the nucleus may be performed by any suitable technique. For example, a detectable marker may be fused to the fusion polypeptide such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

Guide Nucleic Acid

As noted above, a VLP of the present disclosure comprises a CRISPR-Cas effector polypeptide guide nucleic acid (e.g., RNA) or a nucleic acid comprising a nucleotide sequence encoding a CRISPR-Cas effector polypeptide guide RNA.

A nucleic acid molecule that binds to a CRISPR-Cas effector polypeptide protein and targets the complex to a specific location within a target nucleic acid is referred to herein as a "CRISPR-Cas effector polypeptide guide RNA" or simply a "guide RNA."

A guide RNA (can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule. The "targeting segment" is also referred to herein as a "variable region" of a guide RNA. The "protein-binding segment" is also referred to herein as a "constant region" of a guide RNA. In some cases, the guide RNA is a Cas9 guide RNA.

The first segment (targeting segment) of a guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a CRISPR-Cas effector polypeptide. The protein-binding segment of a guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the guide RNA (the guide sequence of the guide RNA) and the target nucleic acid.

A guide RNA and a CRISPR-Cas effector polypeptide form a complex (e.g., bind via non-covalent interactions). The guide RNA provides target specificity to the complex by including a targeting segment, which includes a guide sequence (a nucleotide sequence that is complementary to a sequence of a target nucleic acid). The CRISPR-Cas effector polypeptide of the complex provides the site-specific activity (e.g., cleavage activity or an activity provided by the CRISPR-Cas effector polypeptide when the CRISPR-Cas effector polypeptide is a CRISPR-Cas effector polypeptide fusion polypeptide, i.e., has a fusion partner). In other words, the CRISPR-Cas effector polypeptide is guided to a target nucleic acid sequence (e.g. a target sequence in a chromosomal nucleic acid, e.g., a chromosome; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the guide RNA.

The "guide sequence" also referred to as the "targeting sequence" of a guide RNA can be modified so that the guide RNA can target a CRISPR-Cas effector polypeptide to any desired sequence of any desired target nucleic acid, with the exception that the protospacer adjacent motif (PAM) sequence can be taken into account. Thus, for example, a guide RNA can have a targeting segment with a sequence (a guide sequence) that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a guide RNA includes two separate nucleic acid molecules: an "activator" and a "targeter" and is referred to herein as a "dual guide RNA", a "double-molecule guide RNA", or a "two-molecule guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

A guide RNA comprises a crRNA-like ("CRISPR RNA"/ "targeter"/"crRNA"/"crRNA repeat") molecule and a corresponding tracrRNA-like ("trans-acting CRISPR RNA"/"activator"/"tracrRNA") molecule. A crRNA-like molecule (targeter) comprises both the targeting segment (single stranded) of the guide RNA and a stretch ("duplex-forming segment") of nucleotides that forms one half of the dsRNA duplex of the protein-binding segment of the guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a guide RNA. The exact sequence of a given crRNA or tracrRNA molecule is characteristic of the species in which the RNA molecules are found. A dual guide RNA can include any corresponding activator and targeter pair.

The term "activator" or "activator RNA" is used herein to mean a tracrRNA-like molecule (tracrRNA: "trans-acting CRISPR RNA") of a dual guide RNA (and therefore of a single guide RNA when the "activator" and the "targeter" are linked together by, e.g., intervening nucleotides). Thus, for example, a guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases, the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a dual guide RNA (and therefore of a single guide RNA when the "activator" and the "targeter" are linked together, e.g., by intervening nucleotides). Thus, for example, a guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

A guide RNA can also be said to include 3 parts: (i) a targeting sequence (a nucleotide sequence that hybridizes with a sequence of the target nucleic acid); (ii) an activator sequence (as described above)(in some cases, referred to as a tracr sequence); and (iii) a sequence that hybridizes to at least a portion of the activator sequence to form a double stranded duplex. A targeter has (i) and (iii); while an activator has (ii).

A guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the guide RNA and a stretch ("duplex-forming segment") of nucleotides that forms one half of the dsRNA duplex of the protein-binding segment of the guide RNA. A corresponding tracrRNA-like molecule (activator) comprises a stretch of nucleotides (a duplex-forming segment) that forms the other half of the dsRNA duplex of the protein-binding segment of the guide RNA. In other words, a stretch of nucleotides of the targeter is complementary to and hybridizes with a stretch of nucleotides of the activator to form the dsRNA duplex of the protein-binding segment of a guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a guide RNA. The particular sequence of a given naturally existing crRNA or tracrRNA molecule is characteristic of the species in which the RNA molecules are found. Examples of suitable activator and targeter are well known in the art.

Therapeutic Proteins

As noted above, a VLP of the present disclosure comprises a recombinant lentiviral nucleic acid comprising a nucleotide sequence encoding a therapeutic polypeptide.

A therapeutic polypeptide encoded by a recombinant lentiviral nucleic acid present in a VLP of the present disclosure has a length of from about 250 amino acids to about 3000 amino acids. For example, a therapeutic polypeptide encoded by a recombinant lentiviral nucleic acid present in a VLP of the present disclosure has a length of from about 250 amino acids to about 500 amino acids, from about 500 amino acids to about 1000 amino acids, from about 500 amino acids to about 750 amino acids, from about 750 amino acids to about 1500 amino acids, from about 750 amino acids to about 1000 amino acids, from about 1000 amino acids to about 1250 amino acids, from about 1000 amino acids to about 1500 amino acids, from about 1250 amino acids to about 1500 amino acids, from about 1250 amino acids to about 1750 amino acids, from about 1500 amino acids to about 1750 amino acids, from about 1500 amino acids to about 2000 amino acids, from about 1500 amino acids to about 2500 amino acids, from about 2000 amino acids to about 2500 amino acids, from about 2000 amino acids to about 3000 amino acids, or from about 2500 amino acids to about 3000 amino acids.

Suitable therapeutic proteins include, but are not limited to, a chimeric antigen receptor (CAR), a T cell receptor (TCR), a natural killer cell receptor (NKR), a synNotch polypeptide, an antibody, a Modular Extracellular Sensor Architecture (MESA) receptor, and the like. In some cases, a therapeutic protein is a functional version of a protein, e.g., a cystic fibrosis transmembrane conductance (CFTR) protein, a globin polypeptide (e.g., β-globin), and the like.

Chimeric Antigen Receptor

In some cases, the therapeutic protein is a chimeric antigen receptor (CAR). A CAR generally comprises: a) an extracellular domain comprising an antigen-binding domain (antigen-binding polypeptide); b) a transmembrane region; and c) a cytoplasmic domain comprising an intracellular signaling domain (intracellular signaling polypeptide). In some cases, a CAR comprises: a) an extracellular domain comprising the antigen-binding domain; b) a transmembrane region; and c) a cytoplasmic domain comprising: i) a co-stimulatory polypeptide; and ii) an intracellular signaling domain. In some cases, a CAR comprises hinge region between the extracellular antigen-binding domain and the transmembrane domain Thus, in some cases, a CAR comprises: a) an extracellular domain comprising the antigen-binding domain; b) a hinge region; c) a transmembrane region; and d) a cytoplasmic domain comprising an intracellular signaling domain. In some cases, a CAR comprises: a) an extracellular domain comprising the antigen-binding domain; b) a hinge region; c) a transmembrane region; and d) a cytoplasmic domain comprising: i) a co-stimulatory polypeptide; and ii) an intracellular signaling domain.

Exemplary CAR structures are known in the art (See e.g., WO 2009/091826; US 20130287748; WO 2015/142675; WO 2014/055657; WO 2015/090229; and U.S. Pat. No. 9,587,020.

In some cases, a CAR is a single polypeptide chain. In some cases, a CAR comprises two polypeptide chains.

CARs specific for a variety of tumor antigens are known in the art; for example CD171-specific CARs (Park et al., *Mol Ther* (2007) 15(4):825-833), EGFRvIII-specific CARs (Morgan et al., *Hum Gene Ther* (2012) 23(10):1043-1053), EGF-R-specific CARs (Kobold et al., *J. Natl Cancer Inst* (2014) 107(1):364), carbonic anhydrase IX-specific CARs (Lamers et al., *Biochem Soc Trans* (2016) 44(3):951-959), folate receptor-α (FR-α)-specific CARs (Kershaw et al., *Clin Cancer Res* (2006) 12(20):6106-6015), HER2-specific CARs (Ahmed et al., *J Clin Oncol* (2015) 33(15)1688-1696; Nakazawa et al., *Mol Ther* (2011) 19(12):2133-2143; Ahmed et al., *Mol Ther* (2009) 17(10):1779-1787; Luo et al., *Cell Res* (2016) 26(7):850-853; Morgan et al., *Mol Ther* (2010) 18(4):843-851; Grada et al., *Mol Ther Nucleic Acids* (2013) 9(2):32), CEA-specific CARs (Katz et al., *Clin Cancer Res* (2015) 21(14):3149-3159), IL-13Ra2-specific CARs (Brown et al., *Clin Cancer Res* (2015) 21(18):4062-4072), ganglioside GD2-specific CARs (Louis et al., *Blood* (2011) 118(23):6050-6056; Caruana et al., *Nat Med* (2015) 21(5):524-529; Yu et al. (2018) *J. Hematol. Oncol.* 11:1), ErbB2-specific CARs (Wilkie et al., *J Clin Immunol* (2012) 32(5):1059-1070), VEGF-R-specific CARs (Chinnasamy et al., *Cancer Res* (2016) 22(2):436-447), FAP-specific CARs (Wang et al., *Cancer Immunol Res* (2014) 2(2): 154-166), mesothelin (MSLN)-specific CARs (Moon et al, *Clin Cancer Res* (2011) 17(14):4719-30), NKG2D-specific CARs (VanSeggelen et al., *Mol Ther* (2015) 23(10):1600-1610), CD19-specific CARs (Axicabtagene ciloleucel (Yescarta™) and Tisagenlecleucel (Kymriah™). See also, Li et al., *J Hematol and Oncol* (2018) 11:22, reviewing clinical trials of tumor-specific CARs; Heyman and Yan (2019) *Cancers* 11:pii:E191; Baybutt et al. (2019) *Clin. Pharmacol. Ther.* 105:71.

Antigen-Binding Domain

As noted above, a CAR comprises an extracellular domain comprising an antigen-binding domain. The antigen-binding domain present in a CAR can be any antigen-binding polypeptide, a wide variety of which are known in the art. In some instances, the antigen-binding domain is a single chain Fv (scFv). Other antibody-based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable. In some cases, the antigen-binding domain is a nanobody.

In some cases, the antigen bound by the antigen-binding domain of a CAR is selected from: a MUC1 polypeptide, an LMP2 polypeptide, an epidermal growth factor receptor (EGFR) vIII polypeptide, a HER-2/neu polypeptide, a melanoma antigen family A, 3 (MAGE A3) polypeptide, a p53 polypeptide, a mutant p53 polypeptide, an NY-ESO-1 polypeptide, a folate hydrolase (prostate-specific membrane antigen; PSMA) polypeptide, a carcinoembryonic antigen (CEA) polypeptide, a melanoma antigen recognized by T-cells (melanA/MART1) polypeptide, a Ras polypeptide, a gp100 polypeptide, a proteinase3 (PR1) polypeptide, a bcr-abl polypeptide, a tyrosinase polypeptide, a survivin polypeptide, a prostate specific antigen (PSA) polypeptide, an hTERT polypeptide, a sarcoma translocation breakpoints polypeptide, a synovial sarcoma X (SSX) breakpoint polypeptide, an EphA2 polypeptide, an acid phosphatase, prostate (PAP) polypeptide, a melanoma inhibitor of apoptosis (ML-IAP) polypeptide, an epithelial cell adhesion molecule (EpCAM) polypeptide, an ERG (TMPRSS2 ETS fusion) polypeptide, a NA17 polypeptide, a paired-box-3 (PAX3) polypeptide, an anaplastic lymphoma kinase (ALK) polypeptide, an androgen receptor polypeptide, a cyclin B1 polypeptide, an N-myc proto-oncogene (MYCN) polypeptide, a Ras homolog gene family member C (RhoC) polypeptide, a tyrosinase-related protein-2 (TRP-2) polypeptide, a mesothelin polypeptide, a prostate stem cell antigen (PSCA) polypeptide, a melanoma associated antigen-1 (MAGE A1) polypeptide, a cytochrome P450 1B1 (CYP1B1) polypeptide, a placenta-specific protein 1 (PLAC1) polypeptide, a BORIS polypeptide (also known as CCCTC-binding factor or CTCF), an ETV6-AML polypeptide, a breast cancer antigen NY-BR-1 polypeptide (also referred to as ankyrin repeat domain-containing protein 30A), a regulator of G-protein signaling (RGS5) polypeptide, a squamous cell carcinoma antigen recognized by T-cells (SART3) polypeptide, a carbonic anhydrase IX polypeptide, a paired box-5 (PAX5) polypeptide, an OY-TES1 (testis antigen; also known as acrosin binding protein) polypeptide, a sperm protein 17 polypeptide, a lymphocyte cell-specific protein-tyrosine kinase (LCK) polypeptide, a high molecular weight melanoma associated antigen (HMW-MAA), an A-kinase anchoring protein-4 (AKAP-4), a synovial sarcoma X breakpoint 2 (SSX2) polypeptide, an X antigen family member 1 (XAGE1) polypeptide, a B7 homolog 3 (B7H3; also known as CD276) polypeptide, a legumain polypeptide (LGMN1; also known as asparaginyl endopeptidase), a tyrosine kinase with Ig and EGF homology domains-2 (Tie-2; also known as angiopoietin-1 receptor) polypeptide, a P antigen family member 4 (PAGE4) polypeptide, a vascular endothelial growth factor receptor 2 (VEGF2) polypeptide, a MAD-CT-1 polypeptide, a fibroblast activation protein (FAP) polypeptide, a platelet derived growth factor receptor beta (PDGFl3) polypeptide, a MAD-CT-2 polypeptide, or a Fos-related antigen-1 (FOSL) polypeptide. In some cases, the antigen is a human papilloma virus (HPV) antigen. In some cases, the antigen is an alpha-feto protein (AFP) antigen. In some cases, the antigen is a Wilms tumor-1 (WT1) antigen.

The antigen-binding polypeptide of a CAR can bind any of a variety of cancer-associated antigens, including, e.g., antigens of the immunoglobulin superfamily (see, e.g., Barclay (2003) *Seminars in Immunology* 15:215); antigens of the tumor necrosis factor (TNF) superfamily (see, e.g., Aggarwal et al. (2012) *Blood* 119:651; Locksley et al. (2001) *Cell* 104:487; and Hehlgan and Pfeffer (2005) *Immunol.* 115:1); antigens of the TNF receptor (TNFR) superfamily (see, e.g., Locksley et al. (2001) *Cell* 104:487; and Hehlgan and Pfeffer (2005) *Immunol.* 115:1); antigens of the B7 superfamily (see, e.g., Greenwald et al. (2005) *Ann. Rev. Immunol.* 23:515; and Sharpe and Freeman (2002) *Nat. Rev. Immunol.* 2:116); and antigens of the lectin superfamily (see, e.g., Zelensky and Gready (2005) *FEBS J.* 272:6179).

The antigen-binding polypeptide of a CAR can bind any of a variety of cancer-associated antigens, including, e.g., CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), B-cell maturation antigen (BCMA), high molecular weight-melanoma associated antigen (HMW-MAA), MAGE-A1, IL-13R-a2, GD2, and the like. Cancer-associated antigens also include, e.g., 4-1BB, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvl3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin.

In some cases, the cancer-associated antigen bound by the antigen-binding polypeptide of a CAR is selected from AFP, BCMA, CD10, CD117, CD123, CD133, CD128, CD171, CD19, CD20, CD22, CD30, CD33, CD34, CD38, CD5, CD56, CD7, CD70, CD80, CD86, CEA, CLD18, CLL-1, cMet, EGFR, EGFRvIII, EpCAM, EphA2, GD-2, glypican-3, GPC3, HER-2, kappa immunoglobulin, LeY, LMP1, mesothelin, MG7, MUC1, NKG2D ligand, PD-L1, PSCA, PSMA, ROR1, ROR1R, TACI, and VEGFR2. In some cases, the cancer-associated antigen is BCMA. In some cases, the cancer-associated antigen is MUC1. In some cases, the cancer-associated antigen is CD19. In some cases, the cancer-associated antigen is AFP. In some cases, the cancer-associated antigen is Her-2. In some cases, the cancer-associated antigen is mesothelin. In some cases, the cancer-associated antigen is WT-1.

VH and VL amino acid sequences of various cancer-associated antigen-binding antibodies are known in the art, as are the light chain and heavy chain CDRs of such antibodies. See, e.g., Ling et al. (2018) *Frontiers Immunol.* 9:469; WO 2005/012493; US 2019/0119375; US 2013/0066055.

Hinge Region

As noted above, a CAR can include a hinge region between the extracellular domain and the transmembrane domain. As used herein, the term "hinge region" refers to a flexible polypeptide connector region (also referred to herein as "hinge" or "spacer") providing structural flexibility and spacing to flanking polypeptide regions and can consist of natural or synthetic polypeptides. The hinge region can include complete hinge region derived from an antibody of a different class or subclass from that of the CH1 domain. The term "hinge region" can also include regions derived from CD8 and other receptors that provide a similar function in providing flexibility and spacing to flanking regions.

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

As non-limiting examples, an immunoglobulin hinge region can include one of the following amino acid sequences: DKTHT (SEQ ID NO:18); CPPC (SEQ ID NO:19); CPEPKSCDTPPPCPR (SEQ ID NO:20); ELKTPLGDTTHT (SEQ ID NO:21); KSCDKTHTCP (SEQ ID NO:22); KCCVDCP (SEQ ID NO:23); KYGPPCP (SEQ ID NO:24); EPKSCDKTHTCPPCP (SEQ ID NO:25) (human IgG1 hinge); ERKCCVECPPCP (SEQ ID NO:26) (human IgG2 hinge); ELKTPLGDTTHTCPRCP (SEQ ID NO:27) (human IgG3 hinge); SPNMVPHAHHAQ (SEQ ID NO:28) (human IgG4 hinge); and the like. The hinge region can comprise an amino acid sequence derived from human CD8; e.g., the hinge region can comprise the amino acid sequence: TTTPAPRPPTPAPTIASQPLSLRPEACR-PAAGGAVHTRGLDFACD (SEQ ID NO:29), or a variant thereof.

Transmembrane Domain

Any transmembrane (TM) domain that provides for insertion of a polypeptide into the cell membrane of a eukaryotic (e.g., mammalian) cell is suitable for use. The transmembrane region of a CAR can be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R.alpha., ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. The transmembrane domain can be synthetic, in which case it can comprise predominantly hydrophobic residues such as leucine and valine. In some cases, a triplet of phenylalanine, tryptophan and valine will be found at each end of a synthetic transmembrane domain.

As one non-limiting example, the TM sequence IYI-WAPLAGTCGVLLLSLVITLYC (SEQ ID NO:30) can be used. Additional non-limiting examples of suitable TM sequences include: a) CD8 beta derived TM: LGLL-VAGVLVLLVSLGVAIHLCC (SEQ ID NO:31); b) CD4 derived TM: ALIVLGGVAGLLLFIGLGIFFCVRC (SEQ ID NO:32); c) CD3 zeta derived TM: LCYLLDGIL-FIYGVILTALFLRV (SEQ ID NO:33); d) CD28 derived TM: WVLVVVGGVLACYSLLVTVAFIIFWV (SEQ ID NO:34); e) CD134 (OX40) derived TM: VAAILGLGLVLGLLGPLAILLALYLL (SEQ ID NO:35); and f) CD7 derived TM: ALPAALAVISFLLGLGLG-VACVLA (SEQ ID NO:36).

Intracellular Domain—Co-Stimulatory Polypeptide

The intracellular portion (cytoplasmic domain) of a CAR can comprise one or more co-stimulatory polypeptides.

Non-limiting examples of suitable co-stimulatory polypeptides include, but are not limited to, 4-1BB (CD137), CD28, ICOS, OX-40, BTLA, CD27, CD30, GITR, and HVEM. Suitable co-stimulatory polypeptides include, e.g.: 1) a 4-1BB polypeptide having at least 90%, at least 95%, at least 98%, or 100%, amino acid sequence identity to the following amino acid sequence: KRGRKKLLY-IFKQPFMRPVQTTQEEDGCSCRFPEEEEGGCEL (SEQ ID NO:37); 2) a CD28 polypeptide having at least 90%, at least 95%, at least 98%, or 100%, amino acid sequence identity to the following amino acid sequence: FWVR-SKRSRLLHSDYMNMTPRRPGPTRKHYQPYAPPRD-FAAYRS (SEQ ID NO:38); 3) an ICOS polypeptide having at least 90%, at least 95%, at least 98%, or 100%, amino acid sequence identity to the following amino acid sequence: TKKKYSSSVHDPNGEYMFMRAVNTAKKSRLTDVTL (SEQ ID NO:39); 4) an OX40 polypeptide having at least 90%, at least 95%, at least 98%, or 100%, amino acid sequence identity to the following amino acid sequence: RRDQRLPPDAHKPPGGGSFRTPIQEEQADAHSTLAKI (SEQ ID NO:40); 5) a BTLA polypeptide having at least 90%, at least 95%, at least 98%, or 100%, amino acid sequence identity to the following amino acid sequence: CCLRRHQGKQNELSDTAGREINLVDAHLKSEQTEAS-TRQNSQVLLSETGIYDNDPDLCFRMQEG SEVYSNPCLEENKPGIVYASLNHSVIGPNSR-LARNVKEAPTEYASICVRS (SEQ ID NO:41); 6) a CD27 polypeptide having at least 90%, at least 95%, at least 98%, or 100%, amino acid sequence identity to the following amino acid sequence: HQRRKYRSNKGESPVEPAEPCRY-SCPREEEGSTIPIQEDYRKPEPACSP (SEQ ID NO:42); 7) a CD30 polypeptide having at least 90%, at least 95%, at least 98%, or 100%, amino acid sequence identity to the following amino acid sequence: RRACRKRIRQKLHLCY-PVQTSQPKLELVDSRPRRSSTQLRSGASVTEPVAEER-GLMSQPLMETC HSVGAAYLESLPLQ-DASPAGGPSSPRDLPEPRVSTEHTNNKIEKIYIMKADT-VIVGTVKAELPEG RGLAGPAEPELEEELEADHTPHYPEQETEP-PLGSCSDVMLSVEEEGKEDPLPTAASGK (SEQ ID NO:43); 8) a GITR polypeptide having at least 90%, at least 95%, at least 98%, or 100%, amino acid sequence identity to the following amino acid sequence: HIWQLR-SQCMWPRETQLLLEVPPSTEDARSCQFPEEERGER-SAEEKGRLGDLWV (SEQ ID NO:44); and 9) an HVEM polypeptide having at least 90%, at least 95%, at least 98%, or 100%, amino acid sequence identity to the following amino acid sequence: CVKRRKPRGDVVKVIVSVQRKRQEAEGEAT-VIEALQAPPDVTTVAVEETIPSFTGRSPNH (SEQ ID NO:45). The co-stimulatory polypeptide can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

Intracellular Domain—Signaling Polypeptide

The intracellular portion of a CAR can comprise a signaling polypeptide. Suitable signaling polypeptides include, e.g., an immunoreceptor tyrosine-based activation motif (ITAM)-containing intracellular signaling polypeptide. An ITAM motif is $YX_1X_2L/I$ (SEQ ID NO:46), where $X_1$ and $\chi_2$ are independently any amino acid. In some cases, the intracellular signaling domain of a subject CAR comprises 1, 2, 3, 4, or 5 ITAM motifs. In some cases, an ITAM motif is repeated twice in an intracellular signaling domain, where the first and second instances of the ITAM motif are separated from one another by 6 to 8 amino acids, e.g., $(YX_1X_2L/I)(X_3)_n(YX_1X_2L/I)$ (SEQ ID NO:47), where n is an integer from 6 to 8, and each of the 6-8 $X_3$ can be any amino acid. In some cases, the intracellular signaling domain of a CAR comprises 3 ITAM motifs.

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12; FCER1G (Fc epsilon receptor I gamma chain); CD3D (CD3 delta); CD3E (CD3 epsilon); CD3G (CD3 gamma); CD3Z (CD3 zeta); and CD79A (antigen receptor complex-associated protein alpha chain).

SynNotch Receptor

In some cases, the therapeutic protein is a SynNotch receptor. A synNotch receptor can specifically bind and/or otherwise interact with a SynNotch receptor ligand. SynNotch receptor systems are programmable orthogonal receptor system that can couple binding, detection, or some other interaction with a specific ligand (e.g. a synNotch polypeptide) to an endogenous or engineered function in a cell. Each synNotch receptor can be composed of a core Notch domain flanked by modular extracellular and intracellular domains. Binding of a ligand to the synNotch receptor can trigger protease mediated cleavage of a transcription factor, which can be exogenous. In some embodiments, the SynNotch Receptor can be any SynNotch receptor or variant thereof as described in e.g. Roybal et al. 2016. Cell. Vol. 164(4):599-600; Morsut et al., 2016. Cell. 164:780-791; Roybal et al. Cell (2016) 167(2):419-432, Roybal et al. Cell (2016) 164 (4):770-779; U.S. Pat. App. Pub: 2019/0134093, 2018/0355011; 2018/0079812; 2016/0264665; 2018/0208636; 2017/0233474; 2019/0202918; US2019/0010245; US20190270991; US2018/0346589; US20190269728; U.S. Pat. Nos. 9,670,281; 9,834,608; International Pat. Pub.: WO/2017/1993059; WO/2016/138034; WO2019/175428; WO2019/141270; WO2019/178259; WO 2018/039247; WO/2019/10901; WO/2019/195586; WO/2018/222880; WO/2019/016526; WO/2019/19557; WO/2019/166877.

SynNotch receptors are synthetic receptors that can specifically bind or otherwise interact with a SynNotch ligands. In some cases, the synNotch ligand is not a soluble ligand. In some cases, the synNotch ligand is insoluble and bound to a cell membrane or membrane of a vesicle.

In some embodiments, a synNotch receptor is composed of at least in part an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a Notch receptor. In some instances, the Notch regulatory region of a Notch receptor polypeptide is a mammalian Notch regulatory region, including but not limited to e.g., a mouse Notch (e.g., mouse Notch1, mouse Notch2, mouse Notch3 or mouse Notch4) regulatory region, a rat Notch regulatory region (e.g., rat Notch1, rat Notch2 or rat Notch3), a human Notch regulatory region (e.g., human Notch1, human Notch2, human Notch3 or human Notch4), and the like or a Notch regulatory region derived from a mammalian Notch regulatory region and having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a mammalian Notch regulatory region of a mammalian Notch receptor amino acid sequence.

Such Notch regulatory regions can include or exclude various components (e.g., domains, cleavage sites, etc.) thereof. Examples of such components of Notch regulatory regions that may be present or absent in whole or in part, as appropriate, include e.g., one or more EGF-like repeat domains, one or more Lin12/Notch repeat domains, one or more heterodimerization domains (e.g., HD-N or HD-C), a transmembrane domain, one or more proteolytic cleavage sites (e.g., a furin-like protease site (e.g., an S1 site), an ADAM-family protease site (e.g., an S2 site) and/or a gamma-secretase protease site (e.g., an S3 site)), and the like. Notch receptor polypeptides may, in some instances, exclude all or a portion of one or more Notch extracellular domains, including e.g., Notch-ligand binding domains such as Delta binding domains. Notch receptor polypeptides may, in some instances, include one or more non-functional versions of one or more Notch extracellular domains, including e.g., Notch-ligand binding domains such as Delta-binding domains. Notch receptor polypeptides may, in some instances, exclude all or a portion of one or more Notch intracellular domains, including e.g., Notch Rbp-associated molecule domains (i.e., RAM domains), Notch Ankyrin repeat domains, Notch transactivation domains, Notch PEST domains, and the like. Notch receptor polypeptides may, in some instances, include one or more non-functional versions of one or more Notch intracellular domains, including e.g., non-functional Notch Rbp-associated molecule domains (i.e., RAM domains), non-functional Notch Ankyrin repeat domains, non-functional Notch transactivation domains, non-functional Notch PEST domains, and the like.

In some cases, a synNotch polypeptide comprises, from N-terminus to C-terminus: a) a scFv or a nanobody that specifically binds an antigen; b) a Notch regulatory region comprising a Lin 12-Notch repeat, a heterodimerization domain comprising an S2 proteolytic cleavage site and a transmembrane domain comprising an S3 proteolytic cleavage site; c) an intracellular domain, heterologous to the Notch regulatory region, comprising a transcriptional activator comprising a DNA binding domain, where the transcriptional activator replaces a naturally-occurring intracellular notch domain, and where binding of the scFv or the nanobody to the antigen in trans induces cleavage at the S2 and S3 proteolytic cleavage sites, thereby releasing the intracellular domain and wherein the chimeric Notch polypeptide does not bind its naturally-occurring ligand Delta.

In some cases, the synNotch ligand is expressed on the surface of a target T-cell. In some cases, the synNotch ligand is expressed on the surface of a cell or vesicle that is not a target T-cell.

Antibodies

In some cases, the therapeutic protein is an antibody. Suitable antibodies include, e.g., therapeutic antibodies. In some cases, the antibody is a single-chain Fv (scFv). In some cases, the antibody is a nanobody.

Suitable antibodies include, e.g., Natalizumab (Tysabri; Biogen Idec/Elan) targeting $\alpha 4$ subunit of $\alpha 4\beta 1$ and $\alpha 4\beta 7$ integrins (as used in the treatment of MS and Crohn's disease); Vedolizumab (MLN2; Millennium Pharmaceuticals/Takeda) targeting $\alpha 4\beta 7$ integrin (as used in the treatment of UC and Crohn's disease); Belimumab (Benlysta; Human Genome Sciences/GlaxoSmithKline) targeting BAFF (as used in the treatment of SLE); Atacicept (TACI-Ig; Merck/Serono) targeting BAFF and APRIL (as used in the treatment of SLE); Alefacept (Amevive; Astellas) targeting CD2 (as used in the treatment of Plaque psoriasis, GVHD); Otelixizumab (TRX4; Tolerx/GlaxoSmithKline) targeting CD3 (as used in the treatment of T1D); Teplizumab (MGA031; MacroGenics/Eli Lilly) targeting CD3 (as used in the treatment of T1D); Rituximab (Rituxan/Mabthera; Genentech/Roche/Biogen Idec) targeting CD20 (as used in the treatment of Non-Hodgkin's lymphoma, RA (in patients with inadequate responses to TNF blockade) and CLL); Ofatumumab (Arzerra; Genmab/GlaxoSmithKline) targeting CD20 (as used in the treatment of CLL, RA); Ocrelizumab (2H7; Genentech/Roche/Biogen Idec) targeting CD20 (as used in the treatment of RA and SLE); Epratuzumab (hLL2; Immunomedics/UCB) targeting CD22 (as used in the treatment of SLE and non-Hodgkin's lymphoma); Alemtuzumab (Campath/MabCampath; Genzyme/Bayer) targeting CD52 (as used in the treatment of CLL, MS); Abatacept (Orencia; Bristol-Myers Squibb) targeting CD80 and CD86 (as used in the treatment of RA and JIA, UC and Crohn's disease, SLE); Eculizumab (Soliris; Alexion pharmaceuticals) targeting C5 complement protein (as used in the treatment of Paroxysmal nocturnal haemoglobinuria); Omalizumab (Xolair; Genentech/Roche/Novartis) targeting IgE (as used in the treatment of Moderate to severe persistent allergic asthma); Canakinumab (Ilaris; Novartis) targeting IL-1$\beta$ (as used in the treatment of Cryopyrin-associated periodic syndromes, Systemic JIA, neonatal-onset multisystem inflammatory disease and acute gout); Mepolizumab (Bosatria; GlaxoSmithKline) targeting IL-5 (as used in the treatment of Hyper-eosinophilic syndrome); Reslizumab (SCH55700; Ception Therapeutics) targeting IL-5 (as used in the treatment of Eosinophilic oesophagitis); Tocilizumab (Actemra/RoActemra; Chugai/Roche) targeting IL-6R (as used in the treatment of RA, JIA); Ustekinumab (Stelara; Centocor) targeting IL-12 and IL-23 (as used in the treatment of Plaque psoriasis, Psoriatic arthritis, Crohn's disease); Briakinumab (ABT-874; Abbott) targeting IL-12 and IL-23 (as used in the treatment of Psoriasis and plaque psoriasis); Etanercept (Enbrel; Amgen/Pfizer) targeting TNF (as used in the treatment of RA, JIA, psoriatic arthritis, AS and plaque psoriasis); Infliximab (Remicade; Centocor/Merck) targeting TNF (as used in the treatment of Crohn's disease, RA, psoriatic arthritis, UC, AS and plaque psoriasis); Adalimumab (Humira/Trudexa; Abbott) targeting TNF (as used in the treatment of RA, JIA, psoriatic arthritis, Crohn's disease, AS and plaque psoriasis); Certolizumab pegol (Cimzia; UCB) targeting TNF (as used in the treatment of Crohn's disease and RA); Golimumab (Simponi; Centocor) targeting TNF (as used in the treatment of RA, psoriatic arthritis and AS); and the like. In some cases, the antibody whose production is induced by the intracellular domain of a synNotch polypeptide of the present disclosure is a therapeutic antibody for the treatment of cancer. Such antibodies include, e.g., Ipilimumab targeting CTLA-4 (as used in the treatment of Melanoma, Prostate Cancer, RCC); Tremelimumab targeting CTLA-4 (as used in the treatment of CRC, Gastric, Melanoma, NSCLC); Nivolumab targeting PD-1 (as used in the treatment of Melanoma, NSCLC, RCC); MK-3475 targeting PD-1 (as used in the treatment of Melanoma); Pidilizumab targeting PD-1 (as used in the treatment of Hematologic Malignancies); BMS-936559 targeting PD-L1 (as used in the treatment of Melanoma, NSCLC, Ovarian, RCC); MEDI4736 targeting PD-L1; MPDL33280A targeting PD-L1 (as used in the treatment of Melanoma); Rituximab targeting CD20 (as used in the treatment of Non-Hodgkin's lymphoma); Ibritumomab tiuxetan and tositumomab (as used in the treatment of Lymphoma); Brentuximab vedotin targeting CD30 (as used in the treatment of Hodgkin's lymphoma); Gemtuzumab ozogamicin targeting CD33 (as used in the treatment of Acute myelogenous leukaemia); Alemtuzumab targeting CD52 (as used in the treatment of Chronic lymphocytic leukaemia); IGN101 and adecatumumab targeting EpCAM (as used in the treatment of Epithelial tumors (breast, colon and lung)); Labetuzumab targeting CEA (as used in the treatment of Breast, colon and lung tumors); huA33 targeting gpA33 (as used in the treatment of Colorectal carcinoma); Pemtumomab and oregovomab targeting Mucins (as used in the treatment of Breast, colon, lung and ovarian tumors); CC49 (minretumomab) targeting TAG-72 (as used in the treatment of Breast, colon and lung tumors); cG250 targeting CAIX (as used in the treatment of Renal cell carcinoma); J591 targeting PSMA (as used in the treatment of Prostate carcinoma); MOv18 and MORAb-003 (farletuzumab) targeting Folate-binding protein (as used in the treatment of Ovarian tumors); 3F8, ch14.18 and KW-2871 targeting Gangliosides (such as GD2, GD3 and GM2) (as used in the treatment of Neuroectodermal tumors and some epithelial tumors); hu3S193 and IgN311 targeting Le y (as used in the treatment of Breast, colon, lung and prostate tumors); Bevacizumab targeting VEGF (as used in the treatment of Tumor vasculature); IM-2C6 and CDP791 targeting VEGFR (as used in the treatment of Epithelium-derived solid tumors); Etaracizumab targeting Integrin _V_3 (as used in the treatment of Tumor vasculature); Volociximab targeting Integrin _5_1 (as used in the treatment of Tumor vasculature); Cetuximab, panitumumab, nimotuzumab and 806 targeting EGFR (as used in the treatment of Glioma, lung, breast, colon, and head and neck tumors); Trastuzumab and pertuzumab targeting ERBB2 (as used in the treatment of Breast, colon, lung, ovarian and prostate tumors); MM-121 targeting ERBB3 (as used in the treatment of Breast, colon, lung, ovarian and prostate, tumors); AMG 102, METMAB and SCH 900105 targeting MET (as used in the treatment of Breast, ovary and lung tumors); AVE1642, IMC-A12, MK-0646, R1507 and CP 751871 targeting IGF1R (as used in the treatment of Glioma, lung, breast, head and neck, prostate and thyroid cancer); KB004 and IIIA4 targeting EPHA3 (as used in the treatment of Lung, kidney and colon tumors, melanoma, glioma and haematological malignancies); Mapatumumab (HGS-ETR1) targeting TRAILR1 (as used in the treatment of Colon, lung and pancreas tumors and haematological malignancies); HGS-ETR2 and CS-1008 targeting TRAILR2; Denosumab targeting RANKL (as used in the treatment of Prostate cancer and bone metastases); Sibrotuzumab and F19 targeting FAP (as used in the treatment of Colon, breast, lung, pancreas, and head and neck tumors); 8106 targeting Tenascin (as used in the treatment of Glioma, breast and prostate tumors); Blinatumomab (Blincyto; Amgen) targeting CD3 (as used in the treatment of ALL); pembrolizumab targeting PD-1 as used in cancer immunotherapy; 9E10 antibody targeting c-Myc; and the like.

Suitable antibodies include, e.g., Abagovomab, Abciximab, Abituzumab, Abrilumab, Actoxumab, Aducanumab, Afelimomab, Afutuzumab, Alacizumab pegol, ALD518, Alirocumab, Altumomab pentetate, Amatuximab, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab/tocilizumab, Atorolimumab, Bapineuzumab, Basiliximab, Bavituximab, Bectumomab, Begelomab, Benralizumab, Bertilimumab, Besilesomab, Bevacizumab/Ranibizumab, Bezlotoxumab, Biciromab, Bimagrumab, Bimekizumab, Bivatuzumab mertansine, Blosozumab, Bococizumab, Brentuximabvedotin, Brodalumab, Brolucizumab, Brontictuzumab, Cantuzumab mertansine, Cantuzumab ravtansine, Caplacizumab, Capromab pendetide, Carlumab, Catumaxomab, cBR96-doxorubicin immunoconjugate, Cedelizumab, Ch. 14.18, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Dacetuzumab, Daclizumab, Dalotuzumab, Dapirolizumab pegol, Daratumumab, Dectrekumab, Demcizumab, Denintuzumab mafodotin, Derlotuximab biotin, Detumomab, Dinutuximab, Diridavumab, Dorlimomab aritox, Drozitumab, Duligotumab, Dupilumab, Durvalumab, Dusigitumab, Ecromeximab, Edobacomab, Edrecolomab, Efalizumab, Efungumab, Eldelumab, Elgemtumab, Elotuzumab, Elsilimomab, Emactuzumab, Emibetuzumab, Enavatuzumab, Enfortumab vedotin, Enlimomab pegol, Enoblituzumab, Enokizumab, Enoticumab, Ensituximab, Epitumomab cituxetan, Erlizumab, Ertumaxomab, Etrolizumab, Evinacumab, Evolocumab, Exbivirumab, Fanolesomab, Faralimomab, Farletuzumab, Fasinumab, FBTA05, Felvizumab, Fezakinumab, Ficlatuzumab, Figitumumab, Firivumab, Flanvotumab, Fletikumab, Fontolizumab, Foralumab, Foravirumab, Fresolimumab, Fulranumab, Futuximab, Galiximab, Ganitumab, Gantenerumab, Gavilimomab, Gevokizumab, Girentuximab, Glembatumumab vedotin, Gomiliximab, Guselkumab, Ibalizumab, Ibalizumab, Icrucumab, Idarucizumab, Igovomab, IMAB362, Imalumab, Imciromab, Imgatuzumab, Inclacumab, Indatuximab ravtansine, Indusatumab vedotin, Inolimomab, Inotuzumab ozogamicin, Intetumumab, Iratumumab, Isatuximab, Itolizumab, Ixekizumab, Keliximab, Lambrolizumab, Lampalizumab, Lebrikizumab, Lemalesomab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Margetuximab, Maslimomab, Matuzumab, Mavrilimumab, Metelimumab, Milatuzumab, Minretumomab, Mirvetuximab soravtansine, Mitumomab, Mogamulizumab, Morolimumab, Morolimumab immune, Motavizumab, Moxetumomab pasudotox, Muromonab-CD3, Nacolomab tafenatox, Namilumab, Naptumomab estafenatox, Narnatumab, Nebacumab, Necitumumab, Nemolizumab, Nerelimomab, Nesvacumab, Nofetumomab merpentan, Obiltoxaximab, Obinutuzumab, Ocaratuzumab, Odulimomab, Olaratumab, Olokizumab, Onartuzumab, Ontuxizumab, Opicinumab, Oportuzumab monatox, Orticumab, Otlertuzumab, Oxelumab, Ozanezumab, Ozoralizumab, Pagibaximab, Palivizumab, Pankomab, Panobacumab, Parsatuzumab, Pascolizumab, Pasotuxizumab, Pateclizumab, Patritumab, Perakizumab, Pexelizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Rilotumumab, Rinucumab, Robatumumab, Roledumab, Romosozumab, Rontalizumab, Rovelizumab, Ruplizumab, Sacituzumab govitecan, Samalizumab, Sarilumab, Satumomab pendetide, Secukinumab, Seribantumab, Setoxaximab, Sevirumab, SGN-CD19A, SGN-CD33A, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tarextumab, Tefibazumab, Telimomab aritox, Tenatumomab, Teneliximab, Teprotumumab, Tesidolumab, Tetulomab, TGN1412, Ticilimumab/tremelimumab, Tigatuzumab, Tildrakizumab, TNX-650, Toralizumab, Tosatoxumab, Tovetumab, Tralokinumab, TRB S07, Tregalizumab, Trevogrumab, Tucotuzumab celmoleukin, Tuvirumab, Ublituximab, Ulocuplumab, Urelumab, Urtoxazumab, Vandortuzumab vedotin, Vantictumab, Vanucizumab, Vapaliximab, Varlilumab, Vatelizumab, Veltuzumab, Vepalimomab, Vesencumab, Visilizumab, Vorsetuzumab mafodotin, Votumumab, Zalutumumab, Zanolimumab, Zatuximab, Ziralimumab, Zolimomab aritox, and the like.

Pseudotyping Envelope Proteins

As noted above, a VLP of the present disclosure comprises a pseudotyping envelope protein (e.g., a glycoprotein) and/or a polypeptide that provides for binding to a target cell.

Pseudotyped VLPs include heterologous glycoproteins derived from an enveloped virus other than the virus from which the MA, CA, and NC polypeptides are derived. Such a pseudotyped VLP can be targeted to a cell, tissue, or organ that is targeted by the virus from which the heterologous glycoproteins are derived. A pseudotyped VLP can include, e.g., as the heterologous virus protein used for the pseudotyping, a viral envelope protein selected from a vesicular stomatitis virus (VSV) glycoprotein (VSV-G protein), a Measles virus hemagglutinin (HA) protein and/or a measles virus fusion glycoprotein, Influenza virus neuraminidase (NA) protein, a Measles virus F protein, an Influenza virus HA protein, Moloney virus MLV-A protein, a Moloney virus MLV-E protein, a Baboon Endogenous retrovirus (BAEV) envelope protein, an Ebola virus glycoprotein, a foamy virus envelope protein, or a combination or two or more of the foregoing viral envelope proteins.

In some cases, a VSV-G protein is specifically excluded. In some cases, a measles virus hemagglutinin protein is specifically excluded. In some cases, a measles virus F protein is specifically excluded. In some cases, an influenza virus hemagglutinin protein is specifically excluded. In some cases, a Moloney virus MLV-A protein is specifically excluded. In some cases, a Moloney virus MLV-E protein is specifically excluded. In some cases, a baboon endogenous retrovirus envelope protein is specifically excluded. In some cases, an Ebola virus glycoprotein is specifically excluded. In some cases, a foamy virus envelop protein is specifically excluded.

In some cases, the heterologous glycoprotein used for pseudotyping is a VSV-G protein. A suitable VSV-G protein comprises an amino acid sequence having at least 80%, at least 85%, at least 90%, at least 95%, at least 98%, at least 99%, or 100%, amino acid sequence identity to the following amino acid sequence:

```
                                       (SEQ ID NO: 48)
IMKCLLYLAFLFIGVNCKFTIVFPHNQKGNWKNVPSNYHYCPSSSDLNWH

NDLIGTALQVKMPKSHKAIQADGWMCHASKWVTTCDFRWYGPKYITHSIR

SFTPSVEQCKESIEQTKQGTWLNPGFPPQSCGYATVTDAEAVIVQVTPHH

VLVDEYTGEWVDSQFINGKCSNYICPTVHNSTTWHSDYKVKGLCDSNLIS

MDITFFSEDGELSSLGKEGTGFRSNYFAYETGGKACKMQYCKHWGVRLPS

GVWFEMADKDLFAAARFPECPEGSSISAPSQTSVDVSLIQDVERILDYSL
```

-continued
```
CQETWSKIRAGLPISPVDLSYLAPKNPGTGPAFTIINGTLKYFETRYIRV

DIAAPILSRMVGMISGTTTERELWDDWAPYEDVEIGPNGVLRTSSGYKFP

LYMIGHGMLDSDLHLSSKAQVFEHPHIQDAASQLPDDESLFFGDTGLSKN

PIELVEGWFSSWKSSIASFFFIIGLIIGLFLVLRVGIHLCIKLKHTKKRQ

IYTDIEMNRLGK.
```

In some cases, the heterologous glycoprotein used for pseudotyping is a BAEV-G protein. A suitable BAEV-G protein comprises an amino acid sequence having at least 80%, at least 85%, at least 90%, at least 95%, at least 98%, at least 99%, or 100%, amino acid sequence identity to the following amino acid sequence:

```
                                       (SEQ ID NO: 49)
MGFTTKIIFLYNLVLVYAGFDDPRKAIELVQKRYGRPCDCSGGQVSEPPS

DRVSQVTCSGKTAYLMPDQRWKCKSIPKDTSPSGPLQECPCNSYQSSVHS

SCYTSYQQCRSGNKTYYTATLLKTQTGGTSDVQVLGSTNKLIQSPCNGIK

GQSICWSTTAPIHVSDGGGPLDTTRIKSVQRKLEEIHKALYPELQYHPLA

IPKVRDNLMVDAQTLNILNATYNLLLMSNTSLVDDCWLCLKLGPPTPLAI

PNFLLSYVTRSSDNISCLIIPPLLVQPMQFSNSSCLFSPSYNSTEEIDLG

HVAFSNCTSITNVTGPICAVNGSVFLCGNNMAYTYLPTNWTGLCVLATLL

PDIDIIPGDEPVPIPAIDHFIYRPKRAIQFIPLLAGLGITAAFTTGATGL

GVSVTQYTKLSNQLISDVQILSSTIQDLQDQVDSLAEVVLQNRRGLDLLT

AEQGGICLALQEKCCFYVNKSGIVRDKIKTLQEELERRRKDLASNPLWTG

LQGLLPYLLPFLGPLLTLLLLLTIGPCIFNRLTAFINDKLNIIHAMVLTQ

QYQVLRTDEEAQD.
```

In some cases, the heterologous glycoprotein used for pseudotyping is an influenza virus H1N1 hemagglutinin glycoprotein. A suitable influenza hemagglutinin protein comprises an amino acid sequence having at least 80%, at least 85%, at least 90%, at least 95%, at least 98%, at least 99%, or 100%, amino acid sequence identity to the following amino acid sequence: MKAILVVLLY TFATANADTL CIGYHANNST DTVDTVLEKN VTVTHSVNLL EDKHNGKLCK LRGVAPLHLG KCNIAGWILG NPECESLSTA SSWSYIVETP SSDNGTCYPG DFIDYEELRE QLSSVSSFER FEIFPKTSSW PNHDSNKGVT AACPHAGAKS FYKNLIWLVK KGNSYPKLSK SYINDKGKEV LVLWGIHHPS TSADQQSLYQ NADAYVFVGS SRYSKKFKPE IAIRPKVRXX EGRMNYYWTL VEPGDKITFE ATGNLVVPRY AFAMERNAGS GIIISDTPVH DCNTTCQTPK GAINTSLPFQ NIHPITIGKC PKYVKSTKLR LATGLRNIPS IQSRGLFGAI AGFIEGGWTG MVDGWYGYHH QNEQGSGYAA DLKSTQNAID EITNKVNSVI EKMNTQFTAV GKEFNHLEKR IENLNKKVDD GFLDIWTYNA ELLVLLENER TLDYHDSNVK NLYEKVRSQL KNNAKEIGNG CFEFYHKCDN TCMESVKNGT YDYPKYSEEA KLNREEIDGV KLESTRIYQI LAIYSTVASS LVLVVSLGAI SFWMCSNGSL QCRICI (SEQ ID NO:50; GenBank Accession No: ACP44189). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and natural killer (NK) cells.

In some cases, the heterologous glycoprotein used for pseudotyping is an influenza virus H3N2 hemagglutinin glycoprotein. A suitable influenza hemagglutinin protein comprises an amino acid sequence having at least 80%, at least 85%, at least 90%, at least 95%, at least 98%, at least 99%, or 100%, amino acid sequence identity to the following amino acid sequence: MKTIIALSYI LCLVFAQKLP GNDNSTATLC LGHHAVPNGT IVKTITNDQI EVT-NATELVQ SSSTGGICDS PHQILDGENC TLIDALLGDP QCDGFQNKKW DLFVERSKAY SNCYPYDVPD YASLRSLVAS SGTLEFNNES FNWTGVTQNG TSSACKRRSN NSFFSRLNWL THLKFKYPAL NVTMPNNEKF DKLYIWGVHH PGTDNDQISL YAQASGRITV STKRSQQTVI PSIGSRPRIR DVPSRISIYW TIVKPGDILL INSTGNLIAP RGYFKIRSGK SSIMRSDAPI GKCNSECITP NGSIPNDKPF QNVNRITYGA CPRYVKQNTL KLATGMRNVP EKQTRGIFGA IAGFIENGWE GMVDGWYGFR HQNSEGTGQA ADLKSTQAAI NQINGKLNRL IGKTNEKFHQ IEKEFSEVEG RIQDLEKYVE DTKIDLWSYN AELLVALENQ HTIDLTDSEM NKLFERTKKQ LRENAEDMGN GCF-KIYHKCD NACIGSIRNG TYDHDVYRDE ALNNRFQIKG VELKSGYKDW ILWISFAISC FLLCVALLGF IMWACQKGNI RCNICI (SEQ ID NO:51; GenBank Accession No: YP_308839). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and natural killer (NK) cells.

In some cases, the heterologous glycoprotein used for pseudotyping is an influenza virus A H5N1 hemagglutinin glycoprotein. A suitable influenza hemagglutinin protein comprises an amino acid sequence having at least 80%, at least 85%, at least 90%, at least 95%, at least 98%, at least 99%, or 100%, amino acid sequence identity to the following amino acid sequence: MEKIVLLLAI VSLVKSDQIC IGYHANNSTE QVDTIMEKNV TVTHAQDILE KTH-NGKLCDL NGVKPLILRD CSVAGWLLGN PMCDEF-INVP EWSYIVEKAS PANDLCYPGD FNDYEELKHL LSRTNHFEKI QIIPKSSWSN HDASSGVSSA CPYHGRSSFF RNVVWLIKKN SAYPTIKRSY NNTNQEDLLV LWGIHHPNDA AEQTKLYQNP TTY-ISVGTST LNQRLVPEIA TRPKVNGQSG RMEF-FWTILK PNDAINFESN GNFIAPEYAY KIVKKGDSAI MKSELEYGNC NTKCQTPMGA INSSMPFHNI HPLTIGECPK YVKSNRLVLA TGLRNTPQRE RRRKKRGLFG AIAGFIEGGW QGMVDGWYGY HHS-NEQGSGY AADKESTQKA IDGVTNKVNS IIDKMNTQFE AVGREFNNLE RRIENLNKQM EDGFLDVWTY NAELLVLMEN ERTLDFHDSN VKN-LYDKVRL QLRDNAKELG NGCFEFYHKC DNEC-MESVKN GTYDYPQYSE EARLNREEIS GVKLESMGTY QILSIYSTVA SSLALAIMVA GLSLWMCSNG SLQCRICI (SEQ ID NO:52; GenBank Accession No: YP_308669). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is an influenza virus H7N9 hemagglutinin glycoprotein. A suitable influenza hemagglutinin protein comprises an amino acid sequence having at least 80%, at least 85%, at least 90%, at least 95%, at least 98%, at least 99%, or 100%, amino acid sequence identity to the following amino acid sequence: MNTQILVFAL IAIIPTNADK ICLGHHAVSN GTKVNTLTER GVEVVNATET VERT-NIPRIC SKGKRTVDLG QCGLLGTITG PPQCDQFLEF SADLIIERRE GSDVCYPGKF VNEEALRQIL RESGGID-KEA MGFTYSGIRT NGATSACRRS GSSFYAEMKW LLSNTDNAAF PQMTKSYKNT RKSPALIVWG IHHSVSTAEQ TKLYGSGNKL VTVGSSNYQQ SFVPSP-GARP QVNGLSGRID FHWLMLNPND TVTFSFNGAF IAPDRASFLR GKSMGIQSGV QVDANCEGDC YHSGGTIISN LPFQNIDSRA VGKCPRYVKQ RSLL-LATGMK NVPEIPKGRG LFGAIAGFIE NGWEG-LIDGW YGFRHQNAQG EGTAADYKST QSAIDQITGK LNRLIEKTNQ QFELIDNEFN EVEKQIGNVI NWTRDSITEV WSYNAELLVA MENQHTIDLA DSEMDKLYER VKRQLRENAE EDGTGCFEIF HKCDDDCMAS IRNNTYDHSK YREEAMQNRI QIDPVKLSSG YKDVILWFSF GASCFILLAI VMGLV-FICVK NGNMRCTICI (SEQ ID NO:53; GenBank Accession No: YP_009118475). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is a Hepatitis B Virus (HBV) S glycoprotein. A suitable HBV protein comprises an amino acid sequence having at least 80%, at least 85%, at least 90%, at least 95%, at least 98%, at least 99%, or 100%, amino acid sequence identity to the following amino acid sequence: MENTTSGFLG PLLVLQAGFF LLTRNLTIPQ SLD-SWWTSLN FLGGAPTCPG QNSQSPTSNH SPTSCP-PICP GYRWMCLRRF IIFLFILLLC LIFLLVLLDY QGMLPVCPLL PGTSTTSTGP CKTCTIPAQG TSMFP-SCCCT KPSDGNCTCI PIPSSWAFAR FLWEWASVRF SWLSLLVPFV QWFVGLSPTV WLSVIWMMWY WGPSLYNILS PFLPLLPIFF CLWVYI (SEQ ID NO:54; GenBank Accession No: ABV02793). Such a heterologous glycoprotein may be useful in directing a VLP of the present disclosure to a liver cell.

In some cases, the heterologous glycoprotein used for pseudotyping is a Hepatitis B Virus (HBV) middle S glycoprotein. A suitable HBV protein comprises an amino acid sequence having at least 80%, at least 85%, at least 90%, at least 95%, at least 98%, at least 99%, or 100%, amino acid sequence identity to the following amino acid sequence: MQWNSTAFHQ ALQDPKVRGL YFPAGGSSSG TVN-PAPNIAS HISSISARTG DPVTNMENIT SGFLGPLLVL QAGFFLLTRI LTIPQSLDSW WTSLNFLGGS PVCLGQNSQS PTSNHSPTSC PPICPGYRWM CLRRFII-FLF ILLLCLIFLL VLLDYQGMLP VCPLIPGSTT TSTGPCKTCT TPAQGNSMFP SCCCTKPTDG NCTCIP-IPSS WAFAKYLWEW ASVRFSWLSL LVPFVQWFVG LSPTVWLSAI WMMWYWGPSL YSIVSPFIPL LPIFFCLWVY I (SEQ ID NO:55; GenBank Accession No: ACJ66136). Such a heterologous glycoprotein may be useful in directing a VLP of the present disclosure to a liver cell.

In some cases, the heterologous glycoprotein used for pseudotyping is a Hepatitis B Virus (HBV) large S glycoprotein. A suitable HBV protein comprises an amino acid sequence having at least 80%, at least 85%, at least 90%, at least 95%, at least 98%, at least 99%, or 100%, amino acid sequence identity to the following amino acid sequence: MGLSWTVPLE WGKNHSTTNP LGFFPDHQLD PAFRANTRNP DWDHNPNKDH WTEANKVGVG AFGPGFTPPH GGLLGWSPQA QGMLKTLPAD PPPASTNRQS GRQPTPITPP LRDTHPQAMQ WNSTTFHQAL QDPKVSALYL PAGGSSSGTV NPVPT-TASLI SSIFSRIGDP APNMESITSG FLGPLLVLQA GFFLLTKILT IPQSLDSWWT SLNFLGGAPV CLGQNSQSPT SSHSPTSCPP ICPGYRWMCL RRFIIFL-FIL LLCLIFLLVL LDYQGMLPVC PLIPGSSTTS TGPCRTCTTL AQGTSMFPSC CCSKPSDGNC TCIP-IPSSWA FGKFLWEWAS ARFSWLSLLV PFVQWFAGLS PTVWLSVIWM MWYWGPSLYN ILSPFIPLLP IFFCLWVYI (SEQ ID NO:56; GenBank Accession No: AGR65633). Such a heterologous glycoprotein may be useful in directing a VLP of the present disclosure to a liver cell.

In some cases, the heterologous glycoprotein used for pseudotyping is a Hepatitis B Virus (HBV) small S glycoprotein. A suitable HBV protein comprises an amino acid sequence having at least 80%, at least 85%, at least 90%, at least 95%, at least 98%, at least 99%, or 100%, amino acid sequence identity to the following amino acid sequence: MENITSGFLG PLLVLQAGFF LLTRILTIPQ SLDSWWT-SLN FLGGTTVCLG QNSQSPTSNH SPTSCPPTCP GYRWMCLRRF IIFLFILLLC LIFLLVLLDY QGMLPVCPLI PGSSTTSTGP CRTCTTPAQG TSMYP-SCCCT KPSDGNCTCI PIPSSWAFGK FLWEWASARF SWLSLLVPFV QWFVGLSPTV WLSVIWMMWY WAPNLHNILS PFLPLLPIFL CLWVYI (SEQ ID NO:57; GenBank Accession No: AHC69850. Such a heterologous glycoprotein may be useful in directing a VLP of the present disclosure to a liver cell.

In some cases, the heterologous glycoprotein used for pseudotyping is a Hepatitis B Virus (HBV) pre S glycoprotein. A suitable HBV protein comprises an amino acid sequence having at least 80%, at least 85%, at least 90%, at least 95%, at least 98%, at least 99%, or 100%, amino acid sequence identity to the following amino acid sequence: MGGWSSKPRK GMGTNLAVPN PLGFFPDHQL DPAF-KANSDN PDWDLNTHKD YWPDAWKVGV GAFGPGFTPP HGGLLGWSPQ AQGLLTTVPA APP-PASTNRQ SGRQPTPLSP PLRDTHPQAM KWN-STTFHQT LQDPRVRALY LPAGGSSSGT VSPAQNTVSA ISSILSKTGD PVPNMESIAS GLLGPLL-VLQ AGFFLLTKIL TIPQSLDSWW TSLNFLGGTP VCLGQNSQSQ ISSHSPTCCP PTCPGYRWMC LRRFII-FLCI LLLCLIFLLV LLDYQGMLPV CPLIPGSSTT STGPCKTCTA PAQGTSMFPS CCCTKPTDGN CTCIP-IPSSW AFAKYLWEWA SVRFSWLSLL VPFVQWFVGL SPTVWLSVIW MMWFWGPSLY NILSPFIPLL PIFFCLWVYI (SEQ ID NO:58; GenBank Accession No: CAA66700). Such a heterologous glycoprotein may be useful in directing a VLP of the present disclosure to a liver cell.

In some cases, the heterologous glycoprotein used for pseudotyping is a Hepatitis B Virus (HBV) preS2 glycoprotein. A suitable HBV protein comprises an amino acid sequence having at least 80%, at least 85%, at least 90%, at least 95%, at least 98%, at least 99%, or 100%, amino acid sequence identity to the following amino acid sequence: MQWNSTTFHQ TLQDPRVRGL YFPAGGSSSG TVNPVPTTVS HISSIFSRIG DPALNMENIT SGFLG-PLLVL QAGFFLLTRI LTIPQSLDSW WTSLNFLGGT TVCLGQNSQS PTSNHSPTSC PPTCPGYRWM CLRRFIIFLF ILLLCLIFLL VLLDYQGMLS VCPLIPG-STT TSTGPCKTCTTPAQGTSIHP SCCCTKPSDG NCTWIPIPSS WAFGKFLWEW ASARFSWLSL LVPFVQWFVG LSPTVWLSVI WIMWYWGPSL YSIL-SPFLPL LPIFFCLWVY I (SEQ ID NO:59; GenBank Accession No: AA012662). Such a heterologous glycoprotein may be useful in directing a VLP of the present disclosure to a liver cell.

In some cases, the heterologous glycoprotein used for pseudotyping is a Rabies virus. A suitable Rabies virus protein comprises an amino acid sequence having at least 80%, at least 85%, at least 90%, at least 95%, at least 98%, at least 99%, or 100%, amino acid sequence identity to the following amino acid sequence: MVPQALLFVP LLVFPLCFGK FPIYTIPDKL GPWSPIDIHH LSCPNNLVVE DEGCTNLSGF SYMELKVGYI SAI-KVNGFTC TGVVTEAETY TNFVGYVTTT FKRKHFRPTP DACRSAYNWK MAGDPRYEES LHNPYPDYHW LRTVKTTKES LVIISPSVAD LDPYDKSLHS RVFPSGKCSG ITVSSTYCST NHDYTIWMPE NLRLGTSCDI FINSRGKRAS KGSQTCGFID ERGLYKSLKG ACKLKLCGVL GLRLMDGTWV AMQTSDETKW CPPDQLVNLH DFRSDEIEHL VVEELVKKRE ECLDALESIM TTKSVSFRRL SHLRKLVPGF GKAYTIFNKT LMEA-DAHYKS VRTWNEIIPS KGCLRVGGRC HPHVNGVFFN GIILGPEGHV LIPEMQSSLL QQHMEL-LESS VIPLMHPLAD PSTVFKEGDE AEDFVEVHLP DVHKQVSGVN LGLPNWGKYV LLSAGALIAL MLII-FLLTCC RRVNRPESTQ HSLGGKRRKV SITSQSGKII SSWESYKSGG ETRL (SEQ ID NO:60; GenBank Accession No: AWR88358). Such a glycoprotein may be useful for targeting a VLP of the present disclosure to neurons, astrocytes, oligodendrocyctes, glia, and other cells of the of the central nervous system.

In some cases, the heterologous glycoprotein used for pseudotyping is a Mokola virus glycoprotein. A suitable Mokola virus protein comprises an amino acid sequence having at least 80%, at least 85%, at least 90%, at least 95%, at least 98%, at least 99%, or 100%, amino acid sequence identity to the following amino acid sequence: MNIPCFV-VIL SLATTHSLGE FPLYTIPEKI EKWTPIDMIH LSCPNNLLSE EEGCNAESSF TYFELKSGYL AHQKVPGFTC TGVVNEAETY TNFVGYVTTT FKRKHFRPTV AACRDAYNWK VSGDPRYEES LHTPYPDSSW LRTVTTKES LLIISPSIVE MDIYGRTLHS PMFPSGVCSN VYPSVPSCET NHDYTLWLPE DPSLSLVCDI FTSSNGKKAM NGSRICGFKD ERGFYRSLKG ACKLTLCGRP GIRLFDGTWV SFTKPDVHVW CTPNQLINIH NDRL-DEIEHL IVEDIIKKRE ECLDTLETIL MSQSVSFRRL SHFRKLVPGY GKAYTILNGS LMETNVYYKR VDK-WADILPS KGCLKVGQQC MEPVKGVLFN GIIKGPDGQI LIPEMQSEQL KQHMDLLKAA VFPLRHPLIS REAVFKKDGD ADDFVDLHMP DVHKSVSDVD LGLPHWGFWM LIGATIVAFV VLVCLLRVCC KRVRRRRSGR ATQEIPLSFP SAPVPRAKVV SSWESYKGLP GT (SEQ ID NO:61; GenBank Accession No: AAB26292). Such a glycoprotein may be useful for targeting a VLP of the present disclosure to neurons, astrocytes, oligodendrocyctes, glia, and other cells of the of the central nervous system.

In some cases, the heterologous glycoprotein used for pseudotyping is a lymphocytic choriomeningitis virus (LCMV) glycoprotein. A suitable LCMV protein comprises an amino acid sequence having at least 80%, at least 85%, at least 90%, at least 95%, at least 98%, at least 99%, or 100%, amino acid sequence identity to the following amino acid sequence: MGQIVTMFEA LPHIIDEVIN IVIIVLIIT SIKAVYNFAT CGILALISFL LLAGRSCGLY GLDGPDIYKG IYQFKSVEFD MSHLNLTMPN ACSANNSHHY ISMGNSGLEL TFTNDSIISH NFCNLT- SAFN KKTFDHTLMS IVSSLHLSIR GNSNYKAVSC DFNSGITIQY NLSFSDAQSA LSQCKTFRGR VLDMFR-TAFG GKYMRSGWGW TGSDGKTTWC SQTSYQYLII QNRTWENHCR YAGPFGMARI LFAQEKTKFL TRR-LAGTFTW TLSDSSGVDN PGGYCLTRWM ILAADLKCFG NTAVAKCNMN HDEEFCDMLR LIDYNKAALS KFKEDVESAL HLFKVTVNSL VSDQLLMRNH LRDLMGVPYC NYSRFWYLEH TKT-GETSVPK CWLVTNGSYL NETHFSDQIE QEADN-MITDM LRKDYIKRQG STPLALMDLL MFSTSAYLVS VFLHLVKIPT HRHIKGGSCP KPHRLTNKGI CSCGAFKVPG VKTVWKRR (SEQ ID NO:62; GenBank Accession No: AIW66623).

In some cases, the heterologous glycoprotein used for pseudotyping is a lymphocytic choriomeningitis virus (LCMV) glycoprotein C. A suitable LCMV protein comprises an amino acid sequence having at least 80%, at least 85%, at least 90%, at least 95%, at least 98%, at least 99%, or 100%, amino acid sequence identity to the following amino acid sequence: MGQIVTMFEA LPHIIDEVIN IVIIVLIIIT SIKAVYNFAT CGILALVSFL FLAGRSCGMY GLNGPDIYKG VYQFKSVEFD MSHLNLTMPN ACSANNSHHY ISMGSSGLEL TFTNDSILNH NFCNLTSAFN KKTFDHTLMS IVSSLHLSIR GNSNHKAVSC DFNNGITIQY NLSFSDPQSA ISQCRTFRGR VLDMFRTAFG GKYMRSGWGW AGSDGKTTWC SQTSYQYLII QNRT-WENHCR YAGPFGMSRI LFAQEKTKFL TRR-LAGTFTW TLSDSSGVEN PGGYCLTKWM ILAAEL-KCFG NTAVAKCNVN HDEEFCDMLR LIDYNKAALS KFKQDVESAL HVFKTTVNSL ISDQLLMRNH LRDLMGVPYC NYSKFWYLEH AKTGETSVPK CWLVTNGSYL NETHFSDQIE QEADNMITEM LRKDYIKRQG STPLALMDLL MFSTSAYLIS IFLHLVKIPT HRHIKGGSCP KPHRLTNKGI CSCGAFKVPG VKTIWKRR (SEQ ID NO:63; GenBank Accession No: CAC01231).

In some cases, the heterologous glycoprotein used for pseudotyping is a lymphocytic choriomeningitis virus (LCMV) glycoprotein. A suitable LCMV protein comprises an amino acid sequence having at least 80%, at least 85%, at least 90%, at least 95%, at least 98%, at least 99%, or 100%, amino acid sequence identity to the following amino acid sequence: MGQIVTMFEA LPHIIDEVIN IVIIVLIVIT GIKAVYNFAT CGIFALISFL LLAGRSCGMY GLKGPDIYKG VYQFKSVEFD MSHLNLTMPN ACSANNSHHY ISMGTSGLEL TFTNDSIISH NFCNLT-SAFN KKTFDHTLMS IVSSLHLSIR GNSNYKAVSC DFNNGITIQY NLTFSDAQSA QSQCRTFRGR VLDMFRTAFG GKYMRSGWGW TGSDGKTTWC SQT-SYQYLII QNRTWENHCT YAGPFGMSRI LLSQEKTKFF TRRLAGTFTW TLSDSSGVEN PGGY-CLTKWM ILAAELKCFG NTAVAKCNVN HDAEFCDMLR LIDYNKAALS KFKEDVESAL HLFKTTVNSL ISDQLLMRNH LRDLMGVPYC NYSKFWYLEH AKTGETSVPK CWLVTNGSYL NETH-FSDQIE QEADNMITEM LRKDYIKRQG STPLA-LMDLL MFSTSAYLVS IFLHLVKIPT HRHIKGGSCP KPHRLTNKGI CSCGAFKVPG VKTVWKRR (SEQ ID NO:64; GenBank Accession No: P09991).

In some cases, the heterologous glycoprotein used for pseudotyping is a lymphocytic choriomeningitis virus (LCMV) G1 glycoprotein. A suitable LCMV protein comprises an amino acid sequence having at least 80%, at least 85%, at least 90%, at least 95%, at least 98%, at least 99%, or 100%, amino acid sequence identity to the following amino acid sequence: MYGLKGPDIYKG VYQFKSVEFD MSHLNLTMPN ACSANNSHHY ISMGTSGLEL TFTNDSIISH NFCNLTSAFN KKTFDHTLMS IVSSLHL-SIR GNSNYKAVSC DFNNGITIQY NLTFSDAQSA QSQCRTFRGR VLDMFRTAFG GKYMRSGWGW TGSDGKTTWC SQTSYQYLII QNRTWENHCT YAGPFGMSRI LLSQEKTKFF TRRLA (SEQ ID NO:65; GenBank Accession No: P09991).

In some cases, the heterologous glycoprotein used for pseudotyping is a lymphocytic choriomeningitis virus (LCMV) G2 glycoprotein. A suitable LCMV protein comprises an amino acid sequence having at least 80%, at least 85%, at least 90%, at least 95%, at least 98%, at least 99%, or 100%, amino acid sequence identity to the following amino acid sequence: GTFTW TLSDSSGVEN PGGY-CLTKWM ILAAELKCFG NTAVAKCNVN HDAEFCDMLR LIDYNKAALS KFKEDVESAL HLFKTTVNSL ISDQLLMRNH LRDLMGVPYC NYSKFWYLEH AKTGETSVPK CWLVTNGSYL NETH-FSDQIE QEADNMITEM LRKDYIKRQG STPLA-LMDLL MFSTSAYLVS IFLHLVKIPT HRHIKGGSCP KPHRLTNKGI CSCGAFKVPG VKTVWKRR (SEQ ID NO:66; GenBank Accession No: P09991).

In some cases, the heterologous glycoprotein used for pseudotyping is a Ross River virus E1 glycoprotein. A suitable Ross River virus protein comprises an amino acid sequence having at least 80%, at least 85%, at least 90%, at least 95%, at least 98%, at least 99%, or 100%, amino acid sequence identity to the following amino acid sequence: YEHTATIPNV VGFPYKAHIE RNXFSPMTLQ LEVVXXSLEP TLNLEYITCE YKTVVPSPFI KCCGT-SECSS KEQPDYQCKV YTGVYPFMWG GAYCFCD-SEN TQLSEAYVDR SDVCKHDHAL AYKAHTASLK ATIRISYGTI NQTTEAFVNG EHAVNVGGSK FIFG-PISTAW SPFDNKIVVY KDDVYNQDFP PYGSGQPGRF GDIQSRTVES KDLYANTALK LSRPSPGVVH VPY-TQTPSGF KYWLKEKGSS LNTKAPFGCK IKTNPVRAMD CAVGSIPVSM DIPDSAFTRV VDAPAVTDLS CQVAVCTHSS DFGXVATLSY KTDKPGKCAV HSHSNVATLQ EATVDVKEDG KVTVHFSXXS ASPAFKVSVC DAKTTCTAAC EPPK-DHIVPY GASHNNQVFP DMSGTAMTWV QRMASGLGGL ALIAVVVLVL VTCITMRR (SEQ ID NO:67; GenBank Accession No: NP_740686). Such a glycoprotein may be useful for targeting a VLP of the present disclosure to skeletal muscle, and cells that make up the joints, joint-associated connective tissue, bone, neurons, and lymphatic cells.

In some cases, the heterologous glycoprotein used for pseudotyping is a Ross River virus E2 glycoprotein. A suitable Ross River virus protein comprises an amino acid sequence having at least 80%, at least 85%, at least 90%, at least 95%, at least 98%, at least 99%, or 100%, amino acid sequence identity to the following amino acid sequence: SVIEHFNVYK ATRPYLAXCA DCGDGYFCYS PVAIEKIRDE ASDGMLKIQV SAQIGLDKAG THAHTKMRYM AGHDVQESKR DSLRVYTSAA CSIHGTMGHF IVAHCPPGDY LKXSFEDANS HVKACKVQYK HDPLPVGREK FVVRPHFGVE LPCT-SYQLTT APTDEEIDMH TPPDIPDRTL LSQTAGNVKI TAGGRTIRYN CTCGRDNVGT TSTDKTINTC KIDQCHAAVT SHDKWXFTSP FVPRADQTAR KGKVHVPFPL TNVTCRVPLA RAPDVTYGKK EVTLRLHPDH PTXFSYRSLG AVPHPYEEWV DKF-SERIIPV TEEGIEYQWG NNPPVRLWAQ LTTEGKPHGW PHEIIQYYYG LYPAATIAAV SGASL-MALLT LAATCCMLAT ARRKCLTPYA LTPGAVVPLT LGLLXCAPRA NA (SEQ ID NO:68; GenBank Accession No: NP_740684). Such a glycoprotein may be useful for targeting a VLP of the present disclosure to skeletal muscle, and cells that make up the joints, joint-associated connective tissue, bone, neurons, and lymphatic cells.

In some cases, the heterologous glycoprotein used for pseudotyping is a Semliki Forest virus E1 glycoprotein. A suitable Semliki Forest virus protein comprises an amino acid sequence having at least 80%, at least 85%, at least 90%, at least 95%, at least 98%, at least 99%, or 100%, amino acid sequence identity to the following amino acid sequence: YEHSTVMPNV VGFPYKAHIE RPGYSPLTLQ MQVVETSLEP TLNLEYITCE YKTVVPSPYV KCC-GASECST KEKPDYQCKV YTGVYPFMWG GAYCFCDSEN TQLSEAYVDR SDVCRHDHAS AYKAHTASLK AKVRVMYGNV NQTVDVYVNG DHAVTIGGTQ FIFGPLSSAW TPFDNKIVVY KDEVFNQDFP PYGSGQPGRF GDIQSRTVES NDLY-ANTALK LARPSPGMVH VPYTQTPSGF KYWLKEKGTA LNTKAPFGCQ IKTNPVRAMN CAVGNIPVSM NLPDSAFTRI VEAPTIIDLT CTVATCTHSS DFGGVLTLTY KTNKNGDCSV HSHSN-VATLQ EATAKVKTAG KVTLHFSTAS ASPSFVVSLC SARATCSASC EPPKDHIVPY AASHSNVVFP DMSGTALSWV QKISGGLGAF AIGAILVLVV VTCIGLRR (SEQ ID NO:69; GenBank Accession No: NP_819008). Such a glycoprotein may be useful for targeting a VLP of the present disclosure to muscle, pancreas, neurons, astrocytes, oligodendrocytes, glia, and other cells of the of the central nervous system.

In some cases, the heterologous glycoprotein used for pseudotyping is a Semliki Forest virus E2 glycoprotein. A suitable Semliki Forest virus protein comprises an amino acid sequence having at least 80%, at least 85%, at least 90%, at least 95%, at least 98%, at least 99%, or 100%, amino acid sequence identity to the following amino acid sequence: SVSQHFNVYK ATRPYIAYCA DCGAGH-SCHS PVAIEAVRSE ATDGMLKIQF SAQIGIDKSD NHDYTKIRYA DGHAIENAVR SSLKVATSGD CFVHGTMGHF ILAKCPPGEF LQVSIQDTRN AVRAC-RIQYH HDPQPVGREK FTIRPHYGKE IPCTTYQQTT AETVEEIDMH MPPDTPDRTL LSQQSGNVKI TVGGKKVKYN CTCGTGNVGT TNSDMTINTC LIEQCHVSVT DHKKWQFNSP FVPRADEPAR KGKVHIPFPL DNITCRVPMA REPTVIHGKR EVTLHLHPDH PTLFSYRTLG EDPQYHEEWV TAAVERTIPV PVDGMEYHWG NNDPVRLWSQ LTTEGKPHGW PHQIVQYYYG LYPAATVSAV VGMSL-LALIS IFASCYMLVA ARSKCLTPYA LTPGAAVPWT LGILCCAPRA HA (SEQ ID NO:216; GenBank Accession No: NP_819006). Such a glycoprotein may be useful for targeting a VLP of the present disclosure to muscle, pancreas, neurons, astrocytes, oligodendrocytes, glia, and other cells of the of the central nervous system.

In some cases, the heterologous glycoprotein used for pseudotyping is a Sindbis virus E1 glycoprotein. A suitable Sindbis virus protein comprises an amino acid sequence having at least 80%, at least 85%, at least 90%, at least 95%, at least 98%, at least 99%, or 100%, amino acid sequence identity to the following amino acid sequence: YEHAT-TVPNV PQIPYKALVE RAGYAPLNLE ITVMSSEVLP STNQEYITCK FTTVVPSPKI KCCGSLECQP AAHADYTCKV FGGVYPFMWG GAQCFCDSEN SQM-SEAYVEL SADCASDHAQ AIKVHTAAMK VGL-RIVYGNT TSFLDVYVNG VTPGTSKDLK VIAG-PISASF TPFDHKVVIH RGLVYNYDFP EYGAMKPGAF GDIQATSLTS KDLIASTDIR LLKPSAKNVH VPY-TQASSGF EMWKNNSGRP LQETAPFGCK IAVNPL- RAVD CSYGNIPISI DIPNAAFIRT SDAPLVSTVK CEV-SECTYSA DFGGMATLQY VSDREGQCPV HSHSSTATLQ ESTVHVLEKG AVTVHFSTAS PQAN-FIVSLC GKKTTCNAEC KPPADHIVST PHKNDQEFQA AISKTSWSWL FALFGGASSL LIIGLMIFAC SMMLT-STRR (SEQ ID NO:70; GenBank Accession No: NP_740677). Such a glycoprotein may be useful for targeting a VLP of the present disclosure to muscle, pancreas, neurons, astrocytes, oligodendrocytes, glia, and other cells of the of the central nervous system.

In some cases, the heterologous glycoprotein used for pseudotyping is a Sindbis virus E2 glycoprotein. A suitable Sindbis virus protein comprises an amino acid sequence having at least 80%, at least 85%, at least 90%, at least 95%, at least 98%, at least 99%, or 100%, amino acid sequence identity to the following amino acid sequence: SVIDDFTLTS PYLGTCSYCH HTVPCFSPVK IEQVWDEADD NTIRIQTSAQ FGYDQSGAAS ANKYRYMSLK QDHTVKEGTM DDIKISTSGP CRRL-SYKGYF LLAKCPPGDS VTVSIVSSNS ATSCTLARKI KPKFVGREKY DLPPVHGKKI PCTVYDRLKE TTAGYITMHR PRPHAYTSYL EESSGKVYAK PPSGKNITYE CKCGDYKTGT VSTRTEITGC TAI-KQCVAYK SDQTKWVFNS PDLIRHDDHT AQGKLHLPFK LIPSTCMVPV AHAPNVIHGF KHIS-LQLDTD HLTLLTTRRL GANPEPTTEW IVGKTVRNFT VDRDGLEYIW GNHEPVRVYA QESAPGDPHG WPHEIVQHYY HRHPVYTILA VASATVAMMI GVTVA-VLCAC KARRECLTPY ALAPNAVIPT SLALLCCVRS ANA (SEQ ID NO:71; GenBank Accession No: NP_740675). Such a glycoprotein may be useful for targeting a VLP of the present disclosure to skeletal muscle, and cells that make up the joints, joint-associated connective tissue, bone, neurons, and lymphatic cells.

In some cases, the heterologous glycoprotein used for pseudotyping is an Ebola Zaire virus glycoprotein. A suitable Ebola Zaire virus protein comprises an amino acid sequence having at least 80%, at least 85%, at least 90%, at least 95%, at least 98%, at least 99%, or 100%, amino acid sequence identity to the following amino acid sequence: MGVTGILQLP RDRFKRTSFF LWVIILFQRT FSIPLGVIHN STLQVSDVDK LVCRDKLSST NQLRSVGLNL EGNGVATDVP SATKRWGFRS GVPPKVVNYE AGEWAENCYN LEIKKPDGSE CLPAAPDGIR GFPRCRYVHK VSGTGPCAGD FAFH-KEGAFF LYDRLASTVI YRGTTFAEGV VAFLILPQAK KDFFSSHPLR EPVNATEDPS SGYYSTTIRY QATGFGT-NET EYLFEVDNLT YVQLESRFTP QFLLQLNETI YTSGKRSNTT GKLIWKVNPE IDTTIGEWAF WETK-KNLTRK IRSEELSFTV VSNGAKNISG QSPARTSSDP GTNTTTEDHK IMASENSSAM VQVHSQGREA AVSHLTTLAT ISTSPQSLTT KPGPDNSTHN TPVYKLD-ISE ATQVEQHHRR TDNDSTASDT PSATTAAGPP KAE-NTNTSKS TDFLDPATTT SPQNHSETAG NNNTHHQDTG EESASSGKLG LITNTIAGVA GLITG-GRRTR REAIVNAQPK CNPNLHYWTT QDEGAAIGLA WIPYFGPAAE GIYIEGLMHN QDGLICGLRQ LAN-ETTQALQ LFLRATTELR TFSILNRKAI DFLLQRWGGT CHILGPDCCI EPHDWTKNIT DKIDQIIHDF VDKTLPDQGD NDNWWTGWRQ WIPA-GIGVTG VIIAVIALFC ICKFVF (SEQ ID NO:72; Gen-Bank Accession No: AAB81004). Such a glycoprotein may be useful for targeting a VLP of the present disclosure to hepatocytes, endothelial cells, dendritic cells, macrophages, and monocytes.

In some cases, the heterologous glycoprotein used for pseudotyping is an Ebola Zaire virus glycoprotein. A suitable Ebola Zaire virus protein comprises an amino acid sequence having at least 80%, at least 85%, at least 90%, at least 95%, at least 98%, at least 99%, or 100%, amino acid sequence identity to the following amino acid sequence: IPLGVIHN STLQVSDVDK LVCRDKLSST NQLRSVGLNL EGNGVATDVP SATKRWGFRS GVPPKVVNYE AGEWAENCYN LEIKKPDGSECL-PAAPDGIR GFPRCRYVHK VSGTGPCAGD FAFHKEG-AFF LYDRLASTVI YRGTTFAEGV VAFLILPQAK KDFFSSHPLR EPVNATEDPS SGYYSTTIRY QATGFGT-NET EYLFEVDNLT YVQLESRFTP QFLLQLNETI YTSGKRSNTT GKLIWKVNPE IDTTIGEWAF WETK-KNLTRK IRSEELSFTV VSNGAKNISG QSPARTSSDP GTNTTTEDHK IMASENSSAM VQVHSQGREA AVSHLTTLAT ISTSPQSLTT KPGPDNSTHN TPVYKLD-ISE ATQVEQHHRR TDNDSTASDT PSATTAAGPP KAE-NTNTSKS TDFLDPATTT SPQNHSETAG NNNTHHQDTG EESASSGKLG LITNTIAGVA GLITG-GRRTR REAIVNAQPK CNPNLHYWTT QDEGAAIGLA WIPYFGPAAE GIYIEGLMHN QDGLICGLRQ LAN-ETTQALQ LFLRATTELR TFSILNRKAI DFLLQRWGGT CHILGPDCCI EPHDWTKNIT DKIDQIIHDF VDKTLPDQGD NDNWWTGWRQ WIPA-GIGVTG VIIAVIALFC ICKFVF (SEQ ID NO:73). Such a glycoprotein may be useful for targeting a VLP of the present disclosure to hepatocytes, endothelial cells, dendritic cells, macrophages, and monocytes.

In some cases, the heterologous glycoprotein used for pseudotyping is an Ebola Reston virus glycoprotein. A suitable Ebola Reston virus protein comprises an amino acid sequence having at least 80%, at least 85%, at least 90%, at least 95%, at least 98%, at least 99%, or 100%, amino acid sequence identity to the following amino acid sequence: MGSGYQLLQL PRERFRKTSF LVWVIILFQR AISMPL-GIVT NSTLKATEID QLVCRDKLSS TSQLKSVGLN LEGNGIATDV PSATKRWGFR SGVPPKVVSY EAGE-WAENCY NLEIKKSDGS ECLPLPPDGV RGFPR-CRYVH KVQGTGPCPG DLAFHKNGAF FLYDRLASTV IYRGTTFAEG VVAFLILSEP KKHFWKATPA HEP-VNTTDDS TSYYMTLTLS YEMSNFGGNE SNTLFKVDNH TYVQLDRPHT PQFLVQLNET LRRNNRLSNS TGRLTWTLDP KIEPDVGEWA FWETK-KNFSQ QLHGENLHFQ IPSTHTNNSS DQSPAGTVQG KISYHPPANN SELVPTDSPP VVSVLTAGRT EEM-STQGLTN GETITGFTAN PMTTTIAPSP TMT-SEVDNNV PSEQPNNTAS IEDSPPSASN ETIYHSEMDP IQGSNNSAQS PQTKTTPAPT TSPMTQDPQE TANSSKPGTS PGSAAGPSQP GLTINTVSKV ADSLSP-TRKQ KRSVRQNTAN KCNPDLYYWT AVDEGAAVGL AWIPYFGPAA EGIYIEGVMH NQNGLICGLR QLAN-ETTQAL QLFLRATTEL RTYSLLNRKA IDFLLQRWGG TCRILGPSCC IEPHDWTKNI TDEINQIKHD FIDN-PLPDHG DDLNLWTGWR QWIPAGIGII GVIIAIIALL CICKILC (SEQ ID NO:74; GenBank Accession No: NP_690583). Such a glycoprotein may be useful for target-ing a VLP of the present disclosure to hepatocytes, endothe-lial cells, dendritic cells, macrophages, and monocytes.

In some cases, the heterologous glycoprotein used for pseudotyping is a Marburg virus glycoprotein. A suitable Marburg virus protein comprises an amino acid sequence having at least 80%, at least 85%, at least 90%, at least 95%, at least 98%, at least 99%, or 100%, amino acid sequence identity to the following amino acid sequence: MKTTCFLISL ILIQGTKNLP ILEIASNNQP QNVDSVCSGT LQKTEDVHLM GFTLSGQKVA DSPLEASKRW AFRTGVPPKN VEYTEGEEAK TCYN-ISVTDP SGKSLLLDPP TNIRDYPKCK TIHHIQGQNP HAQGIALHLW GAFFLYDRIA STTMYRGKVF TEGNIAAMIV NKTVHKMIFS RQGQGYRHMN LTSTNKYWTS SNGTQTNDTG CFGALQEYNS TKNQTCAPSK IPPPLPTARP EIKLTSTPTD ATKLNTTDPS SDDEDLATSG SGSGEREPHT TSDAVTKQGL SSTMPPTPSP QPSTPQQGGN NTNHSQDAVT ELDKNNTTAQ PSMPPHNTTT ISTNNTSKHN FSTLSAPLQN TTNDNTQSTI TENEQT-SAPS ITTLPPTGNP TTAKSTSSKK GPATTAPNTT NEHFTSPPPT PSSTAQHLVY FRRKRSILWR EGDMFP-FLDG LINAPIDFDP VPNTKTIFDE SSSSGASAEE DQHASPNISL TLSYFPNINE NTAYSGENEN DCDAEL-RIWS VQEDDLAAGL SWIPFFGPGI EGLYTAVLIK NQNNLVCRLR RLANQTAKSL ELLLRVTTEE RTFSLINRHA IDFLLTRWGG TCKVLGPDCC IGIEDL-SKNI SEQIDQIKKD EQKEGTGWGL GGKWWTSDWG VLTNLGILLL LSIAVLIALS CICRIFTKYI G (SEQ ID NO:75); GenBank Accession No: CAA78117). Such a gly-coprotein may be useful for targeting a VLP of the present disclosure to hepatocytes, endothelial cells, dendritic cells, macrophages, and monocytes.

In some cases, the heterologous glycoprotein used for pseudotyping is a murine leukemia virus (MLV) glycopro-tein. A suitable MLV protein comprises an amino acid sequence having at least 80%, at least 85%, at least 90%, at least 95%, at least 98%, at least 99%, or 100%, amino acid sequence identity to the following amino acid sequence: MESTTLSKPF KNQVNPWGPL IVLLILGGVN PVAL-GNSPHQ VFNLTWEVTN GDRETVWAIA GNHPLWTWWP DLTPDLCMLA LHGPSYWGLE YRAPFSPPPG PPCCSGSSDS TPGCSRDCEE PLTSYT-PRCN TAWNRLKLSK VTHAHNEGFY VCPGPHRPRW ARSCGGPESF YCASWGCETT GRASWKPSSS WDYITVSNNL TSDQATPVCK GNEWCNSLTI RFTSFGKQAT SWVTGHWWGL RLYVSGHDPG LIF-GIRLKIT DSGPRVPIGP NPVLSDRRPP SRPRPTRSPP PSNSTPTETP LTLPEPPPAG VENRLLNLVK GAYQAL-NLTS PDKTQECWLC LVSGPPYYEG VAVLGTYSNH TSAPANCSVA SQHKLTLSEV TGQGLCIGAV PKTHQVLCNT TQKTSDGSYY LAAPTGTTWA CSTGLTPCIS TTILDLTTDY CVLVELWPRV TYHSPSYVYH QFEGRAKYKR EPVSLTLALL LGGLTMGGIA AGVGTGTTAL VATQQFQQLQ AAM-HDDLKEV EKSITNLEKS LTSLSEVVLQ NRRGLD-LLFL KEGGLCAALK EECCFYADHT GLVRDSMAKL RERLSQRQKL FESQQGWFEG LFNKSPWFTT LIST-IMGPLI ILLLILLFGP CILNRLVQFI KDRISVVQAL VLTQQYHQLK TIRDCKSRE (SEQ ID NO:76; GenBank Accession No: AAA51037).

In some cases, the heterologous glycoprotein used for pseudotyping is an MLV glycoprotein. A suitable MLV protein comprises an amino acid sequence having at least 80%, at least 85%, at least 90%, at least 95%, at least 98%, at least 99%, or 100%, amino acid sequence identity to the following amino acid sequence: MESTTLSKPF KNQVNPWGPL IVLLILRGVN PVTLGNSPHQ VFNLTWEVTN GDRETVWAIT GNHPLWTWWP DLTPDLCMLA LHGPSYWGLE YRAPFSPPPG PPCCSGSSDS TPGCSRDCEE PLTSYTPRCN TAW-NRLKLSK VTHAHNGGFY VCPGPHRPRW ARSCGG-PESF YCASWGCETT GRASWKPSSS WDYITVSNNL TSDQATPVCK GNKWCNSLTI RFTSFGKQAT SWVTGHWWGL RLYVSGHDPG LIFGIRLKIT DSGPRVPIGP NPVLSDRRPP SRPRPTRSPP PSN-STPTETP LTLPEPPPAG VENRLLNLVK GAYQALNLTS PDKTQECWLC LVSGPPYYEG VAVLGTYSNH TSAPANCSVA SQHKLTLSEV TGQGLCIGAV PKTHQVLCNT TQKTSDGSYY LAAPTGTTWA CSTGLTPCIS TTILDLTTDY CVLVELWPRV TYHSPSYVYH QFERRAKYKR EPVSLTLALL LGGLTMGGIA AGVGTGTTAL VATQQFQQLQ AAM-HDDLKEV EKSITNLEKS LTSLSEVVLQ NRRGLD-LLFL KEGGLCAALK EECCFYADHT GLVRDSMAKL RERLSQRQKL FESQQGWFEG LFNKSPWFTT LIST-IMGPLI ILLLILLFGP CILNRLVQFI KDRISVVQAL VLTQQYHQLK IIEDCKSRE (SEQ ID NO:77; GenBank Accession No: AID54959).

In some cases, the heterologous glycoprotein used for pseudotyping is an MLV glycoprotein. A suitable MLV protein comprises an amino acid sequence having at least 80%, at least 85%, at least 90%, at least 95%, at least 98%, at least 99%, or 100%, amino acid sequence identity to the following amino acid sequence: MARSTLSKPP QDKINPWKPL IVMGVLLGVG MAESPHQVFN VTWRVTNLMT GRTANATSLL GTVQDAFPKL YFDLCDLVGE EWDPSDQEPY VGYGCKYPAG RQR-TRTFDFY VCPGHTVKSG CGGPGEGYCG KWGC-ETTGQA YWKPTSSWDL ISLKRGNTPW DTGCSK-VACG PCYDLSKVSN SFQGATRGGR CNPLVLEFTD AGKKANWDGP KSWGLRLYRT GTDPITMFSL TRQVLNVGPR VPIGPNPVLP DQRLPSSPIE IVPAPQPPSP LNTSYPPSTT STPSTSPTSP SVPQPPPGTG DRLLALVKGA YQALNLTNPD KTQECWLCLV SGPPYYEGVA VVGTYTNHST APANCTATSQ HKLTLSEVTG QGLCMGAVPK THQAL-CNTTQ SAGSGSYYLA APAGTMWACS TGLTPCLSTT VLNLTTDYCV LVELWPRVIY HSPDYMYGQL EQRT-KYKREP VSLTLALLLG GLTMGGIAAG IGTGTTALIK TQQFEQLHAA IQTDLNEVEK SITNLEKSLT SLSEVVLQNR RGLDLLFLKE GGLCAALKEE CCFY-ADHTGL VRDSMAKLRE RLNQRQKLFE TGQGWFEGLF NRSPWFTTLI STIMGPLIVL LLILL-FGPCI LNRLVQFVKD RISVVQALVL TQQYHQLKPI EYEP (SEQ ID NO:78; GenBank Accession No: AAA46515).

In some cases, the heterologous glycoprotein used for pseudotyping is an MLV glycoprotein. A suitable MLV protein comprises an amino acid sequence having at least 80%, at least 85%, at least 90%, at least 95%, at least 98%, at least 99%, or 100%, amino acid sequence identity to the following amino acid sequence: MEGPAFSKPL KDKINPWKSL MVMGVYLRVG MAESPHQVFN VTWRVTNLMT GRTANATSLL GTVQDAFPRL YFDLCDLVGE EWDPSDQEPY VGYGCKYPGG RKR-TRTFDFY VCPGHTVKSG CGGPREGYCG EWGC-ETTGQA YWKPTSSWDL ISLKRGNTPW DTGCSK-MACG PCYDLSKVSN SFQGATRGGR CNPLVLEFTD AGKKANWDGP KSWGLRLYRT GTDPITMFSL TRQVLNIGPR IPIGPNPVIT GQLPPSRPVQ IRL-PRPPQPP PTGAASIVPE TAPPSQQPGT GDRLLNLVEG AYQALNLTNP DKTQECWLCL VSGPPYYEGV AVVGTYTNHS TAPASCTATS QHKLTLSEVT GQGLCMGALP KTHQALCNTT QSAGSGSYYL AAPAGTMWAC STGLTPCLST TMLNLTTDYC VLVELWPRII YHSPDYMYGQ LEQRTKYKRE PVSLT-LALLL GGLTMGGIAA GIGTGTTALI KTQQFEQLHA AIQTDLNEVE KSITNLEKSL TSLSEVVLQN RRGLD-LLFLK EGGLCAALKE ECCFYADHTG LVRDSMAKLR ERLNQRQKLF ESGQGWFEGQ FNRSPWFTTL ISTIMGPLIV LLLILLFGPC ILNRLVQFVK DRISVVQALV LTQQYHQLKP IEYEP (SEQ ID NO:79; GenBank Accession No: AAA46514).

In some cases, the heterologous glycoprotein used for pseudotyping is an MLV glycoprotein. A suitable MLV protein comprises an amino acid sequence having at least 80%, at least 85%, at least 90%, at least 95%, at least 98%, at least 99%, or 100%, amino acid sequence identity to the following amino acid sequence: MEGSAFSKPL KDKINPWGPL IVMGILVRAG ASVQRDSPHQ IFNVTWRVTN LMTGQTANAT SLLGTMTDTF PKLYFDLCDL VGDYWDDPEP DIGDGCRTPG GRRR-TRLYDF YVCPGHTVPI GCGGPGEGYC GKWGC-ETTGQ AYWKPSSSWD LISLKRGNTP KDQGPCYDSS VSSGVQGATP GGRCNPLVLE FTDAGRKASW DAPKVWGLRL YRSTGADPVT RFSLTRQVLN VGPRVPIGPN PVITDQLPPS QPVQIMLPRP PHPPPSGTVS MVPGAPPPSQ QPGTGDRLLN LVEG-AYQALN LTSPDKTQEC WLCLVSGPPY YEGVA-VLGTY SNHTSAPANC SVASQHKLTL SEVTGQGLCV GAVPKTHQAL CNTTQKTSDG SYYLAAPAGT IWACNTGLTP CLSTTVLNLT TDYCVLVELW PKVT-YHSPDY VYGQFEKKTK YKREPVSLTL ALLLG-GLTMG GIAAGVGTGT TALVATKQFE QLQAAIHTDL GALEKSVSAL EKSLTSLSEV VLQNRRGLDL LFLKEGGLCA ALKEECCFYA DHTGVVRDSM AKLR-ERLNQR QKLFESGQGW FEGLFNRSPW FTTLISTIMG PLIVLLLILL LGPCILNRLV QFVKDRISVV QAL-ILTQQYH QLKSIEPEEV ESRE (SEQ ID NO:80; Gen-Bank Accession No: AAA46531).

In some cases, the heterologous glycoprotein used for pseudotyping is a polytropic mink cell focus-forming virus glycoprotein. A suitable polytropic mink cell focus-forming virus protein comprises an amino acid sequence having at least 80%, at least 85%, at least 90%, at least 95%, at least 98%, at least 99%, or 100%, amino acid sequence identity to the following amino acid sequence: VQHDSPHQVF NVTWRVTNLM TGQTANATSL LGTMTDAFPK LYFDLCDLIG DDWDETGLGC RTPGGRKRAR TFDFYVCPGH TVPTGCGGPR EGYCGKWGCE TTGQAYWKPS SLWDLISLKR GNTPQNQGPC YDS-SAVSSDI KGATPGGRCN PLVLEFTDAG KKAS-WDGPKV WGLRLYRSTG TDPVTRFSLT RRVLNIGPRV PIGPNPVIID QLPPSRPVQI MLPRPPQPPP PGAASIVPET APPSNQPGTG DRLLNLVDGA YQALNLTSPD KTQECWLCLV AEP-PYYEGVA VLGTYSNHTS APANCSVASQ HKLTL-SEVTG RGLCIGTVPK THQALCNTTL KTNKGSYYLV APAGTTWACN TGLTPCLSAT VLNRTTDYCV LVELWPRVTY HPPSYVYSQF EKSYRHKR (SEQ ID NO:81; GenBank Accession No: 2016415A).

In some cases, the heterologous glycoprotein used for pseudotyping is a gibbon ape leukemia virus (GALV) gly-coprotein. A suitable GALV protein comprises an amino acid sequence having at least 80%, at least 85%, at least 90%, at least 95%, at least 98%, at least 99%, or 100%, amino acid sequence identity to the following amino acid sequence: MVLLPGSMLL TSNLHHLRHQ MSPGSWKRLI ILLSCVFGGG GTSLQNKNPH QPMTLTWQVL SQTGDVVWDT KAVQPPWTWW PTLKPDVCAL AASLESWDIP GTDVSSSKRV RPPDSDYTAA YKQITWGAIG CSYPRARTRM ASSTFYVCPR DGRTLSEARR CGGLESLYCK EWDC-ETTGTG YWLSKSSKDL ITVKWDQNSE WTQKFQQCHQ TGWCNPLKID FTDKGKLSKD WITGKTWGLR FYVSGHPGVQ FTIRLKITNM PAVA-VGPDLV LVEQGPPRTS LALPPPLPPR EAPPPSLPDS NSTALATSAQ TPTVRKTIVT LNTPPPTTGD RLFDLVQGAF LTLNATNPGA TESCWLCLAM GPPY-YEAIAS SGEVAYSTDL DRCRWGTQGK LTLTEVSGHG LCIGKVPFTH QHLCNQTLSI NSSGDHQYLL PSNHSWWACS TGLTPCLSTS VFNQTRDFCI QVQLIP- RIYY YPEEVLLQAY DNSHPRTKRE AVSLTLAVLL GLGITAGIGT GSTALIKGPI DLQQGLTSLQ IAIDADL-RAL QDSVSKLEDS LTSLSEVVLQ NRRGLDLLFL KEGGLCAALK EECCFYIDHS GAVRDSMKKL KEKLDKRQLE RQKSQNWYEG WFNNSPWFTT LLSTIAGPLL LLLLLLILGP CIINKLVQFI NDRISAVKIL VLRQKYQALE NEGNL (SEQ ID NO:82; GenBank Accession No: P21415).

In some cases, the heterologous glycoprotein used for pseudotyping is a GALV glycoprotein. A suitable GALV protein comprises an amino acid sequence having at least 80%, at least 85%, at least 90%, at least 95%, at least 98%, at least 99%, or 100%, amino acid sequence identity to the following amino acid sequence: TSLQNKNPH QPMTLTWQVL SQTGDVVWDT KAVQPPWTWW PTLKPDVCAL AASLESWDIP GTDVSSSKRV RPPDSDYTAA YKQITWGAIG CSYPRARTRM ASSTFYVCPR DGRTLSEARR CGGLESLYCK EWDC-ETTGTG YWLSKSSKDL ITVKWDQNSE WTQKFQQCHQ TGWCNPLKID FTDKGKLSKD WITGKTWGLR FYVSGHPGVQ FTIRLKITNM PAVA-VGPDLV LVEQGPPRTS LALPPPLPPR EAPPPSLPDS NSTALATSAQ TPTVRKTIVT LNTPPPTTGD RLFDLVQGAF LTLNATNPGA TESCWLCLAM GPPY-YEAIAS SGEVAYSTDL DRCRWGTQGK LTLTEVSGHG LCIGKVPFTH QHLCNQTLSI NSSGDHQYLL PSNHSWWACS TGLTPCLSTS VFNQTRDFCI QVQLIP-RIYY YPEEVLLQAY DNSHPRTKRE AVSLTLAVLL GLGITAGIGT GSTALIKGPI DLQQGLTSLQ IAIDADL-RAL QDSVSKLEDS LTSLSEVVLQ NRRGLDLLFL KEGGLCAALK EECCFYIDHS GAVRDSMKKL KEKLDKRQLE RQKSQNWYEG WFNNSPWFTT LLSTIAGPLL LLLLLLILGP CIINKLVQFI NDRISAVKIL VLRQKYQALE NEGNL (SEQ ID NO:83).

In some cases, the heterologous glycoprotein used for pseudotyping is a GALV glycoprotein. A suitable GALV protein comprises an amino acid sequence having at least 80%, at least 85%, at least 90%, at least 95%, at least 98%, at least 99%, or 100%, amino acid sequence identity to the following amino acid sequence: TSLQNKNPH QPMTLTWQVL SQTGDVVWDT KAVQPPWTWW PTLKPDVCAL AASLESWDIP GTDVSSSKRV RPPDSDYTAA YKQITWGAIG CSYPRARTRM ASSTFYVCPR DGRTLSEARR CGGLESLYCK EWDC-ETTGTG YWLSKSSKDL ITVKWDQNSE WTQKFQQCHQ TGWCNPLKID FTDKGKLSKD WITGKTWGLR FYVSGHPGVQ FTIRLKITNM PAVA-VGPDLV LVEQGPPRTS LALPPPLPPR EAPPPSLPDS NSTALATSAQ TPTVRKTIVT LNTPPPTTGD RLFDLVQGAF LTLNATNPGA TESCWLCLAM GPPY-YEAIAS SGEVAYSTDL DRCRWGTQGK LTLTEVSGHG LCIGKVPFTH QHLCNQTLSI NSSGDHQYLL PSNHSWWACS TGLTPCLSTS VFNQTRDFCI QVQLIP-RIYY YPEEVLLQAY DNSHPRTKRE AVSLTLAVLL GLGITAGIGT GSTALIKGPI DLQQGLTSLQ IAIDADL-RAL QDSVSKLEDS LTSLSEVVLQ NRRGLDLLFL KEGGLCAALK EECCFYIDHS GAVRDSMKKL KEKLDKRQLE RQKSQNWYEG WFNNSPWFTT LLSTIAGPLL LLLLLLILGP CIINKLVQFI NDRISAVKIL VLRQKYQALE NEGNL (SEQ ID NO:83).

In some cases, the heterologous glycoprotein used for pseudotyping is a GALV glycoprotein. A suitable GALV protein comprises an amino acid sequence having at least 80%, at least 85%, at least 90%, at least 95%, at least 98%, at least 99%, or 100%, amino acid sequence identity to the following amino acid sequence: TSLQNKNPH QPMTLTWQVL SQTGDVVWDT KAVQPPWTWW PTLKPDVCAL AASLESWDIP GTDVSSSKRV RPPDSDYTAA YKQITWGAIG CSYPRARTRM ASSTFYVCPR DGRTLSEARR CGGLESLYCK EWDC-ETTGTG YWLSKSSKDL ITVKWDQNSE WTQKFQQCHQ TGWCNPLKID FTDKGKLSKD WITGKTWGLR FYVSGHPGVQ FTIRLKITNM PAVA-VGPDLV LVEQGPPRTS LALPPPLPPR EAPPPSLPDS NSTALATSAQ TPTVRKTIVT LNTPPPTTGD RLFDLVQGAF LTLNATNPGA TESCWLCLAM GPPY-YEAIAS SGEVAYSTDL DRCRWGTQGK LTLTEVSGHG LCIGKVPFTH QHLCNQTLSI NSSGDHQYLL PSNHSWWACS TGLTPCLSTS VFNQTRDFCI QVQLIP-RIYY YPEEVLLQAY DNSHPRTKR (SEQ ID NO:84).

In some cases, the heterologous glycoprotein used for pseudotyping is a GALV glycoprotein. A suitable GALV protein comprises an amino acid sequence having at least 80%, at least 85%, at least 90%, at least 95%, at least 98%, at least 99%, or 100%, amino acid sequence identity to the following amino acid sequence: E AVSLTLAVLL GLGI-TAGIGT GSTALIKGPI DLQQGLTSLQ IAIDADLRAL QDSVSKLEDS LTSLSEVVLQ NRRGLDLLFL KEGGL-CAALK EECCFYIDHS GAVRDSMKKL KEKLDKRQLE RQKSQNWYEG WFNNSPWFTT LLSTIAGPLL LLLLL-LILGP CIINKLVQFI NDRISAVKIL (SEQ ID NO:85).

In some cases, the heterologous glycoprotein used for pseudotyping is a RD114 retrovirus glycoprotein. A suitable RD114 retrovirus protein comprises an amino acid sequence having at least 80%, at least 85%, at least 90%, at least 95%, at least 98%, at least 99%, or 100%, amino acid sequence identity to the following amino acid sequence: MKLPTGMVIL CSLIIVRAGF DDPRKAIALV QKQHGKPCEC SGGQVSEAPP NSIQQVTCPG KTAY-LMTNQK WKCRVTPKNL TPSGGELQNC PCNTFQDSMH SSCYTEYRQC RANNKTYYTA TLLKIRSGSL NEVQILQNPN QLLQSPCRGS INQPVCWSAT APIHISDGGG PLDTKRVWTV QKR-LEQIHKA MHPELQYHPL ALPKVRDDLS LDART-FDILN TTFRLLQMSN FSLAQDCWLC LKLGTPTPLA IPTPSLTYSL ADSLANASCQ IIPPLLVQPM QFSNSS-CLSS PFINDTEQID LGAVTFTNCT SVANVSSPLC ALNGSVFLCG NNMAYTYLPQ NWTGLCVQAS LLP-DIDIIPG DEPVPIPAID HYIHRPKRAV QFIPLLAGLG ITAAFTTGAT GLGVSVTQYT KLSHQLISDV QVLSG-TIQDL QDQVDSLAEV VLQNRRGLDL LTAEQGGICL ALQEKCCFYA NKSGIVRNKI RTLQEELQKR RESLASNPLW TGLQGFLPYL LPLLGPLLTL LLILT-IGPCV FSRLMAFIND RLNVVHAMVL AQQYQALKAE EEAQD (SEQ ID NO:86; GenBank Accession No: YP_001497149).

In some cases, the heterologous glycoprotein used for pseudotyping is a Sendai virus (SeV) glycoprotein. A suitable SeV protein comprises an amino acid sequence having at least 80%, at least 85%, at least 90%, at least 95%, at least 98%, at least 99%, or 100%, amino acid sequence identity to the following amino acid sequence: MTAYIQRSQC ISTSLLVVLT TLVSCQIPRD RLSNIGVIVD EGKSLKI-AGS HESRYIVLSL VPGVDFENGC GTAQVIQYKS LLNRLLIPLR DALDLQEALI TVTNDTTQNA GAPQSRFFGA VIGTIALGVA TSAQITAGIA LAEAREAKRD IALIKESMTK THKSIELLQN AVGEQILALK TLQDFVNDEI KPAISELGCE TAALRLGIKL TQHYSELLTA FGSNFGTIGE KSLTLQALSS LYSANITEIM TTIKTGQSNI YDVIYTE-QIK GTVIDVDLER YMVTLSVKIP ILSEVPGVLI HKASSISYNI DGEEWYVTVP SHILSRASFL GGA-DITDCVE SRLTYICPRD PAQLIPDSQQ KCILGDTTRC PVTKVVDSLI PKFAFVNGGV VANCIASTCT CGT- GRRPISQ DRSKGVVFLT HDNCGLIGVN GVELY-ANRRG HDATWGVQNL TVGPAIAIRP IDISLNLADA TNFLQDSKAE LEKARKILSE VGRWYNSRET VITIIV-VMVV ILVVIIVIII VLYRLRRSML MGNPDDRIPR DTYTLEPKIR HMYTNGGFDA MAKER (SEQ ID NO:87; GenBank Accession No: P04855).

In some cases, the heterologous glycoprotein used for pseudotyping is an SeV F0 glycoprotein. A suitable SeV protein comprises an amino acid sequence having at least 80%, at least 85%, at least 90%, at least 95%, at least 98%, at least 99%, or 100%, amino acid sequence identity to the following amino acid sequence: QIPRD RLSNIGVIVD EGKSLKIAGS HESRYIVLSL VPGVDFENGC GTAQVIQYKS LLNRLLIPLR DALDLQEALI TVTNDTTQNA GAPQSRFFGA VIGTIALGVA TSAQI-TAGIA LAEAREAKRD IALIKESMTK THKSIELLQN AVGEQILALK TLQDFVNDEI KPAISELGCE TAALRLGIKL TQHYSELLTA FGSNFGTIGE KSLTLQALSS LYSANITEIM TTIKTGQSNI YDVIYTE-QIK GTVIDVDLER YMVTLSVKIP ILSEVPGVLI HKASSISYNI DGEEWYVTVP SHILSRASFL GGA-DITDCVE SRLTYICPRD PAQLIPDSQQ KCILGDTTRC PVTKVVDSLI PKFAFVNGGV VANCIASTCT CGT-GRRPISQ DRSKGVVFLT HDNCGLIGVN GVELY-ANRRG HDATWGVQNL TVGPAIAIRP IDISLNLADA TNFLQDSKAE LEKARKILSE VGRWYNSRET VITIIV-VMVV ILVVIIVIII VLYRLRRSML MGNPDDRIPR DTYTLEPKIR HMYTNGGFDA MAEKR (SEQ ID NO:88; GenBank Accession No: P04855).

In some cases, the heterologous glycoprotein used for pseudotyping is an SeV F2 glycoprotein. A suitable SeV protein comprises an amino acid sequence having at least 80%, at least 85%, at least 90%, at least 95%, at least 98%, at least 99%, or 100%, amino acid sequence identity to the following amino acid sequence: QIPRD RLSNIGVIVD EGKSLKIAGS HESRYIVLSL VPGVDFENGC GTAQVIQYKS LLNRLLIPLR DALDLQEALI TVTNDTTQNA GAPQSR (SEQ ID NO:89; GenBank Accession No: P04855).

In some cases, the heterologous glycoprotein used for pseudotyping is an SeV F1 glycoprotein. A suitable SeV protein comprises an amino acid sequence having at least 80%, at least 85%, at least 90%, at least 95%, at least 98%, at least 99%, or 100%, amino acid sequence identity to the following amino acid sequence: FFGA VIGTIALGVA TSAQITAGIA LAEAREAKRD IALIKESMTK THKS-IELLQN AVGEQILALK TLQDFVNDEI KPAISELGCE TAALRLGIKL TQHYSELLTA FGSNFGTIGE KSLTLQALSS LYSANITEIM TTIKTGQSNI YDVIYTE-QIK GTVIDVDLER YMVTLSVKIP ILSEVPGVLI HKASSISYNI DGEEWYVTVP SHILSRASFL GGA-DITDCVE SRLTYICPRD PAQLIPDSQQ KCILGDTTRC PVTKVVDSLI PKFAFVNGGV VANCIASTCT CGT-GRRPISQ DRSKGVVFLT HDNCGLIGVN GVELY-ANRRG HDATWGVQNL TVGPAIAIRP IDISLNLADA TNFLQDSKAE LEKARKILSE VGRWYNSRET VITIIV-VMVV ILVVIIVIII VLYRLRRSML MGNPDDRIPR DTYTLEPKIR HMYTNGGFDA MAKER (SEQ ID NO:90; GenBank Accession No: P04855).

In some cases, the heterologous glycoprotein used for pseudotyping is an SeV hemagglutinin-neuraminidase gly-coprotein. A suitable SeV protein comprises an amino acid sequence having at least 80%, at least 85%, at least 90%, at least 95%, at least 98%, at least 99%, or 100%, amino acid sequence identity to the following amino acid sequence: MDGDRSKRDS YWSTSPGGST TKLVSDSERS GKVDTWLLIL AFTQWALSIA TVIICIVIAA RQGYS- MERYS MTVEALNTSN KEVKESLTSL IRQEVITRAA NIQSSVQTGI PVLLNKNSRD VIRLIEKSCN RQELTQLCDS TIAVHHAEGI APLEPHSFWR CPAGEPYLSS DPEVSLLPGP SLLSGSTTIS GCVRLPSLSI GEAIYAYSSN LITQGCADIG KSYQVLQLGY ISLNSDMFPD LNPVVSHTYD INDNRKSCSV VATGTRGYQL CSMPIVDERT DYSSDGIEDL VLDILDLKGR TKSHRYSNSE IDLDHPFSAL YPSVGSGIAT EGSLIFLGYG GLTTPLQGDT KCRIQGCQQV SQDTCNEALK ITWLGGKQVV SVLIQVNDYL SERPRIRVTT IPITQ-NYLGA EGRLLKLGDQ VYIYTRSSGW HSQLQIGVLD VSHPLTISWT PHEALSRPGN EDCNWYNTCP KECIS-GVYTD AYPLSPDAAN VATVTLYANT SRVNPTIMYS NTTNIINMLR IKDVQLEAAY TTTSCITHFG KGYCFHIIEI NQKSLNTLQP MLFKTSIPKL CKAES (SEQ ID NO:91; GenBank Accession No: BAA24391).

In some cases, the heterologous glycoprotein used for pseudotyping is a Jaagsiekte sheep retrovirus (JSRV) gly-coprotein. A suitable JSRV protein comprises an amino acid sequence having at least 80%, at least 85%, at least 90%, at least 95%, at least 98%, at least 99%, or 100%, amino acid sequence identity to the following amino acid sequence: MPKRRAGFRK GWYARQRNSL THQMQRMTLS EPT-SELPTQR QIEALMRYAW NEAHVQPPVT PTNIL-IMLLL LLQRIQNGAA ATFWAYIPDP PMLQSLGWDK ETVPVYVNDT SLLGGKSDIH ISPQQANISF YGLTTQYPMC FSYQSQHPHC IQVSADISYP RVTIS-GIDEK TGMRSYRDGT GPLDIPFCDK HLSIGIGIDT PWTLCRARIA SVYNINNANT TLLWDWAPGG TPDFPEYRGQ HPPISSVNTA PIYQTELWKL LAAF-GHGNSL YLQPNISGSK YGDVGVTGFL YPRACVPYPF MVIQGHMEIT PSLNIYYLNC SNCILTNCIR GVAKGEQVII VKQPAFVMLP VEITEEWYDE TALELLQRIN TALSRPKRGL SLIILGIVSL ITLIATAVTA SVSLAQSIQV AHTVDSLSSN VTKVMGTQEN IDK-KIEDRLP ALYDVVRVLG EQVQSINFRM KIQCH-ANYKW ICVTKKPYNT SDFPWDKVKK HLQGIWFNTT VSLDLLQLHN EILDIENSPK ATL-NIADTVD NFLQNLFSNF PSLHSLWRSI IAMGAVLTFV LIIICLAPCL IRSIVKEFLH MRVLIHKNML QHQHLMELLN NKERGAAGDD P (SEQ ID NO:92; Gen-Bank Accession No: ABI50237).

In some cases, the heterologous glycoprotein used for pseudotyping is a baculovirus gp64 glycoprotein. A suitable baculovirus protein comprises an amino acid sequence hav-ing at least 80%, at least 85%, at least 90%, at least 95%, at least 98%, at least 99%, or 100%, amino acid sequence identity to the following amino acid sequence: MFHLLTLLLL LFINMNLYLA GEHCNVQMKN GPY-RIKNLAI TPPRETLKKD VTVTIVETDY EENVLIGYKG YYQAYGYNGG SLDANTRLEE TMESLPLTKE DLLTWTYRQE CEVGEELIDR WGSDSDDCYR NKDGRGVWVK TKELVKRQNN NHFAHHTCNR SWRCGFSTAK MYSKLVCDDE TNDCKVFILD NTGK-PINITT NEVLYRDGVN MMLKSKPTFT RREEKVACLL VKDELNPDKT REHCLIDSDI YDLSNNNWFC MFNKCIKRNV DSVVKKRPNK WMHNLAPKYS EGA-TATKGDM MHIQEELMYE NDLLKMNIEL VHAHMNKLNN IIHDLIVSIA KVDERLIGNL MNISVSSVFL SDDTFLLMPC TNPPQHTSNC YNN-SIYREGR WVFNEDTSEC IDFNNYRELS IDDDIEFWIP TIGNTTYHDS WKDASGWSFV AQQKSNLIMT MENTKFGGVG TSLSDITSMS EGELTAKLTT FVFSHIVTFI LIIILIILCI CLLKK (SEQ ID NO:93; Gen-Bank Accession No: YP_009182316).

In some cases, the heterologous glycoprotein used for pseudotyping is a baculovirus gp64 glycoprotein. A suitable baculovirus protein comprises an amino acid sequence having at least 80%, at least 85%, at least 90%, at least 95%, at least 98%, at least 99%, or 100%, amino acid sequence identity to the following amino acid sequence: MLRITL-LILF LVRFVSGAEH CNAQMKSGPW RIKNLPIAPP KETLQKDVDV EIVETDLDEN VIIGYKGYYQ AYAYN-GGSLD PNTSVDETTQ TLNIDKDDLI TWGDRRKCEV GEELIDQWGS DSDSCFKDKL GRGVWVAGKE LVKRKNNNHF AHHTCNRSWR CGVSTAKMYT RLECDNETDD CKVTILDING TVINVTENEV LHRDGVSMIL KQKSTFTRRT EKVACLLIKD DKSDPYSITR EHCLIDNDIF DLSKNTWNCK FNR-CIKRRSE NVVKKRPPTW RHNEPPKHSE GTTATKGDLM HIQEELMYEN DLLRMNLELL HAHI-NKLNNM MHDLIVSVAK VDERLIGNLM NNSVSST-FLS DDTFLLMPCT NPPPHTSNCY NNSIYKEGRW VANTDSSQCI DFRNYKELAI DDDIEFWIPT IGNTSY-HESW KDASGWSFIA QQKSNLISTM ENTKFGGHTT SLSDIGDMAK GELNATLYSF MLGHGFSFFL IIGVIVFLIC MVRSRVRAF (SEQ ID NO:94; GenBank Accession No: YP_473216).

In some cases, the heterologous glycoprotein used for pseudotyping is a Chandipura virus glycoprotein. A suitable Chandipura virus protein comprises an amino acid sequence having at least 80%, at least 85%, at least 90%, at least 95%, at least 98%, at least 99%, or 100%, amino acid sequence identity to the following amino acid sequence: MTSSVTISVI LLISFIAPSY SSLSIAFPEN TKLDWKPVTK NTRYCPMGGE WFLEPGLQEE SFLSSTPIGA TPSKSDGFLC HAAKWVTTCD FRWYGPKYIT HSIHNIKPTR SDCDTALASY KSGTLVSPGF PPESCGYASV TDSEFLVIMI TPHHVGVDDY RGHWVDPLFV GGECDQSYCD TIHNSSVWIP ADQTKKNICG QSFTPLTVTV AYDKTKEIAA GAIVFKSKYH SHMEGARTCR LSYCGRNGIK FPNGEWVSLD VKTKIQEKPL LPLFKE-CPAG TEVRSTLQSD GAQVLTSEIQ RILDYSLCQN TWDKVERKEP LSPLDLSYLA SKSPGKGLAY TVINGTLSFA HTRYVRMWID GPVLKEMKGK RESPS-GISSD IWTQWFKYGD MEIGPNGLLK TAGGYKFPWH LIGMGIVDNE LHELSEANPL DHPQLPHAQS IADD-SEEIFF GDTGVSKNPV ELVTGWFTSW KES-LAAGVVL ILVVVLIYGV LRCFPVLCTT CRKPKWKKGV ERSDSFEMRI FKPNNMRARV (SEQ ID NO:95; GenBank Accession No: YP_007641380).

In some cases, the heterologous glycoprotein used for pseudotyping is a Venezuelan equine encephalitis virus glycoprotein. A suitable Venezuelan equine encephalitis virus protein comprises an amino acid sequence having at least 80%, at least 85%, at least 90%, at least 95%, at least 98%, at least 99%, or 100%, amino acid sequence identity to the following amino acid sequence: MFPFQPMYPM QPMPYRNPFA APRRPWFPRT DPFLAMQVQE LTRS-MANLTF KQRRDAPPEG PSAKKPKKEA SQKQKGGGQG KKKKNQGKKK AKTGPPNPKA QNG-NKKKTNK KPGKRQRMVM KLESDKTFPI MLEGK-INGYA CVVGGKLFRP MHVEGKIDND VLAALKTKKA SKYDLEYADV PQNMRADTFK YTHEKPQGYY SWHHGAVQYE NGRFTVPKGV GAKGDSGRPI LDNQGRVVAI VLGGVNEGSR TAL-SVVMWNE KGVTVKYTPE NCEQWSLVTT MCL-LANVTFP CAQPPICYDR KPAETLAMLS VNVDNPGYDE LLEAAVKCPG STEELFKEYK LTRPY-MARCI RCAVGSCHSP IAIEAVKSDG HDGYVRLQTS SQYGLDSSGN LKGRTMRYDM HGTIKEIPLH QVSLHTSRPC HIVDGHGYFL LARCPAGDSI TMEFKKDSVT HSCSVPYEVK FNPVGRELYT HPPEHGVEQA CQVYAHDAQN RGAYVEMHLP GSEVDSSLVS LSGSSVTVTP PVGTSALVEC ECGGT-KISET INKTKQFSQC TKKEQCRAYR LQNDKWVYIS DKLPKAAGAT LKGKLHVPFL LADGKCTVPL APEPMITFGF RSVSLKLHPK NPTYLTTRQL ADE-PHYTHEL ISEPAVRNFT VTGKGWEFVW GNHPPKRFWA QETAPGNPHG LPHEVITHYY HRYPM-STILG LSICAAIATV SVAASTWLFC RSRVACLTPY RLTPNARIPF CLAVLCCART ARAETTWESL DHLWNNNQQM FWIQLLIPLA ALIVVTRLLR CVCCVVPFLV MAGAAGAGAY EHATTMPSQA GISYNTIVNR AGYAPLPISI TPTKIKLIPT VNLEYVTCHY KTGMDSPAIK CCGSQECTPT YRPD-EQCKVF TGVYPFMWGG AYCFCDTENT QVSKAY-VMKS DDCLADHAEA YKAHTASVQA FLNITVGEHS IVTTVYVNGE TPVNFNGVKL TAGPLSTAWT PFDRKIVQYA GEIYNYDFPE YGAGQPGAFG DIQSRTVSSS DLYANTNLVL QRPKAGAIHV PYTQAPSGFE QWKKDKAPSL KSTAPFGCEI YTN-PIRAENC AVGSIPLAFD IPDALFTRVS ETPTLSAAEC TLNECVYSSD FGGIATVKYS ASKSGKCAVH VPSGTATLKE AAVELTEQGS ATIHFSTANI HPE-FRLQICT SYVTCKGDCH PPKDHIVTHP QYHAQTFTAA VSKTAWTWLT SLLGGSAVII IIGLV-LATIV AMYVLTNQKH N (SEQ ID NO:96; GenBank Accession No: AAU89534). Such a glycoprotein may be useful for targeting a VLP of the present disclosure to dendritic cells, macrophages, and cells of the spleen, lymph node, thymus, pancreas, skeletal muscle, and central nervous system.

In some cases, the heterologous glycoprotein used for pseudotyping is a Venezuelan equine encephalitis virus E2 glycoprotein. A suitable Venezuelan equine encephalitis virus protein comprises an amino acid sequence having at least 80%, at least 85%, at least 90%, at least 95%, at least 98%, at least 99%, or 100%, amino acid sequence identity to the following amino acid sequence: STEELFKEYK LTRPYMARCI RCAVGSCHSP IAIEAVKSDG HDGYVRLQTS SQYGLDSSGN LKGRTMRYDM HGTIKEIPLH QVSLHTSRPC HIVDGHGYFL LARCPAGDSI TMEFKKDSVT HSCSVPYEVK FNPVGRELYT HPPEHGVEQA CQVYAHDAQN RGAY-VEMHLP GSEVDSSLVS LSGSSVTVTP PVGTSALVEC ECGGTKISET INKTKQFSQC TKKEQCRAYR LQNDKWVYIS DKLPKAAGAT LKGKLHVPFL LADGKCTVPL APEPMITFGF RSVSLKLHPK NPTYLT-TRQL ADEPHYTHEL ISEPAVRNFT VTGKGWEFVW GNHPPKRFWA QETAPGNPHG LPHEVITHYY HRYPM-STILG LSICAAIATV SVAASTWLFC RSRVACLTPY RLTPNARIPF CLAVLCCART ARA (SEQ ID NO:97; Gen-Bank Accession No: AAU89534). Such a glycoprotein may be useful for targeting a VLP of the present disclosure to dendritic cells, macrophages, and cells of the spleen, lymph node, thymus, pancreas, skeletal muscle, and central nervous system.

In some cases, the heterologous glycoprotein used for pseudotyping is a Venezuelan equine encephalitis virus E1 glycoprotein. A suitable Venezuelan equine encephalitis virus protein comprises an amino acid sequence having at least 80%, at least 85%, at least 90%, at least 95%, at least 98%, at least 99%, or 100%, amino acid sequence identity to the following amino acid sequence: Y EHATTMPSQA GISYNTIVNR AGYAPLPISI TPTKIKLIPT VNLEYVTCHY KTGMDSPAIK CCGSQECTPT YRPD-EQCKVF TGVYPFMWGG AYCFCDTENT QVSKAY- VMKS DDCLADHAEA YKAHTASVQA FLNITVGEHS IVTTVYVNGE TPVNFNGVKL TAGPLSTAWT PFDRKIVQYA GEIYNYDFPE YGAGQPGAFG DIQSRTVSSS DLYANTNLVL QRPKAGAIHV PYTQAPSGFE QWKKDKAPSL KSTAPFGCEI YTN- PIRAENC AVGSIPLAFD IPDALFTRVS ETPTLSAAEC TLNECVYSSD FGGIATVKYS ASKSGKCAVH VPSGTATLKE AAVELTEQGS ATIHFSTANI HPE- FRLQICT SYVTCKGDCH PPKDHIVTHP QYHAQTFTAA VSKTAWTWLT SLLGGSAVII IIGLV- LATIV AMYVLTNQKH N (SEQ ID NO:98; GenBank Accession No: AAU89534). Such a glycoprotein may be useful for targeting a VLP of the present disclosure to dendritic cells, macrophages, and cells of the spleen, lymph node, thymus, pancreas, skeletal muscle, and central nervous system.

In some cases, the heterologous glycoprotein used for pseudotyping is a Lassa virus glycoprotein. A suitable Lassa virus protein comprises an amino acid sequence having at least 80%, at least 85%, at least 90%, at least 95%, at least 98%, at least 99%, or 100%, amino acid sequence identity to the following amino acid sequence: MGQIVTFFQE VPHVIEEVMN IVLIALSVLA VLKGLYNFAT CGLVGLVTFL LLCGRSCTTS LYKGVYELQT LELN- METLNM TMPLSCTKNN SHHYIMVGNE TGLELTLTNT SIINHKFCNL SDAHKKNLYD HALMSI- ISTF HLSIPNFNQY EAMSCDFNGG KISVQYNLSH SYAGDAANHC GTVANGVLQT FMRMAWGGSY IALDSGRGNW DCIMTSYQYL IIQNTTWEDH CQFSRPSPIG YLGLLSQRTR DIYISRRLLG TFTWTLSDSE GKDTPGGYCL TRWMLIEAEL KCFGN- TAVAK CNEKHDEEFC DMLRLFDFNK QAIQRLKAEA QMSIQLINKA VNALINDQLI MKNHLRDIMG IPYC- NYSKYW YLNHTTTGRT SLPKCWLVSN GSYL- NETHFS DDIEQQADNM ITEMLQKEYM ERQGKTPLGL VDLFVFSTSF YLISIFLHLV KIP- THRHIVG KSCPKPHRLN HMGICSCGLY KQPGVPVKWK R (SEQ ID NO:99; GenBank Accession No: ADY11070).

In some cases, the heterologous glycoprotein used for pseudotyping is an avian leukosis virus glycoprotein. A suitable avian leukosis virus protein comprises an amino acid sequence having at least 80%, at least 85%, at least 90%, at least 95%, at least 98%, at least 99%, or 100%, amino acid sequence identity to the following amino acid sequence: MEAVIKMRRA LFLQAFLTGR PGKASKKDPK KNPLATSKKD PEKTPLLPTR VNYIL- IIGVL VLCEVTGVRA DVHLLEQPGN LWITWANRTG QTDFCLSTQS ATSPFQTCLI GIPSPISEGD FKGYVSDNCT TLGTDRLVSS ASITGGPDNS TTL- TYRKVSC LLLKLNVSMW NEPPELQLLG SQSLPNITDI TQISGVAGGC VGFRPKGVPW YLGWSQGEAT RFLLRHPSFS NLTGPFTVVT ADRHNLFMGS EYCGAYGYRF WEIYNCSQEG QQYRCGKARR PRPQSPETQC TRQGGIWVNR SKEI- NETEPF SFTVNCTASN LGNASGCCGK AGTILPGIWV DSTQGNFTKP KALPPAIFLI CGDRAWQGIP SRPVGGPCYL GKLTMLAPNH TDILKILANS SRT- GIRRRRS VSHLDDTCSD EVQLWGPTAR IFASILAPGV AAAQALREIE RLACWSVKQA NLTTSLLGDL LDDVT- SIRHA VLQNRAAIDF LLLAHGHGCE DIAGMCCFNL SDHSESIQKK FQLMKEHVNK IGVDSDPIGS WLR- GLFGGIG GWAVHLLKGL LLGLVVILLL VVCLPCFLQF VSSSIRKMIN NSVSYHTEYR KMQG- GAV (SEQ ID NO:100; GenBank Accession No: AD034853).

In some cases, the heterologous glycoprotein used for pseudotyping is an avian leukosis virus glycoprotein. A suitable avian leukosis virus protein comprises an amino acid sequence having at least 80%, at least 85%, at least 90%, at least 95%, at least 98%, at least 99%, or 100%, amino acid sequence identity to the following amino acid sequence: MEAVIKMRRA LFLQAFLTGH PGKV- SKKDSK KKPPATGKRD PEKTPLLPTR VNYILIIGVL VLCEVTGVRA DVHLLEQPGN LWITWANRTG QTDFCLSTQS ATSPFQTCLI GIPSPISEGD FKGYVSGNCT ALGTHRLVSS GIHGGPDNST TLTYRKVSCL LLKLNVSLLD EPSELQLLGS QSLPNIT- NIT QIPSVAGGCI GFTPYGSPAG VYGWDRRQVT HILLTDPGSN PFFNKASNSS KPFTVVTADR HNLFMG- SEYC GAYGYRFWEM YNCSQMRQNW SICMDVWGRG LPESWCTSTG GIWVNQSKEI NETEPFSFTA NCTGSNLGNV SGCCGESITI LPP- GAWVDST QGSFTKPKAL PPGIFLICGD RAWQ- GIPSRP VGGPCYLGKL TMLAPNHTDI LKILANSSQT GVRHKRSVTH LDDTCSDEVQ LWGPTARIFA SILAPGVAAA QALREIERLA CWSVKQANLT TSLLGDLLDD VTSIRHAVLQ NRAAIDFLLL AHGHG- CEDIA GMCCFNLSDH SESIQKKFQL MKEHVNKIGV DSDPIGSWLR GLFGGIGEWA VHLLKGLLLG LVVILLLVVC LPCFLQFVSS SIRKMINNSI SYHTEY- RKMQ GGAV (SEQ ID NO:101; GenBank Accession No: AEF97639).

In some cases, the heterologous glycoprotein used for pseudotyping is an avian leukosis virus glycoprotein. A suitable avian leukosis virus protein comprises an amino acid sequence having at least 80%, at least 85%, at least 90%, at least 95%, at least 98%, at least 99%, or 100%, amino acid sequence identity to the following amino acid sequence: MEAVIKAFLT GHPGKVSKKD SKKKPPATSK KDPEKTPLLP SRGYFFFPTI LVCVVIISVV PGVGGVHLLR QPGNVWVTWA NKTGRTDFCL SLQSATSPFR TCLIGIPQYP LNTFKGYVTN VTACDN- DADL ASQTACLIKA LNTTLPWDPQ ELDILGSQMI KNGTTRTCVT FGSVCYKENN RSRVCHNFDG NFNGTGGAEA ELRDFIAKWK SDDLLIRPYV NQSWTMVSPI NVESFSISRR YCGFTSNETR YYRGDLSNWC GSKRGKWSAG YSNRTKCSSN TTGCGGNCTT EWNYYAYGFT FGKQPEVLWN NGTAKALPPG IFLICGDRAW QGIPRNALGG PCYLGQLTML SPNFTTWITY GPNITGHRRS RRAI- RGLSPD CSDEVQLWSA TARIFASFFA PGVAAAQALK EIERLACWSV KQANLTSLIL NAMLEDMNSI RHAVLQNRAA IDFLLLAQGH GCQDVEGMCC FNLSDHSESI HKALQAMKEH TEKIQVEDDP IGDWFTRTFG DLGRWLAKGV KTLLFALLVI VCL- LAIIPCI IKCFQDCLSR TMNQFMDERI RYHRIREQL (SEQ ID NO:102; GenBank Accession No: AWM62167).

In some cases, the heterologous glycoprotein used for pseudotyping is a human T-lymphotropic virus 1 (HTLV-1) glycoprotein. A suitable HTLV-1 protein comprises an amino acid sequence having at least 80%, at least 85%, at least 90%, at least 95%, at least 98%, at least 99%, or 100%, amino acid sequence identity to the following amino acid sequence: MGKFLATLIL FFQFCPLILG DYSPSCCTLT VGVSSYHSKP CNPAQPVCSW TLDLLALSAD QALQPPCPNL VSYSSYHATY SLYLFPHWIK KPNRNGGGYY SASYSDPCSL KCPYLGCQSW TCPY- TGAVSS PYWKFQQDVN FTQEVSHLNI NLHFSKCGFP FSLLVDAPGY DPIWFLNTEP SQLPPTAPPL LSHSNLDHIL EPSIPWKSKL LTLVQLTLQS TNYTCIVCID RASLSTWHVL YSPNVSVPSL SSTPLLYPSL ALPAPHLTLP FNWTHCFDPQ IQAIVSSPCH NSLILPPFSL SPVPTLGSRS RRAVPVAVWL VSALAMGAGV AGGITGSMSL ASGKSLLHEV DKDISQLTQA IVKNHKNLLK IAQYAAQNRR GLDLLFWEQG GLCKALQEQC CFLNITNSHV SILQERPPLE NRVLTGWGLN WDLGLSQWAR EALQTGITLV ALLLLVILAG PCILRQLRHL PSRVRYPHYS LINPESSL (SEQ ID NO:103; GenBank Accession No: AAU04884). Such a glycoprotein may be useful for targeting a VLP of the present disclosure to CD4+ and CD8+ T cells.

In some cases, the heterologous glycoprotein used for pseudotyping is a human foamy virus gp130 glycoprotein. A suitable human foamy virus protein comprises an amino acid sequence having at least 80%, at least 85%, at least 90%, at least 95%, at least 98%, at least 99%, or 100%, amino acid sequence identity to the following amino acid sequence: MAPPMTLQQW IIWKKMNKAH EALQNTTTVT EQQKEQIILD IQNEEVQPTR RDKFRYLLYT CCATSSRVLA WMFLVCILLI IVLVSCFVTI SRIQWNKDIQ VLGPVIDWNV TQRAVYQPLQ TRRIARSLRM QHPVPKYVEV NMTSIPQGVY YEPHPEPIVV KERVLGLSQI LMINSENIAN NANLTQEVKK LLTEMVNEEM QSLSDVMIDF EIPLGDPRDQ EQYIHRKCYQ EFANCYLVKY KEPKPWPKEG LIADQCPLPG YHAGLTYNRQ SIWDYYIKVE SIRPANWTTK SKYGQARLGS FYIPSSLRQI NVSHVLFCSD QLYSKWYNIE NTIEQNERFL LNKLNNLTSG TSVLKKRALP KDWSSQGKNA LFREINVLDI CSKPESVILL NTSYYSFSLW EGDCNFTKDM ISQLVPECDG FYNNSKWMHM HPYACRFWRS KKNEKEETKC RDGETKRCLY YPLWDSPEST YDFGYLAYQK NFPSPICIEQ QKIRDQDYEV YSLYQERKIA SKAYGIDTVL FSLKNFLNYT GTPVNEMPNA RAFVGLIDPK FPPSYPNVTR EHYTSCNNRK RRSVDNNYAK LRSMGYALTG AVQTLSQISD INDENLQQGI YLLRDHVITL MEATLHDISV MEGMFAVQHL HTHLNHLKTM LLERRIDWTY MSSTWLQQQL QKSDDEMKVI KRIARSLVYY VKQTHSSPTA TAWEIGLYYE LVIPKHIYLN NWNVVNIGHL VKSAGQLTHV TIAHPYEIIN KECVETIYLH LEDCTRQDYV ICDVVKIVQP CGNSSDTSDC PVWAEAVKEP FVQVNPLKNG SYLVLASSTD CQIPPYVPSI VTVNETTSCF GLDFKRPLVA EERLSFEPRL PNLQLRLPHL VGIIAKIKGI KIEVTSSGES IKEQIERAKA ELLRLDIHEG DTPAWIQQLA AATKDVWPAA ASALQGIGNF LSGTAQGIFG TAFSLLGYLK PILIGVGVIL LVILIFKIVS WIPTKKKNQ (SEQ ID NO:104; GenBank Accession No: P14351).

In some cases, the heterologous glycoprotein used for pseudotyping is a human foamy virus glycoprotein. A suitable human foamy virus protein comprises an amino acid sequence having at least 80%, at least 85%, at least 90%, at least 95%, at least 98%, at least 99%, or 100%, amino acid sequence identity to the following amino acid sequence: SLRM QHPVPKYVEV NMTSIPQGVY YEPHPEPIVV KERVLGLSQI LMINSENIAN NANLTQEVKK LLTEMVNEEM QSLSDVMIDF EIPLGDPRDQ EQYIHRKCYQ EFANCYLVKY KEPKPWPKEG LIADQCPLPG YHAGLTYNRQ SIWDYYIKVE SIRPANWTTK SKYGQARLGS FYIPSSLRQI NVSHVLFCSD QLYSKWYNIE NTIEQNERFL LNKLNNLTSG TSVLKKRALP KDWSSQGKNA LFREINVLDI CSKPESVILL NTSYYSFSLW EGDCNFTKDM ISQLVPECDG FYNNSKWMHM HPYACRFWRS KKNEKEETKC RDGETKRCLY YPLWDSPEST YDFGYLAYQK NFPSPICIEQ QKIRDQDYEV YSLYQERKIA SKAYGIDTVL FSLKNFLNYT GTPVNEMPNA RAFVGLIDPK FPPSYPNVTR EHYTSCNNRK RR (SEQ ID NO:105).

In some cases, the heterologous glycoprotein used for pseudotyping is a human foamy virus glycoprotein. A suitable human foamy virus protein comprises an amino acid sequence having at least 80%, at least 85%, at least 90%, at least 95%, at least 98%, at least 99%, or 100%, amino acid sequence identity to the following amino acid sequence: SVDNNYAK LRSMGYALTG AVQTLSQISD INDENLQQGI YLLRDHVITL MEATLHDISV MEGMFAVQHL HTHLNHLKTM LLERRIDWTY MSSTWLQQQL QKSDDEMKVI KRIARSLVYY VKQTHSSPTA TAWEIGLYYE LVIPKHIYLN NWNVVNIGHL VKSAGQLTHV TIAHPYEIIN KECVETIYLH LEDCTRQDYV ICDVVKIVQP CGNSSDTSDC PVWAEAVKEP FVQVNPLKNG SYLVLASSTD CQIPPYVPSI VTVNETTSCF GLDFKRPLVA EERLSFEPRL PNLQLRLPHL VGIIAKIKGI KIEVTSSGES IKEQIERAKA ELLRLDIHEG DTPAWIQQLA AATKDVWPAA ASALQGIGNF LSGTAQGIFG TAFSLLGYLK PILIGVGVIL LVILIFKIVS WIPTKKKNQ (SEQ ID NO:106).

In some cases, the heterologous glycoprotein used for pseudotyping is a visna-maedi virus gp160 glycoprotein. A suitable visna-maedi virus protein comprises an amino acid sequence having at least 80%, at least 85%, at least 90%, at least 95%, at least 98%, at least 99%, or 100%, amino acid sequence identity to the following amino acid sequence: MASKESKPSR TTRRGMEPPL RETWNQVLQE LVKRQQQEEE EQQGLVSGKK KSWVSIDLLG TEGKDIKKVN IWEPCEKWFA QVVWGVLWVL QIVLWGCLMW EVRKGNQCQA EEVIALVSDP GGFQRVQHVE TVPVTCVTKN FTQWGCQPEG AYPDPELEYR NISREILEEV YKQDWPWNTY HWPLWQMENM RQWMKENEKE YKERTNKTKE DIDDLVAGRI RGRFCVPYPY ALLRCEEWCW YPESINQETG HAEKIKINCT KAKAVSCTEK MSLAAVQRVY WEKEDEESMK FLNIKACNIS LRCQDEGKSP GGCVQGYPIP KGAEIIPEAM KYLRGKKSRY GGIKDKNGEL KLPLSVRVWV RMANLSGWVN GTPPYWSARI NGSTGINGTR WYGIGTLHHL GCNISSNPER GICNFTGELW IGGDKFPYYY TPSWNCSQNW TGHPVWHVFR YLDMTEHMTS RCIQRPKRHN ITVGNGTITG NCSVTNWDGC NCTRSGNHLY NSTSGGLLVI ICRQNSTITG IMGTNTNWTT MWNIYQNCSR CNNSSLDRTG SGTLGTVNNL KCSLPHRNES NKWTCKSQRD SYIAGRDFWG KVKAKYSCES NLGGLDSMMH QQMLLQRYQV IRVRAYTYGV VEMPQSYMEA QGENKRSRRN LQRKKRGIGL VIVLAIMAII AAAGAGLGVA NAVQQSYTRT AVQSLANATA AQQEVLEASY AMVQHIAKGI RILEARVARV EALVDRMMVY QELDCWHYQH YCVTSTRSEV ANYVNWTRFK DNCTWQQWEE EIEQHEGNLS LLLREAALQV HIAQRDARRI PDAWKAIQEA FNWSSWFSWL KYIPWIIMGI VGLMCFRILM CVISMCLQAY KQVKQIRYTQ VTVVIEAPVE LEEKQKRNGD GTNGCASLER ERRTSHRSFI QIWRATWWAW KTSPWRHNWR TMPYITLLPI LVIWQWMEEN GWNGENQHKK KKERVDCQDR EQMPTLENDY VEL (SEQ ID NO:107; GenBank Accession No: P35954).

In some cases, the heterologous glycoprotein used for pseudotyping is a visna-maedi virus glycoprotein. A suitable visna-maedi virus protein comprises an amino acid sequence having at least 80%, at least 85%, at least 90%, at least 95%, at least 98%, at least 99%, or 100%, amino acid sequence identity to the following amino acid sequence: QCQA EEVIALVSDP GGFQRVQHVE TVPVTCVTKN FTQWGCQPEG AYPDPELEYR NISREILEEV YKQDWPWNTY HWPLWQMENM RQWMKENEKE YKERTNKTKE DIDDLVAGRI RGRFCVPYPY ALLR-CEEWCW YPESINQETG HAEKIKINCT KAKAVSCTEK MSLAAVQRVY WEKEDEESMK FLNIKACNIS LRCQ-DEGKSP GGCVQGYPIP KGAEIIPEAM KYLRGKKSRY GGIKDKNGEL KLPLSVRVWV RMANLSGWVN GTP-PYWSARI NGSTGINGTR WYGIGTLHHL GCNISSNPER GICNFTGELW IGGDKFPYYY TPSWNCSQNW TGHPVWHVFR YLDMTEHMTS RCI-QRPKRHN ITVGNGTITG NCSVTNWDGC NCTRSGNHLY NSTSGGLLVI ICRQNSTITG IMGTNTNWTT MWNIYQNCSR CNNSSLDRTG SGTLGTVNNL KCSLPHRNES NKWTCKSQRD SYIAGRDFWG KVKAKYSCES NLGGLDSMMH QQMLLQRYQV IRVRAYTYGV VEMPQSYMEA QGENKRSRRN LQRKKRGIGL VIVLAIMAII AAAGAGLGVA NAVQQSYTRT AVQSLANATA AQQEVLEASY AMVQHIAKGI RILEARVARV EALVDRMMVY QELDCWHYQH YCVTSTRSEV ANY-VNWTRFK DNCTWQQWEE EIEQHEGNLS LLL-REAALQV HIAQRDARRI PDAWKAIQEA FNWSS-WFSWL KYIPWIIMGI VGLMCFRILM CVISMCLQAY KQVKQIRYTQ VTVVIEAPVE LEEKQKRNGD GTNGCASLER ERRTSHRSFI QIWRATWWAW KTSPWRHNWR TMPYITLLPI LVIWQWMEEN GWN-GENQHKK KKERVDCQDR EQMPTLENDY VEL (SEQ ID NO:108).

In some cases, the heterologous glycoprotein used for pseudotyping is a visna-maedi virus glycoprotein. A suitable visna-maedi virus protein comprises an amino acid sequence having at least 80%, at least 85%, at least 90%, at least 95%, at least 98%, at least 99%, or 100%, amino acid sequence identity to the following amino acid sequence: QCQA EEVIALVSDP GGFQRVQHVE TVPVTCVTKN FTQWGCQPEG AYPDPELEYR NISREILEEV YKQDWPWNTY HWPLWQMENM RQWMKENEKE YKERTNKTKE DIDDLVAGRI RGRFCVPYPY ALLR-CEEWCW YPESINQETG HAEKIKINCT KAKAVSCTEK MSLAAVQRVY WEKEDEESMK FLNIKACNIS LRCQ-DEGKSP GGCVQGYPIP KGAEIIPEAM KYLRGKKSRY GGIKDKNGEL KLPLSVRVWV RMANLSGWVN GTP-PYWSARI NGSTGINGTR WYGIGTLHHL GCNISSNPER GICNFTGELW IGGDKFPYYY TPSWNCSQNW TGHPVWHVFR YLDMTEHMTS RCI-QRPKRHN ITVGNGTITG NCSVTNWDGC NCTRSGNHLY NSTSGGLLVI ICRQNSTITG IMGTNTNWTT MWNIYQNCSR CNNSSLDRTG SGTLGTVNNL KCSLPHRNES NKWTCKSQRD SYIAGRDFWG KVKAKYSCES NLGGLDSMMH QQMLLQRYQV IRVRAYTYGV VEMPQSYMEA QGENKRSRRN LQRKKRGIGL VIVLAIMAII AAAGAGLGVA NAVQQSYTRT AVQSLANATA AQQEVLEASY AMVQHIAKGI RILEARVARV EALVDRMMVY QELDCWHYQH YCVTSTRSEV ANY-VNWTRFK DNCTWQQWEE EIEQHEGNLS LLL-REAALQV HIAQRDARRI PDAWKAIQEA FNWSS-WFSWL KYIPWIIMGI VGLMCFRILM CVISMCLQAY KQVKQIRYTQ VTVVIEAPVE LEEKQKRNGD GTNGCASLER ERRTSHRSFI QIWRATWWAW KTSPWRHNWR TMPYITLLPI LVIWQWMEEN GWN-GENQHKK KKERVDCQDR EQMPTLENDY VEL (SEQ ID NO:108).

In some cases, the heterologous glycoprotein used for pseudotyping is a visna-maedi virus glycoprotein. A suitable visna-maedi virus protein comprises an amino acid sequence having at least 80%, at least 85%, at least 90%, at least 95%, at least 98%, at least 99%, or 100%, amino acid sequence identity to the following amino acid sequence: QCQA EEVIALVSDP GGFQRVQHVE TVPVTCVTKN FTQWGCQPEG AYPDPELEYR NISREILEEV YKQDWPWNTY HWPLWQMENM RQWMKENEKE YKERTNKTKE DIDDLVAGRI RGRFCVPYPY ALLR-CEEWCW YPESINQETG HAEKIKINCT KAKAVSCTEK MSLAAVQRVY WEKEDEESMK FLNIKACNIS LRCQ-DEGKSP GGCVQGYPIP KGAEIIPEAM KYLRGKKSRY GGIKDKNGEL KLPLSVRVWV RMANLSGWVN GTP-PYWSARI NGSTGINGTR WYGIGTLHHL GCNISSNPER GICNFTGELW IGGDKFPYYY TPSWNCSQNW TGHPVWHVFR YLDMTEHMTS RCI-QRPKRHN ITVGNGTITG NCSVTNWDGC NCTRSGNHLY NSTSGGLLVI ICRQNSTITG IMGTNTNWTT MWNIYQNCSR CNNSSLDRTG SGTLGTVNNL KCSLPHRNES NKWTCKSQRD SYIAGRDFWG KVKAKYSCES NLGGLDSMMH QQMLLQRYQV IRVRAYTYGV VEMPQSYMEA QGENKRSRRN LQRKKR (SEQ ID NO:109).

In some cases, the heterologous glycoprotein used for pseudotyping is a visna-maedi virus glycoprotein. A suitable visna-maedi virus protein comprises an amino acid sequence having at least 80%, at least 85%, at least 90%, at least 95%, at least 98%, at least 99%, or 100%, amino acid sequence identity to the following amino acid sequence: GIGL VIV-LAIMAII AAAGAGLGVA NAVQQSYTRT AVQSLA-NATA AQQEVLEASY AMVQHIAKGI RILEARVARV EALVDRMMVY QELDCWHYQH YCVTSTRSEV ANY-VNWTRFK DNCTWQQWEE EIEQHEGNLS LLL-REAALQV HIAQRDARRI PDAWKAIQEA FNWSS-WFSWL KYIPWIIMGI VGLMCFRILM CVISMCLQAY KQVKQIRYTQ VTVVIEAPVE LEEKQKRNGD GTNGCASLER ERRTSHRSFI QIWRATWWAW KTSPWRHNWR TMPYITLLPI LVIWQWMEEN GWN-GENQHKK KKERVDCQDR EQMPTLENDY VEL (SEQ ID NO:110).

In some cases, the heterologous glycoprotein used for pseudotyping is a severe acute respiratory syndrome-associated coronavirus (SARS-CoV) spike glycoprotein. A suitable SARS-CoV protein comprises an amino acid sequence having at least 80%, at least 85%, at least 90%, at least 95%, at least 98%, at least 99%, or 100%, amino acid sequence identity to the following amino acid sequence: MFIFLL-FLTL TSGSDLDRCT TFDDVQAPNY TQHTSSMRGV YYPDEIFRSD TLYLTQDLFL PFYSNVTGFH TINHTFGNPV IPFKDGIYFA ATEKSNVVRG WVFG-STMNNK SQSVIIINNS TNVVIRACNF ELCDNPFFAV SKPMGTQTHT MIFDNAFNCT FEYISDAFSL DVSEKSGNFK HLREFVFKNK DGFLYVYKGY QPIDVVRDLP SGFNTLKPIF KLPLGINITN FRAILT-AFSP AQDIWGTSAA AYFVGYLKPT TFMLKYDENG TITDAVDCSQ NPLAELKCSV KSFEIDKGIY QTSN-FRVVPS GDVVRFPNIT NLCPFGEVFN ATKFPSVYAW ERKKISNCVA DYSVLYNSTF FSTFKCYGVS ATKLNDLCFS NVYADSFVVK GDDVRQIAPG QTGVIADYNY KLPDDFMGCV LAWNTRNIDA TSTGNYNYKY RYLRHGKLRP FERDISNVPF SPDGKPCTPP ALNCYWPLND YGFYTTTGIG YQPYRVVVLS FELLNAPATV CGPKLSTDLI KNQCVNFNFN GLTGTGVLTP SSKRFQPFQQ FGRDVSDFTD SVRDPKTSEI LDISPCSFGG VSVITPGTNA SSEVAVLYQD VNCTDVSTAI HADQLT-PAWR IYSTGNNVFQ TQAGCLIGAE HVDTSYECDI PIGAGICASY HTVSLLRSTS QKSIVAYTMS LGADS- SIAYS NNTIAIPTNF SISITTEVMP VSMAKTSVDC NMYICGDSTE CANLLLQYGS FCTQLNRALS GIAAEQDRNT REVFAQVKQM YKTPTLKYFG GFNFSQILPD PLKPTKRSFI EDLLFNKVTL ADAGFMKQYG ECLGDINARD LICAQKFNGL TVLP-PLLTDD MIAAYTAALV SGTATAGWTF GAGAALQIPF AMQMAYRFNG IGVTQNVLYE NQKQIANQFN KAI-SQIQESL TTTSTALGKL QDVVNQNAQA LNTLVKQLSS NFGAISSVLN DILSRLDKVE AEVQIDRLIT GRLQSLQTYV TQQLIRAAEI RASAN-LAATK MSECVLGQSK RVDFCGKGYH LMSFPQAAPH GVVFLHVTYV PSQERNFTTA PAICHEGKAY FPREGVFVFN GTSWFITQRN FFSPQIITTD NTFVSGNCDV VIGIINNTVY DPLQPELDSF KEELDKYFKN HTSPDVDLGD ISGI-NASVVN IQKEIDRLNE VAKNLNESLI DLQELGKYEQ YIKWPWYVWL GFIAGLIAIV MVTILLCCMT SCCSCLKGAC SCGSCCKFDE DDSEPVLKGV KLHYT (SEQ ID NO:111; GenBank Accession No: ABA02260). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is a SARS-CoV S2 glycoprotein. A suitable SARS-CoV protein comprises an amino acid sequence having at least 80%, at least 85%, at least 90%, at least 95%, at least 98%, at least 99%, or 100%, amino acid sequence identity to the following amino acid sequence: CDI PIGAG-ICASY HTVSLLRSTS QKSIVAYTMS LGADSSIAYS NNTIAIPTNF SISITTEVMP VSMAKTSVDC NMYICGDSTE CANLLLQYGS FCTQLNRALS GIAAEQDRNT REVFAQVKQM YKTPTLKYFG GFNFSQILPD PLKPTKRSFI EDLLFNKVTL ADAGFMKQYG ECLGDINARD LICAQKFNGL TVLP-PLLTDD MIAAYTAALV SGTATAGWTF GAGAALQIPF AMQMAYRFNG IGVTQNVLYE NQKQIANQFN KAI-SQIQESL TTTSTALGKL QDVVNQNAQA LNTLVKQLSS NFGAISSVLN DILSRLDKVE AEVQIDRLIT GRLQSLQTYV TQQLIRAAEI RASAN-LAATK MSECVLGQSK RVDFCGKGYH LMSFPQAAPH GVVFLHVTYV PSQERNFTTA PAICHEGKAY FPREGVFVFN GTSWFITQRN FFSPQIITTD NTFVSGNCDV VIGIINNTVY DPLQPELDSF KEELDKYFKN HTSPDVDLGD ISGI-NASVVN IQKEIDRLNE VAKNLNESLI DLQELGKYEQ YIKWPWYVWL GFIAGLIVIV MVTILLCCMT SCCSCLKGAC SCGSCCKFDE DDSEPVLKGV KL (SEQ ID NO:112; GenBank Accession No: ABD73002). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is a SARS-CoV spike receptor binding domain glycoprotein. A suitable SARS-CoV protein comprises an amino acid sequence having at least 80%, at least 85%, at least 90%, at least 95%, at least 98%, at least 99%, or 100%, amino acid sequence identity to the following amino acid sequence: PNIT NLCPFGEVFN ATKFPSVYAW ERKKISNCVA DYSVLYNSTF FSTFKCYGVS ATKLNDLCFS NVYADSFVVK GDDVRQIAPG QTGVIADYNY KLPDDFMGCV LAWN- TRNIDA TSTGNYNYKY RYLRHGKLRP FERDISNVPF SPDGKPCTPP ALNCYWPLND YGFYTTTGIG YQPYRVVVLS FELLNAPATV CGPKLSTDLI KNQCVNFNFN GLTGTGVLTP SSKRFQPFQQ FGRDVSDFTD SVRDPKTSE (SEQ ID NO:113; GenBank Accession No: ABD73002). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is a respiratory syncytial virus (RSV) glycoprotein G. A suitable RSV protein comprises an amino acid sequence having at least 80%, at least 85%, at least 90%, at least 95%, at least 98%, at least 99%, or 100%, amino acid sequence identity to the following amino acid sequence: MSKNKDQRTA KTLERTWDTL NHLLFISSCL YKLNLKSVAQ ITLSILAMII STSLIIAAII FIASANHKVT PTTAIIQDAT SQIKNTTPTY LTQNPQL-GIS PSNPSEITSQ ITTILASTTP GVKSTLQSTT VKT-KNTTTTQ TQPSKPTTKQRQNKPPSKPN NDFHFE-VFNF VPCSICSNNP TCWAICKRIP NKKPGKKTTTKPTKKPTLKT TKKDPKPQTT KSKEV-PTTKP TEEPTINTTK TNIITTLLTS NTTGNPELTS QMETFHSTSS EGNPSPSQVS TTSEYPSQPS SPPNT-PRQ (SEQ ID NO:114; UniProtKB: P03423-1). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is an RSV glycoprotein F. A suitable RSV protein comprises an amino acid sequence having at least 80%, at least 85%, at least 90%, at least 95%, at least 98%, at least 99%, or 100%, amino acid sequence identity to the following amino acid sequence: MELLILKANA ITTILT-AVTF CFASGQNITE EFYQSTCSAV SKGYLSALRT GWYTSVITIE LSNIKENKCN GTDAKVKLIK QELDKYKNAV TELQLLMQST PPTNNRARRE LPRFMNYTLN NAKKTNVTLS KKRKRRFLGF LLGVGSAIAS GVAVSKVLHL EGEVNKIKSA LLSTNKAVVS LSNGVSVLTS KVLDLKNYID KQLLPIVNKQ SCSISNIETV IEFQQKNNRL LEITRE-FSVN AGVTTPVSTY MLTNSELLSL INDMPITNDQ KKLMSNNVQI VRQQSYSIMS IIKEEVLAYV VQLPLYGVID TPCWKLHTSP LCTTNTKEGS NICL-TRTDRG WYCDNAGSVS FFPQAETCKV QSNRVFCDTM NSLTLPSEIN LCNVDIFNPK YDC-KIMTSKT DVSSSVITSL GAIVSCYGKT KCTASNKNRG IIKTFSNGCD YVSNKGMDTV SVGNT-LYYVN KQEGKSLYVK GEPIINFYDP LVFPSDEFDA SISQVNEKIN QSLAFIRKSD ELLHNVNAGK STT-NIMITTI IIVIIVILLS LIAVGLLLYC KARSTPVTLS KDQLSGINNI AFSN (SEQ ID NO:115; GenBank Accession No: P03420). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is an RSV glycoprotein. A suitable RSV protein comprises an amino acid sequence having at least 80%, at least 85%, at least 90%, at least 95%, at least 98%, at least 99%, or 100%, amino acid sequence identity to the following amino acid sequence: QNITE EFYQSTCSAV SKGYLSALRT GWYTSVITIE LSNIKENKCN GTDAKVKLIK QELDKYKNAV TELQLLMQST PPTNNRARRE LPRFMNYTLN NAKKTNVTLS KKRKRRFLGF LLGVGSAIAS GVAVSKVLHL EGEVNKIKSA LLSTNKAVVS LSNGVSVLTS KVLD-LKNYID KQLLPIVNKQ SCSISNIETV IEFQQKNNRL LEITREFSVN AGVTTPVSTY MLTNSELLSL INDMPITNDQ KKLMSNNVQI VRQQSYSIMS IIKEEV-LAYV VQLPLYGVID TPCWKLHTSP LCTTNTKEGS NICLTRTDRG WYCDNAGSVS FFPQAETCKV QSNRVFCDTM NSLTLPSEIN LCNVDIFNPK YDC-KIMTSKT DVSSSVITSL GAIVSCYGKT KCTASNKNRG IIKTFSNGCD YVSNKGMDTV SVGNT-LYYVN KQEGKSLYVK GEPIINFYDP LVFPSDEFDA SISQVNEKIN QSLAFIRKSD ELLHNVNAGK STT-NIMITTI IIVIIVILLS LIAVGLLLYC KARSTPVTLS KDQLSGINNI AFSN (SEQ ID NO:116). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is an RSV F0 glycoprotein. A suitable RSV protein comprises an amino acid sequence having at least 80%, at least 85%, at least 90%, at least 95%, at least 98%, at least 99%, or 100%, amino acid sequence identity to the following amino acid sequence: QNITE EFYQSTCSAV SKGYLSALRT GWYTSVITIE LSNIKENKCN GTDAKVKLIK QELDKYKNAV TELQLLMQST PPTNNRARRE LPRFMNYTLN NAKKTNVTLS KKRKRRFLGF LLGVGSAIAS GVAVSKVLHL EGEVNKIKSA LLSTNKAVVS LSNGVSVLTS KVLD-LKNYID KQLLPIVNKQ SCSISNIETV IEFQQKNNRL LEITREFSVN AGVTTPVSTY MLTNSELLSL INDMPITNDQ KKLMSNNVQI VRQQSYSIMS IIKEEV-LAYV VQLPLYGVID TPCWKLHTSP LCTTNTKEGS NICLTRTDRG WYCDNAGSVS FFPQAETCKV QSNRVFCDTM NSLTLPSEIN LCNVDIFNPK YDC-KIMTSKT DVSSSVITSL GAIVSCYGKT KCTASNKNRG IIKTFSNGCD YVSNKGMDTV SVGNT-LYYVN KQEGKSLYVK GEPIINFYDP LVFPSDEFDA SISQVNEKIN QSLAFIRKSD ELLHNVNAGK STT-NIMITTI IIVIIVILLS LIAVGLLLYC KARSTPVTLS KDQLSGINNI AFSN (SEQ ID NO:116; GenBank Accession No: P03420). Such a glycoprotein may be useful for targeting a VLP of the present disclosure to cells of respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is an RSV F2 glycoprotein. A suitable RSV protein comprises an amino acid sequence having at least 80%, at least 85%, at least 90%, at least 95%, at least 98%, at least 99%, or 100%, amino acid sequence identity to the following amino acid sequence: QNITE EFYQSTCSAV SKGYLSALRT GWYTSVITIE LSNIKENKCN GTDAKVKLIK QELDKYKNAV TELQLLMQST PPTNNRARRE LPRFMNYTLN NAKKTNVTLS KKRKRR (SEQ ID NO:117; GenBank Accession No: P03420). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is an RSV F1 glycoprotein. A suitable RSV protein comprises an amino acid sequence having at least 80%, at least 85%, at least 90%, at least 95%, at least 98%, at least 99%, or 100%, amino acid sequence identity to the following amino acid sequence: FLGF LLGVGSAIAS GVAVSKVLHL EGEVNKIKSA LLSTNKAVVS LSNGVSVLTS KVLDLKNYID KQLLPIVNKQ SCSISNI-ETV IEFQQKNNRL LEITREFSVN AGVTTPVSTY MLTNSELLSL INDMPITNDQ KKLMSNNVQI VRQQ-SYSIMS IIKEEVLAYV VQLPLYGVID TPCWKLHTSP LCTTNTKEGS NICLTRTDRG WYCDNAGSVS FFPQAETCKV QSNRVFCDTM NSLTLPSEIN LCNVDIFNPK YDCKIMTSKT DVSSSVITSL GAIVSCYGKT KCTASNKNRG IIKTFSNGCD YVSNKGMDTV SVGNTLYYVN KQEGKSLYVK GEPI-INFYDP LVFPSDEFDA SISQVNEKIN QSLAFIRKSD ELLHNVNAGK STTNIMITTI IIVIIVILLS LIAVGLL-LYC KARSTPVTLS KDQLSGINNI AFSN (SEQ ID NO:118; GenBank Accession No: P03420). Such a glyco-protein may be useful for targeting a VLP of the present disclosure to cells of the lung/respiratory tract.

In some cases, the heterologous glycoprotein used for pseudotyping is an RSV glycoprotein. A suitable RSV protein comprises an amino acid sequence having at least 80%, at least 85%, at least 90%, at least 95%, at least 98%, at least 99%, or 100%, amino acid sequence identity to the following amino acid sequence: QNITE EFYQSTCSAV SKGYLSALRT GWYTSVITIE LSNIKENKCN GTDAKVKLIK QELDKYKNAV TELQLLMQST PPTNNRARRE LPRFMNYTLN NAKKTNVTLS KKRKRRFLGF LLGVGSAIAS GVAVSKVLHL EGEVNKIKSA LLSTNKAVVS LSNGVSVLTS KVLD-LKNYID KQLLPIVNKQ SCSISNIETV IEFQQKNNRL LEITREFSVN AGVTTPVSTY MLTNSELLSL INDMPITNDQ KKLMSNNVQI VRQQSYSIMS IIKEEV-LAYV VQLPLYGVID TPCWKLHTSP LCTTNTKEGS NICLTRTDRG WYCDNAGSVS FFPQAETCKV QSNRVFCDTM NSLTLPSEIN LCNVDIFNPK YDC-KIMTSKT DVSSSVITSL GAIVSCYGKT KCTASNKNRG IIKTFSNGCD YVSNKGMDTV SVGNT-LYYVN KQEGKSLYVK GEPIINFYDP LVFPSDEFDA SISQVNEKIN QSLAFIRKSD ELLHNVNAGK STT-NIMITTI IIVIIVILLS LIAVGLLLYC KARSTPVTLS KDQLSGINNI AFSN (SEQ ID NO:116). Such a glycopro-tein may be useful for targeting a VLP of the present disclosure to cells of the lung/respiratory tract.

In some cases, the heterologous glycoprotein used for pseudotyping is a human parainfluenza virus type 3 hemag-glutinin-neuraminidase glycoprotein. A suitable human parainfluenza virus type 3 protein comprises an amino acid sequence having at least 80%, at least 85%, at least 90%, at least 95%, at least 98%, at least 99%, or 100%, amino acid sequence identity to the following amino acid sequence: MEYWKHTNHG KDAGNELETS MATHGNKLTN KITYILWTII LVLLSIVFII VLINSIKSEK AHESLLQNIN NEFMEITEKI QMASDNTNDL IQSGVNTRLL TIQSHVQNYI PISLTQQMSD LRKFISEITI RNDNQEVLPQ RITHDVGIKP LNPDDFWRCT SGLPSLMKTP KIRLMPGPGL LAMPTTVDGC IRTPSLVIND LIYAYTSNLI TRGCQDIGKS YQVLQI-GIIT VNSDLVPDLN PRISHTFNIN DNRKSCSLAL LNTDVYQLCS TPKVDERSDY ASPGIEDIVL DIVNY-DGSIS TTRFKNNNIS FDQPYAALYP SVGPGIYYKG KIIFLGYGGL EHPINENVIC NTTGCPGKTQ RDCNQASHSP WFSDRRMVNS IIVVDKGLNS IPKLKVWTIS MRQNYWGSEG RLLLLGNKIY IYTRST- SWHS KLQLGIIDIT DYSDIRIKWT WHNVLSRPGN NECPWGHSCP DGCITGVYTD AYPLNPTGSI VSSVILDSQK SRVNPVITYS TATERVNELA ILNRTL- SAGY TTTSCITHYN KGYCFHIVEI NHKSLNTLQP MLFKTEIPKS CS (SEQ ID NO:119; GenBank Accession No: AAP35240). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is a human parainfluenza virus type 3 glycoprotein F0. A suitable human parainfluenza virus type 3 protein comprises an amino acid sequence having at least 80%, at least 85%, at least 90%, at least 95%, at least 98%, at least 99%, or 100%, amino acid sequence identity to the following amino acid sequence: MPISILLIIT TMI- MASHCQI DITKLQHVGV LVNSPKGMKI SQN- FETRYLI LSLIPKIDDS NSCGDQQIKQ YKRLLDRLII PLYDGLRLQK DVIVANQESN ENTDPRTERF FGGVIG- TIAL GVATSAQITA AVALVEAKQA RSDIEKLKEA IRDTNKAVQS VQSSVGNLIV AIKSVQDYVN KEIVP- SIARL GCEAAGLQLG IALTQHYSEL TNIFGDNIGS LQEKGIKLQG IASLYRTNIT EIFTTSTVDK YDIYDLL- FTE SIKVRVIDVD LNDYSITLQV RLPLLTRLLN TQIYKVDSIS YNIQNREWYI PLPSHIMTKG AFLGGA- DVKE CIEAFSSYIC PSDPGFVLNH EMESCLSGNI SQCPRTTVTS DIVPRYAFVN GGVVANCITT TCTCN- GIGNR INQPPDQGVK IITHKECNTI GINGMLFNTN KEGTLAFYTP ADITLNNSVA LDPIDISIEL NKAKSDLEES KEWIRRSNQK LDSIGSWHQS STTIIV- ILIM MIILFIINIT IITIAIKYYR IQKRNRVDQN DKPYVLTNK (SEQ ID NO:120; GenBank Accession No: AXA52708). Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is a Hepatitis C virus (HCV) E1 glycoprotein. A suitable HCV protein comprises an amino acid sequence having at least 80%, at least 85%, at least 90%, at least 95%, at least 98%, at least 99%, or 100%, amino acid sequence identity to the following amino acid sequence: YQVRN- SSGLY HVTNDCPNSS IVYEAADAIL HTPGCVPCVR EGNASRCWVA VTPTVATRDG KLPTTQLRRH IDLL- VGSATL CSALYVGDLC GSVFLVGQLF TFSPRRHWTT QDCNCSIYPG HITGHRMAWD MMMNWSPTAA LVVAQLLRIP QAIMDMIAGA HWGVLAGIAY FSMVGNWAKV LVVLLLFAGV DA (SEQ ID NO:121; GenBank Accession No: NP_751920). Such a glycoprotein may be useful for targeting a VLP of the present disclosure to a liver cell.

In some cases, the heterologous glycoprotein used for pseudotyping is an HCV E2 glycoprotein. A suitable HCV protein comprises an amino acid sequence having at least 80%, at least 85%, at least 90%, at least 95%, at least 98%, at least 99%, or 100%, amino acid sequence identity to the following amino acid sequence: ETHVTGGSAG RTTA- GLVGLL TPGAKQNIQL INTNGSWHIN STALNCNESL NTGWLAGLFY QHKFNSSGCP ERLASCRRLT DFAQGWGPIS YANGSGLDER PYCWHYPPRP CGIVPAKSVC GPVYCFTPSP VVVGTTDRSG APTYSWGAND TDVFVLNNTR PPLGNWFGCT WMN- STGFTKV CGAPPCVIGG VGNNTLLCPT DCFRKHPEAT YSRCGSGPWI TPRCMVDYPY RLWHY- PCTIN YTIFKVRMYV GGVEHRLEAA CNWTRGERCD LEDRDRSELS PLLLSTTQWQ VLPCSFTTLP ALSTG- LIHLH QNIVDVQYLY GVGSSIASWA IKWEYVVLLF LLLADARVCS CLWMMLLISQ AEA (SEQ ID NO:122; GenBank Accession No: NP_751921). Such a glycoprotein may be useful for targeting a VLP of the present disclosure to a liver cell.

In some cases, the heterologous glycoprotein used for pseudotyping is a fowl plague virus glycoprotein. A suitable fowl plague virus protein comprises an amino acid sequence having at least 80%, at least 85%, at least 90%, at least 95%, at least 98%, at least 99%, or 100%, amino acid sequence identity to the following amino acid sequence: MNTQIL- VFAL VAVIPTNADK ICLGHHAVSN GTKVNTLTER GVEVVNATET VERTNIPKIC SKGKRTTDLG QCGLLGTITG PPQCDQFLEF SADLIIERRE GNDVCY- PGKF VNEEALRQIL RGSGGIDKET MGFTYSGIRT NGTTSACRRS GSSFYAEMEW LLSNTDNASF PQMTKSYKNT RRESALIVWG IHHSGSTTEQ TKLYGSGNKL ITVGSSKYHQ SFVPSPGTRP QINGQS- GRID FHWLILDPND TVTFSFNGAF IAPNRASFLR GKSMGIQSDV QVDANCEGEC YHSGGTITSR LPFQNINSRA VGKCPRYVKQ ESLLLATGMK NVPEPSKKRE KRGLFGAIAG FIENGWEGLV DGWYGFRHQN AQGEGTAADY KSTQSAIDQI TGKLNRLIEK TNQQFELIDN EFTEVEKQIG NLINWTKDFI TEVWSYNAEL LVAMENQHTI DLAD- SEMNKL YERVRKQLRE NAEEDGTGCF EIFHKCDDDC MASIRNNTYD HSKYREEAMQ NRIQIDPVKL SSGYKDVILW FSFGASCFLL LAI- AVGLVFI CVKNGNMRCT ICI (SEQ ID NO:123; GenBank Accession No: 0601245A).

In some cases, the heterologous glycoprotein used for pseudotyping is an *Autographa californica* nuclear polyhedrosis virus (AcMNPV) major envelope glycoprotein gp64. A suitable AcMNPV protein comprises an amino acid sequence having at least 80%, at least 85%, at least 90%, at least 95%, at least 98%, at least 99%, or 100%, amino acid sequence identity to the following amino acid sequence: MVSAIVLYVL LAAAAHSAFA AEHCNAQMKT GPYKIKNLDI TPPKETLQKD VEITIVETDY NENVII- GYKG YYQAYAYNGG SLDPNTRVEE TMKTLNVGKE DLLMWSIRQQ CEVGEELIDR WGSDSDDCFR DNE- GRGQWVK GKELVKRQNN NHFAHHTCNK SWRC- GISTSK MYSRLECQDD TDECQVYILD AEGNPINVTV DTVLHRDGVS MILKQKSTFT TRQIKAACLL IKDDKNNPES VTREHCLIDN DIYDLSKNTW NCKFNRCIKR KVEHRVKKRP PTWRHNVRAK YTEGDTATKG DLMHIQEELM YENDLLKMNI ELMHAHINKL NNMLHDLIVS VAKVDERLIG NLMNNSVSST FLSDDTFLLM PCTNPPAHTS NCYNN- SIYKE GRWVANTDSS QCIDFSNYKE LAIDDDVEFW IPTIGNTTYH DSWKDASGWS FIAQQKSNLI TTMENTKFGG VGTSLSDITS MAEGELAAKL TSFMFGHVVN FVIILIVILF LYCMIRNRNR QY (SEQ ID NO:217; UniProt Accession No: P17501-1).

In some cases, the heterologous glycoprotein used for pseudotyping is an AcMNPV glycoprotein. A suitable AcMNPV protein comprises an amino acid sequence having at least 80%, at least 85%, at least 90%, at least 95%, at least 98%, at least 99%, or 100%, amino acid sequence identity to the following amino acid sequence: AEHCNAQMKT GPYKIKNLDI TPPKETLQKD VEITIVETDY NENVII- GYKG YYQAYAYNGG SLDPNTRVEE TMKTLNVGKE DLLMWSIRQQ CEVGEELIDR WGSDSDDCFR DNE- GRGQWVK GKELVKRQNN NHFAHHTCNK SWRC- GISTSK MYSRLECQDD TDECQVYILD AEGNPINVTV DTVLHRDGVS MILKQKSTFT TRQIKAACLL IKDDKNNPES VTREHCLIDN DIYDLSKNTW NCKFNRCIKR KVEHRVKKRP PTWRHNVRAK YTEGDTATKG DLMHIQEELM YENDLLKMNI ELMHAHINKL NNMLHDLIVS VAKVDERLIG NLMNNSVSST FLSDDTFLLM PCTNPPAHTS NCYNN- SIYKE GRWVANTDSS QCIDFSNYKE LAIDDDVEFW IPTIGNTTYH DSWKDASGWS FIAQQKSNLI TTMENTKFGG VGTSLSDITS MAEGELAAKL TSFMFGHVVN FVIILIVILF LYCMIRNRNR QY (SEQ ID NO:124).

In some cases, the heterologous glycoprotein used for pseudotyping is a measles virus hemagglutinin (H) polypeptide. See, e.g., Levy et al. (2017) Blood Adv. 1:2088. A suitable measles virus H polypeptide comprises an amino acid sequence having at least 80%, at least 85%, at least 90%, at least 95%, at least 98%, at least 99%, or 100%, amino acid sequence identity to the following amino acid sequence: MSPQRDRINA FYKDNPHPKG SRIVINREHL MIDRPYVLLA VLFVMFLSLI GLLAIAGIRL HRAAIY- TAEI HKSLSTNLDV TNSIEHQVKD VLTPLFKIIG DEVGLRTPQR FTDLVKFISD KIKFLNPDRE YDFRDLTWCI NPPERIKLDY DQYCADVAAE ELM- NALVNST LLETRTTNQF LAVSKGNCSG PTTIR- GQFSN MSLSLLDLYL SRGYNVSSIV TMTSQGMYGG TYLVEKPNLS SKGSELSQLS MYRVFEVGVI RNPGL- GAPVF HMTNYFEQPV SNDLSNCMVA LGELK- LAALC HGGDSITIPY QGSGKGVSFQ LVKLGVWKSP TDMQSWVPLS TDDPVIDRLY LSSHRGVIAD NQAK- WAVPTT RTDDKLRMET CFQQACKGKI QALCEN- PEWA PLKDNRIPSY GVLSVDLSLT VELKIKIASG FGPLITHGSG MDLYKSNHNN VYWLTIPPMK NLAL- GVINTL EWIPRFKVSP YLFTVPIKEA GEDCHAPTYL PAEVDGDVKL SSNLVILPGQ DLQYVLATYD TSRVE- HAVVY YVYSPSRSFS YFYPFRLPIK GIPIELQVEC FTWDQKLWCR HFCVLADSES GGHITHSGMV GMGVSCTVTR EDGTNSR (SEQ ID NO:125). Such a glycoprotein may be useful for targeting a VLP of the present disclosure to T cells, B cells, monocytes, macro- phages, dendritic cells, and hematopoietic stem cells (e.g., CD34$^+$ cells).

In some cases, the heterologous glycoprotein used for pseudotyping is a measles virus fusion (F) polypeptide. A suitable measles virus F polypeptide comprises an amino acid sequence having at least 80%, at least 85%, at least 90%, at least 95%, at least 98%, at least 99%, or 100%, amino acid sequence identity to the following amino acid sequence: MSIMGLKVNV SAIFMAVLLT LQTPTGQIHW GNLSKIGVVG IGSASYKVMT RSSHQSLVIK LMPNITLLNN CTRVEIAEYR RLLRTVLEPI RDALNAMTQN IRPVQSVASS RRHKRF- AGVV LAGAALGVAT AAQITAGIAL HQSMLNSQAI DNLRASLETT NQAIETIRQA GQEMILAVQG VQDYINNELI PSMNQLSCDL IGQKLGLKLL RYYTEILSLF GPSLRDPISA EISIQALSYA LGGDIN- KVLE KLGYSGGDLL GILESGGIKA RITHVDTESY FIVLSIAYPT LSEIKGVIVH RLEGVSYNIG SQEWYTTVPK YVATQGYLIS NFDESSCTFM PEGTVCSQNA LYPMSPLLQE CLRGYTKSCA RTLVSGSFGN RFILSQGNLI ANCASILCKC YTTGTI- INQD PDKILTYIAA DHCPVVEVNG VTIQVGSRRY PDAVYLHRID LGPPISLERL DVGTNLGNAI AKLEDAKELL ESSDQILRSM KGLSSTSIVY ILI- AVCLGGL IGIPALICCC RGRCNKKGEQ VGMSRPGLKP DLTGTSKSYV RSL (SEQ ID NO:126). Such a glycoprotein may be useful for targeting a VLP of the present disclosure to T cells, B cells, monocytes, macro- phages, dendritic cells, and hematopoietic stem cells (e.g., CD34+ cells). In some cases, both measles virus hemagglu- tinin and measles virus F protein are used to pseudotype a VLP of the present disclosure.

In some cases, both measles virus L and measles virus H polypeptides are used to pseudotype a VLP of the present disclosure.

Polypeptides that Bind to a Target Cell or Target Cell Type

In some cases, a VLP of the present disclosure comprises a polypeptide that provides for binding to a target cell or target cell type. Such polypeptides include antibodies (e.g., scFv; nanobody; and the like) and antibody mimetics (e.g., DARPins).

In some cases, the antibody targets a cancer antigen, thereby targeting the VLP to a cancerous cell that displays the cancer antigen on its cell surface. In some cases, the antibody provides for selective binding to an organ such as kidney, liver, bone, pancreas, brain, lung, heart, and the like. In some cases, the antibody provides for selective binding to a particular cell type. For example, in some cases, the antibody provides for selective binding to a cell such as a skeletal muscle cell, a cardiomyocyte, an adipocyte, an epithelial cell, an endothelial cell, a macrophage, a beta islet cell, or an immune cell (e.g., a T cell, a B cell, a monocyte, a natural killer cell, a dendritic cell, etc.). In some cases, the antibody provides for selective binding to a diseased cell, relative to a non-diseased cell of the same cell type.

Suitable antigens bound by an antibody present in a VLP of the present disclosure include, e.g., CD3, epidermal growth factor receptor (EGFR), CA-125 (highly expressed on epithelial ovarian cancer cells), CD80, CD86, glycopro- tein IIb/IIIa receptor, CD51, TNF-α, epithelial adhesion molecule EpcAM (CD326), vascular endothelial growth factor receptor-2 (VEGFR-2), CD52, mesothelin, activin receptor-like kinase 1 (ALK-1), phosphatidyl serine, CD19, vascular endothelial growth factor A (VEGF-A), IL-6 recep- tor, CD11a, CD25, CD2, CD3 receptor, and the like.

Suitable antigens bound by an antibody present in a VLP of the present disclosure include, e.g., carbonic anhydrase IX, alpha-fetoprotein (AFP), α-actinin-4, A3, ART-4, B7, Ba 733, BAGE, BrE3-antigen, CA125, CAMEL, CAP-1, CASP-8/m, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/ m, CDKN2A, CTLA-4, CXCR4, CXCR7, CXCL12, HIF- 1α, colon-specific antigen-p (CSAp), CEACAM5, CEACAM6, c-Met, DAM, epidermal growth factor receptor (EGFR), EGFRvIII, EGP-1 (TROP-2), EGP-2, ELF2-M, Ep-CAM, fibroblast growth factor (FGF), Flt-1, Flt-3, folate receptor, G250 antigen, GAGE, gp100, GRO-13, HLA-DR, HM1.24, human chorionic gonadotropin (HCG) and its subunits, HER2/neu, histone H2B, histone H3, histone H4, HMGB-1, hypoxia inducible factor (HIF-1), HSP70-2M, HST-2, insulin-like growth factor-1 receptor (IGF-1R), IFN- γ, IFN-α, IFN-β, INF-λ, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), KC4-antigen, KS-1-antigen, KS1-4, Le-Y, LDR/FUT, mac- rophage migration inhibitory factor (MIF), MAGE, MAGE- 3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PAM4 antigen, PD-1, PD-L1, PD-1 receptor, placental growth factor, p53, PLAGL2, prostatic acid phosphatase, PSA, PRAME, PSMA, P1GF, ILGF, ILGF-1R, IL-6, IL-25, RS5, RANTES, T101, SAGE, 5100, survivin, survivin-2B, TAC, TAG-72, tenascin, TRAIL receptors, TNF-α, Tn antigen, tumor necrosis antigens, VEGFR, ED-B fibronectin, WT-1, 17-1A-antigen, complement factors C3, C3a, C3b, C5a, C5; and the like.

Examples of suitable antibodies include, e.g., abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), trastuzumab (anti-ErbB2), lambrolizumab (anti-PD-1 receptor), nivolumab (anti-PD-1 receptor), ipilimumab (anti-CTLA-4), abagovomab (anti-CA-125), adecatumumab (anti-EpCAM), atlizumab (anti-IL-6 receptor), benralizumab (anti-CD125), obinutuzumab (GA101, anti-CD20), CC49 (anti-TAG-72), tocilizumab (anti-IL-6 receptor), basiliximab (anti-CD25), daclizumab (anti-CD25), efalizumab (anti-CD11a), GA101 (anti-CD20; Glycart Roche), muromonab-CD3 (anti-CD3 receptor), natalizumab (anti-α-4 integrin), and the like.

Antibody Mimetics

In some cases, a VLP of the present disclosure comprises an antibody mimetic. Non-limiting examples of antibody mimetics include peptide aptamers, affimers, affilins, affibodies, affitins, alphabodies, anticalins, avimers, DARPins, fynomers, Kunitz domain peptides, nanoCLAMPs, affinity reagents, and scaffold proteins.

Compositions Comprising a VLP

The present disclosure provides compositions, including pharmaceutical compositions, comprising a VLP of the present disclosure. The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19$^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

A composition of the present disclosure can include: a) a VLP of the present disclosure; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl) amino-tris(hydroxymethyl)methane (BIS-Tris), N-(2-hydroxyethyl)piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris(hydroxymethyl)-aminomethane (Tris), etc.). Suitable salts include, e.g., NaCl, MgCl$_2$, KCl, MgSO$_4$, etc.

In some cases, the composition is sterile. In some cases, the composition is suitable for administration to a human subject, e.g., where the composition is sterile and is free of detectable pyrogens and/or other toxins.

In some cases, a composition of the present disclosure comprises: i) a VLP that does not include a donor template nucleic acid; and ii) a donor template nucleic acid (provided separately from the VLP).

Systems

The present disclosure provides a system that can be used to generate a VLP of the present disclosure. A system of the present disclosure comprises: a) a first nucleic acid comprising a nucleotide sequence encoding a fusion polypeptide comprising: i) a lentiviral gag polyprotein comprising a matrix (MA) polypeptide, a capsid (CA) polypeptide, and a nucleocapsid (NC) polypeptide; and ii) a CRISPR-Cas effector polypeptide; wherein the fusion polypeptide comprises proteolytically cleavable linker between the gag polyprotein and the CRISPR-Cas effector polypeptide; b) a second nucleic acid comprising a nucleotide sequence encoding a therapeutic polypeptide, wherein the second nucleic acid is a recombinant lentiviral nucleic acid; c) a third nucleic acid comprising a nucleotide sequence encoding a pseudotyping viral envelope protein and/or a polypeptide that provides for binding to a target cell; and d) a fourth nucleic acid comprising a nucleotide sequence encoding a lentiviral pol polyprotein comprising a reverse transcriptase and an integrase. The system also comprises a nucleic acid comprising a nucleotide sequence encoding a CRISPR-Cas guide RNA. The CRISPR-Cas guide RNA-encoding nucleic acid is in some cases a separate (fifth) nucleic acid. In other cases, the CRISPR-Cas guide RNA-encoding nucleic acid part of the second nucleic acid; in other words, in some cases, the second nucleic acid comprises: i) a nucleotide sequence encoding a therapeutic polypeptide; and ii) a nucleotide sequence encoding the CRISPR-Cas guide RNA. In some cases, the fourth nucleic acid comprise a nucleotide sequence encoding lentivirus Gag and Pol.

In some cases, a system of the present disclosure comprises: a) a first nucleic acid comprising a nucleotide sequence encoding a fusion polypeptide comprising: i) a lentiviral gag polyprotein comprising a MA polypeptide, a CA polypeptide, and an NC polypeptide; and ii) a CRISPR-Cas effector polypeptide; wherein the fusion polypeptide comprises proteolytically cleavable linker between the gag polyprotein and the CRISPR-Cas effector polypeptide; b) a second nucleic acid comprising: i) a first nucleotide sequence encoding a therapeutic polypeptide; and ii) a second nucleotide sequence encoding a CRISPR-Cas guide RNA, wherein the second nucleic acid is a recombinant lentiviral nucleic acid; c) a third nucleic acid comprising a nucleotide sequence encoding a pseudotyping viral envelope protein and/or a polypeptide that provides for binding to a target cell; and d) a fourth nucleic acid comprising a nucleotide sequence encoding a lentiviral pol polyprotein comprising a reverse transcriptase and an integrase. In some cases, the fourth nucleic acid also comprises a nucleotide sequence encoding the lentiviral gag polyprotein.

In some cases, a system of the present disclosure comprises: a) a first nucleic acid comprising a nucleotide sequence encoding a fusion polypeptide comprising: i) a lentiviral gag polyprotein comprising a MA polypeptide, a CA polypeptide, and an NC polypeptide; and ii) a CRISPR-Cas effector polypeptide, wherein the fusion polypeptide comprises proteolytically cleavable linker between the gag polyprotein and the CRISPR-Cas effector polypeptide; b) a second nucleic acid comprising a nucleotide sequence encoding a therapeutic polypeptide; c) a third nucleic acid comprising a nucleotide sequence encoding a pseudotyping viral envelope protein and/or a polypeptide that provides for binding to a target cell; d) a fourth nucleic acid comprising a nucleotide sequence encoding a lentiviral pol polyprotein comprising a reverse transcriptase and an integrase; and e) a fifth nucleic acid comprising a nucleotide sequence encoding a CRISPR-Cas guide RNA. In some cases, the fourth nucleic acid also comprises a nucleotide sequence encoding the lentiviral gag polyprotein.

As noted above, in some cases, the fourth nucleic acid also comprises a nucleotide sequence encoding the lentiviral gag polyprotein; in other words, in some cases, the fourth nucleic acid comprises nucleotide sequences encoding lentiviral Gag and Pol polyproteins. Thus, e.g., in some cases, the first nucleic acid comprises a nucleotide sequence encoding a Gag-CRISPR-Cas fusion polypeptide, wherein the fusion polypeptide comprises proteolytically cleavable linker between the gag polyprotein and the CRISPR-Cas effector polypeptide; and the fourth nucleic acid comprises nucleotide sequences encoding lentiviral Gag and Pol polyproteins. In some cases, the fourth nucleic acid and the first nucleic acid are present in the system in a ratio of from 1.5:1 to 3:1. In some cases, the fourth nucleic acid and the first nucleic acid are present in the system in a ratio of about 2:1. In some cases, a system of the present disclosure comprises: i) about 3 μg of the first nucleic acid; and ii) about 6-7 μg of the fourth nucleic acid.

In some cases, a system of the present disclosure comprises: i) about 3 μg of a first nucleic acid comprising a nucleotide sequence encoding a Gag-CRISPR-Cas fusion polypeptide, wherein the fusion polypeptide comprises proteolytically cleavable linker between the gag polyprotein and the CRISPR-Cas effector polypeptide; about 6 or 7 μg of a fourth nucleic acid comprising nucleotide sequences encoding lentiviral Gag and Pol polyproteins; iii) about 2-3 μg of a second nucleic acid comprising a nucleotide sequence encoding a therapeutic protein; and iv) about 7-8 μg of a fifth nucleic acid comprising a nucleotide sequence encoding a CRISPR-Cas guide RNA.

In some cases, retroviral (e.g. lentiviral) Gag polypeptides include CA (p24), MA (p17) and NC (p'7) polypeptides. In some cases, retroviral Gag polypeptides include CA, MA, and NC polypeptides, and in addition one or more of p1, p2, and p6 polypeptides. In some cases, retroviral Gag polypeptides include CA, MA, NC, and p6 polypeptides. In some cases, retroviral Gag polypeptides include CA, MA, NC, p1, p2, and p6 polypeptides. See, e.g., Muriaux and Darlix (2010) RNA Biol. 7:744.

As noted above, the first nucleic acid comprises a nucleotide sequence encoding a fusion polypeptide comprising: i) a lentiviral gag polyprotein comprising a MA polypeptide, a CA polypeptide, and an NC polypeptide; and ii) a CRISPR-Cas effector polypeptide, wherein the fusion polypeptide comprises proteolytically cleavable linker between the gag polyprotein and the CRISPR-Cas effector polypeptide. One of the nucleic acids in the system comprises a nucleotide sequence encoding a protease that cleaves the proteolytically cleavable linker. In some cases, the second nucleic acid of the system comprises a nucleotide sequence encoding a protease that cleaves the proteolytically cleavable linker. In some cases, the fourth nucleic acid of the system comprises a nucleotide sequence encoding a protease that cleaves the proteolytically cleavable linker. The proteolytically cleavable linker can be one that is cleaved by a lentiviral protease.

The proteolytically cleavable linker can be one that is cleaved by a protease other than a lentiviral protease (i.e., the protease is heterologous to the lentivirus).

A proteolytically cleavable linker comprises a protease cleavage site. A proteolytically cleavable linker can comprise a matrix metalloproteinase cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue (SEQ ID NO:218)), e.g., Pro-X-X-Hy-(Ser/Thr) (SEQ ID NO:219), e.g., Pro-Leu/Gln-Gly-Met-Thr-Ser (SEQ ID NO:220) or Pro-Leu/Gln-Gly-Met-Thr (SEQ ID NO:221). Another example of a protease cleavage site is a plasminogen activator cleavage site, e.g., a uPA or a tissue plasminogen activator (tPA) cleavage site. In some cases, the cleavage site is a furin cleavage site. Specific examples of cleavage sequences of uPA and tPA include sequences comprising Val-Gly-Arg. Another example of a protease cleavage site that can be included in a proteolytically cleavable linker is a tobacco etch virus (TEV) protease cleavage site, e.g., ENLYTQS (SEQ ID NO:127), where the protease cleaves between the glutamine and the serine. Another example of a protease cleavage site that can be included in a proteolytically cleavable linker is an enterokinase cleavage site, e.g., DDDDK (SEQ ID NO:128), where cleavage occurs after the lysine residue. Another example of a protease cleavage site that can be included in a proteolytically cleavable linker is a thrombin cleavage site, e.g., LVPR (SEQ ID NO:129). Additional suitable linkers comprising protease cleavage sites include linkers comprising one or more of the following amino acid sequences: LEVLFQGP (SEQ ID NO:130), cleaved by PreScission protease (a fusion protein comprising human rhinovirus 3C protease and glutathione-S-transferase; Walker et al. (1994) Biotechnol. 12:601); a thrombin cleavage site, e.g., CGLVPAGSGP (SEQ ID NO:131); SLLKSRMVPNFN (SEQ ID NO:132) or SLLIARRM-PNFN (SEQ ID NO:133), cleaved by cathepsin B; SKLVQASASGVN (SEQ ID NO:134) or SSYLKAS-DAPDN (SEQ ID NO:135), cleaved by an Epstein-Barr virus protease; RPKPQQFFGLMN (SEQ ID NO:136) cleaved by MMP-3 (stromelysin); SLRPLALWRSFN (SEQ ID NO:137) cleaved by MMP-7 (matrilysin); SPQ-GIAGQRNFN (SEQ ID NO:138) cleaved by MMP-9; DVDERDVRGFASFL SEQ ID NO:139) cleaved by a thermolysin-like MMP; SLPLGLWAPNFN (SEQ ID NO:140) cleaved by matrix metalloproteinase 2 (MMP-2); SLLIFR-SWANFN (SEQ ID NO:141) cleaved by cathespin L; SGV-VIATVIVIT (SEQ ID NO:142) cleaved by cathepsin D; SLGPQGIWGQFN (SEQ ID NO:143) cleaved by matrix metalloproteinase 1(MMP-1); KKSPGRVVGGSV (SEQ ID NO:144) cleaved by urokinase-type plasminogen activator; PQGLLGAPGILG (SEQ ID NO:145) cleaved by membrane type 1 matrix metalloproteinase (MT-MMP); HGPEGLRVGFYESDVMGRGHARLVHVEEPHT (SEQ ID NO:146) cleaved by stromelysin 3 (or MMP-11), thermolysin, fibroblast collagenase and stromelysin-1; GPQGLAGQRGIV (SEQ ID NO:147) cleaved by matrix metalloproteinase 13 (collagenase-3); GGSGQRGRKALE (SEQ ID NO:148) cleaved by tissue-type plasminogen activator (tPA); SLSALLSSDIFN (SEQ ID NO:149) cleaved by human prostate-specific antigen; SLPRFKIIGGFN (SEQ ID NO:150) cleaved by kallikrein (hK3); SLLGIAVPGNFN (SEQ ID NO:151) cleaved by neutrophil elastase; and FFKNIVTPRTPP (SEQ ID NO:152) cleaved by calpain (calcium activated neutral protease). In some cases, the protease cleavage site is a TEV protease cleavage site, e.g., ENLYFQS (SEQ ID NO:153), where cleavage occurs between the Gln and the Ser. In some cases, the protease cleavage site is the TEV protease cleavage site ENLYFQP (SEQ ID NO:154). ENLYFQS (SEQ ID NO:153) and ENLYFQP (SEQ ID NO:154) are wildtype recognition sequences (cleavage substrates) for TEV protease (see e.g. Stols et al. (2002) *Prot. Exp. Purif.* 25: 8-12). In some cases, the proteolytically cleavable linker comprises an HIV-1 protease cleavage site (e.g. SQNYPIVQ (SEQ ID NO:155)), where cleavage occurs between the tyrosine and the proline. In some cases, an HIV-1 protease cleavage site (e.g. SQNYPIVQ (SEQ ID NO:155)) is specifically excluded.

Figures 6A, 6B, 6C, 6D, 6E, 6F:
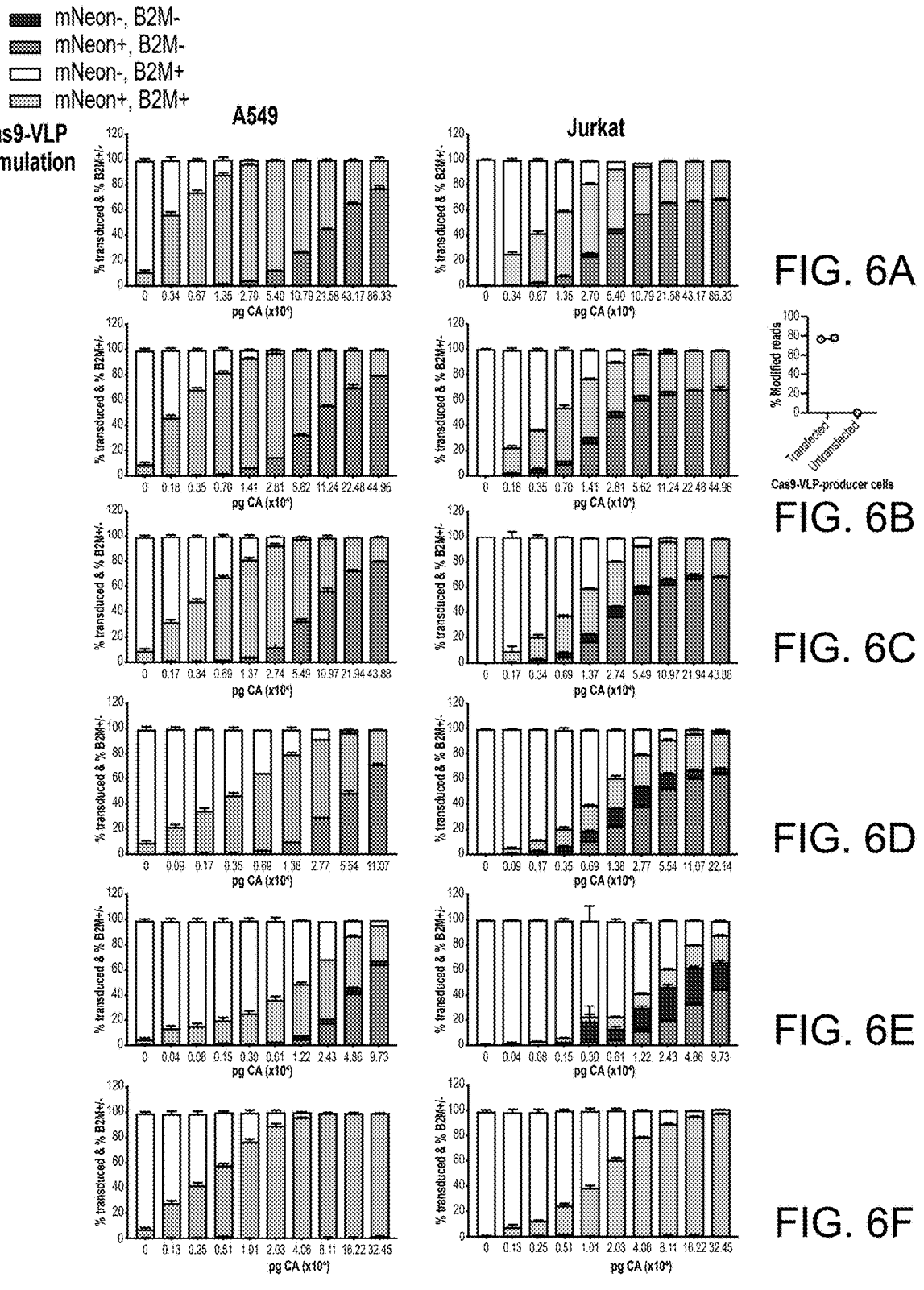
FIG. 6A-6F depict genome editing using various Cas9-VLP formulations.

In some cases, the protease cleavage site is a TEV protease cleavage site, e.g., ENLYTQS (SEQ ID NO:127), where the protease cleaves between the glutamine and the serine. In some cases, the protease cleavage site is a variant TEV-cleavage substrate, where the variant TEV cleavage site is cleaved by a TEV protease (e.g., a TEV protease comprising the TEV protease amino acid sequence provided in FIG. 6B) less efficiently than cleavage of ENLYTQS (SEQ ID NO:127) by the TEV protease. In some cases, a variant TEV-cleavage site can: (1) mimic the temporal cleavage observed with wild-type gag polyprotein maturation; and/or (2) maximize packaging of a CRISPR/Cas effector polypeptide into a VLP. Suitable variant TEV cleavage sites are described in Tözsér et al. (2005) *FEBS J.* 272:514. Suitable variant TEV cleavage sites include: ENAYFQS (SEQ ID NO:156), ENLRFQS (SEQ ID NO:157), ENLFFQS (SEQ ID NO:158), ETVRFQS (SEQ ID NO:159), ETLRFQS (SEQ ID NO:160), ETARFQS (SEQ ID NO:161), ETVYFQS (SEQ ID NO:162), and ENVYFQS (SEQ ID NO:163).

In some cases, a system of the present disclosure comprises a CRISPR/Cas effector guide RNA. For example, a VLP produced using a system of the present disclosure can comprise, encapsulated within the VLP a guide RNA. In some cases, the guide RNA is a dual guide RNA, e.g., two separate nucleic acids that together comprise a guide RNA. In other instances, the guide RNA is a single-molecule guide RNA (also referred to herein as a "single guide RNA" or "sgRNA"). Suitable guide RNAs are described hereinbelow. In some cases, the guide RNA comprises one or more of: i) a modified base; ii) a modified sugar; and iii) a modified backbone.

A coding sequence (e.g., a nucleotide sequence encoding a Gag-CRISPR-Cas fusion polypeptide; a nucleotide sequence encoding a CRISPR-Cas guide RNA; a nucleotide sequence encoding a therapeutic protein) present in a nucleic acid in a system of the present disclosure can be operably linked to a transcriptional control element (e.g., a promoter). The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a protein-encoding nucleotide sequence present in a nucleic acid of a system of the present disclosure is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA in a eukaryotic cell it may sometimes be necessary to modify the sequence encoding the guide RNA to eliminate runs of Ts. In some cases, a nucleotide sequence encoding guide RNA is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Donor Nucleic Acid

In some cases, a system of the present disclosure comprises a donor nucleic acid. By a "donor nucleic acid" or "donor sequence" or "donor polynucleotide" or "donor template" it is meant a nucleic acid sequence to be inserted at the site cleaved by a CRISPR/Cas effector protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair or a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance.

Compositions Comprising a System

The present disclosure provides a composition comprising a system of the present disclosure. A composition of the present disclosure can include: a) a system of the present disclosure; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl)amino-tris(hydroxymethyl) methane (BIS-Tris), N-(2-hydroxyethyl)piperazine-N'3-pro-panesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), pipera-zine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxym-ethyl)methyl-2-aminoethanesulfonic acid (TES), N-tris(hy-droxymethyl)methyl-glycine (Tricine), tris (hydroxymethyl)-aminomethane (Tris), etc.). Suitable salts include, e.g., NaCl, MgCl$_2$, KCl, MgSO$_4$, etc. In some cases, the composition is sterile. In some cases, the composition is sterile and is free of detectable pyrogens and/or other toxins.

Methods of Making a VLP

The present disclosure provides methods of making a VLP of the present disclosure. The methods generally involve introducing into a packaging cell a system of the present disclosure; and harvesting the VLPs produced by the packaging cell. In some cases, the VLPs are harvested from the supernatant (e.g., the cell culture medium) in which the packaging cells are cultures. In some cases, the cell culture medium is filtered (e.g., with a 0.45 μm filter).

Any suitable permissive or packaging cell known in the art may be employed in the production of a VLP of the present disclosure. In some cases, the cell is a mammalian cell. In some cases, the cell is an insect cell. Examples of cells suitable for production of a VLP of the present disclo-sure include, e.g., human cell lines, such as VERO, WI38, MRCS, A549, HEK293, HEK293T, B-50 or any other HeLa cells, HepG2, Saos-2, HuH7, Chinese Hamster Ovary (CHO) cells, and HT1080 cell lines.

Also suitable for use as packaging cells are insect cell lines. Any insect cell that allows for production of a VLP of the present disclosure and which can be maintained in culture can be used. Examples include *Spodoptera fru-giperda*, such as the Sf9 or Sf21 cell lines, *Drosophila* spp. cell lines, or mosquito cell lines, e.g., *Aedes albopictus* derived cell lines.

The nucleic acids present in a system of the present disclosure can extra-chromosomal or integrated into the cell's chromosomal DNA. In some cases, the packaging cell is a cell line with one or more packaging functions incor-porated extrachromosomally or integrated into the cell's chromosomal DNA, or a cell line with helper functions incorporated extra-chromosomally or integrated into the cell's chromosomal DNA.

Cells

The present disclosure provides a eukaryotic cell com-prising a system of the present disclosure, where the cell is a packaging cell. Any suitable permissive or packaging cell known in the art is suitable. In some cases, the cell is a mammalian cell. In some cases, the cell is an insect cell. Examples of cells suitable for production of a VLP of the present disclosure include, e.g., human cell lines, such as VERO, WI38, MRCS, A549, HEK293, HEK293T, B-50 or any other HeLa cells, HepG2, Saos-2, HuH7, Chinese Hamster Ovary (CHO) cells, and HT1080 cell lines.

Also suitable for use as packaging cells are insect cell lines. Any insect cell that allows for production of a VLP of the present disclosure and which can be maintained in culture can be used. Examples include *Spodoptera fru-giperda*, such as the Sf9 or Sf21 cell lines, *Drosophila* spp. cell lines, or mosquito cell lines, e.g., *Aedes albopictus* derived cell lines.

Methods of Delivering a Therapeutic Protein

The present disclosure provides methods of delivering a therapeutic protein, e.g. to a eukaryotic cell (e.g., a target cell) or to an organism (e.g., an individual). The methods generally involve contacting the cell with a VLP of the present disclosure or administering a VLP to an organism. In some cases, the target cell is in vitro. In some cases, the target cell is in vivo and the method comprises administering the VLP to an individual.

Where a VLP of the present disclosure comprises a guide RNA, in some instances, the guide RNA provides for knockout of a nucleic acid targeted by the guide RNA. Thus, in some cases, a VLP of the present disclosure provides for: i) delivery of a therapeutic protein; and ii) knockout of a target nucleic acid. As one non-limiting example, a VLP of the present disclosure can both: i) provide for delivery of a therapeutic protein (such as a chimeric antigen receptor (CAR)); and ii) knock out an endogenous nucleic acid encoding a beta-2 microglobulin (β2M) polypeptide, where the guide RNA present in the VLP (or encoded by a nucleic acid present in the VLP) would comprise a nucleotide sequence targeting a β2M-encoding nucleic acid in a target cell. Such a VLP would be useful for generating T cells that express a CAR ("CAR-T cells") that do not express endog-enous major histocompatibility complex (MHC) class I antigens on their cell surface and thus could be useful for delivery of allogeneic CAR-T cells. As another non-limiting example, a VLP of the present disclosure can both: i) provide for delivery of a therapeutic protein (such as an antibody, e.g., a cancer-specific antibody or other therapeu-tic antibody); and ii) knock out an endogenous nucleic acid encoding an antibody light chain (e.g., a kappa light chain) or an immunoglobulin (Ig) Fc polypeptide (e.g., an Ig Fc polypeptide of a particular isotype such as IgG1). Such a VLP would be useful for generating B cells that produce a therapeutic antibody.

In some cases, a VLP of the present disclosure provides for homology directed repair (HDR) of a defective target nucleic acid. In some cases, a VLP of the present disclosure provides for non-homologous end joining (NHEJ) of a target nucleic acid, e.g., to provide for a knockout of a target nucleic acid.

In some cases, a method of the present disclosure com-prises: a) electroporating VLPs with a donor DNA template (e.g., a single-stranded donor DNA template); and b) con-tacting target cells with the electroporated VLP/donor DNA template mixture. Electroporating VLPs with a donor DNA template (e.g., a single-stranded donor DNA template) prior to contacting with target cells can increase HDR, compared to the level of HDR when the VLPs are simply admixed with the donor DNA template (not electroporated).

A cell that serves as a recipient for a VLP of the present disclosure can be any of a variety of eukaryotic cells, including, e.g., in vitro cells; in vivo cells; ex vivo cells; primary cells; cancer cells; animal cells; plant cells; algal cells; fungal cells; etc. A cell that serves as a recipient for a VLP of the present disclosure is referred to as a "host cell" or a "target cell."

In some cases, the target cell is in vitro. In some cases, cells are removed from an individual, contacted with a VLP of the present disclosure in vitro, such that the cells are modified to produce the therapeutic protein encoded by the recombinant lentiviral nucleic acid present in the VLP; and returning the modified cells to the individual from whom the cells were obtained. In some cases, cells are removed from an individual, contacted with a VLP of the present disclosure in vitro, such that the cells are modified to produce the therapeutic protein encoded by the recombinant lentiviral nucleic acid present in the VLP; and administering the modified cells to an individual other than the individual from whom the cells were obtained.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogeneic cells, allogeneic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34+ and CD3-. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

In some cases, the pseudotyping viral glycoprotein is selected from an influenza virus hemagglutinin, a SARS-CoV glycoprotein, a respiratory syncytial virus glycoprotein, a human parainfluenza virus glycoprotein, and a VSV-G; and the target cell is a lung cell. In some cases, the VLP comprises a guide RNA, or a nucleic acid comprising a nucleotide sequence encoding a guide RNA, where the guide RNA comprises a targeting sequence that targets a CFTR (cystic fibrosis transmembrane conductance regulator) gene. For example, targeting a CFTR gene can treat cystic fibrosis. Where the target gene comprises a defect that leads to pathology, a donor nucleic acid comprising a nucleotide sequence without the defect can be included in the VLP, such that the defect is corrected.

In some cases, the pseudotyping viral glycoprotein is a measles virus hemagglutinin and/or a measles virus fusion glycoprotein, and the target cell is a CD34+ cell. In some cases, the VLP comprises a guide RNA, or a nucleic acid comprising a nucleotide sequence encoding a guide RNA, where the guide RNA comprises a targeting sequence that targets an HbF (fetal hemoglobin) gene. For example, targeting an HbF gene can treat sickle cell disease or beta-thalassemia. Where the target gene comprises a defect that leads to pathology, a donor nucleic acid comprising a nucleotide sequence without the defect can be included in the VLP, such that the defect is corrected.

In some cases, the pseudotyping viral glycoprotein is selected from a measles virus hemagglutinin and/or a measles virus fusion glycoprotein, an HTLV-1 glycoprotein, and a VSV-G glycoprotein; and the target cell is a CD8+ T cell. In some cases, the VLP comprises a guide RNA, or a nucleic acid comprising a nucleotide sequence encoding a guide RNA, where the guide RNA comprises a targeting sequence that targets a gene selected from PD1 (programmed cell death 1), CTLA4 (cytotoxic T-lymphocyte-associated protein 4), and TCR (T-cell receptor). For example, targeting a PD-1 gene, a CTLA-4 gene, or a TCR gene, can be used in the generation of chimeric antigen receptor (CAR)-T cells.

In some cases, the pseudotyping viral glycoprotein is selected from a HIV-1 envelope, a HTLV-1 glycoprotein, a measles virus hemagglutinin, and a VSV-G glycoprotein;

and the target cell is a CD4+ T cell. In some cases, the VLP comprises a guide RNA, or a nucleic acid comprising a nucleotide sequence encoding a guide RNA, where the guide RNA comprises a targeting sequence that targets a CCR5 gene, or targets an integrated and proviral HIV-1. Targeting a CCR5 gene can be used to enhance resistance to HIV. Targeting an integrated and proviral HIV-1 can be used to reduce the pool of T cells that are reservoirs for latent HIV.

In some cases, the pseudotyping viral glycoprotein is a Ross River virus glycoprotein or a VSV-G; and the target cell is a skeletal muscle cell. In some cases, the VLP comprises a guide RNA, or a nucleic acid comprising a nucleotide sequence encoding a guide RNA, where the guide RNA comprises a targeting sequence that targets a Duchenne muscular dystrophy (DMD) gene. Targeting a DMD gene can be used to treat Duchenne muscular dystrophy. Where the target gene comprises a defect that leads to pathology, a donor nucleic acid comprising a nucleotide sequence without the defect can be included in the VLP, such that the defect is corrected.

In some cases, the pseudotyping viral glycoprotein is selected from an Ebola virus glycoprotein, a Marburg virus glycoprotein, and a VSV-G; and the target cell is an ocular cell (e.g., in a retinal cell, a photoreceptor cell, etc.). In some cases, the VLP comprises a guide RNA, or a nucleic acid comprising a nucleotide sequence encoding a guide RNA, and wherein the guide RNA comprises a targeting sequence that targets a CEP290 (centrosomal protein 290) gene. Targeting a CEP290 gene can be used to treat Leber congenital amaurosis 10 (LCA10). Where the target gene comprises a defect that leads to pathology, a donor nucleic acid comprising a nucleotide sequence without the defect can be included in the VLP, such that the defect is corrected.

In some cases, the pseudotyping viral glycoprotein is selected from an Ebola virus glycoprotein, a Marburg virus glycoprotein, and a VSV-G; and the target cell is an auditory cell (e.g., hair cells, cochlear cells, etc.). In some cases, the VLP comprises a guide RNA, or a nucleic acid comprising a nucleotide sequence encoding a guide RNA, where the guide RNA comprises a targeting sequence that targets a USH2A (Usher syndrome 2A) gene. Targeting a USH2A gene can be used to treat Usher Syndrome type 2A. Where the target gene comprises a defect that leads to pathology, a donor nucleic acid comprising a nucleotide sequence without the defect can be included in the VLP, such that the defect is corrected.

In some cases, the pseudotyping viral glycoprotein is selected from aa rabies glycoprotein, a Mokola virus glycoprotein, a Semliki Forest virus glycoprotein, a Sindbis virus glycoprotein, a Venezuelan equine encephalitis virus glycoprotein, an influenza hemagglutinin glycoprotein, and a VSV-G; and wherein the target cell is a central nervous system cell (e.g., neurons (e.g., excitatory and inhibitory neurons); and glial cells (e.g., oligodendrocytes, astrocytes and microglia)). In some cases, the VLP comprises a guide RNA, or a nucleic acid comprising a nucleotide sequence encoding a guide RNA, and wherein the guide RNA comprises a targeting sequence that targets a gene selected from Tau/MAPT-1, HTT (Huntingtin), SOD1 (superoxide dismutase 1), SOCS3 (suppressor of cytokine signaling 3), USP8 (ubiquitin specific peptidase 8), DOT1L (DOT1-like histone lysine methyltransferase), UFM1 (ufmylation; ubiquitin fold modifier 1), SOCS2 (suppressor of cytokine signaling 2), SOCS9 (suppressor of cytokine signaling 9), SOCS13 (suppressor of cytokine signaling 13), SOCS11 (suppressor of cytokine signaling 11), and SOCS5 (suppressor of cytokine signaling 5). For example, targeting a Tau gene can treat Alzheimer's disease. As another example, targeting an HTT gene can treat Huntington Disease. As another example, targeting a SOD1 gene can treat amyotrophic lateral sclerosis. As another example, targeting a Ufmylation, USP8, DOT1L, SOCS2, SOCS3, SOCS9, SOCS13, SOCS11, or SOCS5 gene can treat glioblastoma. Where the target gene comprises a defect that leads to pathology, a donor nucleic acid comprising a nucleotide sequence without the defect can be included in the VLP, such that the defect is corrected.

In some cases, a single dose of a composition comprising a VLP of the present disclosure comprises from about $10^2$ VLPs to about $10^9$ VLPs. For example, a single dose of a composition comprising a VLP of the present disclosure comprises from about $10^2$ VLPs to about $10^3$ VLPs, from about $10^3$ VLPs to about $10^4$ VLPs, from about $10^4$ VLPs to about $10^5$ VLPs, from about $10^5$ VLPs to about $10^6$ VLPs, from about $10^6$ VLPs to about $10^7$ VLPs, from about $10^7$ VLPs to about $10^8$ VLPs, from about $10^8$ VLPs to about $10^9$ VLPs, or from about $10^9$ VLPs to about $10^{10}$ VLPs.

A composition comprising a VLP of the present disclosure can be administered via any of a variety of parenteral and non-parenteral routes of administration. For example, a composition comprising a VLP of the present disclosure can be administered intravenously, intramuscularly, intratumorally, peritumorally, subcutaneously, intraperitoneally, and the like. A VLP of the present disclosure can be administered via convection enhanced delivery (CED) injection.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A system comprising:
a) a first nucleic acid comprising a nucleotide sequence encoding a fusion polypeptide comprising:
  i) a lentiviral gag polyprotein comprising a matrix (MA) polypeptide, a capsid (CA) polypeptide, and a nucleocapsid (NC) polypeptide; and
  ii) a CRISPR-Cas effector polypeptide;
wherein the fusion polypeptide comprises proteolytically cleavable linker between the gag polyprotein and the CRISPR-Cas effector polypeptide;
b) a second nucleic acid comprising a nucleotide sequence encoding a therapeutic polypeptide, wherein the second nucleic acid comprises a recombinant lentiviral nucleic acid;
c) a third nucleic acid comprising a nucleotide sequence encoding a pseudotyping viral envelope protein and/or a polypeptide that provides for binding to a target cell; and
d) a fourth nucleic acid comprising a nucleotide sequence encoding a lentiviral pol polyprotein comprising a reverse transcriptase and an integrase;
wherein the system comprises a nucleic acid comprising a nucleotide sequence encoding a CRISPR-Cas guide RNA, wherein the CRISPR-Cas guide RNA-encoding nucleic acid is either:

i) part of the second nucleic acid; or ii) a fifth nucleic acid.

Aspect 2. The system of aspect 1, wherein the therapeutic polypeptide has a length of from about 250 amino acids to about 3,000 amino acids.

Aspect 3. The system of aspect 2, wherein the therapeutic polypeptide has a length of from about 500 amino acids to about 2,500 amino acids.

Aspect 4. The system of any one of aspects 1-3, wherein the therapeutic polypeptide is a chimeric antigen receptor (CAR), a T-cell receptor, a synNotch polypeptide, a natural killer cell receptor, or an antibody.

Aspect 5. The system of aspect 4, wherein the CAR comprises an antigen-binding domain specific for a cancer-associated antigen.

Aspect 6. The system of any one of aspects 1-5, wherein the recombinant lentiviral nucleic acid is a recombinant human immunodeficiency virus-1 nucleic acid.

Aspect 7. The system of any one of aspects 1-6, wherein the lentiviral gag polyprotein is a human immunodeficiency virus (HIV) gag polyprotein comprising a MA polypeptide, a CA polypeptide, a p2 polypeptide, an NC polypeptide, a p1 polypeptide, and a p6 polypeptide.

Aspect 8. The system of any one of aspects 1-7, wherein the CRISPR-Cas effector polypeptide is a type II CRISPR-Cas effector polypeptide, a type V CRISPR-Cas effector polypeptide, or a type VI CRISPR-Cas effector polypeptide.

Aspect 9. The system of aspect 8, wherein the type II CRISPR/Cas effector polypeptide is a Cas9 polypeptide.

Aspect 10. The system of any one of aspects 1-9, wherein the CRISPR/Cas effector polypeptide is a fusion polypeptide comprising one or more nuclear localization signals.

Aspect 11. The system of any one of aspects 1-10, further comprising a donor template nucleic acid, or a nucleotide sequence encoding the donor template nucleic acid.

Aspect 12. A eukaryotic cell comprising the system of any one of aspects 1-11.

Aspect 13. The eukaryotic cell of aspect 12, wherein the cell is a packaging cell.

Aspect 14. A virus-like particle (VLP) comprising:

a) a CRISPR-Cas effector polypeptide; and b) a recombinant lentivirus comprising a nucleotide sequence encoding a therapeutic polypeptide having a length of from about 250 amino acids to about 3,000 amino acids, wherein the VLP comprises a pseudotyping viral glycoprotein and/or a polypeptide that provides for binding to a target cell.

Aspect 15. The VLP of aspect 14, wherein the therapeutic polypeptide has a length of from about 500 amino acids to about 2,500 amino acids.

Aspect 16. The VLP of aspect 14 or 15, wherein the therapeutic polypeptide is a chimeric antigen receptor (CAR), a T-cell receptor, a synNotch polypeptide, a natural killer cell receptor, or an antibody.

Aspect 17. The VLP of aspect 16, wherein the CAR comprises an antigen-binding domain specific for a cancer-associated antigen.

Aspect 18. The VLP of any one of aspects 14-17, wherein the pseudotyping viral glycoprotein is a human immunodeficiency virus-1 envelope protein, a measles virus hemagglutinin, an HTLV-1 glycoprotein, or a VSV-G glycoprotein.

Aspect 19. The VLP of any one of aspects 14-17, wherein the polypeptide that provides for binding to a target cell is an antibody, optionally wherein the antibody is a single-chain Fv or a nanobody.

Aspect 20. The VLP of any one of aspects 14-17, wherein the polypeptide that provides for binding to a target cell is a DARPin.

Aspect 21. The VLP of any one of aspects 14-20, wherein the CRISPR-Cas effector polypeptide is a type II CRISPR-Cas effector polypeptide, a type V CRISPR-Cas effector polypeptide, or a type VI CRISPR-Cas effector polypeptide.

Aspect 22. The VLP of aspect 21, wherein the type II CRISPR/Cas effector polypeptide is a Cas9 polypeptide.

Aspect 23. The VLP of any one of aspects 14-22, wherein the CRISPR/Cas effector polypeptide is a fusion polypeptide comprising one or more nuclear localization signals.

Aspect 24. The VLP of any one of aspects 14-23, comprising a CRISPR/Cas guide RNA.

Aspect 25. The VLP of any one of aspects 14-24, comprising a donor template nucleic acid.

Aspect 26. A composition comprising the VLP of any one of aspects 14-25.

Aspect 27. The composition of aspect 26, further comprising a donor template nucleic acid.

Aspect 28. A method of delivering a therapeutic polypeptide to a eukaryotic cell, the method comprising contacting the cell with the VLP of any one of aspects 14-25, or the composition of aspect 26 or aspect 27.

Aspect 29. The method of aspect 28, wherein the eukaryotic cell is in vivo.

Aspect 30. The method of aspect 24, wherein the eukaryotic cell is in vitro.

Aspect 31. The method of any one of aspects 28-30 wherein the eukaryotic cell is a T cell.

Aspect 32. The method of any one of aspects 28-30 wherein the eukaryotic cell is a B cell.

Aspect 33. The method of any one of aspects 28-30 wherein the eukaryotic cell is a stem cell.

Aspect 34. A method of making a virus-like particle (VLP) comprising a therapeutic polypeptide, the method comprising: a) introducing the system of any one of aspects 1-11 into a packaging cell; and b) harvesting VLPs produced by the packaging cell.

Aspect 35. A method of delivering a therapeutic polypeptide to a eukaryotic cell, and carrying out homology-directed repair (HDR) in the cell, the method comprising:

a) electroporating a solution comprising: i) a VLP of any one of aspects 14-24; and ii) a donor template nucleic acid, forming an electroporated VLP/donor template solution; and b) contacting the cell with the electroporated VLP/donor template solution, wherein said contacting results in HDR and in synthesis of the therapeutic polypeptide in the cell.

Aspect 36. The method of aspect 35, wherein the eukaryotic cell is a T cell, a B cell, or a stem cell.

Aspect 37. The method of aspect 35, wherein the eukaryotic cell is a T cell, wherein the therapeutic polypeptide is a chimeric antigen receptor, and wherein the guide RNA present in the VLP provides for knockout, via HDR, of endogenous β-2 microglobulin such that, following HDR, the cell does not substantially display MHC class I polypeptides on its surface.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); p1, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Generating VLPs

VLPs are an unexplored strategy for linking the delivery of pre-formed Cas9 RNPs with a clinically relevant transgene and leveraging viral glycoprotein pseudotyping to direct genome editing to specific cell types. Here, it is demonstrated that engineered lentiviral particles can deliver Cas9 RNP complexes for genome editing, either tracelessly or while simultaneously integrating a lentiviral-encoded transgene (Cas9-VLPs) in immortalized cell lines and primary human T cells. Treatment of primary human T cells with Cas9-VLPs packaging a lentiviral-encoded CAR resulted in simultaneous knockout of genetic targets relevant to allogeneic T cell production while effectively mediating CAR expression, an approach that was amenable to multiplexing. Additionally, treatment of T cells with broadly-transducing Cas9-VLPs resulted in targeted genetic knockout in CD4+ and CD8+ T cells, while treatment with Cas9-VLPs pseudotyped with the CD4-tropic HIV-1 envelope glycoprotein drove the exclusive transduction and genome editing of CD4+ T cells within a mixed cell population. These data establish Cas9-VLPs as an effective approach for mediating cell-type specific genome editing using Cas9 RNPs. As Cas9-VLPs circumvent the requirement for ex vivo Cas9 RNP delivery via electroporation, this strategy indicates a path forward for leveraging the tropism of viral glycoproteins in targeting specific cell types for genome engineering in vivo.

Materials and Methods

Culture of Human Cell Lines

Lenti-X, 293T, A549, CCRF-CEM, HuT 78 and Jurkat cell lines were obtained from the UC Berkeley Cell Culture Facility. All cells were cultured with 10% fetal bovine sera (VWR) and 100 U/mL penicillin-streptomycin (Gibco). LentiX, 293T, and A549 cells were cultured in DMEM (Corning), Jurkat and CCRF-CEM cells were cultured in RPMI 1640 (Thermo Fisher) and 1 mM sodium pyruvate, while HuT 78 cells were cultured in IMEM (Thermo Fisher). Cell lines were routinely checked for mycoplasma using the MycoAlert mycoplasma detection kit (Lonza) according to the manufacturer's instructions.

Isolation and Culture of Human Primary T Cells

Primary adult blood cells were obtained from anonymous healthy human donors as a leukoreduction pack purchased from Stemcell Technologies or Allcells Inc, or as a Trima residual from Vitalant, under a protocol approved by the University of California San Francisco Institutional Review Board (IRB). If needed, peripheral blood mononuclear cells were isolated by Ficoll-Paque (GE Healthcare) centrifugation. Bulk CD3+T lymphocytes were then further isolated by magnetic negative selection using an EasySep magnetic Cell Isolation kit (STEMCELL, as per the manufacturer's instructions). 96-well flat bottom plates were primed for stimulation by incubating with anti-human CD3 (10 μg/mL) and anti-human CD28 (5 μg/mL) antibodies in PBS for 1 hour at 37° C. prior to washing. Primary T cells were activated by plating at 250,000 cells/mL and culturing for one day in XVivo15 medium (Lonza) containing fetal bovine serum (5%), 2-mercaptoethanol (50 μM), N-acetyl L-cysteine (10 mM), IL-2 (300 U/mL), IL-7 (5 ng/mL), and IL-15 (5 ng/mL). Cas9-VLPs in RPMI 1640 were added to primary human T cells 24 hours later along with IL-2 (500 U/mL) and protamine sulfate (4 μg/mL). Media and growth factors were replaced as needed, approximately every 5-6 days. The number of unique primary human T cell donors used for each experiment is listed in Supplementary Table 4 (FIG. 17).

Plasmid Construction

The Gag-pol expression plasmid psPax2 was a gift from Didier Trono (Addgene plasmid #12260). pCMV-VSV-G was a gift from Bob Weinberg (Addgene plasmid #8454). Gag-Cas9 was constructed by amplifying Gag from psPax2 and Cas9 from pMJ920 (Addgene plasmid #42234). HIV-1 Env amino acid sequence was obtained from UniProt (P04578), human codon optimized (IDT), and ordered as a gBlock (IDT). In-Fusion (Takara Bio) cloning was used to clone Gag-Cas9 and Env into the pCAGGS expression vector. pCF221 (Addgene plasmid #121669) was modified to express mNeonGreen (Allele Biotechnology) or the α-CD19-4-1BBζ-P2A-mCherry (CAR-P2A-mCherry) construct (Hill et al., 2018; Muller et al., 2020) in place of mCherry and was used as the sgRNA-expressing lentiviral transfer plasmid. For generation of hybrid Cas9-VLPs, the guide RNA expression cassette was removed from the CAR-P2A-mCherry lentiviral plasmid via digestion with EcoRI and KpnI (NEB). The following primers (IDT) were phosphorylated, annealed, and ligated into the digested vector: 5'-cATCGATCTTAAGTCGCGACTCGAg (SEQ ID NO:164) and 5'-aattcTCGAGTCGCGACTTAAGATC-GATggtac (SEQ ID NO:165). The U6-sgRNA CAG-mTagBFP2 expression plasmid used for traceless Cas9-VLP and CAR-Cas9 VLP production was a gift from Benjamin Oakes. Oligos encoding guide RNA spacers were ordered from IDT, phosphorylated, annealed and ligated into digested sgRNA expression vectors.

Cas9-VLP Production

Cas9-VLPs were produced in mammalian cell culture by transient transfection of Lenti-X cells (Takara Bio). 3.5-4 million cells were seeded into 10 cm tissue culture dishes (Corning). The following day, cells were transfected with psPax2, Gag-Cas9, 1 μg pCMV-VSV-G or 0.2 μg HIV Env glycoprotein, and 10 μg of plasmid encoding the sgRNA-expression cassette (either transiently or in the context of a lentiviral transfer plasmid). Plasmids were diluted in Opti-MEM (Gibco) and mixed with polyethylenimine (PEI, Polysciences Inc.) at a 3:1 PEI:plasmid ratio. Quantities of transfected Gag-Cas9 and psPax2 plasmid are listed in FIG. 1C for VLP formulations A-F. A549 and Jurkat experiments used Cas9-VLP formulation D, unless indicated otherwise, and supernatant was harvested at 48 hours post transfection. Cas9-VLP experiments with primary human T cells used Cas9-VLP formulation B, where the Lenti-X media was replaced with Opti-MEM 6-18 hours post transfection. Cas9-VLP-containing Opti-MEM was collected at 48 and 96 hours post media change, with fresh Opti-MEM being added to the cells after 48 hours. Harvested supernatants were centrifuged at 1,500 rpm for 10 minutes and filtered through a 0.45 μM PES membrane bottle top filter (Thermo Fisher) or syringe filter (VWR). Cas9-VLPs were concentrated via ultracentrifugation by floating Cas9-VLP-containing supernatant on top of a cushioning buffer of 30% (w/v) sucrose in 100 mM NaCl, 10 mM Tris-HCl pH 7.5, 1 mM EDTA pH 8.0, at 25,000 rpm with a SW28 or SW41 Ti rotor (Beckman Coulter) for 2 hours at 4° C. in polypropylene tubes (Beckman Coulter). After ultracentrifugation, the Cas9-VLP pellet was resuspended in RPMI 1640 (Gibco) or XVivo15 (Lonza) for treatment of primary T cells or Opti-MEM. Cas9-VLPs were either stored at 4° C. or frozen at −80° C. within a isopropanol-filled freezing container until use.

Cas9-VLP Quantification

Western blots were performed to assess protein components of Cas9-VLPs. Cas9-VLPs were denatured by mixing with Laemmli buffer with 10% 2-mercaptoethanol and heating at 90° C. for 5 minutes. Samples were run on 4-20% SDS-PAGE gels (Bio-Rad) prior to transfer onto a methanol soaked polyvinylidene difluoride (PVDF, Bio-Rad) membrane. PVDF membranes were blocked with 5% non-fat milk (Apex) in PBS (Gibco) with 0.1% Tween (Sigma) (PBS-T) for one hour at room temperature (~22-25° C.). The solution was replaced with 1% non-fat milk in PBS-T and a 1:5000 primary antibody dilution containing anti-FLAG (Sigma) or a 1:2000 dilution of anti-p24 (Abcam) antibodies prior to shaking at 4° C. overnight. The following day, the solution was replaced with 1% non-fat milk in PBS-T and a 1:5000 secondary antibody dilution containing IR680 or IR800 conjugated antibodies (LI-COR) and shaken for 1 hour. Western blot membranes were washed with PBS-T three times prior to imaging on a LI-COR OdysseyCLx.

Lenti-X p24 rapid titer kits (Takara Bio) were used to quantify the titer of Cas9-VLPs after concentration. Cas9-VLPs were diluted 1:1,000-100,000 and the ELISA was performed according to the manufacturer's directions. Absorbance was measured at 450 nm on a BioTek plate reader. Cas9-VLP p24 content was calculated by comparison to serial dilution of a p24 standard (Takara Bio). To calculate transducing units per mL (TU/mL), Cas9-VLP preps were serially diluted and used to treat 15 k Jurkats or 25 k primary T cells in 96-well u-bottom plates. The percent of cells transduced (mNeonGreen+) was quantified at 6-7 days post treatment using an Attune NxT flow cytometer with a 96-well autosampler (Thermo Fisher Scientific) and titer was quantified as TU/mL=(number of cells transduced x percent mNeonGreen+)/(virus treatment volume). Wells where Cas9-VLP transduction was <25% were used for titer calculation. MOI was plotted against indels and a sigmoidal four parameter logistic fit was applied to each data set to interpolate the MOI at which 50% indels would be expected, using a 95% confidence interval.

Cas-VLP Homology-Directed Repair

Cas9-VLPs targeting BFP were produced as previously described (see Supplementary Table 1 (FIG. 14) for guide sequence). Cas9-VLPs were mixed with a single-stranded DNA template (IDT) in either DPBS (Thermo Fisher Scientific), Opti-MEM (Thermo Fisher Scientific), or SE/SF/SG buffer (Lonza). Unless otherwise noted, SE buffer (Lonza) with pulse code CM-150 was utilized. The mixture was electroporated using a 4D-nucleofector (Lonza) before immediately adding to 293T cells stably expressing a BFP-to-GFP reporter (Addgene plasmid #71825). A three-nucleotide conversion within the BFP gene results in GFP expression. Cells were analyzed for loss of BFP (non-homologous end joining) and gain of GFP (homology-directed repair)

expression after 5-7 days on a Attune NxT flow cytometer with a 96-well autosampler (Thermo Fisher Scientific).

Targeted Integration Analysis 15 k 293T cells treated with B2M-targeting or non-targeting Cas9-VLPs and DNA was isolated 3 days post treatment by resuspending in Quick Extract (Lucigen) and heating at 65° C. for 20 minutes followed by 95° C. for 20 minutes before storing at −20° C. A nested PCR approach using PrimeStar GXL DNA polymerase (Takara Bio) was used to detect integration of the lentiviral genome into the B2M genomic site targeted by Cas9. For PCR analysis of lentiviral integration, the B2M targeted region was first amplified using nested primer set #1 and cleaned up (NucleoSpin Gel and PCR Clean-Up kit, Takara Bio) followed by amplification with primer sets a-g (Supp. Table 2 (FIG. 15)). For MiSeq next generation sequencing analysis of targeted integration, the B2M targeted region was first amplified with nested primer set #2 and cleaned up (SPRI beads, UC Berkeley Sequencing Core) followed by amplification with primer sets to detect both integration orientations (primer pairs NGS Fwd and NGS Rev, Supp. Table 2 (FIG. 15)). Pair-end reads were merged, trimmed, and aligned to the expected sequence of lentiviral insertion into the expected Cas9 target site in the B2M gene (Geneious).

RNP Nucleofection

Cas9 RNPs were formed as previously described (Nguyen et al., 2020) at a 1:2 molar ratio between Cas9-NLS (UC Berkeley QB3 MacroLab) and annealed crRNA and tracrRNA (Horizon Discovery) in IDT duplex buffer with a polyglutamic acid electroporation enhancer, aliquoted and stored frozen at −80° C. until use. Cas9 RNPs (50 pmol) were electroporated into primary human T cells using a 96-well format 4D-nucleofector (Lonza) with the P3 buffer and the EH-115 pulse code Immediately after electroporation cells were rescued by adding growth media and incubating for 20 minutes prior to diluting to 0.5 to 1e6 cells/mL for culturing.

Flow Cytometry

Figures 5A, 5B, 5C, 5D, 5E:
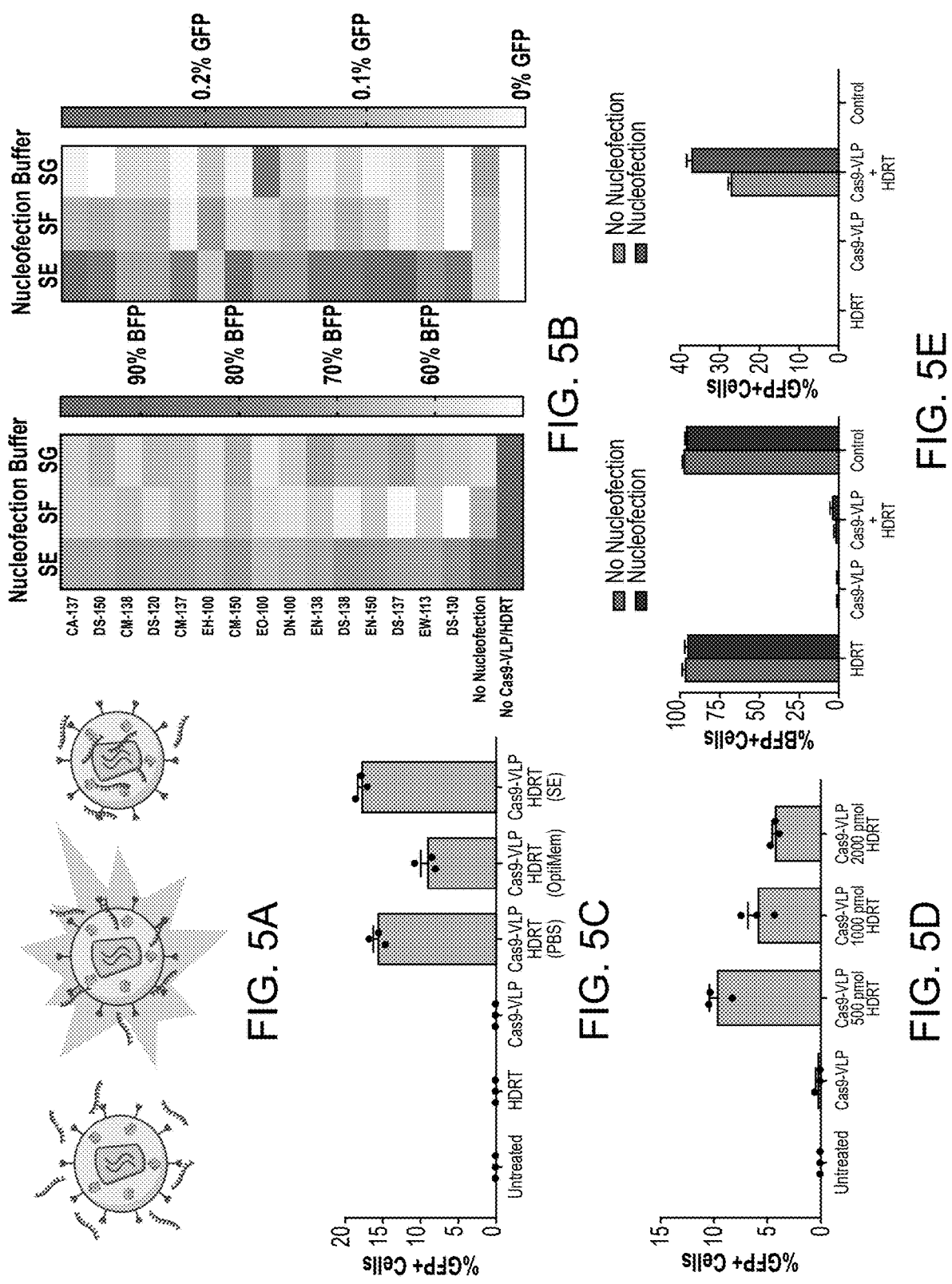
FIG. 5A-5E depict Cas9-VLP-mediated homology-directed repair (HDR).

All flow cytometry was performed on an Attune NxT flow cytometer with a 96-well autosampler (Thermo Fisher Scientific). Cells were resuspended in FACS buffer (1-2% BSA in PBS) and stained with the surface marker-targeting antibodies: B2M-FITC (Biolegend), B2M-PE (Biolegend), B2M-APC (Biolegend), CD4-FITC (Biolegend), CD8-PeCy7 (BD Biosciences), and TCRa/b-BV421 (Biolegend) and live/dead stains Ghost Dye red 780 (Tonbo) or Ghost Dye violet 450 (Tonbo), prior to analyzing. All analysis was done using the FlowJo v10 software. The gating strategy for flow cytometry can be seen in Supplementary FIGS. 5, 6, and 9.

Cytotoxicity Assay

Nalm-6 target cells were labelled using CellTrace Violet Cell Proliferation Kit (Thermo Fisher Scientific) according to the supplier's information. T cells were co-cultured with labelled target cells at various Effector:Target ratios for 16-24 hours. The percent of transduced cells were normalized by adding untransduced T cells. Absolute count of remaining living target cells was analyzed and percent killing was calculated by comparing to control wells (target cells only). Measurement was performed on an Attune NxT Flow Cytometer (Thermo Fisher Scientific).

Intracellular Cytokine and Activation Assay

Cells were stimulated with Nalm-6 target cells at an E:T ratio of 1:1. Transduction rates were normalized by adding untransduced T cells. 24 hours later, eBioscience Brefeldin A Solution (1000×) was added and incubated for 4 hours at 37° C. Cells were stained with extracellular antibodies eBioscience Fixable Viability Dye eFluor 780 (Thermo Fisher Scientific), CD25 PE-Cy7 (BD), CD69 PerCP (BioLegend), 4-1BB BV711 (BioLegend) and intracellular antibodies TNF-α Pacific Blue (BioLegend), IL-2 APC (BD) and IFN-g FITC (BioLegend) using the FIX & PERM Cell Fixation & Cell Permeabilization Kit (Thermo Fisher Scientific). CAR samples were gated on mCherry+ cells. Measurement was performed on an Attune NxT Flow Cytometer (Thermo Fisher Scientific).

Amplicon Sequencing

Genome editing was determined either by Sanger sequencing or next-generation sequencing; in both cases, the presence of insertions or deletions around the Cas9-targeted sequence was used to determine genome editing efficiency. Cells were pelleted and resuspended in QuickExtract (Lucigen) and heated at 65° C. for 20 minutes followed by 95° C. for 20 minutes before storing at −80° C. An amplicon containing the target sequence was amplified via PCR with Q5 polymerase (NEB) or PrimeStar GXL DNA polymerase (Takara Bio) and the resulting sample was cleaned with magnetic SPRI beads (UC Berkeley Sequencing Core). PCR amplicons were analyzed via Sanger sequencing (UC Berkeley Sequencing Core) and the resulting traces were deconvolved with Synthego's Inference of CRISPR Edits (ICE) program (https://ice.synthego.com). NGS sequencing was prepared similarly, but with PCR primers containing Illumina adapter sequences. PCR amplicons were analyzed on an Illumina MiSeq by QB3 Genomics at UC Berkeley. Paired-end NGS reads were analyzed for indels with CRISPResso2 (https://crispresso.pinellolab.partners.org).

Statistical Analysis

Statistical analysis was performed in Prism v7, v8, and v9. Statistical details for all experiments, including value and definition of n, error bars, and significance thresholds can be found in the Figure Legends.

Results

Engineering Lentivirus-Based VLPs for the Controlled Delivery of Cas9 RNP Complexes Lentiviral production involves the co-transfection of producer cells with plasmids encoding the viral structural components, viral glycoprotein, and lentiviral transfer plasmid with a transgenic sequence flanked by long terminal repeat (LTR) sequences. To promote packaging of Cas9 protein in HIV-1 VLPs (Cas9-VLPs), a plasmid was constructed to express *S. pyogenes* Cas9 fused to the C-terminus of the Gag polypeptide and included this during lentiviral production. A lentiviral transfer plasmid encoding expression cassettes for both an mNeonGreen fluorescent reporter and a single guide RNA (sgRNA) was included (FIG. 1A). To promote the separation of Cas9 from Gag during proteolytic virion maturation, an HIV-1 protease-cleavable linker was inserted between Gag and Cas9 (FIG. 1B). Cas9-VLPs pseudotyped with the broadly-transducing vesicular stomatitis virus glycoprotein (VSV-G) was produced. The ratio of Gag-pol and Gag-Cas9 plasmids was varied to optimize Cas9 incorporation in budded particles. Bands corresponding to the expected size of Cas9 fused to Gag (55 kDa+160 kDa=215 kDa) and proteolytically released Cas9 (160 kDa) were detectable by western blot in all Cas9-VLP formulations tested (FIG. 1C). A component of the Gag polypeptide, capsid (CA), was used for quantifying Cas9-VLP production by ELISA. CA-containing particles were detected for all formulations except for Cas9-VLP formulation F (FIG. 1D). Formulation F is composed entirely of Gag-Cas9 polypeptides which may interfere with the successful budding of Cas9-VLPs from transfected cells.

Figure 1F:
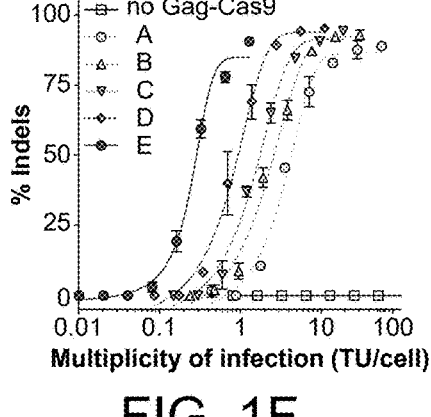
Figure 1G:
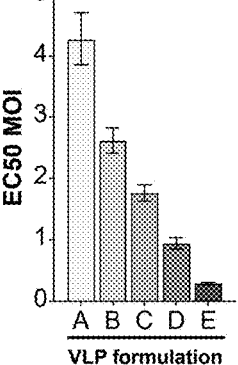

It was hypothesized that Cas9-VLPs packaging relatively high Gag-Cas9 polypeptide content would require fewer individual Cas9-VLPs to deliver a sufficient quantity of Cas9 RNPs for successful genome editing. To assess genome editing activity, Cas9-VLPs were produced with a lentiviral transfer plasmid expressing a sgRNA targeting the beta-2 microglobulin (B2M) gene. The transduction-competent Cas9-VLP titer (TU/mL) was quantified for each Cas9-VLP preparation (FIG. 1E), and was used to calculate the multiplicity of infection (MOI, TU/cell) required to achieve 50% editing (effective concentration 50, EC50 MOI) in the Jurkat cells (FIG. 1F). It was confirmed that as increasing amounts of Gag-Cas9 are packaged per particle, a lower EC50 MOI is needed to achieve genome editing (FIG. 1G) with an approximate MOI=2.6 required to achieve 50% indels using Cas9-VLP formulation B and MOI=0.9 using Cas9-VLP formulation D.

FIG. 1A-1G. Production and characterization of Cas9-VLPs. (A) Schematic of plasmids for Cas9-VLP production. GP=glycoprotein. LV=lentiviral transfer plasmid. LTR=long terminal repeat. (B) Schematic of an immature Cas9-VLP produced through transient transfection. An HIV-1 protease cleavable linker (SQNYPIVQ; SEQ ID NO:155) was inserted between Gag and Cas9. (C) Western blot of Cas9-VLP content with various ratios of Gag-pol and Gag-Cas9 plasmids used for production. Anti-FLAG (Cas9) and anti-p24 (capsid, CA) antibodies were used for detection. (D) Quantification of Cas9-VLPs produced per transfected p100 dish by CA ELISA, n=2 technical replicates. (E) Jurkat cell ("Jurkats") were treated with B2M-targeting Cas9-VLP and the transducing units (TU) per mL titer was calculated. (F) Percent B2M indels plotted against the multiplicity of infection (MOI) using a sigmoidal four parameter logistic fit. Indels were quantified using Synthego's ICE analysis tool. (G) The predicted MOI for each Cas9-VLP formulation to achieve 50% indels, (interpolated from F). EC50=effective concentration at which a drug gives a half-maximal response. n=3 technical replicates (E, F), except for formulation A (n=2) (F). Error bars indicate standard error of the mean (D, E, F) and 95% confidence interval (G). ND=not detected.

Characterization of Cas9-VLPs for Genome Editing

Figures 2A, 2B, 2C, 2D, 2E, 2F:
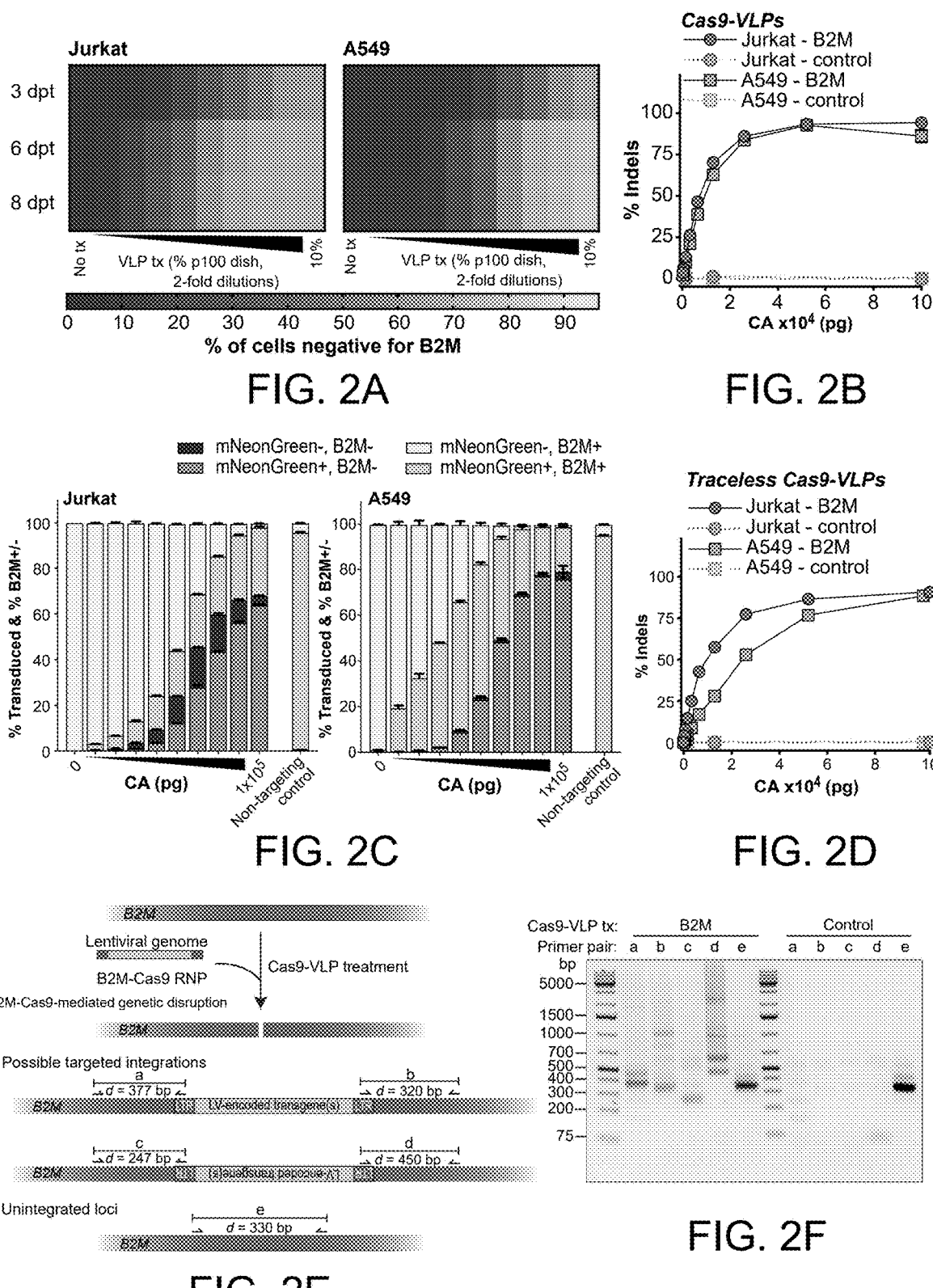
FIG. 2A-2F depict efficient genome editing by Cas9 VLPs.

The kinetics of genome editing following Cas9-VLP treatment was assessed. Jurkat and A549 cells were treated with formulation D B2M-targeting Cas9-VLPs and cell-surface expressed B2M protein was assessed by flow cytometry at 3, 6, and 8 days post treatment. Dose-dependent knockout of B2M protein was observed by day 3 (FIG. 2A), with a maximum loss of protein expression achieved by day 6. Genetic knockout was further confirmed by next-generation sequencing and observed B2M-guide specific indels at the B2M locus (FIG. 2B). Similar to what has been observed for Cas9-packaging MLV VLPs (Mangeot et al., 2019), mixing Cas9-VLPs with a DNA template was sufficient to mediate homology-directed repair (HDR) in a fluorescence reporter assay (Richardson et al., 2016). It was found that Cas9-VLP-directed HDR activity could be further enhanced by electroporating Cas9-VLPs with the DNA template prior to the treatment of target cells, which may promote complexing of Cas9-VLPs with the HDR template (FIG. 5A-5E).

Current RNP-based genome editing approaches have not permitted the quantification of cells edited as a function of the number of cells receiving RNPs. It was reasoned that Cas9-VLPs co-delivering Cas9 RNPs and a lentiviral genome may enable tracking cells that receive Cas9 RNPs. To assess whether transduction is a marker of RNP-edited cells, A549s and Jurkats were treated with serial dilutions of B2M-Cas9-VLPs delivering the mNeonGreen transgene and quantified B2M expression at day 6 post treatment (FIG. 2C, FIG. 6A-6F). For Jurkats, successfully-edited cells largely correlated with the transduction marker mNeonGreen; however, a population of B2M-knockout cells that did not express mNeonGreen was observed. It was hypothesized that this discordance could be explained by a proportion of Cas9-VLPs not co-packaging both the lentiviral genome and Cas9 RNPs. However, in A549 cells treated with the same Cas9-VLP preparation, cells lacking B2M overwhelmingly expressed the transduction marker. This suggests that in the A549 cell line, transduction is a reliable marker for identifying the cell population edited by Cas9 RNPs and that Jurkats may employ a cell-intrinsic mechanism restricting reverse transcription of the lentiviral genome, nuclear import, or integration independent of Cas9-mediated genome editing.

Figures 7A, 7B, 7C, 7D, 7E, 7F:
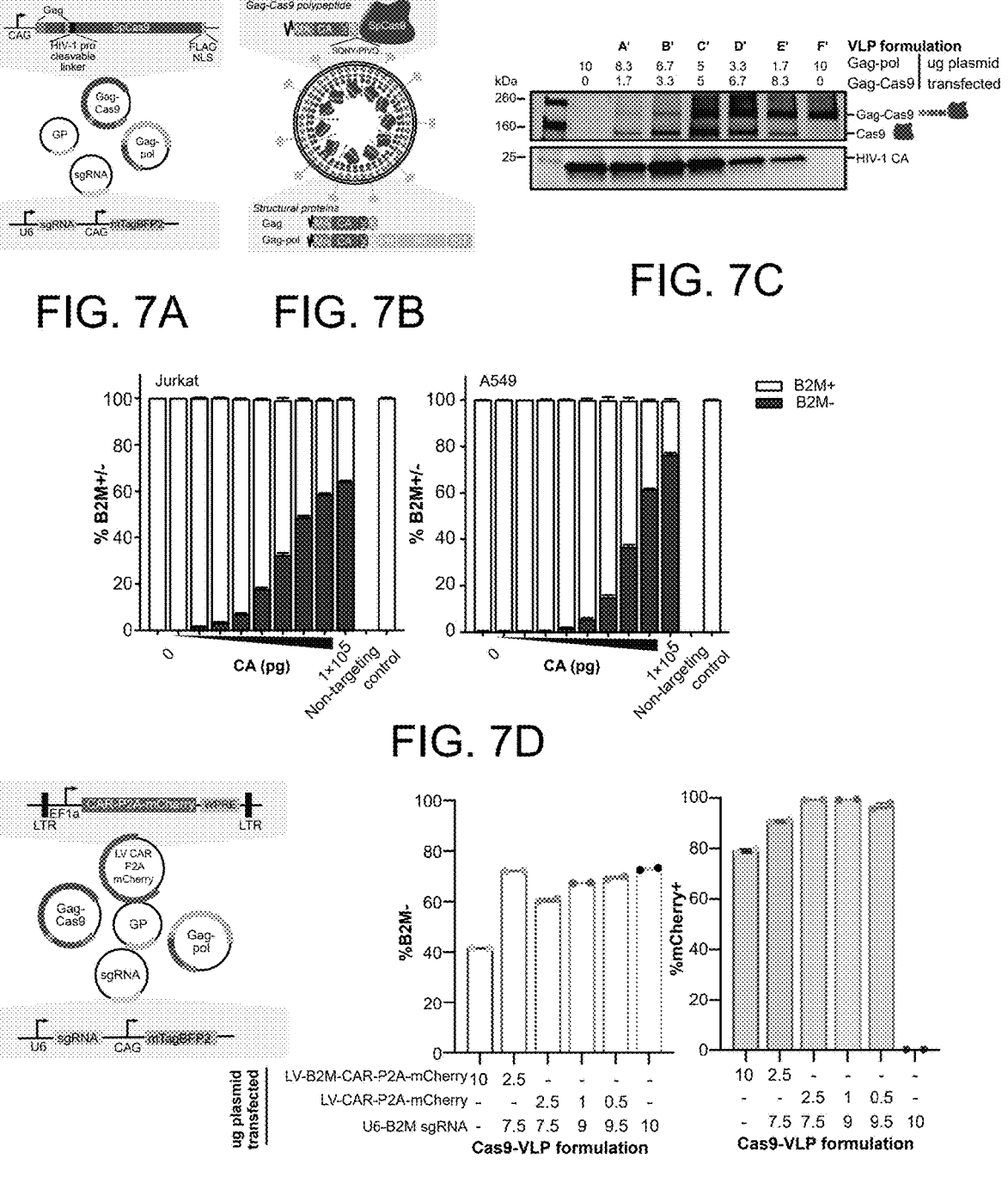
FIG. 7A-7F depict data showing that traceless Cas9-VLPs mediate genome editing without viral transgene insertion and hybrid Cas9-VLPs do not require a lentiviral-encoded guide RNA expression cassette.

As the sgRNA expression cassette is embedded within the lentiviral genome, sgRNA transcription could occur both in the packaging cell line during Cas9-VLP production and in transduced cells. To assess whether Cas9 RNP formation occurs predominantly in the packaging cells or in the treated cells, Cas9-VLPs lacking a lentiviral genome were produced; the B2M sgRNA was expressed instead from an orthogonal expression plasmid. It was found that treatment with "traceless" Cas9-VLPs mediated high levels of editing (FIG. 2D, FIG. 7A-7D) suggesting the majority of Cas9 RNPs are formed within the packaging cell line. A slight increase in editing efficiency was noted when a lentiviral genome including the sgRNA expression cassette was co-packaged within the Cas9-VLP (FIG. 2B vs. FIG. 2D) suggesting, at this concentration, a fraction of VLP-packaged Cas9 may remain in the guideless apo-Cas9 state until sgRNA transcription occurs in treated cells. It was also possible to generate hybrid Cas9-VLPs that co-package a lentiviral genome but do not require a lentiviral-encoded guide RNA expression cassette (FIG. 7E-7F). Together, the ability of Cas9-VLPs to deliver Cas9 RNPs without co-packaging a lentiviral genome enables Cas9-VLPs to mediate genome editing in the absence of transgene integration, which may be advantageous for clinical applications.

As Cas9-VLPs deliver the reverse-transcribed viral genome concomitantly with dsDNA-break inducing Cas9 RNPs, it was reasoned that targeted lentiviral insertion may occur at the genomic site targeted for genome editing. To investigate this possibility, DNA was isolated from cells treated with either B2M-targeting or non-targeting Cas9-VLPs co-packaging a lentiviral genome. Amplification of cellular genomic DNA with primers specific to the B2M locus and the lentiviral LTR resulted in detectable viral insertion at the Cas9-targeted region (FIG. 2E-F). This was further validated using primers specific to the B2M locus and the lentiviral Psi sequence, and next-generation sequencing confirmed targeted lentiviral integration (FIG. 8A-8D).

FIG. 2A-2F. Cas9-VLPs efficiently mediate genome editing. B2M-targeting Cas9-VLP treatment results in genome editing of Jurkat and A549 cells. (A) Flow cytometry quantification of B2M expression at 3, 6, and 8 days post treatment (dpt). Heat maps represent the mean of technical replicates, n=3, except for A549 at 8 dpt (n=2). The highest treatment dose=10% of Cas9-VLPs produced in a p100 dish. (B) Amplicon sequencing quantification of indels, 3 dpt. Control=tdTom298 sgRNA. n=3 technical replicates, except for A549 treated with $10\times10^4$ pg CA (n=2). (C) Flow cytometry quantification of B2M expression and transduction (mNeonGreen+), 6 dpt. Non-targeting control=guideless Cas9-VLP. n=3 technical replicates. (D) Treatment with Cas9-VLPs that target B2M but do not co-package a lentiviral genome. Amplicon sequencing quantification of indels, 3 dpt. Control=tdTom298 sgRNA. n=3 technical replicates, except for Jurkats treated with $10\times10^4$ pg CA traceless B2M Cas9-VLPs (n=2). (E) Schematic of hypothetical lentiviral insertion at the Cas9 RNP-induced DNA break. (F) PCR assessment of targeted lentiviral integration. DNA was isolated from 293T cells 3 dpt with B2M-targeting or non-targeting Cas9-VLPs and indicated primer pairs were used for analysis. Error bars indicate standard error of the mean.

FIG. 5A-5E. Cas9-VLPs mediate homology-directed repair (HDR). (A) Schematic of nucleofection of Cas9-VLPs and single-stranded DNA homology-directed repair templates (HDRT, purple). (B) Assessment of different Lonza nucleofection buffers and pulse codes, 5 days post treatment. Cas9-VLPs packaging BFP-targeting RNPs were mixed with 80 pmol HDRT and nucleofected using the indicated nucleofection buffers and pulse codes. Nucleofected HDRT/Cas9-VLPs were subsequently used to treat a BFP-to-GFP HDR reporter HEK293 cell line (Richardson et al., 2016) where BFP knockout is indicative of non-homologous end joining and GFP expression is representative of HDR. (C) HDR-mediated GFP expression induced treatment with Cas9-VLPs nucleofected (Lonza, CM-150) with 500 pmol HDRT in different buffers, 7 days post treatment. (D) HDR-mediated GFP expression with varying concentrations of HDRT nucleofected (Lonza, CM-150) with Cas9-VLPs in SE buffer (Lonza), 7 days post treatment. (E) Pre-nucleofection of Cas9-VLPs and HDRT enhances HDR activity. Cas9-VLPs ($2.59\times10^6$ pg CA) and 500 pmol HDRT were mixed in SE buffer and either directly added to BFP-to-GFP reporter cells or subjected to nucleofection (Lonza, CM-150) prior to cell treatment. BFP-positive and GFP-positive cells were quantitated by flow cytometry at 7 days post treatment. All error bars represent standard error of the mean.

FIG. 6A-6F. All Cas9-VLP formulations mediate genome editing, Jurkat or A549 cells were treated with B2M-Cas9-VLP formulations A-E and transduction (mNeonGreen+) and B2M expression were assessed by flow cytometry 6 days post treatment. Of note, cells transfected to produce B2M-targeted Cas9-VLPs themselves undergo genome editing (DNA isolated 3 days post transfection). n=3 technical replicates were performed at each Cas9-VLP treatment dose and error bars represent standard error of the mean.

FIG. 7A-7F. Traceless Cas9-VLPs mediate genome editing without viral transgene insertion and hybrid Cas9-VLPs do not require a lentiviral-encoded guide RNA expression cassette. (A) Schematic of plasmids used for the production of traceless Cas9-VLPs. GP=glycoprotein. (B) Schematic of an immature, pre-proteolytically processed Cas9-VLP, produced through transient transfection and lacking a lentiviral genome. An HIV-1 protease cleavable linker containing SQNY/PIVQ was inserted between the c-termini of Gag and the n-termini of Cas9 to promote the separation during proteolytic virion maturation. (C) Western blot of Cas9-VLP content when various ratios of Gag-pol to Gag-Cas9 plasmids are used for production. An anti-Flag antibody was used for Cas9 detection and an anti-HIV-1 capsid (CA) antibody was used to detect Cas9-VLP production. A' is used to indicate VLP formulation "A" lacking a packaged lentiviral genome. (D) Flow cytometry quantification of B2M expression in A549 and Jurkats 6 days post treatment with traceless Cas9-VLPs. Non-targeting control=Cas9-VLPs packaging the tdTom298 sgRNA. n=3 technical replicates were performed at each Cas9-VLP treatment dose and error bars indicate standard error of the mean. (E) Schematic of plasmids used for the production of Cas9-VLPs that co-package Cas9 RNPs and a lentiviral genome that lacks a guide RNA expression cassette ("hybrid Cas9-VLPs"). (F) Optimization of hybrid Cas9-VLPs. Cas9-VLPs were produced as indicated and used to treat Jurkat cells. Targeted protein disruption (% of cells negative for B2M expression) and transduction (% of cells mCherry positive) was quantified at day 7. LV-B2M-CAR-P2A-mCherry=lentiviral transfer plasmid that encodes the U6-promoter driven expression of a B2M-targeting guide RNA and the EF1a-promoter driven expression of a CAR-P2A-mCherry transgene. LV-CAR-P2A-mCherry=lentiviral transfer plasmid that encodes the CAR-P2A-mCherry expression cassette alone. U6-B2M=a transient guide RNA expression plasmid.

FIG. 8A-8D. Targeted integration of the lentiviral genome into the Cas9 RNP target site. (A) Schematic of hypothetical lentiviral insertion at the Cas9 RNP-induced double-stranded DNA break. (B) PCR to assess targeted lentiviral integration. DNA was isolated from 293T cells 3 days post treatment with B2M-targeting or non-targeting Cas9-VLPs and the indicated primer pairs were used for analysis. (C) MiSeq analysis of the targeted "forward" lentiviral integration in cells treated with B2M Cas9-VLPs. Reads mapped to the hypothetical B2M-lentiviral junction are shown. (D) MiSeq analysis of the targeted "reverse" lentiviral integration in cells treated with B2M Cas9-VLPs. Reads mapped to the hypothetical B2M-lentiviral junction are shown. Amplicon sizes include Illumina adaptor sequences, see Table S2 (FIG. 15).

Example 2: Cas9-VLPs Efficiently Edit Primary Human T Cells

Figures 3A, 3B, 3C, 3D, 3E, 3F:
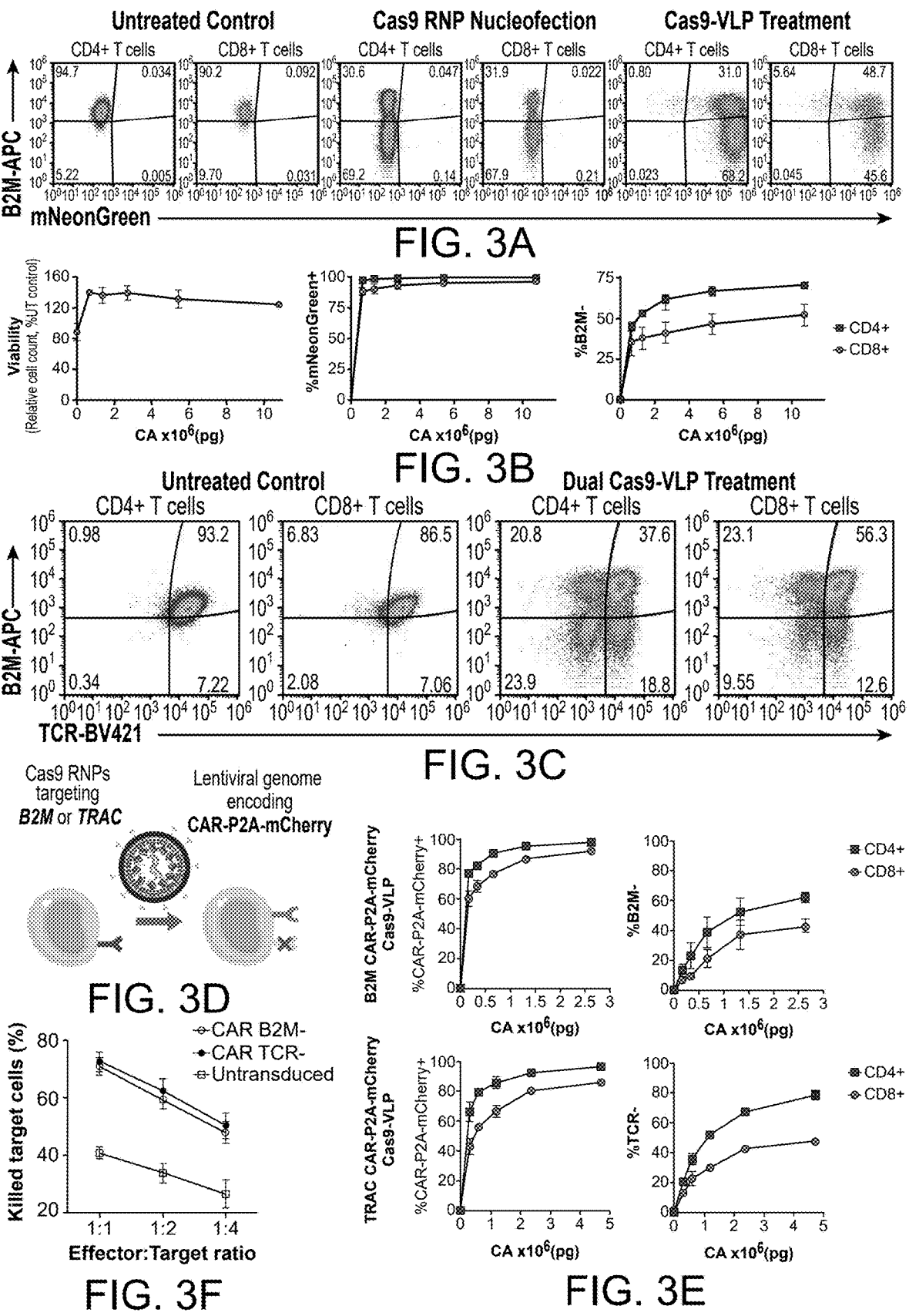
FIG. 3A-3F depict generation of highly engineered CAR-expressing primary human T cells using Cas9-VLPs.

Engineered T cell therapies are transforming the treatment of certain cancers by retargeting T cell activity through introduction of antigen-specific receptors such as chimeric antigen receptors (CARs) (Fesnak et al., 2016; Sadelain et al., 2017). It was tested if Cas9-VLPs could mediate genome editing in primary human T cells. Transducing bulk CD4+ and CD8+ primary human T cells with Cas9-VLPs resulted in B2M knockout levels comparable to Cas9 RNP electroporation, the current clinical standard (FIG. 3A, FIG. 3B, FIG. 9A-9B). Cas9-VLP-mediated transduction and B2M knockout was dose-dependent and cellular viability (as measured by relative cell count) was improved compared to previous reports employing Cas9 RNP nucleofection (Roth et al., 2018) (FIG. 3B).

Figures 10A, 10B, 10C, 10D:
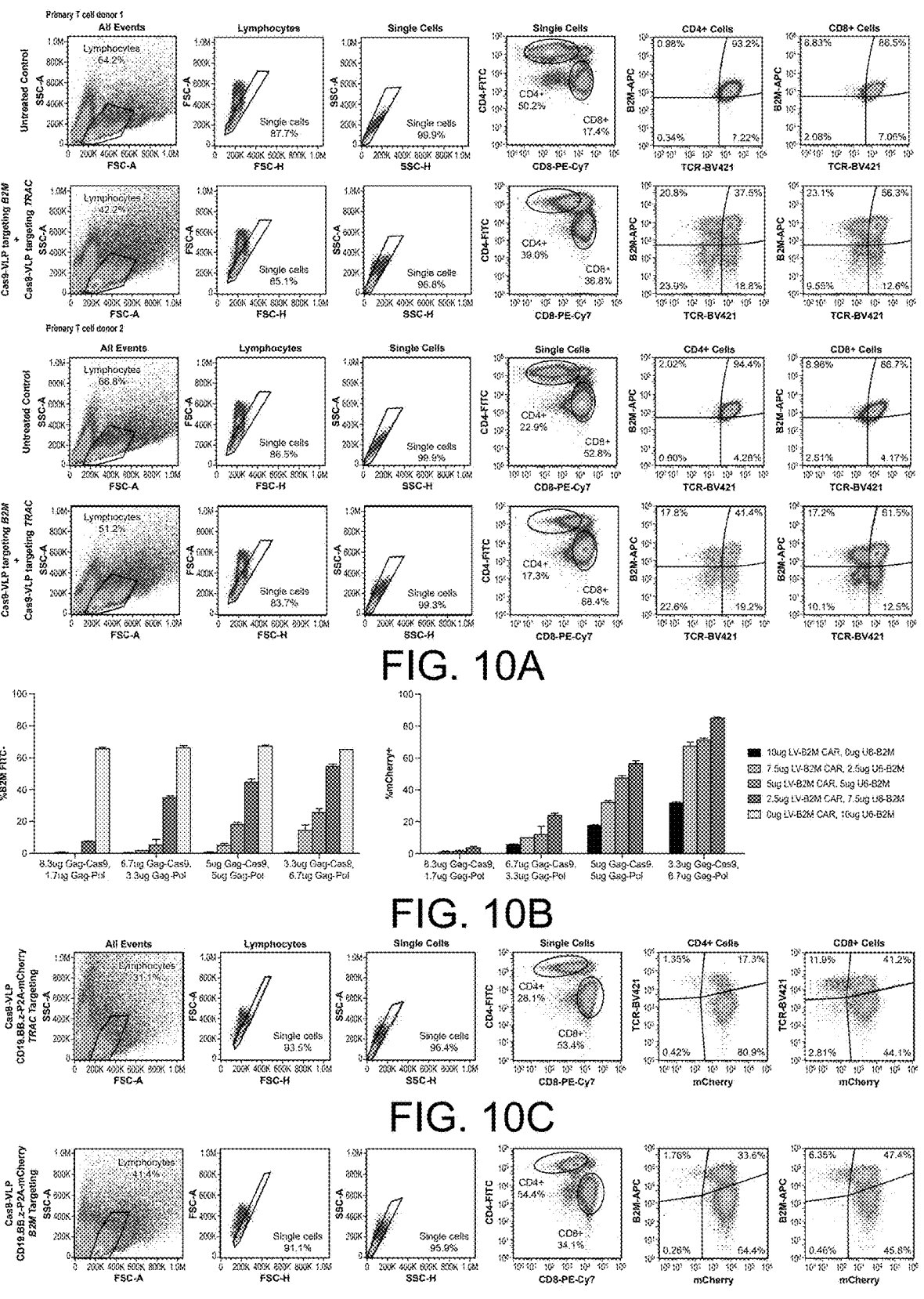
FIG. 10A-10D depict optimization of CAR-Cas9-VLP production & representative flow cytometry gating strategy for Cas9-VLP-mediated multiplexed genome engineering of primary human CAR-T cells.
Figures 11A, 11B:
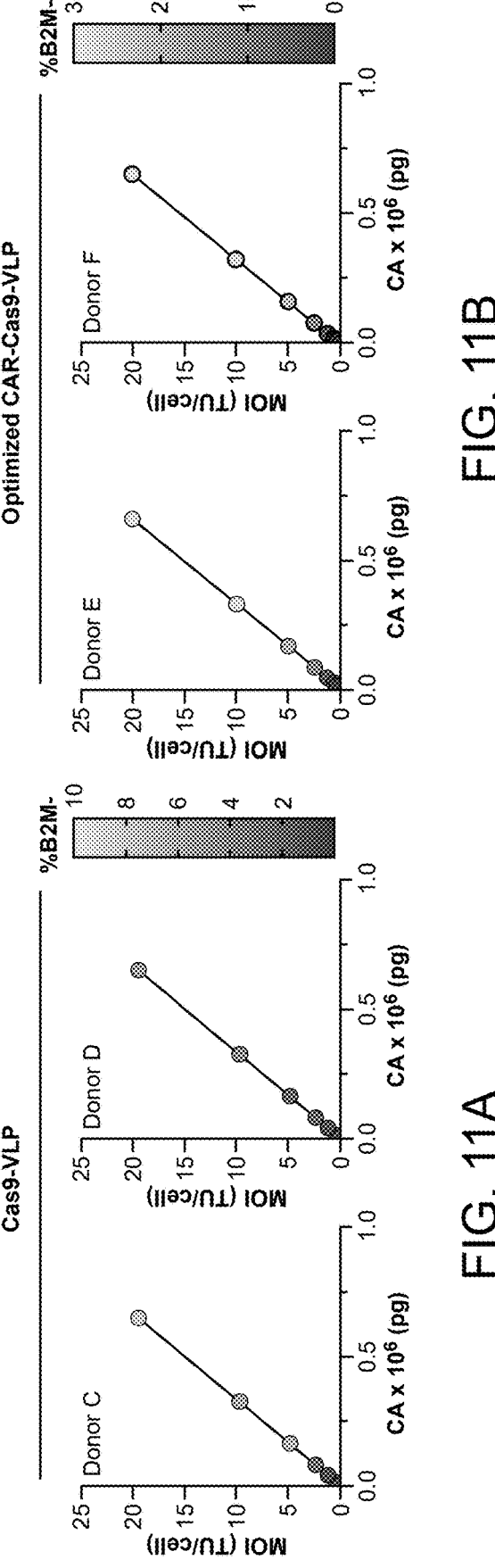
FIG. 11A-11B depict Cas9-VLP genome editing as a function of multiplicity of infection (MOI) and quantity of CA.
Figure 12:
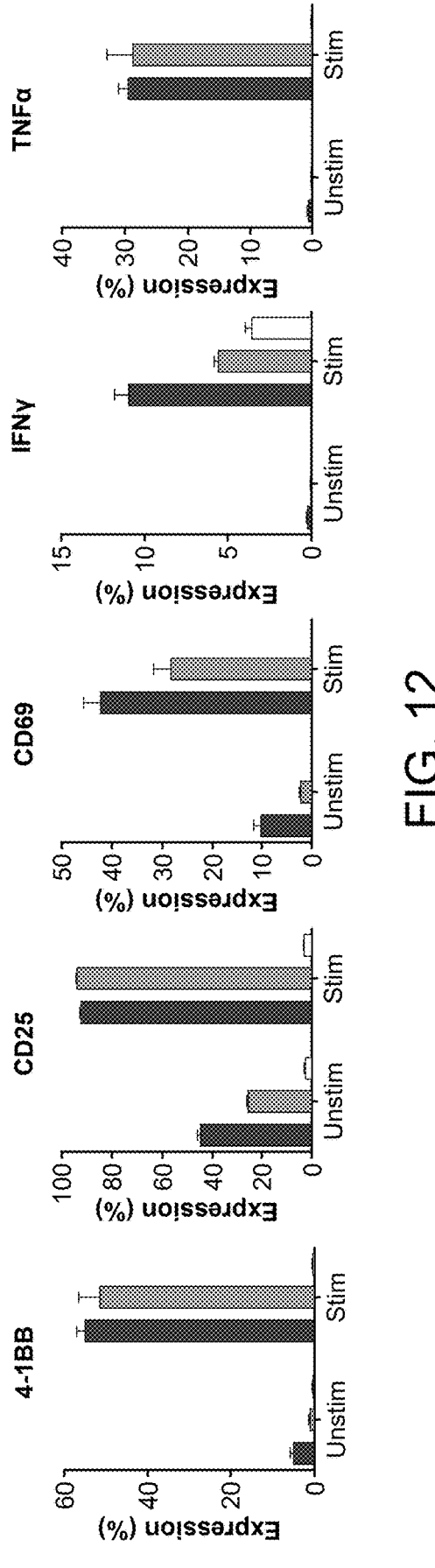
FIG. 12 depicts functional cytokine production and surface receptor expression in Cas9-VLP generated CAR-T cells.

Recently, transgenic T cell receptor (TCR) T cells modified by CRISPR-Cas9 were tested in the first phase I clinical trial (Stadtmauer et al., 2020). The engineered T cell product was produced by electroporation of Cas9 RNPs to first disrupt expression of PD-1 and the endogenous TCR (by targeting PDCD1 and TRAC, respectively) followed by subsequent lentiviral transduction to integrate an exogenous TCR for retargeting antigen specificity. It was hypothesized that Cas9-VLPs could simplify the production of multiply-edited engineered T cells by simultaneously delivering Cas9 RNPs and a lentiviral genome encoding a transgenic TCR or CAR (FIG. 3D). To test this, it was assessed whether it was possible to multiplex genetic knockout by treating primary human T cells with Cas9-VLPs targeting two genetic loci for disruption. Treatment of primary human T cells with separate Cas9-VLPs targeting B2M or TRAC resulted in 23.9% CD4+ and 9.55% CD8+ double-knockout cells by 13 days post treatment (FIG. 3C, FIG. 10A). The production of Cas9-VLPs was optimized to maximize the simultaneous integration of a lentiviral-encoded CAR and knockout of B2M expression in Jurkats ("CAR-Cas9-VLPs") (FIG. 10B). To determine how capsid quantity correlates to MOI in primary T cells, genome editing levels generated using both mNeonGreen and CAR Cas9-VLPs were assessed. An approximate MOI=20 for mNeonGreen Cas9-VLPs resulted in ~7% of cells lacking B2M protein while the equivalent MOI for CAR-Cas9-VLPs resulted in ~28% B2M-negative cells (FIG. 11A-11B). The enhanced editing efficiency of CAR-Cas9-VLPs may be explained by a higher proportion of VLP-packaged Cas9 being associated with guide RNA, as the optimized CAR-Cas9-VLP production involves over-expression of guide RNA in VLP producer cells (FIG. 10B). CAR-Cas9-VLPs packaging Cas9 RNPs targeting either B2M or TRAC for disruption were generated. Primary T cells treated with such RNPs exhibited dose-dependent CAR-P2A-mCherry expression and reduction in surface-expressed B2M or TCR (FIG. 3E, FIG. 10D-10D). Additionally, Cas9-VLP-engineered CAR-T cells were functionalized to kill CD19+ Nalm-6 target cells (FIG. 3F) and stimulation resulted in effector profiles for cytokine production and activation marker expression (FIG. 12). Together, Cas9-VLPs provide a simplified workflow for manufacturing complex CRISPR-modified CAR-T cells in a single step which compares favorably to current clinical manufacturing methods.

FIG. 3A-3F. Generation of highly engineered CAR-expressing primary human T cells using Cas9-VLPs. (A) Cas9 RNP nucleofection and Cas9-VLP treatment of primary human T cells. Flow cytometry quantification of the mNeon-Green transduction marker and B2M expression, 7dpt. (B) Viability, transduction, and B2M expression in primary human T cells treated with Cas9-VLPs. B2M expression is plotted for CD4+(red squares) and CD8+(blue circles) sub-populations. (C) Simultaneous treatment with two Cas9-VLPs results in multiplexed genome editing. Cas9-VLPs targeting B2M and Cas9-VLPs targeting TRAC were used to co-treat primary human T cells. Surface expression of B2M and TCR was assessed by flow cytometry, 13 dpt. n=2 biological replicates from independent donors were used (A, B, C) and representative flow cytometry plots are shown for one donor (A, C). (D) Schematic of a single-step method to generate highly engineered CAR-T cells. (E) Primary human T cells were treated with CAR-Cas9-VLPs targeting B2M (top panels) or TRAC (bottom panels). Knockout was assessed for both CD4+(red squares) and CD8+(blue circles) subpopulations, 12 dpt. (F) CAR-T cells generated by Cas9-VLP treatment, or untreated primary human T cells, were co-cultured with CD19+Nalm-6 cells and cytotoxic killing activity was measured at 24 h. Error bars indicate standard error of the mean.

Figures 9A, 9B:
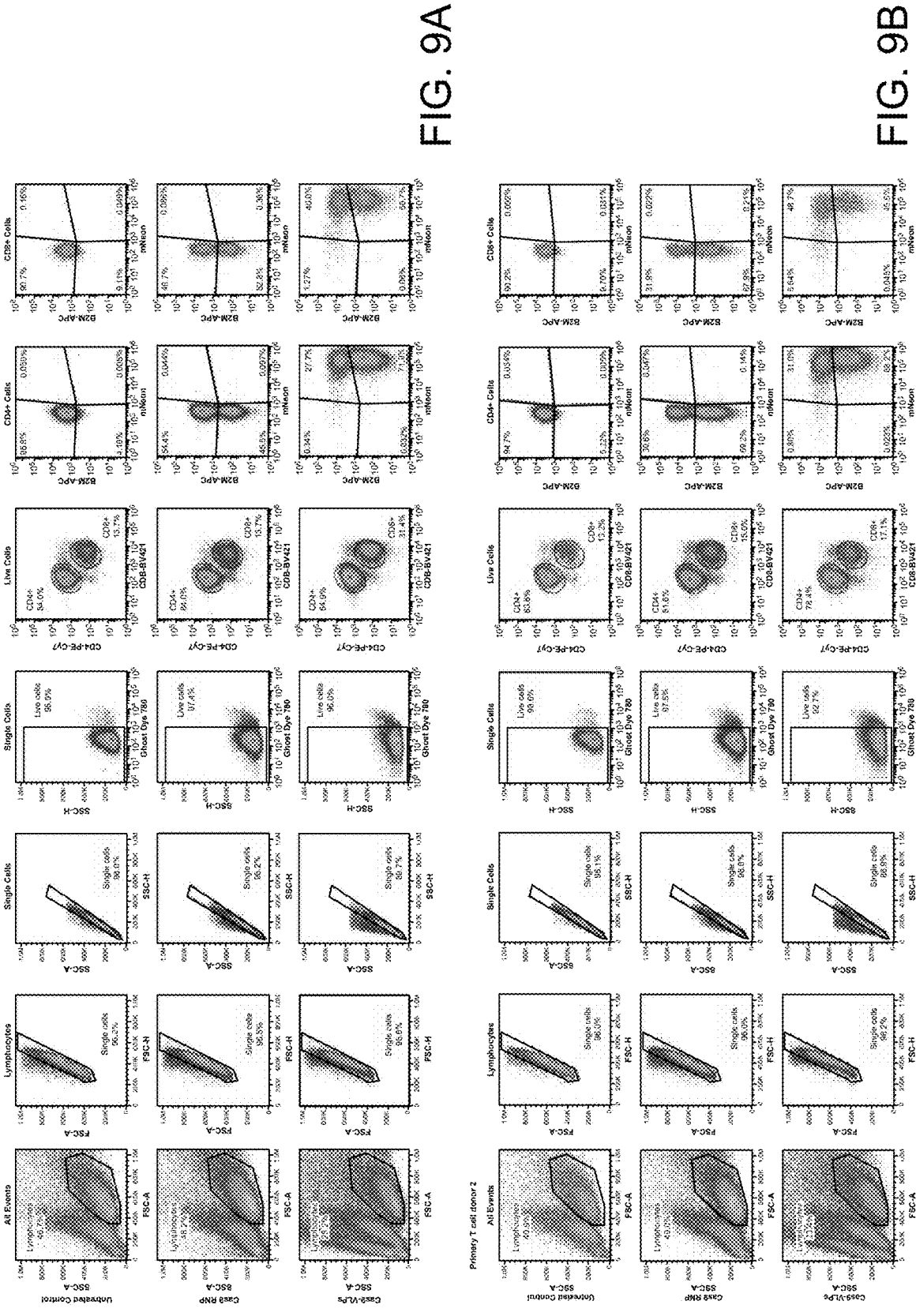
FIG. 9A-9B depict representative flow cytometry gating strategy for quantifying genome editing in primary human T cells.

FIG. 9A-9B. Representative flow cytometry gating strategy for quantifying genome editing in primary human T cells. (A) Flow cytometry gating strategy to assess surface-expressed B2M in primary human T cells after no treatment, nucleofection of Cas9 RNPs, and treatment with Cas9-VLPs from donor 1. (B) Flow cytometry gating strategy to assess surface-expressed B2M in primary human T cells after no treatment, nucleofection of Cas9 RNPs, and treatment with Cas9-VLPs from donor 2.

FIG. 10A-10D. Optimization of CAR-Cas9-VLP production & representative flow cytometry gating strategy for Cas9-VLP-mediated multiplexed genome engineering of primary human CAR-T cells. (A) Flow cytometry gating strategy to assess the dual knockout of surface-expressed TCR and B2M by simultaneous treatment with Cas9-VLPs targeting TRAC and Cas9-VLPs targeting B2M in two independent T cell donors. Cas9-VLPs optimized for simultaneous CAR transgene insertion and B2M knockout were used (FIG. 9B). (B) Optimization of Cas9-VLP production to maximize simultaneous CAR transgene integration and genome editing. Cas9-VLPs were produced with various ratios of plasmids encoding the Gag-Cas9 and Gag-pol structural proteins, and with various ratios of plasmids encoding a lentiviral transfer plasmid (encoding expression cassettes for U6-B2M CAR-P2A-mCherry) and a U6-B2M guide RNA expression plasmid. Jurkats were treated, passed at day 4 post treatment to maintain subconfluent culture conditions and flow cytometry was performed at 6 days post treatment to quantify B2M expression (B, left) and CAR-P2A-mCherry expression (B, right). Cas9-VLPs produced through transient transfection with the following plasmids were most efficient at mediating simultaneous knockout of B2M and CAR-P2A-mCherry transgene expression: 1 μg VSV-G, 3.3 μg Gag-Cas9, 6.7 μg Gag-pol plasmid, 2.5 μg LV-B2M, and 7.5 U6-B2M. n=2 replicates per treatment, error bars represent standard error of the mean. (C) How cytometry gating strategy to assess the knockout of surface-expressed TCR and expression of CAR-P2A-mCherry in primary human T cells by treatment with Cas9-VLPs. (D) Flow cytometry gating strategy to assess the knockout of surface-expressed B2M and expression of CAR-P2A-mCherry in primary human T cells by treatment with Cas9-VLPs.

FIG. 11A-11B. Cas9-VLP genome editing as a function of MOI and quantity of CA. (A) Cas9-VLPs co-packaging B2M-targeting Cas9 RNPs and a lentiviral genome encoding mNeonGreen were generated (as used in FIG. 3) and (B) Cas9-VLPs optimized to co-package B2M-targeting Cas9 RNPs and a lentiviral genome encoding CAR-P2A-mCherry were produced. The transducing units/mL (TU/mL) titer and capsid (CA) content were quantified for each Cas9-VLP preparation. Primary T cells from two human donors were treated with indicated multiplicity of infection (MOI) and picogram (pg) CA and cells negative for B2M protein were quantified by flow cytometry at day 7.

FIG. 12. Functional cytokine production and surface receptor expression in Cas9-VLP generated CAR-T cells. Cytokine and surface receptor expression were quantified in stimulated and unstimulated CAR-T cells generated from Cas9-VLPs at 24 h. For all, n=2 biological replicates from independent donors were used and error bars indicate standard error of the mean.

Example 3: Cell-Type Specific Editing Via Pseudotyping of Cas9-VLPs

Figures 4A, 4B, 4C:
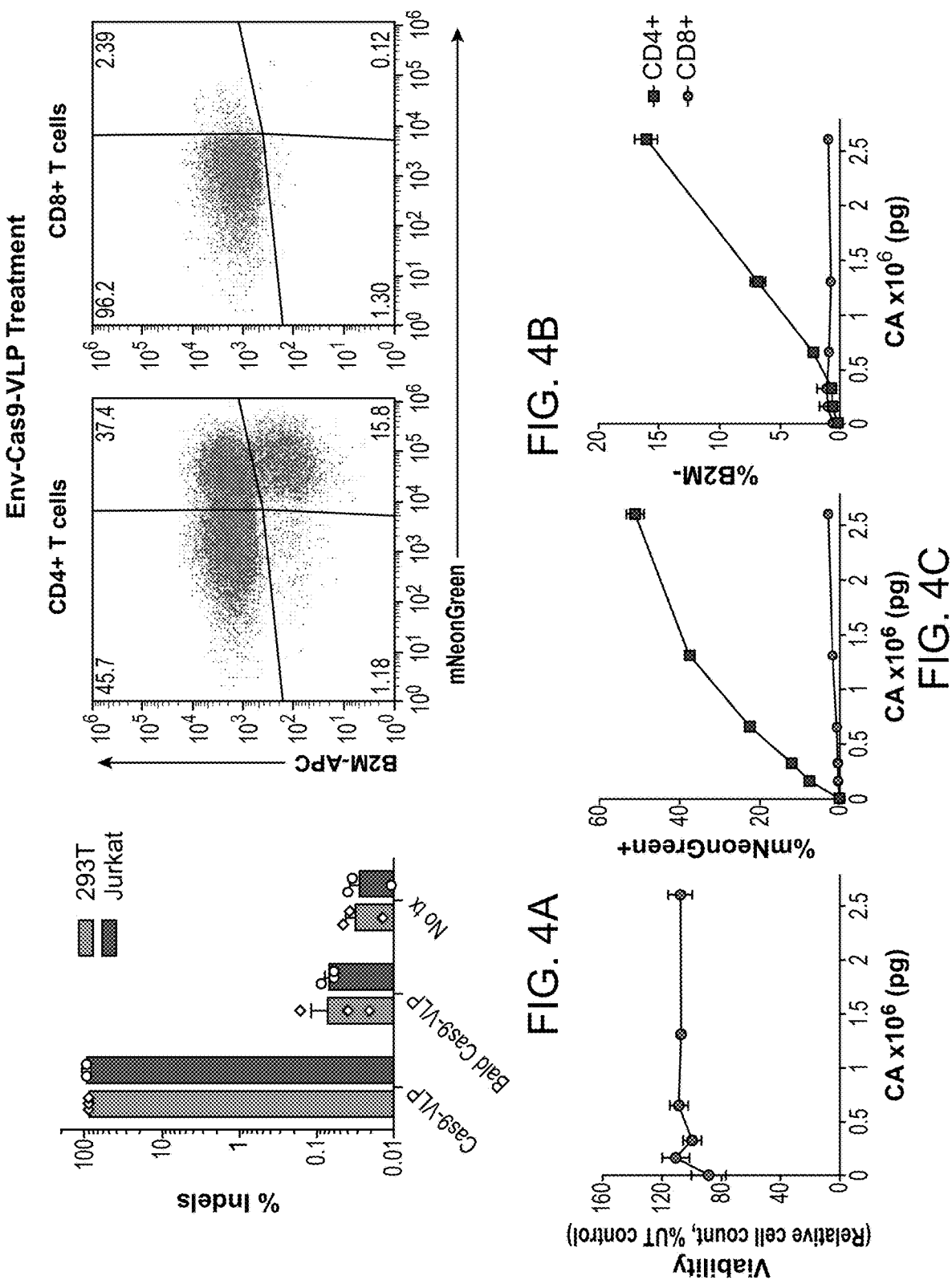
FIG. 4A-4C depict targeting Cas9-VLP genome editing to CD4+ T cells by HIV-1 Envelope pseudotyping.
Figures 13A, 13B, 13C, 13D, 13E, 13F, 13G:
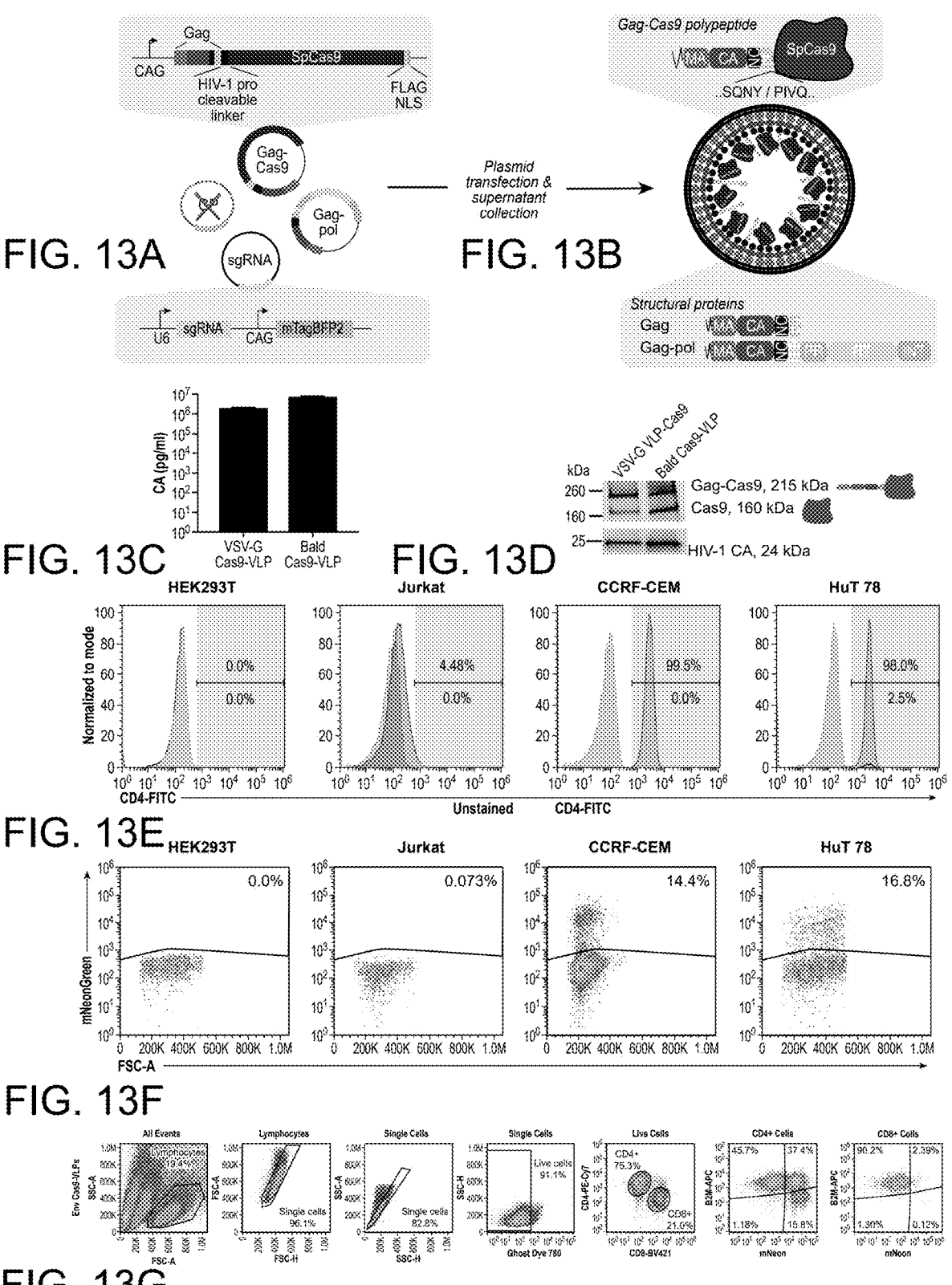
FIG. 13A-13G depict characterization of bald and HIV-1 Env pseudotyped Cas9-VLPs.

Virus and VLP cell-type specificity may be altered through pseudotyping with varied surface glycoproteins (Cronin et al., 2005). To test whether the Cas9-VLP glycoproteins were essential for the genome editing of mammalian cells, Cas9-VLPs lacking viral glycoproteins ("bald" Cas9-VLPs) were produced and their ability to mediate genome editing was assessed. "Bald" Cas9-VLPs were effectively produced (FIG. 13A-13D) but cellular treatment resulted in <0.1% of reads containing indels by deep sequencing, a 3-log reduction in genome editing compared to treatment with VSV-G pseudotyped Cas9-VLPs (FIG. 4A). Efficient delivery of VLP-packaged Cas9 RNPs is therefore dependent upon the expression of viral glycoproteins. To test whether Cas9-VLPs could be engineered to target a specific cell type for genome editing, Cas9-VLPs pseudotyped with the HIV-1 envelope glycoprotein (Env), the viral determinant for HIV-1's CD4+ T cell tropism (Clapham and McKnight, 2001), were produced (FIG. 13E-13F). Env-Cas9-VLPs were produced packaging Cas9 RNPs targeting human B2M locus and an mNeonGreen-expressing lentiviral genome. A mixture of CD4+ and CD8+ T cells were treated with Env-Cas9-VLPs and transduction and B2M protein expression were assessed. At the highest treatment dose, Env-Cas9-VLPs preferentially transduced CD4+ cells over CD8+ cells (53.20% vs. 2.51%, respectively) (FIG. 4B-C, FIG. 13G). Concomitantly, Env-Cas9-VLP treatment resulted in knockout of B2M in CD4+ T cells while co-cultured CD8+ T cells remained unmodified. This establishes Cas9-VLP pseudotyping as a promising approach to specifically retarget Cas9 RNP-mediated genome editing to predetermined cell types within a mixed cell population without unintended modification of bystander cells.

FIG. 4A-4C. HIV-1 Envelope pseudotyping targets Cas9-VLP genome editing to CD4+ T cells. (A) A viral glycoprotein is essential for Cas9-VLP-mediated genome editing. 293T and Jurkat cells were treated with B2M-targeting Cas9-VLPs pseudotyped with VSV-G (Cas9-VLP), without VSV-G (Bald Cas9-VLP) or were left untreated (No tx). Indels were quantified by amplicon sequencing, 3 dpt, n=3. (B) B2M-targeting Cas9-VLPs pseudotyped with the HIV-1 envelope glycoprotein (Env-Cas9-VLPs) were used to treat primary human T cells (a mixture of CD4+ and CD8+ cells). (C) Viability, transduction (mNeonGreen) and B2M expression were assessed for CD4+(red squares) and CD8+(blue circles) subpopulations 7 dpt. n=2 biological replicates from independent donors were used (B, C) and representative flow cytometry plots are shown for one donor (B). Error bars indicate standard error of the mean.

FIG. 13A-13G. Characterization of bald and HIV-1 Env pseudotyped Cas9-VLPs. (A) Production of "bald" Cas9-VLPs. Schematic of plasmids used for the production of bald Cas9-VLPs that lack a glycoprotein. (B) Schematic of an immature, pre-proteolytically processed Cas9-VLP produced through transient transfection. (C) Quantification of Cas9-VLP production by CA ELISA. Amount of CA produced per transfected p100 dish is shown. (D) Western blot of Cas9-VLP content. An anti-Flag antibody was used for Cas9 detection and an anti-HIV-1 capsid (CA) antibody was used to detect Cas9-VLP production. (E) Env-Cas9-VLPs are specific for CD4+ cells. Cell surface expression of CD4 in HEK293T, Jurkat, CCRF-CEM, and HuT 78 cell lines. (F) Transduction of Cas9-VLPs pseudotyped with the HIV-1 envelope correlates with cellular CD4 expression. (G) Representative flow cytometry gating strategy to assess the cell-type specificity of B2M knockout by Env-Cas9-VLPs within a mixed population of primary human T cells.

REFERENCES

Aoki, T., Miyauchi, K., Urano, E., Ichikawa, R., and Komano, J. (2011). Protein transduction by pseudotyped lentivirus-like nanoparticles. Gene Ther. 18, 936-941.

Bailey, S. R., and Maus, M. V. (2019). Gene editing for immune cell therapies. Nature Biotechnology 37, 1425-1434.

Cai, Y., Bak, R. O., Krogh, L. B., Staunstrup, N. H., Moldt, B., Corydon, T. J., Schrøder, L. D., and Mikkelsen, J. G. (2014a). DNA transposition by protein transduction of the piggyBac transposase from lentiviral Gag precursors. Nucleic Acids Res. 42, e28.

Cai, Y., Bak, R. O., and Mikkelsen, J. G. (2014b). Targeted genome editing by lentiviral protein transduction of zinc-finger and TAL-effector nucleases. Elife 3, e01911.

Chen, G., Abdeen, A. A., Wang, Y., Shahi, P. K., Robertson, S., Xie, R., Suzuki, M., Pattnaik, B. R., Saha, K., and Gong, S. (2019). A biodegradable nanocapsule delivers a Cas9 ribonucleoprotein complex for in vivo genome editing. Nat. Nanotechnol. 14, 974-980.

Choi, J. G., Dang, Y., Abraham, S., Ma, H., Zhang, J., Guo, H., Cai, Y., Mikkelsen, J. G., Wu, H., Shankar, P., et al. (2016). Lentivirus pre-packed with Cas9 protein for safer gene editing. Gene Ther. 23, 627-633.

Clapham, P. R., and McKnight, A. (2001). HIV-1 receptors and cell tropism. British Medical Bulletin 58, 43-59.

Cronin, J., Zhang, X.-Y., and Reiser, J. (2005). Altering the tropism of lentiviral vectors through pseudotyping. Curr. Gene Ther. 5, 387-398.

Del'Guidice, T., Lepetit-Stoffaes, J.-P., Bordeleau, L.-J., Roberge, J., Theberge, V., Lauvaux, C., Barbeau, X., Trottier, J., Dave, V., Roy, D.-C., et al. (2018). Membrane permeabilizing amphiphilic peptide delivers recombinant transcription factor and CRISPR-Cas9/Cpf1 ribonucleoproteins in hard-to-modify cells. PLoS One 13, e0195558.

Doudna, J. A. (2020). The promise and challenge of therapeutic genome editing. Nature 578, 229-236.

Fesnak, A. D., June, C. H., and Levine, B. L. (2016). Engineered T cells: the promise and challenges of cancer immunotherapy. Nat. Rev. Cancer 16, 566-581.

van Haasteren, J., Li, J., Scheideler, O. J., Murthy, N., and Schaffer, D. V. (2020). The delivery challenge: fulfilling the promise of therapeutic genome editing. Nat. Biotechnol. 38, 845-855.

Hill, Z. B., Martinko, A. J., Nguyen, D. P., and Wells, J. A. (2018). Human antibody-based chemically induced dimerizers for cell therapeutic applications. Nat. Chem. Biol. 14, 112-117.

Hu, W., Zi, Z., Jin, Y., Li, G., Shao, K., Cai, Q., Ma, X., and Wei, F. (2019). CRISPR/Cas9-mediated PD-1 disruption enhances human mesothelin-targeted CAR T cell effector functions. Cancer Immunology, Immunotherapy 68, 365-377.

Indikova, I., and Indik, S. (2020). Highly efficient "hit-and-run" genome editing with unconcentrated lentivectors carrying Vpr.Prot.Cas9 protein produced from RRE-containing transcripts. Nucleic Acids Research 48, 8178-8187.

Izmiryan, A., Basmaciogullari, S., Henry, A., Paques, F., and Danos, 0. (2011). Efficient gene targeting mediated by a lentiviral vector-associated meganuclease. Nucleic Acids Res. 39, 7610-7619.

Jinek, M., Chylinski, K., Fonfara, I., Hauer, M., Doudna, J. A., and Charpentier, E. (2012). A programmable dual-RNA-guided DNA endonuclease in adaptive bacterial immunity Science 337, 816-821.

Lim, W. A., and June, C. H. (2017). The Principles of Engineering Immune Cells to Treat Cancer. Cell 168, 724-740.

Lyu, P., Javidi-Parsijani, P., Atala, A., and Lu, B. (2019). Delivering Cas9/sgRNA ribonucleoprotein (RNP) by lentiviral capsid-based bionanoparticles for efficient "hit-and-run" genome editing. Nucleic Acids Research 47, e99-e99.

Mangeot, P. E., Risson, V., Fusil, F., Marnef, A., Laurent, E., Blin, J., Mournetas, V., Massourides, E., Sohier, T. J. M., Corbin, A., et al. (2019). Genome editing in primary cells and in vivo using viral-derived Nano-blades loaded with Cas9-sgRNA ribonucleoproteins. Nat. Commun. 10, 45.

Michel, G., Yu, Y., Chang, T., and Yee, J.-K. (2010). Site-specific gene insertion mediated by a Cre-loxP-carrying lentiviral vector. Mol. Ther. 18, 1814-1821.

Miyauchi, K., Urano, E., Takizawa, M., Ichikawa, R., and Komano, J. (2012). Therapeutic potential of HIV protease-activable CASP3. Sci. Rep. 2, 359.

Muller, Y. D., Nguyen, D. P., Ferreira, L. M. R., Ho, P., and Raffin, C. (2020). The CD28-transmembrane domain mediates chimeric antigen receptor heterodimerization with CD28. bioRxiv.

Newick, K., O'Brien, S., Moon, E., and Albelda, S. M. (2017). CAR T Cell Therapy for Solid Tumors. Annu. Rev. Med. 68, 139-152.

Nguyen, D. N., Roth, T. L., Li, P. J., Chen, P. A., Apathy, R., Mamedov, M. R., Vo, L. T., Tobin, V. R., Goodman, D., Shifrut, E., et al. (2020). Polymer-stabilized Cas9 nanoparticles and modified repair templates increase genome editing efficiency. Nat. Biotechnol. 38, 44-49.

Porteus, M. H. (2019). A New Class of Medicines through DNA Editing. N. Engl. J. Med. 380, 947-959.

Ramakrishna, S.-B. Kwaku Dad, A., Beloor, J., Gopalappa, R., Lee, S.-K., and Kim, H. (2014). Gene disruption by cell-penetrating peptide-mediated delivery of Cas9 protein and guide RNA. Genome Research 24, 1020-1027.

Richardson, C. D., Ray, G. J., DeWitt, M. A., Curie, G. L., and Corn, J. E. (2016). Enhancing homology-directed genome editing by catalytically active and inactive CRISPR-Cas9 using asymmetric donor DNA. Nat. Biotechnol. 34, 339-344.

Roth, T. L., Puig-Saus, C., Yu, R., Shifrut, E., Carnevale, J., Li, P. J., Hiatt, J., Saco, J., Krystofinski, P., Li, H., et al. (2018). Reprogramming human T cell function and specificity with non-viral genome targeting. Nature 559, 405-409.

Rouet, R., Thuma, B. A., Roy, M. D., Lintner, N. G., Rubitski, D. M., Finley, J. E., Wisniewska, H. M., Mendonsa, R., Hirsh, A., de Oñate, L., et al. (2018). Receptor-Mediated Delivery of CRISPR-Cas9 Endonuclease for Cell-Type-Specific Gene Editing. J. Am. Chem. Soc. 140, 6596-6603.

Rupp, L. J., Schumann, K., Roybal, K. T., Gate, R. E., Ye, C. J., Lim, W. A., and Marson, A. (2017). CRISPR/Cas9-mediated PD-1 disruption enhances anti-tumor efficacy of human chimeric antigen receptor T cells. Sci. Rep. 7, 737.

Sadelain, M., Rivière, I., and Riddell, S. (2017). Therapeutic T cell engineering. Nature 545, 423-431.

Schenkwein, D., Turkki, V., Kärkkäinen, H.-R., Airenne, K., and Ylä-Herttuala, S. (2010). Production of HIV-1 integrase fusion protein-carrying lentiviral vectors for gene therapy and protein transduction. Hum. Gene Ther. 21, 589-602.

Staahl, B. T., Benekareddy, M., Coulon-Bainier, C., Banfal, A. A., Floor, S. N., Sabo, J. K., Urnes, C., Munares, G. A., Ghosh, A., and Doudna, J. A. (2017). Efficient genome editing in the mouse brain by local delivery of engineered Cas9 ribonucleoprotein complexes. Nat. Biotechnol. 35, 431-434.

Stadtmauer, E. A., Fraietta, J. A., Davis, M. M., Cohen, A. D., Weber, K. L., Lancaster, E., Mangan, P. A., Kulikovskaya, I., Gupta, M., Chen, F., et al. (2020). CRISPR-engineered T cells in patients with refractory cancer. Science 367.

Tang, N., Cheng, C., Zhang, X., Qiao, M., Li, N., Mu, W., Wei, X.-F., Han, W., and Wang, H. (2020). TGF-β inhibition via CRISPR promotes the long-term efficacy of CAR T cells against solid tumors. JCI Insight 5.

Wagner, J., Wickman, E., DeRenzo, C., and Gottschalk, S. (2020). CAR T Cell Therapy for Solid Tumors: Bright Future or Dark Reality? Mol. Ther. 28, 2320-2339.

Wang, H.-X., Song, Z., Lao, Y.-H., Xu, X., Gong, J., Cheng, D., Chakraborty, S., Park, J. S., Li, M., Huang, D., et al. (2018). Nonviral gene editing via CRISPR/Cas9 delivery by membrane-disruptive and endosomolytic helical polypeptide. Proc. Natl. Acad. Sci. U.S.A. 115, 4903-4908.

Weber, E. W., Maus, M. V., and Mackall, C. L. (2020). The Emerging Landscape of Immune Cell Therapies. Cell 181, 46-62.

Wei, T., Cheng, Q., Min, Y.-L., Olson, E. N., and Siegwart, D. J. (2020). Systemic nanoparticle delivery of CRISPR-Cas9 ribonucleoproteins for effective tissue specific genome editing. Nat. Commun. 11, 3232.

Wilson, R. C., and Gilbert, L. A. (2018). The Promise and Challenge of In Vivo Delivery for Genome Therapeutics. ACS Chem. Biol. 13, 376-382.

Wu, X., Liu, H., Xiao, H., Kim, J., Seshaiah, P., Natsoulis, G., Boeke, J. D., Hahn, B. H., and Kappes, J. C. (1995). Targeting foreign proteins to human immunodeficiency virus particles via fusion with Vpr and Vpx. J. Virol. 69, 3389-3398.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A virus-like particle (VLP) comprising:

a) a Cas9 polypeptide, wherein the Cas9 polypeptide is present inside of the VLP as both:

(i) a Gag-Cas9 fusion polypeptide, wherein the Cas9 polypeptide is linked to the C-terminus of a Gag polyprotein through a cleavable linker between the Gag polyprotein and the Cas9 polypeptide; and (ii) a proteolytically released form following proteolytic cleavage of the cleavable linker;

b) a Pol polyprotein;

c) lentiviral structural components comprising:

(i) a matrix (MA) polypeptide;

(ii) a capsid (CA) polypeptide; and (iii) a nucleocapsid (NC) polypeptide;

d) a recombinant lentiviral vector comprising a nucleotide sequence encoding a therapeutic polypeptide selected from the group consisting of: a chimeric antigen receptor (CAR), a T-cell receptor, s synNotch polypeptide, a natural killer cell receptor, and an antibody; and e) a pseudotyping viral glycoprotein; and optionally f) a polypeptide that provides for binding to a target cell.

2. The VLP of claim 1, wherein the therapeutic polypeptide has a length of from about 500 amino acids to about 2,500 amino acids.

3. The VLP of claim 1, wherein the pseudotyping viral glycoprotein is a human immunodeficiency virus-1 envelope protein, a measles virus hemagglutinin, an HTLV-1 glycoprotein, or a VSV-G glycoprotein.

4. The VLP of claim 1, wherein the polypeptide that provides for binding to a target cell is an antibody or a designed ankyrin repeat protein (DARPin).

5. A composition comprising the VLP of claim 1.

6. The VLP of claim 1, wherein the CAR comprises an antigen-binding domain specific for a cancer-associated antigen.

7. The VLP of claim 1, wherein the Cas9 polypeptide is fused to one or more nuclear localization signals at the C-terminus of the Cas9 polypeptide.

8. The VLP of claim 1, comprising one or more CRISPR/Cas guide RNAs each comprising a nucleotide sequence that is complementary to a sequence of a target nucleic acid.

9. The VLP of claim 1, wherein the recombinant lentivirus further comprises one or more nucleotide sequences, each operably linked to a U6 promoter, that encode one or more CRISPR/Cas guide RNAs.

10. The VLP of claim 8, wherein the one or more CRISPR/Cas guide RNAs comprises:

(a) a CRISPR/Cas guide RNA targeting a beta-2-microglobulin (B2M) gene; or (b) a CRISPR/Cas guide RNA targeting a T-cell receptor a constant (TRAC) gene; or (c) both (a) and (b).

11. The VLP of claim 9, wherein the one or more CRISPR/Cas guide RNAs comprises:

(a) a CRISPR/Cas guide RNA targeting a B2M gene; or (b) a CRISPR/Cas guide RNA targeting a TRAC gene; or (c) both (a) and (b).

12. The VLP of claim 1, wherein at least 50% of the Cas9 polypeptide present inside of the VLP is in the form of the Gag-Cas9 fusion polypeptide relative to the proteolytically released form.

13. The VLP of claim 1, wherein the Gag polyprotein of the Gag-Cas9 fusion polypeptide comprises an HIV-1 Gag polyprotein, the Pol polyprotein comprises an HIV-1 Pol polyprotein, and the lentiviral structural components comprise HIV-1 lentiviral structural components.

14. The VLP of claim 1, wherein more than 50% of the lentiviral structural components are from the Gag polyprotein of the Gag-Cas9 fusion polypeptide.

15. The VLP of claim 1, wherein the polypeptide that provides for binding to the target cell is present.

16. The VLP of claim 15, wherein the target cell is a T cell.

17. The VLP of claim 8, wherein the nucleotide sequence encoding the therapeutic polypeptide is flanked by homology regions, wherein each homology region is between 10-200 nucleotides in length and at least 50% homologous to corresponding nucleotide sequences flanking the sequence of the target nucleic acid.

18. The VLP of claim 8, wherein the sequence of the target nucleic acid is a genomic sequence.

19. A VLP comprising:

a) a Cas9 polypeptide, wherein the Cas9 polypeptide is present inside of the VLP as both:

(i) a Gag-Cas9 fusion polypeptide, wherein the Cas9 polypeptide is linked to the C-terminus of an HIV-1 Gag polyprotein through an HIV-1 protease cleavage site between the HIV-1 Gag polyprotein and the Cas9 polypeptide; and (ii) a proteolytically released form following proteolytic cleavage of the HIV-1 protease cleavage site;

b) an HIV-1 Pol polyprotein;

c) HIV-1 lentiviral structural components comprising:

(i) a MA polypeptide;

(ii) a CA polypeptide; and (iii) a NC polypeptide;

d) a recombinant lentiviral vector comprising a nucleotide sequence encoding a CAR;

e) a pseudotyping viral glycoprotein;

f) a polypeptide that provides for binding to a T cell; and g) one or more CRISPR/Cas guide RNAs comprising:

(a) a CRISPR/Cas guide RNA targeting a B2M gene; or (b) a CRISPR/Cas guide RNA targeting a TRAC gene; or (c) both (a) and (b).

20. The VLP of claim 19, wherein at least 50% of the Cas9 polypeptide present inside of the VLP is in the form of the Gag-Cas9 fusion polypeptide relative to the proteolytically released form.

21. The VLP of claim 19, wherein the pseudotyping viral glycoprotein is a HIV-1 envelope protein, a measles virus hemagglutinin, an HTLV-1 glycoprotein, or a VSV-G glycoprotein.

22. The VLP of claim 19, wherein the polypeptide that provides for binding to the T cell is an antibody or a DARPin.

23. A composition comprising the VLP of claim 19.

24. The VLP of claim 19, wherein the CAR comprises an antigen-binding domain specific for a cancer-associated antigen.

25. The VLP of claim 19, wherein the Cas9 polypeptide is fused to one or more nuclear localization signals at the C-terminus of the Cas9 polypeptide.

26. The VLP of claim 19, wherein the recombinant lentiviral vector further comprises one or more nucleotide sequences, each operably linked to a U6 promoter, that encode one or more CRISPR/Cas guide RNAs.

27. The VLP of claim 19, wherein the nucleotide sequence encoding the CAR is flanked by homology regions corresponding to nucleotide sequences flanking a sequence of the B2M gene targeted by the one or more CRISPR/Cas guide RNAs or a sequence of the TRAC gene targeted by the one or more CRISPR/Cas guide RNAs.

28. The VLP of claim 19, wherein the B2M gene or the TRAC gene is a genomic sequence.

29. A VLP comprising:

a) a Cas9 polypeptide, wherein the Cas9 polypeptide is present inside of the VLP as both:

(i) a Gag-Cas9 fusion polypeptide, wherein the Cas9 polypeptide is linked to the C-terminus of an HIV-1 Gag polyprotein through an HIV-1 protease cleavage site between the HIV-1 Gag polyprotein and the Cas9 polypeptide; and (ii) a proteolytically released form following proteolytic cleavage of the HIV-1 protease cleavage site;

b) an HIV-1 Pol polyprotein;

c) HIV-1 lentiviral structural components comprising:

(i) a MA polypeptide;

(ii) a CA polypeptide; and (iii) a NC polypeptide;

d) a CRISPR/Cas guide RNA targeting a genomic sequence of a TRAC gene;

e) a recombinant lentiviral vector comprising a nucleotide sequence encoding a CAR, wherein the CAR comprises an antigen-binding domain specific for a cancer-associated antigen, wherein the nucleotide sequence encoding the CAR is flanked by homology regions corresponding to nucleotide sequences flanking a sequence of the TRAC gene targeted by the one or more CRISPR/Cas guide RNAs;

f) a pseudotyping viral glycoprotein; and g) a polypeptide that provides for binding to a T cell, wherein the polypeptide that provides for binding to the T cell is an antibody.

30. The VLP of claim 29, wherein at least 50% of the Cas9 polypeptide present inside of the VLP is in the form of the Gag-Cas9 fusion polypeptide relative to the proteolytically released form.

31. The VLP of claim 29, wherein the pseudotyping viral glycoprotein is a HIV-1 envelope protein, a measles virus hemagglutinin, an HTLV-1 glycoprotein, or a VSV-G glycoprotein.

32. A composition comprising the VLP of claim 29.

33. The VLP of claim 29, wherein the Cas9 polypeptide is fused to one or more nuclear localization signals at the C-terminus of the Cas9 polypeptide.

\* \* \* \* \*

SEQUENCE LISTING

```
<160> NUMBER OF SEQ ID NOS: 221

<210> SEQ ID NO 1
<211> LENGTH: 7
<212> TYPE: PRT
<213> ORGANISM: SV40 virus

<400> SEQUENCE: 1

Pro Lys Lys Lys Arg Lys Val
1               5

<210> SEQ ID NO 2
<211> LENGTH: 16
<212> TYPE: PRT
<213> ORGANISM: Unknown
<220> FEATURE:
<223> OTHER INFORMATION: nucleoplasmin bipartite NLS

<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 9
<212> TYPE: PRT
<213> ORGANISM: Unknown
<220> FEATURE:
<223> OTHER INFORMATION: c-myc NLS

<400> SEQUENCE: 3

Pro Ala Ala Lys Arg Val Lys Leu Asp
1               5

<210> SEQ ID NO 4
<211> LENGTH: 11
<212> TYPE: PRT
<213> ORGANISM: Unknown
<220> FEATURE:
<223> OTHER INFORMATION: c-myc NLS

<400> SEQUENCE: 4

Arg Gln Arg Arg Asn Glu Leu Lys Arg Ser Pro
1               5                   10
```

```
<210> SEQ ID NO 5
<211> LENGTH: 38
<212> TYPE: PRT
<213> ORGANISM: Unknown
<220> FEATURE:
<223> OTHER INFORMATION: hRNPA1 M9 NLS

<400> SEQUENCE: 5

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 6
<211> LENGTH: 42
<212> TYPE: PRT
<213> ORGANISM: Unknown
<220> FEATURE:
<223> OTHER INFORMATION: IBB domain from importin-alpha

<400> SEQUENCE: 6

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 7
<211> LENGTH: 8
<212> TYPE: PRT
<213> ORGANISM: Unknown
<220> FEATURE:
<223> OTHER INFORMATION: myoma T protein

<400> SEQUENCE: 7

Val Ser Arg Lys Arg Pro Arg Pro
1               5

<210> SEQ ID NO 8
<211> LENGTH: 8
<212> TYPE: PRT
<213> ORGANISM: Unknown
<220> FEATURE:
<223> OTHER INFORMATION: myoma T protein

<400> SEQUENCE: 8

Pro Pro Lys Lys Ala Arg Glu Asp
1               5

<210> SEQ ID NO 9
<211> LENGTH: 8
<212> TYPE: PRT
<213> ORGANISM: Homo sapiens

<400> SEQUENCE: 9

Pro Gln Pro Lys Lys Lys Pro Leu
1               5

<210> SEQ ID NO 10
<211> LENGTH: 12
<212> TYPE: PRT
```

```
<213> ORGANISM: Mus musculus

<400> SEQUENCE: 10

Ser Ala Leu Ile Lys Lys Lys Lys Lys Met Ala Pro
1               5               10

<210> SEQ ID NO 11
<211> LENGTH: 5
<212> TYPE: PRT
<213> ORGANISM: Influenza virus

<400> SEQUENCE: 11

Asp Arg Leu Arg Arg
1               5

<210> SEQ ID NO 12
<211> LENGTH: 10
<212> TYPE: PRT
<213> ORGANISM: Hepatitus virus

<400> SEQUENCE: 12

Arg Lys Leu Lys Lys Lys Ile Lys Lys Leu
1               5               10

<210> SEQ ID NO 13
<211> LENGTH: 10
<212> TYPE: PRT
<213> ORGANISM: Mus musculus

<400> SEQUENCE: 13

Arg Glu Lys Lys Lys Phe Leu Lys Arg Arg
1               5               10

<210> SEQ ID NO 14
<211> LENGTH: 20
<212> TYPE: PRT
<213> ORGANISM: Homo sapiens

<400> SEQUENCE: 14

Lys Arg Lys Gly Asp Glu Val Asp Gly Val Asp Glu Val Ala Lys Lys
1               5               10              15

Lys Ser Lys Lys
            20

<210> SEQ ID NO 15
<211> LENGTH: 17
<212> TYPE: PRT
<213> ORGANISM: Homo sapiens

<400> SEQUENCE: 15

Arg Lys Cys Leu Gln Ala Gly Met Asn Leu Glu Ala Arg Lys Thr Lys
1               5               10              15

Lys

<210> SEQ ID NO 16
<211> LENGTH: 7
<212> TYPE: PRT
<213> ORGANISM: Influenza virus

<400> SEQUENCE: 16

Pro Lys Gln Lys Lys Arg Lys
1               5
```

-continued

```
<210> SEQ ID NO 17
<211> LENGTH: 30
<212> TYPE: PRT
<213> ORGANISM: Artificial sequence
<220> FEATURE:
<223> OTHER INFORMATION: synthetic sequence

<400> SEQUENCE: 17

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys
            20                  25                  30

<210> SEQ ID NO 18
<211> LENGTH: 5
<212> TYPE: PRT
<213> ORGANISM: Artificial sequence
<220> FEATURE:
<223> OTHER INFORMATION: immunoglobulin hinge region

<400> SEQUENCE: 18

Asp Lys Thr His Thr
1               5

<210> SEQ ID NO 19
<211> LENGTH: 4
<212> TYPE: PRT
<213> ORGANISM: Artificial sequence
<220> FEATURE:
<223> OTHER INFORMATION: immunoglobulin hinge region

<400> SEQUENCE: 19

Cys Pro Pro Cys
1

<210> SEQ ID NO 20
<211> LENGTH: 15
<212> TYPE: PRT
<213> ORGANISM: Artificial sequence
<220> FEATURE:
<223> OTHER INFORMATION: immunoglobulin hinge region

<400> SEQUENCE: 20

Cys Pro Glu Pro Lys Ser Cys Asp Thr Pro Pro Pro Cys Pro Arg
1               5                   10                  15

<210> SEQ ID NO 21
<211> LENGTH: 12
<212> TYPE: PRT
<213> ORGANISM: Artificial sequence
<220> FEATURE:
<223> OTHER INFORMATION: immunoglobulin hinge region

<400> SEQUENCE: 21

Glu Leu Lys Thr Pro Leu Gly Asp Thr Thr His Thr
1               5                   10

<210> SEQ ID NO 22
<211> LENGTH: 10
<212> TYPE: PRT
<213> ORGANISM: Artificial sequence
<220> FEATURE:
<223> OTHER INFORMATION: immunoglobulin hinge region

<400> SEQUENCE: 22

Lys Ser Cys Asp Lys Thr His Thr Cys Pro
1               5                   10
```

```
<210> SEQ ID NO 23
<211> LENGTH: 7
<212> TYPE: PRT
<213> ORGANISM: Artificial sequence
<220> FEATURE:
<223> OTHER INFORMATION: immunoglobulin hinge region

<400> SEQUENCE: 23

Lys Cys Cys Val Asp Cys Pro
1               5

<210> SEQ ID NO 24
<211> LENGTH: 7
<212> TYPE: PRT
<213> ORGANISM: Artificial sequence
<220> FEATURE:
<223> OTHER INFORMATION: immunoglobulin hinge region

<400> SEQUENCE: 24

Lys Tyr Gly Pro Pro Cys Pro
1               5

<210> SEQ ID NO 25
<211> LENGTH: 15
<212> TYPE: PRT
<213> ORGANISM: Homo sapiens

<400> SEQUENCE: 25

Glu Pro Lys Ser Cys Asp Lys Thr His Thr Cys Pro Pro Cys Pro
1               5                   10                  15

<210> SEQ ID NO 26
<211> LENGTH: 12
<212> TYPE: PRT
<213> ORGANISM: Homo sapiens

<400> SEQUENCE: 26

Glu Arg Lys Cys Cys Val Glu Cys Pro Pro Cys Pro
1               5                   10

<210> SEQ ID NO 27
<211> LENGTH: 17
<212> TYPE: PRT
<213> ORGANISM: Homo sapiens

<400> SEQUENCE: 27

Glu Leu Lys Thr Pro Leu Gly Asp Thr Thr His Thr Cys Pro Arg Cys
1               5                   10                  15

Pro

<210> SEQ ID NO 28
<211> LENGTH: 12
<212> TYPE: PRT
<213> ORGANISM: Homo sapiens

<400> SEQUENCE: 28

Ser Pro Asn Met Val Pro His Ala His His Ala Gln
1               5                   10

<210> SEQ ID NO 29
<211> LENGTH: 45
<212> TYPE: PRT
<213> ORGANISM: Homo sapiens
```

```
<400> SEQUENCE: 29

Thr Thr Thr Pro Ala Pro Arg Pro Pro Thr Pro Ala Pro Thr Ile Ala
1               5               10              15

Ser Gln Pro Leu Ser Leu Arg Pro Glu Ala Cys Arg Pro Ala Ala Gly
            20              25              30

Gly Ala Val His Thr Arg Gly Leu Asp Phe Ala Cys Asp
        35              40              45

<210> SEQ ID NO 30
<211> LENGTH: 24
<212> TYPE: PRT
<213> ORGANISM: Unknown
<220> FEATURE:
<223> OTHER INFORMATION: transmembrane sequence

<400> SEQUENCE: 30

Ile Tyr Ile Trp Ala Pro Leu Ala Gly Thr Cys Gly Val Leu Leu Leu
1               5               10              15

Ser Leu Val Ile Thr Leu Tyr Cys
            20

<210> SEQ ID NO 31
<211> LENGTH: 23
<212> TYPE: PRT
<213> ORGANISM: Unknown
<220> FEATURE:
<223> OTHER INFORMATION: CD8 beta derived transmembrane sequence

<400> SEQUENCE: 31

Leu Gly Leu Leu Val Ala Gly Val Leu Val Leu Leu Val Ser Leu Gly
1               5               10              15

Val Ala Ile His Leu Cys Cys
            20

<210> SEQ ID NO 32
<211> LENGTH: 25
<212> TYPE: PRT
<213> ORGANISM: Unknown
<220> FEATURE:
<223> OTHER INFORMATION: CD4 derived transmembranse sequence

<400> SEQUENCE: 32

Ala Leu Ile Val Leu Gly Gly Val Ala Gly Leu Leu Leu Phe Ile Gly
1               5               10              15

Leu Gly Ile Phe Phe Cys Val Arg Cys
            20              25

<210> SEQ ID NO 33
<211> LENGTH: 23
<212> TYPE: PRT
<213> ORGANISM: Unknown
<220> FEATURE:
<223> OTHER INFORMATION: CD3 zeta derived transmembrane sequence

<400> SEQUENCE: 33

Leu Cys Tyr Leu Leu Asp Gly Ile Leu Phe Ile Tyr Gly Val Ile Leu
1               5               10              15

Thr Ala Leu Phe Leu Arg Val
            20

<210> SEQ ID NO 34
<211> LENGTH: 26
<212> TYPE: PRT
```

```
<213> ORGANISM: Unknown
<220> FEATURE:
<223> OTHER INFORMATION: CD28 derived transmembrane sequence

<400> SEQUENCE: 34

Trp Val Leu Val Val Val Gly Gly Val Leu Ala Cys Tyr Ser Leu Leu
1               5                   10                  15

Val Thr Val Ala Phe Ile Ile Phe Trp Val
            20                  25

<210> SEQ ID NO 35
<211> LENGTH: 26
<212> TYPE: PRT
<213> ORGANISM: Unknown
<220> FEATURE:
<223> OTHER INFORMATION: CD134 (OX40) derived transmembrane sequence

<400> SEQUENCE: 35

Val Ala Ala Ile Leu Gly Leu Gly Leu Val Leu Gly Leu Leu Gly Pro
1               5                   10                  15

Leu Ala Ile Leu Leu Ala Leu Tyr Leu Leu
            20                  25

<210> SEQ ID NO 36
<211> LENGTH: 24
<212> TYPE: PRT
<213> ORGANISM: Unknown
<220> FEATURE:
<223> OTHER INFORMATION: CD7 derived transmembrane sequence

<400> SEQUENCE: 36

Ala Leu Pro Ala Ala Leu Ala Val Ile Ser Phe Leu Leu Gly Leu Gly
1               5                   10                  15

Leu Gly Val Ala Cys Val Leu Ala
            20

<210> SEQ ID NO 37
<211> LENGTH: 42
<212> TYPE: PRT
<213> ORGANISM: Unknown
<220> FEATURE:
<223> OTHER INFORMATION: 4-1BB polypeptide

<400> SEQUENCE: 37

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 38
<211> LENGTH: 44
<212> TYPE: PRT
<213> ORGANISM: Unknown
<220> FEATURE:
<223> OTHER INFORMATION: CD28 polypeptide

<400> SEQUENCE: 38

Phe Trp Val Arg Ser Lys Arg Ser Arg Leu Leu His Ser Asp Tyr Met
1               5                   10                  15

Asn Met Thr Pro Arg Arg Pro Gly Pro Thr Arg Lys His Tyr Gln Pro
            20                  25                  30
```

```
Tyr Ala Pro Pro Arg Asp Phe Ala Ala Tyr Arg Ser
        35                  40

<210> SEQ ID NO 39
<211> LENGTH: 35
<212> TYPE: PRT
<213> ORGANISM: Unknown
<220> FEATURE:
<223> OTHER INFORMATION: ICOS polypeptide

<400> SEQUENCE: 39

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35

<210> SEQ ID NO 40
<211> LENGTH: 37
<212> TYPE: PRT
<213> ORGANISM: Unknown
<220> FEATURE:
<223> OTHER INFORMATION: OX40 polypeptide

<400> SEQUENCE: 40

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35

<210> SEQ ID NO 41
<211> LENGTH: 114
<212> TYPE: PRT
<213> ORGANISM: Unknown
<220> FEATURE:
<223> OTHER INFORMATION: BTLA polypeptide

<400> SEQUENCE: 41

Cys Cys Leu Arg Arg His Gln Gly Lys Gln Asn Glu Leu Ser Asp Thr
1               5                   10                  15

Ala Gly Arg Glu Ile Asn Leu Val Asp Ala His Leu Lys Ser Glu Gln
            20                  25                  30

Thr Glu Ala Ser Thr Arg Gln Asn Ser Gln Val Leu Leu Ser Glu Thr
        35                  40                      45

Gly Ile Tyr Asp Asn Asp Pro Asp Leu Cys Phe Arg Met Gln Glu Gly
    50                  55                  60

Ser Glu Val Tyr Ser Asn Pro Cys Leu Glu Glu Asn Lys Pro Gly Ile
65                  70                  75                  80

Val Tyr Ala Ser Leu Asn His Ser Val Ile Gly Pro Asn Ser Arg Leu
                85                  90                  95

Ala Arg Asn Val Lys Glu Ala Pro Thr Glu Tyr Ala Ser Ile Cys Val
            100                 105                 110

Arg Ser

<210> SEQ ID NO 42
<211> LENGTH: 49
<212> TYPE: PRT
<213> ORGANISM: Unknown
```

<220> FEATURE:
<223> OTHER INFORMATION: CD27 polypeptide

<400> SEQUENCE: 42

His Gln Arg Arg Lys Tyr Arg Ser Asn Lys Gly Glu Ser Pro Val Glu
1               5                   10                  15

Pro Ala Glu Pro Cys Arg Tyr Ser Cys Pro Arg Glu Glu Glu Gly Ser
            20                  25                  30

Thr Ile Pro Ile Gln Glu Asp Tyr Arg Lys Pro Glu Pro Ala Cys Ser
        35                  40                  45

Pro

<210> SEQ ID NO 43
<211> LENGTH: 187
<212> TYPE: PRT
<213> ORGANISM: Unknown
<220> FEATURE:
<223> OTHER INFORMATION: CD30 polypeptide

<400> SEQUENCE: 43

Arg Arg Ala Cys Arg Lys Arg Ile Arg Gln Lys Leu His Leu Cys Tyr
1               5                   10                  15

Pro Val Gln Thr Ser Gln Pro Lys Leu Glu Leu Val Asp Ser Arg Pro
            20                  25                  30

Arg Arg Ser Ser Thr Gln Leu Arg Ser Gly Ala Ser Val Thr Glu Pro
        35                  40                  45

Val Ala Glu Glu Arg Gly Leu Met Ser Gln Pro Leu Met Glu Thr Cys
    50                  55                  60

His Ser Val Gly Ala Ala Tyr Leu Glu Ser Leu Pro Leu Gln Asp Ala
65                  70                  75                  80

Ser Pro Ala Gly Gly Pro Ser Ser Pro Arg Asp Leu Pro Glu Pro Arg
                85                  90                  95

Val Ser Thr Glu His Thr Asn Asn Lys Ile Glu Lys Ile Tyr Ile Met
            100                 105                 110

Lys Ala Asp Thr Val Ile Val Gly Thr Val Lys Ala Glu Leu Pro Glu
        115                 120                 125

Gly Arg Gly Leu Ala Gly Pro Ala Glu Pro Glu Leu Glu Glu Glu Leu
    130                 135                 140

Glu Ala Asp His Thr Pro His Tyr Pro Glu Gln Glu Thr Glu Pro Pro
145                 150                 155                 160

Leu Gly Ser Cys Ser Asp Val Met Leu Ser Val Glu Glu Glu Gly Lys
                165                 170                 175

Glu Asp Pro Leu Pro Thr Ala Ala Ser Gly Lys
            180                 185

<210> SEQ ID NO 44
<211> LENGTH: 54
<212> TYPE: PRT
<213> ORGANISM: Unknown
<220> FEATURE:
<223> OTHER INFORMATION: GITR polypeptide

<400> SEQUENCE: 44

His Ile Trp Gln Leu Arg Ser Gln Cys Met Trp Pro Arg Glu Thr Gln
1               5                   10                  15

Leu Leu Leu Glu Val Pro Pro Ser Thr Glu Asp Ala Arg Ser Cys Gln
            20                  25                  30

Phe Pro Glu Glu Glu Arg Gly Glu Arg Ser Ala Glu Glu Lys Gly Arg

-continued

```
              35                    40                    45

Leu Gly Asp Leu Trp Val
    50

<210> SEQ ID NO 45
<211> LENGTH: 60
<212> TYPE: PRT
<213> ORGANISM: Unknown
<220> FEATURE:
<223> OTHER INFORMATION: HVEM polypeptide

<400> SEQUENCE: 45

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60

<210> SEQ ID NO 46
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (2)..(3)
<223> OTHER INFORMATION: The amino acid at position 2 and the amino acid
      at position 3 are independently any amino acid
<220> FEATURE:
<221> NAME/KEY: VARIANT
<222> LOCATION: (4)..(4)
<223> OTHER INFORMATION: The amino acid at position 4 is Leu or Ile

<400> SEQUENCE: 46

Tyr Xaa Xaa Xaa
1

<210> SEQ ID NO 47
<211> LENGTH: 16
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (2)..(3)
<223> OTHER INFORMATION: The amino acid at position 2 and the amino acid
      at position 3 are independently any amino acid
<220> FEATURE:
<221> NAME/KEY: VARIANT
<222> LOCATION: (4)..(4)
<223> OTHER INFORMATION: The amino acid at position 4 is Leu or Ile
<220> FEATURE:
<221> NAME/KEY: VARIANT
<222> LOCATION: (5)..(12)
<223> OTHER INFORMATION: Each amino acid at positions 5 to 12 may
      independently be any amino acid and may be present or absent such
      that the number of amino acids ranges from 6 to 8
<220> FEATURE:
<221> NAME/KEY: VARIANT
<222> LOCATION: (14)..(15)
<223> OTHER INFORMATION: The amino acid at position 14 and the amino
      acid at position 15 are independently any amino acid
<220> FEATURE:
<221> NAME/KEY: VARIANT
<222> LOCATION: (16)..(16)
```

-continued

<223> OTHER INFORMATION: The amino acid at position 16 may be Leu or Ile

<400> SEQUENCE: 47

Tyr Xaa Xaa Xaa Xaa Xaa Xaa Xaa Xaa Xaa Xaa Tyr Xaa Xaa Xaa
1               5                   10                  15

<210> SEQ ID NO 48
<211> LENGTH: 512
<212> TYPE: PRT
<213> ORGANISM: Vesicular stomatitis virus

<400> SEQUENCE: 48

Ile Met Lys Cys Leu Leu Tyr Leu Ala Phe Leu Phe Ile Gly Val Asn
1               5                   10                  15

Cys Lys Phe Thr Ile Val Phe Pro His Asn Gln Lys Gly Asn Trp Lys
                20                  25                  30

Asn Val Pro Ser Asn Tyr His Tyr Cys Pro Ser Ser Ser Asp Leu Asn
            35                  40                  45

Trp His Asn Asp Leu Ile Gly Thr Ala Leu Gln Val Lys Met Pro Lys
        50                  55                  60

Ser His Lys Ala Ile Gln Ala Asp Gly Trp Met Cys His Ala Ser Lys
65                  70                  75                  80

Trp Val Thr Thr Cys Asp Phe Arg Trp Tyr Gly Pro Lys Tyr Ile Thr
                85                  90                  95

His Ser Ile Arg Ser Phe Thr Pro Ser Val Glu Gln Cys Lys Glu Ser
            100                 105                 110

Ile Glu Gln Thr Lys Gln Gly Thr Trp Leu Asn Pro Gly Phe Pro Pro
            115                 120                 125

Gln Ser Cys Gly Tyr Ala Thr Val Thr Asp Ala Glu Ala Val Ile Val
        130                 135                 140

Gln Val Thr Pro His His Val Leu Val Asp Glu Tyr Thr Gly Glu Trp
145                 150                 155                 160

Val Asp Ser Gln Phe Ile Asn Gly Lys Cys Ser Asn Tyr Ile Cys Pro
                165                 170                 175

Thr Val His Asn Ser Thr Thr Trp His Ser Asp Tyr Lys Val Lys Gly
            180                 185                 190

Leu Cys Asp Ser Asn Leu Ile Ser Met Asp Ile Thr Phe Phe Ser Glu
        195                 200                 205

Asp Gly Glu Leu Ser Ser Leu Gly Lys Glu Gly Thr Gly Phe Arg Ser
        210                 215                 220

Asn Tyr Phe Ala Tyr Glu Thr Gly Gly Lys Ala Cys Lys Met Gln Tyr
225                 230                 235                 240

Cys Lys His Trp Gly Val Arg Leu Pro Ser Gly Val Trp Phe Glu Met
                245                 250                 255

Ala Asp Lys Asp Leu Phe Ala Ala Ala Arg Phe Pro Glu Cys Pro Glu
                260                 265                 270

Gly Ser Ser Ile Ser Ala Pro Ser Gln Thr Ser Val Asp Val Ser Leu
        275                 280                 285

Ile Gln Asp Val Glu Arg Ile Leu Asp Tyr Ser Leu Cys Gln Glu Thr
        290                 295                 300

Trp Ser Lys Ile Arg Ala Gly Leu Pro Ile Ser Pro Val Asp Leu Ser
305                 310                 315                 320

Tyr Leu Ala Pro Lys Asn Pro Gly Thr Gly Pro Ala Phe Thr Ile Ile
                325                 330                 335

Asn Gly Thr Leu Lys Tyr Phe Glu Thr Arg Tyr Ile Arg Val Asp Ile

-continued

```
              340              345              350

Ala Ala Pro Ile Leu Ser Arg Met Val Gly Met Ile Ser Gly Thr Thr
        355              360              365

Thr Glu Arg Glu Leu Trp Asp Asp Trp Ala Pro Tyr Glu Asp Val Glu
        370              375              380

Ile Gly Pro Asn Gly Val Leu Arg Thr Ser Ser Gly Tyr Lys Phe Pro
385              390              395              400

Leu Tyr Met Ile Gly His Gly Met Leu Asp Ser Asp Leu His Leu Ser
              405              410              415

Ser Lys Ala Gln Val Phe Glu His Pro His Ile Gln Asp Ala Ala Ser
              420              425              430

Gln Leu Pro Asp Asp Glu Ser Leu Phe Phe Gly Asp Thr Gly Leu Ser
        435              440              445

Lys Asn Pro Ile Glu Leu Val Glu Gly Trp Phe Ser Ser Trp Lys Ser
        450              455              460

Ser Ile Ala Ser Phe Phe Phe Ile Ile Gly Leu Ile Ile Gly Leu Phe
465              470              475              480

Leu Val Leu Arg Val Gly Ile His Leu Cys Ile Lys Leu Lys His Thr
              485              490              495

Lys Lys Arg Gln Ile Tyr Thr Asp Ile Glu Met Asn Arg Leu Gly Lys
        500              505              510
```

```
<210> SEQ ID NO 49
<211> LENGTH: 563
<212> TYPE: PRT
<213> ORGANISM: Baboon endogenous retrovirus

<400> SEQUENCE: 49

Met Gly Phe Thr Thr Lys Ile Ile Phe Leu Tyr Asn Leu Val Leu Val
1              5              10              15

Tyr Ala Gly Phe Asp Asp Pro Arg Lys Ala Ile Glu Leu Val Gln Lys
              20              25              30

Arg Tyr Gly Arg Pro Cys Asp Cys Ser Gly Gly Gln Val Ser Glu Pro
        35              40              45

Pro Ser Asp Arg Val Ser Gln Val Thr Cys Ser Gly Lys Thr Ala Tyr
        50              55              60

Leu Met Pro Asp Gln Arg Trp Lys Cys Lys Ser Ile Pro Lys Asp Thr
65              70              75              80

Ser Pro Ser Gly Pro Leu Gln Glu Cys Pro Cys Asn Ser Tyr Gln Ser
              85              90              95

Ser Val His Ser Ser Cys Tyr Thr Ser Tyr Gln Gln Cys Arg Ser Gly
              100              105              110

Asn Lys Thr Tyr Tyr Thr Ala Thr Leu Leu Lys Thr Gln Thr Gly Gly
        115              120              125

Thr Ser Asp Val Gln Val Leu Gly Ser Thr Asn Lys Leu Ile Gln Ser
        130              135              140

Pro Cys Asn Gly Ile Lys Gly Gln Ser Ile Cys Trp Ser Thr Thr Ala
145              150              155              160

Pro Ile His Val Ser Asp Gly Gly Gly Pro Leu Asp Thr Thr Arg Ile
              165              170              175

Lys Ser Val Gln Arg Lys Leu Glu Glu Ile His Lys Ala Leu Tyr Pro
              180              185              190

Glu Leu Gln Tyr His Pro Leu Ala Ile Pro Lys Val Arg Asp Asn Leu
        195              200              205
```

```
Met Val Asp Ala Gln Thr Leu Asn Ile Leu Asn Ala Thr Tyr Asn Leu
    210             215             220

Leu Leu Met Ser Asn Thr Ser Leu Val Asp Asp Cys Trp Leu Cys Leu
225             230             235             240

Lys Leu Gly Pro Pro Thr Pro Leu Ala Ile Pro Asn Phe Leu Leu Ser
            245             250             255

Tyr Val Thr Arg Ser Ser Asp Asn Ile Ser Cys Leu Ile Ile Pro Pro
            260             265             270

Leu Leu Val Gln Pro Met Gln Phe Ser Asn Ser Ser Cys Leu Phe Ser
        275             280             285

Pro Ser Tyr Asn Ser Thr Glu Glu Ile Asp Leu Gly His Val Ala Phe
    290             295             300

Ser Asn Cys Thr Ser Ile Thr Asn Val Thr Gly Pro Ile Cys Ala Val
305             310             315             320

Asn Gly Ser Val Phe Leu Cys Gly Asn Asn Met Ala Tyr Thr Tyr Leu
            325             330             335

Pro Thr Asn Trp Thr Gly Leu Cys Val Leu Ala Thr Leu Leu Pro Asp
            340             345             350

Ile Asp Ile Ile Pro Gly Asp Glu Pro Val Pro Ile Pro Ala Ile Asp
        355             360             365

His Phe Ile Tyr Arg Pro Lys Arg Ala Ile Gln Phe Ile Pro Leu Leu
    370             375             380

Ala Gly Leu Gly Ile Thr Ala Ala Phe Thr Thr Gly Ala Thr Gly Leu
385             390             395             400

Gly Val Ser Val Thr Gln Tyr Thr Lys Leu Ser Asn Gln Leu Ile Ser
            405             410             415

Asp Val Gln Ile Leu Ser Ser Thr Ile Gln Asp Leu Gln Asp Gln Val
            420             425             430

Asp Ser Leu Ala Glu Val Val Leu Gln Asn Arg Arg Gly Leu Asp Leu
        435             440             445

Leu Thr Ala Glu Gln Gly Gly Ile Cys Leu Ala Leu Gln Glu Lys Cys
    450             455             460

Cys Phe Tyr Val Asn Lys Ser Gly Ile Val Arg Asp Lys Ile Lys Thr
465             470             475             480

Leu Gln Glu Glu Leu Glu Arg Arg Lys Asp Leu Ala Ser Asn Pro
            485             490             495

Leu Trp Thr Gly Leu Gln Gly Leu Leu Pro Tyr Leu Leu Pro Phe Leu
            500             505             510

Gly Pro Leu Leu Thr Leu Leu Leu Leu Leu Thr Ile Gly Pro Cys Ile
            515             520             525

Phe Asn Arg Leu Thr Ala Phe Ile Asn Asp Lys Leu Asn Ile Ile His
    530             535             540

Ala Met Val Leu Thr Gln Gln Tyr Gln Val Leu Arg Thr Asp Glu Glu
545             550             555             560

Ala Gln Asp
```

```
<210> SEQ ID NO 50
<211> LENGTH: 566
<212> TYPE: PRT
<213> ORGANISM: Influenza virus
<220> FEATURE:
<221> NAME/KEY: VARIANT
<222> LOCATION: (239)..(240)
<223> OTHER INFORMATION: Xaa can be any naturally occurring amino acid

<400> SEQUENCE: 50
```

-continued

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
        50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
        130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Ala Tyr Val Phe Val Gly Ser Ser Arg Tyr Ser
        210                 215                 220

Lys Lys Phe Lys Pro Glu Ile Ala Ile Arg Pro Lys Val Arg Xaa Xaa
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
        290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
        370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415
```

-continued

```
Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
            450                 455                 460

Lys Val Arg Ser Gln Leu Lys Asn Asn Ala Lys Glu Ile Gly Asn Gly
        465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
            530                 535                 540

Val Ser Leu Gly Ala Ile Ser Phe Trp Met Cys Ser Asn Gly Ser Leu
        545                 550                 555                 560

Gln Cys Arg Ile Cys Ile
            565

<210> SEQ ID NO 51
<211> LENGTH: 566
<212> TYPE: PRT
<213> ORGANISM: Influenza virus

<400> SEQUENCE: 51

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
        50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Thr
            130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
            195                 200                 205

Ser Leu Tyr Ala Gln Ala Ser Gly Arg Ile Thr Val Ser Thr Lys Arg
        210                 215                 220
```

```
Ser Gln Gln Thr Val Ile Pro Ser Ile Gly Ser Arg Pro Arg Ile Arg
225             230             235             240

Asp Val Pro Ser Arg Ile Ser Ile Tyr Trp Thr Ile Val Lys Pro Gly
            245             250             255

Asp Ile Leu Leu Ile Asn Ser Thr Gly Asn Leu Ile Ala Pro Arg Gly
            260             265             270

Tyr Phe Lys Ile Arg Ser Gly Lys Ser Ser Ile Met Arg Ser Asp Ala
            275             280             285

Pro Ile Gly Lys Cys Asn Ser Glu Cys Ile Thr Pro Asn Gly Ser Ile
            290             295             300

Pro Asn Asp Lys Pro Phe Gln Asn Val Asn Arg Ile Thr Tyr Gly Ala
305             310             315             320

Cys Pro Arg Tyr Val Lys Gln Asn Thr Leu Lys Leu Ala Thr Gly Met
            325             330             335

Arg Asn Val Pro Glu Lys Gln Thr Arg Gly Ile Phe Gly Ala Ile Ala
            340             345             350

Gly Phe Ile Glu Asn Gly Trp Glu Gly Met Val Asp Gly Trp Tyr Gly
            355             360             365

Phe Arg His Gln Asn Ser Glu Gly Thr Gly Gln Ala Ala Asp Leu Lys
            370             375             380

Ser Thr Gln Ala Ala Ile Asn Gln Ile Asn Gly Lys Leu Asn Arg Leu
385             390             395             400

Ile Gly Lys Thr Asn Glu Lys Phe His Gln Ile Glu Lys Glu Phe Ser
            405             410             415

Glu Val Glu Gly Arg Ile Gln Asp Leu Glu Lys Tyr Val Glu Asp Thr
            420             425             430

Lys Ile Asp Leu Trp Ser Tyr Asn Ala Glu Leu Leu Val Ala Leu Glu
            435             440             445

Asn Gln His Thr Ile Asp Leu Thr Asp Ser Glu Met Asn Lys Leu Phe
            450             455             460

Glu Arg Thr Lys Lys Gln Leu Arg Glu Asn Ala Glu Asp Met Gly Asn
465             470             475             480

Gly Cys Phe Lys Ile Tyr His Lys Cys Asp Asn Ala Cys Ile Gly Ser
            485             490             495

Ile Arg Asn Gly Thr Tyr Asp His Asp Val Tyr Arg Asp Glu Ala Leu
            500             505             510

Asn Asn Arg Phe Gln Ile Lys Gly Val Glu Leu Lys Ser Gly Tyr Lys
            515             520             525

Asp Trp Ile Leu Trp Ile Ser Phe Ala Ile Ser Cys Phe Leu Leu Cys
            530             535             540

Val Ala Leu Leu Gly Phe Ile Met Trp Ala Cys Gln Lys Gly Asn Ile
545             550             555             560

Arg Cys Asn Ile Cys Ile
            565

<210> SEQ ID NO 52
<211> LENGTH: 568
<212> TYPE: PRT
<213> ORGANISM: Influenza virus

<400> SEQUENCE: 52

Met Glu Lys Ile Val Leu Leu Leu Ala Ile Val Ser Leu Val Lys Ser
1               5               10              15

Asp Gln Ile Cys Ile Gly Tyr His Ala Asn Asn Ser Thr Glu Gln Val
```

-continued

```
                20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asn Gly Val Lys
        50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Asp Leu Cys Tyr Pro Gly Asp Phe Asn
                100                 105                 110

Asp Tyr Glu Glu Leu Lys His Leu Leu Ser Arg Thr Asn His Phe Glu
            115                 120                 125

Lys Ile Gln Ile Ile Pro Lys Ser Ser Trp Ser Asn His Asp Ala Ser
        130                 135                 140

Ser Gly Val Ser Ser Ala Cys Pro Tyr His Gly Arg Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
        210                 215                 220

Leu Val Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Met Lys Ser Glu Leu Glu Tyr Gly
            275                 280                 285

Asn Cys Asn Thr Lys Cys Gln Thr Pro Met Gly Ala Ile Asn Ser Ser
        290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Thr
            325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Gln Met Glu Asp
            420                 425                 430

Gly Phe Leu Asp Val Trp Thr Tyr Asn Ala Glu Leu Leu Val Leu Met
            435                 440                 445
```

```
Glu Asn Glu Arg Thr Leu Asp Phe His Asp Ser Asn Val Lys Asn Leu
    450             455             460

Tyr Asp Lys Val Arg Leu Gln Leu Arg Asp Asn Ala Lys Glu Leu Gly
465             470             475             480

Asn Gly Cys Phe Glu Phe Tyr His Lys Cys Asp Asn Glu Cys Met Glu
            485             490             495

Ser Val Lys Asn Gly Thr Tyr Asp Tyr Pro Gln Tyr Ser Glu Glu Ala
            500             505             510

Arg Leu Asn Arg Glu Glu Ile Ser Gly Val Lys Leu Glu Ser Met Gly
            515             520             525

Thr Tyr Gln Ile Leu Ser Ile Tyr Ser Thr Val Ala Ser Ser Leu Ala
    530             535             540

Leu Ala Ile Met Val Ala Gly Leu Ser Leu Trp Met Cys Ser Asn Gly
545             550             555             560

Ser Leu Gln Cys Arg Ile Cys Ile
            565

<210> SEQ ID NO 53
<211> LENGTH: 560
<212> TYPE: PRT
<213> ORGANISM: Influenza virus

<400> SEQUENCE: 53

Met Asn Thr Gln Ile Leu Val Phe Ala Leu Ile Ala Ile Ile Pro Thr
1               5               10              15

Asn Ala Asp Lys Ile Cys Leu Gly His His Ala Val Ser Asn Gly Thr
            20              25              30

Lys Val Asn Thr Leu Thr Glu Arg Gly Val Glu Val Val Asn Ala Thr
            35              40              45

Glu Thr Val Glu Arg Thr Asn Ile Pro Arg Ile Cys Ser Lys Gly Lys
    50              55              60

Arg Thr Val Asp Leu Gly Gln Cys Gly Leu Leu Gly Thr Ile Thr Gly
65              70              75              80

Pro Pro Gln Cys Asp Gln Phe Leu Glu Phe Ser Ala Asp Leu Ile Ile
            85              90              95

Glu Arg Arg Glu Gly Ser Asp Val Cys Tyr Pro Gly Lys Phe Val Asn
            100             105             110

Glu Glu Ala Leu Arg Gln Ile Leu Arg Glu Ser Gly Gly Ile Asp Lys
    115             120             125

Glu Ala Met Gly Phe Thr Tyr Ser Gly Ile Arg Thr Asn Gly Ala Thr
    130             135             140

Ser Ala Cys Arg Arg Ser Gly Ser Ser Phe Tyr Ala Glu Met Lys Trp
145             150             155             160

Leu Leu Ser Asn Thr Asp Asn Ala Ala Phe Pro Gln Met Thr Lys Ser
            165             170             175

Tyr Lys Asn Thr Arg Lys Ser Pro Ala Leu Ile Val Trp Gly Ile His
            180             185             190

His Ser Val Ser Thr Ala Glu Gln Thr Lys Leu Tyr Gly Ser Gly Asn
            195             200             205

Lys Leu Val Thr Val Gly Ser Ser Asn Tyr Gln Gln Ser Phe Val Pro
    210             215             220

Ser Pro Gly Ala Arg Pro Gln Val Asn Gly Leu Ser Gly Arg Ile Asp
225             230             235             240

Phe His Trp Leu Met Leu Asn Pro Asn Asp Thr Val Thr Phe Ser Phe
```

-continued

```
                    245              250              255

Asn Gly Ala Phe Ile Ala Pro Asp Arg Ala Ser Phe Leu Arg Gly Lys
                260              265              270

Ser Met Gly Ile Gln Ser Gly Val Gln Val Asp Ala Asn Cys Glu Gly
                275              280              285

Asp Cys Tyr His Ser Gly Gly Thr Ile Ile Ser Asn Leu Pro Phe Gln
                290              295              300

Asn Ile Asp Ser Arg Ala Val Gly Lys Cys Pro Arg Tyr Val Lys Gln
305              310              315              320

Arg Ser Leu Leu Leu Ala Thr Gly Met Lys Asn Val Pro Glu Ile Pro
                325              330              335

Lys Gly Arg Gly Leu Phe Gly Ala Ile Ala Gly Phe Ile Glu Asn Gly
                340              345              350

Trp Glu Gly Leu Ile Asp Gly Trp Tyr Gly Phe Arg His Gln Asn Ala
                355              360              365

Gln Gly Glu Gly Thr Ala Ala Asp Tyr Lys Ser Thr Gln Ser Ala Ile
                370              375              380

Asp Gln Ile Thr Gly Lys Leu Asn Arg Leu Ile Glu Lys Thr Asn Gln
385              390              395              400

Gln Phe Glu Leu Ile Asp Asn Glu Phe Asn Glu Val Glu Lys Gln Ile
                405              410              415

Gly Asn Val Ile Asn Trp Thr Arg Asp Ser Ile Thr Glu Val Trp Ser
                420              425              430

Tyr Asn Ala Glu Leu Leu Val Ala Met Glu Asn Gln His Thr Ile Asp
                435              440              445

Leu Ala Asp Ser Glu Met Asp Lys Leu Tyr Glu Arg Val Lys Arg Gln
                450              455              460

Leu Arg Glu Asn Ala Glu Glu Asp Gly Thr Gly Cys Phe Glu Ile Phe
465              470              475              480

His Lys Cys Asp Asp Asp Cys Met Ala Ser Ile Arg Asn Asn Thr Tyr
                485              490              495

Asp His Ser Lys Tyr Arg Glu Glu Ala Met Gln Asn Arg Ile Gln Ile
                500              505              510

Asp Pro Val Lys Leu Ser Ser Gly Tyr Lys Asp Val Ile Leu Trp Phe
                515              520              525

Ser Phe Gly Ala Ser Cys Phe Ile Leu Leu Ala Ile Val Met Gly Leu
                530              535              540

Val Phe Ile Cys Val Lys Asn Gly Asn Met Arg Cys Thr Ile Cys Ile
545              550              555              560

<210> SEQ ID NO 54
<211> LENGTH: 226
<212> TYPE: PRT
<213> ORGANISM: Hepatitis B Virus

<400> SEQUENCE: 54

Met Glu Asn Thr Thr Ser Gly Phe Leu Gly Pro Leu Leu Val Leu Gln
1               5               10              15

Ala Gly Phe Phe Leu Leu Thr Arg Asn Leu Thr Ile Pro Gln Ser Leu
                20              25              30

Asp Ser Trp Trp Thr Ser Leu Asn Phe Leu Gly Gly Ala Pro Thr Cys
                35              40              45

Pro Gly Gln Asn Ser Gln Ser Pro Thr Ser Asn His Ser Pro Thr Ser
                50              55              60
```

-continued

```
Cys Pro Pro Ile Cys Pro Gly Tyr Arg Trp Met Cys Leu Arg Arg Phe
65              70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Leu Pro Gly
            100                 105             110

Thr Ser Thr Thr Ser Thr Gly Pro Cys Lys Thr Cys Thr Ile Pro Ala
        115                 120             125

Gln Gly Thr Ser Met Phe Pro Ser Cys Cys Cys Thr Lys Pro Ser Asp
        130                 135             140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170             175

Val Pro Phe Val Gln Trp Phe Val Gly Leu Ser Pro Thr Val Trp Leu
                180                 185             190

Ser Val Ile Trp Met Met Trp Tyr Trp Gly Pro Ser Leu Tyr Asn Ile
                195                 200             205

Leu Ser Pro Phe Leu Pro Leu Leu Pro Ile Phe Phe Cys Leu Trp Val
        210                 215             220

Tyr Ile
225
```

```
<210> SEQ ID NO 55
<211> LENGTH: 281
<212> TYPE: PRT
<213> ORGANISM: Hepatitis B Virus

<400> SEQUENCE: 55

Met Gln Trp Asn Ser Thr Ala Phe His Gln Ala Leu Gln Asp Pro Lys
1                   5                   10                  15

Val Arg Gly Leu Tyr Phe Pro Ala Gly Gly Ser Ser Ser Gly Thr Val
                20                  25                  30

Asn Pro Ala Pro Asn Ile Ala Ser His Ile Ser Ser Ile Ser Ala Arg
            35                  40                  45

Thr Gly Asp Pro Val Thr Asn Met Glu Asn Ile Thr Ser Gly Phe Leu
        50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Ser Pro Val Cys Leu Gly Gln Asn Ser Gln Ser Pro Thr
                100                 105             110

Ser Asn His Ser Pro Thr Ser Cys Pro Pro Ile Cys Pro Gly Tyr Arg
        115                 120             125

Trp Met Cys Leu Arg Arg Phe Ile Ile Phe Leu Phe Ile Leu Leu Leu
        130                 135             140

Cys Leu Ile Phe Leu Leu Val Leu Leu Asp Tyr Gln Gly Met Leu Pro
145                 150                 155                 160

Val Cys Pro Leu Ile Pro Gly Ser Thr Thr Thr Ser Thr Gly Pro Cys
                165                 170             175

Lys Thr Cys Thr Thr Pro Ala Gln Gly Asn Ser Met Phe Pro Ser Cys
                180                 185             190

Cys Cys Thr Lys Pro Thr Asp Gly Asn Cys Thr Cys Ile Pro Ile Pro
                195                 200             205
```

```
Ser Ser Trp Ala Phe Ala Lys Tyr Leu Trp Glu Trp Ala Ser Val Arg
    210             215             220
```

```
Phe Ser Trp Leu Ser Leu Leu Val Pro Phe Val Gln Trp Phe Val Gly
225             230             235             240
```

```
Leu Ser Pro Thr Val Trp Leu Ser Ala Ile Trp Met Met Trp Tyr Trp
            245             250             255
```

```
Gly Pro Ser Leu Tyr Ser Ile Val Ser Pro Phe Ile Pro Leu Leu Pro
            260             265             270
```

```
Ile Phe Phe Cys Leu Trp Val Tyr Ile
        275             280
```

```
<210> SEQ ID NO 56
<211> LENGTH: 399
<212> TYPE: PRT
<213> ORGANISM: Hepatitis B Virus
```

```
<400> SEQUENCE: 56
```

```
Met Gly Leu Ser Trp Thr Val Pro Leu Glu Trp Gly Lys Asn His Ser
1               5               10              15
```

```
Thr Thr Asn Pro Leu Gly Phe Phe Pro Asp His Gln Leu Asp Pro Ala
            20              25              30
```

```
Phe Arg Ala Asn Thr Arg Asn Pro Asp Trp Asp His Asn Pro Asn Lys
        35              40              45
```

```
Asp His Trp Thr Glu Ala Asn Lys Val Gly Val Gly Ala Phe Gly Pro
    50              55              60
```

```
Gly Phe Thr Pro Pro His Gly Gly Leu Leu Gly Trp Ser Pro Gln Ala
65              70              75              80
```

```
Gln Gly Met Leu Lys Thr Leu Pro Ala Asp Pro Pro Ala Ser Thr
            85              90              95
```

```
Asn Arg Gln Ser Gly Arg Gln Pro Thr Pro Ile Thr Pro Pro Leu Arg
            100             105             110
```

```
Asp Thr His Pro Gln Ala Met Gln Trp Asn Ser Thr Thr Phe His Gln
        115             120             125
```

```
Ala Leu Gln Asp Pro Lys Val Ser Ala Leu Tyr Leu Pro Ala Gly Gly
    130             135             140
```

```
Ser Ser Ser Gly Thr Val Asn Pro Val Pro Thr Thr Ala Ser Leu Ile
145             150             155             160
```

```
Ser Ser Ile Phe Ser Arg Ile Gly Asp Pro Ala Pro Asn Met Glu Ser
            165             170             175
```

```
Ile Thr Ser Gly Phe Leu Gly Pro Leu Leu Val Leu Gln Ala Gly Phe
            180             185             190
```

```
Phe Leu Leu Thr Lys Ile Leu Thr Ile Pro Gln Ser Leu Asp Ser Trp
            195             200             205
```

```
Trp Thr Ser Leu Asn Phe Leu Gly Gly Ala Pro Val Cys Leu Gly Gln
    210             215             220
```

```
Asn Ser Gln Ser Pro Thr Ser Ser His Ser Pro Thr Ser Cys Pro Pro
225             230             235             240
```

```
Ile Cys Pro Gly Tyr Arg Trp Met Cys Leu Arg Arg Phe Ile Ile Phe
            245             250             255
```

```
Leu Phe Ile Leu Leu Leu Cys Leu Ile Phe Leu Leu Val Leu Leu Asp
            260             265             270
```

```
Tyr Gln Gly Met Leu Pro Val Cys Pro Leu Ile Pro Gly Ser Ser Thr
            275             280             285
```

```
Thr Ser Thr Gly Pro Cys Arg Thr Cys Thr Thr Leu Ala Gln Gly Thr
```

-continued

```
            290                 295                 300

Ser Met Phe Pro Ser Cys Cys Cys Ser Lys Pro Ser Asp Gly Asn Cys
305                 310                 315                 320

Thr Cys Ile Pro Ile Pro Ser Ser Trp Ala Phe Gly Lys Phe Leu Trp
                325                 330                 335

Glu Trp Ala Ser Ala Arg Phe Ser Trp Leu Ser Leu Leu Val Pro Phe
                340                 345                 350

Val Gln Trp Phe Ala Gly Leu Ser Pro Thr Val Trp Leu Ser Val Ile
            355                 360                 365

Trp Met Met Trp Tyr Trp Gly Pro Ser Leu Tyr Asn Ile Leu Ser Pro
        370                 375                 380

Phe Ile Pro Leu Leu Pro Ile Phe Phe Cys Leu Trp Val Tyr Ile
385                 390                 395

<210> SEQ ID NO 57
<211> LENGTH: 226
<212> TYPE: PRT
<213> ORGANISM: Hepatitis B Virus

<400> SEQUENCE: 57

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Thr Thr Val Cys
            35                  40                  45

Leu Gly Gln Asn Ser Gln Ser Pro Thr Ser Asn His Ser Pro Thr Ser
        50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Thr Thr Pro Ala
            115                 120                 125

Gln Gly Thr Ser Met Tyr Pro Ser Cys Cys Cys Thr Lys Pro Ser Asp
        130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Ala Pro Asn Leu His Asn Ile
            195                 200                 205

Leu Ser Pro Phe Leu Pro Leu Leu Pro Ile Phe Leu Cys Leu Trp Val
        210                 215                 220

Tyr Ile
225

<210> SEQ ID NO 58
<211> LENGTH: 400
<212> TYPE: PRT
<213> ORGANISM: Hepatitis B Virus
```

```
<400> SEQUENCE: 58

Met Gly Gly Trp Ser Ser Lys Pro Arg Lys Gly Met Gly Thr Asn Leu
1               5                   10                  15

Ala Val Pro Asn Pro Leu Gly Phe Phe Pro Asp His Gln Leu Asp Pro
                20                  25                  30

Ala Phe Lys Ala Asn Ser Asp Asn Pro Asp Trp Asp Leu Asn Thr His
            35                  40                  45

Lys Asp Tyr Trp Pro Asp Ala Trp Lys Val Gly Val Gly Ala Phe Gly
        50                  55                  60

Pro Gly Phe Thr Pro Pro His Gly Gly Leu Leu Gly Trp Ser Pro Gln
65                  70                  75                  80

Ala Gln Gly Leu Leu Thr Thr Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala Met Lys Trp Asn Ser Thr Thr Phe His
            115                 120                 125

Gln Thr Leu Gln Asp Pro Arg Val Arg Ala Leu Tyr Leu Pro Ala Gly
        130                 135                 140

Gly Ser Ser Ser Gly Thr Val Ser Pro Ala Gln Asn Thr Val Ser Ala
145                 150                 155                 160

Ile Ser Ser Ile Leu Ser Lys Thr Gly Asp Pro Val Pro Asn Met Glu
                165                 170                 175

Ser Ile Ala Ser Gly Leu Leu Gly Pro Leu Leu Val Leu Gln Ala Gly
            180                 185                 190

Phe Phe Leu Leu Thr Lys Ile Leu Thr Ile Pro Gln Ser Leu Asp Ser
            195                 200                 205

Trp Trp Thr Ser Leu Asn Phe Leu Gly Gly Thr Pro Val Cys Leu Gly
        210                 215                 220

Gln Asn Ser Gln Ser Gln Ile Ser Ser His Ser Pro Thr Cys Cys Pro
225                 230                 235                 240

Pro Thr Cys Pro Gly Tyr Arg Trp Met Cys Leu Arg Arg Phe Ile Ile
                245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
        275                 280                 285

Thr Thr Ser Thr Gly Pro Cys Lys Thr Cys Thr Ala Pro Ala Gln Gly
        290                 295                 300

Thr Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
            355                 360                 365

Ile Trp Met Met Trp Phe Trp Gly Pro Ser Leu Tyr Asn Ile Leu Ser
        370                 375                 380

Pro Phe Ile Pro Leu Leu Pro Ile Phe Phe Cys Leu Trp Val Tyr Ile
385                 390                 395                 400

<210> SEQ ID NO 59
```

```
<211> LENGTH: 281
<212> TYPE: PRT
<213> ORGANISM: Hepatitis B Virus

<400> SEQUENCE: 59

Met Gln Trp Asn Ser Thr Thr Phe His Gln Thr Leu Gln Asp Pro Arg
1               5                   10                  15

Val Arg Gly Leu Tyr Phe Pro Ala Gly Gly Ser Ser Ser Gly Thr Val
                20                  25                  30

Asn Pro Val Pro Thr Thr Val Ser His Ile Ser Ser Ile Phe Ser Arg
            35                  40                  45

Ile Gly Asp Pro Ala Leu Asn Met Glu Asn Ile Thr Ser Gly Phe Leu
        50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Thr Thr Val Cys Leu Gly Gln Asn Ser Gln Ser Pro Thr
                100                 105                 110

Ser Asn His Ser Pro Thr Ser Cys Pro Pro Thr Cys Pro Gly Tyr Arg
            115                 120                 125

Trp Met Cys Leu Arg Arg Phe Ile Ile Phe Leu Phe Ile Leu Leu Leu
        130                 135                 140

Cys Leu Ile Phe Leu Leu Val Leu Leu Asp Tyr Gln Gly Met Leu Ser
145                 150                 155                 160

Val Cys Pro Leu Ile Pro Gly Ser Thr Thr Thr Ser Thr Gly Pro Cys
                165                 170                 175

Lys Thr Cys Thr Thr Pro Ala Gln Gly Thr Ser Ile His Pro Ser Cys
            180                 185                 190

Cys Cys Thr Lys Pro Ser Asp Gly Asn Cys Thr Trp Ile Pro Ile Pro
            195                 200                 205

Ser Ser Trp Ala Phe Gly Lys Phe Leu Trp Glu Trp Ala Ser Ala Arg
        210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Ile Trp Ile Met Trp Tyr Trp
                245                 250                 255

Gly Pro Ser Leu Tyr Ser Ile Leu Ser Pro Phe Leu Pro Leu Leu Pro
                260                 265                 270

Ile Phe Phe Cys Leu Trp Val Tyr Ile
            275                 280

<210> SEQ ID NO 60
<211> LENGTH: 524
<212> TYPE: PRT
<213> ORGANISM: Rabies virus

<400> SEQUENCE: 60

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
                20                  25                  30

Trp Ser Pro Ile Asp Ile His His Leu Ser Cys Pro Asn Asn Leu Val
            35                  40                  45

Val Glu Asp Glu Gly Cys Thr Asn Leu Ser Gly Phe Ser Tyr Met Glu
        50                  55                  60
```

-continued

```
Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ser Ala Tyr Asn Trp Lys Met Ala Gly Asp Pro Arg Tyr Glu
            115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Lys Ser Leu His Ser Arg Val Phe Pro Ser Gly
                165                 170                 175

Lys Cys Ser Gly Ile Thr Val Ser Ser Thr Tyr Cys Ser Thr Asn His
            180                 185                 190

Asp Tyr Thr Ile Trp Met Pro Glu Asn Leu Arg Leu Gly Thr Ser Cys
            195                 200                 205

Asp Ile Phe Ile Asn Ser Arg Gly Lys Arg Ala Ser Lys Gly Ser Gln
    210                 215                 220

Thr Cys Gly Phe Ile Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
            260                 265                 270

Pro Asp Gln Leu Val Asn Leu His Asp Phe Arg Ser Asp Glu Ile Glu
            275                 280                 285

His Leu Val Val Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Arg Val Gly Gly
            355                 360                 365

Arg Cys His Pro His Val Asn Gly Val Phe Phe Asn Gly Ile Ile Leu
    370                 375                 380

Gly Pro Glu Gly His Val Leu Ile Pro Glu Met Gln Ser Ser Leu Leu
385                 390                 395                 400

Gln Gln His Met Glu Leu Leu Glu Ser Ser Val Ile Pro Leu Met His
                405                 410                 415

Pro Leu Ala Asp Pro Ser Thr Val Phe Lys Glu Gly Asp Glu Ala Glu
            420                 425                 430

Asp Phe Val Glu Val His Leu Pro Asp Val His Lys Gln Val Ser Gly
            435                 440                 445

Val Asn Leu Gly Leu Pro Asn Trp Gly Lys Tyr Val Leu Leu Ser Ala
    450                 455                 460

Gly Ala Leu Ile Ala Leu Met Leu Ile Ile Phe Leu Leu Thr Cys Cys
465                 470                 475                 480
```

Arg Arg Val Asn Arg Pro Glu Ser Thr Gln His Ser Leu Gly Gly Lys
            485              490              495

Arg Arg Lys Val Ser Ile Thr Ser Gln Ser Gly Lys Ile Ile Ser Ser
            500              505              510

Trp Glu Ser Tyr Lys Ser Gly Gly Glu Thr Arg Leu
            515              520

<210> SEQ ID NO 61
<211> LENGTH: 522
<212> TYPE: PRT
<213> ORGANISM: Mokola virus

<400> SEQUENCE: 61

Met Asn Ile Pro Cys Phe Val Val Ile Leu Ser Leu Ala Thr Thr His
1               5                   10                  15

Ser Leu Gly Glu Phe Pro Leu Tyr Thr Ile Pro Glu Lys Ile Glu Lys
            20                  25                  30

Trp Thr Pro Ile Asp Met Ile His Leu Ser Cys Pro Asn Asn Leu Leu
            35                  40                  45

Ser Glu Glu Glu Gly Cys Asn Ala Glu Ser Ser Phe Thr Tyr Phe Glu
            50                  55                  60

Leu Lys Ser Gly Tyr Leu Ala His Gln Lys Val Pro Gly Phe Thr Cys
65                  70                  75                  80

Thr Gly Val Val Asn Glu Ala Glu Thr Tyr Thr Asn Phe Val Gly Tyr
            85                  90                  95

Val Thr Thr Thr Phe Lys Arg Lys His Phe Arg Pro Thr Val Ala Ala
            100                 105                 110

Cys Arg Asp Ala Tyr Asn Trp Lys Val Ser Gly Asp Pro Arg Tyr Glu
            115                 120                 125

Glu Ser Leu His Thr Pro Tyr Pro Asp Ser Ser Trp Leu Arg Thr Val
            130                 135                 140

Thr Thr Thr Lys Glu Ser Leu Leu Ile Ile Ser Pro Ser Ile Val Glu
145                 150                 155                 160

Met Asp Ile Tyr Gly Arg Thr Leu His Ser Pro Met Phe Pro Ser Gly
            165                 170                 175

Val Cys Ser Asn Val Tyr Pro Ser Val Pro Ser Cys Glu Thr Asn His
            180                 185                 190

Asp Tyr Thr Leu Trp Leu Pro Glu Asp Pro Ser Leu Ser Leu Val Cys
            195                 200                 205

Asp Ile Phe Thr Ser Ser Asn Gly Lys Lys Ala Met Asn Gly Ser Arg
            210                 215                 220

Ile Cys Gly Phe Lys Asp Glu Arg Gly Phe Tyr Arg Ser Leu Lys Gly
225                 230                 235                 240

Ala Cys Lys Leu Thr Leu Cys Gly Arg Pro Gly Ile Arg Leu Phe Asp
            245                 250                 255

Gly Thr Trp Val Ser Phe Thr Lys Pro Asp Val His Val Trp Cys Thr
            260                 265                 270

Pro Asn Gln Leu Ile Asn Ile His Asn Asp Arg Leu Asp Glu Ile Glu
            275                 280                 285

His Leu Ile Val Glu Asp Ile Ile Lys Lys Arg Glu Glu Cys Leu Asp
            290                 295                 300

Thr Leu Glu Thr Ile Leu Met Ser Gln Ser Val Ser Phe Arg Arg Leu
305                 310                 315                 320

Ser His Phe Arg Lys Leu Val Pro Gly Tyr Gly Lys Ala Tyr Thr Ile
            325                 330                 335

```
Leu Asn Gly Ser Leu Met Glu Thr Asn Val Tyr Tyr Lys Arg Val Asp
            340                 345                 350

Lys Trp Ala Asp Ile Leu Pro Ser Lys Gly Cys Leu Lys Val Gly Gln
            355                 360                 365

Gln Cys Met Glu Pro Val Lys Gly Val Leu Phe Asn Gly Ile Ile Lys
        370                 375                 380

Gly Pro Asp Gly Gln Ile Leu Ile Pro Glu Met Gln Ser Glu Gln Leu
385                 390                 395                 400

Lys Gln His Met Asp Leu Leu Lys Ala Ala Val Phe Pro Leu Arg His
                405                 410                 415

Pro Leu Ile Ser Arg Glu Ala Val Phe Lys Lys Asp Gly Asp Ala Asp
            420                 425                 430

Asp Phe Val Asp Leu His Met Pro Asp Val His Lys Ser Val Ser Asp
            435                 440                 445

Val Asp Leu Gly Leu Pro His Trp Gly Phe Trp Met Leu Ile Gly Ala
        450                 455                 460

Thr Ile Val Ala Phe Val Val Leu Val Cys Leu Leu Arg Val Cys Cys
465                 470                 475                 480

Lys Arg Val Arg Arg Arg Ser Gly Arg Ala Thr Gln Glu Ile Pro
                485                 490                 495

Leu Ser Phe Pro Ser Ala Pro Val Pro Arg Ala Lys Val Val Ser Ser
            500                 505                 510

Trp Glu Ser Tyr Lys Gly Leu Pro Gly Thr
            515                 520
```

```
<210> SEQ ID NO 62
<211> LENGTH: 498
<212> TYPE: PRT
<213> ORGANISM: Lymphocytic choriomeningitis virus

<400> SEQUENCE: 62
```

```
Met Gly Gln Ile Val Thr Met Phe Glu Ala Leu Pro His Ile Ile Asp
1               5                   10                  15

Glu Val Ile Asn Ile Val Ile Ile Val Leu Ile Ile Ile Thr Ser Ile
            20                  25                  30

Lys Ala Val Tyr Asn Phe Ala Thr Cys Gly Ile Leu Ala Leu Ile Ser
        35                  40                  45

Phe Leu Leu Leu Ala Gly Arg Ser Cys Gly Leu Tyr Gly Leu Asp Gly
    50                  55                  60

Pro Asp Ile Tyr Lys Gly Ile Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Asn Ser Gly Leu Glu Leu Thr Phe
            100                 105                 110

Thr Asn Asp Ser Ile Ile Ser His Asn Phe Cys Asn Leu Thr Ser Ala
            115                 120                 125

Phe Asn Lys Lys Thr Phe Asp His Thr Leu Met Ser Ile Val Ser Ser
        130                 135                 140

Leu His Leu Ser Ile Arg Gly Asn Ser Asn Tyr Lys Ala Val Ser Cys
145                 150                 155                 160

Asp Phe Asn Ser Gly Ile Thr Ile Gln Tyr Asn Leu Ser Phe Ser Asp
                165                 170                 175

Ala Gln Ser Ala Leu Ser Gln Cys Lys Thr Phe Arg Gly Arg Val Leu
```

-continued

```
                180             185             190

Asp Met Phe Arg Thr Ala Phe Gly Gly Lys Tyr Met Arg Ser Gly Trp
        195             200             205

Gly Trp Thr Gly Ser Asp Gly Lys Thr Thr Trp Cys Ser Gln Thr Ser
        210             215             220

Tyr Gln Tyr Leu Ile Ile Gln Asn Arg Thr Trp Glu Asn His Cys Arg
225             230             235             240

Tyr Ala Gly Pro Phe Gly Met Ala Arg Ile Leu Phe Ala Gln Glu Lys
            245             250             255

Thr Lys Phe Leu Thr Arg Arg Leu Ala Gly Thr Phe Thr Trp Thr Leu
        260             265             270

Ser Asp Ser Ser Gly Val Asp Asn Pro Gly Gly Tyr Cys Leu Thr Arg
        275             280             285

Trp Met Ile Leu Ala Ala Asp Leu Lys Cys Phe Gly Asn Thr Ala Val
        290             295             300

Ala Lys Cys Asn Met Asn His Asp Glu Glu Phe Cys Asp Met Leu Arg
305             310             315             320

Leu Ile Asp Tyr Asn Lys Ala Ala Leu Ser Lys Phe Lys Glu Asp Val
            325             330             335

Glu Ser Ala Leu His Leu Phe Lys Val Thr Val Asn Ser Leu Val Ser
        340             345             350

Asp Gln Leu Leu Met Arg Asn His Leu Arg Asp Leu Met Gly Val Pro
        355             360             365

Tyr Cys Asn Tyr Ser Arg Phe Trp Tyr Leu Glu His Thr Lys Thr Gly
        370             375             380

Glu Thr Ser Val Pro Lys Cys Trp Leu Val Thr Asn Gly Ser Tyr Leu
385             390             395             400

Asn Glu Thr His Phe Ser Asp Gln Ile Glu Gln Glu Ala Asp Asn Met
            405             410             415

Ile Thr Asp Met Leu Arg Lys Asp Tyr Ile Lys Arg Gln Gly Ser Thr
            420             425             430

Pro Leu Ala Leu Met Asp Leu Leu Met Phe Ser Thr Ser Ala Tyr Leu
        435             440             445

Val Ser Val Phe Leu His Leu Val Lys Ile Pro Thr His Arg His Ile
        450             455             460

Lys Gly Gly Ser Cys Pro Lys Pro His Arg Leu Thr Asn Lys Gly Ile
465             470             475             480

Cys Ser Cys Gly Ala Phe Lys Val Pro Gly Val Lys Thr Val Trp Lys
            485             490             495

Arg Arg
```

```
<210> SEQ ID NO 63
<211> LENGTH: 498
<212> TYPE: PRT
<213> ORGANISM: Lymphocytic choriomeningitis virus

<400> SEQUENCE: 63

Met Gly Gln Ile Val Thr Met Phe Glu Ala Leu Pro His Ile Ile Asp
1               5               10              15

Glu Val Ile Asn Ile Val Ile Ile Val Leu Ile Ile Ile Thr Ser Ile
            20              25              30

Lys Ala Val Tyr Asn Phe Ala Thr Cys Gly Ile Leu Ala Leu Val Ser
        35              40              45

Phe Leu Phe Leu Ala Gly Arg Ser Cys Gly Met Tyr Gly Leu Asn Gly
```

-continued

```
           50                   55                    60

Pro Asp Ile Tyr Lys Gly Val Tyr Gln Phe Lys Ser Val Glu Phe Asp
65                   70                    75                    80

Met Ser His Leu Asn Leu Thr Met Pro Asn Ala Cys Ser Ala Asn Asn
                85                    90                    95

Ser His His Tyr Ile Ser Met Gly Ser Ser Gly Leu Glu Leu Thr Phe
                100                   105                   110

Thr Asn Asp Ser Ile Leu Asn His Asn Phe Cys Asn Leu Thr Ser Ala
                115                   120                   125

Phe Asn Lys Lys Thr Phe Asp His Thr Leu Met Ser Ile Val Ser Ser
        130                   135                   140

Leu His Leu Ser Ile Arg Gly Asn Ser Asn His Lys Ala Val Ser Cys
145                   150                   155                   160

Asp Phe Asn Asn Gly Ile Thr Ile Gln Tyr Asn Leu Ser Phe Ser Asp
                165                   170                   175

Pro Gln Ser Ala Ile Ser Gln Cys Arg Thr Phe Arg Gly Arg Val Leu
                180                   185                   190

Asp Met Phe Arg Thr Ala Phe Gly Gly Lys Tyr Met Arg Ser Gly Trp
                195                   200                   205

Gly Trp Ala Gly Ser Asp Gly Lys Thr Thr Trp Cys Ser Gln Thr Ser
        210                   215                   220

Tyr Gln Tyr Leu Ile Ile Gln Asn Arg Thr Trp Glu Asn His Cys Arg
225                   230                   235                   240

Tyr Ala Gly Pro Phe Gly Met Ser Arg Ile Leu Phe Ala Gln Glu Lys
                245                   250                   255

Thr Lys Phe Leu Thr Arg Arg Leu Ala Gly Thr Phe Thr Trp Thr Leu
                260                   265                   270

Ser Asp Ser Ser Gly Val Glu Asn Pro Gly Gly Tyr Cys Leu Thr Lys
                275                   280                   285

Trp Met Ile Leu Ala Ala Glu Leu Lys Cys Phe Gly Asn Thr Ala Val
        290                   295                   300

Ala Lys Cys Asn Val Asn His Asp Glu Glu Phe Cys Asp Met Leu Arg
305                   310                   315                   320

Leu Ile Asp Tyr Asn Lys Ala Ala Leu Ser Lys Phe Lys Gln Asp Val
                325                   330                   335

Glu Ser Ala Leu His Val Phe Lys Thr Thr Val Asn Ser Leu Ile Ser
                340                   345                   350

Asp Gln Leu Leu Met Arg Asn His Leu Arg Asp Leu Met Gly Val Pro
        355                   360                   365

Tyr Cys Asn Tyr Ser Lys Phe Trp Tyr Leu Glu His Ala Lys Thr Gly
        370                   375                   380

Glu Thr Ser Val Pro Lys Cys Trp Leu Val Thr Asn Gly Ser Tyr Leu
385                   390                   395                   400

Asn Glu Thr His Phe Ser Asp Gln Ile Glu Gln Glu Ala Asp Asn Met
                405                   410                   415

Ile Thr Glu Met Leu Arg Lys Asp Tyr Ile Lys Arg Gln Gly Ser Thr
                420                   425                   430

Pro Leu Ala Leu Met Asp Leu Leu Met Phe Ser Thr Ser Ala Tyr Leu
        435                   440                   445

Ile Ser Ile Phe Leu His Leu Val Lys Ile Pro Thr His Arg His Ile
        450                   455                   460

Lys Gly Gly Ser Cys Pro Lys Pro His Arg Leu Thr Asn Lys Gly Ile
465                   470                   475                   480
```

-continued

```
Cys Ser Cys Gly Ala Phe Lys Val Pro Gly Val Lys Thr Ile Trp Lys
            485                 490                 495

Arg Arg

<210> SEQ ID NO 64
<211> LENGTH: 498
<212> TYPE: PRT
<213> ORGANISM: Lymphocytic choriomeningitis virus

<400> SEQUENCE: 64

Met Gly Gln Ile Val Thr Met Phe Glu Ala Leu Pro His Ile Ile Asp
1               5                   10                  15

Glu Val Ile Asn Ile Val Ile Ile Val Leu Ile Val Ile Thr Gly Ile
                20                  25                  30

Lys Ala Val Tyr Asn Phe Ala Thr Cys Gly Ile Phe Ala Leu Ile Ser
            35                  40                  45

Phe Leu Leu Leu Ala Gly Arg Ser Cys Gly Met Tyr Gly Leu Lys Gly
        50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Thr Ser Gly Leu Glu Leu Thr Phe
            100                 105                 110

Thr Asn Asp Ser Ile Ile Ser His Asn Phe Cys Asn Leu Thr Ser Ala
            115                 120                 125

Phe Asn Lys Lys Thr Phe Asp His Thr Leu Met Ser Ile Val Ser Ser
        130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asp
                165                 170                 175

Ala Gln Ser Ala Gln Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
            195                 200                 205

Gly Trp Thr Gly Ser Asp Gly Lys Thr Thr Trp Cys Ser Gln Thr Ser
        210                 215                 220

Tyr Gln Tyr Leu Ile Ile Gln Asn Arg Thr Trp Glu Asn His Cys Thr
225                 230                 235                 240

Tyr Ala Gly Pro Phe Gly Met Ser Arg Ile Leu Leu Ser Gln Glu Lys
                245                 250                 255

Thr Lys Phe Phe Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
            275                 280                 285

Trp Met Ile Leu Ala Ala Glu Leu Lys Cys Phe Gly Asn Thr Ala Val
        290                 295                 300

Ala Lys Cys Asn Val Asn His Asp Ala Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
            340                 345                 350
```

-continued

```
Asp Gln Leu Leu Met Arg Asn His Leu Arg Asp Leu Met Gly Val Pro
        355              360              365

Tyr Cys Asn Tyr Ser Lys Phe Trp Tyr Leu Glu His Ala Lys Thr Gly
    370              375              380

Glu Thr Ser Val Pro Lys Cys Trp Leu Val Thr Asn Gly Ser Tyr Leu
385              390              395              400

Asn Glu Thr His Phe Ser Asp Gln Ile Glu Gln Glu Ala Asp Asn Met
            405              410              415

Ile Thr Glu Met Leu Arg Lys Asp Tyr Ile Lys Arg Gln Gly Ser Thr
            420              425              430

Pro Leu Ala Leu Met Asp Leu Leu Met Phe Ser Thr Ser Ala Tyr Leu
        435              440              445

Val Ser Ile Phe Leu His Leu Val Lys Ile Pro Thr His Arg His Ile
    450              455              460

Lys Gly Gly Ser Cys Pro Lys Pro His Arg Leu Thr Asn Lys Gly Ile
465              470              475              480

Cys Ser Cys Gly Ala Phe Lys Val Pro Gly Val Lys Thr Val Trp Lys
            485              490              495

Arg Arg

<210> SEQ ID NO 65
<211> LENGTH: 207
<212> TYPE: PRT
<213> ORGANISM: Lymphocytic choriomeningitis virus

<400> SEQUENCE: 65

Met Tyr Gly Leu Lys Gly Pro Asp Ile Tyr Lys Gly Val Tyr Gln Phe
1              5              10              15

Lys Ser Val Glu Phe Asp Met Ser His Leu Asn Leu Thr Met Pro Asn
            20              25              30

Ala Cys Ser Ala Asn Asn Ser His His Tyr Ile Ser Met Gly Thr Ser
        35              40              45

Gly Leu Glu Leu Thr Phe Thr Asn Asp Ser Ile Ile Ser His Asn Phe
    50              55              60

Cys Asn Leu Thr Ser Ala Phe Asn Lys Lys Thr Phe Asp His Thr Leu
65              70              75              80

Met Ser Ile Val Ser Ser Leu His Leu Ser Ile Arg Gly Asn Ser Asn
            85              90              95

Tyr Lys Ala Val Ser Cys Asp Phe Asn Asn Gly Ile Thr Ile Gln Tyr
            100              105              110

Asn Leu Thr Phe Ser Asp Ala Gln Ser Ala Gln Ser Gln Cys Arg Thr
        115              120              125

Phe Arg Gly Arg Val Leu Asp Met Phe Arg Thr Ala Phe Gly Gly Lys
        130              135              140

Tyr Met Arg Ser Gly Trp Gly Trp Thr Gly Ser Asp Gly Lys Thr Thr
145              150              155              160

Trp Cys Ser Gln Thr Ser Tyr Gln Tyr Leu Ile Ile Gln Asn Arg Thr
            165              170              175

Trp Glu Asn His Cys Thr Tyr Ala Gly Pro Phe Gly Met Ser Arg Ile
            180              185              190

Leu Leu Ser Gln Glu Lys Thr Lys Phe Phe Thr Arg Arg Leu Ala
        195              200              205

<210> SEQ ID NO 66
```

<211> LENGTH: 233
<212> TYPE: PRT
<213> ORGANISM: Lymphocytic choriomeningitis virus

<400> SEQUENCE: 66

Gly Thr Phe Thr Trp Thr Leu Ser Asp Ser Ser Gly Val Glu Asn Pro
1               5                   10                  15

Gly Gly Tyr Cys Leu Thr Lys Trp Met Ile Leu Ala Ala Glu Leu Lys
            20                  25                  30

Cys Phe Gly Asn Thr Ala Val Ala Lys Cys Asn Val Asn His Asp Ala
        35                  40                  45

Glu Phe Cys Asp Met Leu Arg Leu Ile Asp Tyr Asn Lys Ala Ala Leu
    50                  55                  60

Ser Lys Phe Lys Glu Asp Val Glu Ser Ala Leu His Leu Phe Lys Thr
65                  70                  75                  80

Thr Val Asn Ser Leu Ile Ser Asp Gln Leu Leu Met Arg Asn His Leu
                85                  90                  95

Arg Asp Leu Met Gly Val Pro Tyr Cys Asn Tyr Ser Lys Phe Trp Tyr
            100                 105                 110

Leu Glu His Ala Lys Thr Gly Glu Thr Ser Val Pro Lys Cys Trp Leu
        115                 120                 125

Val Thr Asn Gly Ser Tyr Leu Asn Glu Thr His Phe Ser Asp Gln Ile
    130                 135                 140

Glu Gln Glu Ala Asp Asn Met Ile Thr Glu Met Leu Arg Lys Asp Tyr
145                 150                 155                 160

Ile Lys Arg Gln Gly Ser Thr Pro Leu Ala Leu Met Asp Leu Leu Met
            165                 170                 175

Phe Ser Thr Ser Ala Tyr Leu Val Ser Ile Phe Leu His Leu Val Lys
            180                 185                 190

Ile Pro Thr His Arg His Ile Lys Gly Gly Ser Cys Pro Lys Pro His
        195                 200                 205

Arg Leu Thr Asn Lys Gly Ile Cys Ser Cys Gly Ala Phe Lys Val Pro
    210                 215                 220

Gly Val Lys Thr Val Trp Lys Arg Arg
225                 230

<210> SEQ ID NO 67
<211> LENGTH: 438
<212> TYPE: PRT
<213> ORGANISM: Ross River virus
<220> FEATURE:
<221> NAME/KEY: VARIANT
<222> LOCATION: (23)..(23)
<223> OTHER INFORMATION: Xaa can be any naturally occurring amino acid
<220> FEATURE:
<221> NAME/KEY: VARIANT
<222> LOCATION: (35)..(36)
<223> OTHER INFORMATION: Xaa can be any naturally occurring amino acid
<220> FEATURE:
<221> NAME/KEY: VARIANT
<222> LOCATION: (314)..(314)
<223> OTHER INFORMATION: Xaa can be any naturally occurring amino acid
<220> FEATURE:
<221> NAME/KEY: VARIANT
<222> LOCATION: (358)..(359)
<223> OTHER INFORMATION: Xaa can be any naturally occurring amino acid

<400> SEQUENCE: 67

Tyr Glu His Thr Ala Thr Ile Pro Asn Val Val Gly Phe Pro Tyr Lys
1               5                   10                  15

Ala His Ile Glu Arg Asn Xaa Phe Ser Pro Met Thr Leu Gln Leu Glu

-continued

```
               20                 25                 30
Val Val Xaa Xaa Ser Leu Glu Pro Thr Leu Asn Leu Glu Tyr Ile Thr
            35                 40                 45

Cys Glu Tyr Lys Thr Val Val Pro Ser Pro Phe Ile Lys Cys Cys Gly
        50                 55                 60

Thr Ser Glu Cys Ser Ser Lys Glu Gln Pro Asp Tyr Gln Cys Lys Val
65                 70                 75                 80

Tyr Thr Gly Val Tyr Pro Phe Met Trp Gly Gly Ala Tyr Cys Phe Cys
                85                 90                 95

Asp Ser Glu Asn Thr Gln Leu Ser Glu Ala Tyr Val Asp Arg Ser Asp
            100                105                110

Val Cys Lys His Asp His Ala Leu Ala Tyr Lys Ala His Thr Ala Ser
        115                120                125

Leu Lys Ala Thr Ile Arg Ile Ser Tyr Gly Thr Ile Asn Gln Thr Thr
        130                135                140

Glu Ala Phe Val Asn Gly Glu His Ala Val Asn Val Gly Gly Ser Lys
145                150                155                160

Phe Ile Phe Gly Pro Ile Ser Thr Ala Trp Ser Pro Phe Asp Asn Lys
                165                170                175

Ile Val Val Tyr Lys Asp Asp Val Tyr Asn Gln Asp Phe Pro Pro Tyr
            180                185                190

Gly Ser Gly Gln Pro Gly Arg Phe Gly Asp Ile Gln Ser Arg Thr Val
            195                200                205

Glu Ser Lys Asp Leu Tyr Ala Asn Thr Ala Leu Lys Leu Ser Arg Pro
        210                215                220

Ser Pro Gly Val Val His Val Pro Tyr Thr Gln Thr Pro Ser Gly Phe
225                230                235                240

Lys Tyr Trp Leu Lys Glu Lys Gly Ser Ser Leu Asn Thr Lys Ala Pro
                245                250                255

Phe Gly Cys Lys Ile Lys Thr Asn Pro Val Arg Ala Met Asp Cys Ala
            260                265                270

Val Gly Ser Ile Pro Val Ser Met Asp Ile Pro Asp Ser Ala Phe Thr
            275                280                285

Arg Val Val Asp Ala Pro Ala Val Thr Asp Leu Ser Cys Gln Val Ala
        290                295                300

Val Cys Thr His Ser Ser Asp Phe Gly Xaa Val Ala Thr Leu Ser Tyr
305                310                315                320

Lys Thr Asp Lys Pro Gly Lys Cys Ala Val His Ser His Ser Asn Val
                325                330                335

Ala Thr Leu Gln Glu Ala Thr Val Asp Val Lys Glu Asp Gly Lys Val
            340                345                350

Thr Val His Phe Ser Xaa Xaa Ser Ala Ser Pro Ala Phe Lys Val Ser
            355                360                365

Val Cys Asp Ala Lys Thr Thr Cys Thr Ala Ala Cys Glu Pro Pro Lys
        370                375                380

Asp His Ile Val Pro Tyr Gly Ala Ser His Asn Asn Gln Val Phe Pro
385                390                395                400

Asp Met Ser Gly Thr Ala Met Thr Trp Val Gln Arg Met Ala Ser Gly
                405                410                415

Leu Gly Gly Leu Ala Leu Ile Ala Val Val Val Leu Val Leu Val Thr
            420                425                430

Cys Ile Thr Met Arg Arg
            435
```

```
<210> SEQ ID NO 68
<211> LENGTH: 422
<212> TYPE: PRT
<213> ORGANISM: Ross River virus
<220> FEATURE:
<221> NAME/KEY: VARIANT
<222> LOCATION: (18)..(18)
<223> OTHER INFORMATION: Xaa can be any naturally occurring amino acid
<220> FEATURE:
<221> NAME/KEY: VARIANT
<222> LOCATION: (113)..(113)
<223> OTHER INFORMATION: Xaa can be any naturally occurring amino acid
<220> FEATURE:
<221> NAME/KEY: VARIANT
<222> LOCATION: (236)..(236)
<223> OTHER INFORMATION: Xaa can be any naturally occurring amino acid
<220> FEATURE:
<221> NAME/KEY: VARIANT
<222> LOCATION: (293)..(293)
<223> OTHER INFORMATION: Xaa can be any naturally occurring amino acid
<220> FEATURE:
<221> NAME/KEY: VARIANT
<222> LOCATION: (415)..(415)
<223> OTHER INFORMATION: Xaa can be any naturally occurring amino acid

<400> SEQUENCE: 68

Ser Val Ile Glu His Phe Asn Val Tyr Lys Ala Thr Arg Pro Tyr Leu
1               5                   10                  15

Ala Xaa Cys Ala Asp Cys Gly Asp Gly Tyr Phe Cys Tyr Ser Pro Val
                20                  25                  30

Ala Ile Glu Lys Ile Arg Asp Glu Ala Ser Asp Gly Met Leu Lys Ile
            35                  40                  45

Gln Val Ser Ala Gln Ile Gly Leu Asp Lys Ala Gly Thr His Ala His
        50                  55                  60

Thr Lys Met Arg Tyr Met Ala Gly His Asp Val Gln Glu Ser Lys Arg
65                  70                  75                  80

Asp Ser Leu Arg Val Tyr Thr Ser Ala Ala Cys Ser Ile His Gly Thr
                85                  90                  95

Met Gly His Phe Ile Val Ala His Cys Pro Pro Gly Asp Tyr Leu Lys
                100                 105                 110

Xaa Ser Phe Glu Asp Ala Asn Ser His Val Lys Ala Cys Lys Val Gln
        115                 120                 125

Tyr Lys His Asp Pro Leu Pro Val Gly Arg Glu Lys Phe Val Val Arg
        130                 135                 140

Pro His Phe Gly Val Glu Leu Pro Cys Thr Ser Tyr Gln Leu Thr Thr
145                 150                 155                 160

Ala Pro Thr Asp Glu Glu Ile Asp Met His Thr Pro Pro Asp Ile Pro
                165                 170                 175

Asp Arg Thr Leu Leu Ser Gln Thr Ala Gly Asn Val Lys Ile Thr Ala
                180                 185                 190

Gly Gly Arg Thr Ile Arg Tyr Asn Cys Thr Cys Gly Arg Asp Asn Val
            195                 200                 205

Gly Thr Thr Ser Thr Asp Lys Thr Ile Asn Thr Cys Lys Ile Asp Gln
        210                 215                 220

Cys His Ala Ala Val Thr Ser His Asp Lys Trp Xaa Phe Thr Ser Pro
225                 230                 235                 240

Phe Val Pro Arg Ala Asp Gln Thr Ala Arg Lys Gly Lys Val His Val
                245                 250                 255

Pro Phe Pro Leu Thr Asn Val Thr Cys Arg Val Pro Leu Ala Arg Ala
        260                 265                 270
```

-continued

```
Pro Asp Val Thr Tyr Gly Lys Lys Glu Val Thr Leu Arg Leu His Pro
        275             280             285

Asp His Pro Thr Xaa Phe Ser Tyr Arg Ser Leu Gly Ala Val Pro His
        290             295             300

Pro Tyr Glu Glu Trp Val Asp Lys Phe Ser Glu Arg Ile Ile Pro Val
305             310             315             320

Thr Glu Glu Gly Ile Glu Tyr Gln Trp Gly Asn Asn Pro Pro Val Arg
            325             330             335

Leu Trp Ala Gln Leu Thr Thr Glu Gly Lys Pro His Gly Trp Pro His
            340             345             350

Glu Ile Ile Gln Tyr Tyr Tyr Gly Leu Tyr Pro Ala Ala Thr Ile Ala
            355             360             365

Ala Val Ser Gly Ala Ser Leu Met Ala Leu Leu Thr Leu Ala Ala Thr
        370             375             380

Cys Cys Met Leu Ala Thr Ala Arg Arg Lys Cys Leu Thr Pro Tyr Ala
385             390             395             400

Leu Thr Pro Gly Ala Val Val Pro Leu Thr Leu Gly Leu Leu Xaa Cys
            405             410             415

Ala Pro Arg Ala Asn Ala
            420

<210> SEQ ID NO 69
<211> LENGTH: 438
<212> TYPE: PRT
<213> ORGANISM: Semliki Forest virus

<400> SEQUENCE: 69

Tyr Glu His Ser Thr Val Met Pro Asn Val Val Gly Phe Pro Tyr Lys
1               5               10              15

Ala His Ile Glu Arg Pro Gly Tyr Ser Pro Leu Thr Leu Gln Met Gln
            20              25              30

Val Val Glu Thr Ser Leu Glu Pro Thr Leu Asn Leu Glu Tyr Ile Thr
            35              40              45

Cys Glu Tyr Lys Thr Val Val Pro Ser Pro Tyr Val Lys Cys Cys Gly
        50              55              60

Ala Ser Glu Cys Ser Thr Lys Glu Lys Pro Asp Tyr Gln Cys Lys Val
65              70              75              80

Tyr Thr Gly Val Tyr Pro Phe Met Trp Gly Gly Ala Tyr Cys Phe Cys
            85              90              95

Asp Ser Glu Asn Thr Gln Leu Ser Glu Ala Tyr Val Asp Arg Ser Asp
            100             105             110

Val Cys Arg His Asp His Ala Ser Ala Tyr Lys Ala His Thr Ala Ser
            115             120             125

Leu Lys Ala Lys Val Arg Val Met Tyr Gly Asn Val Asn Gln Thr Val
        130             135             140

Asp Val Tyr Val Asn Gly Asp His Ala Val Thr Ile Gly Gly Thr Gln
145             150             155             160

Phe Ile Phe Gly Pro Leu Ser Ser Ala Trp Thr Pro Phe Asp Asn Lys
            165             170             175

Ile Val Val Tyr Lys Asp Glu Val Phe Asn Gln Asp Phe Pro Pro Tyr
            180             185             190

Gly Ser Gly Gln Pro Gly Arg Phe Gly Asp Ile Gln Ser Arg Thr Val
            195             200             205

Glu Ser Asn Asp Leu Tyr Ala Asn Thr Ala Leu Lys Leu Ala Arg Pro
```

-continued

```
            210                 215                 220

Ser Pro Gly Met Val His Val Pro Tyr Thr Gln Thr Pro Ser Gly Phe
225                 230                 235                 240

Lys Tyr Trp Leu Lys Glu Lys Gly Thr Ala Leu Asn Thr Lys Ala Pro
                245                 250                 255

Phe Gly Cys Gln Ile Lys Thr Asn Pro Val Arg Ala Met Asn Cys Ala
                260                 265                 270

Val Gly Asn Ile Pro Val Ser Met Asn Leu Pro Asp Ser Ala Phe Thr
            275                 280                 285

Arg Ile Val Glu Ala Pro Thr Ile Ile Asp Leu Thr Cys Thr Val Ala
        290                 295                 300

Thr Cys Thr His Ser Ser Asp Phe Gly Gly Val Leu Thr Leu Thr Tyr
305                 310                 315                 320

Lys Thr Asn Lys Asn Gly Asp Cys Ser Val His Ser His Ser Asn Val
                325                 330                 335

Ala Thr Leu Gln Glu Ala Thr Ala Lys Val Lys Thr Ala Gly Lys Val
                340                 345                 350

Thr Leu His Phe Ser Thr Ala Ser Ala Ser Pro Ser Phe Val Val Ser
                355                 360                 365

Leu Cys Ser Ala Arg Ala Thr Cys Ser Ala Ser Cys Glu Pro Pro Lys
        370                 375                 380

Asp His Ile Val Pro Tyr Ala Ala Ser His Ser Asn Val Val Phe Pro
385                 390                 395                 400

Asp Met Ser Gly Thr Ala Leu Ser Trp Val Gln Lys Ile Ser Gly Gly
                405                 410                 415

Leu Gly Ala Phe Ala Ile Gly Ala Ile Leu Val Leu Val Val Val Thr
                420                 425                 430

Cys Ile Gly Leu Arg Arg
                435

<210> SEQ ID NO 70
<211> LENGTH: 439
<212> TYPE: PRT
<213> ORGANISM: Sindbis virus

<400> SEQUENCE: 70

Tyr Glu His Ala Thr Thr Val Pro Asn Val Pro Gln Ile Pro Tyr Lys
1               5                   10                  15

Ala Leu Val Glu Arg Ala Gly Tyr Ala Pro Leu Asn Leu Glu Ile Thr
                20                  25                  30

Val Met Ser Ser Glu Val Leu Pro Ser Thr Asn Gln Glu Tyr Ile Thr
            35                  40                  45

Cys Lys Phe Thr Thr Val Val Pro Ser Pro Lys Ile Lys Cys Cys Gly
    50                  55                  60

Ser Leu Glu Cys Gln Pro Ala Ala His Ala Asp Tyr Thr Cys Lys Val
65                  70                  75                  80

Phe Gly Gly Val Tyr Pro Phe Met Trp Gly Gly Ala Gln Cys Phe Cys
                85                  90                  95

Asp Ser Glu Asn Ser Gln Met Ser Glu Ala Tyr Val Glu Leu Ser Ala
                100                 105                 110

Asp Cys Ala Ser Asp His Ala Gln Ala Ile Lys Val His Thr Ala Ala
            115                 120                 125

Met Lys Val Gly Leu Arg Ile Val Tyr Gly Asn Thr Thr Ser Phe Leu
    130                 135                 140
```

-continued

```
Asp Val Tyr Val Asn Gly Val Thr Pro Gly Thr Ser Lys Asp Leu Lys
145             150                 155                 160

Val Ile Ala Gly Pro Ile Ser Ala Ser Phe Thr Pro Phe Asp His Lys
                165                 170                 175

Val Val Ile His Arg Gly Leu Val Tyr Asn Tyr Asp Phe Pro Glu Tyr
            180                 185                 190

Gly Ala Met Lys Pro Gly Ala Phe Gly Asp Ile Gln Ala Thr Ser Leu
            195                 200                 205

Thr Ser Lys Asp Leu Ile Ala Ser Thr Asp Ile Arg Leu Leu Lys Pro
    210                 215                 220

Ser Ala Lys Asn Val His Val Pro Tyr Thr Gln Ala Ser Ser Gly Phe
225                 230                 235                 240

Glu Met Trp Lys Asn Asn Ser Gly Arg Pro Leu Gln Glu Thr Ala Pro
                245                 250                 255

Phe Gly Cys Lys Ile Ala Val Asn Pro Leu Arg Ala Val Asp Cys Ser
                260                 265                 270

Tyr Gly Asn Ile Pro Ile Ser Ile Asp Ile Pro Asn Ala Ala Phe Ile
            275                 280                 285

Arg Thr Ser Asp Ala Pro Leu Val Ser Thr Val Lys Cys Glu Val Ser
    290                 295                 300

Glu Cys Thr Tyr Ser Ala Asp Phe Gly Gly Met Ala Thr Leu Gln Tyr
305                 310                 315                 320

Val Ser Asp Arg Glu Gly Gln Cys Pro Val His Ser His Ser Ser Thr
                325                 330                 335

Ala Thr Leu Gln Glu Ser Thr Val His Val Leu Glu Lys Gly Ala Val
            340                 345                 350

Thr Val His Phe Ser Thr Ala Ser Pro Gln Ala Asn Phe Ile Val Ser
            355                 360                 365

Leu Cys Gly Lys Lys Thr Thr Cys Asn Ala Glu Cys Lys Pro Pro Ala
    370                 375                 380

Asp His Ile Val Ser Thr Pro His Lys Asn Asp Gln Glu Phe Gln Ala
385                 390                 395                 400

Ala Ile Ser Lys Thr Ser Trp Ser Trp Leu Phe Ala Leu Phe Gly Gly
                405                 410                 415

Ala Ser Ser Leu Leu Ile Ile Gly Leu Met Ile Phe Ala Cys Ser Met
            420                 425                 430

Met Leu Thr Ser Thr Arg Arg
            435
```

```
<210> SEQ ID NO 71
<211> LENGTH: 423
<212> TYPE: PRT
<213> ORGANISM: Sindbis virus

<400> SEQUENCE: 71

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
                20                  25                  30

Gln Val Trp Asp Glu Ala Asp Asp Asn Thr Ile Arg Ile Gln Thr Ser
            35                  40                  45

Ala Gln Phe Gly Tyr Asp Gln Ser Gly Ala Ala Ser Ala Asn Lys Tyr
    50                  55                  60

Arg Tyr Met Ser Leu Lys Gln Asp His Thr Val Lys Glu Gly Thr Met
65                  70                  75                  80
```

```
Asp Asp Ile Lys Ile Ser Thr Ser Gly Pro Cys Arg Arg Leu Ser Tyr
            85              90              95

Lys Gly Tyr Phe Leu Leu Ala Lys Cys Pro Pro Gly Asp Ser Val Thr
            100             105             110

Val Ser Ile Val Ser Ser Asn Ser Ala Thr Ser Cys Thr Leu Ala Arg
            115             120             125

Lys Ile Lys Pro Lys Phe Val Gly Arg Glu Lys Tyr Asp Leu Pro Pro
        130             135             140

Val His Gly Lys Lys Ile Pro Cys Thr Val Tyr Asp Arg Leu Lys Glu
145             150             155             160

Thr Thr Ala Gly Tyr Ile Thr Met His Arg Pro Arg Pro His Ala Tyr
                165             170             175

Thr Ser Tyr Leu Glu Glu Ser Ser Gly Lys Val Tyr Ala Lys Pro Pro
            180             185             190

Ser Gly Lys Asn Ile Thr Tyr Glu Cys Lys Cys Gly Asp Tyr Lys Thr
            195             200             205

Gly Thr Val Ser Thr Arg Thr Glu Ile Thr Gly Cys Thr Ala Ile Lys
        210             215             220

Gln Cys Val Ala Tyr Lys Ser Asp Gln Thr Lys Trp Val Phe Asn Ser
225             230             235             240

Pro Asp Leu Ile Arg His Asp Asp His Thr Ala Gln Gly Lys Leu His
            245             250             255

Leu Pro Phe Lys Leu Ile Pro Ser Thr Cys Met Val Pro Val Ala His
            260             265             270

Ala Pro Asn Val Ile His Gly Phe Lys His Ile Ser Leu Gln Leu Asp
            275             280             285

Thr Asp His Leu Thr Leu Leu Thr Thr Arg Arg Leu Gly Ala Asn Pro
        290             295             300

Glu Pro Thr Thr Glu Trp Ile Val Gly Lys Thr Val Arg Asn Phe Thr
305             310             315             320

Val Asp Arg Asp Gly Leu Glu Tyr Ile Trp Gly Asn His Glu Pro Val
            325             330             335

Arg Val Tyr Ala Gln Glu Ser Ala Pro Gly Asp Pro His Gly Trp Pro
            340             345             350

His Glu Ile Val Gln His Tyr Tyr His Arg His Pro Val Tyr Thr Ile
            355             360             365

Leu Ala Val Ala Ser Ala Thr Val Ala Met Met Ile Gly Val Thr Val
            370             375             380

Ala Val Leu Cys Ala Cys Lys Ala Arg Arg Glu Cys Leu Thr Pro Tyr
385             390             395             400

Ala Leu Ala Pro Asn Ala Val Ile Pro Thr Ser Leu Ala Leu Leu Cys
            405             410             415

Cys Val Arg Ser Ala Asn Ala
            420

<210> SEQ ID NO 72
<211> LENGTH: 676
<212> TYPE: PRT
<213> ORGANISM: Ebola Zaire virus

<400> SEQUENCE: 72

Met Gly Val Thr Gly Ile Leu Gln Leu Pro Arg Asp Arg Phe Lys Arg
1               5               10              15

Thr Ser Phe Phe Leu Trp Val Ile Ile Leu Phe Gln Arg Thr Phe Ser
```

-continued

```
                20              25                30

Ile Pro Leu Gly Val Ile His Asn Ser Thr Leu Gln Val Ser Asp Val
            35              40              45

Asp Lys Leu Val Cys Arg Asp Lys Leu Ser Ser Thr Asn Gln Leu Arg
        50              55              60

Ser Val Gly Leu Asn Leu Glu Gly Asn Gly Val Ala Thr Asp Val Pro
65              70              75              80

Ser Ala Thr Lys Arg Trp Gly Phe Arg Ser Gly Val Pro Pro Lys Val
                85              90              95

Val Asn Tyr Glu Ala Gly Glu Trp Ala Glu Asn Cys Tyr Asn Leu Glu
            100             105             110

Ile Lys Lys Pro Asp Gly Ser Glu Cys Leu Pro Ala Ala Pro Asp Gly
        115             120             125

Ile Arg Gly Phe Pro Arg Cys Arg Tyr Val His Lys Val Ser Gly Thr
        130             135             140

Gly Pro Cys Ala Gly Asp Phe Ala Phe His Lys Glu Gly Ala Phe Phe
145             150             155             160

Leu Tyr Asp Arg Leu Ala Ser Thr Val Ile Tyr Arg Gly Thr Thr Phe
                165             170             175

Ala Glu Gly Val Val Ala Phe Leu Ile Leu Pro Gln Ala Lys Lys Asp
            180             185             190

Phe Phe Ser Ser His Pro Leu Arg Glu Pro Val Asn Ala Thr Glu Asp
            195             200             205

Pro Ser Ser Gly Tyr Tyr Ser Thr Thr Ile Arg Tyr Gln Ala Thr Gly
        210             215             220

Phe Gly Thr Asn Glu Thr Glu Tyr Leu Phe Glu Val Asp Asn Leu Thr
225             230             235             240

Tyr Val Gln Leu Glu Ser Arg Phe Thr Pro Gln Phe Leu Leu Gln Leu
                245             250             255

Asn Glu Thr Ile Tyr Thr Ser Gly Lys Arg Ser Asn Thr Thr Gly Lys
            260             265             270

Leu Ile Trp Lys Val Asn Pro Glu Ile Asp Thr Thr Ile Gly Glu Trp
            275             280             285

Ala Phe Trp Glu Thr Lys Lys Asn Leu Thr Arg Lys Ile Arg Ser Glu
        290             295             300

Glu Leu Ser Phe Thr Val Val Ser Asn Gly Ala Lys Asn Ile Ser Gly
305             310             315             320

Gln Ser Pro Ala Arg Thr Ser Ser Asp Pro Gly Thr Asn Thr Thr Thr
            325             330             335

Glu Asp His Lys Ile Met Ala Ser Glu Asn Ser Ser Ala Met Val Gln
            340             345             350

Val His Ser Gln Gly Arg Glu Ala Ala Val Ser His Leu Thr Thr Leu
            355             360             365

Ala Thr Ile Ser Thr Ser Pro Gln Ser Leu Thr Thr Lys Pro Gly Pro
        370             375             380

Asp Asn Ser Thr His Asn Thr Pro Val Tyr Lys Leu Asp Ile Ser Glu
385             390             395             400

Ala Thr Gln Val Glu Gln His His Arg Arg Thr Asp Asn Asp Ser Thr
            405             410             415

Ala Ser Asp Thr Pro Ser Ala Thr Thr Ala Ala Gly Pro Pro Lys Ala
            420             425             430

Glu Asn Thr Asn Thr Ser Lys Ser Thr Asp Phe Leu Asp Pro Ala Thr
            435             440             445
```

```
Thr Thr Ser Pro Gln Asn His Ser Glu Thr Ala Gly Asn Asn Asn Thr
    450                 455             460

His His Gln Asp Thr Gly Glu Glu Ser Ala Ser Ser Gly Lys Leu Gly
465                 470             475             480

Leu Ile Thr Asn Thr Ile Ala Gly Val Ala Gly Leu Ile Thr Gly Gly
                485             490             495

Arg Arg Thr Arg Arg Glu Ala Ile Val Asn Ala Gln Pro Lys Cys Asn
            500             505             510

Pro Asn Leu His Tyr Trp Thr Thr Gln Asp Glu Gly Ala Ala Ile Gly
        515             520             525

Leu Ala Trp Ile Pro Tyr Phe Gly Pro Ala Ala Glu Gly Ile Tyr Ile
    530             535             540

Glu Gly Leu Met His Asn Gln Asp Gly Leu Ile Cys Gly Leu Arg Gln
545             550             555             560

Leu Ala Asn Glu Thr Thr Gln Ala Leu Gln Leu Phe Leu Arg Ala Thr
            565             570             575

Thr Glu Leu Arg Thr Phe Ser Ile Leu Asn Arg Lys Ala Ile Asp Phe
            580             585             590

Leu Leu Gln Arg Trp Gly Gly Thr Cys His Ile Leu Gly Pro Asp Cys
        595             600             605

Cys Ile Glu Pro His Asp Trp Thr Lys Asn Ile Thr Asp Lys Ile Asp
    610             615             620

Gln Ile Ile His Asp Phe Val Asp Lys Thr Leu Pro Asp Gln Gly Asp
625             630             635             640

Asn Asp Asn Trp Trp Thr Gly Trp Arg Gln Trp Ile Pro Ala Gly Ile
            645             650             655

Gly Val Thr Gly Val Ile Ile Ala Val Ile Ala Leu Phe Cys Ile Cys
            660             665             670

Lys Phe Val Phe
        675

<210> SEQ ID NO 73
<211> LENGTH: 644
<212> TYPE: PRT
<213> ORGANISM: Ebola Zaire virus

<400> SEQUENCE: 73

Ile Pro Leu Gly Val Ile His Asn Ser Thr Leu Gln Val Ser Asp Val
1               5               10              15

Asp Lys Leu Val Cys Arg Asp Lys Leu Ser Ser Thr Asn Gln Leu Arg
            20              25              30

Ser Val Gly Leu Asn Leu Glu Gly Asn Gly Val Ala Thr Asp Val Pro
        35              40              45

Ser Ala Thr Lys Arg Trp Gly Phe Arg Ser Gly Val Pro Pro Lys Val
    50              55              60

Val Asn Tyr Glu Ala Gly Glu Trp Ala Glu Asn Cys Tyr Asn Leu Glu
65              70              75              80

Ile Lys Lys Pro Asp Gly Ser Glu Cys Leu Pro Ala Ala Pro Asp Gly
                85              90              95

Ile Arg Gly Phe Pro Arg Cys Arg Tyr Val His Lys Val Ser Gly Thr
            100             105             110

Gly Pro Cys Ala Gly Asp Phe Ala Phe His Lys Glu Gly Ala Phe Phe
        115             120             125

Leu Tyr Asp Arg Leu Ala Ser Thr Val Ile Tyr Arg Gly Thr Thr Phe
```

-continued

```
            130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
                180                 185                 190

Phe Gly Thr Asn Glu Thr Glu Tyr Leu Phe Glu Val Asp Asn Leu Thr
                195                 200                 205

Tyr Val Gln Leu Glu Ser Arg Phe Thr Pro Gln Phe Leu Leu Gln Leu
                210                 215                 220

Asn Glu Thr Ile Tyr Thr Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
                260                 265                 270

Glu Leu Ser Phe Thr Val Val Ser Asn Gly Ala Lys Asn Ile Ser Gly
                275                 280                 285

Gln Ser Pro Ala Arg Thr Ser Ser Asp Pro Gly Thr Asn Thr Thr Thr
                290                 295                 300

Glu Asp His Lys Ile Met Ala Ser Glu Asn Ser Ser Ala Met Val Gln
305                 310                 315                 320

Val His Ser Gln Gly Arg Glu Ala Ala Val Ser His Leu Thr Thr Leu
                325                 330                 335

Ala Thr Ile Ser Thr Ser Pro Gln Ser Leu Thr Thr Lys Pro Gly Pro
                340                 345                 350

Asp Asn Ser Thr His Asn Thr Pro Val Tyr Lys Leu Asp Ile Ser Glu
                355                 360                 365

Ala Thr Gln Val Glu Gln His His Arg Arg Thr Asp Asn Asp Ser Thr
                370                 375                 380

Ala Ser Asp Thr Pro Ser Ala Thr Thr Ala Ala Gly Pro Pro Lys Ala
385                 390                 395                 400

Glu Asn Thr Asn Thr Ser Lys Ser Thr Asp Phe Leu Asp Pro Ala Thr
                405                 410                 415

Thr Thr Ser Pro Gln Asn His Ser Glu Thr Ala Gly Asn Asn Asn Thr
                420                 425                 430

His His Gln Asp Thr Gly Glu Glu Ser Ala Ser Ser Gly Lys Leu Gly
                435                 440                 445

Leu Ile Thr Asn Thr Ile Ala Gly Val Ala Gly Leu Ile Thr Gly Gly
                450                 455                 460

Arg Arg Thr Arg Arg Glu Ala Ile Val Asn Ala Gln Pro Lys Cys Asn
465                 470                 475                 480

Pro Asn Leu His Tyr Trp Thr Thr Gln Asp Glu Gly Ala Ala Ile Gly
                485                 490                 495

Leu Ala Trp Ile Pro Tyr Phe Gly Pro Ala Ala Glu Gly Ile Tyr Ile
                500                 505                 510

Glu Gly Leu Met His Asn Gln Asp Gly Leu Ile Cys Gly Leu Arg Gln
                515                 520                 525

Leu Ala Asn Glu Thr Thr Gln Ala Leu Gln Leu Phe Leu Arg Ala Thr
                530                 535                 540

Thr Glu Leu Arg Thr Phe Ser Ile Leu Asn Arg Lys Ala Ile Asp Phe
545                 550                 555                 560
```

-continued

```
Leu Leu Gln Arg Trp Gly Gly Thr Cys His Ile Leu Gly Pro Asp Cys
            565                 570                 575

Cys Ile Glu Pro His Asp Trp Thr Lys Asn Ile Thr Asp Lys Ile Asp
            580                 585                 590

Gln Ile Ile His Asp Phe Val Asp Lys Thr Leu Pro Asp Gln Gly Asp
            595                 600                 605

Asn Asp Asn Trp Trp Thr Gly Trp Arg Gln Trp Ile Pro Ala Gly Ile
        610                 615                 620

Gly Val Thr Gly Val Ile Ile Ala Val Ile Ala Leu Phe Cys Ile Cys
625                 630                 635                 640

Lys Phe Val Phe

<210> SEQ ID NO 74
<211> LENGTH: 677
<212> TYPE: PRT
<213> ORGANISM: Ebola Reston virus

<400> SEQUENCE: 74

Met Gly Ser Gly Tyr Gln Leu Leu Gln Leu Pro Arg Glu Arg Phe Arg
1               5                   10                  15

Lys Thr Ser Phe Leu Val Trp Val Ile Ile Leu Phe Gln Arg Ala Ile
            20                  25                  30

Ser Met Pro Leu Gly Ile Val Thr Asn Ser Thr Leu Lys Ala Thr Glu
            35                  40                  45

Ile Asp Gln Leu Val Cys Arg Asp Lys Leu Ser Ser Thr Ser Gln Leu
        50                  55                  60

Lys Ser Val Gly Leu Asn Leu Glu Gly Asn Gly Ile Ala Thr Asp Val
65                  70                  75                  80

Pro Ser Ala Thr Lys Arg Trp Gly Phe Arg Ser Gly Val Pro Pro Lys
            85                  90                  95

Val Val Ser Tyr Glu Ala Gly Glu Trp Ala Glu Asn Cys Tyr Asn Leu
            100                 105                 110

Glu Ile Lys Lys Ser Asp Gly Ser Glu Cys Leu Pro Leu Pro Pro Asp
            115                 120                 125

Gly Val Arg Gly Phe Pro Arg Cys Arg Tyr Val His Lys Val Gln Gly
        130                 135                 140

Thr Gly Pro Cys Pro Gly Asp Leu Ala Phe His Lys Asn Gly Ala Phe
145                 150                 155                 160

Phe Leu Tyr Asp Arg Leu Ala Ser Thr Val Ile Tyr Arg Gly Thr Thr
            165                 170                 175

Phe Ala Glu Gly Val Val Ala Phe Leu Ile Leu Ser Glu Pro Lys Lys
            180                 185                 190

His Phe Trp Lys Ala Thr Pro Ala His Glu Pro Val Asn Thr Thr Asp
            195                 200                 205

Asp Ser Thr Ser Tyr Tyr Met Thr Leu Thr Leu Ser Tyr Glu Met Ser
        210                 215                 220

Asn Phe Gly Gly Asn Glu Ser Asn Thr Leu Phe Lys Val Asp Asn His
225                 230                 235                 240

Thr Tyr Val Gln Leu Asp Arg Pro His Thr Pro Gln Phe Leu Val Gln
            245                 250                 255

Leu Asn Glu Thr Leu Arg Arg Asn Asn Arg Leu Ser Asn Ser Thr Gly
            260                 265                 270

Arg Leu Thr Trp Thr Leu Asp Pro Lys Ile Glu Pro Asp Val Gly Glu
            275                 280                 285
```

```
Trp Ala Phe Trp Glu Thr Lys Lys Asn Phe Ser Gln Gln Leu His Gly
    290                 295                 300

Glu Asn Leu His Phe Gln Ile Pro Ser Thr His Thr Asn Asn Ser Ser
305                 310                 315                 320

Asp Gln Ser Pro Ala Gly Thr Val Gln Gly Lys Ile Ser Tyr His Pro
            325                 330                 335

Pro Ala Asn Asn Ser Glu Leu Val Pro Thr Asp Ser Pro Pro Val Val
            340                 345                 350

Ser Val Leu Thr Ala Gly Arg Thr Glu Glu Met Ser Thr Gln Gly Leu
            355                 360                 365

Thr Asn Gly Glu Thr Ile Thr Gly Phe Thr Ala Asn Pro Met Thr Thr
    370                 375                 380

Thr Ile Ala Pro Ser Pro Thr Met Thr Ser Glu Val Asp Asn Asn Val
385                 390                 395                 400

Pro Ser Glu Gln Pro Asn Asn Thr Ala Ser Ile Glu Asp Ser Pro Pro
            405                 410                 415

Ser Ala Ser Asn Glu Thr Ile Tyr His Ser Glu Met Asp Pro Ile Gln
            420                 425                 430

Gly Ser Asn Asn Ser Ala Gln Ser Pro Gln Thr Lys Thr Thr Pro Ala
            435                 440                 445

Pro Thr Thr Ser Pro Met Thr Gln Asp Pro Gln Glu Thr Ala Asn Ser
    450                 455                 460

Ser Lys Pro Gly Thr Ser Pro Gly Ser Ala Ala Gly Pro Ser Gln Pro
465                 470                 475                 480

Gly Leu Thr Ile Asn Thr Val Ser Lys Val Ala Asp Ser Leu Ser Pro
            485                 490                 495

Thr Arg Lys Gln Lys Arg Ser Val Arg Gln Asn Thr Ala Asn Lys Cys
            500                 505                 510

Asn Pro Asp Leu Tyr Tyr Trp Thr Ala Val Asp Glu Gly Ala Ala Val
            515                 520                 525

Gly Leu Ala Trp Ile Pro Tyr Phe Gly Pro Ala Ala Glu Gly Ile Tyr
    530                 535                 540

Ile Glu Gly Val Met His Asn Gln Asn Gly Leu Ile Cys Gly Leu Arg
545                 550                 555                 560

Gln Leu Ala Asn Glu Thr Thr Gln Ala Leu Gln Leu Phe Leu Arg Ala
            565                 570                 575

Thr Thr Glu Leu Arg Thr Tyr Ser Leu Leu Asn Arg Lys Ala Ile Asp
            580                 585                 590

Phe Leu Leu Gln Arg Trp Gly Gly Thr Cys Arg Ile Leu Gly Pro Ser
    595                 600                 605

Cys Cys Ile Glu Pro His Asp Trp Thr Lys Asn Ile Thr Asp Glu Ile
    610                 615                 620

Asn Gln Ile Lys His Asp Phe Ile Asp Asn Pro Leu Pro Asp His Gly
625                 630                 635                 640

Asp Asp Leu Asn Leu Trp Thr Gly Trp Arg Gln Trp Ile Pro Ala Gly
            645                 650                 655

Ile Gly Ile Ile Gly Val Ile Ile Ala Ile Ile Ala Leu Leu Cys Ile
            660                 665                 670

Cys Lys Ile Leu Cys
            675
```

```
<210> SEQ ID NO 75
<211> LENGTH: 681
```

-continued

```
<212> TYPE: PRT
<213> ORGANISM: Marburg virus

<400> SEQUENCE: 75

Met Lys Thr Thr Cys Phe Leu Ile Ser Leu Ile Leu Ile Gln Gly Thr
1               5                   10                  15

Lys Asn Leu Pro Ile Leu Glu Ile Ala Ser Asn Asn Gln Pro Gln Asn
                20                  25                  30

Val Asp Ser Val Cys Ser Gly Thr Leu Gln Lys Thr Glu Asp Val His
            35                  40                  45

Leu Met Gly Phe Thr Leu Ser Gly Gln Lys Val Ala Asp Ser Pro Leu
        50                  55                  60

Glu Ala Ser Lys Arg Trp Ala Phe Arg Thr Gly Val Pro Pro Lys Asn
65                  70                  75                  80

Val Glu Tyr Thr Glu Gly Glu Glu Ala Lys Thr Cys Tyr Asn Ile Ser
                85                  90                  95

Val Thr Asp Pro Ser Gly Lys Ser Leu Leu Leu Asp Pro Pro Thr Asn
                100                 105                 110

Ile Arg Asp Tyr Pro Lys Cys Lys Thr Ile His His Ile Gln Gly Gln
            115                 120                 125

Asn Pro His Ala Gln Gly Ile Ala Leu His Leu Trp Gly Ala Phe Phe
        130                 135                 140

Leu Tyr Asp Arg Ile Ala Ser Thr Thr Met Tyr Arg Gly Lys Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
                180                 185                 190

Ser Thr Asn Lys Tyr Trp Thr Ser Ser Asn Gly Thr Gln Thr Asn Asp
            195                 200                 205

Thr Gly Cys Phe Gly Ala Leu Gln Glu Tyr Asn Ser Thr Lys Asn Gln
        210                 215                 220

Thr Cys Ala Pro Ser Lys Ile Pro Pro Pro Leu Pro Thr Ala Arg Pro
225                 230                 235                 240

Glu Ile Lys Leu Thr Ser Thr Pro Thr Asp Ala Thr Lys Leu Asn Thr
                245                 250                 255

Thr Asp Pro Ser Ser Asp Asp Glu Asp Leu Ala Thr Ser Gly Ser Gly
            260                 265                 270

Ser Gly Glu Arg Glu Pro His Thr Thr Ser Asp Ala Val Thr Lys Gln
            275                 280                 285

Gly Leu Ser Ser Thr Met Pro Pro Thr Pro Ser Pro Gln Pro Ser Thr
        290                 295                 300

Pro Gln Gln Gly Gly Asn Asn Thr Asn His Ser Gln Asp Ala Val Thr
305                 310                 315                 320

Glu Leu Asp Lys Asn Asn Thr Thr Ala Gln Pro Ser Met Pro Pro His
                325                 330                 335

Asn Thr Thr Thr Ile Ser Thr Asn Asn Thr Ser Lys His Asn Phe Ser
                340                 345                 350

Thr Leu Ser Ala Pro Leu Gln Asn Thr Thr Asn Asp Asn Thr Gln Ser
            355                 360                 365

Thr Ile Thr Glu Asn Glu Gln Thr Ser Ala Pro Ser Ile Thr Thr Leu
        370                 375                 380

Pro Pro Thr Gly Asn Pro Thr Thr Ala Lys Ser Thr Ser Ser Lys Lys
385                 390                 395                 400
```

-continued

```
Gly Pro Ala Thr Thr Ala Pro Asn Thr Thr Asn Glu His Phe Thr Ser
            405                 410                 415

Pro Pro Pro Thr Pro Ser Ser Thr Ala Gln His Leu Val Tyr Phe Arg
            420                 425                 430

Arg Lys Arg Ser Ile Leu Trp Arg Glu Gly Asp Met Phe Pro Phe Leu
            435                 440                 445

Asp Gly Leu Ile Asn Ala Pro Ile Asp Phe Asp Pro Val Pro Asn Thr
    450                 455                 460

Lys Thr Ile Phe Asp Glu Ser Ser Ser Gly Ala Ser Ala Glu Glu
465                 470                 475                 480

Asp Gln His Ala Ser Pro Asn Ile Ser Leu Thr Leu Ser Tyr Phe Pro
            485                 490                 495

Asn Ile Asn Glu Asn Thr Ala Tyr Ser Gly Glu Asn Glu Asn Asp Cys
            500                 505                 510

Asp Ala Glu Leu Arg Ile Trp Ser Val Gln Glu Asp Asp Leu Ala Ala
            515                 520                 525

Gly Leu Ser Trp Ile Pro Phe Phe Gly Pro Gly Ile Glu Gly Leu Tyr
    530                 535                 540

Thr Ala Val Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Leu Arg Val
            565                 570                 575

Thr Thr Glu Glu Arg Thr Phe Ser Leu Ile Asn Arg His Ala Ile Asp
            580                 585                 590

Phe Leu Leu Thr Arg Trp Gly Gly Thr Cys Lys Val Leu Gly Pro Asp
            595                 600                 605

Cys Cys Ile Gly Ile Glu Asp Leu Ser Lys Asn Ile Ser Glu Gln Ile
    610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
            645                 650                 655

Ile Leu Leu Leu Leu Ser Ile Ala Val Leu Ile Ala Leu Ser Cys Ile
            660                 665                 670

Cys Arg Ile Phe Thr Lys Tyr Ile Gly
            675                 680
```

```
<210> SEQ ID NO 76
<211> LENGTH: 669
<212> TYPE: PRT
<213> ORGANISM: Murine leukemia virus

<400> SEQUENCE: 76

Met Glu Ser Thr Thr Leu Ser Lys Pro Phe Lys Asn Gln Val Asn Pro
1               5                   10                  15

Trp Gly Pro Leu Ile Val Leu Leu Ile Leu Gly Gly Val Asn Pro Val
            20                  25                  30

Ala Leu Gly Asn Ser Pro His Gln Val Phe Asn Leu Thr Trp Glu Val
            35                  40                  45

Thr Asn Gly Asp Arg Glu Thr Val Trp Ala Ile Ala Gly Asn His Pro
    50                  55                  60

Leu Trp Thr Trp Trp Pro Asp Leu Thr Pro Asp Leu Cys Met Leu Ala
65                  70                  75                  80

Leu His Gly Pro Ser Tyr Trp Gly Leu Glu Tyr Arg Ala Pro Phe Ser
```

-continued

```
                85                    90                    95

Pro Pro Pro Gly Pro Pro Cys Cys Ser Gly Ser Ser Asp Ser Thr Pro
            100                 105                 110

Gly Cys Ser Arg Asp Cys Glu Glu Pro Leu Thr Ser Tyr Thr Pro Arg
            115                 120                 125

Cys Asn Thr Ala Trp Asn Arg Leu Lys Leu Ser Lys Val Thr His Ala
            130                 135                 140

His Asn Glu Gly Phe Tyr Val Cys Pro Gly Pro His Arg Pro Arg Trp
145                 150                 155                 160

Ala Arg Ser Cys Gly Gly Pro Glu Ser Phe Tyr Cys Ala Ser Trp Gly
                165                 170                 175

Cys Glu Thr Thr Gly Arg Ala Ser Trp Lys Pro Ser Ser Ser Trp Asp
                180                 185                 190

Tyr Ile Thr Val Ser Asn Asn Leu Thr Ser Asp Gln Ala Thr Pro Val
                195                 200                 205

Cys Lys Gly Asn Glu Trp Cys Asn Ser Leu Thr Ile Arg Phe Thr Ser
            210                 215                 220

Phe Gly Lys Gln Ala Thr Ser Trp Val Thr Gly His Trp Trp Gly Leu
225                 230                 235                 240

Arg Leu Tyr Val Ser Gly His Asp Pro Gly Leu Ile Phe Gly Ile Arg
                245                 250                 255

Leu Lys Ile Thr Asp Ser Gly Pro Arg Val Pro Ile Gly Pro Asn Pro
                260                 265                 270

Val Leu Ser Asp Arg Arg Pro Pro Ser Arg Pro Arg Pro Thr Arg Ser
            275                 280                 285

Pro Pro Pro Ser Asn Ser Thr Pro Thr Glu Thr Pro Leu Thr Leu Pro
            290                 295                 300

Glu Pro Pro Pro Ala Gly Val Glu Asn Arg Leu Leu Asn Leu Val Lys
305                 310                 315                 320

Gly Ala Tyr Gln Ala Leu Asn Leu Thr Ser Pro Asp Lys Thr Gln Glu
                325                 330                 335

Cys Trp Leu Cys Leu Val Ser Gly Pro Pro Tyr Tyr Glu Gly Val Ala
                340                 345                 350

Val Leu Gly Thr Tyr Ser Asn His Thr Ser Ala Pro Ala Asn Cys Ser
            355                 360                 365

Val Ala Ser Gln His Lys Leu Thr Leu Ser Glu Val Thr Gly Gln Gly
            370                 375                 380

Leu Cys Ile Gly Ala Val Pro Lys Thr His Gln Val Leu Cys Asn Thr
385                 390                 395                 400

Thr Gln Lys Thr Ser Asp Gly Ser Tyr Tyr Leu Ala Ala Pro Thr Gly
                405                 410                 415

Thr Thr Trp Ala Cys Ser Thr Gly Leu Thr Pro Cys Ile Ser Thr Thr
            420                 425                 430

Ile Leu Asp Leu Thr Thr Asp Tyr Cys Val Leu Val Glu Leu Trp Pro
            435                 440                 445

Arg Val Thr Tyr His Ser Pro Ser Tyr Val Tyr His Gln Phe Glu Gly
            450                 455                 460

Arg Ala Lys Tyr Lys Arg Glu Pro Val Ser Leu Thr Leu Ala Leu Leu
465                 470                 475                 480

Leu Gly Gly Leu Thr Met Gly Gly Ile Ala Ala Gly Val Gly Thr Gly
                485                 490                 495

Thr Thr Ala Leu Val Ala Thr Gln Gln Phe Gln Gln Leu Gln Ala Ala
            500                 505                 510
```

-continued

```
Met His Asp Asp Leu Lys Glu Val Glu Lys Ser Ile Thr Asn Leu Glu
        515             520             525

Lys Ser Leu Thr Ser Leu Ser Glu Val Val Leu Gln Asn Arg Arg Gly
    530             535             540

Leu Asp Leu Leu Phe Leu Lys Glu Gly Gly Leu Cys Ala Ala Leu Lys
545             550             555             560

Glu Glu Cys Cys Phe Tyr Ala Asp His Thr Gly Leu Val Arg Asp Ser
            565             570             575

Met Ala Lys Leu Arg Glu Arg Leu Ser Gln Arg Gln Lys Leu Phe Glu
        580             585             590

Ser Gln Gln Gly Trp Phe Glu Gly Leu Phe Asn Lys Ser Pro Trp Phe
        595             600             605

Thr Thr Leu Ile Ser Thr Ile Met Gly Pro Leu Ile Ile Leu Leu Leu
        610             615             620

Ile Leu Leu Phe Gly Pro Cys Ile Leu Asn Arg Leu Val Gln Phe Ile
625             630             635             640

Lys Asp Arg Ile Ser Val Val Gln Ala Leu Val Leu Thr Gln Gln Tyr
            645             650             655

His Gln Leu Lys Thr Ile Arg Asp Cys Lys Ser Arg Glu
        660             665
```

```
<210> SEQ ID NO 77
<211> LENGTH: 669
<212> TYPE: PRT
<213> ORGANISM: Murine leukemia virus

<400> SEQUENCE: 77
```

```
Met Glu Ser Thr Thr Leu Ser Lys Pro Phe Lys Asn Gln Val Asn Pro
1               5               10              15

Trp Gly Pro Leu Ile Val Leu Leu Ile Leu Arg Gly Val Asn Pro Val
            20              25              30

Thr Leu Gly Asn Ser Pro His Gln Val Phe Asn Leu Thr Trp Glu Val
        35              40              45

Thr Asn Gly Asp Arg Glu Thr Val Trp Ala Ile Thr Gly Asn His Pro
    50              55              60

Leu Trp Thr Trp Trp Pro Asp Leu Thr Pro Asp Leu Cys Met Leu Ala
65              70              75              80

Leu His Gly Pro Ser Tyr Trp Gly Leu Glu Tyr Arg Ala Pro Phe Ser
            85              90              95

Pro Pro Pro Gly Pro Pro Cys Cys Ser Gly Ser Ser Asp Ser Thr Pro
            100             105             110

Gly Cys Ser Arg Asp Cys Glu Glu Pro Leu Thr Ser Tyr Thr Pro Arg
        115             120             125

Cys Asn Thr Ala Trp Asn Arg Leu Lys Leu Ser Lys Val Thr His Ala
    130             135             140

His Asn Gly Gly Phe Tyr Val Cys Pro Gly Pro His Arg Pro Arg Trp
145             150             155             160

Ala Arg Ser Cys Gly Gly Pro Glu Ser Phe Tyr Cys Ala Ser Trp Gly
            165             170             175

Cys Glu Thr Thr Gly Arg Ala Ser Trp Lys Pro Ser Ser Ser Trp Asp
            180             185             190

Tyr Ile Thr Val Ser Asn Asn Leu Thr Ser Asp Gln Ala Thr Pro Val
        195             200             205

Cys Lys Gly Asn Lys Trp Cys Asn Ser Leu Thr Ile Arg Phe Thr Ser
```

-continued

```
                210                 215                 220
Phe Gly Lys Gln Ala Thr Ser Trp Val Thr Gly His Trp Trp Gly Leu
225                 230                 235                 240

Arg Leu Tyr Val Ser Gly His Asp Pro Gly Leu Ile Phe Gly Ile Arg
                245                 250                 255

Leu Lys Ile Thr Asp Ser Gly Pro Arg Val Pro Ile Gly Pro Asn Pro
                260                 265                 270

Val Leu Ser Asp Arg Arg Pro Pro Ser Arg Pro Arg Pro Thr Arg Ser
                275                 280                 285

Pro Pro Pro Ser Asn Ser Thr Pro Thr Glu Thr Pro Leu Thr Leu Pro
                290                 295                 300

Glu Pro Pro Pro Ala Gly Val Glu Asn Arg Leu Leu Asn Leu Val Lys
305                 310                 315                 320

Gly Ala Tyr Gln Ala Leu Asn Leu Thr Ser Pro Asp Lys Thr Gln Glu
                325                 330                 335

Cys Trp Leu Cys Leu Val Ser Gly Pro Pro Tyr Tyr Glu Gly Val Ala
                340                 345                 350

Val Leu Gly Thr Tyr Ser Asn His Thr Ser Ala Pro Ala Asn Cys Ser
                355                 360                 365

Val Ala Ser Gln His Lys Leu Thr Leu Ser Glu Val Thr Gly Gln Gly
                370                 375                 380

Leu Cys Ile Gly Ala Val Pro Lys Thr His Gln Val Leu Cys Asn Thr
385                 390                 395                 400

Thr Gln Lys Thr Ser Asp Gly Ser Tyr Tyr Leu Ala Ala Pro Thr Gly
                405                 410                 415

Thr Thr Trp Ala Cys Ser Thr Gly Leu Thr Pro Cys Ile Ser Thr Thr
                420                 425                 430

Ile Leu Asp Leu Thr Thr Asp Tyr Cys Val Leu Val Glu Leu Trp Pro
                435                 440                 445

Arg Val Thr Tyr His Ser Pro Ser Tyr Val Tyr His Gln Phe Glu Arg
                450                 455                 460

Arg Ala Lys Tyr Lys Arg Glu Pro Val Ser Leu Thr Leu Ala Leu Leu
465                 470                 475                 480

Leu Gly Gly Leu Thr Met Gly Gly Ile Ala Ala Gly Val Gly Thr Gly
                485                 490                 495

Thr Thr Ala Leu Val Ala Thr Gln Gln Phe Gln Gln Leu Gln Ala Ala
                500                 505                 510

Met His Asp Asp Leu Lys Glu Val Glu Lys Ser Ile Thr Asn Leu Glu
                515                 520                 525

Lys Ser Leu Thr Ser Leu Ser Glu Val Val Leu Gln Asn Arg Arg Gly
                530                 535                 540

Leu Asp Leu Leu Phe Leu Lys Glu Gly Gly Leu Cys Ala Ala Leu Lys
545                 550                 555                 560

Glu Glu Cys Cys Phe Tyr Ala Asp His Thr Gly Leu Val Arg Asp Ser
                565                 570                 575

Met Ala Lys Leu Arg Glu Arg Leu Ser Gln Arg Gln Lys Leu Phe Glu
                580                 585                 590

Ser Gln Gln Gly Trp Phe Glu Gly Leu Phe Asn Lys Ser Pro Trp Phe
                595                 600                 605

Thr Thr Leu Ile Ser Thr Ile Met Gly Pro Leu Ile Ile Leu Leu Leu
                610                 615                 620

Ile Leu Leu Phe Gly Pro Cys Ile Leu Asn Arg Leu Val Gln Phe Ile
625                 630                 635                 640
```

-continued

```
Lys Asp Arg Ile Ser Val Val Gln Ala Leu Val Leu Thr Gln Gln Tyr
            645             650             655

His Gln Leu Lys Ile Ile Glu Asp Cys Lys Ser Arg Glu
            660             665

<210> SEQ ID NO 78
<211> LENGTH: 654
<212> TYPE: PRT
<213> ORGANISM: Murine leukemia virus

<400> SEQUENCE: 78

Met Ala Arg Ser Thr Leu Ser Lys Pro Pro Gln Asp Lys Ile Asn Pro
1               5               10              15

Trp Lys Pro Leu Ile Val Met Gly Val Leu Leu Gly Val Gly Met Ala
            20              25              30

Glu Ser Pro His Gln Val Phe Asn Val Thr Trp Arg Val Thr Asn Leu
            35              40              45

Met Thr Gly Arg Thr Ala Asn Ala Thr Ser Leu Leu Gly Thr Val Gln
            50              55              60

Asp Ala Phe Pro Lys Leu Tyr Phe Asp Leu Cys Asp Leu Val Gly Glu
65              70              75              80

Glu Trp Asp Pro Ser Asp Gln Glu Pro Tyr Val Gly Tyr Gly Cys Lys
            85              90              95

Tyr Pro Ala Gly Arg Gln Arg Thr Arg Thr Phe Asp Phe Tyr Val Cys
            100             105             110

Pro Gly His Thr Val Lys Ser Gly Cys Gly Gly Pro Gly Glu Gly Tyr
            115             120             125

Cys Gly Lys Trp Gly Cys Glu Thr Thr Gly Gln Ala Tyr Trp Lys Pro
    130             135             140

Thr Ser Ser Trp Asp Leu Ile Ser Leu Lys Arg Gly Asn Thr Pro Trp
145             150             155             160

Asp Thr Gly Cys Ser Lys Val Ala Cys Gly Pro Cys Tyr Asp Leu Ser
            165             170             175

Lys Val Ser Asn Ser Phe Gln Gly Ala Thr Arg Gly Gly Arg Cys Asn
            180             185             190

Pro Leu Val Leu Glu Phe Thr Asp Ala Gly Lys Lys Ala Asn Trp Asp
            195             200             205

Gly Pro Lys Ser Trp Gly Leu Arg Leu Tyr Arg Thr Gly Thr Asp Pro
    210             215             220

Ile Thr Met Phe Ser Leu Thr Arg Gln Val Leu Asn Val Gly Pro Arg
225             230             235             240

Val Pro Ile Gly Pro Asn Pro Val Leu Pro Asp Gln Arg Leu Pro Ser
            245             250             255

Ser Pro Ile Glu Ile Val Pro Ala Pro Gln Pro Pro Ser Pro Leu Asn
            260             265             270

Thr Ser Tyr Pro Pro Ser Thr Thr Ser Thr Pro Ser Thr Ser Pro Thr
            275             280             285

Ser Pro Ser Val Pro Gln Pro Pro Gly Thr Gly Asp Arg Leu Leu
    290             295             300

Ala Leu Val Lys Gly Ala Tyr Gln Ala Leu Asn Leu Thr Asn Pro Asp
305             310             315             320

Lys Thr Gln Glu Cys Trp Leu Cys Leu Val Ser Gly Pro Pro Tyr Tyr
            325             330             335

Glu Gly Val Ala Val Val Gly Thr Tyr Thr Asn His Ser Thr Ala Pro
```

-continued

```
                340                 345                 350

Ala Asn Cys Thr Ala Thr Ser Gln His Lys Leu Thr Leu Ser Glu Val
            355                 360                 365

Thr Gly Gln Gly Leu Cys Met Gly Ala Val Pro Lys Thr His Gln Ala
        370                 375                 380

Leu Cys Asn Thr Thr Gln Ser Ala Gly Ser Gly Ser Tyr Tyr Leu Ala
385                 390                 395                 400

Ala Pro Ala Gly Thr Met Trp Ala Cys Ser Thr Gly Leu Thr Pro Cys
                405                 410                 415

Leu Ser Thr Thr Val Leu Asn Leu Thr Thr Asp Tyr Cys Val Leu Val
            420                 425                 430

Glu Leu Trp Pro Arg Val Ile Tyr His Ser Pro Asp Tyr Met Tyr Gly
            435                 440                 445

Gln Leu Glu Gln Arg Thr Lys Tyr Lys Arg Glu Pro Val Ser Leu Thr
        450                 455                 460

Leu Ala Leu Leu Leu Gly Gly Leu Thr Met Gly Gly Ile Ala Ala Gly
465                 470                 475                 480

Ile Gly Thr Gly Thr Thr Ala Leu Ile Lys Thr Gln Gln Phe Glu Gln
                485                 490                 495

Leu His Ala Ala Ile Gln Thr Asp Leu Asn Glu Val Glu Lys Ser Ile
            500                 505                 510

Thr Asn Leu Glu Lys Ser Leu Thr Ser Leu Ser Glu Val Val Leu Gln
        515                 520                 525

Asn Arg Arg Gly Leu Asp Leu Leu Phe Leu Lys Glu Gly Gly Leu Cys
        530                 535                 540

Ala Ala Leu Lys Glu Glu Cys Cys Phe Tyr Ala Asp His Thr Gly Leu
545                 550                 555                 560

Val Arg Asp Ser Met Ala Lys Leu Arg Glu Arg Leu Asn Gln Arg Gln
                565                 570                 575

Lys Leu Phe Glu Thr Gly Gln Gly Trp Phe Glu Gly Leu Phe Asn Arg
            580                 585                 590

Ser Pro Trp Phe Thr Thr Leu Ile Ser Thr Ile Met Gly Pro Leu Ile
            595                 600                 605

Val Leu Leu Leu Ile Leu Leu Phe Gly Pro Cys Ile Leu Asn Arg Leu
        610                 615                 620

Val Gln Phe Val Lys Asp Arg Ile Ser Val Val Gln Ala Leu Val Leu
625                 630                 635                 640

Thr Gln Gln Tyr His Gln Leu Lys Pro Ile Glu Tyr Glu Pro
                645                 650

<210> SEQ ID NO 79
<211> LENGTH: 645
<212> TYPE: PRT
<213> ORGANISM: Murine leukemia virus

<400> SEQUENCE: 79

Met Glu Gly Pro Ala Phe Ser Lys Pro Leu Lys Asp Lys Ile Asn Pro
1                   5                   10                  15

Trp Lys Ser Leu Met Val Met Gly Val Tyr Leu Arg Val Gly Met Ala
                20                  25                  30

Glu Ser Pro His Gln Val Phe Asn Val Thr Trp Arg Val Thr Asn Leu
            35                  40                  45

Met Thr Gly Arg Thr Ala Asn Ala Thr Ser Leu Leu Gly Thr Val Gln
        50                  55                  60
```

-continued

Asp Ala Phe Pro Arg Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95

Tyr Pro Gly Gly Arg Lys Arg Thr Arg Thr Phe Asp Phe Tyr Val Cys
            100                 105                 110

Pro Gly His Thr Val Lys Ser Gly Cys Gly Gly Pro Arg Glu Gly Tyr
            115                 120                 125

Cys Gly Glu Trp Gly Cys Glu Thr Thr Gly Gln Ala Tyr Trp Lys Pro
    130                 135                 140

Thr Ser Ser Trp Asp Leu Ile Ser Leu Lys Arg Gly Asn Thr Pro Trp
145                 150                 155                 160

Asp Thr Gly Cys Ser Lys Met Ala Cys Gly Pro Cys Tyr Asp Leu Ser
                165                 170                 175

Lys Val Ser Asn Ser Phe Gln Gly Ala Thr Arg Gly Gly Arg Cys Asn
                180                 185                 190

Pro Leu Val Leu Glu Phe Thr Asp Ala Gly Lys Lys Ala Asn Trp Asp
            195                 200                 205

Gly Pro Lys Ser Trp Gly Leu Arg Leu Tyr Arg Thr Gly Thr Asp Pro
    210                 215                 220

Ile Thr Met Phe Ser Leu Thr Arg Gln Val Leu Asn Ile Gly Pro Arg
225                 230                 235                 240

Ile Pro Ile Gly Pro Asn Pro Val Ile Thr Gly Gln Leu Pro Pro Ser
                245                 250                 255

Arg Pro Val Gln Ile Arg Leu Pro Arg Pro Pro Gln Pro Pro Pro Thr
            260                 265                 270

Gly Ala Ala Ser Ile Val Pro Glu Thr Ala Pro Pro Ser Gln Gln Pro
            275                 280                 285

Gly Thr Gly Asp Arg Leu Leu Asn Leu Val Glu Gly Ala Tyr Gln Ala
    290                 295                 300

Leu Asn Leu Thr Asn Pro Asp Lys Thr Gln Glu Cys Trp Leu Cys Leu
305                 310                 315                 320

Val Ser Gly Pro Pro Tyr Tyr Glu Gly Val Ala Val Val Gly Thr Tyr
                325                 330                 335

Thr Asn His Ser Thr Ala Pro Ala Ser Cys Thr Ala Thr Ser Gln His
                340                 345                 350

Lys Leu Thr Leu Ser Glu Val Thr Gly Gln Gly Leu Cys Met Gly Ala
            355                 360                 365

Leu Pro Lys Thr His Gln Ala Leu Cys Asn Thr Thr Gln Ser Ala Gly
    370                 375                 380

Ser Gly Ser Tyr Tyr Leu Ala Ala Pro Ala Gly Thr Met Trp Ala Cys
385                 390                 395                 400

Ser Thr Gly Leu Thr Pro Cys Leu Ser Thr Thr Met Leu Asn Leu Thr
                405                 410                 415

Thr Asp Tyr Cys Val Leu Val Glu Leu Trp Pro Arg Ile Ile Tyr His
            420                 425                 430

Ser Pro Asp Tyr Met Tyr Gly Gln Leu Glu Gln Arg Thr Lys Tyr Lys
            435                 440                 445

Arg Glu Pro Val Ser Leu Thr Leu Ala Leu Leu Leu Gly Gly Leu Thr
    450                 455                 460

Met Gly Gly Ile Ala Ala Gly Ile Gly Thr Gly Thr Thr Ala Leu Ile
465                 470                 475                 480

Lys Thr Gln Gln Phe Glu Gln Leu His Ala Ala Ile Gln Thr Asp Leu

-continued

```
                      485               490               495
Asn Glu Val Glu Lys Ser Ile Thr Asn Leu Glu Lys Ser Leu Thr Ser
                500               505               510
Leu Ser Glu Val Val Leu Gln Asn Arg Arg Gly Leu Asp Leu Leu Phe
                515               520               525
Leu Lys Glu Gly Gly Leu Cys Ala Ala Leu Lys Glu Glu Cys Cys Phe
            530               535               540
Tyr Ala Asp His Thr Gly Leu Val Arg Asp Ser Met Ala Lys Leu Arg
545               550               555               560
Glu Arg Leu Asn Gln Arg Gln Lys Leu Phe Glu Ser Gly Gln Gly Trp
                565               570               575
Phe Glu Gly Gln Phe Asn Arg Ser Pro Trp Phe Thr Thr Leu Ile Ser
                580               585               590
Thr Ile Met Gly Pro Leu Ile Val Leu Leu Leu Ile Leu Leu Phe Gly
                595               600               605
Pro Cys Ile Leu Asn Arg Leu Val Gln Phe Val Lys Asp Arg Ile Ser
            610               615               620
Val Val Gln Ala Leu Val Leu Thr Gln Gln Tyr His Gln Leu Lys Pro
625               630               635               640
Ile Glu Tyr Glu Pro
                645

<210> SEQ ID NO 80
<211> LENGTH: 644
<212> TYPE: PRT
<213> ORGANISM: Polytropic mink cell focus-forming virus

<400> SEQUENCE: 80

Met Glu Gly Ser Ala Phe Ser Lys Pro Leu Lys Asp Lys Ile Asn Pro
1               5                 10                15
Trp Gly Pro Leu Ile Val Met Gly Ile Leu Val Arg Ala Gly Ala Ser
                20                25                30
Val Gln Arg Asp Ser Pro His Gln Ile Phe Asn Val Thr Trp Arg Val
            35                40                45
Thr Asn Leu Met Thr Gly Gln Thr Ala Asn Ala Thr Ser Leu Leu Gly
        50                55                60
Thr Met Thr Asp Thr Phe Pro Lys Leu Tyr Phe Asp Leu Cys Asp Leu
65                70                75                80
Val Gly Asp Tyr Trp Asp Asp Pro Glu Pro Asp Ile Gly Asp Gly Cys
                85                90                95
Arg Thr Pro Gly Gly Arg Arg Arg Thr Arg Leu Tyr Asp Phe Tyr Val
                100               105               110
Cys Pro Gly His Thr Val Pro Ile Gly Cys Gly Gly Pro Gly Glu Gly
            115               120               125
Tyr Cys Gly Lys Trp Gly Cys Glu Thr Thr Gly Gln Ala Tyr Trp Lys
        130               135               140
Pro Ser Ser Ser Trp Asp Leu Ile Ser Leu Lys Arg Gly Asn Thr Pro
145               150               155               160
Lys Asp Gln Gly Pro Cys Tyr Asp Ser Ser Val Ser Ser Gly Val Gln
            165               170               175
Gly Ala Thr Pro Gly Gly Arg Cys Asn Pro Leu Val Leu Glu Phe Thr
            180               185               190
Asp Ala Gly Arg Lys Ala Ser Trp Asp Ala Pro Lys Val Trp Gly Leu
            195               200               205
```

-continued

```
Arg Leu Tyr Arg Ser Thr Gly Ala Asp Pro Val Thr Arg Phe Ser Leu
210                 215                 220

Thr Arg Gln Val Leu Asn Val Gly Pro Arg Val Pro Ile Gly Pro Asn
225                 230                 235                 240

Pro Val Ile Thr Asp Gln Leu Pro Pro Ser Gln Pro Val Gln Ile Met
                245                 250                 255

Leu Pro Arg Pro Pro His Pro Pro Pro Ser Gly Thr Val Ser Met Val
                260                 265                 270

Pro Gly Ala Pro Pro Pro Ser Gln Gln Pro Gly Thr Gly Asp Arg Leu
                275                 280                 285

Leu Asn Leu Val Glu Gly Ala Tyr Gln Ala Leu Asn Leu Thr Ser Pro
    290                 295                 300

Asp Lys Thr Gln Glu Cys Trp Leu Cys Leu Val Ser Gly Pro Pro Tyr
305                 310                 315                 320

Tyr Glu Gly Val Ala Val Leu Gly Thr Tyr Ser Asn His Thr Ser Ala
                325                 330                 335

Pro Ala Asn Cys Ser Val Ala Ser Gln His Lys Leu Thr Leu Ser Glu
                340                 345                 350

Val Thr Gly Gln Gly Leu Cys Val Gly Ala Val Pro Lys Thr His Gln
                355                 360                 365

Ala Leu Cys Asn Thr Thr Gln Lys Thr Ser Asp Gly Ser Tyr Tyr Leu
    370                 375                 380

Ala Ala Pro Ala Gly Thr Ile Trp Ala Cys Asn Thr Gly Leu Thr Pro
385                 390                 395                 400

Cys Leu Ser Thr Thr Val Leu Asn Leu Thr Thr Asp Tyr Cys Val Leu
                405                 410                 415

Val Glu Leu Trp Pro Lys Val Thr Tyr His Ser Pro Asp Tyr Val Tyr
                420                 425                 430

Gly Gln Phe Glu Lys Lys Thr Lys Tyr Lys Arg Glu Pro Val Ser Leu
                435                 440                 445

Thr Leu Ala Leu Leu Leu Gly Gly Leu Thr Met Gly Gly Ile Ala Ala
    450                 455                 460

Gly Val Gly Thr Gly Thr Thr Ala Leu Val Ala Thr Lys Gln Phe Glu
465                 470                 475                 480

Gln Leu Gln Ala Ala Ile His Thr Asp Leu Gly Ala Leu Glu Lys Ser
                485                 490                 495

Val Ser Ala Leu Glu Lys Ser Leu Thr Ser Leu Ser Glu Val Val Leu
                500                 505                 510

Gln Asn Arg Arg Gly Leu Asp Leu Leu Phe Leu Lys Glu Gly Gly Leu
                515                 520                 525

Cys Ala Ala Leu Lys Glu Glu Cys Cys Phe Tyr Ala Asp His Thr Gly
    530                 535                 540

Val Val Arg Asp Ser Met Ala Lys Leu Arg Glu Arg Leu Asn Gln Arg
545                 550                 555                 560

Gln Lys Leu Phe Glu Ser Gly Gln Gly Trp Phe Glu Gly Leu Phe Asn
                565                 570                 575

Arg Ser Pro Trp Phe Thr Thr Leu Ile Ser Thr Ile Met Gly Pro Leu
                580                 585                 590

Ile Val Leu Leu Leu Ile Leu Leu Leu Gly Pro Cys Ile Leu Asn Arg
                595                 600                 605

Leu Val Gln Phe Val Lys Asp Arg Ile Ser Val Val Gln Ala Leu Ile
    610                 615                 620

Leu Thr Gln Gln Tyr His Gln Leu Lys Ser Ile Glu Pro Glu Glu Val
```

-continued

```
625              630              635              640

Glu Ser Arg Glu

<210> SEQ ID NO 81
<211> LENGTH: 408
<212> TYPE: PRT
<213> ORGANISM: Polytropic mink cell focus-forming virus

<400> SEQUENCE: 81

Val Gln His Asp Ser Pro His Gln Val Phe Asn Val Thr Trp Arg Val
1               5                   10                  15

Thr Asn Leu Met Thr Gly Gln Thr Ala Asn Ala Thr Ser Leu Leu Gly
            20                  25                  30

Thr Met Thr Asp Ala Phe Pro Lys Leu Tyr Phe Asp Leu Cys Asp Leu
        35                  40                  45

Ile Gly Asp Asp Trp Asp Glu Thr Gly Leu Gly Cys Arg Thr Pro Gly
    50                  55                  60

Gly Arg Lys Arg Ala Arg Thr Phe Asp Phe Tyr Val Cys Pro Gly His
65                  70                  75                  80

Thr Val Pro Thr Gly Cys Gly Gly Pro Arg Glu Gly Tyr Cys Gly Lys
                85                  90                  95

Trp Gly Cys Glu Thr Thr Gly Gln Ala Tyr Trp Lys Pro Ser Ser Leu
            100                 105                 110

Trp Asp Leu Ile Ser Leu Lys Arg Gly Asn Thr Pro Gln Asn Gln Gly
            115                 120                 125

Pro Cys Tyr Asp Ser Ser Ala Val Ser Ser Asp Ile Lys Gly Ala Thr
        130                 135                 140

Pro Gly Gly Arg Cys Asn Pro Leu Val Leu Glu Phe Thr Asp Ala Gly
145                 150                 155                 160

Lys Lys Ala Ser Trp Asp Gly Pro Lys Val Trp Gly Leu Arg Leu Tyr
                165                 170                 175

Arg Ser Thr Gly Thr Asp Pro Val Thr Arg Phe Ser Leu Thr Arg Arg
            180                 185                 190

Val Leu Asn Ile Gly Pro Arg Val Pro Ile Gly Pro Asn Pro Val Ile
            195                 200                 205

Ile Asp Gln Leu Pro Pro Ser Arg Pro Val Gln Ile Met Leu Pro Arg
    210                 215                 220

Pro Pro Gln Pro Pro Pro Gly Ala Ala Ser Ile Val Pro Glu Thr
225                 230                 235                 240

Ala Pro Pro Ser Asn Gln Pro Gly Thr Gly Asp Arg Leu Leu Asn Leu
                245                 250                 255

Val Asp Gly Ala Tyr Gln Ala Leu Asn Leu Thr Ser Pro Asp Lys Thr
            260                 265                 270

Gln Glu Cys Trp Leu Cys Leu Val Ala Glu Pro Pro Tyr Tyr Glu Gly
        275                 280                 285

Val Ala Val Leu Gly Thr Tyr Ser Asn His Thr Ser Ala Pro Ala Asn
    290                 295                 300

Cys Ser Val Ala Ser Gln His Lys Leu Thr Leu Ser Glu Val Thr Gly
305                 310                 315                 320

Arg Gly Leu Cys Ile Gly Thr Val Pro Lys Thr His Gln Ala Leu Cys
                325                 330                 335

Asn Thr Thr Leu Lys Thr Asn Lys Gly Ser Tyr Tyr Leu Val Ala Pro
            340                 345                 350

Ala Gly Thr Thr Trp Ala Cys Asn Thr Gly Leu Thr Pro Cys Leu Ser
```

-continued

```
            355                 360                 365

Ala Thr Val Leu Asn Arg Thr Thr Asp Tyr Cys Val Leu Val Glu Leu
    370                 375                 380

Trp Pro Arg Val Thr Tyr His Pro Pro Ser Tyr Val Tyr Ser Gln Phe
385                 390                 395                 400

Glu Lys Ser Tyr Arg His Lys Arg
                405

<210> SEQ ID NO 82
<211> LENGTH: 685
<212> TYPE: PRT
<213> ORGANISM: Gibbon ape leukemia virus

<400> SEQUENCE: 82

Met Val Leu Leu Pro Gly Ser Met Leu Leu Thr Ser Asn Leu His His
1                   5                   10                  15

Leu Arg His Gln Met Ser Pro Gly Ser Trp Lys Arg Leu Ile Ile Leu
                20                  25                  30

Leu Ser Cys Val Phe Gly Gly Gly Thr Ser Leu Gln Asn Lys Asn
        35                  40                  45

Pro His Gln Pro Met Thr Leu Thr Trp Gln Val Leu Ser Gln Thr Gly
    50                  55                  60

Asp Val Val Trp Asp Thr Lys Ala Val Gln Pro Pro Trp Thr Trp Trp
65                  70                  75                  80

Pro Thr Leu Lys Pro Asp Val Cys Ala Leu Ala Ala Ser Leu Glu Ser
                85                  90                  95

Trp Asp Ile Pro Gly Thr Asp Val Ser Ser Ser Lys Arg Val Arg Pro
            100                 105                 110

Pro Asp Ser Asp Tyr Thr Ala Ala Tyr Lys Gln Ile Thr Trp Gly Ala
            115                 120                 125

Ile Gly Cys Ser Tyr Pro Arg Ala Arg Thr Arg Met Ala Ser Ser Thr
    130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Val Lys Trp Asp Gln Asn Ser Glu Trp Thr Gln Lys Phe Gln Gln Cys
            195                 200                 205

His Gln Thr Gly Trp Cys Asn Pro Leu Lys Ile Asp Phe Thr Asp Lys
    210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
                245                 250                 255

Ile Thr Asn Met Pro Ala Val Ala Val Gly Pro Asp Leu Val Leu Val
                260                 265                 270

Glu Gln Gly Pro Pro Arg Thr Ser Leu Ala Leu Pro Pro Pro Leu Pro
            275                 280                 285

Pro Arg Glu Ala Pro Pro Pro Ser Leu Pro Asp Ser Asn Ser Thr Ala
    290                 295                 300

Leu Ala Thr Ser Ala Gln Thr Pro Thr Val Arg Lys Thr Ile Val Thr
305                 310                 315                 320
```

-continued

```
Leu Asn Thr Pro Pro Pro Thr Thr Gly Asp Arg Leu Phe Asp Leu Val
            325             330             335

Gln Gly Ala Phe Leu Thr Leu Asn Ala Thr Asn Pro Gly Ala Thr Glu
            340             345             350

Ser Cys Trp Leu Cys Leu Ala Met Gly Pro Pro Tyr Tyr Glu Ala Ile
            355             360             365

Ala Ser Ser Gly Glu Val Ala Tyr Ser Thr Asp Leu Asp Arg Cys Arg
    370             375             380

Trp Gly Thr Gln Gly Lys Leu Thr Leu Thr Glu Val Ser Gly His Gly
385             390             395             400

Leu Cys Ile Gly Lys Val Pro Phe Thr His Gln His Leu Cys Asn Gln
            405             410             415

Thr Leu Ser Ile Asn Ser Ser Gly Asp His Gln Tyr Leu Leu Pro Ser
            420             425             430

Asn His Ser Trp Trp Ala Cys Ser Thr Gly Leu Thr Pro Cys Leu Ser
            435             440             445

Thr Ser Val Phe Asn Gln Thr Arg Asp Phe Cys Ile Gln Val Gln Leu
    450             455             460

Ile Pro Arg Ile Tyr Tyr Tyr Pro Glu Glu Val Leu Leu Gln Ala Tyr
465             470             475             480

Asp Asn Ser His Pro Arg Thr Lys Arg Glu Ala Val Ser Leu Thr Leu
            485             490             495

Ala Val Leu Leu Gly Leu Gly Ile Thr Ala Gly Ile Gly Thr Gly Ser
            500             505             510

Thr Ala Leu Ile Lys Gly Pro Ile Asp Leu Gln Gln Gly Leu Thr Ser
            515             520             525

Leu Gln Ile Ala Ile Asp Ala Asp Leu Arg Ala Leu Gln Asp Ser Val
    530             535             540

Ser Lys Leu Glu Asp Ser Leu Thr Ser Leu Ser Glu Val Val Leu Gln
545             550             555             560

Asn Arg Arg Gly Leu Asp Leu Leu Phe Leu Lys Glu Gly Gly Leu Cys
            565             570             575

Ala Ala Leu Lys Glu Glu Cys Cys Phe Tyr Ile Asp His Ser Gly Ala
            580             585             590

Val Arg Asp Ser Met Lys Lys Leu Lys Glu Lys Leu Asp Lys Arg Gln
    595             600             605

Leu Glu Arg Gln Lys Ser Gln Asn Trp Tyr Glu Gly Trp Phe Asn Asn
    610             615             620

Ser Pro Trp Phe Thr Thr Leu Leu Ser Thr Ile Ala Gly Pro Leu Leu
625             630             635             640

Leu Leu Leu Leu Leu Leu Ile Leu Gly Pro Cys Ile Ile Asn Lys Leu
            645             650             655

Val Gln Phe Ile Asn Asp Arg Ile Ser Ala Val Lys Ile Leu Val Leu
            660             665             670

Arg Gln Lys Tyr Gln Ala Leu Glu Asn Glu Gly Asn Leu
            675             680             685
```

```
<210> SEQ ID NO 83
<211> LENGTH: 644
<212> TYPE: PRT
<213> ORGANISM: Gibbon ape leukemia virus

<400> SEQUENCE: 83

Thr Ser Leu Gln Asn Lys Asn Pro His Gln Pro Met Thr Leu Thr Trp
1               5               10              15
```

-continued

```
Gln Val Leu Ser Gln Thr Gly Asp Val Val Trp Asp Thr Lys Ala Val
            20                  25                  30

Gln Pro Pro Trp Thr Trp Trp Pro Thr Leu Lys Pro Asp Val Cys Ala
            35                  40                  45

Leu Ala Ala Ser Leu Glu Ser Trp Asp Ile Pro Gly Thr Asp Val Ser
            50                  55                  60

Ser Ser Lys Arg Val Arg Pro Pro Asp Ser Asp Tyr Thr Ala Ala Tyr
65                      70                  75                  80

Lys Gln Ile Thr Trp Gly Ala Ile Gly Cys Ser Tyr Pro Arg Ala Arg
                85                  90                  95

Thr Arg Met Ala Ser Ser Thr Phe Tyr Val Cys Pro Arg Asp Gly Arg
            100                 105                 110

Thr Leu Ser Glu Ala Arg Arg Cys Gly Gly Leu Glu Ser Leu Tyr Cys
            115                 120                 125

Lys Glu Trp Asp Cys Glu Thr Thr Gly Thr Gly Tyr Trp Leu Ser Lys
    130                 135                 140

Ser Ser Lys Asp Leu Ile Thr Val Lys Trp Asp Gln Asn Ser Glu Trp
145                 150                 155                 160

Thr Gln Lys Phe Gln Gln Cys His Gln Thr Gly Trp Cys Asn Pro Leu
                165                 170                 175

Lys Ile Asp Phe Thr Asp Lys Gly Lys Leu Ser Lys Asp Trp Ile Thr
            180                 185                 190

Gly Lys Thr Trp Gly Leu Arg Phe Tyr Val Ser Gly His Pro Gly Val
            195                 200                 205

Gln Phe Thr Ile Arg Leu Lys Ile Thr Asn Met Pro Ala Val Ala Val
    210                 215                 220

Gly Pro Asp Leu Val Leu Val Glu Gln Gly Pro Pro Arg Thr Ser Leu
225                 230                 235                 240

Ala Leu Pro Pro Pro Leu Pro Pro Arg Glu Ala Pro Pro Pro Ser Leu
            245                 250                 255

Pro Asp Ser Asn Ser Thr Ala Leu Ala Thr Ser Ala Gln Thr Pro Thr
            260                 265                 270

Val Arg Lys Thr Ile Val Thr Leu Asn Thr Pro Pro Thr Thr Gly
    275                 280                 285

Asp Arg Leu Phe Asp Leu Val Gln Gly Ala Phe Leu Thr Leu Asn Ala
    290                 295                 300

Thr Asn Pro Gly Ala Thr Glu Ser Cys Trp Leu Cys Leu Ala Met Gly
305                 310                 315                 320

Pro Pro Tyr Tyr Glu Ala Ile Ala Ser Ser Gly Glu Val Ala Tyr Ser
            325                 330                 335

Thr Asp Leu Asp Arg Cys Arg Trp Gly Thr Gln Gly Lys Leu Thr Leu
            340                 345                 350

Thr Glu Val Ser Gly His Gly Leu Cys Ile Gly Lys Val Pro Phe Thr
            355                 360                 365

His Gln His Leu Cys Asn Gln Thr Leu Ser Ile Asn Ser Ser Gly Asp
    370                 375                 380

His Gln Tyr Leu Leu Pro Ser Asn His Ser Trp Trp Ala Cys Ser Thr
385                 390                 395                 400

Gly Leu Thr Pro Cys Leu Ser Thr Ser Val Phe Asn Gln Thr Arg Asp
            405                 410                 415

Phe Cys Ile Gln Val Gln Leu Ile Pro Arg Ile Tyr Tyr Tyr Pro Glu
            420                 425                 430
```

-continued

```
Glu Val Leu Leu Gln Ala Tyr Asp Asn Ser His Pro Arg Thr Lys Arg
        435                 440             445

Glu Ala Val Ser Leu Thr Leu Ala Val Leu Leu Gly Leu Gly Ile Thr
    450             455             460

Ala Gly Ile Gly Thr Gly Ser Thr Ala Leu Ile Lys Gly Pro Ile Asp
465             470             475             480

Leu Gln Gln Gly Leu Thr Ser Leu Gln Ile Ala Ile Asp Ala Asp Leu
                485             490             495

Arg Ala Leu Gln Asp Ser Val Ser Lys Leu Glu Asp Ser Leu Thr Ser
            500             505             510

Leu Ser Glu Val Val Leu Gln Asn Arg Arg Gly Leu Asp Leu Leu Phe
            515             520             525

Leu Lys Glu Gly Gly Leu Cys Ala Ala Leu Lys Glu Glu Cys Cys Phe
    530             535             540

Tyr Ile Asp His Ser Gly Ala Val Arg Asp Ser Met Lys Lys Leu Lys
545             550             555             560

Glu Lys Leu Asp Lys Arg Gln Leu Glu Arg Gln Lys Ser Gln Asn Trp
            565             570             575

Tyr Glu Gly Trp Phe Asn Asn Ser Pro Trp Phe Thr Thr Leu Leu Ser
            580             585             590

Thr Ile Ala Gly Pro Leu Leu Leu Leu Leu Leu Leu Ile Leu Gly
            595             600             605

Pro Cys Ile Ile Asn Lys Leu Val Gln Phe Ile Asn Asp Arg Ile Ser
    610             615             620

Ala Val Lys Ile Leu Val Leu Arg Gln Lys Tyr Gln Ala Leu Glu Asn
625             630             635             640

Glu Gly Asn Leu

<210> SEQ ID NO 84
<211> LENGTH: 448
<212> TYPE: PRT
<213> ORGANISM: Gibbon ape leukemia virus

<400> SEQUENCE: 84

Thr Ser Leu Gln Asn Lys Asn Pro His Gln Pro Met Thr Leu Thr Trp
1               5               10              15

Gln Val Leu Ser Gln Thr Gly Asp Val Val Trp Asp Thr Lys Ala Val
            20              25              30

Gln Pro Pro Trp Thr Trp Trp Pro Thr Leu Lys Pro Asp Val Cys Ala
        35              40              45

Leu Ala Ala Ser Leu Glu Ser Trp Asp Ile Pro Gly Thr Asp Val Ser
    50              55              60

Ser Ser Lys Arg Val Arg Pro Pro Asp Ser Asp Tyr Thr Ala Ala Tyr
65              70              75              80

Lys Gln Ile Thr Trp Gly Ala Ile Gly Cys Ser Tyr Pro Arg Ala Arg
                85              90              95

Thr Arg Met Ala Ser Ser Thr Phe Tyr Val Cys Pro Arg Asp Gly Arg
            100             105             110

Thr Leu Ser Glu Ala Arg Arg Cys Gly Gly Leu Glu Ser Leu Tyr Cys
            115             120             125

Lys Glu Trp Asp Cys Glu Thr Thr Gly Thr Gly Tyr Trp Leu Ser Lys
            130             135             140

Ser Ser Lys Asp Leu Ile Thr Val Lys Trp Asp Gln Asn Ser Glu Trp
145             150             155             160
```

```
Thr Gln Lys Phe Gln Gln Cys His Gln Thr Gly Trp Cys Asn Pro Leu
            165                 170                 175

Lys Ile Asp Phe Thr Asp Lys Gly Lys Leu Ser Lys Asp Trp Ile Thr
            180                 185                 190

Gly Lys Thr Trp Gly Leu Arg Phe Tyr Val Ser Gly His Pro Gly Val
            195                 200                 205

Gln Phe Thr Ile Arg Leu Lys Ile Thr Asn Met Pro Ala Val Ala Val
    210                 215                 220

Gly Pro Asp Leu Val Leu Val Glu Gln Gly Pro Pro Arg Thr Ser Leu
225                 230                 235                 240

Ala Leu Pro Pro Pro Leu Pro Pro Arg Glu Ala Pro Pro Pro Ser Leu
            245                 250                 255

Pro Asp Ser Asn Ser Thr Ala Leu Ala Thr Ser Ala Gln Thr Pro Thr
            260                 265                 270

Val Arg Lys Thr Ile Val Thr Leu Asn Thr Pro Pro Pro Thr Thr Gly
            275                 280                 285

Asp Arg Leu Phe Asp Leu Val Gln Gly Ala Phe Leu Thr Leu Asn Ala
    290                 295                 300

Thr Asn Pro Gly Ala Thr Glu Ser Cys Trp Leu Cys Leu Ala Met Gly
305                 310                 315                 320

Pro Pro Tyr Tyr Glu Ala Ile Ala Ser Ser Gly Glu Val Ala Tyr Ser
            325                 330                 335

Thr Asp Leu Asp Arg Cys Arg Trp Gly Thr Gln Gly Lys Leu Thr Leu
            340                 345                 350

Thr Glu Val Ser Gly His Gly Leu Cys Ile Gly Lys Val Pro Phe Thr
            355                 360                 365

His Gln His Leu Cys Asn Gln Thr Leu Ser Ile Asn Ser Ser Gly Asp
    370                 375                 380

His Gln Tyr Leu Leu Pro Ser Asn His Ser Trp Trp Ala Cys Ser Thr
385                 390                 395                 400

Gly Leu Thr Pro Cys Leu Ser Thr Ser Val Phe Asn Gln Thr Arg Asp
            405                 410                 415

Phe Cys Ile Gln Val Gln Leu Ile Pro Arg Ile Tyr Tyr Tyr Pro Glu
            420                 425                 430

Glu Val Leu Leu Gln Ala Tyr Asp Asn Ser His Pro Arg Thr Lys Arg
            435                 440                 445

<210> SEQ ID NO 85
<211> LENGTH: 181
<212> TYPE: PRT
<213> ORGANISM: Gibbon ape leukemia virus

<400> SEQUENCE: 85

Glu Ala Val Ser Leu Thr Leu Ala Val Leu Leu Gly Leu Gly Ile Thr
1               5                   10                  15

Ala Gly Ile Gly Thr Gly Ser Thr Ala Leu Ile Lys Gly Pro Ile Asp
            20                  25                  30

Leu Gln Gln Gly Leu Thr Ser Leu Gln Ile Ala Ile Asp Ala Asp Leu
        35                  40                  45

Arg Ala Leu Gln Asp Ser Val Ser Lys Leu Glu Asp Ser Leu Thr Ser
    50                  55                  60

Leu Ser Glu Val Val Leu Gln Asn Arg Arg Gly Leu Asp Leu Leu Phe
65                  70                  75                  80

Leu Lys Glu Gly Gly Leu Cys Ala Ala Leu Lys Glu Glu Cys Cys Phe
            85                  90                  95
```

-continued

```
Tyr Ile Asp His Ser Gly Ala Val Arg Asp Ser Met Lys Lys Leu Lys
            100                 105                 110

Glu Lys Leu Asp Lys Arg Gln Leu Glu Arg Gln Lys Ser Gln Asn Trp
            115                 120                 125

Tyr Glu Gly Trp Phe Asn Asn Ser Pro Trp Phe Thr Thr Leu Leu Ser
        130                 135                 140

Thr Ile Ala Gly Pro Leu Leu Leu Leu Leu Leu Leu Ile Leu Gly
145                 150                 155                 160

Pro Cys Ile Ile Asn Lys Leu Val Gln Phe Ile Asn Asp Arg Ile Ser
                165                 170                 175

Ala Val Lys Ile Leu
            180

<210> SEQ ID NO 86
<211> LENGTH: 565
<212> TYPE: PRT
<213> ORGANISM: RD114 retrovirus

<400> SEQUENCE: 86

Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
                20                  25                  30

Gln His Gly Lys Pro Cys Glu Cys Ser Gly Gly Gln Val Ser Glu Ala
            35                  40                  45

Pro Pro Asn Ser Ile Gln Gln Val Thr Cys Pro Gly Lys Thr Ala Tyr
        50                  55                  60

Leu Met Thr Asn Gln Lys Trp Lys Cys Arg Val Thr Pro Lys Asn Leu
65                  70                  75                  80

Thr Pro Ser Gly Gly Glu Leu Gln Asn Cys Pro Cys Asn Thr Phe Gln
                85                  90                  95

Asp Ser Met His Ser Ser Cys Tyr Thr Glu Tyr Arg Gln Cys Arg Ala
            100                 105                 110

Asn Asn Lys Thr Tyr Tyr Thr Ala Thr Leu Leu Lys Ile Arg Ser Gly
            115                 120                 125

Ser Leu Asn Glu Val Gln Ile Leu Gln Asn Pro Asn Gln Leu Leu Gln
        130                 135                 140

Ser Pro Cys Arg Gly Ser Ile Asn Gln Pro Val Cys Trp Ser Ala Thr
145                 150                 155                 160

Ala Pro Ile His Ile Ser Asp Gly Gly Gly Pro Leu Asp Thr Lys Arg
                165                 170                 175

Val Trp Thr Val Gln Lys Arg Leu Glu Gln Ile His Lys Ala Met His
            180                 185                 190

Pro Glu Leu Gln Tyr His Pro Leu Ala Leu Pro Lys Val Arg Asp Asp
            195                 200                 205

Leu Ser Leu Asp Ala Arg Thr Phe Asp Ile Leu Asn Thr Thr Phe Arg
        210                 215                 220

Leu Leu Gln Met Ser Asn Phe Ser Leu Ala Gln Asp Cys Trp Leu Cys
225                 230                 235                 240

Leu Lys Leu Gly Thr Pro Thr Pro Leu Ala Ile Pro Thr Pro Ser Leu
                245                 250                 255

Thr Tyr Ser Leu Ala Asp Ser Leu Ala Asn Ala Ser Cys Gln Ile Ile
            260                 265                 270

Pro Pro Leu Leu Val Gln Pro Met Gln Phe Ser Asn Ser Ser Cys Leu
```

```
              275                 280                 285
Ser Ser Pro Phe Ile Asn Asp Thr Glu Gln Ile Asp Leu Gly Ala Val
    290                 295                 300

Thr Phe Thr Asn Cys Thr Ser Val Ala Asn Val Ser Ser Pro Leu Cys
305                 310                 315                 320

Ala Leu Asn Gly Ser Val Phe Leu Cys Gly Asn Asn Met Ala Tyr Thr
                325                 330                 335

Tyr Leu Pro Gln Asn Trp Thr Gly Leu Cys Val Gln Ala Ser Leu Leu
            340                 345                 350

Pro Asp Ile Asp Ile Ile Pro Gly Asp Glu Pro Val Pro Ile Pro Ala
            355                 360                 365

Ile Asp His Tyr Ile His Arg Pro Lys Arg Ala Val Gln Phe Ile Pro
    370                 375                 380

Leu Leu Ala Gly Leu Gly Ile Thr Ala Ala Phe Thr Thr Gly Ala Thr
385                 390                 395                 400

Gly Leu Gly Val Ser Val Thr Gln Tyr Thr Lys Leu Ser His Gln Leu
                405                 410                 415

Ile Ser Asp Val Gln Val Leu Ser Gly Thr Ile Gln Asp Leu Gln Asp
            420                 425                 430

Gln Val Asp Ser Leu Ala Glu Val Val Leu Gln Asn Arg Arg Gly Leu
            435                 440                 445

Asp Leu Leu Thr Ala Glu Gln Gly Gly Ile Cys Leu Ala Leu Gln Glu
    450                 455                 460

Lys Cys Cys Phe Tyr Ala Asn Lys Ser Gly Ile Val Arg Asn Lys Ile
465                 470                 475                 480

Arg Thr Leu Gln Glu Glu Leu Gln Lys Arg Arg Glu Ser Leu Ala Ser
                485                 490                 495

Asn Pro Leu Trp Thr Gly Leu Gln Gly Phe Leu Pro Tyr Leu Leu Pro
            500                 505                 510

Leu Leu Gly Pro Leu Leu Thr Leu Leu Leu Ile Leu Thr Ile Gly Pro
            515                 520                 525

Cys Val Phe Ser Arg Leu Met Ala Phe Ile Asn Asp Arg Leu Asn Val
    530                 535                 540

Val His Ala Met Val Leu Ala Gln Gln Tyr Gln Ala Leu Lys Ala Glu
545                 550                 555                 560

Glu Glu Ala Gln Asp
                565

<210> SEQ ID NO 87
<211> LENGTH: 565
<212> TYPE: PRT
<213> ORGANISM: Sendai virus

<400> SEQUENCE: 87

Met Thr Ala Tyr Ile Gln Arg Ser Gln Cys Ile Ser Thr Ser Leu Leu
1               5                   10                  15

Val Val Leu Thr Thr Leu Val Ser Cys Gln Ile Pro Arg Asp Arg Leu
                20                  25                  30

Ser Asn Ile Gly Val Ile Val Asp Glu Gly Lys Ser Leu Lys Ile Ala
            35                  40                  45

Gly Ser His Glu Ser Arg Tyr Ile Val Leu Ser Leu Val Pro Gly Val
        50                  55                  60

Asp Phe Glu Asn Gly Cys Gly Thr Ala Gln Val Ile Gln Tyr Lys Ser
65                  70                  75                  80
```

-continued

```
Leu Leu Asn Arg Leu Leu Ile Pro Leu Arg Asp Ala Leu Asp Leu Gln
            85              90                 95

Glu Ala Leu Ile Thr Val Thr Asn Asp Thr Thr Gln Asn Ala Gly Ala
            100             105             110

Pro Gln Ser Arg Phe Phe Gly Ala Val Ile Gly Thr Ile Ala Leu Gly
            115             120             125

Val Ala Thr Ser Ala Gln Ile Thr Ala Gly Ile Ala Leu Ala Glu Ala
        130             135             140

Arg Glu Ala Lys Arg Asp Ile Ala Leu Ile Lys Glu Ser Met Thr Lys
145             150             155             160

Thr His Lys Ser Ile Glu Leu Leu Gln Asn Ala Val Gly Glu Gln Ile
                165             170             175

Leu Ala Leu Lys Thr Leu Gln Asp Phe Val Asn Asp Glu Ile Lys Pro
            180             185             190

Ala Ile Ser Glu Leu Gly Cys Glu Thr Ala Ala Leu Arg Leu Gly Ile
            195             200             205

Lys Leu Thr Gln His Tyr Ser Glu Leu Leu Thr Ala Phe Gly Ser Asn
        210             215             220

Phe Gly Thr Ile Gly Glu Lys Ser Leu Thr Leu Gln Ala Leu Ser Ser
225             230             235             240

Leu Tyr Ser Ala Asn Ile Thr Glu Ile Met Thr Thr Ile Lys Thr Gly
            245             250             255

Gln Ser Asn Ile Tyr Asp Val Ile Tyr Thr Glu Gln Ile Lys Gly Thr
            260             265             270

Val Ile Asp Val Asp Leu Glu Arg Tyr Met Val Thr Leu Ser Val Lys
            275             280             285

Ile Pro Ile Leu Ser Glu Val Pro Gly Val Leu Ile His Lys Ala Ser
        290             295             300

Ser Ile Ser Tyr Asn Ile Asp Gly Glu Glu Trp Tyr Val Thr Val Pro
305             310             315             320

Ser His Ile Leu Ser Arg Ala Ser Phe Leu Gly Gly Ala Asp Ile Thr
            325             330             335

Asp Cys Val Glu Ser Arg Leu Thr Tyr Ile Cys Pro Arg Asp Pro Ala
            340             345             350

Gln Leu Ile Pro Asp Ser Gln Gln Lys Cys Ile Leu Gly Asp Thr Thr
            355             360             365

Arg Cys Pro Val Thr Lys Val Val Asp Ser Leu Ile Pro Lys Phe Ala
        370             375             380

Phe Val Asn Gly Gly Val Val Ala Asn Cys Ile Ala Ser Thr Cys Thr
385             390             395             400

Cys Gly Thr Gly Arg Arg Pro Ile Ser Gln Asp Arg Ser Lys Gly Val
            405             410             415

Val Phe Leu Thr His Asp Asn Cys Gly Leu Ile Gly Val Asn Gly Val
            420             425             430

Glu Leu Tyr Ala Asn Arg Arg Gly His Asp Ala Thr Trp Gly Val Gln
            435             440             445

Asn Leu Thr Val Gly Pro Ala Ile Ala Ile Arg Pro Ile Asp Ile Ser
        450             455             460

Leu Asn Leu Ala Asp Ala Thr Asn Phe Leu Gln Asp Ser Lys Ala Glu
465             470             475             480

Leu Glu Lys Ala Arg Lys Ile Leu Ser Glu Val Gly Arg Trp Tyr Asn
            485             490             495

Ser Arg Glu Thr Val Ile Thr Ile Ile Val Val Met Val Val Ile Leu
```

-continued

```
                500                 505                 510

Val Val Ile Ile Val Ile Ile Ile Val Leu Tyr Arg Leu Arg Arg Ser
            515                 520                 525

Met Leu Met Gly Asn Pro Asp Asp Arg Ile Pro Arg Asp Thr Tyr Thr
        530                 535                 540

Leu Glu Pro Lys Ile Arg His Met Tyr Thr Asn Gly Gly Phe Asp Ala
545                 550                 555                 560

Met Ala Lys Glu Arg
                565

<210> SEQ ID NO 88
<211> LENGTH: 540
<212> TYPE: PRT
<213> ORGANISM: Sendai virus

<400> SEQUENCE: 88

Gln Ile Pro Arg Asp Arg Leu Ser Asn Ile Gly Val Ile Val Asp Glu
1               5                   10                  15

Gly Lys Ser Leu Lys Ile Ala Gly Ser His Glu Ser Arg Tyr Ile Val
            20                  25                  30

Leu Ser Leu Val Pro Gly Val Asp Phe Glu Asn Gly Cys Gly Thr Ala
            35                  40                  45

Gln Val Ile Gln Tyr Lys Ser Leu Leu Asn Arg Leu Leu Ile Pro Leu
        50                  55                  60

Arg Asp Ala Leu Asp Leu Gln Glu Ala Leu Ile Thr Val Thr Asn Asp
65                  70                  75                  80

Thr Thr Gln Asn Ala Gly Ala Pro Gln Ser Arg Phe Phe Gly Ala Val
                85                  90                  95

Ile Gly Thr Ile Ala Leu Gly Val Ala Thr Ser Ala Gln Ile Thr Ala
            100                 105                 110

Gly Ile Ala Leu Ala Glu Ala Arg Glu Ala Lys Arg Asp Ile Ala Leu
        115                 120                 125

Ile Lys Glu Ser Met Thr Lys Thr His Lys Ser Ile Glu Leu Leu Gln
        130                 135                 140

Asn Ala Val Gly Glu Gln Ile Leu Ala Leu Lys Thr Leu Gln Asp Phe
145                 150                 155                 160

Val Asn Asp Glu Ile Lys Pro Ala Ile Ser Glu Leu Gly Cys Glu Thr
                165                 170                 175

Ala Ala Leu Arg Leu Gly Ile Lys Leu Thr Gln His Tyr Ser Glu Leu
            180                 185                 190

Leu Thr Ala Phe Gly Ser Asn Phe Gly Thr Ile Gly Glu Lys Ser Leu
            195                 200                 205

Thr Leu Gln Ala Leu Ser Ser Leu Tyr Ser Ala Asn Ile Thr Glu Ile
        210                 215                 220

Met Thr Thr Ile Lys Thr Gly Gln Ser Asn Ile Tyr Asp Val Ile Tyr
225                 230                 235                 240

Thr Glu Gln Ile Lys Gly Thr Val Ile Asp Val Asp Leu Glu Arg Tyr
                245                 250                 255

Met Val Thr Leu Ser Val Lys Ile Pro Ile Leu Ser Glu Val Pro Gly
            260                 265                 270

Val Leu Ile His Lys Ala Ser Ser Ile Ser Tyr Asn Ile Asp Gly Glu
            275                 280                 285

Glu Trp Tyr Val Thr Val Pro Ser His Ile Leu Ser Arg Ala Ser Phe
        290                 295                 300
```

-continued

```
Leu Gly Gly Ala Asp Ile Thr Asp Cys Val Glu Ser Arg Leu Thr Tyr
305             310             315             320

Ile Cys Pro Arg Asp Pro Ala Gln Leu Ile Pro Asp Ser Gln Gln Lys
            325             330             335

Cys Ile Leu Gly Asp Thr Thr Arg Cys Pro Val Thr Lys Val Val Asp
            340             345             350

Ser Leu Ile Pro Lys Phe Ala Phe Val Asn Gly Gly Val Val Ala Asn
            355             360             365

Cys Ile Ala Ser Thr Cys Thr Cys Gly Thr Gly Arg Arg Pro Ile Ser
            370             375             380

Gln Asp Arg Ser Lys Gly Val Val Phe Leu Thr His Asp Asn Cys Gly
385             390             395             400

Leu Ile Gly Val Asn Gly Val Glu Leu Tyr Ala Asn Arg Arg Gly His
            405             410             415

Asp Ala Thr Trp Gly Val Gln Asn Leu Thr Val Gly Pro Ala Ile Ala
            420             425             430

Ile Arg Pro Ile Asp Ile Ser Leu Asn Leu Ala Asp Ala Thr Asn Phe
            435             440             445

Leu Gln Asp Ser Lys Ala Glu Leu Glu Lys Ala Arg Lys Ile Leu Ser
            450             455             460

Glu Val Gly Arg Trp Tyr Asn Ser Arg Glu Thr Val Ile Thr Ile Ile
465             470             475             480

Val Val Met Val Val Ile Leu Val Val Ile Ile Val Ile Ile Ile Val
            485             490             495

Leu Tyr Arg Leu Arg Arg Ser Met Leu Met Gly Asn Pro Asp Asp Arg
            500             505             510

Ile Pro Arg Asp Thr Tyr Thr Leu Glu Pro Lys Ile Arg His Met Tyr
            515             520             525

Thr Asn Gly Gly Phe Asp Ala Met Ala Glu Lys Arg
            530             535             540
```

<210> SEQ ID NO 89
<211> LENGTH: 91
<212> TYPE: PRT
<213> ORGANISM: Sendai virus

<400> SEQUENCE: 89

```
Gln Ile Pro Arg Asp Arg Leu Ser Asn Ile Gly Val Ile Val Asp Glu
1               5               10              15

Gly Lys Ser Leu Lys Ile Ala Gly Ser His Glu Ser Arg Tyr Ile Val
            20              25              30

Leu Ser Leu Val Pro Gly Val Asp Phe Glu Asn Gly Cys Gly Thr Ala
            35              40              45

Gln Val Ile Gln Tyr Lys Ser Leu Leu Asn Arg Leu Leu Ile Pro Leu
            50              55              60

Arg Asp Ala Leu Asp Leu Gln Glu Ala Leu Ile Thr Val Thr Asn Asp
65              70              75              80

Thr Thr Gln Asn Ala Gly Ala Pro Gln Ser Arg
            85              90
```

<210> SEQ ID NO 90
<211> LENGTH: 449
<212> TYPE: PRT
<213> ORGANISM: Sendai virus

<400> SEQUENCE: 90

```
Phe Phe Gly Ala Val Ile Gly Thr Ile Ala Leu Gly Val Ala Thr Ser
1               5                   10                  15

Ala Gln Ile Thr Ala Gly Ile Ala Leu Ala Glu Ala Arg Glu Ala Lys
            20                  25                  30

Arg Asp Ile Ala Leu Ile Lys Glu Ser Met Thr Lys Thr His Lys Ser
        35                  40                  45

Ile Glu Leu Leu Gln Asn Ala Val Gly Glu Gln Ile Leu Ala Leu Lys
    50                  55                  60

Thr Leu Gln Asp Phe Val Asn Asp Glu Ile Lys Pro Ala Ile Ser Glu
65                  70                  75                  80

Leu Gly Cys Glu Thr Ala Ala Leu Arg Leu Gly Ile Lys Leu Thr Gln
                85                  90                  95

His Tyr Ser Glu Leu Leu Thr Ala Phe Gly Ser Asn Phe Gly Thr Ile
            100                 105                 110

Gly Glu Lys Ser Leu Thr Leu Gln Ala Leu Ser Ser Leu Tyr Ser Ala
            115                 120                 125

Asn Ile Thr Glu Ile Met Thr Thr Ile Lys Thr Gly Gln Ser Asn Ile
    130                 135                 140

Tyr Asp Val Ile Tyr Thr Glu Gln Ile Lys Gly Thr Val Ile Asp Val
145                 150                 155                 160

Asp Leu Glu Arg Tyr Met Val Thr Leu Ser Val Lys Ile Pro Ile Leu
                165                 170                 175

Ser Glu Val Pro Gly Val Leu Ile His Lys Ala Ser Ser Ile Ser Tyr
            180                 185                 190

Asn Ile Asp Gly Glu Glu Trp Tyr Val Thr Val Pro Ser His Ile Leu
            195                 200                 205

Ser Arg Ala Ser Phe Leu Gly Gly Ala Asp Ile Thr Asp Cys Val Glu
    210                 215                 220

Ser Arg Leu Thr Tyr Ile Cys Pro Arg Asp Pro Ala Gln Leu Ile Pro
225                 230                 235                 240

Asp Ser Gln Gln Lys Cys Ile Leu Gly Asp Thr Thr Arg Cys Pro Val
                245                 250                 255

Thr Lys Val Val Asp Ser Leu Ile Pro Lys Phe Ala Phe Val Asn Gly
                260                 265                 270

Gly Val Val Ala Asn Cys Ile Ala Ser Thr Cys Thr Cys Gly Thr Gly
            275                 280                 285

Arg Arg Pro Ile Ser Gln Asp Arg Ser Lys Gly Val Val Phe Leu Thr
    290                 295                 300

His Asp Asn Cys Gly Leu Ile Gly Val Asn Gly Val Glu Leu Tyr Ala
305                 310                 315                 320

Asn Arg Arg Gly His Asp Ala Thr Trp Gly Val Gln Asn Leu Thr Val
            325                 330                 335

Gly Pro Ala Ile Ala Ile Arg Pro Ile Asp Ile Ser Leu Asn Leu Ala
            340                 345                 350

Asp Ala Thr Asn Phe Leu Gln Asp Ser Lys Ala Glu Leu Glu Lys Ala
            355                 360                 365

Arg Lys Ile Leu Ser Glu Val Gly Arg Trp Tyr Asn Ser Arg Glu Thr
    370                 375                 380

Val Ile Thr Ile Ile Val Val Met Val Val Ile Leu Val Val Ile Ile
385                 390                 395                 400

Val Ile Ile Ile Val Leu Tyr Arg Leu Arg Arg Ser Met Leu Met Gly
                405                 410                 415

Asn Pro Asp Asp Arg Ile Pro Arg Asp Thr Tyr Thr Leu Glu Pro Lys
```

-continued

```
                  420                 425                 430
Ile Arg His Met Tyr Thr Asn Gly Gly Phe Asp Ala Met Ala Lys Glu
          435                 440                 445

Arg

<210> SEQ ID NO 91
<211> LENGTH: 575
<212> TYPE: PRT
<213> ORGANISM: Sendai virus

<400> SEQUENCE: 91

Met Asp Gly Asp Arg Ser Lys Arg Asp Ser Tyr Trp Ser Thr Ser Pro
1               5                   10                  15

Gly Gly Ser Thr Thr Lys Leu Val Ser Asp Ser Glu Arg Ser Gly Lys
                20                  25                  30

Val Asp Thr Trp Leu Leu Ile Leu Ala Phe Thr Gln Trp Ala Leu Ser
            35                  40                  45

Ile Ala Thr Val Ile Ile Cys Ile Val Ile Ala Ala Arg Gln Gly Tyr
        50                  55                  60

Ser Met Glu Arg Tyr Ser Met Thr Val Glu Ala Leu Asn Thr Ser Asn
65                  70                  75                  80

Lys Glu Val Lys Glu Ser Leu Thr Ser Leu Ile Arg Gln Glu Val Ile
                85                  90                  95

Thr Arg Ala Ala Asn Ile Gln Ser Ser Val Gln Thr Gly Ile Pro Val
            100                 105                 110

Leu Leu Asn Lys Asn Ser Arg Asp Val Ile Arg Leu Ile Glu Lys Ser
            115                 120                 125

Cys Asn Arg Gln Glu Leu Thr Gln Leu Cys Asp Ser Thr Ile Ala Val
        130                 135                 140

His His Ala Glu Gly Ile Ala Pro Leu Glu Pro His Ser Phe Trp Arg
145                 150                 155                 160

Cys Pro Ala Gly Glu Pro Tyr Leu Ser Ser Asp Pro Glu Val Ser Leu
                165                 170                 175

Leu Pro Gly Pro Ser Leu Leu Ser Gly Ser Thr Thr Ile Ser Gly Cys
            180                 185                 190

Val Arg Leu Pro Ser Leu Ser Ile Gly Glu Ala Ile Tyr Ala Tyr Ser
            195                 200                 205

Ser Asn Leu Ile Thr Gln Gly Cys Ala Asp Ile Gly Lys Ser Tyr Gln
        210                 215                 220

Val Leu Gln Leu Gly Tyr Ile Ser Leu Asn Ser Asp Met Phe Pro Asp
225                 230                 235                 240

Leu Asn Pro Val Val Ser His Thr Tyr Asp Ile Asn Asp Asn Arg Lys
            245                 250                 255

Ser Cys Ser Val Val Ala Thr Gly Thr Arg Gly Tyr Gln Leu Cys Ser
            260                 265                 270

Met Pro Ile Val Asp Glu Arg Thr Asp Tyr Ser Ser Asp Gly Ile Glu
        275                 280                 285

Asp Leu Val Leu Asp Ile Leu Asp Leu Lys Gly Arg Thr Lys Ser His
        290                 295                 300

Arg Tyr Ser Asn Ser Glu Ile Asp Leu Asp His Pro Phe Ser Ala Leu
305                 310                 315                 320

Tyr Pro Ser Val Gly Ser Gly Ile Ala Thr Glu Gly Ser Leu Ile Phe
            325                 330                 335

Leu Gly Tyr Gly Gly Leu Thr Thr Pro Leu Gln Gly Asp Thr Lys Cys
```

-continued

```
               340              345              350
Arg Ile Gln Gly Cys Gln Gln Val Ser Gln Asp Thr Cys Asn Glu Ala
        355              360              365
Leu Lys Ile Thr Trp Leu Gly Gly Lys Gln Val Val Ser Val Leu Ile
        370              375              380
Gln Val Asn Asp Tyr Leu Ser Glu Arg Pro Arg Ile Arg Val Thr Thr
385              390              395              400
Ile Pro Ile Thr Gln Asn Tyr Leu Gly Ala Glu Gly Arg Leu Leu Lys
                405              410              415
Leu Gly Asp Gln Val Tyr Ile Tyr Thr Arg Ser Ser Gly Trp His Ser
                420              425              430
Gln Leu Gln Ile Gly Val Leu Asp Val Ser His Pro Leu Thr Ile Ser
        435              440              445
Trp Thr Pro His Glu Ala Leu Ser Arg Pro Gly Asn Glu Asp Cys Asn
        450              455              460
Trp Tyr Asn Thr Cys Pro Lys Glu Cys Ile Ser Gly Val Tyr Thr Asp
465              470              475              480
Ala Tyr Pro Leu Ser Pro Asp Ala Ala Asn Val Ala Thr Val Thr Leu
                485              490              495
Tyr Ala Asn Thr Ser Arg Val Asn Pro Thr Ile Met Tyr Ser Asn Thr
                500              505              510
Thr Asn Ile Ile Asn Met Leu Arg Ile Lys Asp Val Gln Leu Glu Ala
                515              520              525
Ala Tyr Thr Thr Thr Ser Cys Ile Thr His Phe Gly Lys Gly Tyr Cys
        530              535              540
Phe His Ile Ile Glu Ile Asn Gln Lys Ser Leu Asn Thr Leu Gln Pro
545              550              555              560
Met Leu Phe Lys Thr Ser Ile Pro Lys Leu Cys Lys Ala Glu Ser
                565              570              575
```

```
<210> SEQ ID NO 92
<211> LENGTH: 611
<212> TYPE: PRT
<213> ORGANISM: Jaagsiekte sheep retrovirus

<400> SEQUENCE: 92
```

```
Met Pro Lys Arg Arg Ala Gly Phe Arg Lys Gly Trp Tyr Ala Arg Gln
1               5               10              15
Arg Asn Ser Leu Thr His Gln Met Gln Arg Met Thr Leu Ser Glu Pro
                20              25              30
Thr Ser Glu Leu Pro Thr Gln Arg Gln Ile Glu Ala Leu Met Arg Tyr
                35              40              45
Ala Trp Asn Glu Ala His Val Gln Pro Pro Val Thr Pro Thr Asn Ile
        50              55              60
Leu Ile Met Leu Leu Leu Leu Leu Gln Arg Ile Gln Asn Gly Ala Ala
65              70              75              80
Ala Thr Phe Trp Ala Tyr Ile Pro Asp Pro Pro Met Leu Gln Ser Leu
                85              90              95
Gly Trp Asp Lys Glu Thr Val Pro Val Tyr Val Asn Asp Thr Ser Leu
                100             105             110
Leu Gly Gly Lys Ser Asp Ile His Ile Ser Pro Gln Gln Ala Asn Ile
                115             120             125
Ser Phe Tyr Gly Leu Thr Thr Gln Tyr Pro Met Cys Phe Ser Tyr Gln
        130             135             140
```

-continued

```
Ser Gln His Pro His Cys Ile Gln Val Ser Ala Asp Ile Ser Tyr Pro
145             150             155             160

Arg Val Thr Ile Ser Gly Ile Asp Glu Lys Thr Gly Met Arg Ser Tyr
                165             170             175

Arg Asp Gly Thr Gly Pro Leu Asp Ile Pro Phe Cys Asp Lys His Leu
            180             185             190

Ser Ile Gly Ile Gly Ile Asp Thr Pro Trp Thr Leu Cys Arg Ala Arg
            195             200             205

Ile Ala Ser Val Tyr Asn Ile Asn Asn Ala Asn Thr Thr Leu Leu Trp
    210             215             220

Asp Trp Ala Pro Gly Gly Thr Pro Asp Phe Pro Glu Tyr Arg Gly Gln
225             230             235             240

His Pro Pro Ile Ser Ser Val Asn Thr Ala Pro Ile Tyr Gln Thr Glu
                245             250             255

Leu Trp Lys Leu Leu Ala Ala Phe Gly His Gly Asn Ser Leu Tyr Leu
                260             265             270

Gln Pro Asn Ile Ser Gly Ser Lys Tyr Gly Asp Val Gly Val Thr Gly
            275             280             285

Phe Leu Tyr Pro Arg Ala Cys Val Pro Tyr Pro Phe Met Val Ile Gln
    290             295             300

Gly His Met Glu Ile Thr Pro Ser Leu Asn Ile Tyr Tyr Leu Asn Cys
305             310             315             320

Ser Asn Cys Ile Leu Thr Asn Cys Ile Arg Gly Val Ala Lys Gly Glu
                325             330             335

Gln Val Ile Ile Val Lys Gln Pro Ala Phe Val Met Leu Pro Val Glu
            340             345             350

Ile Thr Glu Glu Trp Tyr Asp Glu Thr Ala Leu Glu Leu Leu Gln Arg
            355             360             365

Ile Asn Thr Ala Leu Ser Arg Pro Lys Arg Gly Leu Ser Leu Ile Ile
    370             375             380

Leu Gly Ile Val Ser Leu Ile Thr Leu Ile Ala Thr Ala Val Thr Ala
385             390             395             400

Ser Val Ser Leu Ala Gln Ser Ile Gln Val Ala His Thr Val Asp Ser
                405             410             415

Leu Ser Ser Asn Val Thr Lys Val Met Gly Thr Gln Glu Asn Ile Asp
                420             425             430

Lys Lys Ile Glu Asp Arg Leu Pro Ala Leu Tyr Asp Val Val Arg Val
            435             440             445

Leu Gly Glu Gln Val Gln Ser Ile Asn Phe Arg Met Lys Ile Gln Cys
    450             455             460

His Ala Asn Tyr Lys Trp Ile Cys Val Thr Lys Lys Pro Tyr Asn Thr
465             470             475             480

Ser Asp Phe Pro Trp Asp Lys Val Lys Lys His Leu Gln Gly Ile Trp
                485             490             495

Phe Asn Thr Thr Val Ser Leu Asp Leu Leu Gln Leu His Asn Glu Ile
            500             505             510

Leu Asp Ile Glu Asn Ser Pro Lys Ala Thr Leu Asn Ile Ala Asp Thr
            515             520             525

Val Asp Asn Phe Leu Gln Asn Leu Phe Ser Asn Phe Pro Ser Leu His
    530             535             540

Ser Leu Trp Arg Ser Ile Ile Ala Met Gly Ala Val Leu Thr Phe Val
545             550             555             560

Leu Ile Ile Ile Cys Leu Ala Pro Cys Leu Ile Arg Ser Ile Val Lys
```

-continued

```
                   565                 570                 575
Glu Phe Leu His Met Arg Val Leu Ile His Lys Asn Met Leu Gln His
            580                 585                 590

Gln His Leu Met Glu Leu Leu Asn Asn Lys Glu Arg Gly Ala Ala Gly
        595                 600                 605

Asp Asp Pro
    610

<210> SEQ ID NO 93
<211> LENGTH: 505
<212> TYPE: PRT
<213> ORGANISM: Baculovirus

<400> SEQUENCE: 93

Met Phe His Leu Leu Thr Leu Leu Leu Leu Phe Ile Asn Met Asn
1               5                   10                  15

Leu Tyr Leu Ala Gly Glu His Cys Asn Val Gln Met Lys Asn Gly Pro
            20                  25                  30

Tyr Arg Ile Lys Asn Leu Ala Ile Thr Pro Pro Arg Glu Thr Leu Lys
        35                  40                  45

Lys Asp Val Thr Val Thr Ile Val Glu Thr Asp Tyr Glu Glu Asn Val
    50                  55                  60

Leu Ile Gly Tyr Lys Gly Tyr Tyr Gln Ala Tyr Gly Tyr Asn Gly Gly
65                  70                  75                  80

Ser Leu Asp Ala Asn Thr Arg Leu Glu Glu Thr Met Glu Ser Leu Pro
            85                  90                  95

Leu Thr Lys Glu Asp Leu Leu Thr Trp Thr Tyr Arg Gln Glu Cys Glu
            100                 105                 110

Val Gly Glu Glu Leu Ile Asp Arg Trp Gly Ser Asp Ser Asp Asp Cys
        115                 120                 125

Tyr Arg Asn Lys Asp Gly Arg Gly Val Trp Val Lys Thr Lys Glu Leu
    130                 135                 140

Val Lys Arg Gln Asn Asn Asn His Phe Ala His His Thr Cys Asn Arg
145                 150                 155                 160

Ser Trp Arg Cys Gly Phe Ser Thr Ala Lys Met Tyr Ser Lys Leu Val
            165                 170                 175

Cys Asp Asp Glu Thr Asn Asp Cys Lys Val Phe Ile Leu Asp Asn Thr
            180                 185                 190

Gly Lys Pro Ile Asn Ile Thr Thr Asn Glu Val Leu Tyr Arg Asp Gly
        195                 200                 205

Val Asn Met Met Leu Lys Ser Lys Pro Thr Phe Thr Arg Arg Glu Glu
    210                 215                 220

Lys Val Ala Cys Leu Leu Val Lys Asp Glu Leu Asn Pro Asp Lys Thr
225                 230                 235                 240

Arg Glu His Cys Leu Ile Asp Ser Asp Ile Tyr Asp Leu Ser Asn Asn
            245                 250                 255

Asn Trp Phe Cys Met Phe Asn Lys Cys Ile Lys Arg Asn Val Asp Ser
            260                 265                 270

Val Val Lys Lys Arg Pro Asn Lys Trp Met His Asn Leu Ala Pro Lys
        275                 280                 285

Tyr Ser Glu Gly Ala Thr Ala Thr Lys Gly Asp Met Met His Ile Gln
    290                 295                 300

Glu Glu Leu Met Tyr Glu Asn Asp Leu Leu Lys Met Asn Ile Glu Leu
305                 310                 315                 320
```

```
Val His Ala His Met Asn Lys Leu Asn Asn Ile Ile His Asp Leu Ile
             325                 330                 335

Val Ser Ile Ala Lys Val Asp Glu Arg Leu Ile Gly Asn Leu Met Asn
             340                 345                 350

Ile Ser Val Ser Ser Val Phe Leu Ser Asp Asp Thr Phe Leu Leu Met
             355                 360                 365

Pro Cys Thr Asn Pro Pro Gln His Thr Ser Asn Cys Tyr Asn Asn Ser
     370                 375                 380

Ile Tyr Arg Glu Gly Arg Trp Val Phe Asn Glu Asp Thr Ser Glu Cys
385                 390                 395                 400

Ile Asp Phe Asn Asn Tyr Arg Glu Leu Ser Ile Asp Asp Asp Ile Glu
             405                 410                 415

Phe Trp Ile Pro Thr Ile Gly Asn Thr Thr Tyr His Asp Ser Trp Lys
             420                 425                 430

Asp Ala Ser Gly Trp Ser Phe Val Ala Gln Gln Lys Ser Asn Leu Ile
             435                 440                 445

Met Thr Met Glu Asn Thr Lys Phe Gly Gly Val Gly Thr Ser Leu Ser
     450                 455                 460

Asp Ile Thr Ser Met Ser Glu Gly Glu Leu Thr Ala Lys Leu Thr Thr
465                 470                 475                 480

Phe Val Phe Ser His Ile Val Thr Phe Ile Leu Ile Ile Leu Ile
             485                 490                 495

Ile Leu Cys Ile Cys Leu Leu Lys Lys
             500                 505

<210> SEQ ID NO 94
<211> LENGTH: 509
<212> TYPE: PRT
<213> ORGANISM: Baculovirus

<400> SEQUENCE: 94

Met Leu Arg Ile Thr Leu Leu Ile Leu Phe Leu Val Arg Phe Val Ser
1               5                   10                  15

Gly Ala Glu His Cys Asn Ala Gln Met Lys Ser Gly Pro Trp Arg Ile
             20                  25                  30

Lys Asn Leu Pro Ile Ala Pro Pro Lys Glu Thr Leu Gln Lys Asp Val
             35                  40                  45

Asp Val Glu Ile Val Glu Thr Asp Leu Asp Glu Asn Val Ile Ile Gly
     50                  55                  60

Tyr Lys Gly Tyr Tyr Gln Ala Tyr Ala Tyr Asn Gly Gly Ser Leu Asp
65                  70                  75                  80

Pro Asn Thr Ser Val Asp Glu Thr Thr Gln Thr Leu Asn Ile Asp Lys
             85                  90                  95

Asp Asp Leu Ile Thr Trp Gly Asp Arg Arg Lys Cys Glu Val Gly Glu
             100                 105                 110

Glu Leu Ile Asp Gln Trp Gly Ser Asp Ser Asp Ser Cys Phe Lys Asp
             115                 120                 125

Lys Leu Gly Arg Gly Val Trp Val Ala Gly Lys Glu Leu Val Lys Arg
     130                 135                 140

Lys Asn Asn Asn His Phe Ala His His Thr Cys Asn Arg Ser Trp Arg
145                 150                 155                 160

Cys Gly Val Ser Thr Ala Lys Met Tyr Thr Arg Leu Glu Cys Asp Asn
             165                 170                 175

Glu Thr Asp Asp Cys Lys Val Thr Ile Leu Asp Ile Asn Gly Thr Val
             180                 185                 190
```

```
Ile Asn Val Thr Glu Asn Glu Val Leu His Arg Asp Gly Val Ser Met
        195                 200                 205

Ile Leu Lys Gln Lys Ser Thr Phe Thr Arg Arg Thr Glu Lys Val Ala
        210                 215                 220

Cys Leu Leu Ile Lys Asp Asp Lys Ser Asp Pro Tyr Ser Ile Thr Arg
225                 230                 235                 240

Glu His Cys Leu Ile Asp Asn Asp Ile Phe Asp Leu Ser Lys Asn Thr
                245                 250                 255

Trp Asn Cys Lys Phe Asn Arg Cys Ile Lys Arg Arg Ser Glu Asn Val
                260                 265                 270

Val Lys Lys Arg Pro Pro Thr Trp Arg His Asn Glu Pro Pro Lys His
        275                 280                 285

Ser Glu Gly Thr Thr Ala Thr Lys Gly Asp Leu Met His Ile Gln Glu
        290                 295                 300

Glu Leu Met Tyr Glu Asn Asp Leu Leu Arg Met Asn Leu Glu Leu Leu
305                 310                 315                 320

His Ala His Ile Asn Lys Leu Asn Asn Met Met His Asp Leu Ile Val
                325                 330                 335

Ser Val Ala Lys Val Asp Glu Arg Leu Ile Gly Asn Leu Met Asn Asn
                340                 345                 350

Ser Val Ser Ser Thr Phe Leu Ser Asp Asp Thr Phe Leu Leu Met Pro
        355                 360                 365

Cys Thr Asn Pro Pro Pro His Thr Ser Asn Cys Tyr Asn Asn Ser Ile
        370                 375                 380

Tyr Lys Glu Gly Arg Trp Val Ala Asn Thr Asp Ser Ser Gln Cys Ile
385                 390                 395                 400

Asp Phe Arg Asn Tyr Lys Glu Leu Ala Ile Asp Asp Asp Ile Glu Phe
                405                 410                 415

Trp Ile Pro Thr Ile Gly Asn Thr Ser Tyr His Glu Ser Trp Lys Asp
                420                 425                 430

Ala Ser Gly Trp Ser Phe Ile Ala Gln Gln Lys Ser Asn Leu Ile Ser
        435                 440                 445

Thr Met Glu Asn Thr Lys Phe Gly Gly His Thr Thr Ser Leu Ser Asp
        450                 455                 460

Ile Gly Asp Met Ala Lys Gly Glu Leu Asn Ala Thr Leu Tyr Ser Phe
465                 470                 475                 480

Met Leu Gly His Gly Phe Ser Phe Phe Leu Ile Ile Gly Val Ile Val
                485                 490                 495

Phe Leu Ile Cys Met Val Arg Ser Arg Val Arg Ala Phe
                500                 505
```

<210> SEQ ID NO 95
<211> LENGTH: 530
<212> TYPE: PRT
<213> ORGANISM: Chandipura virus
<400> SEQUENCE: 95

```
Met Thr Ser Ser Val Thr Ile Ser Val Ile Leu Leu Ile Ser Phe Ile
1               5                   10                  15

Ala Pro Ser Tyr Ser Ser Leu Ser Ile Ala Phe Pro Glu Asn Thr Lys
                20                  25                  30

Leu Asp Trp Lys Pro Val Thr Lys Asn Thr Arg Tyr Cys Pro Met Gly
        35                  40                  45

Gly Glu Trp Phe Leu Glu Pro Gly Leu Gln Glu Glu Ser Phe Leu Ser
```

-continued

```
        50                  55                  60

Ser Thr Pro Ile Gly Ala Thr Pro Ser Lys Ser Asp Gly Phe Leu Cys
65                  70                  75                  80

His Ala Ala Lys Trp Val Thr Thr Cys Asp Phe Arg Trp Tyr Gly Pro
                85                  90                  95

Lys Tyr Ile Thr His Ser Ile His Asn Ile Lys Pro Thr Arg Ser Asp
                100                 105                 110

Cys Asp Thr Ala Leu Ala Ser Tyr Lys Ser Gly Thr Leu Val Ser Pro
        115                 120                 125

Gly Phe Pro Pro Glu Ser Cys Gly Tyr Ala Ser Val Thr Asp Ser Glu
        130                 135                 140

Phe Leu Val Ile Met Ile Thr Pro His His Val Gly Val Asp Asp Tyr
145                 150                 155                 160

Arg Gly His Trp Val Asp Pro Leu Phe Val Gly Gly Glu Cys Asp Gln
                165                 170                 175

Ser Tyr Cys Asp Thr Ile His Asn Ser Ser Val Trp Ile Pro Ala Asp
                180                 185                 190

Gln Thr Lys Lys Asn Ile Cys Gly Gln Ser Phe Thr Pro Leu Thr Val
        195                 200                 205

Thr Val Ala Tyr Asp Lys Thr Lys Glu Ile Ala Ala Gly Ala Ile Val
        210                 215                 220

Phe Lys Ser Lys Tyr His Ser His Met Glu Gly Ala Arg Thr Cys Arg
225                 230                 235                 240

Leu Ser Tyr Cys Gly Arg Asn Gly Ile Lys Phe Pro Asn Gly Glu Trp
                245                 250                 255

Val Ser Leu Asp Val Lys Thr Lys Ile Gln Glu Lys Pro Leu Leu Pro
                260                 265                 270

Leu Phe Lys Glu Cys Pro Ala Gly Thr Glu Val Arg Ser Thr Leu Gln
        275                 280                 285

Ser Asp Gly Ala Gln Val Leu Thr Ser Glu Ile Gln Arg Ile Leu Asp
        290                 295                 300

Tyr Ser Leu Cys Gln Asn Thr Trp Asp Lys Val Glu Arg Lys Glu Pro
305                 310                 315                 320

Leu Ser Pro Leu Asp Leu Ser Tyr Leu Ala Ser Lys Ser Pro Gly Lys
                325                 330                 335

Gly Leu Ala Tyr Thr Val Ile Asn Gly Thr Leu Ser Phe Ala His Thr
                340                 345                 350

Arg Tyr Val Arg Met Trp Ile Asp Gly Pro Val Leu Lys Glu Met Lys
        355                 360                 365

Gly Lys Arg Glu Ser Pro Ser Gly Ile Ser Ser Asp Ile Trp Thr Gln
        370                 375                 380

Trp Phe Lys Tyr Gly Asp Met Glu Ile Gly Pro Asn Gly Leu Leu Lys
385                 390                 395                 400

Thr Ala Gly Gly Tyr Lys Phe Pro Trp His Leu Ile Gly Met Gly Ile
                405                 410                 415

Val Asp Asn Glu Leu His Glu Leu Ser Glu Ala Asn Pro Leu Asp His
                420                 425                 430

Pro Gln Leu Pro His Ala Gln Ser Ile Ala Asp Asp Ser Glu Glu Ile
        435                 440                 445

Phe Phe Gly Asp Thr Gly Val Ser Lys Asn Pro Val Glu Leu Val Thr
        450                 455                 460

Gly Trp Phe Thr Ser Trp Lys Glu Ser Leu Ala Ala Gly Val Val Leu
465                 470                 475                 480
```

-continued

```
Ile Leu Val Val Val Leu Ile Tyr Gly Val Leu Arg Cys Phe Pro Val
                485             490             495

Leu Cys Thr Thr Cys Arg Lys Pro Lys Trp Lys Lys Gly Val Glu Arg
            500             505             510

Ser Asp Ser Phe Glu Met Arg Ile Phe Lys Pro Asn Asn Met Arg Ala
        515             520             525

Arg Val
    530

<210> SEQ ID NO 96
<211> LENGTH: 1251
<212> TYPE: PRT
<213> ORGANISM: Venezuelan equine encephalitis virus

<400> SEQUENCE: 96

Met Phe Pro Phe Gln Pro Met Tyr Pro Met Gln Pro Met Pro Tyr Arg
1               5               10              15

Asn Pro Phe Ala Ala Pro Arg Arg Pro Trp Phe Pro Arg Thr Asp Pro
            20              25              30

Phe Leu Ala Met Gln Val Gln Glu Leu Thr Arg Ser Met Ala Asn Leu
        35              40              45

Thr Phe Lys Gln Arg Arg Asp Ala Pro Pro Glu Gly Pro Ser Ala Lys
    50              55              60

Lys Pro Lys Lys Glu Ala Ser Gln Lys Gln Lys Gly Gly Gly Gln Gly
65              70              75              80

Lys Lys Lys Lys Asn Gln Gly Lys Lys Lys Ala Lys Thr Gly Pro Pro
                85              90              95

Asn Pro Lys Ala Gln Asn Gly Asn Lys Lys Lys Thr Asn Lys Lys Pro
            100             105             110

Gly Lys Arg Gln Arg Met Val Met Lys Leu Glu Ser Asp Lys Thr Phe
        115             120             125

Pro Ile Met Leu Glu Gly Lys Ile Asn Gly Tyr Ala Cys Val Val Gly
    130             135             140

Gly Lys Leu Phe Arg Pro Met His Val Glu Gly Lys Ile Asp Asn Asp
145             150             155             160

Val Leu Ala Ala Leu Lys Thr Lys Lys Ala Ser Lys Tyr Asp Leu Glu
            165             170             175

Tyr Ala Asp Val Pro Gln Asn Met Arg Ala Asp Thr Phe Lys Tyr Thr
        180             185             190

His Glu Lys Pro Gln Gly Tyr Tyr Ser Trp His His Gly Ala Val Gln
        195             200             205

Tyr Glu Asn Gly Arg Phe Thr Val Pro Lys Gly Val Gly Ala Lys Gly
    210             215             220

Asp Ser Gly Arg Pro Ile Leu Asp Asn Gln Gly Arg Val Val Ala Ile
225             230             235             240

Val Leu Gly Gly Val Asn Glu Gly Ser Arg Thr Ala Leu Ser Val Val
            245             250             255

Met Trp Asn Glu Lys Gly Val Thr Val Lys Tyr Thr Pro Glu Asn Cys
            260             265             270

Glu Gln Trp Ser Leu Val Thr Thr Met Cys Leu Leu Ala Asn Val Thr
        275             280             285

Phe Pro Cys Ala Gln Pro Pro Ile Cys Tyr Asp Arg Lys Pro Ala Glu
    290             295             300

Thr Leu Ala Met Leu Ser Val Asn Val Asp Asn Pro Gly Tyr Asp Glu
```

-continued

```
305                 310                 315                 320

Leu Leu Glu Ala Ala Val Lys Cys Pro Gly Ser Thr Glu Glu Leu Phe
            325                 330                 335

Lys Glu Tyr Lys Leu Thr Arg Pro Tyr Met Ala Arg Cys Ile Arg Cys
            340                 345                 350

Ala Val Gly Ser Cys His Ser Pro Ile Ala Ile Glu Ala Val Lys Ser
            355                 360                 365

Asp Gly His Asp Gly Tyr Val Arg Leu Gln Thr Ser Ser Gln Tyr Gly
            370                 375                 380

Leu Asp Ser Ser Gly Asn Leu Lys Gly Arg Thr Met Arg Tyr Asp Met
385                 390                 395                 400

His Gly Thr Ile Lys Glu Ile Pro Leu His Gln Val Ser Leu His Thr
                405                 410                 415

Ser Arg Pro Cys His Ile Val Asp Gly His Gly Tyr Phe Leu Leu Ala
                420                 425                 430

Arg Cys Pro Ala Gly Asp Ser Ile Thr Met Glu Phe Lys Lys Asp Ser
                435                 440                 445

Val Thr His Ser Cys Ser Val Pro Tyr Glu Val Lys Phe Asn Pro Val
        450                 455                 460

Gly Arg Glu Leu Tyr Thr His Pro Pro Glu His Gly Val Glu Gln Ala
465                 470                 475                 480

Cys Gln Val Tyr Ala His Asp Ala Gln Asn Arg Gly Ala Tyr Val Glu
                485                 490                 495

Met His Leu Pro Gly Ser Glu Val Asp Ser Ser Leu Val Ser Leu Ser
                500                 505                 510

Gly Ser Ser Val Thr Val Thr Pro Pro Val Gly Thr Ser Ala Leu Val
                515                 520                 525

Glu Cys Glu Cys Gly Gly Thr Lys Ile Ser Glu Thr Ile Asn Lys Thr
                530                 535                 540

Lys Gln Phe Ser Gln Cys Thr Lys Lys Glu Gln Cys Arg Ala Tyr Arg
545                 550                 555                 560

Leu Gln Asn Asp Lys Trp Val Tyr Ile Ser Asp Lys Leu Pro Lys Ala
                565                 570                 575

Ala Gly Ala Thr Leu Lys Gly Lys Leu His Val Pro Phe Leu Leu Ala
                580                 585                 590

Asp Gly Lys Cys Thr Val Pro Leu Ala Pro Glu Pro Met Ile Thr Phe
                595                 600                 605

Gly Phe Arg Ser Val Ser Leu Lys Leu His Pro Lys Asn Pro Thr Tyr
                610                 615                 620

Leu Thr Thr Arg Gln Leu Ala Asp Glu Pro His Tyr Thr His Glu Leu
625                 630                 635                 640

Ile Ser Glu Pro Ala Val Arg Asn Phe Thr Val Thr Gly Lys Gly Trp
                645                 650                 655

Glu Phe Val Trp Gly Asn His Pro Pro Lys Arg Phe Trp Ala Gln Glu
                660                 665                 670

Thr Ala Pro Gly Asn Pro His Gly Leu Pro His Glu Val Ile Thr His
                675                 680                 685

Tyr Tyr His Arg Tyr Pro Met Ser Thr Ile Leu Gly Leu Ser Ile Cys
                690                 695                 700

Ala Ala Ile Ala Thr Val Ser Val Ala Ala Ser Thr Trp Leu Phe Cys
705                 710                 715                 720

Arg Ser Arg Val Ala Cys Leu Thr Pro Tyr Arg Leu Thr Pro Asn Ala
                725                 730                 735
```

-continued

```
Arg Ile Pro Phe Cys Leu Ala Val Leu Cys Cys Ala Arg Thr Ala Arg
        740                 745                 750

Ala Glu Thr Thr Trp Glu Ser Leu Asp His Leu Trp Asn Asn Asn Gln
        755                 760                 765

Gln Met Phe Trp Ile Gln Leu Leu Ile Pro Leu Ala Ala Leu Ile Val
        770                 775                 780

Val Thr Arg Leu Leu Arg Cys Val Cys Cys Val Val Pro Phe Leu Val
785                 790                 795                 800

Met Ala Gly Ala Ala Gly Ala Gly Ala Tyr Glu His Ala Thr Thr Met
                805                 810                 815

Pro Ser Gln Ala Gly Ile Ser Tyr Asn Thr Ile Val Asn Arg Ala Gly
                820                 825                 830

Tyr Ala Pro Leu Pro Ile Ser Ile Thr Pro Thr Lys Ile Lys Leu Ile
        835                 840                 845

Pro Thr Val Asn Leu Glu Tyr Val Thr Cys His Tyr Lys Thr Gly Met
        850                 855                 860

Asp Ser Pro Ala Ile Lys Cys Cys Gly Ser Gln Glu Cys Thr Pro Thr
865                 870                 875                 880

Tyr Arg Pro Asp Glu Gln Cys Lys Val Phe Thr Gly Val Tyr Pro Phe
                885                 890                 895

Met Trp Gly Gly Ala Tyr Cys Phe Cys Asp Thr Glu Asn Thr Gln Val
                900                 905                 910

Ser Lys Ala Tyr Val Met Lys Ser Asp Asp Cys Leu Ala Asp His Ala
        915                 920                 925

Glu Ala Tyr Lys Ala His Thr Ala Ser Val Gln Ala Phe Leu Asn Ile
        930                 935                 940

Thr Val Gly Glu His Ser Ile Val Thr Thr Val Tyr Val Asn Gly Glu
945                 950                 955                 960

Thr Pro Val Asn Phe Asn Gly Val Lys Leu Thr Ala Gly Pro Leu Ser
                965                 970                 975

Thr Ala Trp Thr Pro Phe Asp Arg Lys Ile Val Gln Tyr Ala Gly Glu
                980                 985                 990

Ile Tyr Asn Tyr Asp Phe Pro Glu  Tyr Gly Ala Gly Gln  Pro Gly Ala
        995                 1000                1005

Phe Gly  Asp Ile Gln Ser Arg  Thr Val Ser Ser Ser  Asp Leu Tyr
    1010                1015                1020

Ala Asn  Thr Asn Leu Val Leu  Gln Arg Pro Lys Ala  Gly Ala Ile
    1025                1030                1035

His Val  Pro Tyr Thr Gln Ala  Pro Ser Gly Phe Glu  Gln Trp Lys
    1040                1045                1050

Lys Asp  Lys Ala Pro Ser Leu  Lys Ser Thr Ala Pro  Phe Gly Cys
    1055                1060                1065

Glu Ile  Tyr Thr Asn Pro Ile  Arg Ala Glu Asn Cys  Ala Val Gly
    1070                1075                1080

Ser Ile  Pro Leu Ala Phe Asp  Ile Pro Asp Ala Leu  Phe Thr Arg
    1085                1090                1095

Val Ser  Glu Thr Pro Thr Leu  Ser Ala Ala Glu Cys  Thr Leu Asn
    1100                1105                1110

Glu Cys  Val Tyr Ser Ser Asp  Phe Gly Gly Ile Ala  Thr Val Lys
    1115                1120                1125

Tyr Ser  Ala Ser Lys Ser Gly  Lys Cys Ala Val His  Val Pro Ser
    1130                1135                1140
```

-continued

```
Gly Thr  Ala Thr Leu Lys Glu  Ala Ala Val Glu Leu  Thr Glu Gln
    1145             1150             1155

Gly Ser  Ala Thr Ile His Phe  Ser Thr Ala Asn Ile  His Pro Glu
    1160             1165             1170

Phe Arg  Leu Gln Ile Cys Thr  Ser Tyr Val Thr Cys  Lys Gly Asp
    1175             1180             1185

Cys His  Pro Pro Lys Asp His  Ile Val Thr His Pro  Gln Tyr His
    1190             1195             1200

Ala Gln  Thr Phe Thr Ala Ala  Val Ser Lys Thr Ala  Trp Thr Trp
    1205             1210             1215

Leu Thr  Ser Leu Leu Gly Gly  Ser Ala Val Ile Ile  Ile Ile Gly
    1220             1225             1230

Leu Val  Leu Ala Thr Ile Val  Ala Met Tyr Val Leu  Thr Asn Gln
    1235             1240             1245

Lys His  Asn
    1250

<210> SEQ ID NO 97
<211> LENGTH: 423
<212> TYPE: PRT
<213> ORGANISM: Venezuelan equine encephalitis virus

<400> SEQUENCE: 97

Ser Thr Glu Glu Leu Phe Lys Glu Tyr Lys Leu Thr Arg Pro Tyr Met
1               5                   10                  15

Ala Arg Cys Ile Arg Cys Ala Val Gly Ser Cys His Ser Pro Ile Ala
            20                  25                  30

Ile Glu Ala Val Lys Ser Asp Gly His Asp Gly Tyr Val Arg Leu Gln
        35                  40                  45

Thr Ser Ser Gln Tyr Gly Leu Asp Ser Ser Gly Asn Leu Lys Gly Arg
    50                  55                  60

Thr Met Arg Tyr Asp Met His Gly Thr Ile Lys Glu Ile Pro Leu His
65                  70                  75                  80

Gln Val Ser Leu His Thr Ser Arg Pro Cys His Ile Val Asp Gly His
                85                  90                  95

Gly Tyr Phe Leu Leu Ala Arg Cys Pro Ala Gly Asp Ser Ile Thr Met
            100                 105                 110

Glu Phe Lys Lys Asp Ser Val Thr His Ser Cys Ser Val Pro Tyr Glu
        115                 120                 125

Val Lys Phe Asn Pro Val Gly Arg Glu Leu Tyr Thr His Pro Pro Glu
    130                 135                 140

His Gly Val Glu Gln Ala Cys Gln Val Tyr Ala His Asp Ala Gln Asn
145                 150                 155                 160

Arg Gly Ala Tyr Val Glu Met His Leu Pro Gly Ser Glu Val Asp Ser
                165                 170                 175

Ser Leu Val Ser Leu Ser Gly Ser Ser Val Thr Val Thr Pro Pro Val
            180                 185                 190

Gly Thr Ser Ala Leu Val Glu Cys Glu Cys Gly Gly Thr Lys Ile Ser
        195                 200                 205

Glu Thr Ile Asn Lys Thr Lys Gln Phe Ser Gln Cys Thr Lys Lys Glu
    210                 215                 220

Gln Cys Arg Ala Tyr Arg Leu Gln Asn Asp Lys Trp Val Tyr Ile Ser
225                 230                 235                 240

Asp Lys Leu Pro Lys Ala Ala Gly Ala Thr Leu Lys Gly Lys Leu His
            245                 250                 255
```

-continued

```
Val Pro Phe Leu Leu Ala Asp Gly Lys Cys Thr Val Pro Leu Ala Pro
            260                 265             270

Glu Pro Met Ile Thr Phe Gly Phe Arg Ser Val Ser Leu Lys Leu His
            275                 280             285

Pro Lys Asn Pro Thr Tyr Leu Thr Thr Arg Gln Leu Ala Asp Glu Pro
            290                 295             300

His Tyr Thr His Glu Leu Ile Ser Glu Pro Ala Val Arg Asn Phe Thr
305                 310                 315                 320

Val Thr Gly Lys Gly Trp Glu Phe Val Trp Gly Asn His Pro Pro Lys
                325                 330                 335

Arg Phe Trp Ala Gln Glu Thr Ala Pro Gly Asn Pro His Gly Leu Pro
                340                 345                 350

His Glu Val Ile Thr His Tyr Tyr His Arg Tyr Pro Met Ser Thr Ile
                355                 360                 365

Leu Gly Leu Ser Ile Cys Ala Ala Ile Ala Thr Val Ser Val Ala Ala
            370                 375                 380

Ser Thr Trp Leu Phe Cys Arg Ser Arg Val Ala Cys Leu Thr Pro Tyr
385                 390                 395                 400

Arg Leu Thr Pro Asn Ala Arg Ile Pro Phe Cys Leu Ala Val Leu Cys
                405                 410                 415

Cys Ala Arg Thr Ala Arg Ala
                420

<210> SEQ ID NO 98
<211> LENGTH: 442
<212> TYPE: PRT
<213> ORGANISM: Venezuelan equine encephalitis virus

<400> SEQUENCE: 98

Tyr Glu His Ala Thr Thr Met Pro Ser Gln Ala Gly Ile Ser Tyr Asn
1               5                   10                  15

Thr Ile Val Asn Arg Ala Gly Tyr Ala Pro Leu Pro Ile Ser Ile Thr
            20                  25                  30

Pro Thr Lys Ile Lys Leu Ile Pro Thr Val Asn Leu Glu Tyr Val Thr
            35                  40                  45

Cys His Tyr Lys Thr Gly Met Asp Ser Pro Ala Ile Lys Cys Cys Gly
    50                  55                  60

Ser Gln Glu Cys Thr Pro Thr Tyr Arg Pro Asp Glu Gln Cys Lys Val
65                  70                  75                  80

Phe Thr Gly Val Tyr Pro Phe Met Trp Gly Gly Ala Tyr Cys Phe Cys
                85                  90                  95

Asp Thr Glu Asn Thr Gln Val Ser Lys Ala Tyr Val Met Lys Ser Asp
            100                 105                 110

Asp Cys Leu Ala Asp His Ala Glu Ala Tyr Lys Ala His Thr Ala Ser
            115                 120                 125

Val Gln Ala Phe Leu Asn Ile Thr Val Gly Glu His Ser Ile Val Thr
            130                 135                 140

Thr Val Tyr Val Asn Gly Glu Thr Pro Val Asn Phe Asn Gly Val Lys
145                 150                 155                 160

Leu Thr Ala Gly Pro Leu Ser Thr Ala Trp Thr Pro Phe Asp Arg Lys
                165                 170                 175

Ile Val Gln Tyr Ala Gly Glu Ile Tyr Asn Tyr Asp Phe Pro Glu Tyr
                180                 185                 190

Gly Ala Gly Gln Pro Gly Ala Phe Gly Asp Ile Gln Ser Arg Thr Val
```

-continued

```
          195                200                205
Ser Ser Ser Asp Leu Tyr Ala Asn Thr Asn Leu Val Leu Gln Arg Pro
    210                215                220
Lys Ala Gly Ala Ile His Val Pro Tyr Thr Gln Ala Pro Ser Gly Phe
225                230                235                240
Glu Gln Trp Lys Lys Asp Lys Ala Pro Ser Leu Lys Ser Thr Ala Pro
                   245                250                255
Phe Gly Cys Glu Ile Tyr Thr Asn Pro Ile Arg Ala Glu Asn Cys Ala
                260                265                270
Val Gly Ser Ile Pro Leu Ala Phe Asp Ile Pro Asp Ala Leu Phe Thr
                275                280                285
Arg Val Ser Glu Thr Pro Thr Leu Ser Ala Ala Glu Cys Thr Leu Asn
                290                295                300
Glu Cys Val Tyr Ser Ser Asp Phe Gly Gly Ile Ala Thr Val Lys Tyr
305                310                315                320
Ser Ala Ser Lys Ser Gly Lys Cys Ala Val His Val Pro Ser Gly Thr
                325                330                335
Ala Thr Leu Lys Glu Ala Ala Val Glu Leu Thr Glu Gln Gly Ser Ala
                340                345                350
Thr Ile His Phe Ser Thr Ala Asn Ile His Pro Glu Phe Arg Leu Gln
                355                360                365
Ile Cys Thr Ser Tyr Val Thr Cys Lys Gly Asp Cys His Pro Pro Lys
    370                375                380
Asp His Ile Val Thr His Pro Gln Tyr His Ala Gln Thr Phe Thr Ala
385                390                395                400
Ala Val Ser Lys Thr Ala Trp Thr Trp Leu Thr Ser Leu Leu Gly Gly
                405                410                415
Ser Ala Val Ile Ile Ile Ile Gly Leu Val Leu Ala Thr Ile Val Ala
                420                425                430
Met Tyr Val Leu Thr Asn Gln Lys His Asn
                435                440

<210> SEQ ID NO 99
<211> LENGTH: 491
<212> TYPE: PRT
<213> ORGANISM: Lassa virus

<400> SEQUENCE: 99

Met Gly Gln Ile Val Thr Phe Phe Gln Glu Val Pro His Val Ile Glu
1               5                  10                 15
Glu Val Met Asn Ile Val Leu Ile Ala Leu Ser Val Leu Ala Val Leu
                20                 25                 30
Lys Gly Leu Tyr Asn Phe Ala Thr Cys Gly Leu Val Gly Leu Val Thr
            35                 40                 45
Phe Leu Leu Leu Cys Gly Arg Ser Cys Thr Thr Ser Leu Tyr Lys Gly
    50                 55                 60
Val Tyr Glu Leu Gln Thr Leu Glu Leu Asn Met Glu Thr Leu Asn Met
65                 70                 75                 80
Thr Met Pro Leu Ser Cys Thr Lys Asn Asn Ser His His Tyr Ile Met
                85                 90                 95
Val Gly Asn Glu Thr Gly Leu Glu Leu Thr Leu Thr Asn Thr Ser Ile
            100                105                110
Ile Asn His Lys Phe Cys Asn Leu Ser Asp Ala His Lys Lys Asn Leu
        115                120                125
```

-continued

```
Tyr Asp His Ala Leu Met Ser Ile Ile Ser Thr Phe His Leu Ser Ile
    130                 135                 140

Pro Asn Phe Asn Gln Tyr Glu Ala Met Ser Cys Asp Phe Asn Gly Gly
145                 150                 155                 160

Lys Ile Ser Val Gln Tyr Asn Leu Ser His Ser Tyr Ala Gly Asp Ala
                165                 170                 175

Ala Asn His Cys Gly Thr Val Ala Asn Gly Val Leu Gln Thr Phe Met
            180                 185                 190

Arg Met Ala Trp Gly Gly Ser Tyr Ile Ala Leu Asp Ser Gly Arg Gly
            195                 200                 205

Asn Trp Asp Cys Ile Met Thr Ser Tyr Gln Tyr Leu Ile Ile Gln Asn
    210                 215                 220

Thr Thr Trp Glu Asp His Cys Gln Phe Ser Arg Pro Ser Pro Ile Gly
225                 230                 235                 240

Tyr Leu Gly Leu Leu Ser Gln Arg Thr Arg Asp Ile Tyr Ile Ser Arg
                245                 250                 255

Arg Leu Leu Gly Thr Phe Thr Trp Thr Leu Ser Asp Ser Glu Gly Lys
            260                 265                 270

Asp Thr Pro Gly Gly Tyr Cys Leu Thr Arg Trp Met Leu Ile Glu Ala
            275                 280                 285

Glu Leu Lys Cys Phe Gly Asn Thr Ala Val Ala Lys Cys Asn Glu Lys
    290                 295                 300

His Asp Glu Glu Phe Cys Asp Met Leu Arg Leu Phe Asp Phe Asn Lys
305                 310                 315                 320

Gln Ala Ile Gln Arg Leu Lys Ala Glu Ala Gln Met Ser Ile Gln Leu
                325                 330                 335

Ile Asn Lys Ala Val Asn Ala Leu Ile Asn Asp Gln Leu Ile Met Lys
            340                 345                 350

Asn His Leu Arg Asp Ile Met Gly Ile Pro Tyr Cys Asn Tyr Ser Lys
            355                 360                 365

Tyr Trp Tyr Leu Asn His Thr Thr Thr Gly Arg Thr Ser Leu Pro Lys
    370                 375                 380

Cys Trp Leu Val Ser Asn Gly Ser Tyr Leu Asn Glu Thr His Phe Ser
385                 390                 395                 400

Asp Asp Ile Glu Gln Gln Ala Asp Asn Met Ile Thr Glu Met Leu Gln
                405                 410                 415

Lys Glu Tyr Met Glu Arg Gln Gly Lys Thr Pro Leu Gly Leu Val Asp
                420                 425                 430

Leu Phe Val Phe Ser Thr Ser Phe Tyr Leu Ile Ser Ile Phe Leu His
            435                 440                 445

Leu Val Lys Ile Pro Thr His Arg His Ile Val Gly Lys Ser Cys Pro
    450                 455                 460

Lys Pro His Arg Leu Asn His Met Gly Ile Cys Ser Cys Gly Leu Tyr
465                 470                 475                 480

Lys Gln Pro Gly Val Pro Val Lys Trp Lys Arg
                485                 490
```

<210> SEQ ID NO 100
<211> LENGTH: 607
<212> TYPE: PRT
<213> ORGANISM: Avian leukosis virus

<400> SEQUENCE: 100

```
Met Glu Ala Val Ile Lys Met Arg Arg Ala Leu Phe Leu Gln Ala Phe
1               5                   10                  15
```

-continued

```
Leu Thr Gly Arg Pro Gly Lys Ala Ser Lys Lys Asp Pro Lys Lys Asn
            20                  25                  30

Pro Leu Ala Thr Ser Lys Lys Asp Pro Glu Lys Thr Pro Leu Leu Pro
            35                  40                  45

Thr Arg Val Asn Tyr Ile Leu Ile Ile Gly Val Leu Val Leu Cys Glu
            50                  55                  60

Val Thr Gly Val Arg Ala Asp Val His Leu Leu Glu Gln Pro Gly Asn
65                  70                  75                  80

Leu Trp Ile Thr Trp Ala Asn Arg Thr Gly Gln Thr Asp Phe Cys Leu
                85                  90                  95

Ser Thr Gln Ser Ala Thr Ser Pro Phe Gln Thr Cys Leu Ile Gly Ile
            100                 105                 110

Pro Ser Pro Ile Ser Glu Gly Asp Phe Lys Gly Tyr Val Ser Asp Asn
            115                 120                 125

Cys Thr Thr Leu Gly Thr Asp Arg Leu Val Ser Ser Ala Ser Ile Thr
        130                 135                 140

Gly Gly Pro Asp Asn Ser Thr Thr Leu Thr Tyr Arg Lys Val Ser Cys
145                 150                 155                 160

Leu Leu Leu Lys Leu Asn Val Ser Met Trp Asn Glu Pro Pro Glu Leu
                165                 170                 175

Gln Leu Leu Gly Ser Gln Ser Leu Pro Asn Ile Thr Asp Ile Thr Gln
            180                 185                 190

Ile Ser Gly Val Ala Gly Gly Cys Val Gly Phe Arg Pro Lys Gly Val
            195                 200                 205

Pro Trp Tyr Leu Gly Trp Ser Gln Gly Glu Ala Thr Arg Phe Leu Leu
        210                 215                 220

Arg His Pro Ser Phe Ser Asn Leu Thr Gly Pro Phe Thr Val Val Thr
225                 230                 235                 240

Ala Asp Arg His Asn Leu Phe Met Gly Ser Glu Tyr Cys Gly Ala Tyr
                245                 250                 255

Gly Tyr Arg Phe Trp Glu Ile Tyr Asn Cys Ser Gln Glu Gly Gln Gln
            260                 265                 270

Tyr Arg Cys Gly Lys Ala Arg Arg Pro Arg Pro Gln Ser Pro Glu Thr
            275                 280                 285

Gln Cys Thr Arg Gln Gly Gly Ile Trp Val Asn Arg Ser Lys Glu Ile
        290                 295                 300

Asn Glu Thr Glu Pro Phe Ser Phe Thr Val Asn Cys Thr Ala Ser Asn
305                 310                 315                 320

Leu Gly Asn Ala Ser Gly Cys Cys Gly Lys Ala Gly Thr Ile Leu Pro
                325                 330                 335

Gly Ile Trp Val Asp Ser Thr Gln Gly Asn Phe Thr Lys Pro Lys Ala
            340                 345                 350

Leu Pro Pro Ala Ile Phe Leu Ile Cys Gly Asp Arg Ala Trp Gln Gly
            355                 360                 365

Ile Pro Ser Arg Pro Val Gly Gly Pro Cys Tyr Leu Gly Lys Leu Thr
        370                 375                 380

Met Leu Ala Pro Asn His Thr Asp Ile Leu Lys Ile Leu Ala Asn Ser
385                 390                 395                 400

Ser Arg Thr Gly Ile Arg Arg Arg Ser Val Ser His Leu Asp Asp
                405                 410                 415

Thr Cys Ser Asp Glu Val Gln Leu Trp Gly Pro Thr Ala Arg Ile Phe
            420                 425                 430
```

```
Ala Ser Ile Leu Ala Pro Gly Val Ala Ala Ala Gln Ala Leu Arg Glu
        435             440             445

Ile Glu Arg Leu Ala Cys Trp Ser Val Lys Gln Ala Asn Leu Thr Thr
    450             455             460

Ser Leu Leu Gly Asp Leu Leu Asp Asp Val Thr Ser Ile Arg His Ala
465             470             475             480

Val Leu Gln Asn Arg Ala Ala Ile Asp Phe Leu Leu Leu Ala His Gly
            485             490             495

His Gly Cys Glu Asp Ile Ala Gly Met Cys Cys Phe Asn Leu Ser Asp
            500             505             510

His Ser Glu Ser Ile Gln Lys Lys Phe Gln Leu Met Lys Glu His Val
            515             520             525

Asn Lys Ile Gly Val Asp Ser Asp Pro Ile Gly Ser Trp Leu Arg Gly
        530             535             540

Leu Phe Gly Gly Ile Gly Gly Trp Ala Val His Leu Leu Lys Gly Leu
545             550             555             560

Leu Leu Gly Leu Val Val Ile Leu Leu Leu Val Val Cys Leu Pro Cys
            565             570             575

Phe Leu Gln Phe Val Ser Ser Ser Ile Arg Lys Met Ile Asn Asn Ser
            580             585             590

Val Ser Tyr His Thr Glu Tyr Arg Lys Met Gln Gly Gly Ala Val
            595             600             605

<210> SEQ ID NO 101
<211> LENGTH: 614
<212> TYPE: PRT
<213> ORGANISM: Avian leukosis virus

<400> SEQUENCE: 101

Met Glu Ala Val Ile Lys Met Arg Arg Ala Leu Phe Leu Gln Ala Phe
1               5               10              15

Leu Thr Gly His Pro Gly Lys Val Ser Lys Lys Asp Ser Lys Lys Lys
            20              25              30

Pro Pro Ala Thr Gly Lys Arg Asp Pro Glu Lys Thr Pro Leu Leu Pro
        35              40              45

Thr Arg Val Asn Tyr Ile Leu Ile Ile Gly Val Leu Val Leu Cys Glu
    50              55              60

Val Thr Gly Val Arg Ala Asp Val His Leu Leu Glu Gln Pro Gly Asn
65              70              75              80

Leu Trp Ile Thr Trp Ala Asn Arg Thr Gly Gln Thr Asp Phe Cys Leu
            85              90              95

Ser Thr Gln Ser Ala Thr Ser Pro Phe Gln Thr Cys Leu Ile Gly Ile
            100             105             110

Pro Ser Pro Ile Ser Glu Gly Asp Phe Lys Gly Tyr Val Ser Gly Asn
            115             120             125

Cys Thr Ala Leu Gly Thr His Arg Leu Val Ser Ser Gly Ile His Gly
        130             135             140

Gly Pro Asp Asn Ser Thr Thr Leu Thr Tyr Arg Lys Val Ser Cys Leu
145             150             155             160

Leu Leu Lys Leu Asn Val Ser Leu Leu Asp Glu Pro Ser Glu Leu Gln
            165             170             175

Leu Leu Gly Ser Gln Ser Leu Pro Asn Ile Thr Asn Ile Thr Gln Ile
            180             185             190

Pro Ser Val Ala Gly Gly Cys Ile Gly Phe Thr Pro Tyr Gly Ser Pro
            195             200             205
```

-continued

```
Ala Gly Val Tyr Gly Trp Asp Arg Arg Gln Val Thr His Ile Leu Leu
    210                 215                 220

Thr Asp Pro Gly Ser Asn Pro Phe Phe Asn Lys Ala Ser Asn Ser Ser
225                 230                 235                 240

Lys Pro Phe Thr Val Val Thr Ala Asp Arg His Asn Leu Phe Met Gly
                245                 250                 255

Ser Glu Tyr Cys Gly Ala Tyr Gly Tyr Arg Phe Trp Glu Met Tyr Asn
                260                 265                 270

Cys Ser Gln Met Arg Gln Asn Trp Ser Ile Cys Met Asp Val Trp Gly
                275                 280                 285

Arg Gly Leu Pro Glu Ser Trp Cys Thr Ser Thr Gly Gly Ile Trp Val
    290                 295                 300

Asn Gln Ser Lys Glu Ile Asn Glu Thr Glu Pro Phe Ser Phe Thr Ala
305                 310                 315                 320

Asn Cys Thr Gly Ser Asn Leu Gly Asn Val Ser Gly Cys Cys Gly Glu
                325                 330                 335

Ser Ile Thr Ile Leu Pro Pro Gly Ala Trp Val Asp Ser Thr Gln Gly
                340                 345                 350

Ser Phe Thr Lys Pro Lys Ala Leu Pro Pro Gly Ile Phe Leu Ile Cys
                355                 360                 365

Gly Asp Arg Ala Trp Gln Gly Ile Pro Ser Arg Pro Val Gly Gly Pro
    370                 375                 380

Cys Tyr Leu Gly Lys Leu Thr Met Leu Ala Pro Asn His Thr Asp Ile
385                 390                 395                 400

Leu Lys Ile Leu Ala Asn Ser Ser Gln Thr Gly Val Arg His Lys Arg
                405                 410                 415

Ser Val Thr His Leu Asp Asp Thr Cys Ser Asp Glu Val Gln Leu Trp
                420                 425                 430

Gly Pro Thr Ala Arg Ile Phe Ala Ser Ile Leu Ala Pro Gly Val Ala
                435                 440                 445

Ala Ala Gln Ala Leu Arg Glu Ile Glu Arg Leu Ala Cys Trp Ser Val
    450                 455                 460

Lys Gln Ala Asn Leu Thr Thr Ser Leu Leu Gly Asp Leu Leu Asp Asp
465                 470                 475                 480

Val Thr Ser Ile Arg His Ala Val Leu Gln Asn Arg Ala Ala Ile Asp
                485                 490                 495

Phe Leu Leu Leu Ala His Gly His Gly Cys Glu Asp Ile Ala Gly Met
                500                 505                 510

Cys Cys Phe Asn Leu Ser Asp His Ser Glu Ser Ile Gln Lys Lys Phe
                515                 520                 525

Gln Leu Met Lys Glu His Val Asn Lys Ile Gly Val Asp Ser Asp Pro
    530                 535                 540

Ile Gly Ser Trp Leu Arg Gly Leu Phe Gly Gly Ile Gly Glu Trp Ala
545                 550                 555                 560

Val His Leu Leu Lys Gly Leu Leu Leu Gly Leu Val Val Ile Leu Leu
                565                 570                 575

Leu Val Val Cys Leu Pro Cys Phe Leu Gln Phe Val Ser Ser Ser Ile
                580                 585                 590

Arg Lys Met Ile Asn Asn Ser Ile Ser Tyr His Thr Glu Tyr Arg Lys
    595                 600                 605

Met Gln Gly Gly Ala Val
    610
```

<210> SEQ ID NO 102
<211> LENGTH: 569
<212> TYPE: PRT
<213> ORGANISM: Avian leukosis virus

<400> SEQUENCE: 102

Met Glu Ala Val Ile Lys Ala Phe Leu Thr Gly His Pro Gly Lys Val
1               5                   10                  15

Ser Lys Lys Asp Ser Lys Lys Lys Pro Pro Ala Thr Ser Lys Lys Asp
            20                  25                  30

Pro Glu Lys Thr Pro Leu Leu Pro Ser Arg Gly Tyr Phe Phe Phe Pro
        35                  40                  45

Thr Ile Leu Val Cys Val Val Ile Ile Ser Val Val Pro Gly Val Gly
    50                  55                  60

Gly Val His Leu Leu Arg Gln Pro Gly Asn Val Trp Val Thr Trp Ala
65                  70                  75                  80

Asn Lys Thr Gly Arg Thr Asp Phe Cys Leu Ser Leu Gln Ser Ala Thr
                85                  90                  95

Ser Pro Phe Arg Thr Cys Leu Ile Gly Ile Pro Gln Tyr Pro Leu Asn
            100                 105                 110

Thr Phe Lys Gly Tyr Val Thr Asn Val Thr Ala Cys Asp Asn Asp Ala
        115                 120                 125

Asp Leu Ala Ser Gln Thr Ala Cys Leu Ile Lys Ala Leu Asn Thr Thr
    130                 135                 140

Leu Pro Trp Asp Pro Gln Glu Leu Asp Ile Leu Gly Ser Gln Met Ile
145                 150                 155                 160

Lys Asn Gly Thr Thr Arg Thr Cys Val Thr Phe Gly Ser Val Cys Tyr
                165                 170                 175

Lys Glu Asn Asn Arg Ser Arg Val Cys His Asn Phe Asp Gly Asn Phe
            180                 185                 190

Asn Gly Thr Gly Gly Ala Glu Ala Glu Leu Arg Asp Phe Ile Ala Lys
        195                 200                 205

Trp Lys Ser Asp Asp Leu Leu Ile Arg Pro Tyr Val Asn Gln Ser Trp
    210                 215                 220

Thr Met Val Ser Pro Ile Asn Val Glu Ser Phe Ser Ile Ser Arg Arg
225                 230                 235                 240

Tyr Cys Gly Phe Thr Ser Asn Glu Thr Arg Tyr Tyr Arg Gly Asp Leu
                245                 250                 255

Ser Asn Trp Cys Gly Ser Lys Arg Gly Lys Trp Ser Ala Gly Tyr Ser
            260                 265                 270

Asn Arg Thr Lys Cys Ser Ser Asn Thr Thr Gly Cys Gly Gly Asn Cys
        275                 280                 285

Thr Thr Glu Trp Asn Tyr Tyr Ala Tyr Gly Phe Thr Phe Gly Lys Gln
    290                 295                 300

Pro Glu Val Leu Trp Asn Asn Gly Thr Ala Lys Ala Leu Pro Pro Gly
305                 310                 315                 320

Ile Phe Leu Ile Cys Gly Asp Arg Ala Trp Gln Gly Ile Pro Arg Asn
                325                 330                 335

Ala Leu Gly Gly Pro Cys Tyr Leu Gly Gln Leu Thr Met Leu Ser Pro
            340                 345                 350

Asn Phe Thr Thr Trp Ile Thr Tyr Gly Pro Asn Ile Thr Gly His Arg
        355                 360                 365

Arg Ser Arg Arg Ala Ile Arg Gly Leu Ser Pro Asp Cys Ser Asp Glu
    370                 375                 380

```
Val Gln Leu Trp Ser Ala Thr Ala Arg Ile Phe Ala Ser Phe Phe Ala
385             390             395             400

Pro Gly Val Ala Ala Ala Gln Ala Leu Lys Glu Ile Glu Arg Leu Ala
                405             410             415

Cys Trp Ser Val Lys Gln Ala Asn Leu Thr Ser Leu Ile Leu Asn Ala
                420             425             430

Met Leu Glu Asp Met Asn Ser Ile Arg His Ala Val Leu Gln Asn Arg
            435             440             445

Ala Ala Ile Asp Phe Leu Leu Leu Ala Gln Gly His Gly Cys Gln Asp
        450             455             460

Val Glu Gly Met Cys Cys Phe Asn Leu Ser Asp His Ser Glu Ser Ile
465             470             475             480

His Lys Ala Leu Gln Ala Met Lys Glu His Thr Glu Lys Ile Gln Val
                485             490             495

Glu Asp Asp Pro Ile Gly Asp Trp Phe Thr Arg Thr Phe Gly Asp Leu
            500             505             510

Gly Arg Trp Leu Ala Lys Gly Val Lys Thr Leu Leu Phe Ala Leu Leu
        515             520             525

Val Ile Val Cys Leu Leu Ala Ile Ile Pro Cys Ile Ile Lys Cys Phe
        530             535             540

Gln Asp Cys Leu Ser Arg Thr Met Asn Gln Phe Met Asp Glu Arg Ile
545             550             555             560

Arg Tyr His Arg Ile Arg Glu Gln Leu
            565

<210> SEQ ID NO 103
<211> LENGTH: 488
<212> TYPE: PRT
<213> ORGANISM: Human T-lymphotropic virus 1

<400> SEQUENCE: 103

Met Gly Lys Phe Leu Ala Thr Leu Ile Leu Phe Phe Gln Phe Cys Pro
1               5               10              15

Leu Ile Leu Gly Asp Tyr Ser Pro Ser Cys Cys Thr Leu Thr Val Gly
            20              25              30

Val Ser Ser Tyr His Ser Lys Pro Cys Asn Pro Ala Gln Pro Val Cys
        35              40              45

Ser Trp Thr Leu Asp Leu Leu Ala Leu Ser Ala Asp Gln Ala Leu Gln
    50              55              60

Pro Pro Cys Pro Asn Leu Val Ser Tyr Ser Ser Tyr His Ala Thr Tyr
65              70              75              80

Ser Leu Tyr Leu Phe Pro His Trp Ile Lys Lys Pro Asn Arg Asn Gly
            85              90              95

Gly Gly Tyr Tyr Ser Ala Ser Tyr Ser Asp Pro Cys Ser Leu Lys Cys
            100             105             110

Pro Tyr Leu Gly Cys Gln Ser Trp Thr Cys Pro Tyr Thr Gly Ala Val
        115             120             125

Ser Ser Pro Tyr Trp Lys Phe Gln Gln Asp Val Asn Phe Thr Gln Glu
        130             135             140

Val Ser His Leu Asn Ile Asn Leu His Phe Ser Lys Cys Gly Phe Pro
145             150             155             160

Phe Ser Leu Leu Val Asp Ala Pro Gly Tyr Asp Pro Ile Trp Phe Leu
            165             170             175

Asn Thr Glu Pro Ser Gln Leu Pro Pro Thr Ala Pro Pro Leu Leu Ser
```

-continued

```
                  180               185                  190

His Ser Asn Leu Asp His Ile Leu Glu Pro Ser Ile Pro Trp Lys Ser
        195               200               205

Lys Leu Leu Thr Leu Val Gln Leu Thr Leu Gln Ser Thr Asn Tyr Thr
        210               215               220

Cys Ile Val Cys Ile Asp Arg Ala Ser Leu Ser Thr Trp His Val Leu
225               230               235               240

Tyr Ser Pro Asn Val Ser Val Pro Ser Leu Ser Ser Thr Pro Leu Leu
                245               250               255

Tyr Pro Ser Leu Ala Leu Pro Ala Pro His Leu Thr Leu Pro Phe Asn
                260               265               270

Trp Thr His Cys Phe Asp Pro Gln Ile Gln Ala Ile Val Ser Ser Pro
        275               280               285

Cys His Asn Ser Leu Ile Leu Pro Pro Phe Ser Leu Ser Pro Val Pro
        290               295               300

Thr Leu Gly Ser Arg Ser Arg Arg Ala Val Pro Val Ala Val Trp Leu
305               310               315               320

Val Ser Ala Leu Ala Met Gly Ala Gly Val Ala Gly Gly Ile Thr Gly
                325               330               335

Ser Met Ser Leu Ala Ser Gly Lys Ser Leu Leu His Glu Val Asp Lys
                340               345               350

Asp Ile Ser Gln Leu Thr Gln Ala Ile Val Lys Asn His Lys Asn Leu
                355               360               365

Leu Lys Ile Ala Gln Tyr Ala Ala Gln Asn Arg Arg Gly Leu Asp Leu
        370               375               380

Leu Phe Trp Glu Gln Gly Gly Leu Cys Lys Ala Leu Gln Glu Gln Cys
385               390               395               400

Cys Phe Leu Asn Ile Thr Asn Ser His Val Ser Ile Leu Gln Glu Arg
                405               410               415

Pro Pro Leu Glu Asn Arg Val Leu Thr Gly Trp Gly Leu Asn Trp Asp
                420               425               430

Leu Gly Leu Ser Gln Trp Ala Arg Glu Ala Leu Gln Thr Gly Ile Thr
        435               440               445

Leu Val Ala Leu Leu Leu Leu Val Ile Leu Ala Gly Pro Cys Ile Leu
        450               455               460

Arg Gln Leu Arg His Leu Pro Ser Arg Val Arg Tyr Pro His Tyr Ser
465               470               475               480

Leu Ile Asn Pro Glu Ser Ser Leu
                485

<210> SEQ ID NO 104
<211> LENGTH: 989
<212> TYPE: PRT
<213> ORGANISM: Human foamy virus

<400> SEQUENCE: 104

Met Ala Pro Pro Met Thr Leu Gln Gln Trp Ile Ile Trp Lys Lys Met
1               5                  10                 15

Asn Lys Ala His Glu Ala Leu Gln Asn Thr Thr Thr Val Thr Glu Gln
                20                25                 30

Gln Lys Glu Gln Ile Ile Leu Asp Ile Gln Asn Glu Glu Val Gln Pro
                35                40                 45

Thr Arg Arg Asp Lys Phe Arg Tyr Leu Leu Tyr Thr Cys Cys Ala Thr
        50                55                 60
```

-continued

```
Ser Ser Arg Val Leu Ala Trp Met Phe Leu Val Cys Ile Leu Leu Ile
65              70                  75                  80

Ile Val Leu Val Ser Cys Phe Val Thr Ile Ser Arg Ile Gln Trp Asn
                85                  90                  95

Lys Asp Ile Gln Val Leu Gly Pro Val Ile Asp Trp Asn Val Thr Gln
            100                 105                 110

Arg Ala Val Tyr Gln Pro Leu Gln Thr Arg Arg Ile Ala Arg Ser Leu
            115                 120                 125

Arg Met Gln His Pro Val Pro Lys Tyr Val Glu Val Asn Met Thr Ser
    130                 135                 140

Ile Pro Gln Gly Val Tyr Tyr Glu Pro His Pro Glu Pro Ile Val Val
145                 150                 155                 160

Lys Glu Arg Val Leu Gly Leu Ser Gln Ile Leu Met Ile Asn Ser Glu
            165                 170                 175

Asn Ile Ala Asn Asn Ala Asn Leu Thr Gln Glu Val Lys Lys Leu Leu
            180                 185                 190

Thr Glu Met Val Asn Glu Glu Met Gln Ser Leu Ser Asp Val Met Ile
            195                 200                 205

Asp Phe Glu Ile Pro Leu Gly Asp Pro Arg Asp Gln Glu Gln Tyr Ile
    210                 215                 220

His Arg Lys Cys Tyr Gln Glu Phe Ala Asn Cys Tyr Leu Val Lys Tyr
225                 230                 235                 240

Lys Glu Pro Lys Pro Trp Pro Lys Glu Gly Leu Ile Ala Asp Gln Cys
            245                 250                 255

Pro Leu Pro Gly Tyr His Ala Gly Leu Thr Tyr Asn Arg Gln Ser Ile
            260                 265                 270

Trp Asp Tyr Tyr Ile Lys Val Glu Ser Ile Arg Pro Ala Asn Trp Thr
            275                 280                 285

Thr Lys Ser Lys Tyr Gly Gln Ala Arg Leu Gly Ser Phe Tyr Ile Pro
    290                 295                 300

Ser Ser Leu Arg Gln Ile Asn Val Ser His Val Leu Phe Cys Ser Asp
305                 310                 315                 320

Gln Leu Tyr Ser Lys Trp Tyr Asn Ile Glu Asn Thr Ile Glu Gln Asn
            325                 330                 335

Glu Arg Phe Leu Leu Asn Lys Leu Asn Asn Leu Thr Ser Gly Thr Ser
            340                 345                 350

Val Leu Lys Lys Arg Ala Leu Pro Lys Asp Trp Ser Ser Gln Gly Lys
            355                 360                 365

Asn Ala Leu Phe Arg Glu Ile Asn Val Leu Asp Ile Cys Ser Lys Pro
    370                 375                 380

Glu Ser Val Ile Leu Leu Asn Thr Ser Tyr Tyr Ser Phe Ser Leu Trp
385                 390                 395                 400

Glu Gly Asp Cys Asn Phe Thr Lys Asp Met Ile Ser Gln Leu Val Pro
            405                 410                 415

Glu Cys Asp Gly Phe Tyr Asn Asn Ser Lys Trp Met His Met His Pro
            420                 425                 430

Tyr Ala Cys Arg Phe Trp Arg Ser Lys Lys Asn Glu Lys Glu Glu Thr
    435                 440                 445

Lys Cys Arg Asp Gly Glu Thr Lys Arg Cys Leu Tyr Tyr Pro Leu Trp
    450                 455                 460

Asp Ser Pro Glu Ser Thr Tyr Asp Phe Gly Tyr Leu Ala Tyr Gln Lys
465                 470                 475                 480

Asn Phe Pro Ser Pro Ile Cys Ile Glu Gln Gln Lys Ile Arg Asp Gln
```

-continued

```
                 485                 490                 495
Asp Tyr Glu Val Tyr Ser Leu Tyr Gln Glu Arg Lys Ile Ala Ser Lys
            500                 505                 510
Ala Tyr Gly Ile Asp Thr Val Leu Phe Ser Leu Lys Asn Phe Leu Asn
            515                 520                 525
Tyr Thr Gly Thr Pro Val Asn Glu Met Pro Asn Ala Arg Ala Phe Val
        530                 535                 540
Gly Leu Ile Asp Pro Lys Phe Pro Pro Ser Tyr Pro Asn Val Thr Arg
545                 550                 555                 560
Glu His Tyr Thr Ser Cys Asn Asn Arg Lys Arg Arg Ser Val Asp Asn
            565                 570                 575
Asn Tyr Ala Lys Leu Arg Ser Met Gly Tyr Ala Leu Thr Gly Ala Val
            580                 585                 590
Gln Thr Leu Ser Gln Ile Ser Asp Ile Asn Asp Glu Asn Leu Gln Gln
        595                 600                 605
Gly Ile Tyr Leu Leu Arg Asp His Val Ile Thr Leu Met Glu Ala Thr
        610                 615                 620
Leu His Asp Ile Ser Val Met Glu Gly Met Phe Ala Val Gln His Leu
625                 630                 635                 640
His Thr His Leu Asn His Leu Lys Thr Met Leu Leu Glu Arg Arg Ile
            645                 650                 655
Asp Trp Thr Tyr Met Ser Ser Thr Trp Leu Gln Gln Gln Leu Gln Lys
            660                 665                 670
Ser Asp Asp Glu Met Lys Val Ile Lys Arg Ile Ala Arg Ser Leu Val
            675                 680                 685
Tyr Tyr Val Lys Gln Thr His Ser Ser Pro Thr Ala Thr Ala Trp Glu
        690                 695                 700
Ile Gly Leu Tyr Tyr Glu Leu Val Ile Pro Lys His Ile Tyr Leu Asn
705                 710                 715                 720
Asn Trp Asn Val Val Asn Ile Gly His Leu Val Lys Ser Ala Gly Gln
            725                 730                 735
Leu Thr His Val Thr Ile Ala His Pro Tyr Glu Ile Ile Asn Lys Glu
            740                 745                 750
Cys Val Glu Thr Ile Tyr Leu His Leu Glu Asp Cys Thr Arg Gln Asp
            755                 760                 765
Tyr Val Ile Cys Asp Val Val Lys Ile Val Gln Pro Cys Gly Asn Ser
        770                 775                 780
Ser Asp Thr Ser Asp Cys Pro Val Trp Ala Glu Ala Val Lys Glu Pro
785                 790                 795                 800
Phe Val Gln Val Asn Pro Leu Lys Asn Gly Ser Tyr Leu Val Leu Ala
            805                 810                 815
Ser Ser Thr Asp Cys Gln Ile Pro Pro Tyr Val Pro Ser Ile Val Thr
            820                 825                 830
Val Asn Glu Thr Thr Ser Cys Phe Gly Leu Asp Phe Lys Arg Pro Leu
            835                 840                 845
Val Ala Glu Glu Arg Leu Ser Phe Glu Pro Arg Leu Pro Asn Leu Gln
        850                 855                 860
Leu Arg Leu Pro His Leu Val Gly Ile Ile Ala Lys Ile Lys Gly Ile
865                 870                 875                 880
Lys Ile Glu Val Thr Ser Ser Gly Glu Ser Ile Lys Glu Gln Ile Glu
            885                 890                 895
Arg Ala Lys Ala Glu Leu Leu Arg Leu Asp Ile His Glu Gly Asp Thr
            900                 905                 910
```

-continued

```
Pro Ala Trp Ile Gln Gln Leu Ala Ala Ala Thr Lys Asp Val Trp Pro
    915                 920                 925

Ala Ala Ala Ser Ala Leu Gln Gly Ile Gly Asn Phe Leu Ser Gly Thr
    930                 935                 940

Ala Gln Gly Ile Phe Gly Thr Ala Phe Ser Leu Leu Gly Tyr Leu Lys
945                 950                 955                 960

Pro Ile Leu Ile Gly Val Gly Val Ile Leu Leu Val Ile Leu Ile Phe
                965                 970                 975

Lys Ile Val Ser Trp Ile Pro Thr Lys Lys Lys Asn Gln
                980                 985

<210> SEQ ID NO 105
<211> LENGTH: 446
<212> TYPE: PRT
<213> ORGANISM: Human foamy virus

<400> SEQUENCE: 105

Ser Leu Arg Met Gln His Pro Val Pro Lys Tyr Val Glu Val Asn Met
1                   5                   10                  15

Thr Ser Ile Pro Gln Gly Val Tyr Tyr Glu Pro His Pro Glu Pro Ile
                20                  25                  30

Val Val Lys Glu Arg Val Leu Gly Leu Ser Gln Ile Leu Met Ile Asn
            35                  40                  45

Ser Glu Asn Ile Ala Asn Asn Ala Asn Leu Thr Gln Glu Val Lys Lys
    50                  55                  60

Leu Leu Thr Glu Met Val Asn Glu Glu Met Gln Ser Leu Ser Asp Val
65                  70                  75                  80

Met Ile Asp Phe Glu Ile Pro Leu Gly Asp Pro Arg Asp Gln Glu Gln
                85                  90                  95

Tyr Ile His Arg Lys Cys Tyr Gln Glu Phe Ala Asn Cys Tyr Leu Val
                100                 105                 110

Lys Tyr Lys Glu Pro Lys Pro Trp Pro Lys Glu Gly Leu Ile Ala Asp
            115                 120                 125

Gln Cys Pro Leu Pro Gly Tyr His Ala Gly Leu Thr Tyr Asn Arg Gln
    130                 135                 140

Ser Ile Trp Asp Tyr Tyr Ile Lys Val Glu Ser Ile Arg Pro Ala Asn
145                 150                 155                 160

Trp Thr Thr Lys Ser Lys Tyr Gly Gln Ala Arg Leu Gly Ser Phe Tyr
                165                 170                 175

Ile Pro Ser Ser Leu Arg Gln Ile Asn Val Ser His Val Leu Phe Cys
            180                 185                 190

Ser Asp Gln Leu Tyr Ser Lys Trp Tyr Asn Ile Glu Asn Thr Ile Glu
            195                 200                 205

Gln Asn Glu Arg Phe Leu Leu Asn Lys Leu Asn Asn Leu Thr Ser Gly
    210                 215                 220

Thr Ser Val Leu Lys Lys Arg Ala Leu Pro Lys Asp Trp Ser Ser Gln
225                 230                 235                 240

Gly Lys Asn Ala Leu Phe Arg Glu Ile Asn Val Leu Asp Ile Cys Ser
                245                 250                 255

Lys Pro Glu Ser Val Ile Leu Leu Asn Thr Ser Tyr Tyr Ser Phe Ser
            260                 265                 270

Leu Trp Glu Gly Asp Cys Asn Phe Thr Lys Asp Met Ile Ser Gln Leu
            275                 280                 285

Val Pro Glu Cys Asp Gly Phe Tyr Asn Asn Ser Lys Trp Met His Met
```

-continued

```
        290            295            300

His Pro Tyr Ala Cys Arg Phe Trp Arg Ser Lys Lys Asn Glu Lys Glu
305             310            315            320

Glu Thr Lys Cys Arg Asp Gly Glu Thr Lys Arg Cys Leu Tyr Tyr Pro
            325            330            335

Leu Trp Asp Ser Pro Glu Ser Thr Tyr Asp Phe Gly Tyr Leu Ala Tyr
            340            345            350

Gln Lys Asn Phe Pro Ser Pro Ile Cys Ile Glu Gln Gln Lys Ile Arg
            355            360            365

Asp Gln Asp Tyr Glu Val Tyr Ser Leu Tyr Gln Glu Arg Lys Ile Ala
            370            375            380

Ser Lys Ala Tyr Gly Ile Asp Thr Val Leu Phe Ser Leu Lys Asn Phe
385             390            395            400

Leu Asn Tyr Thr Gly Thr Pro Val Asn Glu Met Pro Asn Ala Arg Ala
            405            410            415

Phe Val Gly Leu Ile Asp Pro Lys Phe Pro Pro Ser Tyr Pro Asn Val
            420            425            430

Thr Arg Glu His Tyr Thr Ser Cys Asn Asn Arg Lys Arg Arg
            435            440            445

<210> SEQ ID NO 106
<211> LENGTH: 417
<212> TYPE: PRT
<213> ORGANISM: Human foamy virus

<400> SEQUENCE: 106

Ser Val Asp Asn Asn Tyr Ala Lys Leu Arg Ser Met Gly Tyr Ala Leu
1               5              10             15

Thr Gly Ala Val Gln Thr Leu Ser Gln Ile Ser Asp Ile Asn Asp Glu
            20             25             30

Asn Leu Gln Gln Gly Ile Tyr Leu Leu Arg Asp His Val Ile Thr Leu
            35             40             45

Met Glu Ala Thr Leu His Asp Ile Ser Val Met Glu Gly Met Phe Ala
        50             55             60

Val Gln His Leu His Thr His Leu Asn His Leu Lys Thr Met Leu Leu
65             70             75             80

Glu Arg Arg Ile Asp Trp Thr Tyr Met Ser Ser Thr Trp Leu Gln Gln
            85             90             95

Gln Leu Gln Lys Ser Asp Asp Glu Met Lys Val Ile Lys Arg Ile Ala
            100            105            110

Arg Ser Leu Val Tyr Tyr Val Lys Gln Thr His Ser Ser Pro Thr Ala
            115            120            125

Thr Ala Trp Glu Ile Gly Leu Tyr Tyr Glu Leu Val Ile Pro Lys His
        130            135            140

Ile Tyr Leu Asn Asn Trp Asn Val Val Asn Ile Gly His Leu Val Lys
145            150            155            160

Ser Ala Gly Gln Leu Thr His Val Thr Ile Ala His Pro Tyr Glu Ile
            165            170            175

Ile Asn Lys Glu Cys Val Glu Thr Ile Tyr Leu His Leu Glu Asp Cys
            180            185            190

Thr Arg Gln Asp Tyr Val Ile Cys Asp Val Val Lys Ile Val Gln Pro
            195            200            205

Cys Gly Asn Ser Ser Asp Thr Ser Asp Cys Pro Val Trp Ala Glu Ala
        210            215            220
```

-continued

```
Val Lys Glu Pro Phe Val Gln Val Asn Pro Leu Lys Asn Gly Ser Tyr
225             230             235             240

Leu Val Leu Ala Ser Ser Thr Asp Cys Gln Ile Pro Pro Tyr Val Pro
            245             250             255

Ser Ile Val Thr Val Asn Glu Thr Thr Ser Cys Phe Gly Leu Asp Phe
            260             265             270

Lys Arg Pro Leu Val Ala Glu Glu Arg Leu Ser Phe Glu Pro Arg Leu
        275             280             285

Pro Asn Leu Gln Leu Arg Leu Pro His Leu Val Gly Ile Ile Ala Lys
        290             295             300

Ile Lys Gly Ile Lys Ile Glu Val Thr Ser Ser Gly Glu Ser Ile Lys
305             310             315             320

Glu Gln Ile Glu Arg Ala Lys Ala Glu Leu Leu Arg Leu Asp Ile His
            325             330             335

Glu Gly Asp Thr Pro Ala Trp Ile Gln Gln Leu Ala Ala Ala Thr Lys
            340             345             350

Asp Val Trp Pro Ala Ala Ala Ser Ala Leu Gln Gly Ile Gly Asn Phe
        355             360             365

Leu Ser Gly Thr Ala Gln Gly Ile Phe Gly Thr Ala Phe Ser Leu Leu
        370             375             380

Gly Tyr Leu Lys Pro Ile Leu Ile Gly Val Gly Val Ile Leu Leu Val
385             390             395             400

Ile Leu Ile Phe Lys Ile Val Ser Trp Ile Pro Thr Lys Lys Lys Asn
            405             410             415

Gln

<210> SEQ ID NO 107
<211> LENGTH: 983
<212> TYPE: PRT
<213> ORGANISM: Visna-maedi virus

<400> SEQUENCE: 107

Met Ala Ser Lys Glu Ser Lys Pro Ser Arg Thr Thr Arg Arg Gly Met
1               5               10              15

Glu Pro Pro Leu Arg Glu Thr Trp Asn Gln Val Leu Gln Glu Leu Val
            20              25              30

Lys Arg Gln Gln Gln Glu Glu Glu Gln Gln Gly Leu Val Ser Gly
        35              40              45

Lys Lys Lys Ser Trp Val Ser Ile Asp Leu Leu Gly Thr Glu Gly Lys
        50              55              60

Asp Ile Lys Lys Val Asn Ile Trp Glu Pro Cys Glu Lys Trp Phe Ala
65              70              75              80

Gln Val Val Trp Gly Val Leu Trp Val Leu Gln Ile Val Leu Trp Gly
            85              90              95

Cys Leu Met Trp Glu Val Arg Lys Gly Asn Gln Cys Gln Ala Glu Glu
            100             105             110

Val Ile Ala Leu Val Ser Asp Pro Gly Gly Phe Gln Arg Val Gln His
            115             120             125

Val Glu Thr Val Pro Val Thr Cys Val Thr Lys Asn Phe Thr Gln Trp
        130             135             140

Gly Cys Gln Pro Glu Gly Ala Tyr Pro Asp Pro Glu Leu Glu Tyr Arg
145             150             155             160

Asn Ile Ser Arg Glu Ile Leu Glu Glu Val Tyr Lys Gln Asp Trp Pro
            165             170             175
```

-continued

```
Trp Asn Thr Tyr His Trp Pro Leu Trp Gln Met Glu Asn Met Arg Gln
            180                 185                 190

Trp Met Lys Glu Asn Glu Lys Glu Tyr Lys Glu Arg Thr Asn Lys Thr
            195                 200                 205

Lys Glu Asp Ile Asp Asp Leu Val Ala Gly Arg Ile Arg Gly Arg Phe
    210                 215                 220

Cys Val Pro Tyr Pro Tyr Ala Leu Leu Arg Cys Glu Glu Trp Cys Trp
225                 230                 235                 240

Tyr Pro Glu Ser Ile Asn Gln Glu Thr Gly His Ala Glu Lys Ile Lys
                245                 250                 255

Ile Asn Cys Thr Lys Ala Lys Ala Val Ser Cys Thr Glu Lys Met Ser
            260                 265                 270

Leu Ala Ala Val Gln Arg Val Tyr Trp Glu Lys Glu Asp Glu Glu Ser
            275                 280                 285

Met Lys Phe Leu Asn Ile Lys Ala Cys Asn Ile Ser Leu Arg Cys Gln
            290                 295                 300

Asp Glu Gly Lys Ser Pro Gly Gly Cys Val Gln Gly Tyr Pro Ile Pro
305                 310                 315                 320

Lys Gly Ala Glu Ile Ile Pro Glu Ala Met Lys Tyr Leu Arg Gly Lys
                325                 330                 335

Lys Ser Arg Tyr Gly Gly Ile Lys Asp Lys Asn Gly Glu Leu Lys Leu
            340                 345                 350

Pro Leu Ser Val Arg Val Trp Val Arg Met Ala Asn Leu Ser Gly Trp
            355                 360                 365

Val Asn Gly Thr Pro Pro Tyr Trp Ser Ala Arg Ile Asn Gly Ser Thr
    370                 375                 380

Gly Ile Asn Gly Thr Arg Trp Tyr Gly Ile Gly Thr Leu His His Leu
385                 390                 395                 400

Gly Cys Asn Ile Ser Ser Asn Pro Glu Arg Gly Ile Cys Asn Phe Thr
                405                 410                 415

Gly Glu Leu Trp Ile Gly Gly Asp Lys Phe Pro Tyr Tyr Tyr Thr Pro
            420                 425                 430

Ser Trp Asn Cys Ser Gln Asn Trp Thr Gly His Pro Val Trp His Val
            435                 440                 445

Phe Arg Tyr Leu Asp Met Thr Glu His Met Thr Ser Arg Cys Ile Gln
    450                 455                 460

Arg Pro Lys Arg His Asn Ile Thr Val Gly Asn Gly Thr Ile Thr Gly
465                 470                 475                 480

Asn Cys Ser Val Thr Asn Trp Asp Gly Cys Asn Cys Thr Arg Ser Gly
                485                 490                 495

Asn His Leu Tyr Asn Ser Thr Ser Gly Gly Leu Leu Val Ile Ile Cys
            500                 505                 510

Arg Gln Asn Ser Thr Ile Thr Gly Ile Met Gly Thr Asn Thr Asn Trp
            515                 520                 525

Thr Thr Met Trp Asn Ile Tyr Gln Asn Cys Ser Arg Cys Asn Asn Ser
    530                 535                 540

Ser Leu Asp Arg Thr Gly Ser Gly Thr Leu Gly Thr Val Asn Asn Leu
545                 550                 555                 560

Lys Cys Ser Leu Pro His Arg Asn Glu Ser Asn Lys Trp Thr Cys Lys
                565                 570                 575

Ser Gln Arg Asp Ser Tyr Ile Ala Gly Arg Asp Phe Trp Gly Lys Val
            580                 585                 590

Lys Ala Lys Tyr Ser Cys Glu Ser Asn Leu Gly Gly Leu Asp Ser Met
```

-continued

```
            595                 600                 605
Met His Gln Gln Met Leu Leu Gln Arg Tyr Gln Val Ile Arg Val Arg
    610                 615                 620

Ala Tyr Thr Tyr Gly Val Val Glu Met Pro Gln Ser Tyr Met Glu Ala
625                 630                 635                 640

Gln Gly Glu Asn Lys Arg Ser Arg Arg Asn Leu Gln Arg Lys Lys Arg
                645                 650                 655

Gly Ile Gly Leu Val Ile Val Leu Ala Ile Met Ala Ile Ile Ala Ala
                660                 665                 670

Ala Gly Ala Gly Leu Gly Val Ala Asn Ala Val Gln Gln Ser Tyr Thr
                675                 680                 685

Arg Thr Ala Val Gln Ser Leu Ala Asn Ala Thr Ala Ala Gln Gln Glu
    690                 695                 700

Val Leu Glu Ala Ser Tyr Ala Met Val Gln His Ile Ala Lys Gly Ile
705                 710                 715                 720

Arg Ile Leu Glu Ala Arg Val Ala Arg Val Glu Ala Leu Val Asp Arg
                725                 730                 735

Met Met Val Tyr Gln Glu Leu Asp Cys Trp His Tyr Gln His Tyr Cys
                740                 745                 750

Val Thr Ser Thr Arg Ser Glu Val Ala Asn Tyr Val Asn Trp Thr Arg
                755                 760                 765

Phe Lys Asp Asn Cys Thr Trp Gln Gln Trp Glu Glu Glu Ile Glu Gln
    770                 775                 780

His Glu Gly Asn Leu Ser Leu Leu Leu Arg Glu Ala Ala Leu Gln Val
785                 790                 795                 800

His Ile Ala Gln Arg Asp Ala Arg Arg Ile Pro Asp Ala Trp Lys Ala
                805                 810                 815

Ile Gln Glu Ala Phe Asn Trp Ser Ser Trp Phe Ser Trp Leu Lys Tyr
                820                 825                 830

Ile Pro Trp Ile Ile Met Gly Ile Val Gly Leu Met Cys Phe Arg Ile
                835                 840                 845

Leu Met Cys Val Ile Ser Met Cys Leu Gln Ala Tyr Lys Gln Val Lys
    850                 855                 860

Gln Ile Arg Tyr Thr Gln Val Thr Val Val Ile Glu Ala Pro Val Glu
865                 870                 875                 880

Leu Glu Glu Lys Gln Lys Arg Asn Gly Asp Gly Thr Asn Gly Cys Ala
                885                 890                 895

Ser Leu Glu Arg Glu Arg Arg Thr Ser His Arg Ser Phe Ile Gln Ile
                900                 905                 910

Trp Arg Ala Thr Trp Trp Ala Trp Lys Thr Ser Pro Trp Arg His Asn
                915                 920                 925

Trp Arg Thr Met Pro Tyr Ile Thr Leu Leu Pro Ile Leu Val Ile Trp
    930                 935                 940

Gln Trp Met Glu Glu Asn Gly Trp Asn Gly Glu Asn Gln His Lys Lys
945                 950                 955                 960

Lys Lys Glu Arg Val Asp Cys Gln Asp Arg Glu Gln Met Pro Thr Leu
                965                 970                 975

Glu Asn Asp Tyr Val Glu Leu
                980
```

<210> SEQ ID NO 108
<211> LENGTH: 877
<212> TYPE: PRT
<213> ORGANISM: Visna-maedi virus -continued

<400> SEQUENCE: 108

```
Gln Cys Gln Ala Glu Glu Val Ile Ala Leu Val Ser Asp Pro Gly Gly
1               5                   10                  15

Phe Gln Arg Val Gln His Val Glu Thr Val Pro Val Thr Cys Val Thr
            20                  25                  30

Lys Asn Phe Thr Gln Trp Gly Cys Gln Pro Glu Gly Ala Tyr Pro Asp
        35                  40                  45

Pro Glu Leu Glu Tyr Arg Asn Ile Ser Arg Glu Ile Leu Glu Glu Val
    50                  55                  60

Tyr Lys Gln Asp Trp Pro Trp Asn Thr Tyr His Trp Pro Leu Trp Gln
65                  70                  75                  80

Met Glu Asn Met Arg Gln Trp Met Lys Glu Asn Glu Lys Glu Tyr Lys
                85                  90                  95

Glu Arg Thr Asn Lys Thr Lys Glu Asp Ile Asp Asp Leu Val Ala Gly
            100                 105                 110

Arg Ile Arg Gly Arg Phe Cys Val Pro Tyr Pro Tyr Ala Leu Leu Arg
            115                 120                 125

Cys Glu Glu Trp Cys Trp Tyr Pro Glu Ser Ile Asn Gln Glu Thr Gly
        130                 135                 140

His Ala Glu Lys Ile Lys Ile Asn Cys Thr Lys Ala Lys Ala Val Ser
145                 150                 155                 160

Cys Thr Glu Lys Met Ser Leu Ala Ala Val Gln Arg Val Tyr Trp Glu
                165                 170                 175

Lys Glu Asp Glu Glu Ser Met Lys Phe Leu Asn Ile Lys Ala Cys Asn
            180                 185                 190

Ile Ser Leu Arg Cys Gln Asp Glu Gly Lys Ser Pro Gly Gly Cys Val
            195                 200                 205

Gln Gly Tyr Pro Ile Pro Lys Gly Ala Glu Ile Ile Pro Glu Ala Met
    210                 215                 220

Lys Tyr Leu Arg Gly Lys Lys Ser Arg Tyr Gly Gly Ile Lys Asp Lys
225                 230                 235                 240

Asn Gly Glu Leu Lys Leu Pro Leu Ser Val Arg Val Trp Val Arg Met
            245                 250                 255

Ala Asn Leu Ser Gly Trp Val Asn Gly Thr Pro Pro Tyr Trp Ser Ala
            260                 265                 270

Arg Ile Asn Gly Ser Thr Gly Ile Asn Gly Thr Arg Trp Tyr Gly Ile
        275                 280                 285

Gly Thr Leu His His Leu Gly Cys Asn Ile Ser Ser Asn Pro Glu Arg
    290                 295                 300

Gly Ile Cys Asn Phe Thr Gly Glu Leu Trp Ile Gly Gly Asp Lys Phe
305                 310                 315                 320

Pro Tyr Tyr Tyr Thr Pro Ser Trp Asn Cys Ser Gln Asn Trp Thr Gly
                325                 330                 335

His Pro Val Trp His Val Phe Arg Tyr Leu Asp Met Thr Glu His Met
            340                 345                 350

Thr Ser Arg Cys Ile Gln Arg Pro Lys Arg His Asn Ile Thr Val Gly
            355                 360                 365

Asn Gly Thr Ile Thr Gly Asn Cys Ser Val Thr Asn Trp Asp Gly Cys
    370                 375                 380

Asn Cys Thr Arg Ser Gly Asn His Leu Tyr Asn Ser Thr Ser Gly Gly
385                 390                 395                 400

Leu Leu Val Ile Ile Cys Arg Gln Asn Ser Thr Ile Thr Gly Ile Met
```

-continued

```
                    405                 410                 415

Gly Thr Asn Thr Asn Trp Thr Thr Met Trp Asn Ile Tyr Gln Asn Cys
            420                 425                 430

Ser Arg Cys Asn Asn Ser Ser Leu Asp Arg Thr Gly Ser Gly Thr Leu
            435                 440                 445

Gly Thr Val Asn Asn Leu Lys Cys Ser Leu Pro His Arg Asn Glu Ser
        450                 455                 460

Asn Lys Trp Thr Cys Lys Ser Gln Arg Asp Ser Tyr Ile Ala Gly Arg
465                 470                 475                 480

Asp Phe Trp Gly Lys Val Lys Ala Lys Tyr Ser Cys Glu Ser Asn Leu
                485                 490                 495

Gly Gly Leu Asp Ser Met Met His Gln Gln Met Leu Leu Gln Arg Tyr
            500                 505                 510

Gln Val Ile Arg Val Arg Ala Tyr Thr Tyr Gly Val Val Glu Met Pro
            515                 520                 525

Gln Ser Tyr Met Glu Ala Gln Gly Glu Asn Lys Arg Ser Arg Arg Asn
        530                 535                 540

Leu Gln Arg Lys Lys Arg Gly Ile Gly Leu Val Ile Val Leu Ala Ile
545                 550                 555                 560

Met Ala Ile Ile Ala Ala Ala Gly Ala Gly Leu Gly Val Ala Asn Ala
                565                 570                 575

Val Gln Gln Ser Tyr Thr Arg Thr Ala Val Gln Ser Leu Ala Asn Ala
            580                 585                 590

Thr Ala Ala Gln Gln Glu Val Leu Glu Ala Ser Tyr Ala Met Val Gln
            595                 600                 605

His Ile Ala Lys Gly Ile Arg Ile Leu Glu Ala Arg Val Ala Arg Val
        610                 615                 620

Glu Ala Leu Val Asp Arg Met Met Val Tyr Gln Glu Leu Asp Cys Trp
625                 630                 635                 640

His Tyr Gln His Tyr Cys Val Thr Ser Thr Arg Ser Glu Val Ala Asn
                645                 650                 655

Tyr Val Asn Trp Thr Arg Phe Lys Asp Asn Cys Thr Trp Gln Gln Trp
            660                 665                 670

Glu Glu Glu Ile Glu Gln His Glu Gly Asn Leu Ser Leu Leu Leu Arg
            675                 680                 685

Glu Ala Ala Leu Gln Val His Ile Ala Gln Arg Asp Ala Arg Arg Ile
        690                 695                 700

Pro Asp Ala Trp Lys Ala Ile Gln Glu Ala Phe Asn Trp Ser Ser Trp
705                 710                 715                 720

Phe Ser Trp Leu Lys Tyr Ile Pro Trp Ile Ile Met Gly Ile Val Gly
                725                 730                 735

Leu Met Cys Phe Arg Ile Leu Met Cys Val Ile Ser Met Cys Leu Gln
            740                 745                 750

Ala Tyr Lys Gln Val Lys Gln Ile Arg Tyr Thr Gln Val Thr Val Val
            755                 760                 765

Ile Glu Ala Pro Val Glu Leu Glu Glu Lys Gln Lys Arg Asn Gly Asp
        770                 775                 780

Gly Thr Asn Gly Cys Ala Ser Leu Glu Arg Glu Arg Arg Thr Ser His
785                 790                 795                 800

Arg Ser Phe Ile Gln Ile Trp Arg Ala Thr Trp Trp Ala Trp Lys Thr
                805                 810                 815

Ser Pro Trp Arg His Asn Trp Arg Thr Met Pro Tyr Ile Thr Leu Leu
            820                 825                 830
```

```
Pro Ile Leu Val Ile Trp Gln Trp Met Glu Glu Asn Gly Trp Asn Gly
        835                 840                 845

Glu Asn Gln His Lys Lys Lys Lys Glu Arg Val Asp Cys Gln Asp Arg
    850                 855                 860

Glu Gln Met Pro Thr Leu Glu Asn Asp Tyr Val Glu Leu
865                 870                 875

<210> SEQ ID NO 109
<211> LENGTH: 550
<212> TYPE: PRT
<213> ORGANISM: Visna-maedi virus

<400> SEQUENCE: 109

Gln Cys Gln Ala Glu Glu Val Ile Ala Leu Val Ser Asp Pro Gly Gly
1               5                   10                  15

Phe Gln Arg Val Gln His Val Glu Thr Val Pro Val Thr Cys Val Thr
            20                  25                  30

Lys Asn Phe Thr Gln Trp Gly Cys Gln Pro Glu Gly Ala Tyr Pro Asp
        35                  40                  45

Pro Glu Leu Glu Tyr Arg Asn Ile Ser Arg Glu Ile Leu Glu Glu Val
    50                  55                  60

Tyr Lys Gln Asp Trp Pro Trp Asn Thr Tyr His Trp Pro Leu Trp Gln
65                  70                  75                  80

Met Glu Asn Met Arg Gln Trp Met Lys Glu Asn Glu Lys Glu Tyr Lys
                85                  90                  95

Glu Arg Thr Asn Lys Thr Lys Glu Asp Ile Asp Asp Leu Val Ala Gly
            100                 105                 110

Arg Ile Arg Gly Arg Phe Cys Val Pro Tyr Pro Tyr Ala Leu Leu Arg
            115                 120                 125

Cys Glu Glu Trp Cys Trp Tyr Pro Glu Ser Ile Asn Gln Glu Thr Gly
    130                 135                 140

His Ala Glu Lys Ile Lys Ile Asn Cys Thr Lys Ala Lys Ala Val Ser
145                 150                 155                 160

Cys Thr Glu Lys Met Ser Leu Ala Ala Val Gln Arg Val Tyr Trp Glu
                165                 170                 175

Lys Glu Asp Glu Glu Ser Met Lys Phe Leu Asn Ile Lys Ala Cys Asn
            180                 185                 190

Ile Ser Leu Arg Cys Gln Asp Glu Gly Lys Ser Pro Gly Gly Cys Val
            195                 200                 205

Gln Gly Tyr Pro Ile Pro Lys Gly Ala Glu Ile Ile Pro Glu Ala Met
    210                 215                 220

Lys Tyr Leu Arg Gly Lys Lys Ser Arg Tyr Gly Gly Ile Lys Asp Lys
225                 230                 235                 240

Asn Gly Glu Leu Lys Leu Pro Leu Ser Val Arg Val Trp Val Arg Met
            245                 250                 255

Ala Asn Leu Ser Gly Trp Val Asn Gly Thr Pro Pro Tyr Trp Ser Ala
            260                 265                 270

Arg Ile Asn Gly Ser Thr Gly Ile Asn Gly Thr Arg Trp Tyr Gly Ile
        275                 280                 285

Gly Thr Leu His His Leu Gly Cys Asn Ile Ser Ser Asn Pro Glu Arg
    290                 295                 300

Gly Ile Cys Asn Phe Thr Gly Glu Leu Trp Ile Gly Gly Asp Lys Phe
305                 310                 315                 320

Pro Tyr Tyr Tyr Thr Pro Ser Trp Asn Cys Ser Gln Asn Trp Thr Gly
```

-continued

```
            325              330              335

His Pro Val Trp His Val Phe Arg Tyr Leu Asp Met Thr Glu His Met
        340              345              350

Thr Ser Arg Cys Ile Gln Arg Pro Lys Arg His Asn Ile Thr Val Gly
        355              360              365

Asn Gly Thr Ile Thr Gly Asn Cys Ser Val Thr Asn Trp Asp Gly Cys
    370              375              380

Asn Cys Thr Arg Ser Gly Asn His Leu Tyr Asn Ser Thr Ser Gly Gly
385              390              395              400

Leu Leu Val Ile Ile Cys Arg Gln Asn Ser Thr Ile Thr Gly Ile Met
            405              410              415

Gly Thr Asn Thr Asn Trp Thr Thr Met Trp Asn Ile Tyr Gln Asn Cys
        420              425              430

Ser Arg Cys Asn Asn Ser Ser Leu Asp Arg Thr Gly Ser Gly Thr Leu
        435              440              445

Gly Thr Val Asn Asn Leu Lys Cys Ser Leu Pro His Arg Asn Glu Ser
    450              455              460

Asn Lys Trp Thr Cys Lys Ser Gln Arg Asp Ser Tyr Ile Ala Gly Arg
465              470              475              480

Asp Phe Trp Gly Lys Val Lys Ala Lys Tyr Ser Cys Glu Ser Asn Leu
            485              490              495

Gly Gly Leu Asp Ser Met Met His Gln Gln Met Leu Leu Gln Arg Tyr
        500              505              510

Gln Val Ile Arg Val Arg Ala Tyr Thr Tyr Gly Val Val Glu Met Pro
        515              520              525

Gln Ser Tyr Met Glu Ala Gln Gly Glu Asn Lys Arg Ser Arg Arg Asn
    530              535              540

Leu Gln Arg Lys Lys Arg
545              550

<210> SEQ ID NO 110
<211> LENGTH: 327
<212> TYPE: PRT
<213> ORGANISM: Visna-maedi virus

<400> SEQUENCE: 110

Gly Ile Gly Leu Val Ile Val Leu Ala Ile Met Ala Ile Ile Ala Ala
1           5               10              15

Ala Gly Ala Gly Leu Gly Val Ala Asn Ala Val Gln Gln Ser Tyr Thr
        20              25              30

Arg Thr Ala Val Gln Ser Leu Ala Asn Ala Thr Ala Ala Gln Gln Glu
        35              40              45

Val Leu Glu Ala Ser Tyr Ala Met Val Gln His Ile Ala Lys Gly Ile
    50              55              60

Arg Ile Leu Glu Ala Arg Val Ala Arg Val Glu Ala Leu Val Asp Arg
65              70              75              80

Met Met Val Tyr Gln Glu Leu Asp Cys Trp His Tyr Gln His Tyr Cys
            85              90              95

Val Thr Ser Thr Arg Ser Glu Val Ala Asn Tyr Val Asn Trp Thr Arg
        100             105             110

Phe Lys Asp Asn Cys Thr Trp Gln Gln Trp Glu Glu Glu Ile Glu Gln
        115             120             125

His Glu Gly Asn Leu Ser Leu Leu Leu Arg Glu Ala Ala Leu Gln Val
    130             135             140
```

His Ile Ala Gln Arg Asp Ala Arg Arg Ile Pro Asp Ala Trp Lys Ala
145             150                 155                 160

Ile Gln Glu Ala Phe Asn Trp Ser Ser Trp Phe Ser Trp Leu Lys Tyr
                165                 170                 175

Ile Pro Trp Ile Ile Met Gly Ile Val Gly Leu Met Cys Phe Arg Ile
                180                 185                 190

Leu Met Cys Val Ile Ser Met Cys Leu Gln Ala Tyr Lys Gln Val Lys
        195                 200                 205

Gln Ile Arg Tyr Thr Gln Val Thr Val Val Ile Glu Ala Pro Val Glu
        210                 215                 220

Leu Glu Glu Lys Gln Lys Arg Asn Gly Asp Gly Thr Asn Gly Cys Ala
225             230                 235                 240

Ser Leu Glu Arg Glu Arg Arg Thr Ser His Arg Ser Phe Ile Gln Ile
                245                 250                 255

Trp Arg Ala Thr Trp Trp Ala Trp Lys Thr Ser Pro Trp Arg His Asn
                260                 265                 270

Trp Arg Thr Met Pro Tyr Ile Thr Leu Leu Pro Ile Leu Val Ile Trp
                275                 280                 285

Gln Trp Met Glu Glu Asn Gly Trp Asn Gly Glu Asn Gln His Lys Lys
        290                 295                 300

Lys Lys Glu Arg Val Asp Cys Gln Asp Arg Glu Gln Met Pro Thr Leu
305                 310                 315                 320

Glu Asn Asp Tyr Val Glu Leu
                325

<210> SEQ ID NO 111
<211> LENGTH: 1255
<212> TYPE: PRT
<213> ORGANISM: Severe acute respiratory syndrome-associated coronavirus

<400> SEQUENCE: 111

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
                20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
        50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
                100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
        130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
                180                 185                 190

-continued

```
Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
        210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
                260                 265                 270

Thr Asp Ala Val Asp Cys Ser Gln Asn Pro Leu Ala Glu Leu Lys Cys
                275                 280                 285

Ser Val Lys Ser Phe Glu Ile Asp Lys Gly Ile Tyr Gln Thr Ser Asn
        290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
                340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
        370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
                420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
        450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
                500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
        530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
                580                 585                 590

Glu Val Ala Val Leu Tyr Gln Asp Val Asn Cys Thr Asp Val Ser Thr
        595                 600                 605
```

```
Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
                660                 665                 670

Ser Ile Val Ala Tyr Thr Met Ser Leu Gly Ala Asp Ser Ser Ile Ala
                675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Ala Glu Gln Asp Arg Asn Thr Arg Glu Val Phe Ala Gln Val Lys
                755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
                835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
                900                 905                 910

Ile Ser Gln Ile Gln Glu Ser Leu Thr Thr Thr Ser Thr Ala Leu Gly
                915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
                980                 985                 990

Gln Leu Ile Arg Ala Ala Glu Ile  Arg Ala Ser Ala Asn  Leu Ala Ala
    995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
```

-continued

```
        1025                1030                1035

Pro His  Gly Val Val Phe Leu  His Val Thr Tyr Val  Pro Ser Gln
        1040                1045                1050

Glu Arg  Asn Phe Thr Thr Ala  Pro Ala Ile Cys His  Glu Gly Lys
        1055                1060                1065

Ala Tyr  Phe Pro Arg Glu Gly  Val Phe Val Phe Asn  Gly Thr Ser
        1070                1075                1080

Trp Phe  Ile Thr Gln Arg Asn  Phe Phe Ser Pro Gln  Ile Ile Thr
        1085                1090                1095

Thr Asp  Asn Thr Phe Val Ser  Gly Asn Cys Asp Val  Val Ile Gly
        1100                1105                1110

Ile Ile  Asn Asn Thr Val Tyr  Asp Pro Leu Gln Pro  Glu Leu Asp
        1115                1120                1125

Ser Phe  Lys Glu Glu Leu Asp  Lys Tyr Phe Lys Asn  His Thr Ser
        1130                1135                1140

Pro Asp  Val Asp Leu Gly Asp  Ile Ser Gly Ile Asn  Ala Ser Val
        1145                1150                1155

Val Asn  Ile Gln Lys Glu Ile  Asp Arg Leu Asn Glu  Val Ala Lys
        1160                1165                1170

Asn Leu  Asn Glu Ser Leu Ile  Asp Leu Gln Glu Leu  Gly Lys Tyr
        1175                1180                1185

Glu Gln  Tyr Ile Lys Trp Pro  Trp Tyr Val Trp Leu  Gly Phe Ile
        1190                1195                1200

Ala Gly  Leu Ile Ala Ile Val  Met Val Thr Ile Leu  Leu Cys Cys
        1205                1210                1215

Met Thr  Ser Cys Cys Ser Cys  Leu Lys Gly Ala Cys  Ser Cys Gly
        1220                1225                1230

Ser Cys  Cys Lys Phe Asp Glu  Asp Asp Ser Glu Pro  Val Leu Lys
        1235                1240                1245

Gly Val  Lys Leu His Tyr Thr
        1250                1255
```

<210> SEQ ID NO 112
<211> LENGTH: 605
<212> TYPE: PRT
<213> ORGANISM: Severe acute respiratory syndrome-associated coronavirus

<400> SEQUENCE: 112

```
Cys Asp Ile Pro Ile Gly Ala Gly Ile Cys Ala Ser Tyr His Thr Val
1               5                   10                  15

Ser Leu Leu Arg Ser Thr Ser Gln Lys Ser Ile Val Ala Tyr Thr Met
            20                  25                  30

Ser Leu Gly Ala Asp Ser Ser Ile Ala Tyr Ser Asn Asn Thr Ile Ala
        35                  40                  45

Ile Pro Thr Asn Phe Ser Ile Ser Ile Thr Thr Glu Val Met Pro Val
    50                  55                  60

Ser Met Ala Lys Thr Ser Val Asp Cys Asn Met Tyr Ile Cys Gly Asp
65                  70                  75                  80

Ser Thr Glu Cys Ala Asn Leu Leu Leu Gln Tyr Gly Ser Phe Cys Thr
                85                  90                  95

Gln Leu Asn Arg Ala Leu Ser Gly Ile Ala Ala Glu Gln Asp Arg Asn
            100                 105                 110

Thr Arg Glu Val Phe Ala Gln Val Lys Gln Met Tyr Lys Thr Pro Thr
        115                 120                 125
```

```
Leu Lys Tyr Phe Gly Gly Phe Asn Phe Ser Gln Ile Leu Pro Asp Pro
130             135                 140

Leu Lys Pro Thr Lys Arg Ser Phe Ile Glu Asp Leu Leu Phe Asn Lys
145             150             155                 160

Val Thr Leu Ala Asp Ala Gly Phe Met Lys Gln Tyr Gly Glu Cys Leu
            165             170             175

Gly Asp Ile Asn Ala Arg Asp Leu Ile Cys Ala Gln Lys Phe Asn Gly
            180             185             190

Leu Thr Val Leu Pro Pro Leu Leu Thr Asp Asp Met Ile Ala Ala Tyr
            195             200             205

Thr Ala Ala Leu Val Ser Gly Thr Ala Thr Ala Gly Trp Thr Phe Gly
    210             215             220

Ala Gly Ala Ala Leu Gln Ile Pro Phe Ala Met Gln Met Ala Tyr Arg
225             230             235                 240

Phe Asn Gly Ile Gly Val Thr Gln Asn Val Leu Tyr Glu Asn Gln Lys
            245             250             255

Gln Ile Ala Asn Gln Phe Asn Lys Ala Ile Ser Gln Ile Gln Glu Ser
            260             265             270

Leu Thr Thr Thr Ser Thr Ala Leu Gly Lys Leu Gln Asp Val Val Asn
    275             280             285

Gln Asn Ala Gln Ala Leu Asn Thr Leu Val Lys Gln Leu Ser Ser Asn
    290             295             300

Phe Gly Ala Ile Ser Ser Val Leu Asn Asp Ile Leu Ser Arg Leu Asp
305             310             315                 320

Lys Val Glu Ala Glu Val Gln Ile Asp Arg Leu Ile Thr Gly Arg Leu
            325             330             335

Gln Ser Leu Gln Thr Tyr Val Thr Gln Gln Leu Ile Arg Ala Ala Glu
            340             345             350

Ile Arg Ala Ser Ala Asn Leu Ala Ala Thr Lys Met Ser Glu Cys Val
    355             360             365

Leu Gly Gln Ser Lys Arg Val Asp Phe Cys Gly Lys Gly Tyr His Leu
    370             375             380

Met Ser Phe Pro Gln Ala Ala Pro His Gly Val Val Phe Leu His Val
385             390             395                 400

Thr Tyr Val Pro Ser Gln Glu Arg Asn Phe Thr Thr Ala Pro Ala Ile
            405             410             415

Cys His Glu Gly Lys Ala Tyr Phe Pro Arg Glu Gly Val Phe Val Phe
            420             425             430

Asn Gly Thr Ser Trp Phe Ile Thr Gln Arg Asn Phe Phe Ser Pro Gln
            435             440             445

Ile Ile Thr Thr Asp Asn Thr Phe Val Ser Gly Asn Cys Asp Val Val
    450             455             460

Ile Gly Ile Ile Asn Asn Thr Val Tyr Asp Pro Leu Gln Pro Glu Leu
465             470             475                 480

Asp Ser Phe Lys Glu Glu Leu Asp Lys Tyr Phe Lys Asn His Thr Ser
            485             490             495

Pro Asp Val Asp Leu Gly Asp Ile Ser Gly Ile Asn Ala Ser Val Val
            500             505             510

Asn Ile Gln Lys Glu Ile Asp Arg Leu Asn Glu Val Ala Lys Asn Leu
            515             520             525

Asn Glu Ser Leu Ile Asp Leu Gln Glu Leu Gly Lys Tyr Glu Gln Tyr
    530             535             540

Ile Lys Trp Pro Trp Tyr Val Trp Leu Gly Phe Ile Ala Gly Leu Ile
```

-continued

```
545              550              555              560

Val Ile Val Met Val Thr Ile Leu Leu Cys Cys Met Thr Ser Cys Cys
             565              570              575

Ser Cys Leu Lys Gly Ala Cys Ser Cys Gly Ser Cys Cys Lys Phe Asp
         580              585              590

Glu Asp Asp Ser Glu Pro Val Leu Lys Gly Val Lys Leu
         595              600              605
```

```
<210> SEQ ID NO 113
<211> LENGTH: 253
<212> TYPE: PRT
<213> ORGANISM: Severe acute respiratory syndrome-associated coronavirus

<400> SEQUENCE: 113

Pro Asn Ile Thr Asn Leu Cys Pro Phe Gly Glu Val Phe Asn Ala Thr
1               5               10              15

Lys Phe Pro Ser Val Tyr Ala Trp Glu Arg Lys Lys Ile Ser Asn Cys
            20              25              30

Val Ala Asp Tyr Ser Val Leu Tyr Asn Ser Thr Phe Phe Ser Thr Phe
            35              40              45

Lys Cys Tyr Gly Val Ser Ala Thr Lys Leu Asn Asp Leu Cys Phe Ser
        50              55              60

Asn Val Tyr Ala Asp Ser Phe Val Val Lys Gly Asp Asp Val Arg Gln
65              70              75              80

Ile Ala Pro Gly Gln Thr Gly Val Ile Ala Asp Tyr Asn Tyr Lys Leu
            85              90              95

Pro Asp Asp Phe Met Gly Cys Val Leu Ala Trp Asn Thr Arg Asn Ile
            100             105             110

Asp Ala Thr Ser Thr Gly Asn Tyr Asn Tyr Lys Tyr Arg Tyr Leu Arg
            115             120             125

His Gly Lys Leu Arg Pro Phe Glu Arg Asp Ile Ser Asn Val Pro Phe
        130             135             140

Ser Pro Asp Gly Lys Pro Cys Thr Pro Pro Ala Leu Asn Cys Tyr Trp
145             150             155             160

Pro Leu Asn Asp Tyr Gly Phe Tyr Thr Thr Thr Gly Ile Gly Tyr Gln
            165             170             175

Pro Tyr Arg Val Val Val Leu Ser Phe Glu Leu Leu Asn Ala Pro Ala
            180             185             190

Thr Val Cys Gly Pro Lys Leu Ser Thr Asp Leu Ile Lys Asn Gln Cys
            195             200             205

Val Asn Phe Asn Phe Asn Gly Leu Thr Gly Thr Gly Val Leu Thr Pro
        210             215             220

Ser Ser Lys Arg Phe Gln Pro Phe Gln Gln Phe Gly Arg Asp Val Ser
225             230             235             240

Asp Phe Thr Asp Ser Val Arg Asp Pro Lys Thr Ser Glu
            245             250
```

```
<210> SEQ ID NO 114
<211> LENGTH: 298
<212> TYPE: PRT
<213> ORGANISM: Respiratory syncytial virus

<400> SEQUENCE: 114

Met Ser Lys Asn Lys Asp Gln Arg Thr Ala Lys Thr Leu Glu Arg Thr
1               5               10              15

Trp Asp Thr Leu Asn His Leu Leu Phe Ile Ser Ser Cys Leu Tyr Lys
```

-continued

```
                20                  25                  30

Leu Asn Leu Lys Ser Val Ala Gln Ile Thr Leu Ser Ile Leu Ala Met
            35                  40                  45

Ile Ile Ser Thr Ser Leu Ile Ile Ala Ala Ile Ile Phe Ile Ala Ser
        50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
            115                 120                 125

Thr Thr Val Lys Thr Lys Asn Thr Thr Thr Thr Gln Thr Gln Pro Ser
        130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
            195                 200                 205

Lys Thr Thr Lys Lys Asp Pro Lys Pro Gln Thr Thr Lys Ser Lys Glu
        210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
            275                 280                 285

Pro Ser Ser Pro Pro Asn Thr Pro Arg Gln
    290                 295
```

<210> SEQ ID NO 115
<211> LENGTH: 574
<212> TYPE: PRT
<213> ORGANISM: Respiratory syncytial virus

<400> SEQUENCE: 115

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95
```

-continued

```
Met Gln Ser Thr Pro Pro Thr Asn Asn Arg Ala Arg Arg Glu Leu Pro
            100             105             110

Arg Phe Met Asn Tyr Thr Leu Asn Asn Ala Lys Lys Thr Asn Val Thr
            115             120             125

Leu Ser Lys Lys Arg Lys Arg Arg Phe Leu Gly Phe Leu Leu Gly Val
    130             135             140

Gly Ser Ala Ile Ala Ser Gly Val Ala Val Ser Lys Val Leu His Leu
145             150             155             160

Glu Gly Glu Val Asn Lys Ile Lys Ser Ala Leu Leu Ser Thr Asn Lys
                165             170             175

Ala Val Val Ser Leu Ser Asn Gly Val Ser Val Leu Thr Ser Lys Val
            180             185             190

Leu Asp Leu Lys Asn Tyr Ile Asp Lys Gln Leu Leu Pro Ile Val Asn
            195             200             205

Lys Gln Ser Cys Ser Ile Ser Asn Ile Glu Thr Val Ile Glu Phe Gln
    210             215             220

Gln Lys Asn Asn Arg Leu Leu Glu Ile Thr Arg Glu Phe Ser Val Asn
225             230             235             240

Ala Gly Val Thr Thr Pro Val Ser Thr Tyr Met Leu Thr Asn Ser Glu
            245             250             255

Leu Leu Ser Leu Ile Asn Asp Met Pro Ile Thr Asn Asp Gln Lys Lys
            260             265             270

Leu Met Ser Asn Asn Val Gln Ile Val Arg Gln Gln Ser Tyr Ser Ile
            275             280             285

Met Ser Ile Ile Lys Glu Glu Val Leu Ala Tyr Val Val Gln Leu Pro
    290             295             300

Leu Tyr Gly Val Ile Asp Thr Pro Cys Trp Lys Leu His Thr Ser Pro
305             310             315             320

Leu Cys Thr Thr Asn Thr Lys Glu Gly Ser Asn Ile Cys Leu Thr Arg
            325             330             335

Thr Asp Arg Gly Trp Tyr Cys Asp Asn Ala Gly Ser Val Ser Phe Phe
            340             345             350

Pro Gln Ala Glu Thr Cys Lys Val Gln Ser Asn Arg Val Phe Cys Asp
            355             360             365

Thr Met Asn Ser Leu Thr Leu Pro Ser Glu Ile Asn Leu Cys Asn Val
    370             375             380

Asp Ile Phe Asn Pro Lys Tyr Asp Cys Lys Ile Met Thr Ser Lys Thr
385             390             395             400

Asp Val Ser Ser Ser Val Ile Thr Ser Leu Gly Ala Ile Val Ser Cys
            405             410             415

Tyr Gly Lys Thr Lys Cys Thr Ala Ser Asn Lys Asn Arg Gly Ile Ile
            420             425             430

Lys Thr Phe Ser Asn Gly Cys Asp Tyr Val Ser Asn Lys Gly Met Asp
            435             440             445

Thr Val Ser Val Gly Asn Thr Leu Tyr Tyr Val Asn Lys Gln Glu Gly
    450             455             460

Lys Ser Leu Tyr Val Lys Gly Glu Pro Ile Ile Asn Phe Tyr Asp Pro
465             470             475             480

Leu Val Phe Pro Ser Asp Glu Phe Asp Ala Ser Ile Ser Gln Val Asn
            485             490             495

Glu Lys Ile Asn Gln Ser Leu Ala Phe Ile Arg Lys Ser Asp Glu Leu
            500             505             510

Leu His Asn Val Asn Ala Gly Lys Ser Thr Thr Asn Ile Met Ile Thr
```

```
              515                520                525
Thr Ile Ile Ile Val Ile Ile Val Ile Leu Leu Ser Leu Ile Ala Val
    530                535                540
Gly Leu Leu Leu Tyr Cys Lys Ala Arg Ser Thr Pro Val Thr Leu Ser
545                550                555                560
Lys Asp Gln Leu Ser Gly Ile Asn Asn Ile Ala Phe Ser Asn
                565                570

<210> SEQ ID NO 116
<211> LENGTH: 549
<212> TYPE: PRT
<213> ORGANISM: Respiratory syncytial virus

<400> SEQUENCE: 116

Gln Asn Ile Thr Glu Glu Phe Tyr Gln Ser Thr Cys Ser Ala Val Ser
1                5                10                15
Lys Gly Tyr Leu Ser Ala Leu Arg Thr Gly Trp Tyr Thr Ser Val Ile
                20                25                30
Thr Ile Glu Leu Ser Asn Ile Lys Glu Asn Lys Cys Asn Gly Thr Asp
            35                40                45
Ala Lys Val Lys Leu Ile Lys Gln Glu Leu Asp Lys Tyr Lys Asn Ala
        50                55                60
Val Thr Glu Leu Gln Leu Leu Met Gln Ser Thr Pro Pro Thr Asn Asn
65                70                75                80
Arg Ala Arg Arg Glu Leu Pro Arg Phe Met Asn Tyr Thr Leu Asn Asn
                85                90                95
Ala Lys Lys Thr Asn Val Thr Leu Ser Lys Lys Arg Lys Arg Arg Phe
                100                105                110
Leu Gly Phe Leu Leu Gly Val Gly Ser Ala Ile Ala Ser Gly Val Ala
                115                120                125
Val Ser Lys Val Leu His Leu Glu Gly Glu Val Asn Lys Ile Lys Ser
        130                135                140
Ala Leu Leu Ser Thr Asn Lys Ala Val Val Ser Leu Ser Asn Gly Val
145                150                155                160
Ser Val Leu Thr Ser Lys Val Leu Asp Leu Lys Asn Tyr Ile Asp Lys
                165                170                175
Gln Leu Leu Pro Ile Val Asn Lys Gln Ser Cys Ser Ile Ser Asn Ile
                180                185                190
Glu Thr Val Ile Glu Phe Gln Gln Lys Asn Asn Arg Leu Leu Glu Ile
                195                200                205
Thr Arg Glu Phe Ser Val Asn Ala Gly Val Thr Thr Pro Val Ser Thr
    210                215                220
Tyr Met Leu Thr Asn Ser Glu Leu Leu Ser Leu Ile Asn Asp Met Pro
225                230                235                240
Ile Thr Asn Asp Gln Lys Lys Leu Met Ser Asn Asn Val Gln Ile Val
                245                250                255
Arg Gln Gln Ser Tyr Ser Ile Met Ser Ile Ile Lys Glu Glu Val Leu
                260                265                270
Ala Tyr Val Val Gln Leu Pro Leu Tyr Gly Val Ile Asp Thr Pro Cys
                275                280                285
Trp Lys Leu His Thr Ser Pro Leu Cys Thr Thr Asn Thr Lys Glu Gly
        290                295                300
Ser Asn Ile Cys Leu Thr Arg Thr Asp Arg Gly Trp Tyr Cys Asp Asn
305                310                315                320
```

-continued

```
Ala Gly Ser Val Ser Phe Phe Pro Gln Ala Glu Thr Cys Lys Val Gln
            325                 330                 335

Ser Asn Arg Val Phe Cys Asp Thr Met Asn Ser Leu Thr Leu Pro Ser
            340                 345                 350

Glu Ile Asn Leu Cys Asn Val Asp Ile Phe Asn Pro Lys Tyr Asp Cys
            355                 360                 365

Lys Ile Met Thr Ser Lys Thr Asp Val Ser Ser Ser Val Ile Thr Ser
    370                 375                 380

Leu Gly Ala Ile Val Ser Cys Tyr Gly Lys Thr Lys Cys Thr Ala Ser
385                 390                 395                 400

Asn Lys Asn Arg Gly Ile Ile Lys Thr Phe Ser Asn Gly Cys Asp Tyr
                405                 410                 415

Val Ser Asn Lys Gly Met Asp Thr Val Ser Val Gly Asn Thr Leu Tyr
            420                 425                 430

Tyr Val Asn Lys Gln Glu Gly Lys Ser Leu Tyr Val Lys Gly Glu Pro
            435                 440                 445

Ile Ile Asn Phe Tyr Asp Pro Leu Val Phe Pro Ser Asp Glu Phe Asp
    450                 455                 460

Ala Ser Ile Ser Gln Val Asn Glu Lys Ile Asn Gln Ser Leu Ala Phe
465                 470                 475                 480

Ile Arg Lys Ser Asp Glu Leu Leu His Asn Val Asn Ala Gly Lys Ser
                485                 490                 495

Thr Thr Asn Ile Met Ile Thr Thr Ile Ile Val Ile Ile Val Ile
            500                 505                 510

Leu Leu Ser Leu Ile Ala Val Gly Leu Leu Leu Tyr Cys Lys Ala Arg
            515                 520                 525

Ser Thr Pro Val Thr Leu Ser Lys Asp Gln Leu Ser Gly Ile Asn Asn
    530                 535                 540

Ile Ala Phe Ser Asn
545
```

<210> SEQ ID NO 117
<211> LENGTH: 111
<212> TYPE: PRT
<213> ORGANISM: Respiratory syncytial virus

<400> SEQUENCE: 117

```
Gln Asn Ile Thr Glu Glu Phe Tyr Gln Ser Thr Cys Ser Ala Val Ser
1               5                   10                  15

Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
            35                  40                  45

Ala Lys Val Lys Leu Ile Lys Gln Glu Leu Asp Lys Tyr Lys Asn Ala
    50                  55                  60

Val Thr Glu Leu Gln Leu Leu Met Gln Ser Thr Pro Pro Thr Asn Asn
65                  70                  75                  80

Arg Ala Arg Arg Glu Leu Pro Arg Phe Met Asn Tyr Thr Leu Asn Asn
                85                  90                  95

Ala Lys Lys Thr Asn Val Thr Leu Ser Lys Lys Arg Lys Arg Arg
            100                 105                 110
```

<210> SEQ ID NO 118
<211> LENGTH: 438
<212> TYPE: PRT
<213> ORGANISM: Respiratory syncytial virus

<400> SEQUENCE: 118

Phe Leu Gly Phe Leu Leu Gly Val Gly Ser Ala Ile Ala Ser Gly Val
1               5                   10                  15

Ala Val Ser Lys Val Leu His Leu Glu Gly Glu Val Asn Lys Ile Lys
                20                  25                  30

Ser Ala Leu Leu Ser Thr Asn Lys Ala Val Val Ser Leu Ser Asn Gly
            35                  40                  45

Val Ser Val Leu Thr Ser Lys Val Leu Asp Leu Lys Asn Tyr Ile Asp
        50                  55                  60

Lys Gln Leu Leu Pro Ile Val Asn Lys Gln Ser Cys Ser Ile Ser Asn
65                  70                  75                  80

Ile Glu Thr Val Ile Glu Phe Gln Gln Lys Asn Asn Arg Leu Leu Glu
                85                  90                  95

Ile Thr Arg Glu Phe Ser Val Asn Ala Gly Val Thr Thr Pro Val Ser
            100                 105                 110

Thr Tyr Met Leu Thr Asn Ser Glu Leu Leu Ser Leu Ile Asn Asp Met
        115                 120                 125

Pro Ile Thr Asn Asp Gln Lys Lys Leu Met Ser Asn Asn Val Gln Ile
    130                 135                 140

Val Arg Gln Gln Ser Tyr Ser Ile Met Ser Ile Ile Lys Glu Glu Val
145                 150                 155                 160

Leu Ala Tyr Val Val Gln Leu Pro Leu Tyr Gly Val Ile Asp Thr Pro
                165                 170                 175

Cys Trp Lys Leu His Thr Ser Pro Leu Cys Thr Thr Asn Thr Lys Glu
            180                 185                 190

Gly Ser Asn Ile Cys Leu Thr Arg Thr Asp Arg Gly Trp Tyr Cys Asp
        195                 200                 205

Asn Ala Gly Ser Val Ser Phe Phe Pro Gln Ala Glu Thr Cys Lys Val
    210                 215                 220

Gln Ser Asn Arg Val Phe Cys Asp Thr Met Asn Ser Leu Thr Leu Pro
225                 230                 235                 240

Ser Glu Ile Asn Leu Cys Asn Val Asp Ile Phe Asn Pro Lys Tyr Asp
                245                 250                 255

Cys Lys Ile Met Thr Ser Lys Thr Asp Val Ser Ser Ser Val Ile Thr
            260                 265                 270

Ser Leu Gly Ala Ile Val Ser Cys Tyr Gly Lys Thr Lys Cys Thr Ala
        275                 280                 285

Ser Asn Lys Asn Arg Gly Ile Ile Lys Thr Phe Ser Asn Gly Cys Asp
    290                 295                 300

Tyr Val Ser Asn Lys Gly Met Asp Thr Val Ser Val Gly Asn Thr Leu
305                 310                 315                 320

Tyr Tyr Val Asn Lys Gln Glu Gly Lys Ser Leu Tyr Val Lys Gly Glu
                325                 330                 335

Pro Ile Ile Asn Phe Tyr Asp Pro Leu Val Phe Pro Ser Asp Glu Phe
            340                 345                 350

Asp Ala Ser Ile Ser Gln Val Asn Glu Lys Ile Asn Gln Ser Leu Ala
        355                 360                 365

Phe Ile Arg Lys Ser Asp Glu Leu Leu His Asn Val Asn Ala Gly Lys
    370                 375                 380

Ser Thr Thr Asn Ile Met Ile Thr Thr Ile Ile Ile Val Ile Ile Val
385                 390                 395                 400

Ile Leu Leu Ser Leu Ile Ala Val Gly Leu Leu Leu Tyr Cys Lys Ala

-continued

```
                    405                410                415
Arg Ser Thr Pro Val Thr Leu Ser Lys Asp Gln Leu Ser Gly Ile Asn
        420                425                430

Asn Ile Ala Phe Ser Asn
        435

<210> SEQ ID NO 119
<211> LENGTH: 572
<212> TYPE: PRT
<213> ORGANISM: Human parainfluenza virus type 3

<400> SEQUENCE: 119

Met Glu Tyr Trp Lys His Thr Asn His Gly Lys Asp Ala Gly Asn Glu
1               5                10                15

Leu Glu Thr Ser Met Ala Thr His Gly Asn Lys Leu Thr Asn Lys Ile
            20                25                30

Thr Tyr Ile Leu Trp Thr Ile Ile Leu Val Leu Leu Ser Ile Val Phe
        35                40                45

Ile Ile Val Leu Ile Asn Ser Ile Lys Ser Glu Lys Ala His Glu Ser
    50                55                60

Leu Leu Gln Asn Ile Asn Asn Glu Phe Met Glu Ile Thr Glu Lys Ile
65                70                75                80

Gln Met Ala Ser Asp Asn Thr Asn Asp Leu Ile Gln Ser Gly Val Asn
            85                90                95

Thr Arg Leu Leu Thr Ile Gln Ser His Val Gln Asn Tyr Ile Pro Ile
            100                105                110

Ser Leu Thr Gln Gln Met Ser Asp Leu Arg Lys Phe Ile Ser Glu Ile
            115                120                125

Thr Ile Arg Asn Asp Asn Gln Glu Val Leu Pro Gln Arg Ile Thr His
        130                135                140

Asp Val Gly Ile Lys Pro Leu Asn Pro Asp Asp Phe Trp Arg Cys Thr
145                150                155                160

Ser Gly Leu Pro Ser Leu Met Lys Thr Pro Lys Ile Arg Leu Met Pro
            165                170                175

Gly Pro Gly Leu Leu Ala Met Pro Thr Thr Val Asp Gly Cys Ile Arg
            180                185                190

Thr Pro Ser Leu Val Ile Asn Asp Leu Ile Tyr Ala Tyr Thr Ser Asn
            195                200                205

Leu Ile Thr Arg Gly Cys Gln Asp Ile Gly Lys Ser Tyr Gln Val Leu
        210                215                220

Gln Ile Gly Ile Ile Thr Val Asn Ser Asp Leu Val Pro Asp Leu Asn
225                230                235                240

Pro Arg Ile Ser His Thr Phe Asn Ile Asn Asp Asn Arg Lys Ser Cys
            245                250                255

Ser Leu Ala Leu Leu Asn Thr Asp Val Tyr Gln Leu Cys Ser Thr Pro
            260                265                270

Lys Val Asp Glu Arg Ser Asp Tyr Ala Ser Pro Gly Ile Glu Asp Ile
            275                280                285

Val Leu Asp Ile Val Asn Tyr Asp Gly Ser Ile Ser Thr Thr Arg Phe
    290                295                300

Lys Asn Asn Asn Ile Ser Phe Asp Gln Pro Tyr Ala Ala Leu Tyr Pro
305                310                315                320

Ser Val Gly Pro Gly Ile Tyr Tyr Lys Gly Lys Ile Ile Phe Leu Gly
            325                330                335
```

-continued

```
Tyr Gly Gly Leu Glu His Pro Ile Asn Glu Asn Val Ile Cys Asn Thr
            340                 345                 350

Thr Gly Cys Pro Gly Lys Thr Gln Arg Asp Cys Asn Gln Ala Ser His
            355                 360                 365

Ser Pro Trp Phe Ser Asp Arg Arg Met Val Asn Ser Ile Ile Val Val
    370                 375                 380

Asp Lys Gly Leu Asn Ser Ile Pro Lys Leu Lys Val Trp Thr Ile Ser
385                 390                 395                 400

Met Arg Gln Asn Tyr Trp Gly Ser Glu Gly Arg Leu Leu Leu Leu Gly
                405                 410                 415

Asn Lys Ile Tyr Ile Tyr Thr Arg Ser Thr Ser Trp His Ser Lys Leu
            420                 425                 430

Gln Leu Gly Ile Ile Asp Ile Thr Asp Tyr Ser Asp Ile Arg Ile Lys
            435                 440                 445

Trp Thr Trp His Asn Val Leu Ser Arg Pro Gly Asn Asn Glu Cys Pro
    450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Asn Pro Val Ile Thr Tyr Ser Thr Ala
            500                 505                 510

Thr Glu Arg Val Asn Glu Leu Ala Ile Leu Asn Arg Thr Leu Ser Ala
            515                 520                 525

Gly Tyr Thr Thr Thr Ser Cys Ile Thr His Tyr Asn Lys Gly Tyr Cys
    530                 535                 540

Phe His Ile Val Glu Ile Asn His Lys Ser Leu Asn Thr Leu Gln Pro
545                 550                 555                 560

Met Leu Phe Lys Thr Glu Ile Pro Lys Ser Cys Ser
                565                 570
```

```
<210> SEQ ID NO 120
<211> LENGTH: 539
<212> TYPE: PRT
<213> ORGANISM: Human parainfluenza virus type 3

<400> SEQUENCE: 120
```

```
Met Pro Ile Ser Ile Leu Leu Ile Ile Thr Thr Met Ile Met Ala Ser
1               5                   10                  15

His Cys Gln Ile Asp Ile Thr Lys Leu Gln His Val Gly Val Leu Val
            20                  25                  30

Asn Ser Pro Lys Gly Met Lys Ile Ser Gln Asn Phe Glu Thr Arg Tyr
    35                  40                  45

Leu Ile Leu Ser Leu Ile Pro Lys Ile Asp Asp Ser Asn Ser Cys Gly
    50                  55                  60

Asp Gln Gln Ile Lys Gln Tyr Lys Arg Leu Leu Asp Arg Leu Ile Ile
65                  70                  75                  80

Pro Leu Tyr Asp Gly Leu Arg Leu Gln Lys Asp Val Ile Val Ala Asn
                85                  90                  95

Gln Glu Ser Asn Glu Asn Thr Asp Pro Arg Thr Glu Arg Phe Phe Gly
            100                 105                 110

Gly Val Ile Gly Thr Ile Ala Leu Gly Val Ala Thr Ser Ala Gln Ile
            115                 120                 125

Thr Ala Ala Val Ala Leu Val Glu Ala Lys Gln Ala Arg Ser Asp Ile
    130                 135                 140
```

-continued

```
Glu Lys Leu Lys Glu Ala Ile Arg Asp Thr Asn Lys Ala Val Gln Ser
145                 150                 155                 160

Val Gln Ser Ser Val Gly Asn Leu Ile Val Ala Ile Lys Ser Val Gln
                165                 170                 175

Asp Tyr Val Asn Lys Glu Ile Val Pro Ser Ile Ala Arg Leu Gly Cys
                180                 185                 190

Glu Ala Ala Gly Leu Gln Leu Gly Ile Ala Leu Thr Gln His Tyr Ser
            195                 200                 205

Glu Leu Thr Asn Ile Phe Gly Asp Asn Ile Gly Ser Leu Gln Glu Lys
        210                 215                 220

Gly Ile Lys Leu Gln Gly Ile Ala Ser Leu Tyr Arg Thr Asn Ile Thr
225                 230                 235                 240

Glu Ile Phe Thr Thr Ser Thr Val Asp Lys Tyr Asp Ile Tyr Asp Leu
                245                 250                 255

Leu Phe Thr Glu Ser Ile Lys Val Arg Val Ile Asp Val Asp Leu Asn
                260                 265                 270

Asp Tyr Ser Ile Thr Leu Gln Val Arg Leu Pro Leu Leu Thr Arg Leu
            275                 280                 285

Leu Asn Thr Gln Ile Tyr Lys Val Asp Ser Ile Ser Tyr Asn Ile Gln
        290                 295                 300

Asn Arg Glu Trp Tyr Ile Pro Leu Pro Ser His Ile Met Thr Lys Gly
305                 310                 315                 320

Ala Phe Leu Gly Gly Ala Asp Val Lys Glu Cys Ile Glu Ala Phe Ser
                325                 330                 335

Ser Tyr Ile Cys Pro Ser Asp Pro Gly Phe Val Leu Asn His Glu Met
            340                 345                 350

Glu Ser Cys Leu Ser Gly Asn Ile Ser Gln Cys Pro Arg Thr Thr Val
            355                 360                 365

Thr Ser Asp Ile Val Pro Arg Tyr Ala Phe Val Asn Gly Gly Val Val
        370                 375                 380

Ala Asn Cys Ile Thr Thr Thr Cys Thr Cys Asn Gly Ile Gly Asn Arg
385                 390                 395                 400

Ile Asn Gln Pro Pro Asp Gln Gly Val Lys Ile Ile Thr His Lys Glu
                405                 410                 415

Cys Asn Thr Ile Gly Ile Asn Gly Met Leu Phe Asn Thr Asn Lys Glu
            420                 425                 430

Gly Thr Leu Ala Phe Tyr Thr Pro Ala Asp Ile Thr Leu Asn Asn Ser
            435                 440                 445

Val Ala Leu Asp Pro Ile Asp Ile Ser Ile Glu Leu Asn Lys Ala Lys
        450                 455                 460

Ser Asp Leu Glu Glu Ser Lys Glu Trp Ile Arg Arg Ser Asn Gln Lys
465                 470                 475                 480

Leu Asp Ser Ile Gly Ser Trp His Gln Ser Ser Thr Thr Ile Ile Val
            485                 490                 495

Ile Leu Ile Met Met Ile Ile Leu Phe Ile Ile Asn Ile Thr Ile Ile
            500                 505                 510

Thr Ile Ala Ile Lys Tyr Tyr Arg Ile Gln Lys Arg Asn Arg Val Asp
            515                 520                 525

Gln Asn Asp Lys Pro Tyr Val Leu Thr Asn Lys
        530                 535
```

<210> SEQ ID NO 121
<211> LENGTH: 192

<212> TYPE: PRT
<213> ORGANISM: Hepatitis C virus

<400> SEQUENCE: 121

```
Tyr Gln Val Arg Asn Ser Ser Gly Leu Tyr His Val Thr Asn Asp Cys
1               5                   10                  15

Pro Asn Ser Ser Ile Val Tyr Glu Ala Ala Asp Ala Ile Leu His Thr
            20                  25                  30

Pro Gly Cys Val Pro Cys Val Arg Glu Gly Asn Ala Ser Arg Cys Trp
        35                  40                  45

Val Ala Val Thr Pro Thr Val Ala Thr Arg Asp Gly Lys Leu Pro Thr
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Asp
            100                 105                 110

Cys Asn Cys Ser Ile Tyr Pro Gly His Ile Thr Gly His Arg Met Ala
            115                 120                 125

Trp Asp Met Met Met Asn Trp Ser Pro Thr Ala Ala Leu Val Val Ala
        130                 135                 140

Gln Leu Leu Arg Ile Pro Gln Ala Ile Met Asp Met Ile Ala Gly Ala
145                 150                 155                 160

His Trp Gly Val Leu Ala Gly Ile Ala Tyr Phe Ser Met Val Gly Asn
            165                 170                 175

Trp Ala Lys Val Leu Val Val Leu Leu Leu Phe Ala Gly Val Asp Ala
            180                 185                 190
```

<210> SEQ ID NO 122
<211> LENGTH: 363
<212> TYPE: PRT
<213> ORGANISM: Hepatitis C virus

<400> SEQUENCE: 122

```
Glu Thr His Val Thr Gly Gly Ser Ala Gly Arg Thr Thr Ala Gly Leu
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

Ser Leu Asn Thr Gly Trp Leu Ala Gly Leu Phe Tyr Gln His Lys Phe
    50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Pro Arg Pro Cys Gly
            100                 105                 110

Ile Val Pro Ala Lys Ser Val Cys Gly Pro Val Tyr Cys Phe Thr Pro
            115                 120                 125

Ser Pro Val Val Val Gly Thr Thr Asp Arg Ser Gly Ala Pro Thr Tyr
        130                 135                 140

Ser Trp Gly Ala Asn Asp Thr Asp Val Phe Val Leu Asn Asn Thr Arg
145                 150                 155                 160
```

-continued

```
Pro Pro Leu Gly Asn Trp Phe Gly Cys Thr Trp Met Asn Ser Thr Gly
            165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
            195                 200                 205

Ala Thr Tyr Ser Arg Cys Gly Ser Gly Pro Trp Ile Thr Pro Arg Cys
        210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Gln
        275                 280                 285

Trp Gln Val Leu Pro Cys Ser Phe Thr Thr Leu Pro Ala Leu Ser Thr
        290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
                325                 330                 335

Val Leu Leu Phe Leu Leu Leu Ala Asp Ala Arg Val Cys Ser Cys Leu
                340                 345                 350

Trp Met Met Leu Leu Ile Ser Gln Ala Glu Ala
            355                 360
```

```
<210> SEQ ID NO 123
<211> LENGTH: 563
<212> TYPE: PRT
<213> ORGANISM: Autographa californica nuclear polyhedrosis virus

<400> SEQUENCE: 123
```

```
Met Asn Thr Gln Ile Leu Val Phe Ala Leu Val Ala Val Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Thr Val Glu Arg Thr Asn Ile Pro Lys Ile Cys Ser Lys Gly Lys
        50                  55                  60

Arg Thr Thr Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Asn Asp Val Cys Tyr Pro Gly Lys Phe Val Asn
            100                 105                 110

Glu Glu Ala Leu Arg Gln Ile Leu Arg Gly Ser Gly Gly Ile Asp Lys
        115                 120                 125

Glu Thr Met Gly Phe Thr Tyr Ser Gly Ile Arg Thr Asn Gly Thr Thr
        130                 135                 140

Ser Ala Cys Arg Arg Ser Gly Ser Ser Phe Tyr Ala Glu Met Glu Trp
145                 150                 155                 160

Leu Leu Ser Asn Thr Asp Asn Ala Ser Phe Pro Gln Met Thr Lys Ser
                165                 170                 175
```

-continued

```
Tyr Lys Asn Thr Arg Arg Glu Ser Ala Leu Ile Val Trp Gly Ile His
            180                 185                 190

His Ser Gly Ser Thr Thr Glu Gln Thr Lys Leu Tyr Gly Ser Gly Asn
            195                 200                 205

Lys Leu Ile Thr Val Gly Ser Ser Lys Tyr His Gln Ser Phe Val Pro
        210                 215                 220

Ser Pro Gly Thr Arg Pro Gln Ile Asn Gly Gln Ser Gly Arg Ile Asp
225                 230                 235                 240

Phe His Trp Leu Ile Leu Asp Pro Asn Asp Thr Val Thr Phe Ser Phe
                245                 250                 255

Asn Gly Ala Phe Ile Ala Pro Asn Arg Ala Ser Phe Leu Arg Gly Lys
            260                 265                 270

Ser Met Gly Ile Gln Ser Asp Val Gln Val Asp Ala Asn Cys Glu Gly
            275                 280                 285

Glu Cys Tyr His Ser Gly Gly Thr Ile Thr Ser Arg Leu Pro Phe Gln
        290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Pro Ser
                325                 330                 335

Lys Lys Arg Glu Lys Arg Gly Leu Phe Gly Ala Ile Ala Gly Phe Ile
            340                 345                 350

Glu Asn Gly Trp Glu Gly Leu Val Asp Gly Trp Tyr Gly Phe Arg His
            355                 360                 365

Gln Asn Ala Gln Gly Glu Gly Thr Ala Ala Asp Tyr Lys Ser Thr Gln
        370                 375                 380

Ser Ala Ile Asp Gln Ile Thr Gly Lys Leu Asn Arg Leu Ile Glu Lys
385                 390                 395                 400

Thr Asn Gln Gln Phe Glu Leu Ile Asp Asn Glu Phe Thr Glu Val Glu
                405                 410                 415

Lys Gln Ile Gly Asn Leu Ile Asn Trp Thr Lys Asp Phe Ile Thr Glu
            420                 425                 430

Val Trp Ser Tyr Asn Ala Glu Leu Leu Val Ala Met Glu Asn Gln His
            435                 440                 445

Thr Ile Asp Leu Ala Asp Ser Glu Met Asn Lys Leu Tyr Glu Arg Val
        450                 455                 460

Arg Lys Gln Leu Arg Glu Asn Ala Glu Glu Asp Gly Thr Gly Cys Phe
465                 470                 475                 480

Glu Ile Phe His Lys Cys Asp Asp Asp Cys Met Ala Ser Ile Arg Asn
                485                 490                 495

Asn Thr Tyr Asp His Ser Lys Tyr Arg Glu Glu Ala Met Gln Asn Arg
            500                 505                 510

Ile Gln Ile Asp Pro Val Lys Leu Ser Ser Gly Tyr Lys Asp Val Ile
            515                 520                 525

Leu Trp Phe Ser Phe Gly Ala Ser Cys Phe Leu Leu Leu Ala Ile Ala
        530                 535                 540

Val Gly Leu Val Phe Ile Cys Val Lys Asn Gly Asn Met Arg Cys Thr
545                 550                 555                 560

Ile Cys Ile
```

<210> SEQ ID NO 124
<211> LENGTH: 492
<212> TYPE: PRT

-continued

```
<213> ORGANISM: Autographa californica nuclear polyhedrosis virus

<400> SEQUENCE: 124

Ala Glu His Cys Asn Ala Gln Met Lys Thr Gly Pro Tyr Lys Ile Lys
1               5                   10                  15

Asn Leu Asp Ile Thr Pro Pro Lys Glu Thr Leu Gln Lys Asp Val Glu
            20                  25                  30

Ile Thr Ile Val Glu Thr Asp Tyr Asn Glu Asn Val Ile Ile Gly Tyr
        35                  40                  45

Lys Gly Tyr Tyr Gln Ala Tyr Ala Tyr Asn Gly Gly Ser Leu Asp Pro
    50                  55                  60

Asn Thr Arg Val Glu Glu Thr Met Lys Thr Leu Asn Val Gly Lys Glu
65                  70                  75                  80

Asp Leu Leu Met Trp Ser Ile Arg Gln Gln Cys Glu Val Gly Glu Glu
                85                  90                  95

Leu Ile Asp Arg Trp Gly Ser Asp Ser Asp Asp Cys Phe Arg Asp Asn
            100                 105                 110

Glu Gly Arg Gly Gln Trp Val Lys Gly Lys Glu Leu Val Lys Arg Gln
            115                 120                 125

Asn Asn Asn His Phe Ala His His Thr Cys Asn Lys Ser Trp Arg Cys
    130                 135                 140

Gly Ile Ser Thr Ser Lys Met Tyr Ser Arg Leu Glu Cys Gln Asp Asp
145                 150                 155                 160

Thr Asp Glu Cys Gln Val Tyr Ile Leu Asp Ala Glu Gly Asn Pro Ile
                165                 170                 175

Asn Val Thr Val Asp Thr Val Leu His Arg Asp Gly Val Ser Met Ile
            180                 185                 190

Leu Lys Gln Lys Ser Thr Phe Thr Thr Arg Gln Ile Lys Ala Ala Cys
            195                 200                 205

Leu Leu Ile Lys Asp Asp Lys Asn Asn Pro Glu Ser Val Thr Arg Glu
    210                 215                 220

His Cys Leu Ile Asp Asn Asp Ile Tyr Asp Leu Ser Lys Asn Thr Trp
225                 230                 235                 240

Asn Cys Lys Phe Asn Arg Cys Ile Lys Arg Lys Val Glu His Arg Val
                245                 250                 255

Lys Lys Arg Pro Pro Thr Trp Arg His Asn Val Arg Ala Lys Tyr Thr
            260                 265                 270

Glu Gly Asp Thr Ala Thr Lys Gly Asp Leu Met His Ile Gln Glu Glu
            275                 280                 285

Leu Met Tyr Glu Asn Asp Leu Leu Lys Met Asn Ile Glu Leu Met His
    290                 295                 300

Ala His Ile Asn Lys Leu Asn Asn Met Leu His Asp Leu Ile Val Ser
305                 310                 315                 320

Val Ala Lys Val Asp Glu Arg Leu Ile Gly Asn Leu Met Asn Asn Ser
            325                 330                 335

Val Ser Ser Thr Phe Leu Ser Asp Asp Thr Phe Leu Leu Met Pro Cys
            340                 345                 350

Thr Asn Pro Pro Ala His Thr Ser Asn Cys Tyr Asn Asn Ser Ile Tyr
            355                 360                 365

Lys Glu Gly Arg Trp Val Ala Asn Thr Asp Ser Ser Gln Cys Ile Asp
    370                 375                 380

Phe Ser Asn Tyr Lys Glu Leu Ala Ile Asp Asp Asp Val Glu Phe Trp
385                 390                 395                 400
```

-continued

```
Ile Pro Thr Ile Gly Asn Thr Thr Tyr His Asp Ser Trp Lys Asp Ala
            405                 410                 415

Ser Gly Trp Ser Phe Ile Ala Gln Gln Lys Ser Asn Leu Ile Thr Thr
            420             425                 430

Met Glu Asn Thr Lys Phe Gly Gly Val Gly Thr Ser Leu Ser Asp Ile
            435             440                 445

Thr Ser Met Ala Glu Gly Glu Leu Ala Ala Lys Leu Thr Ser Phe Met
    450             455                 460

Phe Gly His Val Val Asn Phe Val Ile Ile Leu Ile Val Ile Leu Phe
465             470                 475                 480

Leu Tyr Cys Met Ile Arg Asn Arg Asn Arg Gln Tyr
                485             490
```

```
<210> SEQ ID NO 125
<211> LENGTH: 617
<212> TYPE: PRT
<213> ORGANISM: Measles virus

<400> SEQUENCE: 125

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
            35              40                  45

Leu Ile Gly Leu Leu Ala Ile Ala Gly Ile Arg Leu His Arg Ala Ala
    50              55                  60

Ile Tyr Thr Ala Glu Ile His Lys Ser Leu Ser Thr Asn Leu Asp Val
65              70                  75                  80

Thr Asn Ser Ile Glu His Gln Val Lys Asp Val Leu Thr Pro Leu Phe
            85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
            115                 120                 125

Arg Glu Tyr Asp Phe Arg Asp Leu Thr Trp Cys Ile Asn Pro Pro Glu
            130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
            165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
            195                 200                 205

Tyr Leu Ser Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Gly Ser Glu Leu Ser Gln Leu Ser Met Tyr Arg Val Phe Glu
            245                 250                 255

Val Gly Val Ile Arg Asn Pro Gly Leu Gly Ala Pro Val Phe His Met
            260                 265                 270

Thr Asn Tyr Phe Glu Gln Pro Val Ser Asn Asp Leu Ser Asn Cys Met
            275                 280                 285
```

-continued

```
Val Ala Leu Gly Glu Leu Lys Leu Ala Ala Leu Cys His Gly Gly Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
                340                 345                 350

Ser His Arg Gly Val Ile Ala Asp Asn Gln Ala Lys Trp Ala Val Pro
            355                 360                 365

Thr Thr Arg Thr Asp Asp Lys Leu Arg Met Glu Thr Cys Phe Gln Gln
    370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
                420                 425                 430

Pro Leu Ile Thr His Gly Ser Gly Met Asp Leu Tyr Lys Ser Asn His
            435                 440                 445

Asn Asn Val Tyr Trp Leu Thr Ile Pro Pro Met Lys Asn Leu Ala Leu
    450                 455                 460

Gly Val Ile Asn Thr Leu Glu Trp Ile Pro Arg Phe Lys Val Ser Pro
465                 470                 475                 480

Tyr Leu Phe Thr Val Pro Ile Lys Glu Ala Gly Glu Asp Cys His Ala
                485                 490                 495

Pro Thr Tyr Leu Pro Ala Glu Val Asp Gly Asp Val Lys Leu Ser Ser
                500                 505                 510

Asn Leu Val Ile Leu Pro Gly Gln Asp Leu Gln Tyr Val Leu Ala Thr
            515                 520                 525

Tyr Asp Thr Ser Arg Val Glu His Ala Val Val Tyr Tyr Val Tyr Ser
    530                 535                 540

Pro Ser Arg Ser Phe Ser Tyr Phe Tyr Pro Phe Arg Leu Pro Ile Lys
545                 550                 555                 560

Gly Ile Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
            580                 585                 590

His Ile Thr His Ser Gly Met Val Gly Met Gly Val Ser Cys Thr Val
            595                 600                 605

Thr Arg Glu Asp Gly Thr Asn Ser Arg
    610                 615
```

```
<210> SEQ ID NO 126
<211> LENGTH: 553
<212> TYPE: PRT
<213> ORGANISM: Measles virus

<400> SEQUENCE: 126
```

```
Met Ser Ile Met Gly Leu Lys Val Asn Val Ser Ala Ile Phe Met Ala
1                   5                   10                  15

Val Leu Leu Thr Leu Gln Thr Pro Thr Gly Gln Ile His Trp Gly Asn
                20                  25                  30

Leu Ser Lys Ile Gly Val Val Gly Ile Gly Ser Ala Ser Tyr Lys Val
```

-continued

```
               35                    40                    45

Met Thr Arg Ser Ser His Gln Ser Leu Val Ile Lys Leu Met Pro Asn
        50                    55                    60

Ile Thr Leu Leu Asn Asn Cys Thr Arg Val Glu Ile Ala Glu Tyr Arg
65                    70                    75                    80

Arg Leu Leu Arg Thr Val Leu Glu Pro Ile Arg Asp Ala Leu Asn Ala
                85                    90                    95

Met Thr Gln Asn Ile Arg Pro Val Gln Ser Val Ala Ser Ser Arg Arg
                100                   105                   110

His Lys Arg Phe Ala Gly Val Val Leu Ala Gly Ala Ala Leu Gly Val
                115                   120                   125

Ala Thr Ala Ala Gln Ile Thr Ala Gly Ile Ala Leu His Gln Ser Met
        130                   135                   140

Leu Asn Ser Gln Ala Ile Asp Asn Leu Arg Ala Ser Leu Glu Thr Thr
145                   150                   155                   160

Asn Gln Ala Ile Glu Thr Ile Arg Gln Ala Gly Gln Glu Met Ile Leu
                165                   170                   175

Ala Val Gln Gly Val Gln Asp Tyr Ile Asn Asn Glu Leu Ile Pro Ser
                180                   185                   190

Met Asn Gln Leu Ser Cys Asp Leu Ile Gly Gln Lys Leu Gly Leu Lys
                195                   200                   205

Leu Leu Arg Tyr Tyr Thr Glu Ile Leu Ser Leu Phe Gly Pro Ser Leu
        210                   215                   220

Arg Asp Pro Ile Ser Ala Glu Ile Ser Ile Gln Ala Leu Ser Tyr Ala
225                   230                   235                   240

Leu Gly Gly Asp Ile Asn Lys Val Leu Glu Lys Leu Gly Tyr Ser Gly
                245                   250                   255

Gly Asp Leu Leu Gly Ile Leu Glu Ser Gly Gly Ile Lys Ala Arg Ile
                260                   265                   270

Thr His Val Asp Thr Glu Ser Tyr Phe Ile Val Leu Ser Ile Ala Tyr
                275                   280                   285

Pro Thr Leu Ser Glu Ile Lys Gly Val Ile Val His Arg Leu Glu Gly
        290                   295                   300

Val Ser Tyr Asn Ile Gly Ser Gln Glu Trp Tyr Thr Thr Val Pro Lys
305                   310                   315                   320

Tyr Val Ala Thr Gln Gly Tyr Leu Ile Ser Asn Phe Asp Glu Ser Ser
                325                   330                   335

Cys Thr Phe Met Pro Glu Gly Thr Val Cys Ser Gln Asn Ala Leu Tyr
                340                   345                   350

Pro Met Ser Pro Leu Leu Gln Glu Cys Leu Arg Gly Tyr Thr Lys Ser
                355                   360                   365

Cys Ala Arg Thr Leu Val Ser Gly Ser Phe Gly Asn Arg Phe Ile Leu
                370                   375                   380

Ser Gln Gly Asn Leu Ile Ala Asn Cys Ala Ser Ile Leu Cys Lys Cys
385                   390                   395                   400

Tyr Thr Thr Gly Thr Ile Ile Asn Gln Asp Pro Asp Lys Ile Leu Thr
                405                   410                   415

Tyr Ile Ala Ala Asp His Cys Pro Val Val Glu Val Asn Gly Val Thr
                420                   425                   430

Ile Gln Val Gly Ser Arg Arg Tyr Pro Asp Ala Val Tyr Leu His Arg
                435                   440                   445

Ile Asp Leu Gly Pro Pro Ile Ser Leu Glu Arg Leu Asp Val Gly Thr
        450                   455                   460
```

```
Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
                485                 490                 495

Ser Ile Val Tyr Ile Leu Ile Ala Val Cys Leu Gly Gly Leu Ile Gly
                500                 505                 510

Ile Pro Ala Leu Ile Cys Cys Cys Arg Gly Arg Cys Asn Lys Lys Gly
            515                 520                 525

Glu Gln Val Gly Met Ser Arg Pro Gly Leu Lys Pro Asp Leu Thr Gly
        530                 535                 540

Thr Ser Lys Ser Tyr Val Arg Ser Leu
545                 550

<210> SEQ ID NO 127
<211> LENGTH: 7
<212> TYPE: PRT
<213> ORGANISM: Artificial sequence
<220> FEATURE:
<223> OTHER INFORMATION: synthetic sequence

<400> SEQUENCE: 127

Glu Asn Leu Tyr Thr Gln Ser
1               5

<210> SEQ ID NO 128
<211> LENGTH: 5
<212> TYPE: PRT
<213> ORGANISM: Artificial sequence
<220> FEATURE:
<223> OTHER INFORMATION: synthetic sequence

<400> SEQUENCE: 128

Asp Asp Asp Asp Lys
1               5

<210> SEQ ID NO 129
<211> LENGTH: 4
<212> TYPE: PRT
<213> ORGANISM: Artificial sequence
<220> FEATURE:
<223> OTHER INFORMATION: synthetic sequence

<400> SEQUENCE: 129

Leu Val Pro Arg
1

<210> SEQ ID NO 130
<211> LENGTH: 8
<212> TYPE: PRT
<213> ORGANISM: Artificial sequence
<220> FEATURE:
<223> OTHER INFORMATION: synthetic sequence

<400> SEQUENCE: 130

Leu Glu Val Leu Phe Gln Gly Pro
1               5

<210> SEQ ID NO 131
<211> LENGTH: 10
<212> TYPE: PRT
<213> ORGANISM: Artificial sequence
<220> FEATURE:
<223> OTHER INFORMATION: synthetic sequence
```

```
<400> SEQUENCE: 131

Cys Gly Leu Val Pro Ala Gly Ser Gly Pro
1               5                   10

<210> SEQ ID NO 132
<211> LENGTH: 12
<212> TYPE: PRT
<213> ORGANISM: Artificial sequence
<220> FEATURE:
<223> OTHER INFORMATION: synthetic sequence

<400> SEQUENCE: 132

Ser Leu Leu Lys Ser Arg Met Val Pro Asn Phe Asn
1               5                   10

<210> SEQ ID NO 133
<211> LENGTH: 12
<212> TYPE: PRT
<213> ORGANISM: Artificial sequence
<220> FEATURE:
<223> OTHER INFORMATION: synthetic sequence

<400> SEQUENCE: 133

Ser Leu Leu Ile Ala Arg Arg Met Pro Asn Phe Asn
1               5                   10

<210> SEQ ID NO 134
<211> LENGTH: 12
<212> TYPE: PRT
<213> ORGANISM: Artificial sequence
<220> FEATURE:
<223> OTHER INFORMATION: synthetic sequence

<400> SEQUENCE: 134

Ser Lys Leu Val Gln Ala Ser Ala Ser Gly Val Asn
1               5                   10

<210> SEQ ID NO 135
<211> LENGTH: 12
<212> TYPE: PRT
<213> ORGANISM: Artificial sequence
<220> FEATURE:
<223> OTHER INFORMATION: synthetic sequence

<400> SEQUENCE: 135

Ser Ser Tyr Leu Lys Ala Ser Asp Ala Pro Asp Asn
1               5                   10

<210> SEQ ID NO 136
<211> LENGTH: 12
<212> TYPE: PRT
<213> ORGANISM: Artificial sequence
<220> FEATURE:
<223> OTHER INFORMATION: synthetic sequence

<400> SEQUENCE: 136

Arg Pro Lys Pro Gln Gln Phe Phe Gly Leu Met Asn
1               5                   10

<210> SEQ ID NO 137
<211> LENGTH: 12
<212> TYPE: PRT
<213> ORGANISM: Artificial sequence
<220> FEATURE:
<223> OTHER INFORMATION: synthetic sequence

<400> SEQUENCE: 137
```

Ser Leu Arg Pro Leu Ala Leu Trp Arg Ser Phe Asn
1               5                   10

<210> SEQ ID NO 138
<211> LENGTH: 12
<212> TYPE: PRT
<213> ORGANISM: Artificial sequence
<220> FEATURE:
<223> OTHER INFORMATION: synthetic sequence

<400> SEQUENCE: 138

Ser Pro Gln Gly Ile Ala Gly Gln Arg Asn Phe Asn
1               5                   10

<210> SEQ ID NO 139
<211> LENGTH: 14
<212> TYPE: PRT
<213> ORGANISM: Artificial sequence
<220> FEATURE:
<223> OTHER INFORMATION: synthetic sequence

<400> SEQUENCE: 139

Asp Val Asp Glu Arg Asp Val Arg Gly Phe Ala Ser Phe Leu
1               5                   10

<210> SEQ ID NO 140
<211> LENGTH: 12
<212> TYPE: PRT
<213> ORGANISM: Artificial sequence
<220> FEATURE:
<223> OTHER INFORMATION: synthetic sequence

<400> SEQUENCE: 140

Ser Leu Pro Leu Gly Leu Trp Ala Pro Asn Phe Asn
1               5                   10

<210> SEQ ID NO 141
<211> LENGTH: 12
<212> TYPE: PRT
<213> ORGANISM: Artificial sequence
<220> FEATURE:
<223> OTHER INFORMATION: synthetic sequence

<400> SEQUENCE: 141

Ser Leu Leu Ile Phe Arg Ser Trp Ala Asn Phe Asn
1               5                   10

<210> SEQ ID NO 142
<211> LENGTH: 12
<212> TYPE: PRT
<213> ORGANISM: Artificial sequence
<220> FEATURE:
<223> OTHER INFORMATION: synthetic sequence

<400> SEQUENCE: 142

Ser Gly Val Val Ile Ala Thr Val Ile Val Ile Thr
1               5                   10

<210> SEQ ID NO 143
<211> LENGTH: 12
<212> TYPE: PRT
<213> ORGANISM: Artificial sequence
<220> FEATURE:
<223> OTHER INFORMATION: synthetic sequence

<400> SEQUENCE: 143

-continued

```
Ser Leu Gly Pro Gln Gly Ile Trp Gly Gln Phe Asn
1               5                   10

<210> SEQ ID NO 144
<211> LENGTH: 12
<212> TYPE: PRT
<213> ORGANISM: Artificial sequence
<220> FEATURE:
<223> OTHER INFORMATION: synthetic sequence

<400> SEQUENCE: 144

Lys Lys Ser Pro Gly Arg Val Val Gly Gly Ser Val
1               5                   10

<210> SEQ ID NO 145
<211> LENGTH: 12
<212> TYPE: PRT
<213> ORGANISM: Artificial sequence
<220> FEATURE:
<223> OTHER INFORMATION: synthetic sequence

<400> SEQUENCE: 145

Pro Gln Gly Leu Leu Gly Ala Pro Gly Ile Leu Gly
1               5                   10

<210> SEQ ID NO 146
<211> LENGTH: 31
<212> TYPE: PRT
<213> ORGANISM: Artificial sequence
<220> FEATURE:
<223> OTHER INFORMATION: synthetic sequence

<400> SEQUENCE: 146

His Gly Pro Glu Gly Leu Arg Val Gly Phe Tyr Glu Ser Asp Val Met
1               5                   10                  15

Gly Arg Gly His Ala Arg Leu Val His Val Glu Glu Pro His Thr
            20                  25                  30

<210> SEQ ID NO 147
<211> LENGTH: 12
<212> TYPE: PRT
<213> ORGANISM: Artificial sequence
<220> FEATURE:
<223> OTHER INFORMATION: synthetic sequence

<400> SEQUENCE: 147

Gly Pro Gln Gly Leu Ala Gly Gln Arg Gly Ile Val
1               5                   10

<210> SEQ ID NO 148
<211> LENGTH: 12
<212> TYPE: PRT
<213> ORGANISM: Artificial sequence
<220> FEATURE:
<223> OTHER INFORMATION: synthetic sequence

<400> SEQUENCE: 148

Gly Gly Ser Gly Gln Arg Gly Arg Lys Ala Leu Glu
1               5                   10

<210> SEQ ID NO 149
<211> LENGTH: 12
<212> TYPE: PRT
<213> ORGANISM: Artificial sequence
<220> FEATURE:
<223> OTHER INFORMATION: synthetic sequence
```

```
<400> SEQUENCE: 149

Ser Leu Ser Ala Leu Leu Ser Ser Asp Ile Phe Asn
1               5                   10

<210> SEQ ID NO 150
<211> LENGTH: 12
<212> TYPE: PRT
<213> ORGANISM: Artificial sequence
<220> FEATURE:
<223> OTHER INFORMATION: synthetic sequence

<400> SEQUENCE: 150

Ser Leu Pro Arg Phe Lys Ile Ile Gly Gly Phe Asn
1               5                   10

<210> SEQ ID NO 151
<211> LENGTH: 12
<212> TYPE: PRT
<213> ORGANISM: Artificial sequence
<220> FEATURE:
<223> OTHER INFORMATION: synthetic sequence

<400> SEQUENCE: 151

Ser Leu Leu Gly Ile Ala Val Pro Gly Asn Phe Asn
1               5                   10

<210> SEQ ID NO 152
<211> LENGTH: 12
<212> TYPE: PRT
<213> ORGANISM: Artificial sequence
<220> FEATURE:
<223> OTHER INFORMATION: synthetic sequence

<400> SEQUENCE: 152

Phe Phe Lys Asn Ile Val Thr Pro Arg Thr Pro Pro
1               5                   10

<210> SEQ ID NO 153
<211> LENGTH: 7
<212> TYPE: PRT
<213> ORGANISM: Artificial sequence
<220> FEATURE:
<223> OTHER INFORMATION: synthetic sequence

<400> SEQUENCE: 153

Glu Asn Leu Tyr Phe Gln Ser
1               5

<210> SEQ ID NO 154
<211> LENGTH: 7
<212> TYPE: PRT
<213> ORGANISM: Artificial sequence
<220> FEATURE:
<223> OTHER INFORMATION: synthetic sequence

<400> SEQUENCE: 154

Glu Asn Leu Tyr Phe Gln Pro
1               5

<210> SEQ ID NO 155
<211> LENGTH: 8
<212> TYPE: PRT
<213> ORGANISM: Artificial sequence
<220> FEATURE:
<223> OTHER INFORMATION: synthetic sequence

<400> SEQUENCE: 155
```

-continued

```
Ser Gln Asn Tyr Pro Ile Val Gln
1               5

<210> SEQ ID NO 156
<211> LENGTH: 7
<212> TYPE: PRT
<213> ORGANISM: Artificial sequence
<220> FEATURE:
<223> OTHER INFORMATION: synthetic sequence

<400> SEQUENCE: 156

Glu Asn Ala Tyr Phe Gln Ser
1               5

<210> SEQ ID NO 157
<211> LENGTH: 7
<212> TYPE: PRT
<213> ORGANISM: Artificial sequence
<220> FEATURE:
<223> OTHER INFORMATION: synthetic sequence

<400> SEQUENCE: 157

Glu Asn Leu Arg Phe Gln Ser
1               5

<210> SEQ ID NO 158
<211> LENGTH: 7
<212> TYPE: PRT
<213> ORGANISM: Artificial sequence
<220> FEATURE:
<223> OTHER INFORMATION: synthetic sequence

<400> SEQUENCE: 158

Glu Asn Leu Phe Phe Gln Ser
1               5

<210> SEQ ID NO 159
<211> LENGTH: 7
<212> TYPE: PRT
<213> ORGANISM: Artificial sequence
<220> FEATURE:
<223> OTHER INFORMATION: synthetic sequence

<400> SEQUENCE: 159

Glu Thr Val Arg Phe Gln Ser
1               5

<210> SEQ ID NO 160
<211> LENGTH: 7
<212> TYPE: PRT
<213> ORGANISM: Artificial sequence
<220> FEATURE:
<223> OTHER INFORMATION: synthetic sequence

<400> SEQUENCE: 160

Glu Thr Leu Arg Phe Gln Ser
1               5

<210> SEQ ID NO 161
<211> LENGTH: 7
<212> TYPE: PRT
<213> ORGANISM: Artificial sequence
<220> FEATURE:
<223> OTHER INFORMATION: synthetic sequence

<400> SEQUENCE: 161
```

-continued

```
Glu Thr Ala Arg Phe Gln Ser
1               5

<210> SEQ ID NO 162
<211> LENGTH: 7
<212> TYPE: PRT
<213> ORGANISM: Artificial sequence
<220> FEATURE:
<223> OTHER INFORMATION: synthetic sequence

<400> SEQUENCE: 162

Glu Thr Val Tyr Phe Gln Ser
1               5

<210> SEQ ID NO 163
<211> LENGTH: 7
<212> TYPE: PRT
<213> ORGANISM: Artificial sequence
<220> FEATURE:
<223> OTHER INFORMATION: synthetic sequence

<400> SEQUENCE: 163

Glu Asn Val Tyr Phe Gln Ser
1               5

<210> SEQ ID NO 164
<211> LENGTH: 25
<212> TYPE: DNA
<213> ORGANISM: Artificial sequence
<220> FEATURE:
<223> OTHER INFORMATION: synthetic sequence

<400> SEQUENCE: 164
catcgatctt aagtcgcgac tcgag                                          25

<210> SEQ ID NO 165
<211> LENGTH: 33
<212> TYPE: DNA
<213> ORGANISM: Artificial sequence
<220> FEATURE:
<223> OTHER INFORMATION: synthetic sequence

<400> SEQUENCE: 165
aattctcgag tcgcgactta agatcgatgg tac                                 33

<210> SEQ ID NO 166
<211> LENGTH: 20
<212> TYPE: DNA
<213> ORGANISM: Artificial sequence
<220> FEATURE:
<223> OTHER INFORMATION: synthetic sequence

<400> SEQUENCE: 166
gagtagcgcg agcacagcta                                                20

<210> SEQ ID NO 167
<211> LENGTH: 20
<212> TYPE: DNA
<213> ORGANISM: Artificial sequence
<220> FEATURE:
<223> OTHER INFORMATION: synthetic sequence

<400> SEQUENCE: 167
agagtctctc agctggtaca                                                20

<210> SEQ ID NO 168
```

-continued

```
<211> LENGTH: 20
<212> TYPE: DNA
<213> ORGANISM: Artificial sequence
<220> FEATURE:
<223> OTHER INFORMATION: synthetic sequence

<400> SEQUENCE: 168
gctgaagcac tgcacgccat                                           20

<210> SEQ ID NO 169
<211> LENGTH: 20
<212> TYPE: DNA
<213> ORGANISM: Artificial sequence
<220> FEATURE:
<223> OTHER INFORMATION: synthetic sequence

<400> SEQUENCE: 169
aagtaaaacc tctacaaatg                                           20

<210> SEQ ID NO 170
<211> LENGTH: 20
<212> TYPE: DNA
<213> ORGANISM: Artificial sequence
<220> FEATURE:
<223> OTHER INFORMATION: synthetic sequence

<400> SEQUENCE: 170
gtattactga tattggtggg                                           20

<210> SEQ ID NO 171
<211> LENGTH: 20
<212> TYPE: DNA
<213> ORGANISM: Artificial sequence
<220> FEATURE:
<223> OTHER INFORMATION: synthetic sequence

<400> SEQUENCE: 171
tcacccagtc tagtgcatgc                                           20

<210> SEQ ID NO 172
<211> LENGTH: 20
<212> TYPE: DNA
<213> ORGANISM: Artificial sequence
<220> FEATURE:
<223> OTHER INFORMATION: synthetic sequence

<400> SEQUENCE: 172
gacgcttatc gacgccctaa                                           20

<210> SEQ ID NO 173
<211> LENGTH: 22
<212> TYPE: DNA
<213> ORGANISM: Artificial sequence
<220> FEATURE:
<223> OTHER INFORMATION: synthetic sequence

<400> SEQUENCE: 173
catcactggc atctggactc ca                                        22

<210> SEQ ID NO 174
<211> LENGTH: 24
<212> TYPE: DNA
<213> ORGANISM: Artificial sequence
<220> FEATURE:
<223> OTHER INFORMATION: synthetic sequence

<400> SEQUENCE: 174
```

-continued tgctcttgaa gtccatagac ctca                                            24

<210> SEQ ID NO 175
<211> LENGTH: 33
<212> TYPE: DNA
<213> ORGANISM: Artificial sequence
<220> FEATURE:
<223> OTHER INFORMATION: synthetic sequence

<400> SEQUENCE: 175
gctcttccga tcttgcgggc cttgtcctga ttg                                  33

<210> SEQ ID NO 176
<211> LENGTH: 33
<212> TYPE: DNA
<213> ORGANISM: Artificial sequence
<220> FEATURE:
<223> OTHER INFORMATION: synthetic sequence

<400> SEQUENCE: 176
gctcttccga tctagatcca gccctggact agc                                  33

<210> SEQ ID NO 177
<211> LENGTH: 32
<212> TYPE: DNA
<213> ORGANISM: Artificial sequence
<220> FEATURE:
<223> OTHER INFORMATION: synthetic sequence

<400> SEQUENCE: 177
gctcttccga tctaagctga cagcattcgg gc                                   32

<210> SEQ ID NO 178
<211> LENGTH: 33
<212> TYPE: DNA
<213> ORGANISM: Artificial sequence
<220> FEATURE:
<223> OTHER INFORMATION: synthetic sequence

<400> SEQUENCE: 178
gctcttccga tctgaagtca cggagcgaga gag                                  33

<210> SEQ ID NO 179
<211> LENGTH: 20
<212> TYPE: DNA
<213> ORGANISM: Artificial sequence
<220> FEATURE:
<223> OTHER INFORMATION: synthetic sequence

<400> SEQUENCE: 179
gttcgggcgc cactgctaga                                                 20

<210> SEQ ID NO 180
<211> LENGTH: 22
<212> TYPE: DNA
<213> ORGANISM: Artificial sequence
<220> FEATURE:
<223> OTHER INFORMATION: synthetic sequence

<400> SEQUENCE: 180
ttaagcctca ataaagcttg cc                                              22

<210> SEQ ID NO 181
<211> LENGTH: 21
<212> TYPE: DNA

<210> ORGANISM: Artificial sequence
<220> FEATURE:
<223> OTHER INFORMATION: synthetic sequence

<400> SEQUENCE: 181
tactgacgct ctcgcaccca t                                                    21

<210> SEQ ID NO 182
<211> LENGTH: 33
<212> TYPE: DNA
<213> ORGANISM: Artificial sequence
<220> FEATURE:
<223> OTHER INFORMATION: synthetic sequence

<400> SEQUENCE: 182
gctcttccga tctaggtccg agcagttaac tgg                                       33

<210> SEQ ID NO 183
<211> LENGTH: 31
<212> TYPE: DNA
<213> ORGANISM: Artificial sequence
<220> FEATURE:
<223> OTHER INFORMATION: synthetic sequence

<400> SEQUENCE: 183
gctcttccga tctacttagc gggcgcctag a                                         31

<210> SEQ ID NO 184
<211> LENGTH: 127
<212> TYPE: DNA
<213> ORGANISM: Artificial sequence
<220> FEATURE:
<223> OTHER INFORMATION: synthetic sequence

<400> SEQUENCE: 184
gccacctacg gcaagctgac cctgaagttc atctgcacca ccggcaagct gcccgtgccc          60
tggcccaccc tcgtgaccac cctgacgtac ggcgtgcagt gcttcagccg ctaccccgac         120
cacatga                                                                   127

<210> SEQ ID NO 185
<211> LENGTH: 330
<212> TYPE: DNA
<213> ORGANISM: Artificial sequence
<220> FEATURE:
<223> OTHER INFORMATION: synthetic sequence

<400> SEQUENCE: 185
aagctgacag cattcgggcc gagatgtctc gctccgtggc cttagtggaa gggctaattc          60
actcccaacg aagacaagat ctgctttttg cttgtactgg gtctctctgg ttagaccaga         120
tctgagcctg ggagctctct ggctaactag ggaacccact gcttaagcct caataaagct         180
tgccttgagt gcttcaagta gtgtgtgccc gtctgttgtg tgactctggt aactagagat         240
ccctcagacc cttttagtca gtgtggaaaa tctctagcag tggcgcccga acagggactt         300
gaaagcgaaa gggaaaccag aggagctctc                                          330

<210> SEQ ID NO 186
<211> LENGTH: 317
<212> TYPE: DNA
<213> ORGANISM: Artificial sequence
<220> FEATURE:
<223> OTHER INFORMATION: synthetic sequence

<400> SEQUENCE: 186

```
aagctgacag cattcgggcc gagatgtctc gctccaaggg ctaattcact cccaacgaag       60
acaagatctg cttttgctt gtactgggtc tctctggtta gaccagatct gagcctggga      120
gctctctggc taactaggga acccactgct taagcctcaa taaagcttgc cttgagtgct      180
tcaagtagtg tgtgcccgtc tgttgtgtga ctctggtaac tagagatccc tcagacccttt      240 ttagtcagtg tggaaaatct ctagcagtgg cgcccgaaca gggacttgaa agcgaaaggg      300
aaaccagagg agctctc                                                     317
```

```
<210> SEQ ID NO 187
<211> LENGTH: 279
<212> TYPE: DNA
<213> ORGANISM: Artificial sequence
<220> FEATURE:
<223> OTHER INFORMATION: synthetic sequence

<400> SEQUENCE: 187
aagctgacag cattcgggcc gagatgtctc gctccgtggc cttagctggg tctctctggt       60
tagaccagat ctgagcctgg gagctctctg gctaactagg gaacccactg cttaagcctc      120
aataaagctt gccttgagtg cttcaagtag tgtgtgcccg tctgttgtgt gactctggta      180
actagagatc cctcagaccc ttttagtcag tgtggaaaat ctctagcagt ggcgcccgaa      240
cagggacttg aaagcgaaag ggaaaccaga ggagctctc                             279
```

```
<210> SEQ ID NO 188
<211> LENGTH: 319
<212> TYPE: DNA
<213> ORGANISM: Artificial sequence
<220> FEATURE:
<223> OTHER INFORMATION: synthetic sequence

<400> SEQUENCE: 188
aagctgacag cattcgggcc gagatgtctc gctccgtggc cttaaattca ctcccaacga       60
agacaagatc tgcttttgc ttgtactggg tctctctggt tagaccagat ctgagcctgg      120
gagctctctg gctaactagg gaacccactg cttaagcctc aataaagctt gccttgagtg      180
cttcaagtag tgtgtgcccg tctgttgtgt gactctggta actagagatc cctcagaccc      240
ttttagtcag tgtggaaaat ctctagcagt ggcgcccgaa cagggacttg aaagcgaaag      300
ggaaaccaga ggagctctc                                                   319
```

```
<210> SEQ ID NO 189
<211> LENGTH: 332
<212> TYPE: DNA
<213> ORGANISM: Artificial sequence
<220> FEATURE:
<223> OTHER INFORMATION: synthetic sequence

<400> SEQUENCE: 189
aagctgacag cattcgggcc gagatgtctc gctccgtggc cttagactgg aagggctaat       60
tcactcccaa cgaagacaag atctgctttt tgcttgtact gggtctctct ggttagacca      120
gatctgagcc tgggagctct ctggctaact agggaaccca ctgcttaagc ctcaataaag      180
cttgccttga gtgcttcaag tagtgtgtgc ccgtctgttg tgtgactctg gtaactagag      240
atccctcaga cccttttagt cagtgtggaa aatctctagc agtggcgccc gaacagggac      300
ttgaaagcga aagggaaacc agaggagctc tc                                    332
```

```
<210> SEQ ID NO 190
```

```
<211> LENGTH: 420
<212> TYPE: DNA
<213> ORGANISM: Artificial sequence
<220> FEATURE:
<223> OTHER INFORMATION: synthetic sequence

<400> SEQUENCE: 190
gagagctcct ctggtttccc tttcgctttc aagtccctgt tcgggcgcca ctgctagaga     60
ttttccacac tgactaaaag ggtctgaggg atctctagtt accagagtca cacaacagac    120
gggcacacac tacttgaagc actcaaggca agctttattg aggcttaagc agtgggttcc    180
ctagttagcc agagagctcc caggctcaga tctggtctaa ccagagagac ccagtacaag    240
caaaaagcag atcttgtctt cgttgggagt gaattagccc ttccactgtg ctcgcgctac    300
tctctctttc tggcctggag gctatccagc gtgagtctct cctaccctcc cgctctggtc    360
cttcctctcc cgctctgcac cctctgtggc cctcgctgtg ctctctcgct ccgtgacttc    420

<210> SEQ ID NO 191
<211> LENGTH: 421
<212> TYPE: DNA
<213> ORGANISM: Artificial sequence
<220> FEATURE:
<223> OTHER INFORMATION: synthetic sequence

<400> SEQUENCE: 191
gagagctcct ctggtttccc tttcgctttc aagtccctgt tcgggcgcca ctgctagaga     60
ttttccacac tgactaaaag ggtctgaggg atctctagtt accagagtca cacaacagac    120
gggcacacac tacttgaagc actcaaggca agctttattg aggcttaagc agtgggttcc    180
ctagttagcc agagagctcc caggctcaga tctggtctaa ccagagagac ccagtacaag    240
caaaaagcag atcttgtctt cgttgggagt gaattagccc ttccagctgt gctcgcgcta    300
ctctctcttt ctggcctgga ggctatccag cgtgagtctc tcctaccctc ccgctctggt    360
ccttcctctc ccgctctgca ccctctgtgg ccctcgctgt gctctctcgc tccgtgactt    420
c                                                                    421

<210> SEQ ID NO 192
<211> LENGTH: 425
<212> TYPE: DNA
<213> ORGANISM: Artificial sequence
<220> FEATURE:
<223> OTHER INFORMATION: synthetic sequence

<400> SEQUENCE: 192
gagagctcct ctggtttccc tttcgctttc aagtccctgt tcgggcgcca ctgctagaga     60
ttttccacac tgactaaaag ggtctgaggg atctctagtt accagagtca cacaacagac    120
gggcacacac tacttgaagc actcaaggca agctttattg aggcttaagc agtgggttcc    180
ctagttagcc agagagctcc caggctcaga tctggtctaa ccagagagac ccagtacaag    240
caaaaagcag atcttgtctt cgttgggagt gaattagccc ttccagtttg ctctgctcgc    300
gctactctct ctttctggcc tggaggctat ccagcgtgag tctctcctac cctcccgctc    360
tggtccttcc tctcccgctc tgcaccctct gtggccctcg ctgtgctctc tcgctccgtg    420
acttc                                                                425

<210> SEQ ID NO 193
<211> LENGTH: 422
<212> TYPE: DNA
<213> ORGANISM: Artificial sequence
```

-continued

```
<220> FEATURE:
<223> OTHER INFORMATION: synthetic sequence

<400> SEQUENCE: 193
gagagctcct ctggtttccc tttcgctttc aagtccctgt tcgggcgcca ctgctagaga      60
ttttccacac tgactaaaag ggtctgaggg atctctagtt accagagtca cacaacagac     120
gggcacacac tacttgaagc actcaaggca agctttattg aggcttaagc agtgggttcc     180
ctagttagcc agagagctcc caggctcaga tctggtctaa ccagagagac ccagtacaag     240
caaaaagcag atcttgtctt cgttgggagt gaattagccc ttccagtctg tgctcgcgct     300
actctctctt tctggcctgg aggctatcca gcgtgagtct ctcctaccct cccgctctgg     360
tccttcctct cccgctctgc accctctgtg gccctcgctg tgctctctcg ctccgtgact     420
tc                                                                     422

<210> SEQ ID NO 194
<211> LENGTH: 421
<212> TYPE: DNA
<213> ORGANISM: Artificial sequence
<220> FEATURE:
<223> OTHER INFORMATION: synthetic sequence

<400> SEQUENCE: 194
gagagctcct ctggtttccc tttcgctttc aagtccctgt tcgggcgcca ctgctagaga      60
ttttccacac tgactaaaag ggtctgaggg atctctagtt accagagtca cacaacagac     120
gggcacacac tacttgaagc actcaaggca agctttattg aggcttaagc agtgggttcc     180
ctagttagcc agagagctcc caggctcaga tctggtctaa ccagagagac ccagtacaag     240
caaaaagcag atcttgtctt cgttgggagt gaattagccc ttccagtagt gctcgcgcta     300
ctctctcttt ctggcctgga ggctatccag cgtgagtctc tcctaccctc ccgctctggt     360
ccttcctctc ccgctctgca ccctctgtgg ccctcgctgt gctctctcgc tccgtgactt     420
c                                                                      421

<210> SEQ ID NO 195
<211> LENGTH: 418
<212> TYPE: DNA
<213> ORGANISM: Artificial sequence
<220> FEATURE:
<223> OTHER INFORMATION: synthetic sequence

<400> SEQUENCE: 195
gagagctcct ctggtttccc tttcgctttc aagtccctgt tcgggcgcca ctgctagaga      60
ttttccacac tgactaaaag ggtctgaggg atctctagtt accagagtca cacaacagac     120
gggcacacac tacttgaagc actcaaggca agctttattg aggcttaagc agtgggttcc     180
ctagttagcc agagagctcc caggctcaga tctggtctaa ccagagagac ccagtacaag     240
caaaaagcag atcttgtctt cgttgggagt gaattagccc ttccagtgct cgcgctactc     300
tctctttctg gcctggaggc tatccagcgt gagtctctcc taccctcccg ctctggtcct     360
tcctctcccg ctctgcaccc tctgtggccc tcgctgtgct ctctcgctcc gtgacttc       418

<210> SEQ ID NO 196
<211> LENGTH: 430
<212> TYPE: DNA
<213> ORGANISM: Artificial sequence
<220> FEATURE:
<223> OTHER INFORMATION: synthetic sequence
```

-continued

<400> SEQUENCE: 196

```
gagagctcct ctggtttccc tttcgctttc aagtccctgt tcgggcgcca ctgctagaga      60
ttttccacac tgactaaaag ggtctgaggg atctctagtt accagagtca cacaacagac     120
gggcacacac tacttgaagc actcaaggca agctttattg aggcttaagc agtgggttcc     180
ctagttagcc agagagctcc caggctcaga tctggtctaa ccagagagac ccagtacaag     240
caaaaagcag atcttgtctt cgttgggagt gaattagccc ttccagttgg cgtccctgtg     300
ctcgcgctac tctctctttc tggcctggag gctatccagc gtgagtctct cctaccctcc     360
cgctctggtc cttcctctcc cgctctgcac cctctgtggc cctcgctgtg ctctctcgct     420
ccgtgacttc                                                           430
```

<210> SEQ ID NO 197
<211> LENGTH: 436
<212> TYPE: DNA
<213> ORGANISM: Artificial sequence
<220> FEATURE:
<223> OTHER INFORMATION: synthetic sequence

<400> SEQUENCE: 197

```
gagagctcct ctggtttccc tttcgctttc aagtccctgt tcgggcgcca ctgctagaga      60
ttttccacac tgactaaaag ggtctgaggg atctctagtt accagagtca cacaacagac     120
gggcacatac tacttgaagc actcaaggca agctttattg aggcttaagc agtgggttcc     180
ctagttagcc agagagctcc caggctcaga tctggtctaa ccagagagac ccagtacaag     240
caaaaagcag atcttgtctt cgttgggagt gaattagccc ttccagtgct ccgtggcctt     300
ccagtgctcg cgctactctc tctttctggc ctggaggcta tccagcgtga gtctctccta     360
ccctcccgct ctggtccttc ctctcccgct ctgcaccctc tgtggccctc gctgtgctct     420
ctcgctccgt gacttc                                                    436
```

<210> SEQ ID NO 198
<211> LENGTH: 448
<212> TYPE: DNA
<213> ORGANISM: Artificial sequence
<220> FEATURE:
<223> OTHER INFORMATION: synthetic sequence

<400> SEQUENCE: 198

```
gagagctcct ctggtttccc tttcgctttc aagtccctgt tcgggcgcca ctgctagaga      60
ttttccacac tgactaaaag ggtctgaggg atctctagtt accagagtca cacaacagac     120
gggcacacac tacttgaagc actcaaggca agctttattg aggcttaagc agtgggttcc     180
ctagttagcc agagagctcc caggctcaga tctggtctaa ccagagagac ccagtacaag     240
caaaaagcag atcttgtctt cgttgggagt gaattagccg gctagagccg gctgaggcgg     300
cgctgccgga agtagtagct cgcgctactc tctctttctg gcctggaggc tatccagcgt     360
gagtctctcc taccctcccg ctctggtcct tcctctcccg ctctgcaccc tctgtggccc     420
tcgctgtgct ctctcgctcc gtgacttc                                       448
```

<210> SEQ ID NO 199
<211> LENGTH: 436
<212> TYPE: DNA
<213> ORGANISM: Artificial sequence
<220> FEATURE:
<223> OTHER INFORMATION: synthetic sequence

<400> SEQUENCE: 199

```
gagagctcct ctggtttccc tttcgctttc aagtccctgt tcgggcgcca ctgctagaga      60
ttttccacac tgactaaaag ggtctgaggg atctctagtt accagagtca cacaacagac     120
gggcacacac tacttgaagc actcaaggca agctttattg aggcttaagc agtgggttcc     180
ctagttagcc agagagctcc caggctcaga tctggtctaa ccagagagac ccagtacaag     240
caaaaagcag atcttgtctt cgttgggagt gaattagccc ttccagtgct ccgtggcctt     300
ccagtgctcg cgctactctc tctttctggc ctggaggcta tccagcgtga gtctctccta     360
ccctcccgct ctggtccttc ctctcccgct ctgcaccctc tgtggccctc gctgtgctct     420
ctcgctccgt gacttc                                                     436
```

```
<210> SEQ ID NO 200
<211> LENGTH: 1368
<212> TYPE: PRT
<213> ORGANISM: Streptococcus pyogenes

<400> SEQUENCE: 200

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285
```

-continued

```
Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
    595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
```

```
705              710              715              720

His Glu His Ile Ala Asn Leu Ala Gly Ser Pro Ala Ile Lys Lys Gly
                 725              730              735

Ile Leu Gln Thr Val Lys Val Val Asp Glu Leu Val Lys Val Met Gly
                 740              745              750

Arg His Lys Pro Glu Asn Ile Val Ile Glu Met Ala Arg Glu Asn Gln
             755              760              765

Thr Thr Gln Lys Gly Gln Lys Asn Ser Arg Glu Arg Met Lys Arg Ile
    770              775              780

Glu Glu Gly Ile Lys Glu Leu Gly Ser Gln Ile Leu Lys Glu His Pro
785              790              795              800

Val Glu Asn Thr Gln Leu Gln Asn Glu Lys Leu Tyr Leu Tyr Tyr Leu
                 805              810              815

Gln Asn Gly Arg Asp Met Tyr Val Asp Gln Glu Leu Asp Ile Asn Arg
                 820              825              830

Leu Ser Asp Tyr Asp Val Asp His Ile Val Pro Gln Ser Phe Leu Lys
                 835              840              845

Asp Asp Ser Ile Asp Asn Lys Val Leu Thr Arg Ser Asp Lys Asn Arg
    850              855              860

Gly Lys Ser Asp Asn Val Pro Ser Glu Glu Val Val Lys Lys Met Lys
865              870              875              880

Asn Tyr Trp Arg Gln Leu Leu Asn Ala Lys Leu Ile Thr Gln Arg Lys
                 885              890              895

Phe Asp Asn Leu Thr Lys Ala Glu Arg Gly Gly Leu Ser Glu Leu Asp
                 900              905              910

Lys Ala Gly Phe Ile Lys Arg Gln Leu Val Glu Thr Arg Gln Ile Thr
                 915              920              925

Lys His Val Ala Gln Ile Leu Asp Ser Arg Met Asn Thr Lys Tyr Asp
    930              935              940

Glu Asn Asp Lys Leu Ile Arg Glu Val Lys Val Ile Thr Leu Lys Ser
945              950              955              960

Lys Leu Val Ser Asp Phe Arg Lys Asp Phe Gln Phe Tyr Lys Val Arg
                 965              970              975

Glu Ile Asn Asn Tyr His His Ala His Asp Ala Tyr Leu Asn Ala Val
                 980              985              990

Val Gly Thr Ala Leu Ile Lys Lys  Tyr Pro Lys Leu Glu  Ser Glu Phe
                 995              1000             1005

Val Tyr  Gly Asp Tyr Lys Val  Tyr Asp Val Arg Lys  Met Ile Ala
    1010             1015             1020

Lys Ser  Glu Gln Glu Ile Gly  Lys Ala Thr Ala Lys  Tyr Phe Phe
    1025             1030             1035

Tyr Ser  Asn Ile Met Asn Phe  Phe Lys Thr Glu Ile  Thr Leu Ala
    1040             1045             1050

Asn Gly  Glu Ile Arg Lys Arg  Pro Leu Ile Glu Thr  Asn Gly Glu
    1055             1060             1065

Thr Gly  Glu Ile Val Trp Asp  Lys Gly Arg Asp Phe  Ala Thr Val
    1070             1075             1080

Arg Lys  Val Leu Ser Met Pro  Gln Val Asn Ile Val  Lys Lys Thr
    1085             1090             1095

Glu Val  Gln Thr Gly Gly Phe  Ser Lys Glu Ser Ile  Leu Pro Lys
    1100             1105             1110

Arg Asn  Ser Asp Lys Leu Ile  Ala Arg Lys Lys Asp  Trp Asp Pro
    1115             1120             1125
```

```
Lys Lys Tyr Gly Gly Phe Asp  Ser Pro Thr Val Ala  Tyr Ser Val
    1130              1135                1140

Leu Val Val Ala Lys Val Glu  Lys Gly Lys Ser Lys  Lys Leu Lys
    1145              1150                1155

Ser Val Lys Glu Leu Leu Gly  Ile Thr Ile Met Glu  Arg Ser Ser
    1160              1165                1170

Phe Glu Lys Asn Pro Ile Asp  Phe Leu Glu Ala Lys  Gly Tyr Lys
    1175              1180                1185

Glu Val Lys Lys Asp Leu Ile  Ile Lys Leu Pro Lys  Tyr Ser Leu
    1190              1195                1200

Phe Glu Leu Glu Asn Gly Arg  Lys Arg Met Leu Ala  Ser Ala Gly
    1205              1210                1215

Glu Leu Gln Lys Gly Asn Glu  Leu Ala Leu Pro Ser  Lys Tyr Val
    1220              1225                1230

Asn Phe Leu Tyr Leu Ala Ser  His Tyr Glu Lys Leu  Lys Gly Ser
    1235              1240                1245

Pro Glu Asp Asn Glu Gln Lys  Gln Leu Phe Val Glu  Gln His Lys
    1250              1255                1260

His Tyr Leu Asp Glu Ile Ile  Glu Gln Ile Ser Glu  Phe Ser Lys
    1265              1270                1275

Arg Val Ile Leu Ala Asp Ala  Asn Leu Asp Lys Val  Leu Ser Ala
    1280              1285                1290

Tyr Asn Lys His Arg Asp Lys  Pro Ile Arg Glu Gln  Ala Glu Asn
    1295              1300                1305

Ile Ile His Leu Phe Thr Leu  Thr Asn Leu Gly Ala  Pro Ala Ala
    1310              1315                1320

Phe Lys Tyr Phe Asp Thr Thr  Ile Asp Arg Lys Arg  Tyr Thr Ser
    1325              1330                1335

Thr Lys Glu Val Leu Asp Ala  Thr Leu Ile His Gln  Ser Ile Thr
    1340              1345                1350

Gly Leu Tyr Glu Thr Arg Ile  Asp Leu Ser Gln Leu  Gly Gly Asp
    1355              1360                1365
```

```
<210> SEQ ID NO 201
<211> LENGTH: 1368
<212> TYPE: PRT
<213> ORGANISM: Artificial sequence
<220> FEATURE:
<223> OTHER INFORMATION: synthetic sequence

<400> SEQUENCE: 201
```

```
Met Asp Lys Lys Tyr Ser Ile Gly Leu Ala Ile Gly Thr Asn Ser Val
1               5                  10                 15

Gly Trp Ala Val Ile Thr Asp Glu Tyr Lys Val Pro Ser Lys Lys Phe
            20                 25                 30

Lys Val Leu Gly Asn Thr Asp Arg His Ser Ile Lys Lys Asn Leu Ile
        35                 40                 45

Gly Ala Leu Leu Phe Asp Ser Gly Glu Thr Ala Glu Ala Thr Arg Leu
    50                 55                 60

Lys Arg Thr Ala Arg Arg Arg Tyr Thr Arg Arg Lys Asn Arg Ile Cys
65                 70                 75                 80

Tyr Leu Gln Glu Ile Phe Ser Asn Glu Met Ala Lys Val Asp Asp Ser
                85                 90                 95

Phe Phe His Arg Leu Glu Glu Ser Phe Leu Val Glu Glu Asp Lys Lys
            100                105                110
```

-continued

```
His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
        210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
        515                 520                 525
```

-continued

```
Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
```

-continued

```
945              950              955              960

Lys Leu Val Ser Asp Phe Arg Lys Asp Phe Gln Phe Tyr Lys Val Arg
                965              970              975

Glu Ile Asn Asn Tyr His His Ala His Asp Ala Tyr Leu Asn Ala Val
            980              985              990

Val Gly Thr Ala Leu Ile Lys Lys  Tyr Pro Lys Leu Glu  Ser Glu Phe
            995              1000             1005

Val Tyr  Gly Asp Tyr Lys Val  Tyr Asp Val Arg Lys  Met Ile Ala
    1010             1015             1020

Lys Ser  Glu Gln Glu Ile Gly  Lys Ala Thr Ala Lys  Tyr Phe Phe
    1025             1030             1035

Tyr Ser  Asn Ile Met Asn Phe  Phe Lys Thr Glu Ile  Thr Leu Ala
    1040             1045             1050

Asn Gly  Glu Ile Arg Lys Arg  Pro Leu Ile Glu Thr  Asn Gly Glu
    1055             1060             1065

Thr Gly  Glu Ile Val Trp Asp  Lys Gly Arg Asp Phe  Ala Thr Val
    1070             1075             1080

Arg Lys  Val Leu Ser Met Pro  Gln Val Asn Ile Val  Lys Lys Thr
    1085             1090             1095

Glu Val  Gln Thr Gly Gly Phe  Ser Lys Glu Ser Ile  Leu Pro Lys
    1100             1105             1110

Arg Asn  Ser Asp Lys Leu Ile  Ala Arg Lys Lys Asp  Trp Asp Pro
    1115             1120             1125

Lys Lys  Tyr Gly Gly Phe Asp  Ser Pro Thr Val Ala  Tyr Ser Val
    1130             1135             1140

Leu Val  Val Ala Lys Val Glu  Lys Gly Lys Ser Lys  Lys Leu Lys
    1145             1150             1155

Ser Val  Lys Glu Leu Leu Gly  Ile Thr Ile Met Glu  Arg Ser Ser
    1160             1165             1170

Phe Glu  Lys Asn Pro Ile Asp  Phe Leu Glu Ala Lys  Gly Tyr Lys
    1175             1180             1185

Glu Val  Lys Lys Asp Leu Ile  Ile Lys Leu Pro Lys  Tyr Ser Leu
    1190             1195             1200

Phe Glu  Leu Glu Asn Gly Arg  Lys Arg Met Leu Ala  Ser Ala Gly
    1205             1210             1215

Glu Leu  Gln Lys Gly Asn Glu  Leu Ala Leu Pro Ser  Lys Tyr Val
    1220             1225             1230

Asn Phe  Leu Tyr Leu Ala Ser  His Tyr Glu Lys Leu  Lys Gly Ser
    1235             1240             1245

Pro Glu  Asp Asn Glu Gln Lys  Gln Leu Phe Val Glu  Gln His Lys
    1250             1255             1260

His Tyr  Leu Asp Glu Ile Ile  Glu Gln Ile Ser Glu  Phe Ser Lys
    1265             1270             1275

Arg Val  Ile Leu Ala Asp Ala  Asn Leu Asp Lys Val  Leu Ser Ala
    1280             1285             1290

Tyr Asn  Lys His Arg Asp Lys  Pro Ile Arg Glu Gln  Ala Glu Asn
    1295             1300             1305

Ile Ile  His Leu Phe Thr Leu  Thr Asn Leu Gly Ala  Pro Ala Ala
    1310             1315             1320

Phe Lys  Tyr Phe Asp Thr Thr  Ile Asp Arg Lys Arg  Tyr Thr Ser
    1325             1330             1335

Thr Lys  Glu Val Leu Asp Ala  Thr Leu Ile His Gln  Ser Ile Thr
    1340             1345             1350
```

-continued

```
Gly Leu  Tyr Glu Thr Arg Ile  Asp Leu Ser Gln Leu  Gly Gly Asp
    1355                1360                1365

<210> SEQ ID NO 202
<211> LENGTH: 1368
<212> TYPE: PRT
<213> ORGANISM: Artificial sequence
<220> FEATURE:
<223> OTHER INFORMATION: synthetic sequence

<400> SEQUENCE: 202

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350
```

-continued

```
Asp Gln Ser Lys Asn Gly Tyr Ala Gly Tyr Ile Asp Gly Gly Ala Ser
        355                 360             365

Gln Glu Glu Phe Tyr Lys Phe Ile Lys Pro Ile Leu Glu Lys Met Asp
    370             375             380

Gly Thr Glu Glu Leu Leu Val Lys Leu Asn Arg Glu Asp Leu Leu Arg
385             390             395             400

Lys Gln Arg Thr Phe Asp Asn Gly Ser Ile Pro His Gln Ile His Leu
            405             410             415

Gly Glu Leu His Ala Ile Leu Arg Arg Gln Glu Asp Phe Tyr Pro Phe
            420             425             430

Leu Lys Asp Asn Arg Glu Lys Ile Glu Lys Ile Leu Thr Phe Arg Ile
            435             440             445

Pro Tyr Tyr Val Gly Pro Leu Ala Arg Gly Asn Ser Arg Phe Ala Trp
    450             455             460

Met Thr Arg Lys Ser Glu Glu Thr Ile Thr Pro Trp Asn Phe Glu Glu
465             470             475             480

Val Val Asp Lys Gly Ala Ser Ala Gln Ser Phe Ile Glu Arg Met Thr
            485             490             495

Asn Phe Asp Lys Asn Leu Pro Asn Glu Lys Val Leu Pro Lys His Ser
            500             505             510

Leu Leu Tyr Glu Tyr Phe Thr Val Tyr Asn Glu Leu Thr Lys Val Lys
            515             520             525

Tyr Val Thr Glu Gly Met Arg Lys Pro Ala Phe Leu Ser Gly Glu Gln
    530             535             540

Lys Lys Ala Ile Val Asp Leu Leu Phe Lys Thr Asn Arg Lys Val Thr
545             550             555             560

Val Lys Gln Leu Lys Glu Asp Tyr Phe Lys Lys Ile Glu Cys Phe Asp
            565             570             575

Ser Val Glu Ile Ser Gly Val Glu Asp Arg Phe Asn Ala Ser Leu Gly
            580             585             590

Thr Tyr His Asp Leu Leu Lys Ile Ile Lys Asp Lys Asp Phe Leu Asp
            595             600             605

Asn Glu Glu Asn Glu Asp Ile Leu Glu Asp Ile Val Leu Thr Leu Thr
    610             615             620

Leu Phe Glu Asp Arg Glu Met Ile Glu Glu Arg Leu Lys Thr Tyr Ala
625             630             635             640

His Leu Phe Asp Asp Lys Val Met Lys Gln Leu Lys Arg Arg Arg Tyr
            645             650             655

Thr Gly Trp Gly Arg Leu Ser Arg Lys Leu Ile Asn Gly Ile Arg Asp
            660             665             670

Lys Gln Ser Gly Lys Thr Ile Leu Asp Phe Leu Lys Ser Asp Gly Phe
            675             680             685

Ala Asn Arg Asn Phe Met Gln Leu Ile His Asp Asp Ser Leu Thr Phe
    690             695             700

Lys Glu Asp Ile Gln Lys Ala Gln Val Ser Gly Gln Gly Asp Ser Leu
705             710             715             720

His Glu His Ile Ala Asn Leu Ala Gly Ser Pro Ala Ile Lys Lys Gly
            725             730             735

Ile Leu Gln Thr Val Lys Val Val Asp Glu Leu Val Lys Val Met Gly
            740             745             750

Arg His Lys Pro Glu Asn Ile Val Ile Glu Met Ala Arg Glu Asn Gln
    755             760             765
```

-continued

```
Thr Thr Gln Lys Gly Gln Lys Asn Ser Arg Glu Arg Met Lys Arg Ile
770             775                 780

Glu Glu Gly Ile Lys Glu Leu Gly Ser Gln Ile Leu Lys Glu His Pro
785             790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865             870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
            995             1000                1005

Val Tyr  Gly Asp Tyr Lys Val  Tyr Asp Val Arg Lys  Met Ile Ala
    1010            1015                1020

Lys Ser  Glu Gln Glu Ile Gly  Lys Ala Thr Ala Lys  Tyr Phe Phe
    1025            1030                1035

Tyr Ser  Asn Ile Met Asn Phe  Phe Lys Thr Glu Ile  Thr Leu Ala
    1040            1045                1050

Asn Gly  Glu Ile Arg Lys Arg  Pro Leu Ile Glu Thr  Asn Gly Glu
    1055            1060                1065

Thr Gly  Glu Ile Val Trp Asp  Lys Gly Arg Asp Phe  Ala Thr Val
    1070            1075                1080

Arg Lys  Val Leu Ser Met Pro  Gln Val Asn Ile Val  Lys Lys Thr
    1085            1090                1095

Glu Val  Gln Thr Gly Gly Phe  Ser Lys Glu Ser Ile  Leu Pro Lys
    1100            1105                1110

Arg Asn  Ser Asp Lys Leu Ile  Ala Arg Lys Lys Asp  Trp Asp Pro
    1115            1120                1125

Lys Lys  Tyr Gly Gly Phe Asp  Ser Pro Thr Val Ala  Tyr Ser Val
    1130            1135                1140

Leu Val  Val Ala Lys Val Glu  Lys Gly Lys Ser Lys  Lys Leu Lys
    1145            1150                1155

Ser Val  Lys Glu Leu Leu Gly  Ile Thr Ile Met Glu  Arg Ser Ser
    1160            1165                1170

Phe Glu  Lys Asn Pro Ile Asp  Phe Leu Glu Ala Lys  Gly Tyr Lys
```

-continued

```
       1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245

Pro Glu Asp Asn Glu Gln Lys Gln Leu Phe Val Glu Gln His Lys
    1250            1255            1260

His Tyr Leu Asp Glu Ile Ile Glu Gln Ile Ser Glu Phe Ser Lys
    1265            1270            1275

Arg Val Ile Leu Ala Asp Ala Asn Leu Asp Lys Val Leu Ser Ala
    1280            1285            1290

Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
    1340            1345            1350

Gly Leu Tyr Glu Thr Arg Ile Asp Leu Ser Gln Leu Gly Gly Asp
    1355            1360            1365
```

```
<210> SEQ ID NO 203
<211> LENGTH: 1368
<212> TYPE: PRT
<213> ORGANISM: Artificial sequence
<220> FEATURE:
<223> OTHER INFORMATION: synthetic sequence

<400> SEQUENCE: 203

Met Asp Lys Lys Tyr Ser Ile Gly Leu Ala Ile Gly Thr Asn Ser Val
1               5               10              15

Gly Trp Ala Val Ile Thr Asp Glu Tyr Lys Val Pro Ser Lys Lys Phe
            20              25              30

Lys Val Leu Gly Asn Thr Asp Arg His Ser Ile Lys Lys Asn Leu Ile
        35              40              45

Gly Ala Leu Leu Phe Asp Ser Gly Glu Thr Ala Glu Ala Thr Arg Leu
    50              55              60

Lys Arg Thr Ala Arg Arg Arg Tyr Thr Arg Arg Lys Asn Arg Ile Cys
65              70              75              80

Tyr Leu Gln Glu Ile Phe Ser Asn Glu Met Ala Lys Val Asp Asp Ser
                85              90              95

Phe Phe His Arg Leu Glu Glu Ser Phe Leu Val Glu Glu Asp Lys Lys
            100             105             110

His Glu Arg His Pro Ile Phe Gly Asn Ile Val Asp Glu Val Ala Tyr
        115             120             125

His Glu Lys Tyr Pro Thr Ile Tyr His Leu Arg Lys Lys Leu Val Asp
    130             135             140

Ser Thr Asp Lys Ala Asp Leu Arg Leu Ile Tyr Leu Ala Leu Ala His
145             150             155             160

Met Ile Lys Phe Arg Gly His Phe Leu Ile Glu Gly Asp Leu Asn Pro
```

-continued

```
                    165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590
```

-continued

```
Thr Tyr His Asp Leu Leu Lys Ile Ile Lys Asp Lys Asp Phe Leu Asp
        595             600             605

Asn Glu Glu Asn Glu Asp Ile Leu Glu Asp Ile Val Leu Thr Leu Thr
    610             615             620

Leu Phe Glu Asp Arg Glu Met Ile Glu Glu Arg Leu Lys Thr Tyr Ala
625             630             635             640

His Leu Phe Asp Asp Lys Val Met Lys Gln Leu Lys Arg Arg Arg Tyr
            645             650             655

Thr Gly Trp Gly Arg Leu Ser Arg Lys Leu Ile Asn Gly Ile Arg Asp
            660             665             670

Lys Gln Ser Gly Lys Thr Ile Leu Asp Phe Leu Lys Ser Asp Gly Phe
        675             680             685

Ala Asn Arg Asn Phe Met Gln Leu Ile His Asp Asp Ser Leu Thr Phe
    690             695             700

Lys Glu Asp Ile Gln Lys Ala Gln Val Ser Gly Gln Gly Asp Ser Leu
705             710             715             720

His Glu His Ile Ala Asn Leu Ala Gly Ser Pro Ala Ile Lys Lys Gly
            725             730             735

Ile Leu Gln Thr Val Lys Val Val Asp Glu Leu Val Lys Val Met Gly
            740             745             750

Arg His Lys Pro Glu Asn Ile Val Ile Glu Met Ala Arg Glu Asn Gln
        755             760             765

Thr Thr Gln Lys Gly Gln Lys Asn Ser Arg Glu Arg Met Lys Arg Ile
    770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
            805             810             815

Gln Asn Gly Arg Asp Met Tyr Val Asp Gln Glu Leu Asp Ile Asn Arg
            820             825             830

Leu Ser Asp Tyr Asp Val Asp Ala Ile Val Pro Gln Ser Phe Leu Lys
        835             840             845

Asp Asp Ser Ile Asp Asn Lys Val Leu Thr Arg Ser Asp Lys Asn Arg
    850             855             860

Gly Lys Ser Asp Asn Val Pro Ser Glu Glu Val Val Lys Lys Met Lys
865             870             875             880

Asn Tyr Trp Arg Gln Leu Leu Asn Ala Lys Leu Ile Thr Gln Arg Lys
            885             890             895

Phe Asp Asn Leu Thr Lys Ala Glu Arg Gly Gly Leu Ser Glu Leu Asp
            900             905             910

Lys Ala Gly Phe Ile Lys Arg Gln Leu Val Glu Thr Arg Gln Ile Thr
        915             920             925

Lys His Val Ala Gln Ile Leu Asp Ser Arg Met Asn Thr Lys Tyr Asp
    930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
            965             970             975

Glu Ile Asn Asn Tyr His His Ala His Asp Ala Tyr Leu Asn Ala Val
            980             985             990

Val Gly Thr Ala Leu Ile Lys Lys  Tyr Pro Lys Leu Glu  Ser Glu Phe
        995             1000             1005
```

-continued

```
Val Tyr  Gly Asp Tyr Lys Val  Tyr Asp Val Arg Lys  Met Ile Ala
    1010             1015              1020

Lys Ser  Glu Gln Glu Ile Gly  Lys Ala Thr Ala Lys  Tyr Phe Phe
    1025             1030              1035

Tyr Ser  Asn Ile Met Asn Phe  Phe Lys Thr Glu Ile  Thr Leu Ala
    1040             1045              1050

Asn Gly  Glu Ile Arg Lys Arg  Pro Leu Ile Glu Thr  Asn Gly Glu
    1055             1060              1065

Thr Gly  Glu Ile Val Trp Asp  Lys Gly Arg Asp Phe  Ala Thr Val
    1070             1075              1080

Arg Lys  Val Leu Ser Met Pro  Gln Val Asn Ile Val  Lys Lys Thr
    1085             1090              1095

Glu Val  Gln Thr Gly Gly Phe  Ser Lys Glu Ser Ile  Leu Pro Lys
    1100             1105              1110

Arg Asn  Ser Asp Lys Leu Ile  Ala Arg Lys Lys Asp  Trp Asp Pro
    1115             1120              1125

Lys Lys  Tyr Gly Gly Phe Asp  Ser Pro Thr Val Ala  Tyr Ser Val
    1130             1135              1140

Leu Val  Val Ala Lys Val Glu  Lys Gly Lys Ser Lys  Lys Leu Lys
    1145             1150              1155

Ser Val  Lys Glu Leu Leu Gly  Ile Thr Ile Met Glu  Arg Ser Ser
    1160             1165              1170

Phe Glu  Lys Asn Pro Ile Asp  Phe Leu Glu Ala Lys  Gly Tyr Lys
    1175             1180              1185

Glu Val  Lys Lys Asp Leu Ile  Ile Lys Leu Pro Lys  Tyr Ser Leu
    1190             1195              1200

Phe Glu  Leu Glu Asn Gly Arg  Lys Arg Met Leu Ala  Ser Ala Gly
    1205             1210              1215

Glu Leu  Gln Lys Gly Asn Glu  Leu Ala Leu Pro Ser  Lys Tyr Val
    1220             1225              1230

Asn Phe  Leu Tyr Leu Ala Ser  His Tyr Glu Lys Leu  Lys Gly Ser
    1235             1240              1245

Pro Glu  Asp Asn Glu Gln Lys  Gln Leu Phe Val Glu  Gln His Lys
    1250             1255              1260

His Tyr  Leu Asp Glu Ile Ile  Glu Gln Ile Ser Glu  Phe Ser Lys
    1265             1270              1275

Arg Val  Ile Leu Ala Asp Ala  Asn Leu Asp Lys Val  Leu Ser Ala
    1280             1285              1290

Tyr Asn  Lys His Arg Asp Lys  Pro Ile Arg Glu Gln  Ala Glu Asn
    1295             1300              1305

Ile Ile  His Leu Phe Thr Leu  Thr Asn Leu Gly Ala  Pro Ala Ala
    1310             1315              1320

Phe Lys  Tyr Phe Asp Thr Thr  Ile Asp Arg Lys Arg  Tyr Thr Ser
    1325             1330              1335

Thr Lys  Glu Val Leu Asp Ala  Thr Leu Ile His Gln  Ser Ile Thr
    1340             1345              1350

Gly Leu  Tyr Glu Thr Arg Ile  Asp Leu Ser Gln Leu  Gly Gly Asp
    1355             1360              1365
```

<210> SEQ ID NO 204
<211> LENGTH: 1368
<212> TYPE: PRT
<213> ORGANISM: Artificial sequence
<220> FEATURE:
<223> OTHER INFORMATION: synthetic sequence -continued

```
<400> SEQUENCE: 204

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
        210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
```

-continued

```
                    405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830
```

-continued

```
Leu Ser Asp Tyr Asp Val Asp His Ile Val Pro Gln Ser Phe Leu Ala
        835             840             845

Asp Asp Ser Ile Asp Asn Lys Val Leu Thr Arg Ser Asp Lys Asn Arg
    850             855             860

Gly Lys Ser Asp Asn Val Pro Ser Glu Glu Val Val Lys Lys Met Lys
865             870             875             880

Asn Tyr Trp Arg Gln Leu Leu Asn Ala Lys Leu Ile Thr Gln Arg Lys
            885             890             895

Phe Asp Asn Leu Thr Lys Ala Glu Arg Gly Gly Leu Ser Glu Leu Asp
            900             905             910

Lys Ala Gly Phe Ile Lys Arg Gln Leu Val Glu Thr Arg Gln Ile Thr
        915             920             925

Lys His Val Ala Gln Ile Leu Asp Ser Arg Met Asn Thr Lys Tyr Asp
    930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
            965             970             975

Glu Ile Asn Asn Tyr His His Ala His Asp Ala Tyr Leu Asn Ala Val
            980             985             990

Val Gly Thr Ala Leu Ile Lys Lys  Tyr Pro Ala Leu Glu  Ser Glu Phe
            995             1000            1005

Val Tyr  Gly Asp Tyr Lys Val  Tyr Asp Val Arg Lys  Met Ile Ala
    1010            1015            1020

Lys Ser  Glu Gln Glu Ile Gly  Lys Ala Thr Ala Lys  Tyr Phe Phe
    1025            1030            1035

Tyr Ser  Asn Ile Met Asn Phe  Phe Lys Thr Glu Ile  Thr Leu Ala
    1040            1045            1050

Asn Gly  Glu Ile Arg Lys Ala  Pro Leu Ile Glu Thr  Asn Gly Glu
    1055            1060            1065

Thr Gly  Glu Ile Val Trp Asp  Lys Gly Arg Asp Phe  Ala Thr Val
    1070            1075            1080

Arg Lys  Val Leu Ser Met Pro  Gln Val Asn Ile Val  Lys Lys Thr
    1085            1090            1095

Glu Val  Gln Thr Gly Gly Phe  Ser Lys Glu Ser Ile  Leu Pro Lys
    1100            1105            1110

Arg Asn  Ser Asp Lys Leu Ile  Ala Arg Lys Lys Asp  Trp Asp Pro
    1115            1120            1125

Lys Lys  Tyr Gly Gly Phe Asp  Ser Pro Thr Val Ala  Tyr Ser Val
    1130            1135            1140

Leu Val  Val Ala Lys Val Glu  Lys Gly Lys Ser Lys  Lys Leu Lys
    1145            1150            1155

Ser Val  Lys Glu Leu Leu Gly  Ile Thr Ile Met Glu  Arg Ser Ser
    1160            1165            1170

Phe Glu  Lys Asn Pro Ile Asp  Phe Leu Glu Ala Lys  Gly Tyr Lys
    1175            1180            1185

Glu Val  Lys Lys Asp Leu Ile  Ile Lys Leu Pro Lys  Tyr Ser Leu
    1190            1195            1200

Phe Glu  Leu Glu Asn Gly Arg  Lys Arg Met Leu Ala  Ser Ala Gly
    1205            1210            1215

Glu Leu  Gln Lys Gly Asn Glu  Leu Ala Leu Pro Ser  Lys Tyr Val
    1220            1225            1230
```

-continued

```
Asn Phe Leu Tyr Leu Ala Ser  His Tyr Glu Lys Leu  Lys Gly Ser
    1235             1240            1245

Pro Glu  Asp Asn Glu Gln Lys  Gln Leu Phe Val Glu  Gln His Lys
    1250             1255            1260

His Tyr  Leu Asp Glu Ile Ile  Glu Gln Ile Ser Glu  Phe Ser Lys
    1265             1270            1275

Arg Val  Ile Leu Ala Asp Ala  Asn Leu Asp Lys Val  Leu Ser Ala
    1280             1285            1290

Tyr Asn  Lys His Arg Asp Lys  Pro Ile Arg Glu Gln  Ala Glu Asn
    1295             1300            1305

Ile Ile  His Leu Phe Thr Leu  Thr Asn Leu Gly Ala  Pro Ala Ala
    1310             1315            1320

Phe Lys  Tyr Phe Asp Thr Thr  Ile Asp Arg Lys Arg  Tyr Thr Ser
    1325             1330            1335

Thr Lys  Glu Val Leu Asp Ala  Thr Leu Ile His Gln  Ser Ile Thr
    1340             1345            1350

Gly Leu  Tyr Glu Thr Arg Ile  Asp Leu Ser Gln Leu  Gly Gly Asp
    1355             1360            1365

<210> SEQ ID NO 205
<211> LENGTH: 1367
<212> TYPE: PRT
<213> ORGANISM: Artificial sequence
<220> FEATURE:
<223> OTHER INFORMATION: synthetic sequence

<400> SEQUENCE: 205

Asp Lys Lys Tyr Ser Ile Gly Leu Ala Ile Gly Thr Asn Ser Val Gly
1               5               10              15

Trp Ala Val Ile Thr Asp Glu Tyr Lys Val Pro Ser Lys Lys Phe Lys
            20              25              30

Val Leu Gly Asn Thr Asp Arg His Ser Ile Lys Lys Asn Leu Ile Gly
        35              40              45

Ala Leu Leu Phe Asp Ser Gly Glu Thr Ala Glu Ala Thr Arg Leu Lys
    50              55              60

Arg Thr Ala Arg Arg Arg Tyr Thr Arg Arg Lys Asn Arg Ile Cys Tyr
65              70              75              80

Leu Gln Glu Ile Phe Ser Asn Glu Met Ala Lys Val Asp Asp Ser Phe
            85              90              95

Phe His Arg Leu Glu Glu Ser Phe Leu Val Glu Glu Asp Lys Lys His
            100             105             110

Glu Arg His Pro Ile Phe Gly Asn Ile Val Asp Glu Val Ala Tyr His
            115             120             125

Glu Lys Tyr Pro Thr Ile Tyr His Leu Arg Lys Lys Leu Val Asp Ser
    130             135             140

Thr Asp Lys Ala Asp Leu Arg Leu Ile Tyr Leu Ala Leu Ala His Met
145             150             155             160

Ile Lys Phe Arg Gly His Phe Leu Ile Glu Gly Asp Leu Asn Pro Asp
            165             170             175

Asn Ser Asp Val Asp Lys Leu Phe Ile Gln Leu Val Gln Thr Tyr Asn
            180             185             190

Gln Leu Phe Glu Glu Asn Pro Ile Asn Ala Ser Gly Val Asp Ala Lys
        195             200             205

Ala Ile Leu Ser Ala Arg Leu Ser Lys Ser Arg Arg Leu Glu Asn Leu
    210             215             220
```

-continued

```
Ile Ala Gln Leu Pro Gly Glu Lys Lys Asn Gly Leu Phe Gly Asn Leu
225             230             235             240

Ile Ala Leu Ser Leu Gly Leu Thr Pro Asn Phe Lys Ser Asn Phe Asp
            245             250             255

Leu Ala Glu Asp Ala Lys Leu Gln Leu Ser Lys Asp Thr Tyr Asp Asp
            260             265             270

Asp Leu Asp Asn Leu Leu Ala Gln Ile Gly Asp Gln Tyr Ala Asp Leu
            275             280             285

Phe Leu Ala Ala Lys Asn Leu Ser Asp Ala Ile Leu Leu Ser Asp Ile
            290             295             300

Leu Arg Val Asn Thr Glu Ile Thr Lys Ala Pro Leu Ser Ala Ser Met
305             310             315             320

Ile Lys Arg Tyr Asp Glu His His Gln Asp Leu Thr Leu Leu Lys Ala
                325             330             335

Leu Val Arg Gln Gln Leu Pro Glu Lys Tyr Lys Glu Ile Phe Phe Asp
                340             345             350

Gln Ser Lys Asn Gly Tyr Ala Gly Tyr Ile Asp Gly Gly Ala Ser Gln
            355             360             365

Glu Glu Phe Tyr Lys Phe Ile Lys Pro Ile Leu Glu Lys Met Asp Gly
            370             375             380

Thr Glu Glu Leu Leu Val Lys Leu Asn Arg Glu Asp Leu Leu Arg Lys
385             390             395             400

Gln Arg Thr Phe Asp Asn Gly Ser Ile Pro His Gln Ile His Leu Gly
                405             410             415

Glu Leu His Ala Ile Leu Arg Arg Gln Glu Asp Phe Tyr Pro Phe Leu
                420             425             430

Lys Asp Asn Arg Glu Lys Ile Glu Lys Ile Leu Thr Phe Arg Ile Pro
            435             440             445

Tyr Tyr Val Gly Pro Leu Ala Arg Gly Asn Ser Arg Phe Ala Trp Met
            450             455             460

Thr Arg Lys Ser Glu Glu Thr Ile Thr Pro Trp Asn Phe Glu Glu Val
465             470             475             480

Val Asp Lys Gly Ala Ser Ala Gln Ser Phe Ile Glu Arg Met Thr Ala
                485             490             495

Phe Asp Lys Asn Leu Pro Asn Glu Lys Val Leu Pro Lys His Ser Leu
            500             505             510

Leu Tyr Glu Tyr Phe Thr Val Tyr Asn Glu Leu Thr Lys Val Lys Tyr
            515             520             525

Val Thr Glu Gly Met Arg Lys Pro Ala Phe Leu Ser Gly Glu Gln Lys
            530             535             540

Lys Ala Ile Val Asp Leu Leu Phe Lys Thr Asn Arg Lys Val Thr Val
545             550             555             560

Lys Gln Leu Lys Glu Asp Tyr Phe Lys Lys Ile Glu Cys Phe Asp Ser
                565             570             575

Val Glu Ile Ser Gly Val Glu Asp Arg Phe Asn Ala Ser Leu Gly Thr
            580             585             590

Tyr His Asp Leu Leu Lys Ile Ile Lys Asp Lys Asp Phe Leu Asp Asn
            595             600             605

Glu Glu Asn Glu Asp Ile Leu Glu Asp Ile Val Leu Thr Leu Thr Leu
            610             615             620

Phe Glu Asp Arg Glu Met Ile Glu Glu Arg Leu Lys Thr Tyr Ala His
625             630             635             640

Leu Phe Asp Asp Lys Val Met Lys Gln Leu Lys Arg Arg Arg Tyr Thr
```

-continued

```
                  645                    650                    655

Gly Trp Gly Ala Leu Ser Arg Lys Leu Ile Asn Gly Ile Arg Asp Lys
              660                    665                    670

Gln Ser Gly Lys Thr Ile Leu Asp Phe Leu Lys Ser Asp Gly Phe Ala
              675                    680                    685

Asn Arg Asn Phe Met Ala Leu Ile His Asp Asp Ser Leu Thr Phe Lys
              690                    695                    700

Glu Asp Ile Gln Lys Ala Gln Val Ser Gly Gln Gly Asp Ser Leu His
705                    710                    715                    720

Glu His Ile Ala Asn Leu Ala Gly Ser Pro Ala Ile Lys Lys Gly Ile
                  725                    730                    735

Leu Gln Thr Val Lys Val Val Asp Glu Leu Val Lys Val Met Gly Arg
              740                    745                    750

His Lys Pro Glu Asn Ile Val Ile Glu Met Ala Arg Glu Asn Gln Thr
              755                    760                    765

Thr Gln Lys Gly Gln Lys Asn Ser Arg Glu Arg Met Lys Arg Ile Glu
              770                    775                    780

Glu Gly Ile Lys Glu Leu Gly Ser Gln Ile Leu Lys Glu His Pro Val
785                    790                    795                    800

Glu Asn Thr Gln Leu Gln Asn Glu Lys Leu Tyr Leu Tyr Tyr Leu Gln
                  805                    810                    815

Asn Gly Arg Asp Met Tyr Val Asp Gln Glu Leu Asp Ile Asn Arg Leu
                  820                    825                    830

Ser Asp Tyr Asp Val Asp His Ile Val Pro Gln Ser Phe Leu Lys Asp
                  835                    840                    845

Asp Ser Ile Asp Asn Lys Val Leu Thr Arg Ser Asp Lys Asn Arg Gly
              850                    855                    860

Lys Ser Asp Asn Val Pro Ser Glu Glu Val Val Lys Lys Met Lys Asn
865                    870                    875                    880

Tyr Trp Arg Gln Leu Leu Asn Ala Lys Leu Ile Thr Gln Arg Lys Phe
                  885                    890                    895

Asp Asn Leu Thr Lys Ala Glu Arg Gly Gly Leu Ser Glu Leu Asp Lys
                  900                    905                    910

Ala Gly Phe Ile Lys Arg Gln Leu Val Glu Thr Arg Ala Ile Thr Lys
              915                    920                    925

His Val Ala Gln Ile Leu Asp Ser Arg Met Asn Thr Lys Tyr Asp Glu
              930                    935                    940

Asn Asp Lys Leu Ile Arg Glu Val Lys Val Ile Thr Leu Lys Ser Lys
945                    950                    955                    960

Leu Val Ser Asp Phe Arg Lys Asp Phe Gln Phe Tyr Lys Val Arg Glu
                  965                    970                    975

Ile Asn Asn Tyr His His Ala His Asp Ala Tyr Leu Asn Ala Val Val
                  980                    985                    990

Gly Thr Ala Leu Ile Lys Lys Tyr  Pro Lys Leu Glu Ser  Glu Phe Val
              995                    1000                   1005

Tyr Gly  Asp Tyr Lys Val Tyr  Asp Val Arg Lys Met  Ile Ala Lys
          1010                   1015                   1020

Ser Glu  Gln Glu Ile Gly Lys  Ala Thr Ala Lys Tyr  Phe Phe Tyr
          1025                   1030                   1035

Ser Asn  Ile Met Asn Phe Phe  Lys Thr Glu Ile Thr  Leu Ala Asn
          1040                   1045                   1050

Gly Glu  Ile Arg Lys Arg Pro  Leu Ile Glu Thr Asn  Gly Glu Thr
          1055                   1060                   1065
```

-continued

```
Gly Glu  Ile Val Trp Asp Lys  Gly Arg Asp Phe Ala  Thr Val Arg
    1070                1075                1080

Lys Val  Leu Ser Met Pro Gln  Val Asn Ile Val Lys  Lys Thr Glu
    1085                1090                1095

Val Gln  Thr Gly Gly Phe Ser  Lys Glu Ser Ile Leu  Pro Lys Arg
    1100                1105                1110

Asn Ser  Asp Lys Leu Ile Ala  Arg Lys Lys Asp Trp  Asp Pro Lys
    1115                1120                1125

Lys Tyr  Gly Gly Phe Asp Ser  Pro Thr Val Ala Tyr  Ser Val Leu
    1130                1135                1140

Val Val  Ala Lys Val Glu Lys  Gly Lys Ser Lys Lys  Leu Lys Ser
    1145                1150                1155

Val Lys  Glu Leu Leu Gly Ile  Thr Ile Met Glu Arg  Ser Ser Phe
    1160                1165                1170

Glu Lys  Asn Pro Ile Asp Phe  Leu Glu Ala Lys Gly  Tyr Lys Glu
    1175                1180                1185

Val Lys  Lys Asp Leu Ile Ile  Lys Leu Pro Lys Tyr  Ser Leu Phe
    1190                1195                1200

Glu Leu  Glu Asn Gly Arg Lys  Arg Met Leu Ala Ser  Ala Gly Glu
    1205                1210                1215

Leu Gln  Lys Gly Asn Glu Leu  Ala Leu Pro Ser Lys  Tyr Val Asn
    1220                1225                1230

Phe Leu  Tyr Leu Ala Ser His  Tyr Glu Lys Leu Lys  Gly Ser Pro
    1235                1240                1245

Glu Asp  Asn Glu Gln Lys Gln  Leu Phe Val Glu Gln  His Lys His
    1250                1255                1260

Tyr Leu  Asp Glu Ile Ile Glu  Gln Ile Ser Glu Phe  Ser Lys Arg
    1265                1270                1275

Val Ile  Leu Ala Asp Ala Asn  Leu Asp Lys Val Leu  Ser Ala Tyr
    1280                1285                1290

Asn Lys  His Arg Asp Lys Pro  Ile Arg Glu Gln Ala  Glu Asn Ile
    1295                1300                1305

Ile His  Leu Phe Thr Leu Thr  Asn Leu Gly Ala Pro  Ala Ala Phe
    1310                1315                1320

Lys Tyr  Phe Asp Thr Thr Ile  Asp Arg Lys Arg Tyr  Thr Ser Thr
    1325                1330                1335

Lys Glu  Val Leu Asp Ala Thr  Leu Ile His Gln Ser  Ile Thr Gly
    1340                1345                1350

Leu Tyr  Glu Thr Arg Ile Asp  Leu Ser Gln Leu Gly  Gly Asp
    1355                1360                1365
```

<210> SEQ ID NO 206
<211> LENGTH: 1053
<212> TYPE: PRT
<213> ORGANISM: Staphylococcus aureus

<400> SEQUENCE: 206

```
Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
```

-continued

```
        50                  55                  60
Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
            115                 120                 125

Gly Asn Glu Leu Ser Thr Lys Glu Gln Ile Ser Arg Asn Ser Lys Ala
        130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
            195                 200                 205

Arg Thr Tyr Tyr Glu Gly Pro Gly Glu Gly Ser Pro Phe Gly Trp Lys
        210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
            275                 280                 285

Lys Gln Lys Lys Lys Pro Thr Leu Lys Gln Ile Ala Lys Glu Ile Leu
        290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
        370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
        450                 455                 460

Ile Lys Lys Tyr Gly Leu Pro Asn Asp Ile Ile Ile Glu Leu Ala Arg
465                 470                 475                 480
```

```
Glu Lys Asn Ser Lys Asp Ala Gln Lys Met Ile Asn Glu Met Gln Lys
            485             490             495

Arg Asn Arg Gln Thr Asn Glu Arg Ile Glu Glu Ile Ile Arg Thr Thr
            500             505             510

Gly Lys Glu Asn Ala Lys Tyr Leu Ile Glu Lys Ile Lys Leu His Asp
            515             520             525

Met Gln Glu Gly Lys Cys Leu Tyr Ser Leu Glu Ala Ile Pro Leu Glu
    530             535             540

Asp Leu Leu Asn Asn Pro Phe Asn Tyr Glu Val Asp His Ile Ile Pro
545             550             555             560

Arg Ser Val Ser Phe Asp Asn Ser Phe Asn Asn Lys Val Leu Val Lys
            565             570             575

Gln Glu Glu Asn Ser Lys Lys Gly Asn Arg Thr Pro Phe Gln Tyr Leu
            580             585             590

Ser Ser Ser Asp Ser Lys Ile Ser Tyr Glu Thr Phe Lys Lys His Ile
            595             600             605

Leu Asn Leu Ala Lys Gly Lys Gly Arg Ile Ser Lys Thr Lys Lys Glu
            610             615             620

Tyr Leu Leu Glu Glu Arg Asp Ile Asn Arg Phe Ser Val Gln Lys Asp
625             630             635             640

Phe Ile Asn Arg Asn Leu Val Asp Thr Arg Tyr Ala Thr Arg Gly Leu
            645             650             655

Met Asn Leu Leu Arg Ser Tyr Phe Arg Val Asn Asn Leu Asp Val Lys
            660             665             670

Val Lys Ser Ile Asn Gly Gly Phe Thr Ser Phe Leu Arg Arg Lys Trp
            675             680             685

Lys Phe Lys Lys Glu Arg Asn Lys Gly Tyr Lys His His Ala Glu Asp
    690             695             700

Ala Leu Ile Ile Ala Asn Ala Asp Phe Ile Phe Lys Glu Trp Lys Lys
705             710             715             720

Leu Asp Lys Ala Lys Lys Val Met Glu Asn Gln Met Phe Glu Glu Lys
            725             730             735

Gln Ala Glu Ser Met Pro Glu Ile Glu Thr Glu Gln Glu Tyr Lys Glu
            740             745             750

Ile Phe Ile Thr Pro His Gln Ile Lys His Ile Lys Asp Phe Lys Asp
            755             760             765

Tyr Lys Tyr Ser His Arg Val Asp Lys Lys Pro Asn Arg Glu Leu Ile
    770             775             780

Asn Asp Thr Leu Tyr Ser Thr Arg Lys Asp Asp Lys Gly Asn Thr Leu
785             790             795             800

Ile Val Asn Asn Leu Asn Gly Leu Tyr Asp Lys Asp Asn Asp Lys Leu
            805             810             815

Lys Lys Leu Ile Asn Lys Ser Pro Glu Lys Leu Leu Met Tyr His His
            820             825             830

Asp Pro Gln Thr Tyr Gln Lys Leu Lys Leu Ile Met Glu Gln Tyr Gly
    835             840             845

Asp Glu Lys Asn Pro Leu Tyr Lys Tyr Glu Glu Thr Gly Asn Tyr
    850             855             860

Leu Thr Lys Tyr Ser Lys Lys Asp Asn Gly Pro Val Ile Lys Lys Ile
865             870             875             880

Lys Tyr Tyr Gly Asn Lys Leu Asn Ala His Leu Asp Ile Thr Asp Asp
            885             890             895
```

```
Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
            930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
            995                 1000                1005

Asn Asp  Lys Arg Pro Pro Arg  Ile Ile Lys Thr Ile  Ala Ser Lys
    1010                1015                1020

Thr Gln  Ser Ile Lys Lys Tyr  Ser Thr Asp Ile Leu  Gly Asn Leu
    1025                1030                1035

Tyr Glu  Val Lys Ser Lys Lys  His Pro Gln Ile Ile  Lys Lys Gly
    1040                1045                1050

<210> SEQ ID NO 207
<211> LENGTH: 1300
<212> TYPE: PRT
<213> ORGANISM: Francisella tularensis

<400> SEQUENCE: 207

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
            35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
            115                 120                 125

Asp Ala Lys Lys Gly Gln Glu Ser Asp Leu Ile Leu Trp Leu Lys Gln
            130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
            195                 200                 205

Pro Lys Phe Leu Glu Asn Lys Ala Lys Tyr Glu Ser Leu Lys Asp Lys
    210                 215                 220
```

```
Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
                260                 265                 270

Leu Asn Gln Ser Gly Ile Thr Lys Phe Asn Thr Ile Ile Gly Gly Lys
                275                 280                 285

Phe Val Asn Gly Glu Asn Thr Lys Arg Lys Gly Ile Asn Glu Tyr Ile
290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
                340                 345                 350

Gln Ser Phe Tyr Glu Gln Ile Ala Ala Phe Lys Thr Val Glu Glu Lys
                355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
                420                 425                 430

Pro Ser Lys Lys Glu Gln Glu Leu Ile Ala Lys Lys Thr Glu Lys Ala
                435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
                500                 505                 510

Asp Leu Leu Gln Ala Ser Ala Glu Asp Asp Val Lys Ala Ile Lys Asp
                515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
                580                 585                 590

Asp Glu Lys Phe Lys Leu Asn Phe Glu Asn Ser Thr Leu Ala Asn Gly
                595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640
```

-continued

```
Phe Asp Asp Lys Ala Ile Lys Glu Asn Lys Gly Glu Gly Tyr Lys Lys
              645                 650                 655

Ile Val Tyr Lys Leu Leu Pro Gly Ala Asn Lys Met Leu Pro Lys Val
              660                 665                 670

Phe Phe Ser Ala Lys Ser Ile Lys Phe Tyr Asn Pro Ser Glu Asp Ile
              675                 680                 685

Leu Arg Ile Arg Asn His Ser Thr His Thr Lys Asn Gly Ser Pro Gln
      690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                  725                 730                 735

Phe Gly Phe Arg Phe Ser Asp Thr Gln Arg Tyr Asn Ser Ile Asp Glu
              740                 745                 750

Phe Tyr Arg Glu Val Glu Asn Gln Gly Tyr Lys Leu Thr Phe Glu Asn
              755                 760                 765

Ile Ser Glu Ser Tyr Ile Asp Ser Val Val Asn Gln Gly Lys Leu Tyr
      770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                  805                 810                 815

Leu Gln Asp Val Val Tyr Lys Leu Asn Gly Glu Ala Glu Leu Phe Tyr
              820                 825                 830

Arg Lys Gln Ser Ile Pro Lys Lys Ile Thr His Pro Ala Lys Glu Ala
              835                 840                 845

Ile Ala Asn Lys Asn Lys Asp Asn Pro Lys Lys Glu Ser Val Phe Glu
      850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                  885                 890                 895

Asn Asp Glu Ile Asn Leu Leu Leu Lys Glu Lys Ala Asn Asp Val His
              900                 905                 910

Ile Leu Ser Ile Asp Arg Gly Glu Arg His Leu Ala Tyr Tyr Thr Leu
              915                 920                 925

Val Asp Gly Lys Gly Asn Ile Ile Lys Gln Asp Thr Phe Asn Ile Ile
      930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                  965                 970                 975

Ile Lys Glu Met Lys Glu Gly Tyr Leu Ser Gln Val Val His Glu Ile
              980                 985                 990

Ala Lys Leu Val Ile Glu Tyr Asn  Ala Ile Val Val Phe  Glu Asp Leu
          995                 1000                 1005

Asn Phe  Gly Phe Lys Arg Gly  Arg Phe Lys Val Glu  Lys Gln Val
      1010                 1015                 1020

Tyr Gln  Lys Leu Glu Lys Met  Leu Ile Glu Lys Leu  Asn Tyr Leu
      1025                 1030                 1035

Val Phe  Lys Asp Asn Glu Phe  Asp Lys Thr Gly Gly  Val Leu Arg
      1040                 1045                 1050

Ala Tyr  Gln Leu Thr Ala Pro  Phe Glu Thr Phe Lys  Lys Met Gly
```

-continued

```
        1055                    1060                    1065

Lys Gln  Thr Gly Ile Ile Tyr  Tyr Val Pro Ala Gly  Phe Thr Ser
        1070                    1075                    1080

Lys Ile  Cys Pro Val Thr Gly  Phe Val Asn Gln Leu  Tyr Pro Lys
        1085                    1090                    1095

Tyr Glu  Ser Val Ser Lys Ser  Gln Glu Phe Phe Ser  Lys Phe Asp
        1100                    1105                    1110

Lys Ile  Cys Tyr Asn Leu Asp  Lys Gly Tyr Phe Glu  Phe Ser Phe
        1115                    1120                    1125

Asp Tyr  Lys Asn Phe Gly Asp  Lys Ala Ala Lys Gly  Lys Trp Thr
        1130                    1135                    1140

Ile Ala  Ser Phe Gly Ser Arg  Leu Ile Asn Phe Arg  Asn Ser Asp
        1145                    1150                    1155

Lys Asn  His Asn Trp Asp Thr  Arg Glu Val Tyr Pro  Thr Lys Glu
        1160                    1165                    1170

Leu Glu  Lys Leu Leu Lys Asp  Tyr Ser Ile Glu Tyr  Gly His Gly
        1175                    1180                    1185

Glu Cys  Ile Lys Ala Ala Ile  Cys Gly Glu Ser Asp  Lys Lys Phe
        1190                    1195                    1200

Phe Ala  Lys Leu Thr Ser Val  Leu Asn Thr Ile Leu  Gln Met Arg
        1205                    1210                    1215

Asn Ser  Lys Thr Gly Thr Glu  Leu Asp Tyr Leu Ile  Ser Pro Val
        1220                    1225                    1230

Ala Asp  Val Asn Gly Asn Phe  Phe Asp Ser Arg Gln  Ala Pro Lys
        1235                    1240                    1245

Asn Met  Pro Gln Asp Ala Asp  Ala Asn Gly Ala Tyr  His Ile Gly
        1250                    1255                    1260

Leu Lys  Gly Leu Met Leu Leu  Gly Arg Ile Lys Asn  Asn Gln Glu
        1265                    1270                    1275

Gly Lys  Lys Leu Asn Leu Val  Ile Lys Asn Glu Glu  Tyr Phe Glu
        1280                    1285                    1290

Phe Val  Gln Asn Arg Asn Asn
        1295                    1300
```

```
<210> SEQ ID NO 208
<211> LENGTH: 1306
<212> TYPE: PRT
<213> ORGANISM: Acidaminococcus sp.

<400> SEQUENCE: 208

Thr Gln Phe Glu Gly Phe Thr Asn Leu Tyr Gln Val Ser Lys Thr Leu
1               5                   10                  15

Arg Phe Glu Leu Ile Pro Gln Gly Lys Thr Leu Lys His Ile Gln Glu
            20                  25                  30

Gln Gly Phe Ile Glu Glu Asp Lys Ala Arg Asn Asp His Tyr Lys Glu
        35                  40                  45

Leu Lys Pro Ile Ile Asp Arg Ile Tyr Lys Thr Tyr Ala Asp Gln Cys
    50                  55                  60

Leu Gln Leu Val Gln Leu Asp Trp Glu Asn Leu Ser Ala Ala Ile Asp
65                  70                  75                  80

Ser Tyr Arg Lys Glu Lys Thr Glu Glu Thr Arg Asn Ala Leu Ile Glu
                85                  90                  95

Glu Gln Ala Thr Tyr Arg Asn Ala Ile His Asp Tyr Phe Ile Gly Arg
            100                 105                 110
```

-continued

```
Thr Asp Asn Leu Thr Asp Ala Ile Asn Lys Arg His Ala Glu Ile Tyr
        115                 120                 125

Lys Gly Leu Phe Lys Ala Glu Leu Phe Asn Gly Lys Val Leu Lys Gln
    130                 135                 140

Leu Gly Thr Val Thr Thr Thr Glu His Glu Asn Ala Leu Leu Arg Ser
145                 150                 155                 160

Phe Asp Lys Phe Thr Thr Tyr Phe Ser Gly Phe Tyr Glu Asn Arg Lys
                165                 170                 175

Asn Val Phe Ser Ala Glu Asp Ile Ser Thr Ala Ile Pro His Arg Ile
            180                 185                 190

Val Gln Asp Asn Phe Pro Lys Phe Lys Glu Asn Cys His Ile Phe Thr
        195                 200                 205

Arg Leu Ile Thr Ala Val Pro Ser Leu Arg Glu His Phe Glu Asn Val
    210                 215                 220

Lys Lys Ala Ile Gly Ile Phe Val Ser Thr Ser Ile Glu Glu Val Phe
225                 230                 235                 240

Ser Phe Pro Phe Tyr Asn Gln Leu Leu Thr Gln Thr Gln Ile Asp Leu
                245                 250                 255

Tyr Asn Gln Leu Leu Gly Gly Ile Ser Arg Glu Ala Gly Thr Glu Lys
            260                 265                 270

Ile Lys Gly Leu Asn Glu Val Leu Asn Leu Ala Ile Gln Lys Asn Asp
        275                 280                 285

Glu Thr Ala His Ile Ile Ala Ser Leu Pro His Arg Phe Ile Pro Leu
    290                 295                 300

Phe Lys Gln Ile Leu Ser Asp Arg Asn Thr Leu Ser Phe Ile Leu Glu
305                 310                 315                 320

Glu Phe Lys Ser Asp Glu Glu Val Ile Gln Ser Phe Cys Lys Tyr Lys
                325                 330                 335

Thr Leu Leu Arg Asn Glu Asn Val Leu Glu Thr Ala Glu Ala Leu Phe
            340                 345                 350

Asn Glu Leu Asn Ser Ile Asp Leu Thr His Ile Phe Ile Ser His Lys
        355                 360                 365

Lys Leu Glu Thr Ile Ser Ser Ala Leu Cys Asp His Trp Asp Thr Leu
    370                 375                 380

Arg Asn Ala Leu Tyr Glu Arg Arg Ile Ser Glu Leu Thr Gly Lys Ile
385                 390                 395                 400

Thr Lys Ser Ala Lys Glu Lys Val Gln Arg Ser Leu Lys His Glu Asp
                405                 410                 415

Ile Asn Leu Gln Glu Ile Ile Ser Ala Ala Gly Lys Glu Leu Ser Glu
            420                 425                 430

Ala Phe Lys Gln Lys Thr Ser Glu Ile Leu Ser His Ala His Ala Ala
        435                 440                 445

Leu Asp Gln Pro Leu Pro Thr Thr Leu Lys Lys Gln Glu Glu Lys Glu
    450                 455                 460

Ile Leu Lys Ser Gln Leu Asp Ser Leu Leu Gly Leu Tyr His Leu Leu
465                 470                 475                 480

Asp Trp Phe Ala Val Asp Glu Ser Asn Glu Val Asp Pro Glu Phe Ser
                485                 490                 495

Ala Arg Leu Thr Gly Ile Lys Leu Glu Met Glu Pro Ser Leu Ser Phe
            500                 505                 510

Tyr Asn Lys Ala Arg Asn Tyr Ala Thr Lys Lys Pro Tyr Ser Val Glu
        515                 520                 525

Lys Phe Lys Leu Asn Phe Gln Met Pro Thr Leu Ala Ser Gly Trp Asp
```

530                535                540

Val Asn Lys Glu Lys Asn Asn Gly Ala Ile Leu Phe Val Lys Asn Gly
545                550                555                560

Leu Tyr Tyr Leu Gly Ile Met Pro Lys Gln Lys Gly Arg Tyr Lys Ala
                565                570                575

Leu Ser Phe Glu Pro Thr Glu Lys Thr Ser Glu Gly Phe Asp Lys Met
                580                585                590

Tyr Tyr Asp Tyr Phe Pro Asp Ala Ala Lys Met Ile Pro Lys Cys Ser
                595                600                605

Thr Gln Leu Lys Ala Val Thr Ala His Phe Gln Thr His Thr Thr Pro
                610                615                620

Ile Leu Leu Ser Asn Asn Phe Ile Glu Pro Leu Glu Ile Thr Lys Glu
625                630                635                640

Ile Tyr Asp Leu Asn Asn Pro Glu Lys Glu Pro Lys Lys Phe Gln Thr
                645                650                655

Ala Tyr Ala Lys Lys Thr Gly Asp Gln Lys Gly Tyr Arg Glu Ala Leu
                660                665                670

Cys Lys Trp Ile Asp Phe Thr Arg Asp Phe Leu Ser Lys Tyr Thr Lys
                675                680                685

Thr Thr Ser Ile Asp Leu Ser Ser Leu Arg Pro Ser Ser Gln Tyr Lys
                690                695                700

Asp Leu Gly Glu Tyr Tyr Ala Glu Leu Asn Pro Leu Leu Tyr His Ile
705                710                715                720

Ser Phe Gln Arg Ile Ala Glu Lys Glu Ile Met Asp Ala Val Glu Thr
                725                730                735

Gly Lys Leu Tyr Leu Phe Gln Ile Tyr Asn Lys Asp Phe Ala Lys Gly
                740                745                750

His His Gly Lys Pro Asn Leu His Thr Leu Tyr Trp Thr Gly Leu Phe
                755                760                765

Ser Pro Glu Asn Leu Ala Lys Thr Ser Ile Lys Leu Asn Gly Gln Ala
                770                775                780

Glu Leu Phe Tyr Arg Pro Lys Ser Arg Met Lys Arg Met Ala His Arg
785                790                795                800

Leu Gly Glu Lys Met Leu Asn Lys Lys Leu Lys Asp Gln Lys Thr Pro
                805                810                815

Ile Pro Asp Thr Leu Tyr Gln Glu Leu Tyr Asp Tyr Val Asn His Arg
                820                825                830

Leu Ser His Asp Leu Ser Asp Glu Ala Arg Ala Leu Leu Pro Asn Val
                835                840                845

Ile Thr Lys Glu Val Ser His Glu Ile Ile Lys Asp Arg Arg Phe Thr
                850                855                860

Ser Asp Lys Phe Phe Phe His Val Pro Ile Thr Leu Asn Tyr Gln Ala
865                870                875                880

Ala Asn Ser Pro Ser Lys Phe Asn Gln Arg Val Asn Ala Tyr Leu Lys
                885                890                895

Glu His Pro Glu Thr Pro Ile Ile Gly Ile Asp Arg Gly Glu Arg Asn
                900                905                910

Leu Ile Tyr Ile Thr Val Ile Asp Ser Thr Gly Lys Ile Leu Glu Gln
                915                920                925

Arg Ser Leu Asn Thr Ile Gln Gln Phe Asp Tyr Gln Lys Lys Leu Asp
                930                935                940

Asn Arg Glu Lys Glu Arg Val Ala Ala Arg Gln Ala Trp Ser Val Val
945                950                955                960

-continued

```
Gly Thr Ile Lys Asp Leu Lys Gln Gly Tyr Leu Ser Gln Val Ile His
                965                 970                 975

Glu Ile Val Asp Leu Met Ile His Tyr Gln Ala Val Val Val Leu Glu
            980                 985                 990

Asn Leu Asn Phe Gly Phe Lys Ser  Lys Arg Thr Gly Ile  Ala Glu Lys
        995                 1000                1005

Ala Val  Tyr Gln Gln Phe Glu  Lys Met Leu Ile Asp  Lys Leu Asn
    1010                1015                1020

Cys Leu  Val Leu Lys Asp Tyr  Pro Ala Glu Lys Val  Gly Gly Val
    1025                1030                1035

Leu Asn  Pro Tyr Gln Leu Thr  Asp Gln Phe Thr Ser  Phe Ala Lys
    1040                1045                1050

Met Gly  Thr Gln Ser Gly Phe  Leu Phe Tyr Val Pro  Ala Pro Tyr
    1055                1060                1065

Thr Ser  Lys Ile Asp Pro Leu  Thr Gly Phe Val Asp  Pro Phe Val
    1070                1075                1080

Trp Lys  Thr Ile Lys Asn His  Glu Ser Arg Lys His  Phe Leu Glu
    1085                1090                1095

Gly Phe  Asp Phe Leu His Tyr  Asp Val Lys Thr Gly  Asp Phe Ile
    1100                1105                1110

Leu His  Phe Lys Met Asn Arg  Asn Leu Ser Phe Gln  Arg Gly Leu
    1115                1120                1125

Pro Gly  Phe Met Pro Ala Trp  Asp Ile Val Phe Glu  Lys Asn Glu
    1130                1135                1140

Thr Gln  Phe Asp Ala Lys Gly  Thr Pro Phe Ile Ala  Gly Lys Arg
    1145                1150                1155

Ile Val  Pro Val Ile Glu Asn  His Arg Phe Thr Gly  Arg Tyr Arg
    1160                1165                1170

Asp Leu  Tyr Pro Ala Asn Glu  Leu Ile Ala Leu Leu  Glu Glu Lys
    1175                1180                1185

Gly Ile  Val Phe Arg Asp Gly  Ser Asn Ile Leu Pro  Lys Leu Leu
    1190                1195                1200

Glu Asn  Asp Asp Ser His Ala  Ile Asp Thr Met Val  Ala Leu Ile
    1205                1210                1215

Arg Ser  Val Leu Gln Met Arg  Asn Ser Asn Ala Ala  Thr Gly Glu
    1220                1225                1230

Asp Tyr  Ile Asn Ser Pro Val  Arg Asp Leu Asn Gly  Val Cys Phe
    1235                1240                1245

Asp Ser  Arg Phe Gln Asn Pro  Glu Trp Pro Met Asp  Ala Asp Ala
    1250                1255                1260

Asn Gly  Ala Tyr His Ile Ala  Leu Lys Gly Gln Leu  Leu Leu Asn
    1265                1270                1275

His Leu  Lys Glu Ser Lys Asp  Leu Lys Leu Gln Asn  Gly Ile Ser
    1280                1285                1290

Asn Gln  Asp Trp Leu Ala Tyr  Ile Gln Glu Leu Arg  Asn
    1295                1300                1305
```

<210> SEQ ID NO 209
<211> LENGTH: 1306
<212> TYPE: PRT
<213> ORGANISM: Artificial sequence
<220> FEATURE:
<223> OTHER INFORMATION: synthetic sequence

<400> SEQUENCE: 209

-continued

```
Thr Gln Phe Glu Gly Phe Thr Asn Leu Tyr Gln Val Ser Lys Thr Leu
1               5                   10                  15

Arg Phe Glu Leu Ile Pro Gln Gly Lys Thr Leu Lys His Ile Gln Glu
                20                  25                  30

Gln Gly Phe Ile Glu Glu Asp Lys Ala Arg Asn Asp His Tyr Lys Glu
            35                  40                  45

Leu Lys Pro Ile Ile Asp Arg Ile Tyr Lys Thr Tyr Ala Asp Gln Cys
    50                  55                  60

Leu Gln Leu Val Gln Leu Asp Trp Glu Asn Leu Ser Ala Ala Ile Asp
65                  70                  75                  80

Ser Tyr Arg Lys Glu Lys Thr Glu Glu Thr Arg Asn Ala Leu Ile Glu
                85                  90                  95

Glu Gln Ala Thr Tyr Arg Asn Ala Ile His Asp Tyr Phe Ile Gly Arg
            100                 105                 110

Thr Asp Asn Leu Thr Asp Ala Ile Asn Lys Arg His Ala Glu Ile Tyr
            115                 120                 125

Lys Gly Leu Phe Lys Ala Glu Leu Phe Asn Gly Lys Val Leu Lys Gln
    130                 135                 140

Leu Gly Thr Val Thr Thr Thr Glu His Glu Asn Ala Leu Leu Arg Ser
145                 150                 155                 160

Phe Asp Lys Phe Thr Thr Tyr Phe Ser Gly Phe Tyr Glu Asn Arg Lys
                165                 170                 175

Asn Val Phe Ser Ala Glu Asp Ile Ser Thr Ala Ile Pro His Arg Ile
            180                 185                 190

Val Gln Asp Asn Phe Pro Lys Phe Lys Glu Asn Cys His Ile Phe Thr
            195                 200                 205

Arg Leu Ile Thr Ala Val Pro Ser Leu Arg Glu His Phe Glu Asn Val
    210                 215                 220

Lys Lys Ala Ile Gly Ile Phe Val Ser Thr Ser Ile Glu Glu Val Phe
225                 230                 235                 240

Ser Phe Pro Phe Tyr Asn Gln Leu Leu Thr Gln Thr Gln Ile Asp Leu
                245                 250                 255

Tyr Asn Gln Leu Leu Gly Gly Ile Ser Arg Glu Ala Gly Thr Glu Lys
            260                 265                 270

Ile Lys Gly Leu Asn Glu Val Leu Asn Leu Ala Ile Gln Lys Asn Asp
            275                 280                 285

Glu Thr Ala His Ile Ile Ala Ser Leu Pro His Arg Phe Ile Pro Leu
    290                 295                 300

Phe Lys Gln Ile Leu Ser Asp Arg Asn Thr Leu Ser Phe Ile Leu Glu
305                 310                 315                 320

Glu Phe Lys Ser Asp Glu Glu Val Ile Gln Ser Phe Cys Lys Tyr Lys
                325                 330                 335

Thr Leu Leu Arg Asn Glu Asn Val Leu Glu Thr Ala Glu Ala Leu Phe
            340                 345                 350

Asn Glu Leu Asn Ser Ile Asp Leu Thr His Ile Phe Ile Ser His Lys
            355                 360                 365

Lys Leu Glu Thr Ile Ser Ser Ala Leu Cys Asp His Trp Asp Thr Leu
    370                 375                 380

Arg Asn Ala Leu Tyr Glu Arg Arg Ile Ser Glu Leu Thr Gly Lys Ile
385                 390                 395                 400

Thr Lys Ser Ala Lys Glu Lys Val Gln Arg Ser Leu Lys His Glu Asp
                405                 410                 415
```

-continued

```
Ile Asn Leu Gln Glu Ile Ile Ser Ala Ala Gly Lys Glu Leu Ser Glu
            420             425             430

Ala Phe Lys Gln Lys Thr Ser Glu Ile Leu Ser His Ala His Ala Ala
            435             440             445

Leu Asp Gln Pro Leu Pro Thr Thr Leu Lys Lys Gln Glu Glu Lys Glu
            450             455             460

Ile Leu Lys Ser Gln Leu Asp Ser Leu Leu Gly Leu Tyr His Leu Leu
465             470             475             480

Asp Trp Phe Ala Val Asp Glu Ser Asn Glu Val Asp Pro Glu Phe Ser
                485             490             495

Ala Arg Leu Thr Gly Ile Lys Leu Glu Met Glu Pro Ser Leu Ser Phe
            500             505             510

Tyr Asn Lys Ala Arg Asn Tyr Ala Thr Lys Lys Pro Tyr Ser Val Glu
            515             520             525

Lys Phe Lys Leu Asn Phe Gln Met Pro Thr Leu Ala Ser Gly Trp Asp
            530             535             540

Val Asn Lys Glu Lys Asn Asn Gly Ala Ile Leu Phe Val Lys Asn Gly
545             550             555             560

Leu Tyr Tyr Leu Gly Ile Met Pro Lys Gln Lys Gly Arg Tyr Lys Ala
            565             570             575

Leu Ser Phe Glu Pro Thr Glu Lys Thr Ser Glu Gly Phe Asp Lys Met
            580             585             590

Tyr Tyr Asp Tyr Phe Pro Asp Ala Ala Lys Met Ile Pro Lys Cys Ser
            595             600             605

Thr Gln Leu Lys Ala Val Thr Ala His Phe Gln Thr His Thr Thr Pro
            610             615             620

Ile Leu Leu Ser Asn Asn Phe Ile Glu Pro Leu Glu Ile Thr Lys Glu
625             630             635             640

Ile Tyr Asp Leu Asn Asn Pro Glu Lys Glu Pro Lys Lys Phe Gln Thr
            645             650             655

Ala Tyr Ala Lys Lys Thr Gly Asp Gln Lys Gly Tyr Arg Glu Ala Leu
            660             665             670

Cys Lys Trp Ile Asp Phe Thr Arg Asp Phe Leu Ser Lys Tyr Thr Lys
            675             680             685

Thr Thr Ser Ile Asp Leu Ser Ser Leu Arg Pro Ser Ser Gln Tyr Lys
            690             695             700

Asp Leu Gly Glu Tyr Tyr Ala Glu Leu Asn Pro Leu Leu Tyr His Ile
705             710             715             720

Ser Phe Gln Arg Ile Ala Glu Lys Glu Ile Met Asp Ala Val Glu Thr
            725             730             735

Gly Lys Leu Tyr Leu Phe Gln Ile Tyr Asn Lys Asp Phe Ala Lys Gly
            740             745             750

His His Gly Lys Pro Asn Leu His Thr Leu Tyr Trp Thr Gly Leu Phe
            755             760             765

Ser Pro Glu Asn Leu Ala Lys Thr Ser Ile Lys Leu Asn Gly Gln Ala
            770             775             780

Glu Leu Phe Tyr Arg Pro Lys Ser Arg Met Lys Arg Met Ala His Arg
785             790             795             800

Leu Gly Glu Lys Met Leu Asn Lys Lys Leu Lys Asp Gln Lys Thr Pro
                805             810             815

Ile Pro Asp Thr Leu Tyr Gln Glu Leu Tyr Asp Tyr Val Asn His Arg
                820             825             830

Leu Ser His Asp Leu Ser Asp Glu Ala Arg Ala Leu Leu Pro Asn Val
```

-continued

```
                 835              840              845

Ile Thr Lys Glu Val Ser His Glu Ile Ile Lys Asp Arg Arg Phe Thr
850              855              860

Ser Asp Lys Phe Phe Phe His Val Pro Ile Thr Leu Asn Tyr Gln Ala
865              870              875              880

Ala Asn Ser Pro Ser Lys Phe Asn Gln Arg Val Asn Ala Tyr Leu Lys
                 885              890              895

Glu His Pro Glu Thr Pro Ile Ile Gly Ile Asp Arg Gly Glu Arg Asn
                 900              905              910

Leu Ile Tyr Ile Thr Val Ile Asp Ser Thr Gly Lys Ile Leu Glu Gln
                 915              920              925

Arg Ser Leu Asn Thr Ile Gln Gln Phe Asp Tyr Gln Lys Lys Leu Asp
                 930              935              940

Asn Arg Glu Lys Glu Arg Val Ala Ala Arg Gln Ala Trp Ser Val Val
945              950              955              960

Gly Thr Ile Lys Asp Leu Lys Gln Gly Tyr Leu Ser Gln Val Ile His
                 965              970              975

Glu Ile Val Asp Leu Met Ile His Tyr Gln Ala Val Val Val Leu Glu
                 980              985              990

Asn Leu Asn Phe Gly Phe Lys Ser  Lys Arg Thr Gly Ile  Ala Glu Lys
                 995              1000             1005

Ala Val  Tyr Gln Gln Phe Glu  Lys Met Leu Ile Asp  Lys Leu Asn
1010             1015             1020

Cys Leu  Val Leu Lys Asp Tyr  Pro Ala Glu Lys Val  Gly Gly Val
1025             1030             1035

Leu Asn  Pro Tyr Gln Leu Thr  Asp Gln Phe Thr Ser  Phe Ala Lys
1040             1045             1050

Met Gly  Thr Gln Ser Gly Phe  Leu Phe Tyr Val Pro  Ala Pro Tyr
1055             1060             1065

Thr Ser  Lys Ile Asp Pro Leu  Thr Gly Phe Val Asp  Pro Phe Val
1070             1075             1080

Trp Lys  Thr Ile Lys Asn His  Glu Ser Arg Lys His  Phe Leu Glu
1085             1090             1095

Gly Phe  Asp Phe Leu His Tyr  Asp Val Lys Thr Gly  Asp Phe Ile
1100             1105             1110

Leu His  Phe Lys Met Asn Arg  Asn Leu Ser Phe Gln  Arg Gly Leu
1115             1120             1125

Pro Gly  Phe Met Pro Ala Trp  Asp Ile Val Phe Glu  Lys Asn Glu
1130             1135             1140

Thr Gln  Phe Asp Ala Lys Gly  Thr Pro Phe Ile Ala  Gly Lys Arg
1145             1150             1155

Ile Val  Pro Val Ile Glu Asn  His Arg Phe Thr Gly  Arg Tyr Arg
1160             1165             1170

Asp Leu  Tyr Pro Ala Asn Glu  Leu Ile Ala Leu Leu  Glu Glu Lys
1175             1180             1185

Gly Ile  Val Phe Arg Asp Gly  Ser Asn Ile Leu Pro  Lys Leu Leu
1190             1195             1200

Glu Asn  Asp Asp Ser His Ala  Ile Asp Thr Met Val  Ala Leu Ile
1205             1210             1215

Arg Ser  Val Leu Gln Met Ala  Asn Ser Asn Ala Ala  Thr Gly Glu
1220             1225             1230

Asp Tyr  Ile Asn Ser Pro Val  Arg Asp Leu Asn Gly  Val Cys Phe
1235             1240             1245
```

-continued

Asp Ser Arg Phe Gln Asn Pro  Glu Trp Pro Met Asp  Ala Asp Ala
    1250              1255              1260

Asn Gly  Ala Tyr His Ile Ala  Leu Lys Gly Gln Leu  Leu Leu Asn
    1265              1270              1275

His Leu  Lys Glu Ser Lys Asp  Leu Lys Leu Gln Asn  Gly Ile Ser
    1280              1285              1290

Asn Gln  Asp Trp Leu Ala Tyr  Ile Gln Glu Leu Arg  Asn
    1295              1300              1305

<210> SEQ ID NO 210
<211> LENGTH: 1120
<212> TYPE: PRT
<213> ORGANISM: Listeria seeligeri

<400> SEQUENCE: 210

Met Trp Ile Ser Ile Lys Thr Leu Ile His His Leu Gly Val Leu Phe
1               5                   10                  15

Phe Cys Asp Tyr Met Tyr Asn Arg Arg Glu Lys Lys Ile Ile Glu Val
            20                  25                  30

Lys Thr Met Arg Ile Thr Lys Val Glu Val Asp Arg Lys Lys Val Leu
        35                  40                  45

Ile Ser Arg Asp Lys Asn Gly Gly Lys Leu Val Tyr Glu Asn Glu Met
    50                  55                  60

Gln Asp Asn Thr Glu Gln Ile Met His His Lys Lys Ser Ser Phe Tyr
65                  70                  75                  80

Lys Ser Val Val Asn Lys Thr Ile Cys Arg Pro Glu Gln Lys Gln Met
                85                  90                  95

Lys Lys Leu Val His Gly Leu Leu Gln Glu Asn Ser Gln Glu Lys Ile
            100                 105                 110

Lys Val Ser Asp Val Thr Lys Leu Asn Ile Ser Asn Phe Leu Asn His
        115                 120                 125

Arg Phe Lys Lys Ser Leu Tyr Tyr Phe Pro Glu Asn Ser Pro Asp Lys
    130                 135                 140

Ser Glu Glu Tyr Arg Ile Glu Ile Asn Leu Ser Gln Leu Leu Glu Asp
145                 150                 155                 160

Ser Leu Lys Lys Gln Gln Gly Thr Phe Ile Cys Trp Glu Ser Phe Ser
                165                 170                 175

Lys Asp Met Glu Leu Tyr Ile Asn Trp Ala Glu Asn Tyr Ile Ser Ser
            180                 185                 190

Lys Thr Lys Leu Ile Lys Lys Ser Ile Arg Asn Asn Arg Ile Gln Ser
        195                 200                 205

Thr Glu Ser Arg Ser Gly Gln Leu Met Asp Arg Tyr Met Lys Asp Ile
    210                 215                 220

Leu Asn Lys Asn Lys Pro Phe Asp Ile Gln Ser Val Ser Glu Lys Tyr
225                 230                 235                 240

Gln Leu Glu Lys Leu Thr Ser Ala Leu Lys Ala Thr Phe Lys Glu Ala
                245                 250                 255

Lys Lys Asn Asp Lys Glu Ile Asn Tyr Lys Leu Lys Ser Thr Leu Gln
            260                 265                 270

Asn His Glu Arg Gln Ile Ile Glu Glu Leu Lys Glu Asn Ser Glu Leu
        275                 280                 285

Asn Gln Phe Asn Ile Glu Ile Arg Lys His Leu Glu Thr Tyr Phe Pro
    290                 295                 300

Ile Lys Lys Thr Asn Arg Lys Val Gly Asp Ile Arg Asn Leu Glu Ile

-continued

```
305                 310                 315                 320

Gly Glu Ile Gln Lys Ile Val Asn His Arg Leu Lys Asn Lys Ile Val
                325                 330                 335

Gln Arg Ile Leu Gln Glu Gly Lys Leu Ala Ser Tyr Glu Ile Glu Ser
                340                 345                 350

Thr Val Asn Ser Asn Ser Leu Gln Lys Ile Lys Ile Glu Glu Ala Phe
                355                 360                 365

Ala Leu Lys Phe Ile Asn Ala Cys Leu Phe Ala Ser Asn Asn Leu Arg
                370                 375                 380

Asn Met Val Tyr Pro Val Cys Lys Lys Asp Ile Leu Met Ile Gly Glu
385                 390                 395                 400

Phe Lys Asn Ser Phe Lys Glu Ile Lys His Lys Lys Phe Ile Arg Gln
                405                 410                 415

Trp Ser Gln Phe Phe Ser Gln Glu Ile Thr Val Asp Asp Ile Glu Leu
                420                 425                 430

Ala Ser Trp Gly Leu Arg Gly Ala Ile Ala Pro Ile Arg Asn Glu Ile
                435                 440                 445

Ile His Leu Lys Lys His Ser Trp Lys Lys Phe Phe Asn Asn Pro Thr
                450                 455                 460

Phe Lys Val Lys Lys Ser Lys Ile Ile Asn Gly Lys Thr Lys Asp Val
465                 470                 475                 480

Thr Ser Glu Phe Leu Tyr Lys Glu Thr Leu Phe Lys Asp Tyr Phe Tyr
                485                 490                 495

Ser Glu Leu Asp Ser Val Pro Glu Leu Ile Ile Asn Lys Met Glu Ser
                500                 505                 510

Ser Lys Ile Leu Asp Tyr Tyr Ser Ser Asp Gln Leu Asn Gln Val Phe
                515                 520                 525

Thr Ile Pro Asn Phe Glu Leu Ser Leu Leu Thr Ser Ala Val Pro Phe
                530                 535                 540

Ala Pro Ser Phe Lys Arg Val Tyr Leu Lys Gly Phe Asp Tyr Gln Asn
545                 550                 555                 560

Gln Asp Glu Ala Gln Pro Asp Tyr Asn Leu Lys Leu Asn Ile Tyr Asn
                565                 570                 575

Glu Lys Ala Phe Asn Ser Glu Ala Phe Gln Ala Gln Tyr Ser Leu Phe
                580                 585                 590

Lys Met Val Tyr Tyr Gln Val Phe Leu Pro Gln Phe Thr Thr Asn Asn
                595                 600                 605

Asp Leu Phe Lys Ser Ser Val Asp Phe Ile Leu Thr Leu Asn Lys Glu
                610                 615                 620

Arg Lys Gly Tyr Ala Lys Ala Phe Gln Asp Ile Arg Lys Met Asn Lys
625                 630                 635                 640

Asp Glu Lys Pro Ser Glu Tyr Met Ser Tyr Ile Gln Ser Gln Leu Met
                645                 650                 655

Leu Tyr Gln Lys Lys Gln Glu Glu Lys Glu Lys Ile Asn His Phe Glu
                660                 665                 670

Lys Phe Ile Asn Gln Val Phe Ile Lys Gly Phe Asn Ser Phe Ile Glu
                675                 680                 685

Lys Asn Arg Leu Thr Tyr Ile Cys His Pro Thr Lys Asn Thr Val Pro
                690                 695                 700

Glu Asn Asp Asn Ile Glu Ile Pro Phe His Thr Asp Met Asp Asp Ser
705                 710                 715                 720

Asn Ile Ala Phe Trp Leu Met Cys Lys Leu Leu Asp Ala Lys Gln Leu
                725                 730                 735
```

-continued

```
Ser Glu Leu Arg Asn Glu Met Ile Lys Phe Ser Cys Ser Leu Gln Ser
        740                 745                 750

Thr Glu Glu Ile Ser Thr Phe Thr Lys Ala Arg Glu Val Ile Gly Leu
        755                 760                 765

Ala Leu Leu Asn Gly Glu Lys Gly Cys Asn Asp Trp Lys Glu Leu Phe
        770                 775                 780

Asp Asp Lys Glu Ala Trp Lys Lys Asn Met Ser Leu Tyr Val Ser Glu
785                 790                 795                 800

Glu Leu Leu Gln Ser Leu Pro Tyr Thr Gln Glu Asp Gly Gln Thr Pro
                805                 810                 815

Val Ile Asn Arg Ser Ile Asp Leu Val Lys Lys Tyr Gly Thr Glu Thr
                820                 825                 830

Ile Leu Glu Lys Leu Phe Ser Ser Ser Asp Asp Tyr Lys Val Ser Ala
                835                 840                 845

Lys Asp Ile Ala Lys Leu His Glu Tyr Asp Val Thr Glu Lys Ile Ala
        850                 855                 860

Gln Gln Glu Ser Leu His Lys Gln Trp Ile Glu Lys Pro Gly Leu Ala
865                 870                 875                 880

Arg Asp Ser Ala Trp Thr Lys Lys Tyr Gln Asn Val Ile Asn Asp Ile
                885                 890                 895

Ser Asn Tyr Gln Trp Ala Lys Thr Lys Val Glu Leu Thr Gln Val Arg
                900                 905                 910

His Leu His Gln Leu Thr Ile Asp Leu Leu Ser Arg Leu Ala Gly Tyr
                915                 920                 925

Met Ser Ile Ala Asp Arg Asp Phe Gln Phe Ser Ser Asn Tyr Ile Leu
        930                 935                 940

Glu Arg Glu Asn Ser Glu Tyr Arg Val Thr Ser Trp Ile Leu Leu Ser
945                 950                 955                 960

Glu Asn Lys Asn Lys Asn Lys Tyr Asn Asp Tyr Glu Leu Tyr Asn Leu
                965                 970                 975

Lys Asn Ala Ser Ile Lys Val Ser Ser Lys Asn Asp Pro Gln Leu Lys
                980                 985                 990

Val Asp Leu Lys Gln Leu Arg Leu  Thr Leu Glu Tyr Leu  Glu Leu Phe
        995                 1000                1005

Asp Asn  Arg Leu Lys Glu Lys  Arg Asn Asn Ile Ser  His Phe Asn
    1010                1015                1020

Tyr Leu  Asn Gly Gln Leu Gly  Asn Ser Ile Leu Glu  Leu Phe Asp
    1025                1030                1035

Asp Ala  Arg Asp Val Leu Ser  Tyr Asp Arg Lys Leu  Lys Asn Ala
    1040                1045                1050

Val Ser  Lys Ser Leu Lys Glu  Ile Leu Ser Ser His  Gly Met Glu
    1055                1060                1065

Val Thr  Phe Lys Pro Leu Tyr  Gln Thr Asn His His  Leu Lys Ile
    1070                1075                1080

Asp Lys  Leu Gln Pro Lys Lys  Ile His His Leu Gly  Glu Lys Ser
    1085                1090                1095

Thr Val  Ser Ser Asn Gln Val  Ser Asn Glu Tyr Cys  Gln Leu Val
    1100                1105                1110

Arg Thr  Leu Leu Thr Met Lys
    1115                1120
```

<210> SEQ ID NO 211
<211> LENGTH: 1159

-continued

```
<212> TYPE: PRT
<213> ORGANISM: Leptotrichia buccalis

<400> SEQUENCE: 211

Met Lys Val Thr Lys Val Gly Gly Ile Ser His Lys Lys Tyr Thr Ser
1               5                   10                  15

Glu Gly Arg Leu Val Lys Ser Glu Ser Glu Glu Asn Arg Thr Asp Glu
            20                  25                  30

Arg Leu Ser Ala Leu Leu Asn Met Arg Leu Asp Met Tyr Ile Lys Asn
        35                  40                  45

Pro Ser Ser Thr Glu Thr Lys Glu Asn Gln Lys Arg Ile Gly Lys Leu
    50                  55                  60

Lys Lys Phe Phe Ser Asn Lys Met Val Tyr Leu Lys Asp Asn Thr Leu
65                  70                  75                  80

Ser Leu Lys Asn Gly Lys Lys Glu Asn Ile Asp Arg Glu Tyr Ser Glu
                85                  90                  95

Thr Asp Ile Leu Glu Ser Asp Val Arg Asp Lys Lys Asn Phe Ala Val
            100                 105                 110

Leu Lys Lys Ile Tyr Leu Asn Glu Asn Val Asn Ser Glu Glu Leu Glu
        115                 120                 125

Val Phe Arg Asn Asp Ile Lys Lys Lys Leu Asn Lys Ile Asn Ser Leu
    130                 135                 140

Lys Tyr Ser Phe Glu Lys Asn Lys Ala Asn Tyr Gln Lys Ile Asn Glu
145                 150                 155                 160

Asn Asn Ile Glu Lys Val Glu Gly Lys Ser Lys Arg Asn Ile Ile Tyr
                165                 170                 175

Asp Tyr Tyr Arg Glu Ser Ala Lys Arg Asp Ala Tyr Val Ser Asn Val
            180                 185                 190

Lys Glu Ala Phe Asp Lys Leu Tyr Lys Glu Glu Asp Ile Ala Lys Leu
        195                 200                 205

Val Leu Glu Ile Glu Asn Leu Thr Lys Leu Glu Lys Tyr Lys Ile Arg
    210                 215                 220

Glu Phe Tyr His Glu Ile Ile Gly Arg Lys Asn Asp Lys Glu Asn Phe
225                 230                 235                 240

Ala Lys Ile Ile Tyr Glu Glu Ile Gln Asn Val Asn Asn Met Lys Glu
                245                 250                 255

Leu Ile Glu Lys Val Pro Asp Met Ser Glu Leu Lys Lys Ser Gln Val
            260                 265                 270

Phe Tyr Lys Tyr Tyr Leu Asp Lys Glu Glu Leu Asn Asp Lys Asn Ile
        275                 280                 285

Lys Tyr Ala Phe Cys His Phe Val Glu Ile Glu Met Ser Gln Leu Leu
    290                 295                 300

Lys Asn Tyr Val Tyr Lys Arg Leu Ser Asn Ile Ser Asn Asp Lys Ile
305                 310                 315                 320

Lys Arg Ile Phe Glu Tyr Gln Asn Leu Lys Lys Leu Ile Glu Asn Lys
                325                 330                 335

Leu Leu Asn Lys Leu Asp Thr Tyr Val Arg Asn Cys Gly Lys Tyr Asn
            340                 345                 350

Tyr Tyr Leu Gln Asp Gly Glu Ile Ala Thr Ser Asp Phe Ile Ala Arg
        355                 360                 365

Asn Arg Gln Asn Glu Ala Phe Leu Arg Asn Ile Ile Gly Val Ser Ser
    370                 375                 380

Val Ala Tyr Phe Ser Leu Arg Asn Ile Leu Glu Thr Glu Asn Glu Asn
385                 390                 395                 400
```

-continued

```
Asp Ile Thr Gly Arg Met Arg Gly Lys Thr Val Lys Asn Asn Lys Gly
                405             410             415

Glu Glu Lys Tyr Val Ser Gly Glu Val Asp Lys Ile Tyr Asn Glu Asn
            420             425             430

Lys Lys Asn Glu Val Lys Glu Asn Leu Lys Met Phe Tyr Ser Tyr Asp
        435             440             445

Phe Asn Met Asp Asn Lys Asn Glu Ile Glu Asp Phe Phe Ala Asn Ile
    450             455             460

Asp Glu Ala Ile Ser Ser Ile Arg His Gly Ile Val His Phe Asn Leu
465             470             475             480

Glu Leu Glu Gly Lys Asp Ile Phe Ala Phe Lys Asn Ile Ala Pro Ser
            485             490             495

Glu Ile Ser Lys Lys Met Phe Gln Asn Glu Ile Asn Glu Lys Lys Leu
        500             505             510

Lys Leu Lys Ile Phe Arg Gln Leu Asn Ser Ala Asn Val Phe Arg Tyr
        515             520             525

Leu Glu Lys Tyr Lys Ile Leu Asn Tyr Leu Lys Arg Thr Arg Phe Glu
    530             535             540

Phe Val Asn Lys Asn Ile Pro Phe Val Pro Ser Phe Thr Lys Leu Tyr
545             550             555             560

Ser Arg Ile Asp Asp Leu Lys Asn Ser Leu Gly Ile Tyr Trp Lys Thr
            565             570             575

Pro Lys Thr Asn Asp Asp Asn Lys Thr Lys Glu Ile Ile Asp Ala Gln
            580             585             590

Ile Tyr Leu Leu Lys Asn Ile Tyr Tyr Gly Glu Phe Leu Asn Tyr Phe
        595             600             605

Met Ser Asn Asn Gly Asn Phe Phe Glu Ile Ser Lys Glu Ile Ile Glu
    610             615             620

Leu Asn Lys Asn Asp Lys Arg Asn Leu Lys Thr Gly Phe Tyr Lys Leu
625             630             635             640

Gln Lys Phe Glu Asp Ile Gln Glu Lys Ile Pro Lys Glu Tyr Leu Ala
            645             650             655

Asn Ile Gln Ser Leu Tyr Met Ile Asn Ala Gly Asn Gln Asp Glu Glu
        660             665             670

Glu Lys Asp Thr Tyr Ile Asp Phe Ile Gln Lys Ile Phe Leu Lys Gly
        675             680             685

Phe Met Thr Tyr Leu Ala Asn Asn Gly Arg Leu Ser Leu Ile Tyr Ile
    690             695             700

Gly Ser Asp Glu Glu Thr Asn Thr Ser Leu Ala Glu Lys Lys Gln Glu
705             710             715             720

Phe Asp Lys Phe Leu Lys Lys Tyr Glu Gln Asn Asn Asn Ile Lys Ile
            725             730             735

Pro Tyr Glu Ile Asn Glu Phe Leu Arg Glu Ile Lys Leu Gly Asn Ile
            740             745             750

Leu Lys Tyr Thr Glu Arg Leu Asn Met Phe Tyr Leu Ile Leu Lys Leu
        755             760             765

Leu Asn His Lys Glu Leu Thr Asn Leu Lys Gly Ser Leu Glu Lys Tyr
        770             775             780

Gln Ser Ala Asn Lys Glu Glu Ala Phe Ser Asp Gln Leu Glu Leu Ile
785             790             795             800

Asn Leu Leu Asn Leu Asp Asn Asn Arg Val Thr Glu Asp Phe Glu Leu
            805             810             815
```

-continued

```
Glu Ala Asp Glu Ile Gly Lys Phe Leu Asp Phe Asn Gly Asn Lys Val
            820                 825                 830

Lys Asp Asn Lys Glu Leu Lys Lys Phe Asp Thr Asn Lys Ile Tyr Phe
        835                 840                 845

Asp Gly Glu Asn Ile Ile Lys His Arg Ala Phe Tyr Asn Ile Lys Lys
    850                 855                 860

Tyr Gly Met Leu Asn Leu Leu Glu Lys Ile Ala Asp Lys Ala Gly Tyr
865                 870                 875                 880

Lys Ile Ser Ile Glu Glu Leu Lys Lys Tyr Ser Asn Lys Lys Asn Glu
                885                 890                 895

Ile Glu Lys Asn His Lys Met Gln Glu Asn Leu His Arg Lys Tyr Ala
            900                 905                 910

Arg Pro Arg Lys Asp Glu Lys Phe Thr Asp Glu Asp Tyr Glu Ser Tyr
        915                 920                 925

Lys Gln Ala Ile Glu Asn Ile Glu Glu Tyr Thr His Leu Lys Asn Lys
    930                 935                 940

Val Glu Phe Asn Glu Leu Asn Leu Leu Gln Gly Leu Leu Leu Arg Ile
945                 950                 955                 960

Leu His Arg Leu Val Gly Tyr Thr Ser Ile Trp Glu Arg Asp Leu Arg
                965                 970                 975

Phe Arg Leu Lys Gly Glu Phe Pro Glu Asn Gln Tyr Ile Glu Glu Ile
            980                 985                 990

Phe Asn Phe Glu Asn Lys Lys Asn  Val Lys Tyr Lys Gly  Gly Gln Ile
        995                 1000                1005

Val Glu Lys Tyr Ile Lys Phe  Tyr Lys Glu Leu His  Gln Asn Asp
    1010                1015                1020

Glu Val Lys Ile Asn Lys Tyr  Ser Ser Ala Asn Ile  Lys Val Leu
    1025                1030                1035

Lys Gln Glu Lys Lys Asp Leu  Tyr Ile Arg Asn Tyr  Ile Ala His
    1040                1045                1050

Phe Asn Tyr Ile Pro His Ala  Glu Ile Ser Leu Leu  Glu Val Leu
    1055                1060                1065

Glu Asn Leu Arg Lys Leu Leu  Ser Tyr Asp Arg Lys  Leu Lys Asn
    1070                1075                1080

Ala Val Met Lys Ser Val Val  Asp Ile Leu Lys Glu  Tyr Gly Phe
    1085                1090                1095

Val Ala Thr Phe Lys Ile Gly  Ala Asp Lys Lys Ile  Gly Ile Gln
    1100                1105                1110

Thr Leu Glu Ser Glu Lys Ile  Val His Leu Lys Asn  Leu Lys Lys
    1115                1120                1125

Lys Lys Leu Met Thr Asp Arg  Asn Ser Glu Glu Leu  Cys Lys Leu
    1130                1135                1140

Val Lys Ile Met Phe Glu Tyr  Lys Met Glu Glu Lys  Lys Ser Glu
    1145                1150                1155

Asn
```

```
<210> SEQ ID NO 212
<211> LENGTH: 1389
<212> TYPE: PRT
<213> ORGANISM: Leptotrichia shahii

<400> SEQUENCE: 212

Met Gly Asn Leu Phe Gly His Lys Arg Trp Tyr Glu Val Arg Asp Lys
1               5                   10                  15
```

-continued

```
Lys Asp Phe Lys Ile Lys Arg Lys Val Lys Val Lys Arg Asn Tyr Asp
            20                  25                  30

Gly Asn Lys Tyr Ile Leu Asn Ile Asn Glu Asn Asn Asn Lys Glu Lys
            35                  40                  45

Ile Asp Asn Asn Lys Phe Ile Arg Lys Tyr Ile Asn Tyr Lys Lys Asn
    50                  55                  60

Asp Asn Ile Leu Lys Glu Phe Thr Arg Lys Phe His Ala Gly Asn Ile
65                  70                  75                  80

Leu Phe Lys Leu Lys Gly Lys Glu Gly Ile Ile Arg Ile Glu Asn Asn
            85                  90                  95

Asp Asp Phe Leu Glu Thr Glu Glu Val Val Leu Tyr Ile Glu Ala Tyr
            100                 105                 110

Gly Lys Ser Glu Lys Leu Lys Ala Leu Gly Ile Thr Lys Lys Lys Ile
            115                 120                 125

Ile Asp Glu Ala Ile Arg Gln Gly Ile Thr Lys Asp Asp Lys Lys Ile
    130                 135                 140

Glu Ile Lys Arg Gln Glu Asn Glu Glu Glu Ile Glu Ile Asp Ile Arg
145                 150                 155                 160

Asp Glu Tyr Thr Asn Lys Thr Leu Asn Asp Cys Ser Ile Ile Leu Arg
            165                 170                 175

Ile Ile Glu Asn Asp Glu Leu Glu Thr Lys Lys Ser Ile Tyr Glu Ile
            180                 185                 190

Phe Lys Asn Ile Asn Met Ser Leu Tyr Lys Ile Ile Glu Lys Ile Ile
            195                 200                 205

Glu Asn Glu Thr Glu Lys Val Phe Glu Asn Arg Tyr Tyr Glu Glu His
    210                 215                 220

Leu Arg Glu Lys Leu Leu Lys Asp Asp Lys Ile Asp Val Ile Leu Thr
225                 230                 235                 240

Asn Phe Met Glu Ile Arg Glu Lys Ile Lys Ser Asn Leu Glu Ile Leu
            245                 250                 255

Gly Phe Val Lys Phe Tyr Leu Asn Val Gly Gly Asp Lys Lys Lys Ser
            260                 265                 270

Lys Asn Lys Lys Met Leu Val Glu Lys Ile Leu Asn Ile Asn Val Asp
            275                 280                 285

Leu Thr Val Glu Asp Ile Ala Asp Phe Val Ile Lys Glu Leu Glu Phe
    290                 295                 300

Trp Asn Ile Thr Lys Arg Ile Glu Lys Val Lys Lys Val Asn Asn Glu
305                 310                 315                 320

Phe Leu Glu Lys Arg Arg Asn Arg Thr Tyr Ile Lys Ser Tyr Val Leu
            325                 330                 335

Leu Asp Lys His Glu Lys Phe Lys Ile Glu Arg Glu Asn Lys Lys Asp
            340                 345                 350

Lys Ile Val Lys Phe Phe Val Glu Asn Ile Lys Asn Asn Ser Ile Lys
            355                 360                 365

Glu Lys Ile Glu Lys Ile Leu Ala Glu Phe Lys Ile Asp Glu Leu Ile
    370                 375                 380

Lys Lys Leu Glu Lys Glu Leu Lys Lys Gly Asn Cys Asp Thr Glu Ile
385                 390                 395                 400

Phe Gly Ile Phe Lys Lys His Tyr Lys Val Asn Phe Asp Ser Lys Lys
            405                 410                 415

Phe Ser Lys Lys Ser Asp Glu Glu Lys Glu Leu Tyr Lys Ile Ile Tyr
            420                 425                 430

Arg Tyr Leu Lys Gly Arg Ile Glu Lys Ile Leu Val Asn Glu Gln Lys
```

-continued

```
                435                   440                   445

Val Arg Leu Lys Lys Met Glu Lys Ile Glu Ile Glu Lys Ile Leu Asn
    450                   455                   460

Glu Ser Ile Leu Ser Glu Lys Ile Leu Lys Arg Val Lys Gln Tyr Thr
465                   470                   475                   480

Leu Glu His Ile Met Tyr Leu Gly Lys Leu Arg His Asn Asp Ile Asp
                485                   490                   495

Met Thr Thr Val Asn Thr Asp Asp Phe Ser Arg Leu His Ala Lys Glu
                500                   505                   510

Glu Leu Asp Leu Glu Leu Ile Thr Phe Phe Ala Ser Thr Asn Met Glu
                515                   520                   525

Leu Asn Lys Ile Phe Ser Arg Glu Asn Ile Asn Asn Asp Glu Asn Ile
    530                   535                   540

Asp Phe Phe Gly Gly Asp Arg Glu Lys Asn Tyr Val Leu Asp Lys Lys
545                   550                   555                   560

Ile Leu Asn Ser Lys Ile Lys Ile Ile Arg Asp Leu Asp Phe Ile Asp
                565                   570                   575

Asn Lys Asn Asn Ile Thr Asn Asn Phe Ile Arg Lys Phe Thr Lys Ile
                580                   585                   590

Gly Thr Asn Glu Arg Asn Arg Ile Leu His Ala Ile Ser Lys Glu Arg
                595                   600                   605

Asp Leu Gln Gly Thr Gln Asp Asp Tyr Asn Lys Val Ile Asn Ile Ile
    610                   615                   620

Gln Asn Leu Lys Ile Ser Asp Glu Glu Val Ser Lys Ala Leu Asn Leu
625                   630                   635                   640

Asp Val Val Phe Lys Asp Lys Lys Asn Ile Ile Thr Lys Ile Asn Asp
                645                   650                   655

Ile Lys Ile Ser Glu Glu Asn Asn Asn Asp Ile Lys Tyr Leu Pro Ser
                660                   665                   670

Phe Ser Lys Val Leu Pro Glu Ile Leu Asn Leu Tyr Arg Asn Asn Pro
                675                   680                   685

Lys Asn Glu Pro Phe Asp Thr Ile Glu Thr Glu Lys Ile Val Leu Asn
    690                   695                   700

Ala Leu Ile Tyr Val Asn Lys Glu Leu Tyr Lys Lys Leu Ile Leu Glu
705                   710                   715                   720

Asp Asp Leu Glu Glu Asn Glu Ser Lys Asn Ile Phe Leu Gln Glu Leu
                725                   730                   735

Lys Lys Thr Leu Gly Asn Ile Asp Glu Ile Asp Glu Asn Ile Ile Glu
                740                   745                   750

Asn Tyr Tyr Lys Asn Ala Gln Ile Ser Ala Ser Lys Gly Asn Asn Lys
                755                   760                   765

Ala Ile Lys Lys Tyr Gln Lys Lys Val Ile Glu Cys Tyr Ile Gly Tyr
    770                   775                   780

Leu Arg Lys Asn Tyr Glu Glu Leu Phe Asp Phe Ser Asp Phe Lys Met
785                   790                   795                   800

Asn Ile Gln Glu Ile Lys Lys Gln Ile Lys Asp Ile Asn Asp Asn Lys
                805                   810                   815

Thr Tyr Glu Arg Ile Thr Val Lys Thr Ser Asp Lys Thr Ile Val Ile
                820                   825                   830

Asn Asp Asp Phe Glu Tyr Ile Ile Ser Ile Phe Ala Leu Leu Asn Ser
    835                   840                   845

Asn Ala Val Ile Asn Lys Ile Arg Asn Arg Phe Phe Ala Thr Ser Val
    850                   855                   860
```

-continued

```
Trp Leu Asn Thr Ser Glu Tyr Gln Asn Ile Ile Asp Ile Leu Asp Glu
865                 870                 875                 880

Ile Met Gln Leu Asn Thr Leu Arg Asn Glu Cys Ile Thr Glu Asn Trp
                885                 890                 895

Asn Leu Asn Leu Glu Glu Phe Ile Gln Lys Met Lys Glu Ile Glu Lys
            900                 905                 910

Asp Phe Asp Asp Phe Lys Ile Gln Thr Lys Lys Glu Ile Phe Asn Asn
        915                 920                 925

Tyr Tyr Glu Asp Ile Lys Asn Asn Ile Leu Thr Glu Phe Lys Asp Asp
    930                 935                 940

Ile Asn Gly Cys Asp Val Leu Glu Lys Lys Leu Glu Lys Ile Val Ile
945                 950                 955                 960

Phe Asp Asp Glu Thr Lys Phe Glu Ile Asp Lys Lys Ser Asn Ile Leu
                965                 970                 975

Gln Asp Glu Gln Arg Lys Leu Ser Asn Ile Asn Lys Lys Asp Leu Lys
            980                 985                 990

Lys Lys Val Asp Gln Tyr Ile Lys  Asp Lys Asp Gln Glu  Ile Lys Ser
        995                 1000                1005

Lys Ile  Leu Cys Arg Ile Ile  Phe Asn Ser Asp Phe  Leu Lys Lys
    1010                1015                1020

Tyr Lys  Lys Glu Ile Asp Asn  Leu Ile Glu Asp Met  Glu Ser Glu
    1025                1030                1035

Asn Glu  Asn Lys Phe Gln Glu  Ile Tyr Tyr Pro Lys  Glu Arg Lys
    1040                1045                1050

Asn Glu  Leu Tyr Ile Tyr Lys  Lys Asn Leu Phe Leu  Asn Ile Gly
    1055                1060                1065

Asn Pro  Asn Phe Asp Lys Ile  Tyr Gly Leu Ile Ser  Asn Asp Ile
    1070                1075                1080

Lys Met  Ala Asp Ala Lys Phe  Leu Phe Asn Ile Asp  Gly Lys Asn
    1085                1090                1095

Ile Arg  Lys Asn Lys Ile Ser  Glu Ile Asp Ala Ile  Leu Lys Asn
    1100                1105                1110

Leu Asn  Asp Lys Leu Asn Gly  Tyr Ser Lys Glu Tyr  Lys Glu Lys
    1115                1120                1125

Tyr Ile  Lys Lys Leu Lys Glu  Asn Asp Asp Phe Phe  Ala Lys Asn
    1130                1135                1140

Ile Gln  Asn Lys Asn Tyr Lys  Ser Phe Glu Lys Asp  Tyr Asn Arg
    1145                1150                1155

Val Ser  Glu Tyr Lys Lys Ile  Arg Asp Leu Val Glu  Phe Asn Tyr
    1160                1165                1170

Leu Asn  Lys Ile Glu Ser Tyr  Leu Ile Asp Ile Asn  Trp Lys Leu
    1175                1180                1185

Ala Ile  Gln Met Ala Arg Phe  Glu Arg Asp Met His  Tyr Ile Val
    1190                1195                1200

Asn Gly  Leu Arg Glu Leu Gly  Ile Ile Lys Leu Ser  Gly Tyr Asn
    1205                1210                1215

Thr Gly  Ile Ser Arg Ala Tyr  Pro Lys Arg Asn Gly  Ser Asp Gly
    1220                1225                1230

Phe Tyr  Thr Thr Thr Ala Tyr  Tyr Lys Phe Phe Asp  Glu Glu Ser
    1235                1240                1245

Tyr Lys  Lys Phe Glu Lys Ile  Cys Tyr Gly Phe Gly  Ile Asp Leu
    1250                1255                1260
```

-continued

```
Ser Glu  Asn Ser Glu Ile Asn  Lys Pro Glu Asn Glu  Ser Ile Arg
    1265              1270              1275

Asn Tyr  Ile Ser His Phe Tyr  Ile Val Arg Asn Pro  Phe Ala Asp
    1280              1285              1290

Tyr Ser  Ile Ala Glu Gln Ile  Asp Arg Val Ser Asn  Leu Leu Ser
    1295              1300              1305

Tyr Ser  Thr Arg Tyr Asn Asn  Ser Thr Tyr Ala Ser  Val Phe Glu
    1310              1315              1320

Val Phe  Lys Lys Asp Val Asn  Leu Asp Tyr Asp Glu  Leu Lys Lys
    1325              1330              1335

Lys Phe  Lys Leu Ile Gly Asn  Asn Asp Ile Leu Glu  Arg Leu Met
    1340              1345              1350

Lys Pro  Lys Lys Val Ser Val  Leu Glu Leu Glu Ser  Tyr Asn Ser
    1355              1360              1365

Asp Tyr  Ile Lys Asn Leu Ile  Ile Glu Leu Leu Thr  Lys Ile Glu
    1370              1375              1380

Asn Thr  Asn Asp Thr Leu
    1385

<210> SEQ ID NO 213
<211> LENGTH: 1285
<212> TYPE: PRT
<213> ORGANISM: Rhodobacter capsulatus

<400> SEQUENCE: 213

Met Gln Ile Gly Lys Val Gln Gly Arg Thr Ile Ser Glu Phe Gly Asp
1               5                   10                  15

Pro Ala Gly Gly Leu Lys Arg Lys Ile Ser Thr Asp Gly Lys Asn Arg
                20                  25                  30

Lys Glu Leu Pro Ala His Leu Ser Ser Asp Pro Lys Ala Leu Ile Gly
            35                  40                  45

Gln Trp Ile Ser Gly Ile Asp Lys Ile Tyr Arg Lys Pro Asp Ser Arg
        50                  55                  60

Lys Ser Asp Gly Lys Ala Ile His Ser Pro Thr Pro Ser Lys Met Gln
65                  70                  75                  80

Phe Asp Ala Arg Asp Asp Leu Gly Glu Ala Phe Trp Lys Leu Val Ser
                85                  90                  95

Glu Ala Gly Leu Ala Gln Asp Ser Asp Tyr Asp Gln Phe Lys Arg Arg
                100                 105                 110

Leu His Pro Tyr Gly Asp Lys Phe Gln Pro Ala Asp Ser Gly Ala Lys
            115                 120                 125

Leu Lys Phe Glu Ala Asp Pro Pro Glu Pro Gln Ala Phe His Gly Arg
            130                 135                 140

Trp Tyr Gly Ala Met Ser Lys Arg Gly Asn Asp Ala Lys Glu Leu Ala
145                 150                 155                 160

Ala Ala Leu Tyr Glu His Leu His Val Asp Glu Lys Arg Ile Asp Gly
                165                 170                 175

Gln Pro Lys Arg Asn Pro Lys Thr Asp Lys Phe Ala Pro Gly Leu Val
            180                 185                 190

Val Ala Arg Ala Leu Gly Ile Glu Ser Ser Val Leu Pro Arg Gly Met
            195                 200                 205

Ala Arg Leu Ala Arg Asn Trp Gly Glu Glu Glu Ile Gln Thr Tyr Phe
            210                 215                 220

Val Val Asp Val Ala Ala Ser Val Lys Glu Val Ala Lys Ala Ala Val
225                 230                 235                 240
```

-continued

```
Ser Ala Ala Gln Ala Phe Asp Pro Pro Arg Gln Val Ser Gly Arg Ser
                245                 250                 255

Leu Ser Pro Lys Val Gly Phe Ala Leu Ala Glu His Leu Glu Arg Val
            260                 265                 270

Thr Gly Ser Lys Arg Cys Ser Phe Asp Pro Ala Ala Gly Pro Ser Val
        275                 280                 285

Leu Ala Leu His Asp Glu Val Lys Lys Thr Tyr Lys Arg Leu Cys Ala
    290                 295                 300

Arg Gly Lys Asn Ala Ala Arg Ala Phe Pro Ala Asp Lys Thr Glu Leu
305                 310                 315                 320

Leu Ala Leu Met Arg His Thr His Glu Asn Arg Val Arg Asn Gln Met
                325                 330                 335

Val Arg Met Gly Arg Val Ser Glu Tyr Arg Gly Gln Gln Ala Gly Asp
            340                 345                 350

Leu Ala Gln Ser His Tyr Trp Thr Ser Ala Gly Gln Thr Glu Ile Lys
        355                 360                 365

Glu Ser Glu Ile Phe Val Arg Leu Trp Val Gly Ala Phe Ala Leu Ala
    370                 375                 380

Gly Arg Ser Met Lys Ala Trp Ile Asp Pro Met Gly Lys Ile Val Asn
385                 390                 395                 400

Thr Glu Lys Asn Asp Arg Asp Leu Thr Ala Ala Val Asn Ile Arg Gln
                405                 410                 415

Val Ile Ser Asn Lys Glu Met Val Ala Glu Ala Met Ala Arg Arg Gly
            420                 425                 430

Ile Tyr Phe Gly Glu Thr Pro Glu Leu Asp Arg Leu Gly Ala Glu Gly
        435                 440                 445

Asn Glu Gly Phe Val Phe Ala Leu Leu Arg Tyr Leu Arg Gly Cys Arg
    450                 455                 460

Asn Gln Thr Phe His Leu Gly Ala Arg Ala Gly Phe Leu Lys Glu Ile
465                 470                 475                 480

Arg Lys Glu Leu Glu Lys Thr Arg Trp Gly Lys Ala Lys Glu Ala Glu
                485                 490                 495

His Val Val Leu Thr Asp Lys Thr Val Ala Ala Ile Arg Ala Ile Ile
            500                 505                 510

Asp Asn Asp Ala Lys Ala Leu Gly Ala Arg Leu Leu Ala Asp Leu Ser
        515                 520                 525

Gly Ala Phe Val Ala His Tyr Ala Ser Lys Glu His Phe Ser Thr Leu
    530                 535                 540

Tyr Ser Glu Ile Val Lys Ala Val Lys Asp Ala Pro Glu Val Ser Ser
545                 550                 555                 560

Gly Leu Pro Arg Leu Lys Leu Leu Lys Arg Ala Asp Gly Val Arg
            565                 570                 575

Gly Tyr Val His Gly Leu Arg Asp Thr Arg Lys His Ala Phe Ala Thr
        580                 585                 590

Lys Leu Pro Pro Pro Ala Pro Arg Glu Leu Asp Asp Pro Ala Thr
            595                 600                 605

Lys Ala Arg Tyr Ile Ala Leu Leu Arg Leu Tyr Asp Gly Pro Phe Arg
    610                 615                 620

Ala Tyr Ala Ser Gly Ile Thr Gly Thr Ala Leu Ala Gly Pro Ala Ala
625                 630                 635                 640

Arg Ala Lys Glu Ala Ala Thr Ala Leu Ala Gln Ser Val Asn Val Thr
                645                 650                 655
```

-continued

```
Lys Ala Tyr Ser Asp Val Met Glu Gly Arg Ser Ser Arg Leu Arg Pro
            660                 665                 670

Pro Asn Asp Gly Glu Thr Leu Arg Glu Tyr Leu Ser Ala Leu Thr Gly
            675                 680                 685

Glu Thr Ala Thr Glu Phe Arg Val Gln Ile Gly Tyr Glu Ser Asp Ser
        690                 695                 700

Glu Asn Ala Arg Lys Gln Ala Glu Phe Ile Glu Asn Tyr Arg Arg Asp
705                 710                 715                 720

Met Leu Ala Phe Met Phe Glu Asp Tyr Ile Arg Ala Lys Gly Phe Asp
                725                 730                 735

Trp Ile Leu Lys Ile Glu Pro Gly Ala Thr Ala Met Thr Arg Ala Pro
            740                 745                 750

Val Leu Pro Glu Pro Ile Asp Thr Arg Gly Gln Tyr Glu His Trp Gln
            755                 760                 765

Ala Ala Leu Tyr Leu Val Met His Phe Val Pro Ala Ser Asp Val Ser
        770                 775                 780

Asn Leu Leu His Gln Leu Arg Lys Trp Glu Ala Leu Gln Gly Lys Tyr
785                 790                 795                 800

Glu Leu Val Gln Asp Gly Asp Ala Thr Asp Gln Ala Asp Ala Arg Arg
                805                 810                 815

Glu Ala Leu Asp Leu Val Lys Arg Phe Arg Asp Val Leu Val Leu Phe
            820                 825                 830

Leu Lys Thr Gly Glu Ala Arg Phe Glu Gly Arg Ala Ala Pro Phe Asp
            835                 840                 845

Leu Lys Pro Phe Arg Ala Leu Phe Ala Asn Pro Ala Thr Phe Asp Arg
        850                 855                 860

Leu Phe Met Ala Thr Pro Thr Thr Ala Arg Pro Ala Glu Asp Asp Pro
865                 870                 875                 880

Glu Gly Asp Gly Ala Ser Glu Pro Glu Leu Arg Val Ala Arg Thr Leu
                885                 890                 895

Arg Gly Leu Arg Gln Ile Ala Arg Tyr Asn His Met Ala Val Leu Ser
            900                 905                 910

Asp Leu Phe Ala Lys His Lys Val Arg Asp Glu Glu Val Ala Arg Leu
            915                 920                 925

Ala Glu Ile Glu Asp Glu Thr Gln Glu Lys Ser Gln Ile Val Ala Ala
        930                 935                 940

Gln Glu Leu Arg Thr Asp Leu His Asp Lys Val Met Lys Cys His Pro
945                 950                 955                 960

Lys Thr Ile Ser Pro Glu Glu Arg Gln Ser Tyr Ala Ala Ala Ile Lys
                965                 970                 975

Thr Ile Glu Glu His Arg Phe Leu Val Gly Arg Val Tyr Leu Gly Asp
            980                 985                 990

His Leu Arg Leu His Arg Leu Met   Met Asp Val Ile Gly  Arg Leu Ile
            995                 1000                 1005

Asp Tyr  Ala Gly Ala Tyr Glu  Arg Asp Thr Gly Thr  Phe Leu Ile
    1010                 1015                 1020

Asn Ala  Ser Lys Gln Leu Gly  Ala Gly Ala Asp Trp  Ala Val Thr
    1025                 1030                 1035

Ile Ala  Gly Ala Ala Asn Thr  Asp Ala Arg Thr Gln  Thr Arg Lys
    1040                 1045                 1050

Asp Leu  Ala His Phe Asn Val  Leu Asp Arg Ala Asp  Gly Thr Pro
    1055                 1060                 1065

Asp Leu  Thr Ala Leu Val Asn  Arg Ala Arg Glu Met  Met Ala Tyr
```

-continued

```
            1070              1075              1080

Asp Arg  Lys Arg Lys Asn Ala  Val Pro Arg Ser Ile  Leu Asp Met
    1085              1090              1095

Leu Ala  Arg Leu Gly Leu Thr  Leu Lys Trp Gln Met  Lys Asp His
    1100              1105              1110

Leu Leu  Gln Asp Ala Thr Ile  Thr Gln Ala Ala Ile  Lys His Leu
    1115              1120              1125

Asp Lys  Val Arg Leu Thr Val  Gly Gly Pro Ala Ala  Val Thr Glu
    1130              1135              1140

Ala Arg  Phe Ser Gln Asp Tyr  Leu Gln Met Val Ala  Ala Val Phe
    1145              1150              1155

Asn Gly  Ser Val Gln Asn Pro  Lys Pro Arg Arg Arg  Asp Asp Gly
    1160              1165              1170

Asp Ala  Trp His Lys Pro Pro  Lys Pro Ala Thr Ala  Gln Ser Gln
    1175              1180              1185

Pro Asp  Gln Lys Pro Pro Asn  Lys Ala Pro Ser Ala  Gly Ser Arg
    1190              1195              1200

Leu Pro  Pro Pro Gln Val Gly  Glu Val Tyr Glu Gly  Val Val Val
    1205              1210              1215

Lys Val  Ile Asp Thr Gly Ser  Leu Gly Phe Leu Ala  Val Glu Gly
    1220              1225              1230

Val Ala  Gly Asn Ile Gly Leu  His Ile Ser Arg Leu  Arg Arg Ile
    1235              1240              1245

Arg Glu  Asp Ala Ile Ile Val  Gly Arg Arg Tyr Arg  Phe Arg Val
    1250              1255              1260

Glu Ile  Tyr Val Pro Pro Lys  Ser Asn Thr Ser Lys  Leu Asn Ala
    1265              1270              1275

Ala Asp  Leu Val Arg Ile Asp
    1280              1285

<210> SEQ ID NO 214
<211> LENGTH: 1175
<212> TYPE: PRT
<213> ORGANISM: Carnobacterium gallinarum

<400> SEQUENCE: 214

Met Arg Ile Thr Lys Val Lys Ile Lys Leu Asp Asn Lys Leu Tyr Gln
1               5                   10                  15

Val Thr Met Gln Lys Glu Glu Lys Tyr Gly Thr Leu Lys Leu Asn Glu
            20                  25                  30

Glu Ser Arg Lys Ser Thr Ala Glu Ile Leu Arg Leu Lys Lys Ala Ser
        35                  40                  45

Phe Asn Lys Ser Phe His Ser Lys Thr Ile Asn Ser Gln Lys Glu Asn
    50                  55                  60

Lys Asn Ala Thr Ile Lys Lys Asn Gly Asp Tyr Ile Ser Gln Ile Phe
65                  70                  75                  80

Glu Lys Leu Val Gly Val Asp Thr Asn Lys Asn Ile Arg Lys Pro Lys
                85                  90                  95

Met Ser Leu Thr Asp Leu Lys Asp Leu Pro Lys Lys Asp Leu Ala Leu
            100                 105                 110

Phe Ile Lys Arg Lys Phe Lys Asn Asp Asp Ile Val Glu Ile Lys Asn
        115                 120                 125

Leu Asp Leu Ile Ser Leu Phe Tyr Asn Ala Leu Gln Lys Val Pro Gly
    130                 135                 140
```

-continued

```
Glu His Phe Thr Asp Glu Ser Trp Ala Asp Phe Cys Gln Glu Met Met
145             150              155              160

Pro Tyr Arg Glu Tyr Lys Asn Lys Phe Ile Glu Arg Lys Ile Ile Leu
                165              170              175

Leu Ala Asn Ser Ile Glu Gln Asn Lys Gly Phe Ser Ile Asn Pro Glu
                180              185              190

Thr Phe Ser Lys Arg Lys Arg Val Leu His Gln Trp Ala Ile Glu Val
            195              200              205

Gln Glu Arg Gly Asp Phe Ser Ile Leu Asp Glu Lys Leu Ser Lys Leu
    210              215              220

Ala Glu Ile Tyr Asn Phe Lys Lys Met Cys Lys Arg Val Gln Asp Glu
225              230              235              240

Leu Asn Asp Leu Glu Lys Ser Met Lys Lys Gly Lys Asn Pro Glu Lys
            245              250              255

Glu Lys Glu Ala Tyr Lys Lys Gln Lys Asn Phe Lys Ile Lys Thr Ile
            260              265              270

Trp Lys Asp Tyr Pro Tyr Lys Thr His Ile Gly Leu Ile Glu Lys Ile
            275              280              285

Lys Glu Asn Glu Glu Leu Asn Gln Phe Asn Ile Glu Ile Gly Lys Tyr
    290              295              300

Phe Glu His Tyr Phe Pro Ile Lys Lys Glu Arg Cys Thr Glu Asp Glu
305              310              315              320

Pro Tyr Tyr Leu Asn Ser Glu Thr Ile Ala Thr Thr Val Asn Tyr Gln
                325              330              335

Leu Lys Asn Ala Leu Ile Ser Tyr Leu Met Gln Ile Gly Lys Tyr Lys
            340              345              350

Gln Phe Gly Leu Glu Asn Gln Val Leu Asp Ser Lys Lys Leu Gln Glu
    355              360              365

Ile Gly Ile Tyr Glu Gly Phe Gln Thr Lys Phe Met Asp Ala Cys Val
    370              375              380

Phe Ala Thr Ser Ser Leu Lys Asn Ile Ile Glu Pro Met Arg Ser Gly
385              390              395              400

Asp Ile Leu Gly Lys Arg Glu Phe Lys Glu Ala Ile Ala Thr Ser Ser
                405              410              415

Phe Val Asn Tyr His His Phe Phe Pro Tyr Phe Pro Phe Glu Leu Lys
            420              425              430

Gly Met Lys Asp Arg Glu Ser Glu Leu Ile Pro Phe Gly Glu Gln Thr
            435              440              445

Glu Ala Lys Gln Met Gln Asn Ile Trp Ala Leu Arg Gly Ser Val Gln
    450              455              460

Gln Ile Arg Asn Glu Ile Phe His Ser Phe Asp Lys Asn Gln Lys Phe
465              470              475              480

Asn Leu Pro Gln Leu Asp Lys Ser Asn Phe Glu Phe Asp Ala Ser Glu
            485              490              495

Asn Ser Thr Gly Lys Ser Gln Ser Tyr Ile Glu Thr Asp Tyr Lys Phe
            500              505              510

Leu Phe Glu Ala Glu Lys Asn Gln Leu Glu Gln Phe Phe Ile Glu Arg
            515              520              525

Ile Lys Ser Ser Gly Ala Leu Glu Tyr Tyr Pro Leu Lys Ser Leu Glu
    530              535              540

Lys Leu Phe Ala Lys Lys Glu Met Lys Phe Ser Leu Gly Ser Gln Val
545              550              555              560

Val Ala Phe Ala Pro Ser Tyr Lys Lys Leu Val Lys Lys Gly His Ser
```

-continued

```
                565              570              575

Tyr Gln Thr Ala Thr Glu Gly Thr Ala Asn Tyr Leu Gly Leu Ser Tyr
                580              585              590

Tyr Asn Arg Tyr Glu Leu Lys Glu Glu Ser Phe Gln Ala Gln Tyr Tyr
                595              600              605

Leu Leu Lys Leu Ile Tyr Gln Tyr Val Phe Leu Pro Asn Phe Ser Gln
        610              615              620

Gly Asn Ser Pro Ala Phe Arg Glu Thr Val Lys Ala Ile Leu Arg Ile
    625              630              635              640

Asn Lys Asp Glu Ala Arg Lys Lys Met Lys Lys Asn Lys Lys Phe Leu
                645              650              655

Arg Lys Tyr Ala Phe Glu Gln Val Arg Glu Met Glu Phe Lys Glu Thr
                660              665              670

Pro Asp Gln Tyr Met Ser Tyr Leu Gln Ser Glu Met Arg Glu Glu Lys
                675              680              685

Val Arg Lys Ala Glu Lys Asn Asp Lys Gly Phe Glu Lys Asn Ile Thr
        690              695              700

Met Asn Phe Glu Lys Leu Leu Met Gln Ile Phe Val Lys Gly Phe Asp
    705              710              715              720

Val Phe Leu Thr Thr Phe Ala Gly Lys Glu Leu Leu Leu Ser Ser Glu
                725              730              735

Glu Lys Val Ile Lys Glu Thr Glu Ile Ser Leu Ser Lys Lys Ile Asn
                740              745              750

Glu Arg Glu Lys Thr Leu Lys Ala Ser Ile Gln Val Glu His Gln Leu
                755              760              765

Val Ala Thr Asn Ser Ala Ile Ser Tyr Trp Leu Phe Cys Lys Leu Leu
        770              775              780

Asp Ser Arg His Leu Asn Glu Leu Arg Asn Glu Met Ile Lys Phe Lys
    785              790              795              800

Gln Ser Arg Ile Lys Phe Asn His Thr Gln His Ala Glu Leu Ile Gln
                805              810              815

Asn Leu Leu Pro Ile Val Glu Leu Thr Ile Leu Ser Asn Asp Tyr Asp
                820              825              830

Glu Lys Asn Asp Ser Gln Asn Val Asp Val Ser Ala Tyr Phe Glu Asp
                835              840              845

Lys Ser Leu Tyr Glu Thr Ala Pro Tyr Val Gln Thr Asp Asp Arg Thr
        850              855              860

Arg Val Ser Phe Arg Pro Ile Leu Lys Leu Glu Lys Tyr His Thr Lys
    865              870              875              880

Ser Leu Ile Glu Ala Leu Leu Lys Asp Asn Pro Gln Phe Arg Val Ala
                885              890              895

Ala Thr Asp Ile Gln Glu Trp Met His Lys Arg Glu Glu Ile Gly Glu
                900              905              910

Leu Val Glu Lys Arg Lys Asn Leu His Thr Glu Trp Ala Glu Gly Gln
                915              920              925

Gln Thr Leu Gly Ala Glu Lys Arg Glu Glu Tyr Arg Asp Tyr Cys Lys
        930              935              940

Lys Ile Asp Arg Phe Asn Trp Lys Ala Asn Lys Val Thr Leu Thr Tyr
    945              950              955              960

Leu Ser Gln Leu His Tyr Leu Ile Thr Asp Leu Leu Gly Arg Met Val
                965              970              975

Gly Phe Ser Ala Leu Phe Glu Arg Asp Leu Val Tyr Phe Ser Arg Ser
                980              985              990
```

-continued

```
Phe Ser Glu Leu Gly Gly Glu Thr  Tyr His Ile Ser Asp  Tyr Lys Asn
        995                 1000                1005

Leu Ser  Gly Val Leu Arg Leu  Asn Ala Glu Val Lys  Pro Ile Lys
        1010                1015                1020

Ile Lys  Asn Ile Lys Val Ile  Asp Asn Glu Glu Asn  Pro Tyr Lys
        1025                1030                1035

Gly Asn  Glu Pro Glu Val Lys  Pro Phe Leu Asp Arg  Leu His Ala
        1040                1045                1050

Tyr Leu  Glu Asn Val Ile Gly  Ile Lys Ala Val His  Gly Lys Ile
        1055                1060                1065

Arg Asn  Gln Thr Ala His Leu  Ser Val Leu Gln Leu  Glu Leu Ser
        1070                1075                1080

Met Ile  Glu Ser Met Asn Asn  Leu Arg Asp Leu Met  Ala Tyr Asp
        1085                1090                1095

Arg Lys  Leu Lys Asn Ala Val  Thr Lys Ser Met Ile  Lys Ile Leu
        1100                1105                1110

Asp Lys  His Gly Met Ile Leu  Lys Leu Lys Ile Asp  Glu Asn His
        1115                1120                1125

Lys Asn  Phe Glu Ile Glu Ser  Leu Ile Pro Lys Glu  Ile Ile His
        1130                1135                1140

Leu Lys  Asp Lys Ala Ile Lys  Thr Asn Gln Val Ser  Glu Glu Tyr
        1145                1150                1155

Cys Gln  Leu Val Leu Ala Leu  Leu Thr Thr Asn Pro  Gly Asn Gln
        1160                1165                1170

Leu Asn
        1175
```

<210> SEQ ID NO 215
<211> LENGTH: 1285
<212> TYPE: PRT
<213> ORGANISM: Herbinix hemicellulosilytica

<400> SEQUENCE: 215

```
Met Lys Leu Thr Arg Arg Arg Ile Ser Gly Asn Ser Val Asp Gln Lys
1               5                   10                  15

Ile Thr Ala Ala Phe Tyr Arg Asp Met Ser Gln Gly Leu Leu Tyr Tyr
            20                  25                  30

Asp Ser Glu Asp Asn Asp Cys Thr Asp Lys Val Ile Glu Ser Met Asp
            35                  40                  45

Phe Glu Arg Ser Trp Arg Gly Arg Ile Leu Lys Asn Gly Glu Asp Asp
        50                  55                  60

Lys Asn Pro Phe Tyr Met Phe Val Lys Gly Leu Val Gly Ser Asn Asp
65                  70                  75                  80

Lys Ile Val Cys Glu Pro Ile Asp Val Asp Ser Asp Pro Asp Asn Leu
                85                  90                  95

Asp Ile Leu Ile Asn Lys Asn Leu Thr Gly Phe Gly Arg Asn Leu Lys
            100                 105                 110

Ala Pro Asp Ser Asn Asp Thr Leu Glu Asn Leu Ile Arg Lys Ile Gln
            115                 120                 125

Ala Gly Ile Pro Glu Glu Glu Val Leu Pro Glu Leu Lys Lys Ile Lys
            130                 135                 140

Glu Met Ile Gln Lys Asp Ile Val Asn Arg Lys Glu Gln Leu Leu Lys
145                 150                 155                 160

Ser Ile Lys Asn Asn Arg Ile Pro Phe Ser Leu Glu Gly Ser Lys Leu
```

-continued

```
                    165                 170                 175
    Val Pro Ser Thr Lys Lys Met Lys Trp Leu Phe Lys Leu Ile Asp Val
                180                 185                 190

Pro Asn Lys Thr Phe Asn Glu Lys Met Leu Glu Lys Tyr Trp Glu Ile
                195                 200                 205

Tyr Asp Tyr Asp Lys Leu Lys Ala Asn Ile Thr Asn Arg Leu Asp Lys
                210                 215                 220

Thr Asp Lys Lys Ala Arg Ser Ile Ser Arg Ala Val Ser Glu Glu Leu
    225                 230                 235                 240

Arg Glu Tyr His Lys Asn Leu Arg Thr Asn Tyr Asn Arg Phe Val Ser
                245                 250                 255

Gly Asp Arg Pro Ala Ala Gly Leu Asp Asn Gly Gly Ser Ala Lys Tyr
                260                 265                 270

Asn Pro Asp Lys Glu Glu Phe Leu Leu Phe Leu Lys Glu Val Glu Gln
                275                 280                 285

Tyr Phe Lys Lys Tyr Phe Pro Val Lys Ser Lys His Ser Asn Lys Ser
                290                 295                 300

Lys Asp Lys Ser Leu Val Asp Lys Tyr Lys Asn Tyr Cys Ser Tyr Lys
    305                 310                 315                 320

Val Val Lys Lys Glu Val Asn Arg Ser Ile Ile Asn Gln Leu Val Ala
                325                 330                 335

Gly Leu Ile Gln Gln Gly Lys Leu Leu Tyr Tyr Phe Tyr Tyr Asn Asp
                340                 345                 350

Thr Trp Gln Glu Asp Phe Leu Asn Ser Tyr Gly Leu Ser Tyr Ile Gln
                355                 360                 365

Val Glu Glu Ala Phe Lys Lys Ser Val Met Thr Ser Leu Ser Trp Gly
                370                 375                 380

Ile Asn Arg Leu Thr Ser Phe Phe Ile Asp Asp Ser Asn Thr Val Lys
    385                 390                 395                 400

Phe Asp Asp Ile Thr Thr Lys Lys Ala Lys Glu Ala Ile Glu Ser Asn
                405                 410                 415

Tyr Phe Asn Lys Leu Arg Thr Cys Ser Arg Met Gln Asp His Phe Lys
                420                 425                 430

Glu Lys Leu Ala Phe Phe Tyr Pro Val Tyr Val Lys Asp Lys Lys Asp
                435                 440                 445

Arg Pro Asp Asp Asp Ile Glu Asn Leu Ile Val Leu Val Lys Asn Ala
    450                 455                 460

Ile Glu Ser Val Ser Tyr Leu Arg Asn Arg Thr Phe His Phe Lys Glu
    465                 470                 475                 480

Ser Ser Leu Leu Glu Leu Leu Lys Glu Leu Asp Asp Lys Asn Ser Gly
                485                 490                 495

Gln Asn Lys Ile Asp Tyr Ser Val Ala Ala Glu Phe Ile Lys Arg Asp
                500                 505                 510

Ile Glu Asn Leu Tyr Asp Val Phe Arg Glu Gln Ile Arg Ser Leu Gly
                515                 520                 525

Ile Ala Glu Tyr Tyr Lys Ala Asp Met Ile Ser Asp Cys Phe Lys Thr
                530                 535                 540

Cys Gly Leu Glu Phe Ala Leu Tyr Ser Pro Lys Asn Ser Leu Met Pro
    545                 550                 555                 560

Ala Phe Lys Asn Val Tyr Lys Arg Gly Ala Asn Leu Asn Lys Ala Tyr
                565                 570                 575

Ile Arg Asp Lys Gly Pro Lys Glu Thr Gly Asp Gln Gly Gln Asn Ser
                580                 585                 590
```

-continued

```
Tyr Lys Ala Leu Glu Glu Tyr Arg Glu Leu Thr Trp Tyr Ile Glu Val
        595                 600                 605

Lys Asn Asn Asp Gln Ser Tyr Asn Ala Tyr Lys Asn Leu Leu Gln Leu
        610                 615                 620

Ile Tyr Tyr His Ala Phe Leu Pro Glu Val Arg Glu Asn Glu Ala Leu
625                 630                 635                 640

Ile Thr Asp Phe Ile Asn Arg Thr Lys Glu Trp Asn Arg Lys Glu Thr
                645                 650                 655

Glu Glu Arg Leu Asn Thr Lys Asn Asn Lys Lys His Lys Asn Phe Asp
                660                 665                 670

Glu Asn Asp Asp Ile Thr Val Asn Thr Tyr Arg Tyr Glu Ser Ile Pro
        675                 680                 685

Asp Tyr Gln Gly Glu Ser Leu Asp Asp Tyr Leu Lys Val Leu Gln Arg
        690                 695                 700

Lys Gln Met Ala Arg Ala Lys Glu Val Asn Glu Lys Glu Glu Gly Asn
705                 710                 715                 720

Asn Asn Tyr Ile Gln Phe Ile Arg Asp Val Val Val Trp Ala Phe Gly
                725                 730                 735

Ala Tyr Leu Glu Asn Lys Leu Lys Asn Tyr Lys Asn Glu Leu Gln Pro
                740                 745                 750

Pro Leu Ser Lys Glu Asn Ile Gly Leu Asn Asp Thr Leu Lys Glu Leu
        755                 760                 765

Phe Pro Glu Glu Lys Val Lys Ser Pro Phe Asn Ile Lys Cys Arg Phe
        770                 775                 780

Ser Ile Ser Thr Phe Ile Asp Asn Lys Gly Lys Ser Thr Asp Asn Thr
785                 790                 795                 800

Ser Ala Glu Ala Val Lys Thr Asp Gly Lys Glu Asp Glu Lys Asp Lys
                805                 810                 815

Lys Asn Ile Lys Arg Lys Asp Leu Leu Cys Phe Tyr Leu Phe Leu Arg
                820                 825                 830

Leu Leu Asp Glu Asn Glu Ile Cys Lys Leu Gln His Gln Phe Ile Lys
        835                 840                 845

Tyr Arg Cys Ser Leu Lys Glu Arg Arg Phe Pro Gly Asn Arg Thr Lys
        850                 855                 860

Leu Glu Lys Glu Thr Glu Leu Leu Ala Glu Leu Glu Glu Leu Met Glu
865                 870                 875                 880

Leu Val Arg Phe Thr Met Pro Ser Ile Pro Glu Ile Ser Ala Lys Ala
                885                 890                 895

Glu Ser Gly Tyr Asp Thr Met Ile Lys Lys Tyr Phe Lys Asp Phe Ile
                900                 905                 910

Glu Lys Lys Val Phe Lys Asn Pro Lys Thr Ser Asn Leu Tyr Tyr His
        915                 920                 925

Ser Asp Ser Lys Thr Pro Val Thr Arg Lys Tyr Met Ala Leu Leu Met
        930                 935                 940

Arg Ser Ala Pro Leu His Leu Tyr Lys Asp Ile Phe Lys Gly Tyr Tyr
945                 950                 955                 960

Leu Ile Thr Lys Lys Glu Cys Leu Glu Tyr Ile Lys Leu Ser Asn Ile
                965                 970                 975

Ile Lys Asp Tyr Gln Asn Ser Leu Asn Glu Leu His Glu Gln Leu Glu
                980                 985                 990

Arg Ile Lys Leu Lys Ser Glu Lys  Gln Asn Gly Lys Asp  Ser Leu Tyr
        995                 1000                1005
```

-continued

```
Leu Asp Lys Lys Asp Phe Tyr  Lys Val Lys Glu Tyr  Val Glu Asn
    1010             1015              1020

Leu Glu  Gln Val Ala Arg Tyr  Lys His Leu Gln His  Lys Ile Asn
    1025             1030              1035

Phe Glu  Ser Leu Tyr Arg Ile  Phe Arg Ile His Val  Asp Ile Ala
    1040             1045              1050

Ala Arg  Met Val Gly Tyr Thr  Gln Asp Trp Glu Arg  Asp Met His
    1055             1060              1065

Phe Leu  Phe Lys Ala Leu Val  Tyr Asn Gly Val Leu  Glu Glu Arg
    1070             1075              1080

Arg Phe  Glu Ala Ile Phe Asn  Asn Asn Asp Asp Asn  Asn Asp Gly
    1085             1090              1095

Arg Ile  Val Lys Lys Ile Gln  Asn Asn Leu Asn Asn  Lys Asn Arg
    1100             1105              1110

Glu Leu  Val Ser Met Leu Cys  Trp Asn Lys Lys Leu  Asn Lys Asn
    1115             1120              1125

Glu Phe  Gly Ala Ile Ile Trp  Lys Arg Asn Pro Ile  Ala His Leu
    1130             1135              1140

Asn His  Phe Thr Gln Thr Glu  Gln Asn Ser Lys Ser  Ser Leu Glu
    1145             1150              1155

Ser Leu  Ile Asn Ser Leu Arg  Ile Leu Leu Ala Tyr  Asp Arg Lys
    1160             1165              1170

Arg Gln  Asn Ala Val Thr Lys  Thr Ile Asn Asp Leu  Leu Leu Asn
    1175             1180              1185

Asp Tyr  His Ile Arg Ile Lys  Trp Glu Gly Arg Val  Asp Glu Gly
    1190             1195              1200

Gln Ile  Tyr Phe Asn Ile Lys  Glu Lys Glu Asp Ile  Glu Asn Glu
    1205             1210              1215

Pro Ile  Ile His Leu Lys His  Leu His Lys Lys Asp  Cys Tyr Ile
    1220             1225              1230

Tyr Lys  Asn Ser Tyr Met Phe  Asp Lys Gln Lys Glu  Trp Ile Cys
    1235             1240              1245

Asn Gly  Ile Lys Glu Glu Val  Tyr Asp Lys Ser Ile  Leu Lys Cys
    1250             1255              1260

Ile Gly  Asn Leu Phe Lys Phe  Asp Tyr Glu Asp Lys  Asn Lys Ser
    1265             1270              1275

Ser Ala  Asn Pro Lys His Thr
    1280             1285
```

<210> SEQ ID NO 216
<211> LENGTH: 422
<212> TYPE: PRT
<213> ORGANISM: Semliki Forest virus

<400> SEQUENCE: 216

```
Ser Val Ser Gln His Phe Asn Val Tyr Lys Ala Thr Arg Pro Tyr Ile
1               5                   10                  15

Ala Tyr Cys Ala Asp Cys Gly Ala Gly His Ser Cys His Ser Pro Val
            20                  25                  30

Ala Ile Glu Ala Val Arg Ser Glu Ala Thr Asp Gly Met Leu Lys Ile
        35                  40                  45

Gln Phe Ser Ala Gln Ile Gly Ile Asp Lys Ser Asp Asn His Asp Tyr
    50                  55                  60

Thr Lys Ile Arg Tyr Ala Asp Gly His Ala Ile Glu Asn Ala Val Arg
65                  70                  75                  80
```

-continued

```
Ser Ser Leu Lys Val Ala Thr Ser Gly Asp Cys Phe Val His Gly Thr
            85                  90                  95

Met Gly His Phe Ile Leu Ala Lys Cys Pro Pro Gly Glu Phe Leu Gln
            100                 105                 110

Val Ser Ile Gln Asp Thr Arg Asn Ala Val Arg Ala Cys Arg Ile Gln
            115                 120                 125

Tyr His His Asp Pro Gln Pro Val Gly Arg Glu Lys Phe Thr Ile Arg
        130                 135                 140

Pro His Tyr Gly Lys Glu Ile Pro Cys Thr Thr Tyr Gln Gln Thr Thr
145                 150                 155                 160

Ala Glu Thr Val Glu Glu Ile Asp Met His Met Pro Pro Asp Thr Pro
                165                 170                 175

Asp Arg Thr Leu Leu Ser Gln Gln Ser Gly Asn Val Lys Ile Thr Val
                180                 185                 190

Gly Gly Lys Lys Val Lys Tyr Asn Cys Thr Cys Gly Thr Gly Asn Val
            195                 200                 205

Gly Thr Thr Asn Ser Asp Met Thr Ile Asn Thr Cys Leu Ile Glu Gln
        210                 215                 220

Cys His Val Ser Val Thr Asp His Lys Lys Trp Gln Phe Asn Ser Pro
225                 230                 235                 240

Phe Val Pro Arg Ala Asp Glu Pro Ala Arg Lys Gly Lys Val His Ile
                245                 250                 255

Pro Phe Pro Leu Asp Asn Ile Thr Cys Arg Val Pro Met Ala Arg Glu
                260                 265                 270

Pro Thr Val Ile His Gly Lys Arg Glu Val Thr Leu His Leu His Pro
            275                 280                 285

Asp His Pro Thr Leu Phe Ser Tyr Arg Thr Leu Gly Glu Asp Pro Gln
        290                 295                 300

Tyr His Glu Glu Trp Val Thr Ala Ala Val Glu Arg Thr Ile Pro Val
305                 310                 315                 320

Pro Val Asp Gly Met Glu Tyr His Trp Gly Asn Asn Asp Pro Val Arg
                325                 330                 335

Leu Trp Ser Gln Leu Thr Thr Glu Gly Lys Pro His Gly Trp Pro His
            340                 345                 350

Gln Ile Val Gln Tyr Tyr Tyr Gly Leu Tyr Pro Ala Ala Thr Val Ser
            355                 360                 365

Ala Val Val Gly Met Ser Leu Leu Ala Leu Ile Ser Ile Phe Ala Ser
        370                 375                 380

Cys Tyr Met Leu Val Ala Ala Arg Ser Lys Cys Leu Thr Pro Tyr Ala
385                 390                 395                 400

Leu Thr Pro Gly Ala Ala Val Pro Trp Thr Leu Gly Ile Leu Cys Cys
            405                 410                 415

Ala Pro Arg Ala His Ala
            420
```

```
<210> SEQ ID NO 217
<211> LENGTH: 512
<212> TYPE: PRT
<213> ORGANISM: Autographa californica nuclear polyhedrosis virus

<400> SEQUENCE: 217

Met Val Ser Ala Ile Val Leu Tyr Val Leu Leu Ala Ala Ala Ala His
1               5                   10                  15

Ser Ala Phe Ala Ala Glu His Cys Asn Ala Gln Met Lys Thr Gly Pro
```

-continued

```
                20              25              30

Tyr Lys Ile Lys Asn Leu Asp Ile Thr Pro Pro Lys Glu Thr Leu Gln
            35              40              45

Lys Asp Val Glu Ile Thr Ile Val Glu Thr Asp Tyr Asn Glu Asn Val
        50              55              60

Ile Ile Gly Tyr Lys Gly Tyr Tyr Gln Ala Tyr Ala Tyr Asn Gly Gly
65              70              75              80

Ser Leu Asp Pro Asn Thr Arg Val Glu Glu Thr Met Lys Thr Leu Asn
                85              90              95

Val Gly Lys Glu Asp Leu Leu Met Trp Ser Ile Arg Gln Gln Cys Glu
            100             105             110

Val Gly Glu Glu Leu Ile Asp Arg Trp Gly Ser Asp Ser Asp Asp Cys
        115             120             125

Phe Arg Asp Asn Glu Gly Arg Gly Gln Trp Val Lys Gly Lys Glu Leu
        130             135             140

Val Lys Arg Gln Asn Asn Asn His Phe Ala His His Thr Cys Asn Lys
145             150             155             160

Ser Trp Arg Cys Gly Ile Ser Thr Ser Lys Met Tyr Ser Arg Leu Glu
            165             170             175

Cys Gln Asp Asp Thr Asp Glu Cys Gln Val Tyr Ile Leu Asp Ala Glu
            180             185             190

Gly Asn Pro Ile Asn Val Thr Val Asp Thr Val Leu His Arg Asp Gly
            195             200             205

Val Ser Met Ile Leu Lys Gln Lys Ser Thr Phe Thr Thr Arg Gln Ile
        210             215             220

Lys Ala Ala Cys Leu Leu Ile Lys Asp Asp Lys Asn Asn Pro Glu Ser
225             230             235             240

Val Thr Arg Glu His Cys Leu Ile Asp Asn Asp Ile Tyr Asp Leu Ser
            245             250             255

Lys Asn Thr Trp Asn Cys Lys Phe Asn Arg Cys Ile Lys Arg Lys Val
            260             265             270

Glu His Arg Val Lys Lys Arg Pro Pro Thr Trp Arg His Asn Val Arg
            275             280             285

Ala Lys Tyr Thr Glu Gly Asp Thr Ala Thr Lys Gly Asp Leu Met His
            290             295             300

Ile Gln Glu Glu Leu Met Tyr Glu Asn Asp Leu Leu Lys Met Asn Ile
305             310             315             320

Glu Leu Met His Ala His Ile Asn Lys Leu Asn Asn Met Leu His Asp
            325             330             335

Leu Ile Val Ser Val Ala Lys Val Asp Glu Arg Leu Ile Gly Asn Leu
            340             345             350

Met Asn Asn Ser Val Ser Ser Thr Phe Leu Ser Asp Asp Thr Phe Leu
            355             360             365

Leu Met Pro Cys Thr Asn Pro Pro Ala His Thr Ser Asn Cys Tyr Asn
        370             375             380

Asn Ser Ile Tyr Lys Glu Gly Arg Trp Val Ala Asn Thr Asp Ser Ser
385             390             395             400

Gln Cys Ile Asp Phe Ser Asn Tyr Lys Glu Leu Ala Ile Asp Asp Asp
                405             410             415

Val Glu Phe Trp Ile Pro Thr Ile Gly Asn Thr Thr Tyr His Asp Ser
            420             425             430

Trp Lys Asp Ala Ser Gly Trp Ser Phe Ile Ala Gln Gln Lys Ser Asn
            435             440             445
```

```
Leu Ile Thr Thr Met Glu Asn Thr Lys Phe Gly Gly Val Gly Thr Ser
    450                 455                 460

Leu Ser Asp Ile Thr Ser Met Ala Glu Gly Glu Leu Ala Ala Lys Leu
465                 470                 475                 480

Thr Ser Phe Met Phe Gly His Val Val Asn Phe Val Ile Ile Leu Ile
                485                 490                 495

Val Ile Leu Phe Leu Tyr Cys Met Ile Arg Asn Arg Asn Arg Gln Tyr
                500                 505                 510
```

```
<210> SEQ ID NO 218
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (2)..(3)
<223> OTHER INFORMATION: Each amino acid at positions 2-3 may be any
      amino acid
<220> FEATURE:
<221> NAME/KEY: VARIANT
<222> LOCATION: (4)..(4)
<223> OTHER INFORMATION: The amino acid at position 4 is a hydrophobic
      residue

<400> SEQUENCE: 218

Pro Xaa Xaa Xaa
1
```

```
<210> SEQ ID NO 219
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (2)..(3)
<223> OTHER INFORMATION: Each amino acid at positions 2-3 may be any
      amino acid
<220> FEATURE:
<221> NAME/KEY: VARIANT
<222> LOCATION: (4)..(4)
<223> OTHER INFORMATION: The amino acid at position 4 is a hydrophobic
      residue
<220> FEATURE:
<221> NAME/KEY: VARIANT
<222> LOCATION: (5)..(5)
<223> OTHER INFORMATION: The amino acid at position 5 is Ser or Thr

<400> SEQUENCE: 219

Pro Xaa Xaa Xaa Xaa
1               5
```

```
<210> SEQ ID NO 220
<211> LENGTH: 6
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (2)..(2)
<223> OTHER INFORMATION: The amino acid at position 2 is Leu or Gln

<400> SEQUENCE: 220

Pro Xaa Gly Met Thr Ser
1               5
```

```
<210> SEQ ID NO 221
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (2)..(2)
<223> OTHER INFORMATION: The amino acid at position 2 is Leu or Gln

<400> SEQUENCE: 221

Pro Xaa Gly Met Thr
1               5
```